US010815463B2

(12) United States Patent
Chivukula et al.

(10) Patent No.: US 10,815,463 B2
(45) Date of Patent: Oct. 27, 2020

(54) MESSENGER UNA MOLECULES AND USES THEREOF

(71) Applicant: Arcturus Therapeutics, Inc., San Diego, CA (US)

(72) Inventors: Padmanabh Chivukula, San Diego, CA (US); Luigi Warren, San Diego, CA (US); Kiyoshi Tachikawa, San Diego, CA (US); Joseph E. Payne, San Diego, CA (US)

(73) Assignee: ARCTURUS THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 15/806,096

(22) Filed: Nov. 7, 2017

(65) Prior Publication Data

US 2018/0051262 A1    Feb. 22, 2018

Related U.S. Application Data

(63) Continuation of application No. 14/929,366, filed on Nov. 1, 2015, now abandoned.

(60) Provisional application No. 62/074,046, filed on Nov. 2, 2014.

(51) Int. Cl.
| | |
|---|---|
| A61K 48/00 | (2006.01) |
| C07H 21/02 | (2006.01) |
| C07H 21/04 | (2006.01) |
| C12N 9/10 | (2006.01) |
| C07K 14/46 | (2006.01) |
| C07K 14/47 | (2006.01) |
| C07K 14/505 | (2006.01) |
| C07K 14/52 | (2006.01) |
| C07K 14/575 | (2006.01) |
| C07K 14/705 | (2006.01) |
| C07K 14/745 | (2006.01) |
| C07K 14/805 | (2006.01) |
| C07K 14/81 | (2006.01) |
| C12N 9/02 | (2006.01) |
| C12N 9/12 | (2006.01) |
| C12N 9/44 | (2006.01) |
| C12N 9/64 | (2006.01) |
| C12N 9/88 | (2006.01) |
| C07K 14/445 | (2006.01) |
| A61K 39/00 | (2006.01) |

(52) U.S. Cl.
CPC .......... *C12N 9/1018* (2013.01); *C07K 14/445* (2013.01); *C07K 14/463* (2013.01); *C07K 14/47* (2013.01); *C07K 14/4712* (2013.01); *C07K 14/4717* (2013.01); *C07K 14/505* (2013.01); *C07K 14/524* (2013.01); *C07K 14/575* (2013.01); *C07K 14/705* (2013.01); *C07K 14/745* (2013.01); *C07K 14/805* (2013.01); *C07K 14/8125* (2013.01); *C12N 9/0071* (2013.01); *C12N 9/1051* (2013.01); *C12N 9/1205* (2013.01); *C12N 9/2451* (2013.01); *C12N 9/644* (2013.01); *C12N 9/88* (2013.01); *C12Y 114/16001* (2013.01); *C12Y 201/03003* (2013.01); *C12Y 204/01025* (2013.01); *C12Y 207/0104* (2013.01); *C12Y 302/01033* (2013.01); *C12Y 304/21022* (2013.01); *C12Y 403/02001* (2013.01); *A61K 39/00* (2013.01); *A61K 48/00* (2013.01); *C12N 2740/16222* (2013.01); *C12N 2840/105* (2013.01); *C12N 2840/60* (2013.01)

(58) Field of Classification Search
CPC .... C12N 15/111; C12N 15/113; A61K 31/713
See application file for complete search history.

(56) References Cited

U.S. PATENT DOCUMENTS

| | | | |
|---|---|---|---|
| 8,278,036 B2 | 10/2012 | Kariko | |
| 8,454,948 B2 | 6/2013 | Pearlman | |
| 8,691,966 B2 | 4/2014 | Kariko | |
| 2002/0064812 A1 | 5/2002 | Connelly | |
| 2002/0090719 A1 | 7/2002 | Yew | |
| 2008/0167219 A1 | 7/2008 | Lin | |
| 2009/0286852 A1 | 11/2009 | Kariko | |
| 2011/0105734 A1 | 5/2011 | Kawasaki | |
| 2011/0143397 A1 | 6/2011 | Kariko | |
| 2013/0096289 A1 | 4/2013 | Wengel | |
| 2013/0123481 A1 | 5/2013 | De Fougerolles | |
| 2013/0259923 A1 | 10/2013 | Bancel et al. | |
| 2014/0371302 A1 | 12/2014 | Afeyan et al. | |
| 2016/0022774 A1 | 1/2016 | Bancel | |
| 2016/0032316 A1 | 2/2016 | Weissman et al. | |

FOREIGN PATENT DOCUMENTS

| | | |
|---|---|---|
| WO | 2007003582 A2 | 1/2007 |
| WO | 2011012316 | 2/2011 |
| WO | 2012145624 A2 | 10/2012 |
| WO | 2013149140 A1 | 10/2013 |
| WO | 2014003580 A1 | 1/2014 |
| WO | 2015051169 A2 | 4/2015 |
| WO | 2015117021 A1 | 8/2015 |
| WO | 2015196128 A2 | 12/2015 |
| WO | 2016131052 A1 | 8/2016 |

OTHER PUBLICATIONS

Kertesz et al. (Developmental Biology, 276, 2004, 101-110).*

(Continued)

*Primary Examiner* — Amy H Bowman
(74) *Attorney, Agent, or Firm* — Mintz, Levin, Cohn, Ferris, Glovsky and Popeo, P.C.

(57) ABSTRACT

This invention provides a range of translatable messenger UNA (mUNA) molecules. The mUNA molecules can be translated in vitro and in vivo to provide an active polypeptide or protein, or to provide an immunization agent or vaccine component. The mUNA molecules can be used as an active agent to express an active polypeptide or protein in cells or subjects. Among other things, the mUNA molecules are useful in methods for treating rare diseases.

19 Claims, 14 Drawing Sheets

Specification includes a Sequence Listing.

(56) References Cited

OTHER PUBLICATIONS

Suto, Dominant-negative mutant of c-Jun gene transfer: a novel therapeutic strategy for colorectal cancer, 2004, Gene Therapy, vol. 11, pp. 187-193.
Benjannet, Loss- and Gain-of-function PCSK9 Variants, 2012, J Biol Chem, vol. 287, pp. 33745-33755.
Niu, Gene Therapy with Dominant-negative Stat3 Suppresses Growth of the Murine Melanoma B16 Tumor in Vivo, 1999, Cancer Research, vol. 59, pp. 5059-5063.
Silva, Meganucleases and Other Tools for Targeted Genome Engineering: Perspectives and Challenges for Gene Therapy, 2011, Current Gene Therapy, vol. 11, pp. 11-27.
Kariko, Increased Erythropoiesis in Mice Injected With Submicrogram Quantities of Pseudouridinecontaining mRNA Encoding Erythropoietin, Molecular Therapy, vol. 20 No. 5, 948-953 May 2012.
Kariko, Incorporation of Pseudouridine Into mRNA Yields Superior Nonimmunogenic Vector with Increased Translational Capacity and Biological Stability, Mol Ther. Nov. 2008 ; 16(11): 1833-1840.
Thess, Sequence-engineered mRNA without Chemical Nucleoside Modifications Enables an Effective Protein Therapy in Large Animals, Molecular Therapy, online publication Jun. 30, 2015, pp. 1-9.
Thess, Sequence-engineered mRNA without Chemical Nucleoside Modifications Enables an Effective Protein Therapy in Large Animals, Molecular Therapy, online publication Jun. 30, 2015, supplementary material pp. 1-11.
Kotkowiak, Unlocked Nucleic Acids: Implications of Increased Conformational Flexibility for RNA/DNA Triplex Formation, Biochemical Journal, Sep. 2014, vol. 464, No. 2; pp. 203-211.
Ferri, Aminoacylase I Deficiency Due to ACY1 mRNA Exon Skipping, Clinical Genetics, Nov. 17, 2013, vol. 86, No. 4; pp. 367-372.
Campbell, Locked vs. unlocked nucleic acids (LNA vs. UNA): contrasting structures work towards common therapeutic goals, Chem Soc Rev, 2011, vol. 40, pp. 5680-5689.
Collins, Generation and initial analysis of more than 15,000 full-length human and mouse cDNA sequences, Proc Nat Academy Sci, 2002, vol. 99, pp. 16899-16903.
Seth, RNAi-based Therapeutics Targeting Survivin and PLK1 for Treatment of Bladder Cancer, Molecular Therapy, 2011, vol. 19, pp. 928-935.
Lucchiari, Molecular Characterisation of GSD III Subjects and Identification of Six Novel Mutations in AGL, Human Mutation, 2002, #564 Online, pp. 1-6.
Pasternak, et al., Unlocked nucleic acid—an RNA modification with broad potential, Org. Biomol. Chem., 2011, pp .3591-3597, vol. 9.

\* cited by examiner

MESSENGER UNA MOLECULES AND USES THEREOF

SEQUENCE LISTING

This application includes a Sequence Listing submitted electronically herewith as an ASCII file created on Nov. 7, 2017, named ARC3146US2_SL.txt, which is 347,990 bytes in size, and is hereby incorporated by reference in its entirety.

BACKGROUND OF THE INVENTION

It has long been difficult to utilize messenger RNA molecules in medicines. Synthetic mRNA can be designed with inherent translational activity for making an active protein, which could be used in various therapeutic strategies. However, the expression of protein involves a number of steps that are localized and/or regulated. Further, plentiful RNase enzymes can degrade mRNA. Moreover, use of a synthetic mRNA requires clinical formulation and delivery to cells. These steps of mRNA delivery, partitioning and dynamics increase the need for stability and longevity of the synthetic mRNA.

For efficient translation, natural mRNA transcripts incorporate a 5' 7-methylguanosine cap and a 3' polyA tail. PolyA binding proteins (PABPs) bind to the tail and cooperate with the 5' cap via looping interactions to recruit the machinery of translation. A 3' polyA tail of at least about 20 nucleotides is needed to activate the mRNA for translation. Translational activity can decrease to low levels in the absence of either the 5' cap or the 3' polyA tail.

One drawback in using mRNA molecules in medicines is that the lifetime of the molecule in the cytoplasm of mammalian cells is relatively short. In general, ubiquitous mRNA degradation pathways actively clear out transcripts from the mRNA pool. The principle pathways for mRNA degradation involve deadenylation or trimming of the 3' polyA tail by 3'-exoribonucleases and cleavage of the 5'-5' triphosphate linkage that attaches the methylguanosine cap by a decapping complex.

One way to increase mRNA longevity might be to increase 3'-nuclease resistance by incorporating nucleotide analogues or chemical modifications in either the phosphodiester backbone or the nucleotides, which are localized to the 3' end to be compatible with enzymatic synthesis and efficient translation. A drawback of this approach is that it may not be possible to selectively incorporate such chemical modifications at 3' termini, or to retain activity.

There is an urgent need for molecules, structures and compositions having specific translational activity to provide active peptides and proteins, both in vitro and in vivo. Such new molecules having functional cytoplasmic half-life for producing active peptides and proteins can yield new drug molecules, therapeutic modalities, vaccines, and immunotherapies.

What is needed are translatable molecules that have increased specific activity and/or lifetime over native mRNA, to be used in methods and compositions for producing and delivering active peptides and proteins in medicines.

BRIEF SUMMARY

This invention relates to the fields of molecular biology and genetics, as well as to biopharmaceuticals and therapeutics generated from translatable molecules. More particularly, this invention relates to methods, structures and compositions for molecules having translational activity for making active peptides or proteins in vivo.

This invention provides methods and compositions for novel molecules having translational activity, which can be used to provide active peptides and proteins.

The molecules of this invention can have functional cytoplasmic half-life for producing peptides and proteins. The peptides and proteins can be active for therapeutic modalities, as well as in vaccines and immunotherapies.

The molecules of this invention can be translatable messenger molecules, which can have long half-life, particularly in the cytoplasm of a cell. The longer duration of the translatable messenger molecules of this invention can be significant for providing a translation product that is active for ameliorating, preventing or treating various diseases. The diseases can be associated with undesirable modulation of protein concentration, or undesirable activity of a protein.

This disclosure provides a range of structures for translatable molecules that have increased specific activity and/or lifetime over native mRNA. The translatable molecules of this invention can be used in medicines, and for methods and compositions for producing and delivering active peptides and proteins.

Embodiments of this disclosure provide a wide range of novel, translatable messenger molecules. The translatable messenger molecules can contain monomers that are unlocked nucleomonomers (UNA monomers). The long duration of translatable messenger UNA molecules (mUNA molecules) of this invention can be useful for providing an active peptide or protein translation product. The mUNA molecules of this invention can be used in medicines for ameliorating, preventing or treating disease.

The translatable mUNA molecules of this invention can be used to provide peptides or proteins in vitro, ex vivo, or in vivo.

The translatable mUNA molecules of this invention can provide high-efficiency expression of virtually any protein.

In some embodiments, the mUNA molecules of this invention have increased cytoplasmic half-life over a native, mature mRNA that provides the same peptide or protein. The mUNA structures and compositions of this invention can provide increased functional half-life with respect to native, mature mRNAs.

In further aspects, a mUNA molecule of this invention can provide increased activity as a drug providing a peptide or protein product, as compared to a native, mature mRNA. In some embodiments, a mUNA molecule can reduce the expected dose level that would be required for efficacious therapy.

Additional embodiments of this invention can provide vaccine compositions for immunization and immunotherapies using mUNA molecules.

Embodiments of this invention include the following:

A mUNA molecule, containing one or more UNA monomers, and containing nucleic acid monomers, wherein the mUNA molecule is translatable to express a polypeptide or protein. The molecule may have from 200 to 12,000 monomers, or from 200 to 4,000 monomers. In some embodiments, the molecule can have from 1 to 8,000 UNA monomers, or from 1 to 100 UNA monomers, or from 1 to 20 UNA monomers.

A mUNA molecule can have one or more modified nucleic acid nucleotides, and/or one or more chemically-modified nucleic acid nucleotides.

In some embodiments, a mUNA molecule can contain a 5' cap, a 5' untranslated region of monomers, a coding region of monomers, a 3' untranslated region of monomers, and a tail region of monomers. In certain embodiments, the molecule can contain a translation enhancer in a 5' or 3' untranslated region.

The mUNA molecules of this invention can be translatable in vivo, or in vitro, or in a mammalian cell, or in a human in vivo. In some embodiments, a translation product of a mUNA molecule can be an active peptide or protein.

In certain embodiments, a translation product of a mUNA molecule is human EPO, human Factor IX, human alpha-1-antitrypsin, human CFTR, human ASL, human PAH, human NIS, or human hepcidin.

In another aspect, a mUNA molecule can exhibit at least 2-fold, 3-fold, 5-fold, or 10-fold increased translation efficiency in vivo as compared to a native mRNA that encodes the same translation product.

In certain embodiments, a mUNA molecule can have a cytoplasmic half-life in a cell at least 2-fold greater than a native mRNA of the cell that encodes the same translation product.

Embodiments of this invention further contemplate therapeutic mUNA agents for a rare disease, a liver disease, or a cancer. A mUNA molecule can be an immunization agent or vaccine component for a rare disease, a liver disease, or a cancer.

This invention further provides compositions containing a mUNA molecule and a pharmaceutically acceptable carrier, and vaccine or immunization compositions containing a mUNA molecule. The carrier can be a nanoparticle or liposome.

In additional embodiments, this invention provides methods for ameliorating, preventing or treating a disease or condition in a subject comprising administering to the subject a composition containing a mUNA molecule. The disease or condition can be a rare disease, liver disease, or cancer.

In certain embodiments, this invention provides methods for producing a polypeptide or protein in vivo, by administering to a mammal a composition containing a mUNA molecule. The polypeptide or protein may be deficient in a disease or condition of a subject or mammal. The protein can be human EPO, human Factor IX, human alpha-1-antitrypsin, human CFTR, human ASL, human PAH, human NIS, or human hepcidin.

This invention further provides methods for producing a polypeptide or protein in vitro, by transfecting a cell with a mUNA molecule. The polypeptide or protein can be deficient in a disease or condition of a subject or mammal. The protein can be human EPO, human Factor IX, human alpha-1-antitrypsin, human CFTR, human ASL, human PAH, human NIS, or human hepcidin.

BRIEF DESCRIPTION OF THE DRAWINGS

FIG. 1 shows the results of expressing human Factor IX (F9) in vivo using a translatable mUNA molecule of this invention, as compared to expression of a native mRNA of Factor IX. FIG. 1 shows that the translation efficiency of this mUNA molecule was doubled as compared to the native mRNA of F9. The mUNA molecule of this embodiment was translated in C57BL/c mouse to produce human F9.

FIG. 2 shows the results of expressing human Factor IX (F9) in vitro using a translatable mUNA molecule of this invention, as compared to expression of a native mRNA of Factor IX. FIG. 2 shows that the translation efficiency of this mUNA molecule was increased by 5-fold after 48 hours, as compared to the native mRNA of F9. The mUNA molecule of this embodiment was translated in mouse hepatocyte cell line Hepa1-6 to produce human F9.

FIG. 3 shows the results of expressing human Erythropoietin (EPO) in vitro using a translatable mUNA molecule of this invention, as compared to expression of a native mRNA of human EPO. FIG. 3 shows that the translation efficiency of this mUNA molecule was increased nearly 3-fold after 48 hours, as compared to the native mRNA of EPO. The mUNA molecule of this embodiment was translated in mouse hepatocyte cell line Hepa1-6 to produce human EPO.

FIG. 4 shows the results of expressing mouse Erythropoietin (EPO) in vitro using several translatable mUNA molecules of this invention, as compared to expression of a native mRNA of mouse EPO. FIG. 4 shows that the translation efficiencies of the mUNA molecules (#2, 3, 4, 5, 6, 7, 8, 9, 10 and 11) were increased by up to 10-fold after 72 hours, as compared to the native mRNA of EPO. The mUNA molecules of this embodiment were translated in mouse hepatocyte cell line Hepa1-6 to produce mouse EPO.

FIG. 5 shows the results of expressing human alpha-1-antitrypsin in vivo using a translatable mUNA molecule of this invention, as compared to expression of a native mRNA of human alpha-1-antitrypsin. FIG. 5 shows that the translation efficiency of this mUNA molecule at 72 hrs was increased more than 3-fold as compared to the native mRNA of human alpha-1-antitrypsin. The mUNA molecule of this embodiment was translated in C57BL/c mouse to produce human alpha-1-antitrypsin.

FIG. 6 shows the results of expressing human erythropoietin (EPO) in vivo using a translatable mUNA molecule of this invention, as compared to expression of a native mRNA of human EPO. FIG. 6 shows that the translation efficiency of this mUNA molecule at 72 hrs was increased more than 10-fold as compared to the native mRNA of human EPO. The mUNA molecule of this embodiment was translated in C57BL/c mouse to produce human EPO.

FIG. 7 shows the primary structure of a functional mRNA transcript in the cytoplasm. The mRNA includes a 5' methylguanosine cap, a protein coding sequence flanked by untranslated regions (UTRs), and a polyadenosine (polyA) tail bound by polyA binding proteins (PABPs).

FIG. 8 shows the 5' cap and PABPs cooperatively interacting with proteins involved in translation to facilitate the recruitment and recycling of ribosome complexes.

FIG. 9 shows the splint-mediated ligation scheme, in which an acceptor RNA with a 30-monomer stub polyA tail (A(30)) was ligated to a 30-monomer donor oligomer A(30). The splint-mediated ligation used a DNA oligomer splint which was complementary to the 3' UTR sequence upstream of the stub polyA tail, and included a 60-monomer oligo(dT) 5' heel (T(60)) to splint the ligation. The anchoring region of the splint was complementary to the UTR sequence to ensure that a 5' $dT_{30}$ overhang was presented upon hybridization to the acceptor. This brings the donor oligomer into juxtaposition with the 3' terminus of the stub tail, dramatically improving the kinetics of ligation.

FIG. 10 shows experimental results of splint-mediated ligation of a donor oligomer to an acceptor. FIG. 10 shows the results of ligation using 2 ug of a 120-monomer acceptor with an $A_{30}$ stub tail that was ligated to a 5'-phosphorylated $A_{30}$ RNA donor oligomer using T4 RNA Ligase 2. The reaction was incubated overnight at 37° C. The ligation and a mock reaction done without enzyme were purified, treated with DNAse I for 1 hour to degrade and detach the splint oligomers, and re-purified in a volume of 30 uL. The ligation efficiency was nearly 100%. The absence of a size shift in the mock-reaction prep shows that the acceptor and donor were truly ligated and not simply held together by undigested splint oligomers.

FIG. 11 shows the results of splint-mediated ligation using an acceptor RNA with a 30-monomer stub polyA tail (A(30)). The ligation reactions were performed with three different donor oligomer species: A(30), A(60), and A(120). Based on the gel shifts, the ligations have attained nearly 100% efficiency.

FIG. 12 shows the results of one-hour splint-mediated ligations that were performed on nGFP-$A_{30}$ transcripts. The resulting ligation products were compared to untreated transcripts and native nGFP-$A_{60}$ IVT products. The native nGFP-$A_{60}$ and the ligated products were up-shifted on the gel relative to the untreated nGFP-$A_{30}$ transcripts and mock-ligated material, showing that the ligation yield was nearly 100%.

FIG. 13 shows increased lifetime and translational activity for an nGFP-$A_{60}$ ligation product. In FIG. 13, nuclearized transcripts were transfected into fibroblasts, and a comparison of fluorescence signals was made for nGFP-$A_{30}$, mock-ligated nGFP-$A_{30}$, and an nGFP-$A_{60}$ ligation product (FIG. 13, left to right). The significantly higher fluorescence signal observed for the nGFP-$A_{60}$ ligation product shows that it has markedly increased translational activity.

FIG. 14 shows the results of a ligation performed with a 100-monomer acceptor RNA that was treated for 3 hours at room temperature with T4 RNA Ligase 2 (truncated KQ mutant) using a 10 uM concentration of a polyA tail 30-monomer donor oligomer. 15% PEG 8000 was included in the reaction as a volume excluder to promote efficient ligation. The ligation reaction showed that a high molecular weight product was formed, having a size in between the 100-monomer acceptor RNA and a 180-monomer RNA transcript included as a size standard. These results show that the ligation reaction produced a predominant product having high molecular weight with nearly 100% ligation of the donor to the acceptor. Additional experiments with concentrations of the polyA tail at 10 uM, 20 uM, and 40 uM showed that from about 50% to about 100% of the acceptor RNA was ligated.

DETAILED DESCRIPTION OF THE INVENTION

Figure 1:
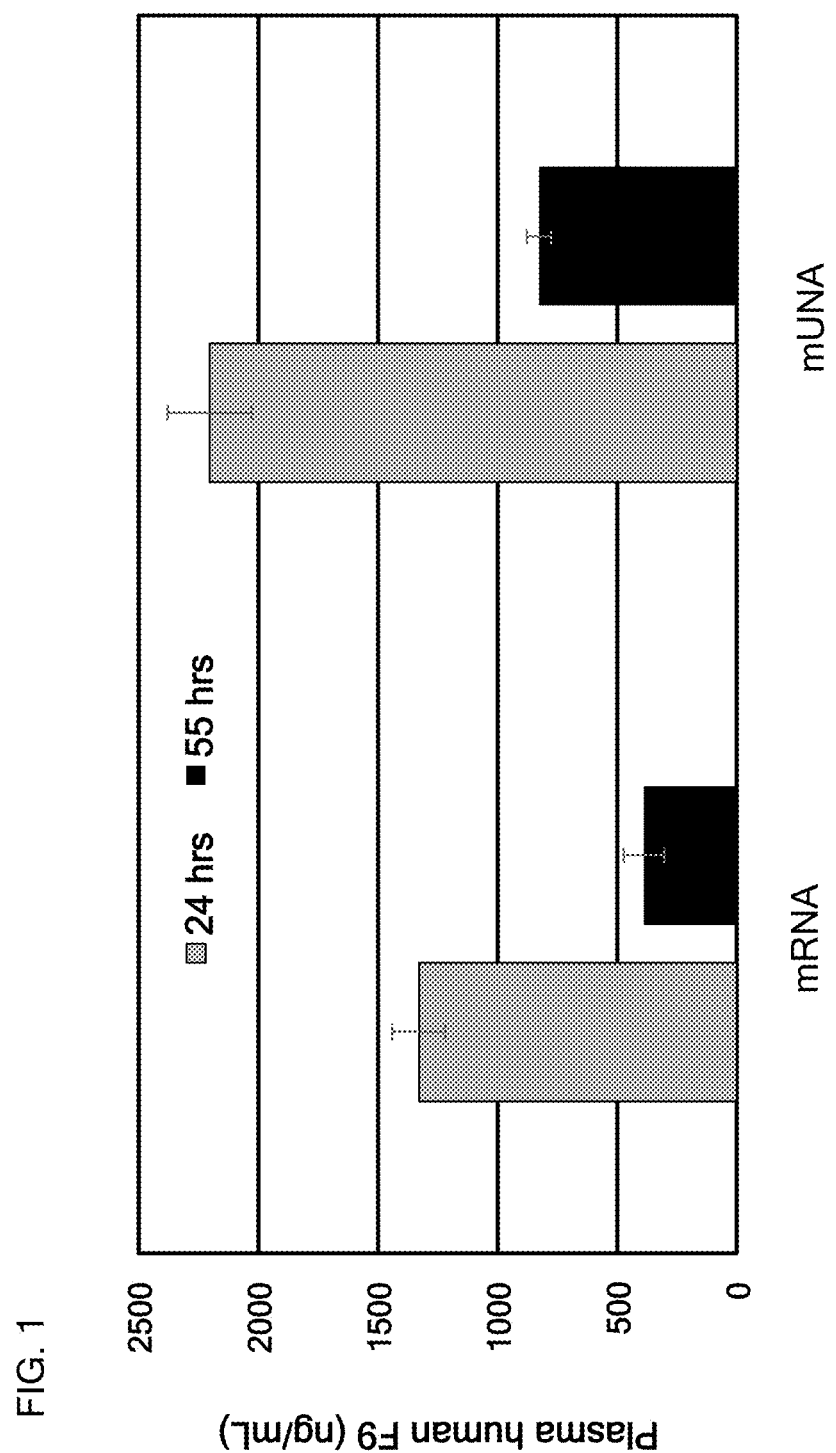
FIG. 1.

This invention provides a range of novel agents and compositions to be used for therapeutic applications. The molecules and compositions of this invention can be used for ameliorating, preventing or treating various diseases associated with genomic functionalities.

The molecules of this invention can be translatable messenger UNA molecules, which can have long half-life, particularly in the cytoplasm. The long duration mUNA molecules (mUNA molecules) can be used for ameliorating, preventing or treating various diseases associated with undesirable modulation of protein concentration, or activity of a protein.

The properties of the mUNA compounds of this invention arise according to their molecular structure, and the structure of the molecule in its entirety, as a whole, can provide significant benefits based on those properties. Embodiments of this invention can provide mUNA molecules having one or more properties that advantageously provide enhanced effectiveness in regulating protein expression or concentration, or modulating protein activity. The molecules and compositions of this invention can provide formulations for therapeutic agents for various diseases and conditions, which can provide clinical agents.

This invention provides a range of mUNA molecules that are surprisingly translatable to provide active peptide or protein, in vitro and in vivo.

The mUNA structures and compositions can have increased translational activity and cytoplasmic half-life. In these embodiments, the mUNA structures and compositions can provide increased functional half-life in the cytoplasm of mammalian cells over native mRNA molecules. The inventive mUNA molecules can have increased half-life of activity with respect to a corresponding native mRNA.

A wide range of novel mUNA molecules are provided herein, each of which can incorporate specialized linker groups. The linker groups can be attached in a chain in the mUNA molecule. Each linker group can also be attached to a nucleobase.

In some aspects, a linker group can be a monomer. Monomers can be attached to form a chain molecule. In a chain molecule of this invention, a linker group monomer can be attached at any point in the chain.

In certain aspects, linker group monomers can be attached in a chain molecule of this invention so that the linker group monomers reside near the ends of the chain, or at any position in the chain.

As used herein, a chain molecule can also be referred to as an oligomer.

In further aspects, the linker groups of a chain molecule can each be attached to a nucleobase. The presence of nucleobases in the chain molecule can provide a sequence of nucleobases in the chain molecule.

In certain embodiments, this invention provides oligomer mUNA molecules having chain structures that incorporate novel combinations of the linker group monomers, along with certain natural nucleotides, or non-natural nucleotides, or modified nucleotides, or chemically-modified nucleotides.

The oligomer mUNA molecules of this invention can display a sequence of nucleobases, and can be designed to express a polypeptide or protein, in vitro, ex vivo, or in vivo. The expressed polypeptide or protein can have activity in various forms, including activity corresponding to protein expressed from natural mRNA, or activity corresponding to a negative or dominant negative protein.

In some aspects, this invention can provide active mUNA oligomer molecules having a base sequence that corresponds to at least a fragment of a native nucleic acid molecule of a cell.

In some embodiments, the cell can be a eukaryotic cell, a mammalian cell, or a human cell.

This invention provides structures, methods and compositions for oligomeric mUNA agents that incorporate the linker group monomers. The oligomeric molecules of this invention can be used as active agents in formulations for therapeutics.

This invention provides a range of mUNA molecules that are useful for providing therapeutic effects because of their longevity of activity in providing an expressed peptide or protein.

In certain embodiments, an active mUNA molecule can be structured as an oligomer composed of monomers. The oligomeric structures of this invention may contain one or more linker group monomers, along with certain nucleotides.

An expressed peptide or protein can be modified or mutated as compared to a native variant, or can be a homolog or ortholog for enhanced expression in a eukaryotic cell. An active mUNA molecule can be human codon optimized. Methodologies for optimizing codons are known in the art.

In certain embodiments, a mUNA molecule may contain a sequence of nucleobases, and can be designed to express a peptide or protein of any isoform, in part by having sufficient homology with a native polynucleotide sequence.

In some embodiments, a mUNA molecule can be from about 200 to about 12,000 monomers in length, or more. In certain embodiments, a mUNA molecule can be from 200 to 12,000 monomers in length, or 200 to 10,000 monomers, or 200 to 8,000 monomers, or 200 to 6000 monomers, or 200 to 5000 monomers, or 200 to 4000 monomers, or 200 to 3600 monomers, or 200 to 3200 monomers, or 200 to 3000 monomers, or 200 to 2800 monomers, or 200 to 2600 monomers, or 200 to 2400 monomers, or 200 to 2200 monomers, or 600 to 3200 monomers, or 600 to 3000 monomers, or 600 to 2600 monomers.

In some embodiments, a mUNA molecule can contain from 1 to about 8,000 UNA monomers. In certain embodiments, a mUNA molecule can contain from 1 to 8,000 UNA monomers, or 1 to 6,000 UNA monomers, or 1 to 4,000 UNA monomers, or 1 to 3,000 UNA monomers, or 1 to 2,000 UNA monomers, or 1 to 1,000 UNA monomers, or 1 to 500 UNA monomers, or 1 to 300 UNA monomers, or 1 to 200 UNA monomers, or 1 to 100 UNA monomers, or 1 to 50 UNA monomers, or 1 to 40 UNA monomers, or 1 to 30 UNA monomers, or 1 to 20 UNA monomers, or 1 to 10 UNA monomers, or 1 to 6 UNA monomers.

In some embodiments, a mUNA molecule can be from about 200 to about 12,000 bases in length, or more. In certain embodiments, a mUNA molecule can be from 200 to 12,000 bases in length, or 200 to 10,000 bases, or 200 to 8,000 bases, or 200 to 6000 bases, or 200 to 5000 bases, or 200 to 4000 bases, or 200 to 3600 bases, or 200 to 3200 bases, or 200 to 3000 bases, or 200 to 2800 bases, or 200 to 2600 bases, or 200 to 2400 bases, or 200 to 2200 bases, or 600 to 3200 bases, or 600 to 3000 bases, or 600 to 2600 bases.

A mUNA molecule of this invention may comprise a 5' cap, a 5' untranslated region of monomers, a coding region of monomers, a 3' untranslated region of monomers, and a tail region of monomers. Any of these regions of monomers may comprise one or more UNA monomers.

A mUNA molecule of this invention may comprise a 5' untranslated region of monomers containing one or more UNA monomers.

A mUNA molecule of this invention may comprise a coding region of monomers containing one or more UNA monomers.

A mUNA molecule of this invention may comprise a 3' untranslated region of monomers containing one or more UNA monomers.

A mUNA molecule of this invention may comprise a tail region of monomers containing one or more UNA monomers.

A mUNA molecule of this invention may comprise a 5' cap containing one or more UNA monomers.

A mUNA molecule of this invention can be translatable, and may comprise regions of sequences or structures that are operable for translation in a cell, or which have the functionality of regions of an mRNA including, for example, a 5' cap, a 5' untranslated region, a coding region, a 3' untranslated region, and a polyA tail.

This invention further contemplates methods for delivering one or more vectors, or one or more mUNA molecules to a cell.

In some embodiments, one or more mUNA molecules can be delivered to a cell, in vitro, ex vivo, or in vivo. Viral and non-viral transfer methods as are known in the art can be used to introduce mUNA molecules in mammalian cells. mUNA molecules can be delivered with a pharmaceutically acceptable vehicle, or for example, encapsulated in a liposome.

A peptide or protein expressed by a mUNA molecule can be any peptide or protein, endogenous or exogenous in nature with respect to a eukaryotic cell, and may be a synthetic or non-natural peptide or protein with activity or effect in the cell.

In some embodiments, mUNA structures and compositions of this invention can reduce the number and frequency of transfections required for cell-fate manipulation in culture as compared to utilizing native compositions.

In additional aspects, this invention provides increased activity for mUNA-based drugs as compared to utilizing native compositions, and can reduce the dose levels required for efficacious therapy.

In further aspects, this invention provides increased activity for mUNA-based molecules, as compared to utilizing a native mRNA as active agent.

In some aspects, this invention can provide mUNA molecules that may reduce the cellular innate immune response, as compared to that induced by a natural nucleic acid, peptide or protein.

In further aspects, embodiments of this invention can provide increased efficacy for single-dose therapeutic modalities, including mUNA immunization and immunotherapies.

This invention can provide synthetic mUNA molecules that are refractory to deadenylation as compared to native molecules.

In certain embodiments, this invention can provide synthetic mUNA molecules with increased specific activity and longer functional half-life as compared to native molecules. The synthetic mUNA molecules of this invention can provide increased levels of ectopic protein expression. When using a mUNA molecule as a vector, cellular-delivery can be at increased levels, and cytotoxic innate immune responses can be restrained so that higher levels of ectopic protein expression can be achieved. The mUNA molecules of this invention can have increased specific activity and longer functional half-life than mRNAs.

In certain aspects, a mUNA molecule may have a number of mutations from a native mRNA, or from a disease associated mRNA.

In further embodiments, this invention can provide mUNA molecules having cleavable delivery and targeting moieties attached at the 3' end.

In general, the specific activity for a synthetic translatable molecule delivered by transfection can be viewed as the number of molecules of protein expressed per delivered transcript per unit time.

As used herein, translation efficiency refers to a measure of the production of a protein or polypeptide by translation of a messenger molecule in vitro or in vivo.

This invention provides a range of mUNA molecules, which can contain one or more UNA monomers, and a number of nucleic acid monomers, wherein the mUNA molecule can be translated to express a polypeptide or protein.

In some embodiments, this invention includes a range of mUNA molecules, which contain one or more UNA monomers in one or more untranslated regions, and a number of nucleic acid monomers, wherein the mUNA molecule can be translated to express a polypeptide or protein.

In some embodiments, this invention includes a range of mUNA molecules, which contain one or more UNA monomers in a tail region or monomers, and a number of nucleic acid monomers, wherein the mUNA molecule can be translated to express a polypeptide or protein.

In some embodiments, a mUNA molecule can contain a modified 5' cap.

In some embodiments, a mUNA molecule can contain one ore more UNA monomers in a 5' cap.

In further embodiments, a mUNA molecule can contain a translation enhancing 5' untranslated region of monomers.

In further embodiments, a mUNA molecule can contain one or more UNA monomers in a 5' untranslated region.

In additional embodiments, a mUNA molecule can contain a translation enhancing 3' untranslated region of monomers.

In additional embodiments, a mUNA molecule can contain one or more UNA monomers in a 3' untranslated region of monomers.

In additional embodiments, a mUNA molecule can contain one or more UNA monomers in a tail region of monomers.

In additional embodiments, a mUNA molecule can contain one or more UNA monomers in a polyA tail.

In another aspect, a mUNA molecule can exhibit at least 2-fold, 3-fold, 5-fold, or 10-fold increased translation efficiency in vivo as compared to a native mRNA that encodes the same translation product.

In another aspect, a mUNA molecule can produce at least 2-fold, 3-fold, 5-fold, or 10-fold increased polypeptide or protein in vivo as compared to a native mRNA that encodes the same polypeptide or protein.

In additional embodiments, this invention provides methods for treating a rare disease or condition in a subject by administering to the subject a composition containing a mUNA molecule.

In additional embodiments, this invention provides methods for treating a liver disease or condition in a subject by administering to the subject a composition containing a mUNA molecule.

Modalities for Peptides and Proteins

A mUNA molecule of this invention may be used for ameliorating, preventing or treating a disease through enzyme modulation or replacement. In these embodiments, a mUNA molecule of this invention can be administered to regulate, modulate, increase, or decrease the concentration or effectiveness of a natural enzyme in a subject.

In some aspects, the enzyme can be an unmodified, natural enzyme for which the patient has an abnormal quantity.

In some embodiments, a mUNA molecule can be delivered to cells or subjects, and translated to supply increased levels of the natural enzyme.

A mUNA molecule of this invention may be used for ameliorating, preventing or treating a disease through modulation or introduction of a peptide or protein. In these embodiments, a mUNA molecule of this invention can be administered to regulate, modulate, increase, or decrease the concentration or effectiveness of a peptide or protein in a subject, where the peptide or protein is non-natural or mutated, as compared to a native peptide or protein.

In some aspects, the peptide or protein can be a modified, non-natural, exogenous, or synthetic peptide or protein, which has a pharmacological effect in a subject.

In some embodiments, a mUNA molecule can be delivered to cells or subjects, and translated to supply a concentration of the peptide or protein.

Examples of diseases for enzyme modulation include lysosomal diseases, for example, Gaucher disease, Fabry disease, Mucopolysaccharidoses (MPS) and related diseases including MPS I, MPS II (Hunter syndrome), and MPS VI, as well as Glycogen storage disease type II.

Examples of diseases for enzyme modulation include hematologic diseases, for example, sickle-cell disease, thalassemia, methemoglobinemia, anemia due to deficiency of hemoglobin or $B_{12}$ intrinsic factor, spherocytosis, glucose-6-phosphate dehydrogenase deficiency, and pyruvate kinase deficiency.

Examples of diseases for enzyme modulation include hemophilia, Von Willebrand disease, Protein S deficiency, age-related macular degeneration, trinucleotide repeat disorders, muscular dystrophy, insertion mutation diseases, DNA repair-deficiency disorders, and deletion mutation diseases.

Rare Diseases

Examples of diseases and/or conditions for which the mUNA molecules of this invention can be translatable to provide an active agent include those in Table 1.

TABLE 1

| Rare diseases | |
|---|---|
| RARE DISEASE | DEFICIENCY |
| Aminoacylase 1 deficiency | Aminoacylase 1 |
| Apo A-I deficiency | Apo A-I |
| Carbamoyl phosphate synthetase 1 deficiency | Carbamoyl phosphate synthetase 1 |
| Ornithine transcarbamylase deficiency | Ornithine transcarbamylase |
| Plasminogen activator inhibitor type 1 deficiency | Plasminogen activator inhibitor type 1 |
| Flaujeac factor deficiency | Flaujeac factor (High-molecular-weight kininogen) |
| High-molecular-weight kininogen deficiency congenital | High-molecular-weight kininogen (Flaujeac factor) |
| PEPCK 1 deficiency | PEPCK 1 |
| Pyruvate kinase deficiency liver type | Pyruvate kinase liver type |
| Alpha 1-antitrypsin deficiency | Alpha 1-antitrypsin |
| Anti-plasmin deficiency congenital | Anti-plasmin |
| Apolipoprotein C 2I deficiency | Apolipoprotein C 2I |

TABLE 1-continued

Rare diseases

| RARE DISEASE | DEFICIENCY |
| --- | --- |
| Butyrylcholinesterase deficiency | Butyrylcholinesterase |
| Complement component 2 deficiency | Complement component 2 |
| Complement component 8 deficiency type 2 | Complement component 8 type 2 |
| Congenital antithrombin deficiency type 1 | Antithrombin |
| Congenital antithrombin deficiency type 2 | Antithrombin, type 2 |
| Congenital antithrombin deficiency type 3 | Antithrombin, type 3 |
| Cortisone reductase deficiency 1 | Cortisone reductase |
| Factor VII deficiency | Factor VII |
| Factor X deficiency | Factor X |
| Factor XI deficiency | Factor XI |
| Factor XII deficiency | Factor XII |
| Factor XIII deficiency | Factor XIII |
| Fibrinogen deficiency congenital | Fibrinogen |
| Fructose-1 6-bisphosphatase deficiency | Fructose-1 6-bisphosphatase |
| Gamma aminobutyric acid transaminase deficiency | Gamma aminobutyric acid transaminase |
| Gamma-cystathionase deficiency | Gamma-cystathionase |
| Glut2 deficiency | Glut2 |
| GTP cyclohydrolase I deficiency | GTP cyclohydrolase I |
| Isolated growth hormone deficiency type 1B | Isolated growth hormone type 1B |
| Molybdenum cofactor deficiency | Molybdenum cofactor |
| Prekallikrein deficiency congenital | Prekallikrein |
| Proconvertin deficiency congenital | Proconvertin |
| Protein S deficiency | Protein S |
| Pseudocholinesterase deficiency | Pseudocholinesterase |
| Stuart factor deficiency congenital | Stuart factor |
| Tetrahydrobiopterin deficiency | Tetrahydrobiopterin |
| Type 1 plasminogen deficiency | Plasminogen |
| Urocanase deficiency | Urocanase |
| Chondrodysplasia punctata with steroid sulfatase deficiency | Chondrodysplasia punctata with steroid sulfatase/X-linked chondrodysplasia punctata 1 |
| Homocystinuria due to CBS deficiency | CBS |
| Guanidinoacetate methyltransferase deficiency | Guanidinoacetate methyltransferase |
| Pulmonary surfactant protein B deficiency | Pulmonary surfactant protein B |
| Aminoacylase 1 deficiency | Aminoacylase 1 |
| Acid Sphingomyelinase Deficiency | Enzyme found in lysosomes, responsible for conversion of lipid sphingomyelin into lipid ceramide |
| Adenylosuccinate Lyase Deficiency | Neurological disorder, brain dysfunction (encephalopathy) and to delayed development of mental and movement abilities, autistic behaviors and seizures |
| Aggressive Angiomyxoma | Myxoid tumor involving the blood vessels, may be a non-metastasizing benign tumor |
| Albrights Hereditary Osteodystrophy | Inherited in an autosomal dominant pattern, lack of responsiveness to parathyroid hormone, low serum calcium, high serum phosphate |
| Carney Stratakis Syndrome | Very rare syndrome characterized by gastrointestinal stromal tumors and paragangliomas. |
| Carney Triad Syndrome | Characterized by the coexistence of 3 types of neoplasms, mainly in young women, including gastric gastrointestinal stromal tumor, pulmonary chondroma, and extra-adrenal paraganglioma |
| CDKL5 Mutation | Results in severe neurodevelopmental impairment and early onset, difficult to control seizures |
| CLOVES Syndrome | Complex vascular anomalies: Congenital, Lipomatous Overgrowth, Vascular malformations, Epidermal nevi and Scoliosis/Skeletal/Spinal anomalies |
| Cockayne Syndrome | Characterized by short stature and an appearance of premature aging, failure to gain weight, abnormally small head size, and impaired development of the nervous system |
| Congenital Disorder of Glycosylation type 1R | Rare inborn errors of metabolism involving deficient or defective glycosylation |

TABLE 1-continued

Rare diseases

| RARE DISEASE | DEFICIENCY |
| --- | --- |
| Cowden Syndrome | Characterized by multiple noncancerous, tumor-like growths called hamartomas and an increased risk of developing certain cancers |
| DEND Syndrome | Generally severe form of neonatal diabetes mellitus characterized by a triad of developmental delay, epilepsy, and neonatal diabetes |
| Dercum's Disease | Characterized by multiple, and painful lipomas. These lipomas mainly occur on the trunk, the upper arms and upper legs |
| Febrile Infection-Related Epilepsy Syndrome | Explosive-onset, potentially fatal acute epileptic encephalopathy, develops in previously healthy children and adolescents following the onset of a non-specific febrile illness |
| Fibular Aplasia Tibial Campomelia Oligosyndactyly Syndrome | Unknown genetic basis and inheritance with variable expressivity and penetrance |
| Food Protein-Induced Enterocolitis Syndrome | A non-IgE mediated immune reaction in the gastrointestinal system to one or more specific foods, commonly characterized by profuse vomiting and diarrhea |
| Foreign Body Giant Cell Reactive Tissue Disease | Collection of fused macrophages which are generated in response to the presence of a large foreign body; particularly evident with implants that cause the body chronic inflammation and foreign body response |
| Galloway-Mowat | Physical features may include an unusually small head and additional abnormalities of the head and facial area; damage to clusters of capillaries in the kidneys resulting in abnormal kidney function; and, in many cases, protrusion of part of the stomach through an abnormal opening in the diaphragm |
| Gitelman syndrome | Autosomal recessive kidney disorder characterized by hypokalemic metabolic alkalosis with hypocalciuria, and hypomagnesemia. |
| Glycerol Kinase Deficiency | X-linked recessive enzyme defect that is heterozygous in nature, responsible gene in a region containing genes in which deletions can cause DMD and adrenal hypoplasia congenita |
| Glycogen Storage Disease type 9 | Caused by the inability to break down glycogen. The different forms of the condition can affect glycogen breakdown in liver cells, muscle cells or both |
| gm1 gangliosidosis | Autosomal recessive lysosomal storage disease characterized by accumulation of ganglioside substrates in lysosomes |
| Hereditary spherocytosis | Affects red blood cells, shortage of red blood cells, yellowing of the eyes and skin, and an enlarged spleen |
| Hidradenitis Suppurativa Stage III | Disorder of the terminal follicular epithelium in the apocrine gland-bearing skin, frequently causing keloids, contractures, and immobility. Stage III is defined as multiple lesions, with more extensive sinus tracts and scarring |
| Horizonatal Gaze Palsy with Progressive Scoliosis | Disorder that affects vision and also causes an abnormal curvature of the spine |
| IMAGe syndrome | The combination of intrauterine growth restriction, metaphyseal dysplasia, adrenal hypoplasia congenita, and genital anomalies (only about 20 cases reported in the medical literature) |
| Isodicentric 15 | Chromosome abnormality in which a child is born with extra genetic material from chromosome 15 |
| isolated hemihyperplasia | One side of the body grows more than other, causing asymmetry |
| Juvenile Xanthogranuloma | Usually benign and self-limiting. It occurs most often in the skin of the head, neck, and trunk but can also occur in the arms, legs, feet, and buttocks |
| Kasabach-Merritt Syndrome | A vascular tumor leads to decreased platelet counts and sometimes other bleeding problems |
| Kniest Dysplasia | Disorder of bone growth characterized by short stature (dwarfism) with other skeletal abnormalities and problems with vision and hearing |
| Koolen de-Vries Syndrome | Disorder characterized by developmental delay and mild to moderate intellectual disability.They usually have weak muscle tone in childhood. About half have recurrent seizures |

TABLE 1-continued

Rare diseases

| RARE DISEASE | DEFICIENCY |
| --- | --- |
| Lennox-Gastaut syndrome | Type of epilepsy with multiple different types of seizures, particularly tonic (stiffening) and atonic (drop) seizures. Intellectual development is usually, but not always, impaired |
| Lymphangiomatosis | Congenital and can affect any of the body's systems except the central nervous system (including the brain) |
| Lymphangiomiomytosis | Can occur either sporadically or in association with the tuberous sclerosis complex (TSC) and is often considered a forme fruste of TSC |
| MASA Syndrome | X-linked recessive neurological disorder |
| Mast Cell Activation disorder | Condition with signs and symptoms involving the skin, gastrointestinal, cardiovascular, respiratory, and neurologic systems |
| Mecp2 Duplication Syndrome | Genetic neurodevelopmental disorder characterized by low muscle tone, potentially severe intellectual disability, developmental delays, recurrent respiratory infections, speech abnormalities, seizures, and progressive spasticity |
| Mucha Habermann | Skin disorder |
| Neonatal Hemochromatosis | Severe liver disease of fetal or perinatal onset, associated with deposition of stainable iron in extrahepatic sites, disordered iron handling due to injury to the perinatal liver, as a form of fulminant hepatic failure |
| N-glycanase deficiency | The encoded enzyme may play a role in the proteasome-mediated degradation of misfolded glycoproteins |
| Opsoclonus Myoclonus Syndrome | Neurological disorder of unknown causes which appears to be the result of an autoimmune process involving the nervous system |
| Persistent genital arousal disorder | Results in a spontaneous, persistent, and uncontrollable genital arousal, with or without orgasm or genital engorgement, unrelated to any feelings of sexual desire |
| Pompe Disease | Inherited disorder caused by the buildup of glycogen in the body's cells. The accumulation of glycogen in certain organs and tissues, especially muscles, impairs their ability to function normally |
| Progressive Familial Intrahepatic Cholestasis | Disorder that causes progressive liver disease, which typically leads to liver failure. In people with PFIC, liver cells are less able to secrete a digestive fluid called bile. The buildup of bile in liver cells causes liver disease in affected individuals |
| Pseudohypoparathyroidism type 1a | Characterized by renal resistance to parathyroid hormone, resulting in hypocalcemia, hyperphosphatemia, and elevated PTH; resistance to other hormones including thyroid stimulating hormone, gonadotropins and growth-hormone-releasing hormone |
| PTEN Hamartoma Tumor Syndrome | The gene was identified as a tumor suppressor that is mutated in a large number of cancers at high frequency |
| Schnitzler syndrome | Characterised by chronic hives and periodic fever, bone pain and joint pain (sometimes with joint inflammation), weight loss, malaise, fatigue, swollen lymph glands and enlarged spleen and liver |
| Scleroderma | Chronic hardening and tightening of the skin and connective tissues |
| Semi Lobar Holoprosencephany | Holoprosencephany: birth defect of the brain, which often can also affect facial features, including closely spaced eyes, small head size, and sometimes clefts of the lip and roof of the mouth. Semilobar holoprosencephaly is a subtype of holoprosencephaly characterised by an incomplete forebrain division |
| Sjogren's Syndrome | Immune system disorder characterized by dry eyes and dry mouth |
| Specific Antibody Deficiency Disease | Immune |
| SYNGAP 1 | A ras GTPase-activating protein that is critical for the development of cognition and proper synapse function |
| Trigeminal Trophic Syndrome | This is the wing of tissue at the end of the nose above the nostril. Trigeminal trophic syndrome is due to damage to the trigeminal nerve |
| Undifferentiated Connective Tissue Disease | Systemic autoimmune disease |

TABLE 1-continued

Rare diseases

| RARE DISEASE | DEFICIENCY |
| --- | --- |
| X-linked hypophosphatemia | X-linked dominant form of rickets (or osteomalacia) that differs from most cases of rickets in that ingestion of vitamin D is relatively ineffective. It can cause bone deformity including short stature and genu varum |

Modalities for Immune Modulation

The mUNA molecules of this invention can be translatable to provide an active protein. In certain embodiments, a translatable mUNA molecule can provide an active mRNA immunization agent, or an mRNA vaccine component.

A mUNA vaccine of this disclosure can advantageously provide a safe and efficacious genetic vaccine by inducing an immune response having both cellular and humoral components. In general, protein can be expressed using a mUNA vaccine of this invention.

In some embodiments, a mUNA vaccine can advantageously provide protein synthesis in the cytoplasm. In certain embodiments, a mUNA vaccine of this invention can provide internalization, release and transport of an exogenous mRNA in the cytoplasm.

In certain aspects, a mUNA vaccine of this invention can encode for a protein antigen that can be translated by host cells.

In further aspects, some mUNA vaccines of this disclosure can encode for tumor antigens, viral antigens, or allergens.

Modalities for administering a mUNA vaccine of this invention can include intravenous, intranodal, intradermal, subcutaneous and intrasplenic.

Embodiments of this invention further provide mUNA vaccines having increased half-life of translation, which can be used to reduce the necessary dose and exposure to antigen, and reduce the risk of inducing tolerance.

A mUNA vaccine of this invention can provide an immunological effect without the risk of integration of a component into the genome, and may reduce the risk of mutagenesis as compared to other genetic vaccines.

Additional embodiments of this disclosure include mUNA molecules having translational activity, where the translational activity can be described by a cytoplasmic half-life in a mammalian cell. The half-life can be determined by the time required for 50% of the mUNA molecule to be degraded in the cell.

A translatable mUNA molecule of this invention can be a precursor of an active molecule, which can be used in the treatment of a condition or disease in a subject.

In some embodiments, a translatable mUNA molecule of this invention can be a pharmacologically active molecule having increased half-life in the cytoplasm of mammalian cells.

Examples of mUNA molecules of this invention include a mUNA molecule that provides an mRNA encoding HIV-1 gag antigen, a mUNA molecule that provides an mRNA encoding antigens overexpressed in lung cancers, a mUNA molecule that provides an mRNA encoding malarial *P. falciparum* reticulocyte-binding protein homologue 5 (PfRH5), and a mUNA molecule that provides an mRNA encoding malarial *Plasmodium falciparum* PfSEA-1, a 244 KD malaria antigen expressed in schizont-infected RBCs.

UNA Monomers and Oligomers

In some embodiments, linker group monomers can be unlocked nucleomonomers (UNA monomers), which are small organic molecules based on a propane-1,2,3-tri-yl-trisoxy structure as shown below:

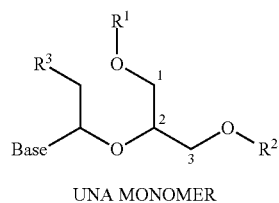

UNA MONOMER where $R^1$ and $R^2$ are H, and $R^1$ and $R^2$ can be phosphodiester linkages, Base can be a nucleobase, and $R^3$ is a functional group described below.

In another view, the UNA monomer main atoms can be drawn in IUPAC notation as follows:

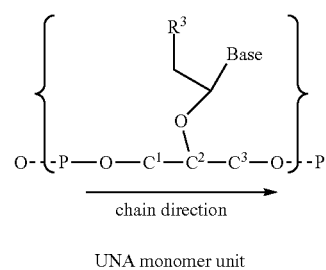

UNA monomer unit where the direction of progress of the oligomer chain is from the 1-end to the 3-end of the propane residue.

Examples of a nucleobase include uracil, thymine, cytosine, 5-methylcytosine, adenine, guanine, inosine, and natural and non-natural nucleobase analogues.

Examples of a nucleobase include pseudouracil, 1-methylpseudouracil, and 5-methoxyuracil.

In general, a UNA monomer, which is not a nucleotide, can be an internal linker monomer in an oligomer. An internal UNA monomer in an oligomer is flanked by other monomers on both sides.

A UNA monomer can participate in base pairing when the oligomer forms a complex or duplex, for example, and there are other monomers with nucleobases in the complex or duplex.

Examples of UNA monomer as internal monomers flanked at both the propane-1-yl position and the propane-3-yl position, where $R^3$ is —OH, are shown below.

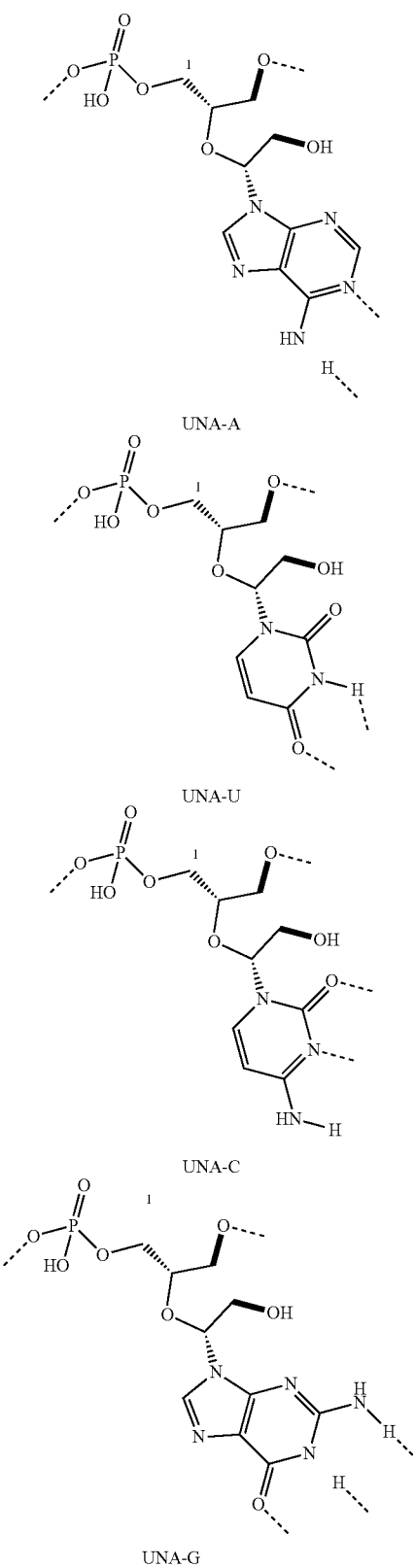

UNA-A

UNA-U

UNA-C

UNA-G organic structures, unlike nucleotides, the terminal UNA monomer can be a flexible terminator for the oligomer.

Examples of a UNA monomer as a terminal monomer attached at the propane-3-yl position are shown below.

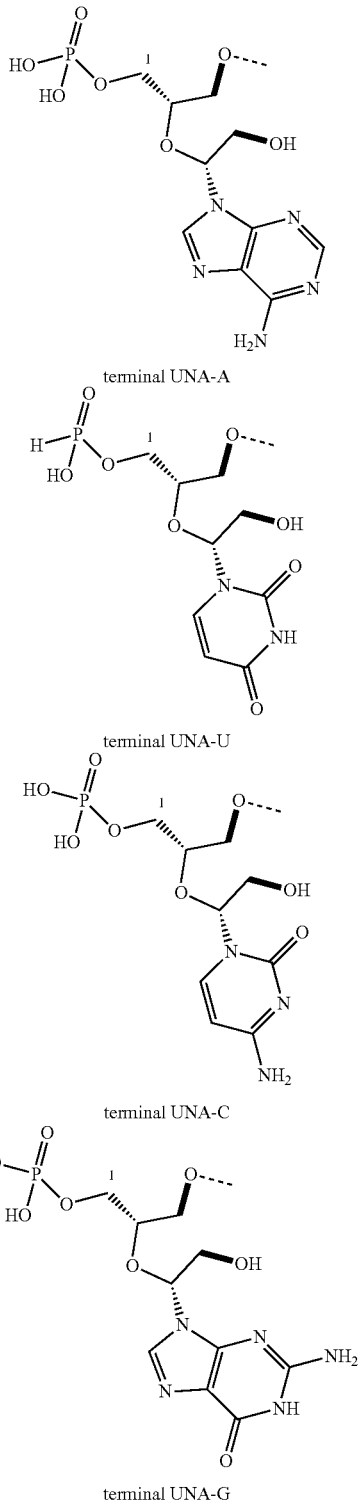

terminal UNA-A terminal UNA-U terminal UNA-C terminal UNA-G

A UNA monomer can be a terminal monomer of an oligomer, where the UNA monomer is attached to only one monomer at either the propane-1-yl position or the propane-3-yl position. Because the UNA monomers are flexible Because a UNA monomer can be a flexible molecule, a UNA monomer as a terminal monomer can assume widely differing conformations. An example of an energy minimized UNA monomer conformation as a terminal monomer attached at the propane-3-yl position is shown below.

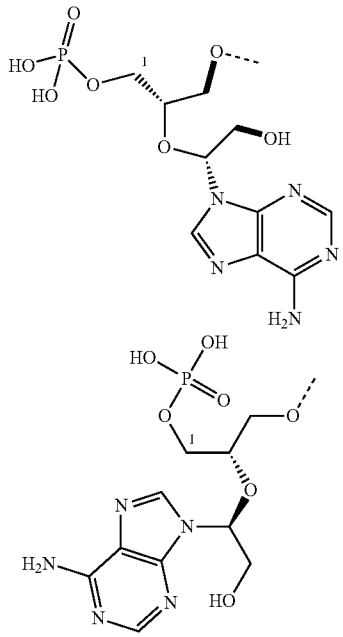

UNA-A terminal forms: the dashed bond shows the propane-3-yl attachment

Among other things, the structure of the UNA monomer allows it to be attached to naturally-occurring nucleotides.

A UNA oligomer can be a chain composed of UNA monomers, as well as various nucleotides that may be based on naturally-occurring nucleosides.

In some embodiments, the functional group $R^3$ of a UNA monomer can be —$OR^4$, —$SR^4$, —$NR^4_2$, —$NH(C=O)R^4$, morpholino, morpholin-1-yl, piperazin-1-yl, or 4-alkanoyl-piperazin-1-yl, where $R^4$ is the same or different for each occurrence, and can be H, alkyl, a cholesterol, a lipid molecule, a polyamine, an amino acid, or a polypeptide.

The UNA monomers are organic molecules. UNA monomers are not nucleic acid monomers or nucleotides, nor are they naturally-occurring nucleosides or modified naturally-occurring nucleosides.

A UNA oligomer of this invention is a synthetic chain molecule.

In some embodiments, as shown above, a UNA monomer can be UNA-A (designated Ã), UNA-U (designated Ũ), UNA-C (designated C̃), and UNA-G (designated G̃).

Designations that may be used herein include mA, mG, mC, and mU, which refer to the 2'-O-Methyl modified ribonucleotides.

Designations that may be used herein include dT, which refers to a 2'-deoxy T nucleotide.

Additional Monomers for Oligomers

As used herein, in the context of oligomer sequences, the symbol X represents a UNA monomer. When a mUNA oligomer is complexed or duplexed with a nucleic acid molecule, the UNA monomers of the mUNA oligomer can have any base attached that would be complementary to the monomer with which it is paired in the nucleic acid molecule.

As used herein, in the context of oligomer sequences, the symbol N can represent any natural nucleotide monomer, or any modified nucleotide monomer. When a mUNA oligomer is complexed or duplexed with a nucleic acid molecule, an N monomer of the mUNA oligomer can have any base attached that would be complementary to the monomer with which it is paired in the nucleic acid molecule.

As used herein, in the context of oligomer sequences, the symbol Q represents a non-natural, modified, or chemically-modified nucleotide monomer. When a mUNA oligomer is complexed or duplexed with a nucleic acid molecule, a Q monomer of the mUNA oligomer can have any base attached that would be complementary to the monomer with which it is paired in the nucleic acid molecule.

Examples of nucleic acid monomers include non-natural, modified, and chemically-modified nucleotides, including any such nucleotides known in the art.

Examples of non-natural, modified, and chemically-modified nucleotide monomers include any such nucleotides known in the art, for example, 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of non-natural, modified, and chemically-modified nucleotide monomers include 3'-end stabilized nucleotides, 3'-glyceryl nucleotides, 3'-inverted abasic nucleotides, and 3'-inverted thymidine.

Examples of non-natural, modified, and chemically-modified nucleotide monomers include locked nucleic acid nucleotides (LNA), 2'-O,4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides.

Examples of non-natural, modified, and chemically-modified nucleotide monomers include 2',4'-Constrained 2'-O-Methoxyethyl (cMOE) and 2'-O-Ethyl (cEt) Modified DNAs.

Examples of non-natural, modified, and chemically-modified nucleotide monomers include 2'-amino nucleotides, 2'-O-amino nucleotides, 2'-C-allyl nucleotides, and 2'-O-allyl nucleotides.

Examples of non-natural, modified, and chemically-modified nucleotide monomers include $N^6$-methyladenosine nucleotides.

Examples of non-natural, modified, and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of non-natural, modified, and chemically-modified nucleotide monomers include 2'-O-aminopropyl substituted nucleotides.

Examples of non-natural, modified, and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Examples of nucleotide monomers include pseudouridine (psi-Uridine) and 1-methylpseudouridine.

Some examples of modified nucleotides are given in Saenger, Principles of Nucleic Acid Structure, Springer-Verlag, 1984.

mUNA Compounds

Aspects of this invention provide structures and compositions for mUNA molecules that are oligomeric compounds. The mUNA compounds can be active agents for pharmaceutical compositions.

An oligomeric mUNA agent of this invention may contain one or more UNA monomers. Oligomeric molecules of this invention can be used as active agents in formulations for supplying peptide and protein therapeutics.

In some embodiments, this invention provides oligomeric mUNA compounds having a structure that incorporates novel combinations of UNA monomers with certain natural nucleotides, non-natural nucleotides, modified nucleotides, or chemically-modified nucleotides.

Oligomeric mUNA compounds of this invention can have a length of from about 200 to about 12,000 bases in length. Oligomeric mUNA compounds of this invention can have a length of about 1800, or about 1900, or about 2000, or about 2100, or about 2200, or about 2300, or about 2400, or about 2500 bases.

In further aspects, the oligomeric mUNA compounds of this invention can be pharmacologically active molecules. A mUNA molecule can be used as an active pharmaceutical ingredient for generating a peptide or protein active agent in vitro, in vivo, or ex vivo.

A mUNA molecule of this invention can have the structure of Formula I

Formula I wherein $L^1$ is a linkage, n is from 200 to 12,000, and for each occurrence $L^2$ is a UNA linker group having the formula —$C^1$—$C^2$—$C^3$— where R is attached to $C^2$ and has the formula —OCH(CH$_2$R$^3$)R$^5$, where R$^3$ is —OR$^4$, —SR$^4$, —NR$^4{}_2$, —NH(C=O)R$^4$, morpholino, morpholin-1-yl, piperazin-1-yl, or 4-alkanoyl-piperazin-1-yl, where R$^4$ is the same or different for each occurrence and is H, alkyl, a cholesterol, a lipid molecule, a polyamine, an amino acid, or a polypeptide, and where R$^5$ is a nucleobase, or $L^2$(R) is a sugar such as a ribose and R is a nucleobase, or $L^2$ is a modified sugar such as a modified ribose and R is a nucleobase. In certain embodiments, a nucleobase can be a modified nucleobase. $L^1$ can be a phosphodiester linkage.

The base sequence of a mUNA molecule can be any sequence of nucleobases.

In some aspects, a mUNA molecule of this invention can have any number of phosphorothioate intermonomer linkages in any intermonomer location.

In some embodiments, any one or more of the intermonomer linkages of a mUNA molecule can be a phosphodiester, a phosphorothioate including dithioates, a chiral phosphorothioate, and other chemically modified forms.

When a mUNA molecule terminates in a UNA monomer, the terminal position has a 1-end, or the terminal position has a 3-end, according to the positional numbering shown above.

mUNA Molecules with Enhanced Translation

A mUNA molecule of this invention can incorporate a region that enhances the translational efficiency of the mUNA molecule.

In general, translational enhancer regions as known in the art can be incorporated into the structure of a mUNA molecule to increase peptide or protein yields.

A mUNA molecule containing a translation enhancer region can provide increased production of peptide or protein.

In some embodiments, a translation enhancer region can comprise, or be located in a 5' or 3' untranslated region of a mUNA molecule.

Examples of translation enhancer regions include naturally-occurring enhancer regions from TEV 5'UTR and Xenopus beta-globin 3'UTR.

mUNA Molecular Structure and Sequences

A mUNA molecule can be designed to express a target peptide or protein. In some embodiments, the target peptide or protein can be associated with a condition or disease in a subject.

In some aspects, the base sequence of a mUNA molecule can include a portion that is identical to at least an effective portion or domain of a base sequence of an mRNA, where an effective portion is sufficient to impart a therapeutic activity to a translation product of the mUNA molecule.

In some aspects, this invention provides active mUNA oligomer molecules having a base sequence identical to at least a fragment of a native nucleic acid molecule of a cell.

In certain embodiments, the base sequence of a mUNA molecule can include a portion that is identical to a base sequence of an mRNA, except for one or more base mutations. The number of mutations for the mUNA molecule should not exceed an amount that would produce a translation product of the mUNA molecule having substantially less activity than the mRNA.

The oligomer mUNA molecules of this invention can display a sequence of nucleobases, and can be designed to express a peptide or protein, in vitro, ex vivo, or in vivo. The expressed peptide or protein can have activity in various forms, including activity corresponding to protein expressed from a native or natural mRNA.

In some embodiments, a mUNA molecule of this invention may have a chain length of about 400 to 15,000 monomers, where any monomer that is not a UNA monomer can be a Q monomer.

mUNA Molecular Cap Structure

A mUNA molecule of this invention may have a 5'-end capped with various groups and their analogues as are known in the art. The 5' cap may be a m7GpppGm cap. The 5' cap may be an ARCA cap (3'-OMe-m7G(5')pppG). The 5' cap may be an mCAP (m7G(5')ppp(5')G, N$^7$-Methyl-Guanosine-5'-Triphosphate-5'-Guanosine). The 5' cap may be resistant to hydrolysis.

Some examples of 5' cap structures are given in WO2015/051169A2.

Genetic Basis for mUNA Molecules

In some embodiments, the mUNA molecules of this invention can be structured to provide peptides or proteins that are nominally expressed by any portion of a genome. Examples of genes for which a mUNA molecule can be used to express the corresponding peptide or protein are set forth below.

Examples of genes for which a mUNA molecule can be used to express the corresponding peptide or protein include: Neoplasia, PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc.

Examples of genes for which a mUNA molecule can be used to express the corresponding peptide or protein include:

Age-related Macular Degeneration, Schizophrenia, Aber; Ccl2; Cc2; cp (ceruloplasmin); Timp3; cathepsinD; Vldlr; Ccr2 Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b.

Examples of genes for which a mUNA molecule can be used to express the corresponding peptide or protein include: 5-HTT (Slc6a4); COMT; DRD (Drd1a); SLC6A3; DAOA; DTNBP1; Dao (Dao1).

Examples of genes for which a mUNA molecule can be used to express the corresponding peptide or protein include: Trinucleotide Repeat Disorders, HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn 1 (DRPLA Dx); CBP (Creb-BP-global instability); VLDLR (Alzheimer's); Atxn7; Atxn10.

Examples of genes for which a mUNA molecule can be used to express the corresponding peptide or protein include: Fragile X Syndrome, FMR2; FXR1; FXR2; mGLUR5.

Examples of genes for which a mUNA molecule can be used to express the corresponding peptide or protein include: Secretase Related Disorders, APH-1 (alpha and beta); Presenilin (Psen1); nicastrin (Ncstn); PEN-2.

Examples of genes for which a mUNA molecule can be used to express the corresponding peptide or protein include: Nos1.

Examples of genes for which a mUNA molecule can be used to express the corresponding peptide or protein include: Parp1.

Examples of genes for which a mUNA molecule can be used to express the corresponding peptide or protein include: Nat1; Nat2.

Examples of genes for which a mUNA molecule can be used to express the corresponding peptide or protein include: Prion-related disorders, Prp.

Examples of genes for which a mUNA molecule can be used to express the corresponding peptide or protein include: ALS disease, SOD1; ALS2; STEX; FUS; TARDBP; VEGF (VEGF-a; VEGF-b; VEGF-c).

Examples of genes for which a mUNA molecule can be used to express the corresponding peptide or protein include: Drug addiction, Prkce (alcohol); Drd2; Drd4; ABAT (alcohol); GRIA2; Grm5; Grin1; Htr1b; Grin2a; Drd3; Pdyn; Gria1 (alcohol).

Examples of genes for which a mUNA molecule can be used to express the corresponding peptide or protein include: Autism, Mecp2; BZRAP1; MDGA2; Sema5A; Neurexin 1; Fragile X (FMR2 (AFF2); FXR1; FXR2; Mglur5).

Examples of genes for which a mUNA molecule can be used to express the corresponding peptide or protein include: Alzheimer's Disease, E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP.

Examples of genes for which a mUNA molecule can be used to express the corresponding peptide or protein include: Inflammation, IL-10; IL-1 (IL-1a; IL-1b); IL-13; IL-17 (IL-17a (CTLA8); IL-17b; IL-17c; IL-17d; IL-17f); Il-23; Cx3er1; ptpn22; TNFa; NOD2/CARD15 for IBD; IL-6; IL-12 (IL-12a; IL-12b); CTLA4; Cx3cl1.

Examples of genes for which a mUNA molecule can be used to express the corresponding peptide or protein include: Parkinson's Disease, x-Synuclein; DJ-1; LRRK2; Parkin; PINK1.

Examples of genes for which a mUNA molecule can be used to express the corresponding peptide or protein include: Blood and coagulation diseases and disorders, Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9 Factor IX, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1).

Examples of genes for which a mUNA molecule can be used to express the corresponding peptide or protein include: Cell dysregulation and oncology diseases and disorders, B-cell non-Hodgkin lymphoma (BCL7A, BCL7); Leukemia (TAL1 TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSCIL1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN).

Examples of genes for which a mUNA molecule can be used to express the corresponding peptide or protein include: Inflammation and immune related diseases and disorders, AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immuno-deficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immuno-deficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f, 11-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs) (JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4).

Examples of genes for which a mUNA molecule can be used to express the corresponding peptide or protein include: Metabolic, liver, kidney and protein diseases and disorders, Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, BG213071, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepato-blastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63).

Examples of genes for which a mUNA molecule can be used to express the corresponding peptide or protein include: Lipoprotein lipase, APOA1, APOC3 and APOA4.

Examples of genes for which a mUNA molecule can be used to express the corresponding peptide or protein include: Muscular/skeletal diseases and disorders, Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facio-scapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1).

Examples of genes for which a mUNA molecule can be used to express the corresponding peptide or protein include: Neurological and neuronal diseases and disorders, ALS (SOD1, ALS2, STEX, FUS, TARDBP, VEGF (VEGF-a, VEGF-b, VEGF-c); Alzheimer's Disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIPIL, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizo-phrenia (Neuregulin1 (Nrg1), Erb4 (receptor for Neuregulin), Complexin1 (Cplx1), Tph1 Trypto-phan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Dis-orders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP-global instability), VLDLR (Alzheimer's), Atxn7, Atxn10).

Examples of genes for which a mUNA molecule can be used to express the corresponding peptide or protein include: Occular diseases and disorders, Age-related macular degeneration (Aber, Ccl2, Cc2, cp (ceruloplasmin), Timp3, cathepsinD, Vld1r, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2).

Examples of genes for which a mUNA molecule can be used to express the corresponding peptide or protein include: Epilepsy, myoclonic, EPM2A, MELF, EPM2 Lafora type, 254780 Epilepsy, myoclonic, NHLRC1, EPM2A, EPM2B Lafora type, 254780.

Examples of genes for which a mUNA molecule can be used to express the corresponding peptide or protein include: Duchenne muscular DMD, BMD dystrophy, 310200 (3) AIDS, delayed/rapid KIR3DL1, NKAT3, NKB1, AMB11, KIR3DS1 progression to (3).

Examples of genes for which a mUNA molecule can be used to express the corresponding peptide or protein include: AIDS, delayed/rapid KIR3DL1, NKAT3, NKB1, AMB11, KIR3DS1 progression to (3) AIDS, rapid IFNG progression to, 609423 (3) AIDS, resistance to CXCL12, SDF1 (3).

Examples of genes for which a mUNA molecule can be used to express the corresponding peptide or protein include: Alpha-1-Antitrypsin Deficiency, SERPINA1 [serpin peptidase inhibitor, clade A (alpha-1 antiproteinase, antitrypsin), member 1]; SERPINA2 [serpin peptidase inhibitor, clade A (alpha-1 antiproteinase, antitrypsin), member 2]; SERPINA3 [serpin peptidase inhibitor, clade A (alpha-1 antiproteinase, antitrypsin), member 3]; SERPINA5 [serpin peptidase inhibitor, clade A (alpha-1 antiproteinase, antitrypsin), member 5]; SERPINA6 [serpin peptidase inhibitor, clade A (alpha-1 antiproteinase, antitrypsin), member 6]; SERPINA7 [serpin peptidase inhibitor, clade A (alpha-1 antiproteinase, antitrypsin), member 7];" AND "SERPLNA6 (serpin peptidase inhibitor, clade A (alpha-1 antiproteinase, antitrypsin), member 6).

Examples of genes for which a mUNA molecule can be used to express the corresponding peptide or protein include:

PI3K/AKT Signaling, PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1.

Examples of genes for which a mUNA molecule can be used to express the corresponding peptide or protein include: ERK/MAPK Signaling, PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK.

Examples of genes for which a mUNA molecule can be used to express the corresponding peptide or protein include: Serine/Threonine-Protein Kinase, CDK16; PCTK1; CDK5R1.

Examples of genes for which a mUNA molecule can be used to express the corresponding peptide or protein include: Glucocorticoid Receptor Signaling, RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1.

Examples of genes for which a mUNA molecule can be used to express the corresponding peptide or protein include: Axonal Guidance Signaling, PRKCE; ITGAM; ROCK1; ITGA5; CXCR4; ADAM12; IGF1; RAC1; RAP1A; E1F4E; PRKCZ; NRP1; NTRK2; ARHGEF7; SMO; ROCK2; MAPK1; PGF; RAC2; PTPN11; GNAS; AKT2; PIK3CA; ERBB2; PRKC1; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA.

Examples of genes for which a mUNA molecule can be used to express the corresponding peptide or protein include: Ephrin Receptor Signaling, PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4, AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK.

Examples of genes for which a mUNA molecule can be used to express the corresponding peptide or protein include: Actin Cytoskeleton Signaling, ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK.

Examples of genes for which a mUNA molecule can be used to express the corresponding peptide or protein include: Huntington's Disease Signaling, PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKC1; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF; AKT3; PRKCA; CLTC; SGK; HDAC6; CASP3.

Examples of genes for which a mUNA molecule can be used to express the corresponding peptide or protein include: Apoptosis Signaling, PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1.

Examples of genes for which a mUNA molecule can be used to express the corresponding peptide or protein include: B Cell Receptor Signaling, RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1.

Examples of genes for which a mUNA molecule can be used to express the corresponding peptide or protein include: Leukocyte Extravasation Signaling, ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9.

Examples of genes for which a mUNA molecule can be used to express the corresponding peptide or protein include: Integrin Signaling, ACTN4; ITGAM; ROCK1; ITGA5; RAC1; PTEN; RAP1A; TLN1; ARHGEF7; MAPK1;

RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3.

Examples of genes for which a mUNA molecule can be used to express the corresponding peptide or protein include: Acute Phase Response Signaling, IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6.

Examples of genes for which a mUNA molecule can be used to express the corresponding peptide or protein include: PTEN Signaling, ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1.

Examples of genes for which a mUNA molecule can be used to express the corresponding peptide or protein include: p53 Signaling, PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; RIK3R1; RRM2B; APAF1; CTNNB1; SIRT1; CCND1; PRKDC; ATM; SFN; CDKN2A; JUN; SNAI2; GSK3B; BAX; AKT3.

Examples of genes for which a mUNA molecule can be used to express the corresponding peptide or protein include: Aryl Hydrocarbon Receptor Signaling, HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1.

Examples of genes for which a mUNA molecule can be used to express the corresponding peptide or protein include: Xenobiotic Metabolism Signaling, PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1.

Examples of genes for which a mUNA molecule can be used to express the corresponding peptide or protein include: SAPK/JNK Signaling, PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK.

Examples of genes for which a mUNA molecule can be used to express the corresponding peptide or protein include: PPAr/RXR Signaling, PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ.

Examples of genes for which a mUNA molecule can be used to express the corresponding peptide or protein include: NF-KB Signaling, IRAK1; EIF2AK2; EP300; INS; MYD88; PRKCZ: TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4: PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1.

Examples of genes for which a mUNA molecule can be used to express the corresponding peptide or protein include: Neuregulin Signaling, ERBB4; PRKCE; ITGAM; ITGA5: PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1.

Examples of genes for which a mUNA molecule can be used to express the corresponding peptide or protein include: Wnt & Beta catenin Signaling, CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2: ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2.

Examples of genes for which a mUNA molecule can be used to express the corresponding peptide or protein include: Insulin Receptor Signaling, PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1.

Examples of genes for which a mUNA molecule can be used to express the corresponding peptide or protein include: IL-6 Signaling, HSPB1; TRAF6; MAPKAPK2; ELK1; MAPK1; PTPN11; IKBKB; FOS; NFKB2: MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6.

Examples of genes for which a mUNA molecule can be used to express the corresponding peptide or protein include: Hepatic Cholestasis, PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6.

Examples of genes for which a mUNA molecule can be used to express the corresponding peptide or protein include: IGF-1 Signaling, IGF1; PRKCZ; ELK1; MAPK1; PTPN11; NEDD4; AKT2; PIK3CA; PRKC1; PTK2; FOS; PIK3CB; PIK3C3; MAPK8; 1GF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1.

Examples of genes for which a mUNA molecule can be used to express the corresponding peptide or protein include: NRF2-mediated Oxidative Stress Response, PRKCE; EP300; SOD2; PRKCZ; MAPK1; SQSTM1; NQO1; PIK3CA; PRKC1; FOS; PIK3CB; P1K3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1.

Examples of genes for which a mUNA molecule can be used to express the corresponding peptide or protein include: Hepatic, Fibrosis/Hepatic Stellate Cell Activation, EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9.

Examples of genes for which a mUNA molecule can be used to express the corresponding peptide or protein include: PPAR Signaling, EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1.

Examples of genes for which a mUNA molecule can be used to express the corresponding peptide or protein include: Fc Epsilon RI Signaling, PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA.

Examples of genes for which a mUNA molecule can be used to express the corresponding peptide or protein include: G-Protein Coupled Receptor Signaling, PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA.

Examples of genes for which a mUNA molecule can be used to express the corresponding peptide or protein include: Inositol Phosphate Metabolism, PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK.

Examples of genes for which a mUNA molecule can be used to express the corresponding peptide or protein include: PDGF Signaling, EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2.

Examples of genes for which a mUNA molecule can be used to express the corresponding peptide or protein include: VEGF Signaling, ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA.

Examples of genes for which a mUNA molecule can be used to express the corresponding peptide or protein include: Natural Killer Cell Signaling, PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA.

Examples of genes for which a mUNA molecule can be used to express the corresponding peptide or protein include: Cell Cycle: G1/S Checkpoint Regulation, HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6.

Examples of genes for which a mUNA molecule can be used to express the corresponding peptide or protein include: T Cell Receptor Signaling, RAC1; ELK1; MAPK1; IKBKB; CBL; PIK3CA; FOS; NFKB2; PIK3CB; PIK3C3; MAPK8; MAPK3; KRAS; RELA, PIK3C2A; BTK; LCK; RAF1; IKBKG; RELB; FYN; MAP2K2; PIK3R1; CHUK; MAP2K1; NFKB1; ITK; BCL10; JUN; VAV3.

Examples of genes for which a mUNA molecule can be used to express the corresponding peptide or protein include: Death Receptor Signaling, CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3.

Examples of genes for which a mUNA molecule can be used to express the corresponding peptide or protein include: FGF Signaling RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF.

Examples of genes for which a mUNA molecule can be used to express the corresponding peptide or protein include: GM-CSF Signaling, LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1.

Examples of genes for which a mUNA molecule can be used to express the corresponding peptide or protein include: Amyotrophic Lateral Sclerosis Signaling, BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3.

Examples of genes for which a mUNA molecule can be used to express the corresponding peptide or protein include: JAK/Stat Signaling, PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A;

MAP2K2; JAK1; AKT1; JAK2; PIK3R1; STAT3; MAP2K1; FRAP1; AKT3; STAT1.

Examples of genes for which a mUNA molecule can be used to express the corresponding peptide or protein include: Nicotinate and Nicotinamide Metabolism, PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK.

Examples of genes for which a mUNA molecule can be used to express the corresponding peptide or protein include: Chemokine Signaling, CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA.

Examples of genes for which a mUNA molecule can be used to express the corresponding peptide or protein include: IL-2 Signaling, ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3.

Examples of genes for which a mUNA molecule can be used to express the corresponding peptide or protein include: Synaptic Long Term Depression, PRKCE; IGF1; PRKCZ; PRDX6; LYN; MAPK1; GNAS; PRKC1; GNAQ; PPP2R1A; IGF1R; PRKID1; MAPK3; KRAS; GRN; PRKCD; NOS3; NOS2A; PPP2CA; YWHAZ; RAF1; MAP2K2; PPP2R5C; MAP2K1; PRKCA.

Examples of genes for which a mUNA molecule can be used to express the corresponding peptide or protein include: Estrogen Receptor Signaling, TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2.

Examples of genes for which a mUNA molecule can be used to express the corresponding peptide or protein include: Protein Ubiquitination Pathway, TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USPS; USP1; VHL; HSP90AA1; BIRC3.

Examples of genes for which a mUNA molecule can be used to express the corresponding peptide or protein include: IL-10 Signaling, TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6.

Examples of genes for which a mUNA molecule can be used to express the corresponding peptide or protein include: VDR/RXR Activation, PRKCE; EP300; PRKCZ; RXRA; GADD45A; HES1; NCOR2; SP1; PRKC1; CDKN1B; PRKD1; PRKCD; RUNX2; KLF4; YY1; NCOA3; CDKN1A; NCOA2; SPP1; LRP5; CEBPB; FOXO1; PRKCA.

Examples of genes for which a mUNA molecule can be used to express the corresponding peptide or protein include: TGF-beta Signaling, EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5.

Examples of genes for which a mUNA molecule can be used to express the corresponding peptide or protein include: Toll-like Receptor Signaling, IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN.

Examples of genes for which a mUNA molecule can be used to express the corresponding peptide or protein include: p38 MAPK Signaling, HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1.

Examples of genes for which a mUNA molecule can be used to express the corresponding peptide or protein include: Neurotrophin/TRK Signaling, NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4.

Examples of genes for which a mUNA molecule can be used to express the corresponding peptide or protein include: FXR/RXR Activation, INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1.

Examples of genes for which a mUNA molecule can be used to express the corresponding peptide or protein include: Synaptic Long Term Potentiation, PRKCE; RAP1A; EP300; PRKCZ; MAPK1; CREB1; PRKC1; GNAQ; CAMK2A; PRKD1; MAPK3; KRAS; PRKCD; PPP1CC; RAF1; CREBBP; MAP2K2; MAP2K1; ATF4; PRKCA.

Examples of genes for which a mUNA molecule can be used to express the corresponding peptide or protein include: Calcium Signaling, RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6.

Examples of genes for which a mUNA molecule can be used to express the corresponding peptide or protein include: EGF Signaling, ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1.

Examples of genes for which a mUNA molecule can be used to express the corresponding peptide or protein include: Hypoxia Signaling in the Cardiovascular System, EDN1; PTEN; EP300; NQO1; UBE21; CREB1; ARNT; HIF1A; SLC2A4; NOS3; TP53; LDHA; AKT1; ATM; VEGFA; JUN; ATF4; VHL; HSP90AA1.

Examples of genes for which a mUNA molecule can be used to express the corresponding peptide or protein include: LPS/IL-1 Mediated Inhibition of RXR Function, IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1.

Examples of genes for which a mUNA molecule can be used to express the corresponding peptide or protein include: LXR/RXR Activation, FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9.

Examples of genes for which a mUNA molecule can be used to express the corresponding peptide or protein include: Amyloid Processing, PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP.

Examples of genes for which a mUNA molecule can be used to express the corresponding peptide or protein include: IL-4 Signaling, AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1.

Examples of genes for which a mUNA molecule can be used to express the corresponding peptide or protein include: Cell Cycle: G2/M DNA Damage Checkpoint Regulation, EP300; PCAF; BRCA1; GADD45A; PLK1; BTRC; CHEK1; ATR; CHEK2; YWHAZ; TP53; CDKN1A; PRKDC; ATM; SFN; CDKN2A.

Examples of genes for which a mUNA molecule can be used to express the corresponding peptide or protein include: Nitric Oxide Signaling in the Cardiovascular System, KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1.

Examples of genes for which a mUNA molecule can be used to express the corresponding peptide or protein include: Purine Metabolism NME2; SMARCA4; MYH9; RRM2; ADAR; EIF2AK4; PKM2; ENTPD1; RAD51; RRM2B; TJP2; RAD51C; NT5E; POLD1; NME1.

Examples of genes for which a mUNA molecule can be used to express the corresponding peptide or protein include: cAMP-mediated Signaling, RAP1A; MAPK1; GNAS; CREB1; CAMK2A; MAPK3; SRC; RAF1; MAP2K2; STAT3; MAP2K1; BRAF; ATF4.

Examples of genes for which a mUNA molecule can be used to express the corresponding peptide or protein include: Mitochondrial Dysfunction Notch Signaling, SOD2; MAPK8; CASP8; MAPK10; MAPK9; CASP9; PARK7; PSEN1; PARK2; APP; CASP3 HES1; JAG1; NUMB; NOTCH4; ADAM17; NOTCH2; PSEN1; NOTCH3; NOTCH1; DLL4.

Examples of genes for which a mUNA molecule can be used to express the corresponding peptide or protein include: Endoplasmic Reticulum Stress Pathway, HSPA5; MAPK8; XBP1; TRAF2; ATF6; CASP9; ATF4; EIF2AK3; CASP3.

Examples of genes for which a mUNA molecule can be used to express the corresponding peptide or protein include: Pyrimidine Metabolism, NME2; AICDA; RRM2; EIF2AK4; ENTPD1; RRM2B; NT5E; POLD1; NME1.

Examples of genes for which a mUNA molecule can be used to express the corresponding peptide or protein include: Parkinson's Signaling, UCHL1; MAPK8; MAPK13; MAPK14; CASP9; PARK7; PARK2; CASP3.

Examples of genes for which a mUNA molecule can be used to express the corresponding peptide or protein include: Cardiac & Beta Adrenergic Signaling, GNAS; GNAQ; PPP2R1A; GNB2L1; PPP2CA; PPP1CC; PPP2R5C.

Examples of genes for which a mUNA molecule can be used to express the corresponding peptide or protein include: Glycolysis/Gluco-neogenesis, HK2; GCK; GPI; ALDH1A1; PKM2; LDHA; HK1.

Examples of genes for which a mUNA molecule can be used to express the corresponding peptide or protein include: Interferon Signaling, IRF1; SOCS1; JAK1; JAK2; IFITM1; STAT1; IFIT3.

Examples of genes for which a mUNA molecule can be used to express the corresponding peptide or protein include: Sonic Hedgehog Signaling, ARRB2; SMO; GLI2; DYRK1A; GLI1; GSK3B; DYRK1B.

Examples of genes for which a mUNA molecule can be used to express the corresponding peptide or protein include: Glycerophospholipid Metabolism, PLD1; GRN; GPAM; YWHAZ; SPHK1; SPHK2.

Examples of genes for which a mUNA molecule can be used to express the corresponding peptide or protein include: Phospholipid Degradation, PRDX6; PLD1; GRN; YWHAZ; SPHK1; SPHK2.

Examples of genes for which a mUNA molecule can be used to express the corresponding peptide or protein include: Tryptophan Metabolism, SIAH2; PRMT5; NEDD4; ALDH1A1; CYP1B1; STAHL Examples of genes for which a mUNA molecule can be used to express the corresponding peptide or protein include: Lysine Degradation, SUV39H1; EHMT2; NSD1; SETD7; PPP2R5C.

Examples of genes for which a mUNA molecule can be used to express the corresponding peptide or protein include: Nucleotide Excision, ERCC5; ERCC4; XPA; XPC; ERCC1.

Examples of genes for which a mUNA molecule can be used to express the corresponding peptide or protein include: Repair Pathway Starch and Sucrose Metabolism, UCHL1; HK2; GCK; GPI; HK1.

Examples of genes for which a mUNA molecule can be used to express the corresponding peptide or protein include: Aminosugars Metabolism, NQO1; HK2; GCK; HK1.

Examples of genes for which a mUNA molecule can be used to express the corresponding peptide or protein include: Arachidonic Acid Metabolism, PRDX6; GRN; YWHAZ; CYP1B1.

Examples of genes for which a mUNA molecule can be used to express the corresponding peptide or protein include: Circadian Rhythm Signaling, CSNK1E; CREB1; ATF4; NR1D1.

Examples of genes for which a mUNA molecule can be used to express the corresponding peptide or protein include: Coagulation System, BDKRB1; F2R; SERPINE1; F3.

Examples of genes for which a mUNA molecule can be used to express the corresponding peptide or protein include: Dopamine Receptor Signaling, PPP2R1A; PPP2CA; PPP1CC; PPP2R5C.

Examples of genes for which a mUNA molecule can be used to express the corresponding peptide or protein include: Glutathione Metabolism, IDH2; GSTP1; ANPEP; IDH1.

Examples of genes for which a mUNA molecule can be used to express the corresponding peptide or protein include: Glycerolipid Metabolism, ALDH1A1; GPAM; SPHK1; SPHK2.

Examples of genes for which a mUNA molecule can be used to express the corresponding peptide or protein include: Linoleic Acid Metabolism, PRDX6; GRN; YWHAZ; CYP1B1.

Examples of genes for which a mUNA molecule can be used to express the corresponding peptide or protein include: Methionine Metabolism, DNMT1; DNMT3B; AHCY; DNMT3A.

Examples of genes for which a mUNA molecule can be used to express the corresponding peptide or protein include: Pyruvate Metabolism, GLO1; ALDH1A1; PKM2; LDHA.

Examples of genes for which a mUNA molecule can be used to express the corresponding peptide or protein include: Arginine and Proline Metabolism, ALDH1A1; NOS3; NOS2A.

Examples of genes for which a mUNA molecule can be used to express the corresponding peptide or protein include: Eicosanoid Signaling, PRDX6; GRN; YWHAZ.

Examples of genes for which a mUNA molecule can be used to express the corresponding peptide or protein include: Fructose and Mannose Metabolism, HK2; GCK; HK1.

Examples of genes for which a mUNA molecule can be used to express the corresponding peptide or protein include: Galactose Metabolism, HK2; GCK; HK1.

Examples of genes for which a mUNA molecule can be used to express the corresponding peptide or protein include: Stilbene, Coumarine and Lignin Biosynthesis, PRDX6; PRDX1; TYR.

Examples of genes for which a mUNA molecule can be used to express the corresponding peptide or protein include: Antigen Presentation Pathway, CALR; B2M.

Examples of genes for which a mUNA molecule can be used to express the corresponding peptide or protein include: Biosynthesis of Steroids, NQO1; DHCR7.

Examples of genes for which a mUNA molecule can be used to express the corresponding peptide or protein include: Butanoate Metabolism, ALDH1A1; NLGN1.

Examples of genes for which a mUNA molecule can be used to express the corresponding peptide or protein include: Citrate Cycle, IDH2; IDH1.

Examples of genes for which a mUNA molecule can be used to express the corresponding peptide or protein include: Fatty Acid Metabolism, ALDH1A1; CYP1B1.

Examples of genes for which a mUNA molecule can be used to express the corresponding peptide or protein include: Glycerophospholipid Metabolism, PRDX6; CHKA.

Examples of genes for which a mUNA molecule can be used to express the corresponding peptide or protein include: Histidine Metabolism, PRMT5; ALDH1A1.

Examples of genes for which a mUNA molecule can be used to express the corresponding peptide or protein include: Inositol Metabolism, ERO1L; APEX1.

Examples of genes for which a mUNA molecule can be used to express the corresponding peptide or protein include: Metabolism of Xenobiotics by Cytochrome p450, GSTP1; CYP1B1.

Examples of genes for which a mUNA molecule can be used to express the corresponding peptide or protein include: Methane Metabolism, PRDX6; PRDX1.

Examples of genes for which a mUNA molecule can be used to express the corresponding peptide or protein include: Phenylalanine Metabolism, PRDX6; PRDX1.

Examples of genes for which a mUNA molecule can be used to express the corresponding peptide or protein include: Propanoate Metabolism, ALDH1A1; LDHA.

Examples of genes for which a mUNA molecule can be used to express the corresponding peptide or protein include: Selenoamino Acid Metabolism, PRMT5; AHCY.

Examples of genes for which a mUNA molecule can be used to express the corresponding peptide or protein include: Sphingolipid Metabolism, SPHK1; SPHK2.

Examples of genes for which a mUNA molecule can be used to express the corresponding peptide or protein include: Aminophosphonate Metabolism, PRMT5.

Examples of genes for which a mUNA molecule can be used to express the corresponding peptide or protein include: Androgen and Estrogen Metabolism, PRMT5.

Examples of genes for which a mUNA molecule can be used to express the corresponding peptide or protein include: Ascorbate and Aldarate Metabolism, ALDH1A1.

Examples of genes for which a mUNA molecule can be used to express the corresponding peptide or protein include: Bile Acid Biosynthesis, ALDH1A1.

Examples of genes for which a mUNA molecule can be used to express the corresponding peptide or protein include: Cysteine Metabolism, LDHA.

Examples of genes for which a mUNA molecule can be used to express the corresponding peptide or protein include: Fatty Acid Biosynthesis, FASN.

Examples of genes for which a mUNA molecule can be used to express the corresponding peptide or protein include: Glutamate Receptor Signaling, GNB2L1.

Examples of genes and/or polynucleotides that can be edited with the guide molecules of this invention include: NRF2-mediated Oxidative Stress Response, PRDX1.

Examples of genes for which a mUNA molecule can be used to express the corresponding peptide or protein include: Pentose Phosphate Pathway, GPI.

Examples of genes for which a mUNA molecule can be used to express the corresponding peptide or protein include: Pentose and Glucuronate Interconversions, UCHL1.

Examples of genes for which a mUNA molecule can be used to express the corresponding peptide or protein include: Retinol Metabolism, ALDH1A1.

Examples of genes for which a mUNA molecule can be used to express the corresponding peptide or protein include: Riboflavin Metabolism, TYR.

Examples of genes for which a mUNA molecule can be used to express the corresponding peptide or protein include: Tyrosine Metabolism, PRMT5, TYR.

Examples of genes for which a mUNA molecule can be used to express the corresponding peptide or protein include: Ubiquinone Biosynthesis, PRMT5.

Examples of genes for which a mUNA molecule can be used to express the corresponding peptide or protein include: Valine, Leucine and Isoleucine Degradation, ALDH1A1.

Examples of genes for which a mUNA molecule can be used to express the corresponding peptide or protein include: Glycine, Serine and Threonine Metabolism, CHKA.

Examples of genes for which a mUNA molecule can be used to express the corresponding peptide or protein include: Lysine Degradation, ALDH1A1.

Examples of genes for which a mUNA molecule can be used to express the corresponding peptide or protein include: Pain/Taste, TRPM5; TRPA1.

Examples of genes for which a mUNA molecule can be used to express the corresponding peptide or protein include: Pain, TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a.

Examples of genes for which a mUNA molecule can be used to express the corresponding peptide or protein include: Mitochondrial Function, AIF; CytC; SMAC (Diablo); Aifm-1; Aifm-2.

Examples of genes for which a mUNA molecule can be used to express the corresponding peptide or protein include: Developmental Neurology, BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4fl or Brn3a); Numb; Reln.

mUNA Methods

In various aspects, this invention provides methods for synthesis of mUNA messenger UNA oligomer molecules.

mUNA oligomer molecules of this invention can be synthesized and isolated using methods disclosed herein, as well as any pertinent techniques known in the art.

Some methods for preparing nucleic acids are given in, for example, Merino, Chemical Synthesis of Nucleoside Analogues, (2013); Gait, Oligonucleotide synthesis: a practical approach (1984); Herdewijn, Oligonucleotide Synthesis, Methods in Molecular Biology, Vol. 288 (2005).

In some embodiments, a ligase can be used to link a synthetic oligomer to the 3' end of an RNA molecule or an RNA transcript to form a mUNA molecule. The synthetic oligomer that is ligated to the 3' end can provide the functionality of a polyA tail, and advantageously provide resistance to its removal by 3'-exoribonucleases. The ligated product mUNA molecule can have increased specific activity and provide increased levels of ectopic protein expression.

In certain embodiments, ligated product mUNA molecules of this invention can be made with an RNA transcript that has native specificity. The ligated product can be a synthetic molecule that retains the structure of the RNA transcript at the 5' end to ensure compatibility with the native specificity.

In further embodiments, ligated product mUNA molecules of this invention can be made with an exogenous RNA transcript or non-natural RNA. The ligated product can be a synthetic molecule that retains the structure of the RNA.

In general, the canonical mRNA degradation pathway in cells includes the steps: (i) the polyA tail is gradually cut back to a stub by 3' exonucleases, shutting down the looping interaction required for efficient translation and leaving the cap open to attack; (ii) decapping complexes remove the 5' cap; (iii) the unprotected and translationally incompetent residuum of the transcript is degraded by 5' and 3' exonuclease activity.

Embodiments of this invention involve new mUNA structures which can have increased translational activity over a native transcript. The mUNA molecules can prevent exonucleases from trimming back the polyA tail in the process of de-adenylation.

Embodiments of this invention provide structures, compositions and methods for translatable mUNA molecules. Embodiments of this invention can provide translatable mUNA molecules containing one or more UNA monomers and having increased functional half-life.

It has been found that ligation of a synthetic oligomer to the 3' end of an mRNA transcript can surprisingly be accomplished with high conversion of the mRNA transcript to the ligation product. The ligase can catalyze the joining of the 3'-hydroxyl terminus of the RNA transcript to a synthetic oligomer bearing a 5' monophosphate group. The 3' end of the synthetic oligomer can be blocked to prevent circularization and concatemerization, while the presence of a triphosphate or cap moiety at the 5' terminus of the mRNA transcript can prevent its entry into undesired side reactions.

In some embodiments, the yield of conversion of the mRNA transcript to the ligation product mUNA molecule can be from 70% to 100%. In some embodiments, the yield of conversion of the mRNA transcript to the ligation product can be 70%, 80%, 90%, 95%, 99%, or 100%.

As used herein, the terms polyA tail and polyA oligomer refer to an oligomer of monomers, wherein the monomers can include nucleotides based on adenine, UNA monomers, naturally-occurring nucleotides, modified nucleotides, or nucleotide analogues.

A modified nucleotide can be base-modified, sugar-modified, or linkage modified.

Splint Ligation Methods

Embodiments of this invention can employ splint ligation to synthesize mUNA molecules.

In some aspects, ligation of a tail oligomer to the 3' end of an RNA molecule can surprisingly be accomplished with high conversion of the RNA molecule to the ligation product by using a DNA splint oligomer. Splint ligation of specific RNA molecules can be done with a DNA ligase and a bridging DNA splint oligomer that is complementary to the RNAs.

As used herein, a molecule to which a tail oligomer is added can be referred to as an acceptor oligomer, and a tail oligomer to be ligated to an acceptor oligomer can be referred to as a donor oligomer.

A donor oligomer of this invention may contain one or more UNA monomers. In some embodiments, a donor oligomer may be composed of UNA monomers and adenylate nucleotides.

A donor oligomer of this invention may include any number of UNA monomers within its total length.

An acceptor oligomer of this invention can be a RNA of any length, an mRNA, or a mammalian gene transcript.

In some aspects, ligation of a donor oligomer of any length to the 3' end of an acceptor RNA molecule can surprisingly be accomplished with high conversion to the ligation product mUNA molecule by using a DNA splint oligomer.

In certain embodiments, a DNA splint oligomer can hybridize to the end of an mRNA having a short polyA tail, anchored in a specific position based on a region complementary to the end of the mRNA's 3' UTR. The polyA tail can be about 30 monomers or less in length. The DNA splint oligomer can incorporate a poly(dT) tail that overhangs beyond the native polyA tail of the mRNA transcript. The poly(dT) tail can bring a polyA oligomer into position for efficient ligation to the synthetic mRNA.

Embodiments of this invention can employ splint ligation to introduce UNA monomers, modified nucleotides, or nucleotide analogues into RNA molecules.

In certain embodiments, in splint ligation the DNA ligase can be used to join RNA molecules in an RNA:DNA hybrid.

In some embodiments, the donor can be from 2 to 120 monomers in length, or from 3 to 120 monomers, or from 4 to 120 monomers, or from 5 to 120 monomers, or from 6 to 120 monomers, or longer.

The splint oligomer can be removed from the ligation product using a DNAse treatment, which can be required post-IVT to remove the DNA template for transcription.

Cohesive End Ligation

In some embodiments, a wild-type T4 RNA ligase can be used to join the 3' hydroxyl terminus of an RNA transcript to a tail oligomer bearing a 5' monophosphate group.

In further embodiments, a KQ mutant variant of T4 RNA Ligase 2, which requires a pre-adenylated donor, was used to join the 3' hydroxyl terminus of an RNA transcript to a pre-adenylated tail oligomer.

In these embodiments, a preponderance of the tail can advantageously be incorporated co-transcriptionally in the IVT synthetic RNA transcript, and the donor oligomer can be correspondingly shortened.

Post-Ligation Treatment

In some aspects, a 3'-exonuclease treatment can be used to remove the unligated fraction of the product of the ligation reaction. Examples of a 3'-exonuclease include Exonuclease T, Ribonuclease R, and analogs thereof.

In certain embodiments, Ribonuclease R can be used with high processivity, and the ligation can be insensitive to sequence content and variations, as well as secondary structure.

Tail Oligomers

In some embodiments, the 100% bulk ligation of a tail oligomer to the 3' end of an RNA has been achieved.

Donor oligomers of this invention for ligation to the 3' end of an mRNA may be from 2 to 120 monomers in length, or from 3 to 120 monomers in length, or from 4 to 120 monomers in length, or from 5 to 120 monomers in length, or longer.

In further embodiments, a donor oligomer may have a 3'-terminal modification to block circularization or oligimerization of the synthetic oligomer in ligation reactions. Examples of a 3'-terminal modification include a 3'-terminal C3 spacer.

A donor oligomer of this invention may contain one or more UNA monomers.

A donor oligomer can include one or more nucleic acid monomers that are naturally-occurring nucleotides, modified naturally-occurring nucleotides, or non-naturally-occurring nucleotides.

A donor oligomer can include a nucleic acid monomer that is base-modified, sugar-modified, or linkage modified.

Pharmaceutical Compositions

In some aspects, this invention provides pharmaceutical compositions containing a mUNA oligomeric compound and a pharmaceutically acceptable carrier.

A pharmaceutical composition can be capable of local or systemic administration. In some aspects, a pharmaceutical composition can be capable of any modality of administration. In certain aspects, the administration can be intravenous, subcutaneous, pulmonary, intramuscular, intraperitoneal, dermal, oral, or nasal administration.

Embodiments of this invention include pharmaceutical compositions containing an oligomeric compound in a lipid formulation.

In some embodiments, a pharmaceutical composition may comprise one or more lipids selected from cationic lipids, anionic lipids, sterols, pegylated lipids, and any combination of the foregoing.

In certain embodiments, a pharmaceutical composition can be substantially free of liposomes.

In further embodiments, a pharmaceutical composition can include liposomes or nanoparticles.

Some examples of lipids and lipid compositions for delivery of an active molecule of this invention are given in WO/2015/074085, which is hereby incorporated by reference in its entirety.

In additional embodiments, a pharmaceutical composition can contain an oligomeric compound within a viral or bacterial vector.

A pharmaceutical composition of this disclosure may include carriers, diluents or excipients as are known in the art. Examples of pharmaceutical compositions and methods are described, for example, in Remington's Pharmaceutical Sciences, Mack Publishing Co. (A. R. Gennaro ed. 1985), and Remington, The Science and Practice of Pharmacy, 21st Edition (2005).

Examples of excipients for a pharmaceutical composition include antioxidants, suspending agents, dispersing agents, preservatives, buffering agents, tonicity agents, and surfactants.

An effective dose of an agent or pharmaceutical formulation of this invention can be an amount that is sufficient to cause translation of a mUNA molecule in a cell.

A therapeutically effective dose can be an amount of an agent or formulation that is sufficient to cause a therapeutic effect. A therapeutically effective dose can be administered in one or more separate administrations, and by different routes.

A therapeutically effective dose, upon administration, can result in serum levels of an active agent of 1-1000 pg/ml, or 1-1000 ng/ml, or 1-1000 µg/ml, or more.

A therapeutically effective dose of an active agent in vivo can be a dose of 0.001-0.01 mg/kg body weight, or 0.01-0.1 mg/kg, or 0.1-1 mg/kg, or 1-10 mg/kg, or 10-100 mg/kg.

A therapeutically effective dose of an active agent in vivo can be a dose of 0.001 mg/kg body weight, or 0.01 mg/kg, or 0.1 mg/kg, or 1 mg/kg, or 2 mg/kg, or 3 mg/kg, or 4 mg/kg, or 5 mg/kg, or more.

A subject can be an animal, or a human subject or patient.

Base sequences show herein are from left to right, 5' to 3', unless stated otherwise.

For the examples below, the mUNA transfection protocol in vitro was as follows:
1. Plate mouse hepatocyte Hepa1-6 cells 5000 cells per well in 96 well plate at least 8 hours before transfection.
2. Replace 90 uL DMEM medium containing 10% FBS and Non-essential amino acid) adding 90 uL into each well of 96 well plate immediately before beginning the transfection experiment.
3. Prepare Messenger Max transfection reagent (Life Technologies) mUNA complex according to manufacturer's instruction.
4. Transfer 10 uL of the complex into a well containing the cells in the 96-well plate.
5. Collect the medium after desired time points and add 100 uL fresh medium into each well. Medium will be kept at −80° C. until ELISA assay is performed using the standard manufacturer protocol.

For the examples below, the mUNA transfection protocol in vivo was as follows:
1. The mUNA is formulated with Lipid nanoparticle (LNP).
2. Inject the LNP-formulated mUNA (1 mg/kg mUNA) into BL57BL/c mice (4-6 week-old) via standard i.v. injection in the lateral tail vein.
3. Collect approximately 50 uL of blood in a Heparin-coated microcentrifuge tube.
4. Centrifuge at 3,000×g for 10 minutes at 4° C.
5. Transfer the supernatant (plasma) into a fresh microcentrifuge tube. Plasma will be kept at −80° C. until ELISA assay is performed using the standard manufacturer protocol.

EXAMPLES

All of the comparative mUNA and mRNA molecules in the examples below were synthesized with the 5' cap being a m7GpppGm cap. Unless otherwise specified, the mUNA molecules in the examples below contained a 5'-UTR of TEV, and a 3' UTR of xenopus beta-globin.

Example 1: mUNA Oligomer Producing Human Factor IX In Vivo

In this example, a translatable mUNA molecule was made and used for expressing human Factor IX (F9) in vivo with advantageously increased efficiency of translation, as compared to the mRNA of Factor IX. The translatable mUNA molecule expressing human Factor IX in vivo exhibited activity suitable for use in methods for ameliorating or treating hemophilia B. In this embodiment, the translatable mUNA molecule comprised a 5' cap (m7GpppGm), a 5' UTR of TEV, a F9 CDS, a 3'UTR of xenopus beta-globin, and a tail region.

The translation efficiency of this mUNA molecule is shown in FIG. 1, as compared to the mRNA of F9.

The mUNA molecule of this embodiment was translated in C57BL/c mouse to produce human F9.

FIG. 1 shows that the translation efficiency of this mUNA molecule was advantageously and surprisingly increased as compared to the mRNA of F9. In particular, after 55 hours, the translation efficiency of this mUNA molecule was increased by more than 2-fold (827/388) as compared to the mRNA of F9.

Details of the base structure of this translatable mUNA molecule are as follows:

(SEQ ID NO: 1)
(m7GpppGm) GGGAAACAUAAGUCAACACAACAUAUACAAAACAAACGAA

UCUCAAGCAAUCAAGCAUUCUACUUCUAUUGCAGCAAUUUAAAUCAUUUC

UUUUAAAGCAAAAGCAAUUUUCUGAAAAUUUUCACCAUUUACGAACGAUA

GCCAUGGCCCAGCGCGUGAACAUGAUCAUGGCAGAAUCACCAGGCCUCAU

CACCAUCUGCCUUUUAGGAUAUCUACUCAGUGCUGAAUGUACAGUUUUUC

UUGAUCAUGAAAACGCCAACAAAAUUCUGAAUCGGCCAAAGAGGUAUAAU

UCAGGUAAAUUGGAAGAGUUUGUUCAAGGGAACCUUGAGAGAGAAUGUAU

GGAAGAAAGUGUAGUUUUGAAGAAGCACGAGAAGUUUUUGAAAACACUG

AAAGAACAACUGAAUUUUGGAAGCAGUAUGUUGAUGGAGAUCAGUGUGAG

UCCAAUCCAUGUUUAAAUGGCGGCAGUUGCAAGGAUGACAUUAAUUCCUA

UGAAUGUUGGUGUCCCUUUGGAUUUGAAGGAAAGAACUGUGAAUUAGAUG

UAACAUGUAACAUUAAGAAUGGCAGAUGCGAGCAGUUUUGUAAAAAUAGU

GCUGAUAACAAGGUGGUUUGCUCCUGUACUGAGGGAUAUCGACUUGCAGA

AAACCAGAAGUCCUGUGAACCAGCAGUGCCAUUUCCAUGUGGAAGAGUUU

CUGUUUCACAAACUUCUAAGCUCACCCGUGCUGAGACUGUUUUUCCUGAU

GUGGACUAUGUAAAUUCUACUGAAGCUGAAACCAUUUUGGAUAACAUCAC

UCAAAGCACCCAAUCAUUUAAUGACUUCACUCGGGUUGUUGGUGGAGAAG

AUGCCAAACCAGGUCAAUUCCCUUGGCAGGUUGUUUUGAAUGGUAAAGUU

GAUGCAUUCUGUGGAGGCUCUAUCGUUAAUGAAAAAUGGAUUGUAACUGC

UGCCCACUGUGUUGAAACUGGUGUUAAAAUUACAGUUGUCGCAGGUGAAC

AUAAUAUUGAGGAGACAGAACAUACAGAGCAAAAGCGAAAUGUGAUUCGA

AUUAUUCCUCACCACAACUACAAUGCAGCUAUUAAUAAGUACAACCAUGA

CAUUGCCCUUCUGGAACUGGACGAACCCUUAGUGCUAAACAGCUACGUUA

CACCUAUUUGCAUUGCUGACAAGGAAUACACGAACAUCUUCCUCAAAUUU

GGAUCUGGCUAUGUAAGUGGCUGGGGAAGAGUCUUCCACAAAGGGAGAUC

AGCUUUAGUUCUUCAGUACCUUAGAGUUCCACUUGUUGACCGAGCCACAU

GUCUUCGAUCUACAAAGUUCACCAUCUAUAACAACAUGUUCUGUGCUGGC

UUCCAUGAAGGAGGUAGAGAUUCAUGUCAAGGAGAUAGUGGGGGACCCCA

UGUUACUGAAGUGGAAGGGACCAGUUUCUUAACUGGAAUUAUUAGCUGGG

GUGAAGAGUGUGCAAUGAAAGGCAAAUAUGGAAUAUAUACCAAGGUAUCC

CGGUAUGUCAACUGGAUUAAGGAAAAAACAAAGCUCACUUGACUAGUGAC

UGACUAGGAUCUGGUUACCACUAAACCAGCCUCAAGAACACCCGAAUGGA

GUCUCUAAGCUACAUAAUACCAACUUACACUUACAAAAUGUUGUCCCCA

AAAUGUAGCCAUUCGUAUCUGCUCCUAAUAAAAAGAAAGUUUCUUCACAU

AAAAAAAAAAAAAAAAAAAAAAAAAAAAAAAAAAAAAAAAAAAAAAAAAA

AAAAAAAAAA

Example 2: mUNA Oligomer Producing Human Factor IX In Vitro

In this example, the translatable mUNA molecule of Example 1 (SEQ ID NO:1) was made and used for expressing human Factor IX (F9) in vitro with advantageously increased efficiency of translation, as compared to the mRNA of Factor IX. The translatable mUNA molecule expressing human Factor IX exhibited activity suitable for use in methods for ameliorating or treating hemophilia B.

Figure 2:
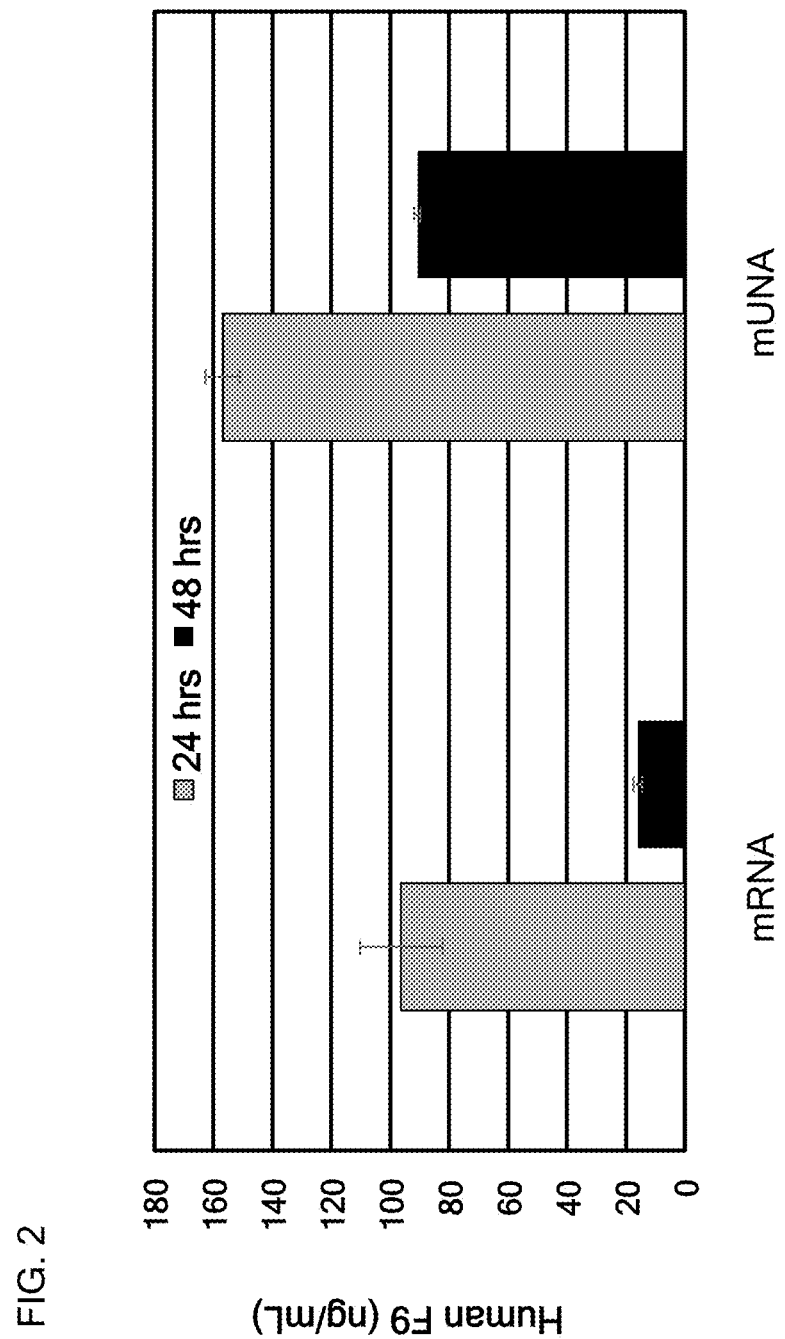
FIG. 2.

The translation efficiency of this mUNA molecule (SEQ ID NO:1) is shown in FIG. 2, as compared to the mRNA of F9.

The mUNA molecule of this embodiment was translated in mouse hepatocyte cell line Hepa1-6 to produce human F9.

FIG. 2 shows that the translation efficiency of this mUNA molecule was advantageously and surprisingly increased as compared to the mRNA of F9. In particular, after 48 hours, the translation efficiency of this mUNA molecule was increased by 5-fold (91/16) as compared to the mRNA of F9.

Example 3: mUNA Oligomer Producing Human Erythropoietin In Vitro

In this example, a translatable mUNA molecule was made and used for expressing human Erythropoietin (EPO) in vitro with advantageously increased efficiency of translation, as compared to the mRNA of EPO. The translatable mUNA molecule expressing human EPO exhibited activity suitable for use in methods for ameliorating or treating certain anemias, inflammatory bowel disease, and/or certain myelodysplasias. In this embodiment, the translatable mUNA molecule comprised a 5' cap (m7 GpppGm), a 5' UTR of TEV, a human EPO CDS, a 3'UTR of xenopus beta-globin, and a tail region.

Figure 3:
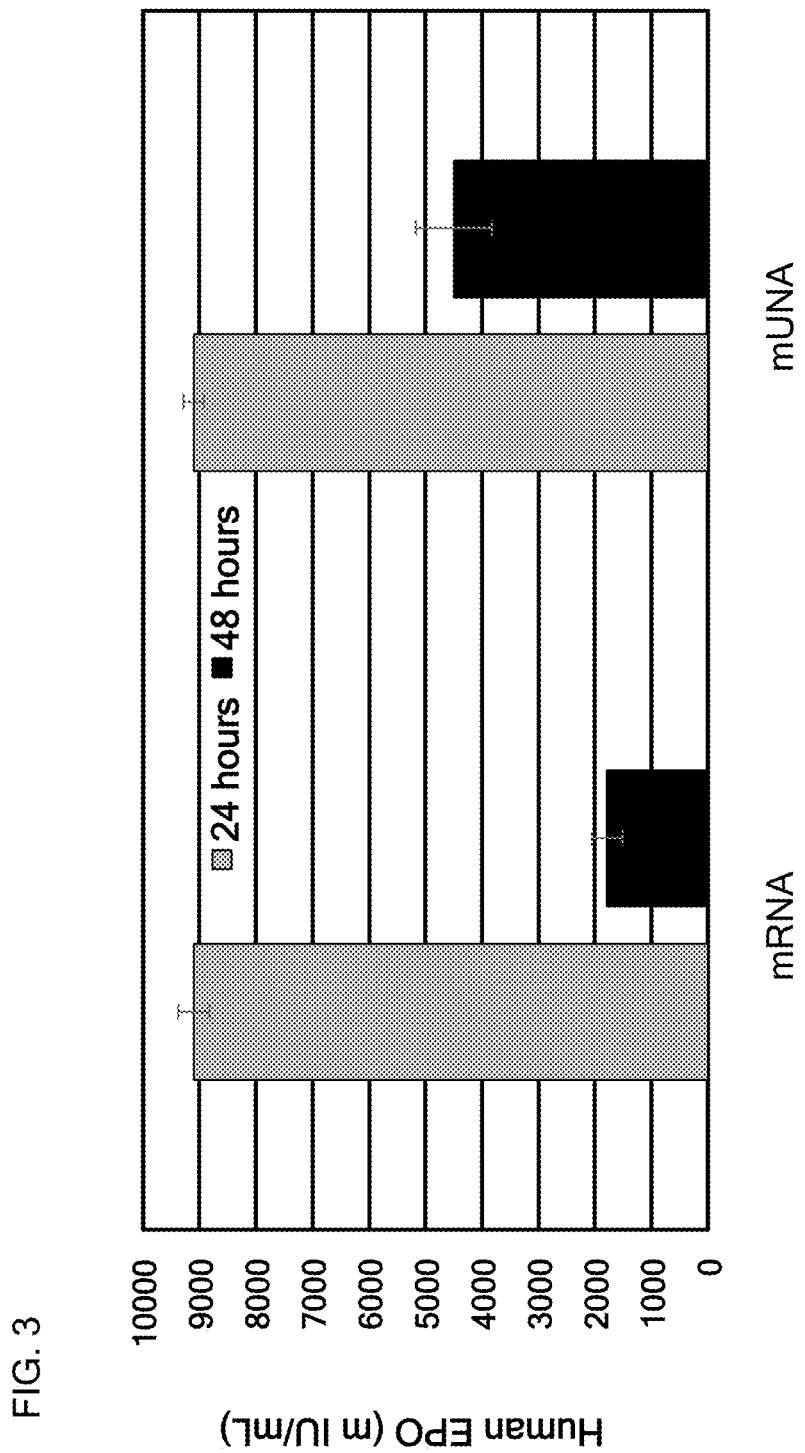
FIG. 3.

The translation efficiency of this mUNA molecule is shown in FIG. 3, as compared to the mRNA of EPO.

The mUNA molecule of this embodiment was translated in mouse hepatocyte cell line Hepa1-6 to produce human EPO.

FIG. 3 shows that the translation efficiency of this mUNA molecule was advantageously and surprisingly increased as compared to the mRNA of F9. In particular, after 48 hours, the translation efficiency of this mUNA molecule was more than doubled (4500/1784) as compared to the mRNA of EPO.

Details of the base structure of this translatable mUNA molecule are as follows:

(SEQ ID NO: 2)
(m7GpppGm) GGGAAACAUAAGUCAACACAACAUAUACAAAACAAACGAA

UCUCAAGCAAUCAAGCAUUCUACUUCUAUUGCAGCAAUUUAAAUCAUUUC

UUUUAAAGCAAAAGCAAUUUUCUGAAAAUUUUCACCAUUUACGAACGAUA

GCCAUGGGGGUGCACGAAUGUCCUGCCUGGCUGUGGCUUCUCCUGUCCCU

GCUGUCGCUCCCUCUGGGCCUCCCAGUCCUGGGCGCCCCACCACGCCUCA

UCUGUGACAGCCGAGUCCUGGAGAGGUACCUCUUGGAGGCCAAGGAGGCC

GAGAAUAUCACGACGGGCUGUGCUGAACACUGCAGCUUGAAUGAGAAUAU

CACUGUCCCAGACACCAAAGUUAAUUUCUAUGCCUGGAAGAGGAUGGAGG

UCGGGCAGCAGGCCGUAGAAGUCUGGCAGGGCCUGGCCCUGCUGUCGGAA

GCUGUCCUGCGGGGCCAGGCCCUGUUGGUCAACUCUUCCCAGCCGUGGGA

-continued
```
GCCCCUGCAGCUGCAUGUGGAUAAAGCCGUCAGUGGCCUUCGCAGCCUCA

CCACUCUGCUUCGGGCUCUGGGAGCCCAGAAGGAAGCCAUCUCCCCUCCA

GAUGCGGCCUCAGCUGCUCCACUCCGAACAAUCACUGCUGACACUUUCCG

CAAACUCUUCCGAGUCUACUCCAAUUUCCUCCGGGGAAAGCUGAAGCUGU

ACACAGGGGAGGCCUGCAGGACAGGGGACAGAUGACUAGUGACUGACUAG

GAUCUGGUUACCACUAAACCAGCCUCAAGAACACCCGAAUGGAGUCUCUA

AGCUACAUAAUACCAACUUACACUUACAAAAUGUUGUCCCCAAAAUGUA

GCCAUUCGUAUCUGCUCCUAAUAAAAAGAAAGUUUCUUCACAUAAAAAAA

AAAAAAAAAAAAAAAAAAAAAAAAAAAAAAAAAAAAAAAAAAAAAAAÃ

ÃAA
```

Example 4: mUNA Oligomers Producing Mouse Erythropoietin In Vitro

In this example, several translatable mUNA molecules were made and used for expressing mouse Erythropoietin (EPO) in vitro with advantageously increased efficiency of translation, as compared to the mRNA of EPO. In this embodiment, the translatable mUNA molecules each comprised a 5' cap (m7GpppGm), a 5' UTR of TEV, a mouse EPO CDS, a 3'UTR of xenopus beta-globin, and a tail region.

Figure 4:
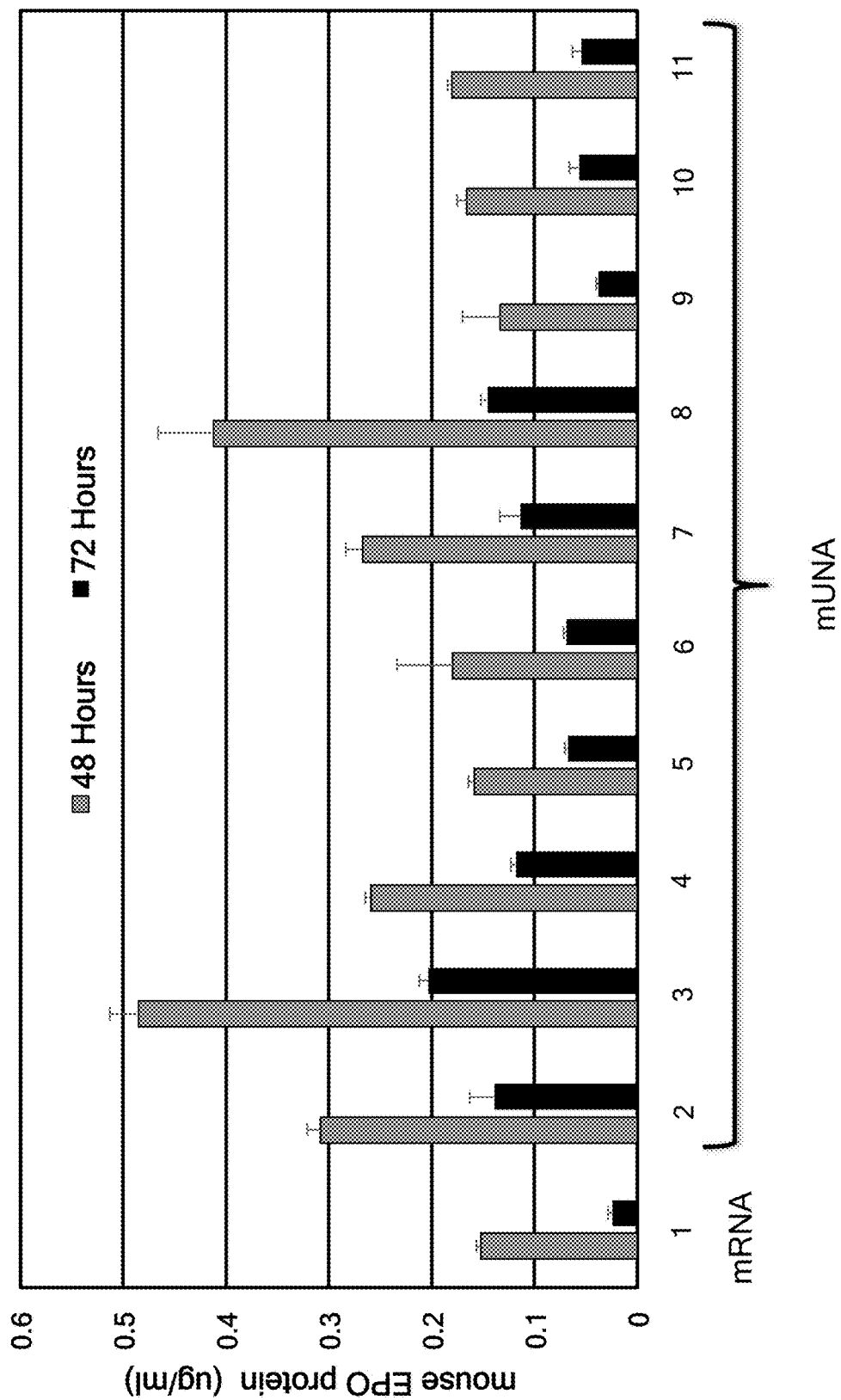
FIG. 4.

The translation efficiency of these mUNA molecules (#2, 3, 4, 5, 6, 7, 8, 9, 10 and 11) are shown in FIG. 4, as compared to the mRNA of EPO (#1).

The mUNA molecules of this embodiment were translated in mouse hepatocyte cell line Hepa1-6 to produce mouse EPO.

FIG. 4 shows that the translation efficiency of the mUNA molecules (#2, 3, 4, 5, 6, 7, 8, 9, 10 and 11) was advantageously and surprisingly increased as compared to the mRNA of EPO (#1). In particular, after 72 hours, the translation efficiency of the mUNA molecules was increased by up to 8-fold (0.203/0.025) as compared to the mRNA of EPO, and the translation efficiency of every mUNA molecule (#2, 3, 4, 5, 6, 7, 8, 9, 10 and 11) was increased as compared to the mRNA of EPO (#1).

Details of the base structure of the translatable mUNA molecule #2 are as follows:

```
                                           (SEQ ID NO: 3)
(m7GpppGm) GGGAAACAUAAGUCAACACAACAUAUACAAAACAAACGAA

UCUCAAGCAAUCAAGCAUUCUACUUCUAUUGCAGCAAUUUAAAUCAUUUC

UUUUAAAGCAAAAGCAAUUUUCUGAAAAUUUUCACCAUUUACGAACGAUA

GCCAUGGGGGUGCCCGAACGUCCCACCCUGCUGCUUUUACUCUCCUUGCU

ACUGAUUCCUCUGGGGCCUCCCAGUCCUCUGUGCUCCCCCACGCCUCAUCU

GCGACAGUCGAGUUCUGGAGAGGUACAUCUUAGAGGCCAAGGAGGCAGAA

AAUGUCACGAUGGGUUGUGCAGAAGGUCCCAGACUGAGUGAAAAUAUUAC

AGUCCCAGAUACCAAAGUCAACUUCUAUGCUUGGAAAAGAAUGGAGGUGG

AAGAACAGGCCAUAGAAGUUUGGCAAGGCCUGUCCCUGCUCUCAGAAGCC

AUCCUGCAGGCCCAGGCCCUGCUAGCCAAUUCCUCCCAGCCACCAGAGAC
```
```
CCUUCAGCUUCAUAUAGACAAAGCCAUCAGUGGUCUACGUAGCCUCACUU

CACUGCUUCGGGUACUGGGAGCUCAGAAGGAAUUGAUGUCGCCUCCAGAU

ACCACCCCACCUGCUCCACUCCGAACACUCACAGUGGAUACUUUCUGCAA

GCUCUUCCGGGUCUACGCCAACUUCCUCCGGGGGAAACUGAAGCUGUACA

CGGGAGAGGUCUGCAGGAGAGGGGACAGGTGACUAGUGACUGACUAGGAU

CUGGUUACCACUAAACCAGCCUCAAGAACACCCGAAUGGAGUCUCUAAGC

UACAUAAUACCAACUUACACUUACAAAAUGUUGUCCCCCAAAAUGUAGCC

AUUCGUAUCUGCUCCUAAUAAAAAGAAAGUUUCUUCACAUAAAAAAAAAA

AAAAAAAAAAAAAAAAAAAAAAAAAAAAAAAAAAAAAAAAAAAAAAÃÃ
```

Details of the base structure of the translatable mUNA molecules #3 through #11 that were made are the same as molecule #2, except that the 3' terminal tail regions, the last 40 monomers are as follows:

```
mUNA molecule #3
                                           (SEQ ID NO: 4)
AAAAAAAAAAAAAAAAAAAAAAAAAAAAAA

AAAAAAAAAAAAAAAAAAAAAAAAAAÃÃAA mUNA molecule #4
                                           (SEQ ID NO: 5)
AAAAAAAAAAAAAAAAAAAAAAAAAAAAAA

AAAAAAAAAAAAAAAAAAAAAAAAÃÃAAAA mUNA molecule #5
                                           (SEQ ID NO: 6)
AAAAAAAAAAAAAAAAAAAAAAAAAAAAAA

AAAAAAAAAAAAAAAAAAAAAAÃÃAAAAAA mUNA molecule #6
                                           (SEQ ID NO: 7)
AAAAAAAAAAAAAAAAAAAAAAAAAAAAAA

AAAAAAAAAAAAAAAAAAAAÃÃAAAAAAAA mUNA molecule #7
                                           (SEQ ID NO: 8)
AAAAAAAAAAAAAAAAAAAAAAAAAAAAAA

AAAAAAAAAAAAAAAAAAÃÃAAAAAAAAAA mUNA molecule #8
                                           (SEQ ID NO: 9)
AAAAAAAAAAAAAAAAAAAAAAAAAAAAAA

AAAAAAAAAAAAAAAAÃÃAAAAAAAAAAAA mUNA molecule #9
                                           (SEQ ID NO: 10)
AAAAAAAAAAAAAAAAAAAAAAAAAAAAAA

AAAAAAAAAAAAAAÃÃAAAAAAAAAAAAAA mUNA molecule #10
                                           (SEQ ID NO: 11)
AAAAAAAAAAAAAAAAAAAAAAAAAAAAAA

AAAAAAAAAAAAÃÃAAAAAAAAAAAAAAAA mUNA molecule #11
                                           (SEQ ID NO: 12)
AAAAAAAAAAAAAAAAAAAAAAAAAAAAAA

AAAAAAAAAAÃÃAAAAAAAAAAAAAAAAAA
```

Example 5: mUNA Oligomer Producing Human Alpha-1-Antitrypsin In Vivo

In this example, a translatable mUNA molecule was made and used for expressing human alpha-1-Antitrypsin in vivo with advantageously increased efficiency of translation, as compared to the mRNA of human alpha-1-Antitrypsin. The translatable mUNA molecule expressing human alpha-1-Antitrypsin exhibited activity suitable for use in methods for ameliorating or treating alpha-1-Antitrypsin deficiency. In this embodiment, the translatable mUNA molecule comprised a 5' cap (m7GpppGm), a 5' UTR of TEV, a human alpha-1-Antitrypsin CDS, a 3'UTR of xenopus beta-globin, and a tail region.

Figure 5:
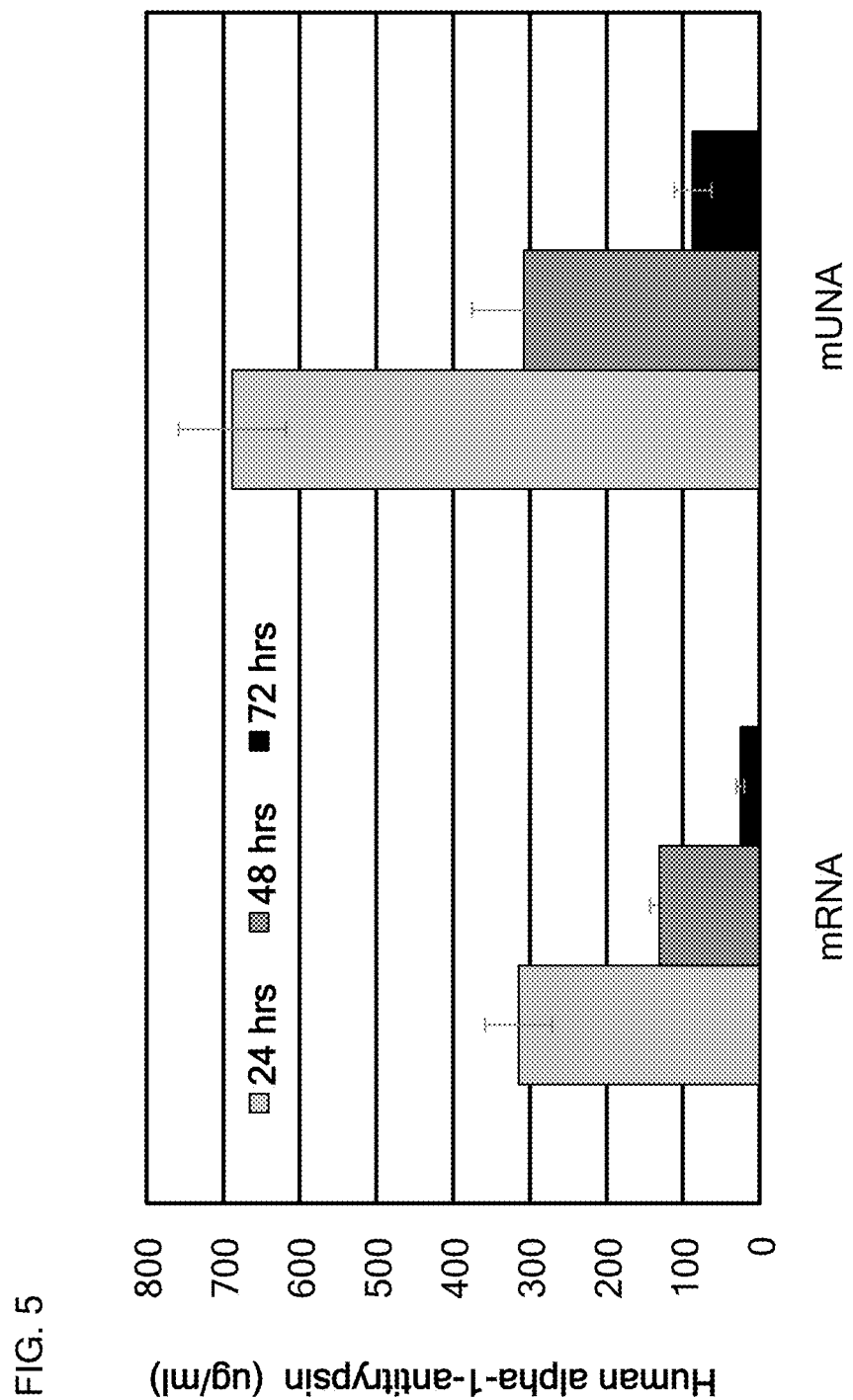
FIG. 5.

The translation efficiency of this mUNA molecule is shown in FIG. 5, as compared to the mRNA of human alpha-1-Antitrypsin.

The mUNA molecule of this embodiment was translated in C57BL/c mouse to produce human alpha-1-Antitrypsin.

FIG. 5 shows that the translation efficiency of this mUNA molecule was advantageously and surprisingly increased as compared to the mRNA of human alpha-1-Antitrypsin. In particular, after 72 hours, the translation efficiency of this mUNA molecule was increased by more than 3-fold (87.8/25.4) as compared to the mRNA of human alpha-1-Antitrypsin.

Details of the base structure of this translatable mUNA molecule were as follows:

```
                                              (SEQ ID NO: 13)
(m7GpppGm) GGGAAACAUAAGUCAACACAACAUAUACAAAACAAACGAA

UCUCAAGCAAUCAAGCAUUCUACUUCUAUUGCAGCAAUUUAAAUCAUUUC

UUUUAAAGCAAAAGCAAUUUUCUGAAAAUUUUCACCAUUUACGAACGAUA

GCCAUGCCGUCUUCUGUCUCGUGGGGCAUCCUCCUGCUGGCAGGCCUGUG

CUGCCUGGUCCCUGUCUCCCUGGCUGAGGAUCCCCAGGGAGAUGCUGCCC

AGAAGACAGAUACAUCCCACCAUGAUCAGGAUCACCCAACCUUCAACAAG

AUCACCCCCAACCUGGCUGAGUUCGCCUUCAGCCUAUACCGCCAGCUGGC

ACACCAGUCCAACAGCACCAAUAUCUUCUUCUCCCCAGUGAGCAUCGCUA

CAGCCUUUGCAAUGCUCUCCCUGGGGACCAAGGCUGACACUCACGAUGAA

AUCCUGGAGGGCCUGAAUUUCAACCUCACGGAGAUUCCGGAGGCUCAGAU

CCAUGAAGGCUUCCAGGAACUCCUCCGUACCCUCAACCAGCCAGACAGCC

AGCUCCAGCUGACCACCGGCAAUGGCCUGUUCCUCAGCGAGGGCCUGAAG

CUAGUGGAUAAGUUUUUGGAGGAUGUUAAAAAGUUGUACCACUCAGAAGC

CUUCACUGUCAACUUCGGGGACACCGAAGAGGCCAAGAAACAGAUCAACG

AUUACGUGGAGAAGGGUACUCAAGGGAAAAUUGUGGAUUUGGUCAAGGAG

CUUGACAGAGACACAGUUUUUGCUCUGGUGAAUUACAUCUUCUUUAAAGG

CAAAUGGGAGAGACCCUUUGAAGUCAAGGACACCGAGGAAGAGGACUUCC

ACGUGGACCAGGUGACCACCGUGAAGGUGCCUAUGAUGAAGCGUUUAGGC

AUGUUUAACAUCCAGCACUGUAAGAAGCUGUCCAGCUGGGUGCUGCUGAU

GAAAUACCUGGGCAAUGCCACCGCCAUCUUCUUCCUGCCUGAUGAGGGA

AACUACAGCACCUGGAAAAUGAACUCACCCACGAUAUCAUCACCAAGUUC

CUGGAAAAUGAAGACAGAAGGUCUGCCAGCUUACAUUUACCCAAACUGUC

CAUUACUGGAACCUAUGAUCUGAAGAGCGUCCUGGGUCAACUGGGCAUCA

CUAAGGUCUUCAGCAAUGGGGCUGACCUCUCCGGGGUCACAGAGGAGGCA

CCCCUGAAGCUCUCCAAGGCCGUGCAUAAGGCUGUGCUGACCAUCGACGA

GAAAGGGACUGAAGCUGCUGGGGCCAUGUUUUUAGAGGCCAUACCCAUGU

CUAUCCCCCCCGAGGUCAAGUUCAACAAACCCUUUGUCUUCUUAAUGAUU

GAACAAAAUACCAAGUCUCCCCUCUUCAUGGGAAAAGUGGUGAAUCCCAC

CCAAAAAUAACUAGUGACUGACUAGGAUCUGGUUACCACUAAACCAGCCU

CAAGAACACCCGAAUGGAGUCUCUAAGCUACAUAAUACCAACUUACACUU

ACAAAAUGUUGUCCCCCAAAAUGUAGCCAUUCGUAUCUGCUCCUAAUAAA

AAGAAAGUUUCUUCACAUAAAAAAAAAAAAAAAAAAAAAAAAAAAAAAAA

AAAAAAAAAAAAAAAAAAAAAAÃÃAAAA
```

Example 6: mUNA Oligomer Producing Human Erythropoietin In Vivo

In this example, a translatable mUNA molecule was made and used for expressing human Erythropoietin (EPO) in vivo with advantageously increased efficiency of translation, as compared to the mRNA of EPO. The translatable mUNA molecule expressing human EPO exhibited activity suitable for use in methods for ameliorating or treating certain anemias, inflammatory bowel disease, and/or certain myelodysplasias. In this embodiment, the translatable mUNA molecule comprised a 5' cap (m7GpppGm), a 5' UTR of TEV, a human EPO CDS, a 3'UTR of xenopus beta-globin, and a tail region.

Figure 6:
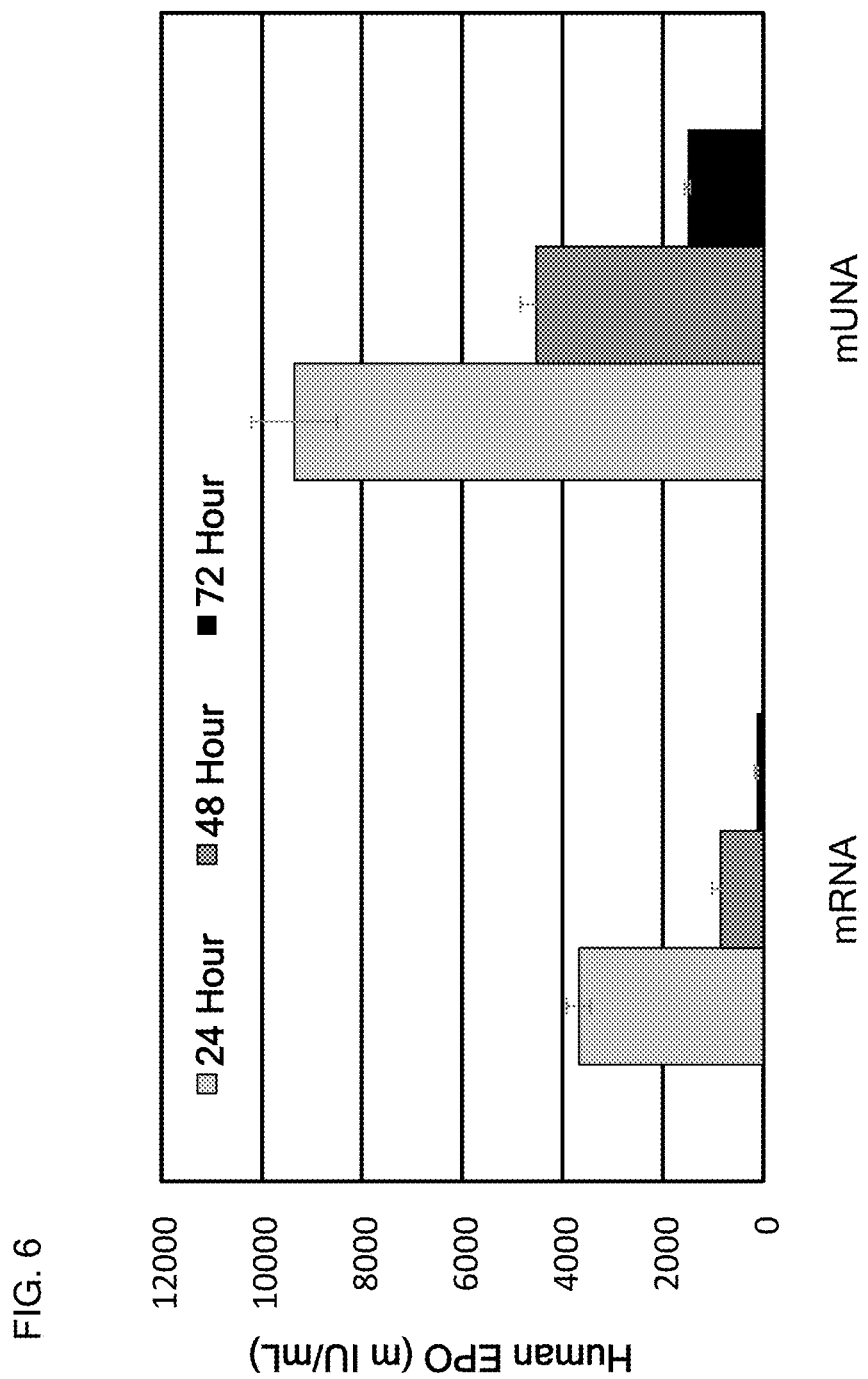
FIG. 6.

The translation efficiency of this mUNA molecule is shown in FIG. 6, as compared to the mRNA of EPO.

The mUNA molecule of this embodiment was translated in C57BL/c mouse to produce human EPO.

FIG. 6 shows that the translation efficiency of this mUNA molecule was advantageously and surprisingly increased as compared to the mRNA of EPO. In particular, after 72 hours, the translation efficiency of this mUNA molecule was increased by more than 10-fold (1517/143) as compared to the mRNA of EPO.

Details of the base structure of this translatable mUNA molecule were as follows:

```
                                              (SEQ ID NO: 14)
(m7GpppGm) GGGAAACAUAAGUCAACACAACAUAUACAAAACAAACGAA

UCUCAAGCAAUCAAGCAUUCUACUUCUAUUGCAGCAAUUUAAAUCAUUUC

UUUUAAAGCAAAAGCAAUUUUCUGAAAAUUUUCACCAUUUACGAACGAUA

GCCAUGGGGGUGCACGAAUGUCCUGCCUGGCUGUGGCUUCUCCUGUCCCU

GCUGUCGCUCCCUCUGGGCCUCCCAGUCCUGGGCGCCCCACCACGCCUCA

UCUGUGACAGCCGAGUCCUGGAGAGGUACCUCUUGGAGGCCAAGGAGGCC

GAGAAUAUCACGACGGGCUGUGCUGAACACUGCAGCUUGAAUGAGAAUAU

CACUGUCCCAGACACCAAAGUUAAUUUCUAUGCCUGGAAGAGGAUGGAGG

UCGGGCAGCAGGCCGUAGAAGUCUGGCAGGGCCUGGCCCUGCUGUCGGAA

GCUGUCCUGCGGGGCCAGGCCCUGUUGGUCAACUCUUCCCAGCCGUGGGA

GCCCCUGCAGCUGCAUGUGGAUAAAGCCGUCAGUGGCCUUCGCAGCCUCA
```

-continued
CCACUCUGCUUCGGGCUCUGGGAGCCCAGAAGGAAGCCAUCUCCCCUCCA

GAUGCGGCCUCAGCUGCUCCACUCCGAACAAUCACUGCUGACACUUUCCG

CAAACUCUUCCGAGUCUACUCCAAUUUCCUCCGGGGAAAGCUGAAGCUGU

ACACAGGGGAGGCCUGCAGGACAGGGGACAGAUGACUAGUGACUGACUAG

GAUCUGGUUACCACUAAACCAGCCUCAAGAACACCCGAAUGGAGUCUCUA

AGCUACAUAAUACCAACUUACACUUACAAAAUGUUGUCCCCCAAAAUGUA

GCCAUUCGUAUCUGCUCCUAAUAAAAAGAAAGUUUCUUCACAUAAAAAAA

AAAAAAAAAAAAAAAAAAAAAAAAAAAAAAAAAAAAAAAAAAAAAAAÃÃA

AAA

Example 7: mUNA Oligomer Producing Human CFTR

In this example, a translatable mUNA molecule is made for use in expressing human CFTR in vivo. The translatable mUNA molecule expressing human CFTR in vivo is suitable for use in methods for ameliorating or treating cystic fibrosis. In this embodiment, the translatable mUNA molecule comprises a 5' cap (m7GpppGm), a 5' UTR of TEV, a CFTR CDS, a 3'UTR of xenopus beta-globin, and a tail region shown in Example 4.

Human CFTR is accession NM_000492.3.

Example 8: mUNA Oligomer Producing Human ASL

In this example, a translatable mUNA molecule is made for use in expressing human argininosuccinate lyase (ASL) in vivo. The translatable mUNA molecule expressing human ASL in vivo is suitable for use in methods for ameliorating or treating ASL deficiency. In this embodiment, the translatable mUNA molecule comprises a 5' cap (m7GpppGm), a 5' UTR of TEV, a ASL CDS, a 3'UTR of xenopus beta-globin, and a tail region shown in Example 4.

Human ASL is accession NM_001024943.1.

Example 9: mUNA Oligomer Producing Human PAH

In this example, a translatable mUNA molecule is made for use in expressing human Phenylalanine-4-hydroxylase (PAH) in vivo. The translatable mUNA molecule expressing human PAH in vivo is suitable for use in methods for ameliorating or treating Phenylketonuria (PKU). In this embodiment, the translatable mUNA molecule comprises a 5' cap (m7GpppGm), a 5' UTR of TEV, a PAH CDS, a 3'UTR of xenopus beta-globin, and a tail region shown in Example 4.

Human PAH is accession NM_000277.1.

Example 10: mUNA Oligomer Producing Human NIS

In this example, a translatable mUNA molecule is made for use in expressing human Sodium/iodide cotransporter (NIS) in vivo. The translatable mUNA molecule expressing human NIS in vivo is suitable for use in methods for ameliorating or treating thyroid disease. In this embodiment, the translatable mUNA molecule comprises a 5' cap (m7GpppGm), a 5' UTR of TEV, a NIS CDS, a 3'UTR of xenopus beta-globin, and a tail region shown in Example 4.

Human NIS is accession BC105047.

Example 11: mUNA Oligomer Producing Human NIS

In this example, a translatable mUNA molecule is made for use in expressing human Sodium/iodide cotransporter (NIS) in vivo. The translatable mUNA molecule expressing human NIS in vivo is suitable for use in methods for ameliorating or treating thyroid disease. In this embodiment, the translatable mUNA molecule comprises a 5' cap (m7GpppGm), a 5' UTR of TEV, a NIS CDS, a 3'UTR of xenopus beta-globin, and a tail region shown in Example 4.

Human NIS is accession BC105047.

Example 12: mUNA Oligomer Producing Human Hepcidin

In this example, a translatable mUNA molecule is made for use in expressing human Hepcidin in vivo. The translatable mUNA molecule expressing human Hepcidin in vivo is suitable for use in methods for ameliorating or treating iron deficiency disease. In this embodiment, the translatable mUNA molecule comprises a 5' cap (m7GpppGm), a 5' UTR of TEV, a Hepcidin CDS, a 3'UTR of xenopus beta-globin, and a tail region shown in Example 4.

Human Hepcidin is accession NM_021175.3.

Example 13: mUNA Oligomer Expressing Factor IX

In this example, the structures of mUNA molecules for use in expressing Factor IX are shown.

Factor IX (F9) is associated with hemophilia B.

The base sequences shown below are the portion of the mUNA molecule that may correspond in functionality to the open reading frame of the native mRNA of human Factor IX. The complete mUNA molecule comprises a 5' cap (m7GpppGm), and a 5'-UTR upstream of the sequence below, and a 3' UTR and polyA tail (SEQ ID Nos:4 to 12) downstream of the sequence below, each of which corresponds to the structure of the native mRNA of human Factor IX.

Human Factor IX is accession NM_000133.3.

(SEQ ID NO: 15)

AUG̃CAGCGCGUGAACAUGAUCAUGGCAGAAUC̃ACCAGGCCUCAUCACCAUCUGCCUUUU

AGG̃AUAUCUACUCAGUGCUGAAUGUACAGUUUŨCUUGAUCAUGAAAACGCCAACAAAA

UUCUG̃AAUCGGCCAAAGAGGUAUAAUUCAGGUAAÃUUGGAAGAGUUUGUUCAAGGGAAC

CUUGAG̃AGAGAAUGUAUGGAAGAAAAGUGUAGUUŨGAAGAAGCACGAGAAGUUUUUGA

AAACACŨGAAAGAACAACUGAAUUUUGGAAGCAGUAŨGUUGAUGGAGAUCAGUGUGAGU

-continued

CCAAUCCAUGUUUAAAUGGCGGCAGUUGCAAGGAUGACAUUAAUUCCUAUGAAUGUUGG
UGUCCCUUUGGAUUUGAAGGAAAGAACUGUGAAUUAGAUGUAACAUGUAACAUUAAGAA
UGGCAGAUCGAGCAGUUUUGUAAAAAUAGUGCUGAUAACAAGGUGGUUUGCUCCUGUA
CUGAGGGAUAUCGACUUGCAGAAAACCAGAAGUCCUGUGAACCAGCAGUGCCAUUCCA
UGUGGAAGAGUUUCUGUUUCACAAACUUCUAAGCUCACCCGUGCUGAGACUGUUUUUCC
UGAUGUGGACUAUGUAAAUUCUACUGAAGCUGAAACCAUUUUGGAUAACAUCACUCAAA
GCACCCAAUCAUUUAAUGACUUCACUCGGGUUGUUGGUGGAGAAGAUGCCAAACCAGGU
CAAUUCCCUUGGCAGGUUGUUUUGAAUGGUAAAGUUGAUGCAUUCUGUGGAGGCUCUAU
CGUUAAUGAAAAAUGGAUUGUAACUGCUGCCCACUGUGUUGAAACUGGUGUUAAAAUUA
CAGUUGUCGCAGGUGAACAUAAUAUUGAGGAGACAGAACAUACAGAGCAAAAGCGAAAU
GUGAUUCGAAUUAUUCCUCACCACAACUACAAUGCAGCUAUUAAUAAGUACAACCAUGA
CAUUGCCCUUCUGGAACUGGACGAACCCUUAGUGCUAAACAGCUACGUUACACCUAUUU
GCAUUGCUGACAAGGAAUACACGAACAUCUUCCUCAAAUUUGGAUCUGGCUAUGUAAGU
GGCUGGGGAAGAGUCUUCCACAAAGGGAGAUCAGCUUUAGUUCUUCAGUACCUUAGAGU
UCCACUUGUUGACCGAGCCACAUGUCUUCGAUCUACAAAGUUCACCAUCUAUAACAACA
UGUUCUGUGCUGGCUUCCAUGAAGGAGGUAGAGAUUCAUGUCAAGGAGAUAGUGGGGGA
CCCCAUGUUACUGAAGUGGAAGGACCAGUUUCUUAACUGGAAUUAUUAGCUGGGGUGA
AGAGUGUGCAAUGAAAGGCAAAUAUGGAAUAUAUACCAAGGUAUCCCGGUAUGUCAACU
GGAUUAAGGAAAAAACAAAGCUCACUUAA (SEQ ID NO: 16)

AUCCAGCGCGUGAACAUGAUCAUGGCAGAAUCACCAGGCCUCAUCACCAUCUGCCUUUU
AGGAUAUCUACUCAGUGCUGAAUGUACAGUUUUUCUUGAUCAUGAAAACGCCAACAAAA
UUCUGAAUCGGCCAAAGAGGUAUAAUUCAGGUAAAUUGGAAGAGUUUGUUCAAGGGAAC
CUUGAGAGAGAAUGUAUGGAAGAAAAGUGUAGUUUUGAAGAAGCACGAGAAGUUUUUGA
AAACACUGAAAGAACAACUGAAUUUUGGAAGCAGUAUGUUGAUGGAGAUCAGUGUGAGU
CCAAUCCAUGUUUAAAUGGCGGCAGUUGCAAGGAUGACAUUAAUUCCUAUGAAUGUUGG
UGUCCCUUUGGAUUUGAAGGAAAGAACUGUGAAUUAGAUGUAACAUGUAACAUUAAGAA
UGGCAGAUGCGAGCAGUUUUGUAAAAAUAGUGCUGAUAACAAGGUGGUUUGCUCCUGUA
CUGAGGGAUAUCGACUUGCAGAAAACCAGAAGUCCUGUGAACCAGCAGUGCCAUUCCA
UGUGGAAGAGUUUCUGUUUCACAAACUUCUAAGCUCACCCGUGCUGAGACUGUUUUUCC
UGAUGUGGACUAUGUAAAUUCUACUGAAGCUGAAACCAUUUUGGAUAACAUCACUCAAA
GCACCCAAUCAUUUAAUGACUUCACUCGGGUUGUUGGUGGAGAAGAUGCCAAACCAGGU
CAAUUCCCUUGGCAGGUUGUUUUGAAUGGUAAAGUUGAUGCAUUCUGUGGAGGCUCUAU
CGUUAAUGAAAAAUGGAUUGUAACUGCUGCCCACUGUGUUGAAACUGGUGUUAAAAUUA
CAGUUGUCGCAGGUGAACAUAAUAUUGAGGAGACAGAACAUACAGAGCAAAAGCGAAAU
GUGAUUCGAAUUAUUCCUCACCACAACUACAAUGCAGCUAUUAAUAAGUACAACCAUGA
CAUUGCCCUUCUGGAACUGGACGAACCCUUAGUGCUAAACAGCUACGUUACACCUAUUU
GCAUUGCUGACAAGGAAUACACGAACAUCUUCCUCAAAUUUGGAUCUGGCUAUGUAAGU
GGCUGGGGAAGAGUCUUCCACAAAGGGAGAUCAGCUUUAGUUCUUCAGUACCUUAGAGU
UCCACUUGUUGACCGAGCCACAUGUCUUCGAUCUACAAAGUUCACCAUCUAUAACAACA

-continued

```
UGUUCUGUGCUGGCUUCCAUGAAGGAGGUAGAGAUUCAUGUCAAGGAGAUAGUGGGGA

CCCCAUGUUACUGAAGUGGAAGGGACCAGUUUCUUAACUGGAAUUAUUAGCUGGGGUGA

AGAGUGUGCAAUGAAAGGCAAAUAUGGAAUAUAUACCAAGGUAUCCCGGUAUGUCAACU

GGAUUAAGGAAAAAACAAAGCUCACUUAA
```

(SEQ ID NO: 17)

```
AUGCAGCGCUGAACAUGAUCAUGGCAGAAUCACCAGGCCUCAUCACCAUCUGCCUG

AGGAUAUCUACUCAGUGCUGAAUGUACAGUUUUCUUGAUCAUGAAAACGCCAACAAAA

UUCUGAAUCGGCCAAAGAGGUAUAAUUCAGGUAAAUUGGAAGAGUUUGUUCAAGGGAAC

CUUGAGAGAAUGUAUGGAAGAAAAGUGUAGUUUGAAGAAGCACGAGAAGUUUUGA

AAACAUGAAAGAACAACUGAAUUUUGGAAGCAGUAUGUUGAUGGAGAUCAGUGUGACU

CCAAUCCAUGUUUAAAUGGCGGCAGUUGCAAGGAUGACAUUAAUUCCUAUGAAUGUUGG

UGUCCCUUUGGAUUUGAAGGAAAGAACUGUGAAUUAGAUGUAACAUGUAACAUUAAGAA

UGGCAGAUGCGAGCAGUUUUGUAAAAAUAGUGCUGAUAACAAGGUGGUUGCUCCUGUA

CUGAGGGAUAUCGACUUGCAGAAAACCAGAAGUCCUGUGAACCAGCAGUGCCAUUCCA

UGUGGAAGAGUUUCUGUUCACAAACUUCUAAGCUCACCCUGCUGAGACUGUUUUCC

UGAUGUGGACUAUGUAAAUUCUACUGAAGCUGAAACCAUUUGGAUAACAUCACUCAAA

GCACCCAAUCAUUUAAUGACUUCACUCGGGUUGUGGUGGAGAAGAUGCCAAACCAGGU

CAAUUCCCUUGGCAGGUUGUUUGAAUGGUAAAGUUGAUGCAUUCUGUGGAGGCUCUAU

CGUUAAUGAAAAAUGGAUUGUAACUGCUGCCCACUGUGUUGAAACUGGUGUAAAAUUA

CAGUUGUCGCAGGUGAACAUAAUAUUGAGGAGGACAGAACAUACAGAGCAAAAGCGAAAU

GUGAUUCGAAUUAUUCCUCACCACAACUACAAUGCAGCUAUUAAUAAGUACAACCAUGA

CAUUGCCCUUCUGGAACUGGACGAACCCUUAGUGCUAAACAGCUACGUUACACCUAUG

GCAUUGCUGACAAGGAAUACACGAACAUCUUCCUCAAAUUUGGAUCUGGCUAUGUAAGU

GGCUGGGGAAGAGUCUUCCACAAAGGGAGAUCAGUUUAGUUCUUCAGUACCUUAGAGU

UCCACUUGUGACCGAGCCACAUGUCUUCGAUCUACAAAGUUCACCAUCUAUAACAACA

UGUUCUGUGCUGGCUUCCAUGAAGGAGGUAGAGAUUCAUGUCAAGGAGAUAGUGGGGA

CCCCAUGUUACUGAAGUGGAAGGGACCAGUUUCUUAACUGGAAUUAUUAGCUGGGGUGA

AGAGUGUGCAAUGAAAGGCAAAUAUGGAAUAUAUACCAAGGUAUCCCGGUAUGUCAACU

GGAUUAAGGAAAAAACAAAGCUCACUUAA
```

Example 14: mUNA Oligomer Expressing Alpha-1-Antitrypsin

In this example, the structures of mUNA molecules for use in expressing alpha-1-Antitrypsin are shown.

Alpha-1-Antitrypsin is associated with alpha-1-Antitrypsin deficiency disease, cystic fibrosis, interstitial lung disease, and pulmonary arterial hypertension.

The base sequences shown below are the portion of the mUNA molecule that may correspond in functionality to the open reading frame of the native mRNA of alpha-1-Antitrypsin. The complete mUNA molecule comprises a 5' cap (m7GpppGm), and a 5'-UTR upstream of the sequence below, and a 3' UTR and polyA tail (SEQ ID Nos:4 to 12) downstream of the sequence below, each of which corresponds to the structure of the native mRNA of alpha-1-Antitrypsin.

Human alpha-1-antitrypsin mRNA is accession NM_000295.4.

(SEQ ID NO: 18)

```
AUGCCGUCUUCUGUCUCGUGGGCAUCCUCCUGCUGGCAGGCCUGUGCUGCCUGGUCCC

UGUCUCCCUGGCUGAGGAUCCCCAGGGAGAUGCUGCCCAGAAGACAGAUACAUCCCACC
```

```
AUGAŨCAGGAUCACCCAACCUUCAACAAGAUCACĊCCCAACCUGGCUGAGUUCGCCUUC

AGCCUÃUACCGCCAGCUGGCACACCAGUCCAACAĠCACCAAUAUCUUCUUCUCCCCAGU

GAGCAUĊGCUACAGCCUUUGCAAUGCUCUCCCUGGGĠACCAAGGCUGACACUCACGAUG

AAAUCCUĠGAGGGCCUGAAUUUCAACCUCACGGAGAUŨCCGGAGGCUCAGAUCCAUGAA

GGCUUCCAĠGAACUCCUCCGUACCCUCAACCAGCCAGAĊAGCCAGCUCCAGCUGACCAC

CGGCAAUGĊCUGUUCCUCAGCGAGGGCCUGAAGCUAGUĠGAUAAGUUUUUGGAGGAUG

UUAAAAAGUUĠUACCACUCAGAAGCCUUCACUGUCAACUUĊGGGGACACCGAAGAGGCC

AAGAAACAGAUĊAACGAUUACGUGGAGAAGGGUACUCAAGGĠAAAAUUGUGGAUUUGGU

CAAGGAGCUUGAĊAGAGACACAGUUUUUGCUCUGGUGAAUUAĊAUCUUCUUUAAAGGCA

AAUGGGAGAGACĊCUUUGAAGUCAAGGACACCGAGGAAGAGGAĊUUCCACGUGGACCAG

GUGACCACCGUGAAĠGUGCCUAUGAUGAAGCGUUUAGGCAUGUUŨAACAUCCAGCACUG

UAAGAAGCUGUCCAĊCUGGGUGCUGCUGAUGAAAUACCUGGGCAAŨGCCACCGCCAUCU

UCUUCCUGCCUGAUGAĠGGGAAACUACAGCACCUGGAAAAUGAACUĊACCCACGAUAUC

AUCACCAAGUUCCUGGAÃAAUGAAGACAGAAGGUCUGCCAGCUUACAŨUUACCCAAACU

GUCCAUUACUGGAACCUAŨGAUCUGAAGAGCGUCCUGGGUCAACUGGĊAUCACUAAGG

UCUUCAGCAAUGGGGCUGAĊCUCUCCGGGGUCACAGAGGAGGCACCCCUĠAAGCUCUCC

AAGGCCGUGCAUAAGGCUGUĠCUGACCAUCGACGAGAAAGGGACUGAAGĊUGCUGGGGC

CAUGUUUUUAGAGGCCAUACCĊAUGUCUAUCCCCCCCGAGGUCAAGUUCAAĊAAACCCU

UUGUCUUCUUAAUGAUUGAACAÃAAUACCAAGUCUCCCCUCUUCAUGGGAAAÃGUGGUG

AAUCCCACCCAAAAAUŨA
                                              (SEQ ID NO: 19)

AŨĊCGUCUUCUGUCUCGUGGGGCAUCCUCCUGCUGGCAGGCCUGUGCUGCCUGGUCCC

UGUCUCCCUGGCUGAGGAUCCCCAGGGAGAUGCUGCCCAGAAGACAGAUACAUCCCACC

AUGAUCAGGAUCACCCAACCUUCAACAAGAUCACCCCCAACCUGGCUGAGUUCGCCUUC

AGCCUAUACCGCCAGCUGGCACACCAGUCCAACAGCACCAAUAUCUUCUUCUCCCCAGU

GAGCAUCGCUACAGCCUUUGCAAUGCUCUCCCUGGGGACCAAGGCUGACACUCACGAUG

AAAUCCUGGAGGGCCUGAAUUUCAACCUCACGGAGAUUCCGGAGGCUCAGAUCCAUGAA

GGCUUCCAGGAACUCCUCCGUACCCUCAACCAGCCAGACAGCCAGCUCCAGCUGACCAC

CGGCAAUGGCCUGUUCCUCAGCGAGGGCCUGAAGCUAGUGGAUAAGUUUUUGGAGGAUG

UUAAAAAGUUGUACCACUCAGAAGCCUUCACUGUCAACUUCGGGGACACCGAAGAGGCC

AAGAAACAGAUCAACGAUUACGUGGAGAAGGGUACUCAAGGGAAAAUUGUGGAUUUGGU

CAAGGAGCUUGACAGAGACACAGUUUUUGCUCUGGUGAAUUACAUCUUCUUUAAAGGCA

AAUGGGAGAGACCCUUUGAAGUCAAGGACACCGAGGAAGAGGACUUCCACGUGGACCAG

GUGACCACCGUGAAGGUGCCUAUGAUGAAGCGUUUAGGCAUGUUUAACAUCCAGCACUG

UAAGAAGCUGUCCAGCUGGGUGCUGCUGAUGAAAUACCUGGGCAAUGCCACCGCCAUCU

UCUUCCUGCCUGAUGAGGGGAAACUACAGCACCUGGAAAAUGAACUCACCCACGAUAUC

AUCACCAAGUUCCUGGAAAAUGAAGACAGAAGGUCUGCCAGCUUACAUUUACCCAAACU

GUCCAUUACUGGAACCUAUGAUCUGAAGAGCGUCCUGGGUCAACUGGGCAUCACUAAGG

UCUUCAGCAAUGGGGCUGACCUCUCCGGGGUCACAGAGGAGGCACCCCUGAAGCUCUCC
```

```
AAGGCCGUGCAUAAGGCUGUGCUGACCAUCGACGAGAAAGGGACUGAAGCUGCUGGGGC

CAUGUUUUUAGAGGCCAUACCCAUGUCUAUCCCCCCCGAGGUCAAGUUCAACAAACCCU

UUGUCUUCUUAAUGAUUGAACAAAAUACCAAGUCUCCCCUCUUCAUGGGAAAAGUGGUG

AAUCCCACCCAAAAAUAA
```

(SEQ ID NO: 20)

```
AUGCCGUCUCUGUCUCGUGGGGCAUCCUCCUGCUGGCAGGCCUGUGCUGCCUGGCUCCC

UGUCUCCCUGGCUGAGGAUCCCCAGGGAGAUGCUGCCCAGAAGACAGAUACAUCCCACC

AUGAUCAGGAUCACCCAACCUUCAACAAGAUCACCCCCAACCUGGCUGAGUUCGCCUUC

AGCCUAUACCGCCAGCUGGCACACCAGUCCAACAGCACCAAUAUCUUCUUCUCCCCAGU

GAGCAUCGCUACAGCCUUUGCAAUGUCUCCCUGGGGACCAAGGCUGACACUCACGAUG

AAAUCCUGGAGGGCCUGAAUUUCAACCUCACGGAGAUCCGGAGGCUCAGAUCCAUGAA

GGCUUCCAGGAACUCCUCCGUACCCUCAACCAGCCAGACAGCCAGCUCCAGCUGACCAC

CGGCAAUGGCCUGUUCCUCAGCGAGGGCCUGAAGCUAGUGGAUAAGUUUUGGAGGAUG

UUAAAAAGUUGUACCACUCAGAAGCCUUCACUGUCAACUUCGGGGACACCGAAGAGGCC

AAGAAACAGAUCAACGAUUACGUGGAGAAGGGUACUCAAGGGAAAAUUGUGGAUUGGU

CAAGGAGCUUGACAGAGACACAGUUUUGCUCUGGUGAAUUACAUCUUCUUUAAAGGCA

AAUGGGAGAGACCCUUUGAAGUCAAGGACACCGAGGAAGAGGACUUCCACGUGGACCAG

GUGACCACCGUGAAGGUGCCUAUGAUGAAGCGUUUAGGCAUGUUUAACAUCCAGCACUG

UAAGAAGCUGUCCAGCUGGGUGCUGCUGAUGAAAUACCUGGGCAAUGCCACCGCCAUCU

UCUUCCUGCCUGAUGAGGGGAAACUACAGCACCUGGAAAAUGAACUCACCCACGAUAUC

AUCACCAAGUUCCUGGAAAAUGAAGACAGAAGGUCUGCCAGCUUACAUUACCCAAACU

GUCCAUUACUGGAACCUAUGAUCUGAAGAGCGUCCUGGGUCAACUGGGCAUCACUAAGG

UCUUCAGCAAUGGGGCUGACCUCUCCGGGGUCACAGAGGAGGCACCCCUGAAGCUCUCC

AAGGCCGUGCAUAAGGCUGUGCUGACCAUCGACGAGAAAGGGACUGAAGCUGCUGGGGC

CAUGUUUUUAGAGGCCAUACCCAUGUCUAUCCCCCCCGAGGUCAAGUUCAACAAACCCU

UUGUCUUCUUAAUGAUUGAACAAAAUACCAAGUCUCCCCUCUUCAUGGGAAAAGUGGUG

AAUCCCACCCAAAAAUAA
```

Example 15: mUNA Oligomer Expressing Alpha-1-Antitrypsin

In this example, the structures of mUNA molecules for use in expressing alpha-1-Antitrypsin are shown.

Alpha-1-Antitrypsin is associated with alpha-1-Antitrypsin deficiency disease, cystic fibrosis, interstitial lung disease, and pulmonary arterial hypertension.

The base sequences shown below are the portion of the mUNA molecule that may correspond in functionality to the 5'-UTR of the native mRNA of alpha-1-Antitrypsin. The complete mUNA molecule comprises a 5' cap (m7GpppGm) upstream of the sequence below, and coding region (CDS) for human alpha-1-Antitrypsin, a 3' UTR and polyA tail (SEQ ID Nos:4 to 12) downstream of the sequence below, each of which corresponds to the structure of the native mRNA of alpha-1-Antitrypsin.

Human alpha-1-antitrypsin mRNA is accession NM_000295.4.

```
                                                    (SEQ ID NO: 21)
GGCACCACCACUGACCUGGGACAGUGAAUCGACAGCCGACC (SEQ ID NO: 22)
GGCACCACCACUGACCUGGGACAGUGAAUCGACAGCCGACC (SEQ ID NO: 23)
GGCACCACCACUGACCUGGGACAGUGAAUCGACAGCCGACC (SEQ ID NO: 24)
GGCACCACCACUGACCUGGGACAGUGAAUCGACAGCCGACC (SEQ ID NO: 25)
GGCACCACCACUGACCUGGGACAGUGAAUCGAAGCCGACC (SEQ ID NO: 26)
GGCACCACCACUGACCUGGGACAGUGAAUCACAGCCGACC (SEQ ID NO: 27)
GGCACCACCACUGACCUGGGACAGUGAAUGACAGCCGACC
```

(SEQ ID NO: 28)
GGCACCACCACUGACCUGGGACAGUGAÄÜCGACAGCCGACC (SEQ ID NO: 29)
GGCACCACCACUGACCUGGGACAGUĊÄAUCGACAGCCGACC (SEQ ID NO: 30)
GGCACCACCACUGACCUGGGACAĊÜGAAUCGACAGCCGACC (SEQ ID NO: 31)
GGCACCACCACUGACCUGGGAĊÄGUGAAUCGACAGCCGACC (SEQ ID NO: 32)
GGCACCACCACUGACCUGĊÄCAGUGAAUCGACAGCCGACC (SEQ ID NO: 33)
GGCACCACCACUGACCUĜĠACAGUGAAUCGACAGCCGACC (SEQ ID NO: 34)
GGCACCACCACUGACÜGGGACAGUGAAUCGACAGCCGACC (SEQ ID NO: 35)
GGCACCACCACUGÄĊUGGGACAGUGAAUCGACAGCCGACC (SEQ ID NO: 36)
GGCACCACCACÜGACCUGGGACAGUGAAUCGACAGCCGACC (SEQ ID NO: 37)
GGCACCACCÄĊUGACCUGGGACAGUGAAUCGACAGCCGACC (SEQ ID NO: 38)
GGCACCAĊĊACUGACCUGGGACAGUGAAUCGACAGCCGACC (SEQ ID NO: 39)
GGCACĊÄCCACUGACCUGGGACAGUGAAUCGACAGCCGACC (SEQ ID NO: 40)
GGCÄĊCACCACUGACCUGGGACAGUGAAUCGACAGCCGACC (SEQ ID NO: 41)
GĠĊACCACCACUGACCUGGGACAGUGAAUCGACAGCCGACC (SEQ ID NO: 42)
GGCACCACCACUGACCUGGGACAGUGAAUCGACAGCCÄĊĊ

(SEQ ID NO: 43)
GGCACCACCACUGACCUGGGACAGUGAAUCGACAGCCĠACĊ

(SEQ ID NO: 44)
GGCACCACCACUGACCUGGGACAGUGAAUCGACAGĊGACĊ

(SEQ ID NO: 45)
GGCACCACCACUGACCUGGGACAGUGAAUCGACAĠĊGACĊ

(SEQ ID NO: 46)
GGCACCACCACUGACCUGGGACAGUGAAUCGACAĠCCGACĊ

(SEQ ID NO: 47)
GGCACCACCACUGACCUGGGACAGUGAAUCGAĊÄGCCGACĊ

(SEQ ID NO: 48)
GGCACCACCACUGACCUGGGACAGUGAAUCGAĊAGCCGACĊ

(SEQ ID NO: 49)
GGCACCACCACUGACCUGGGACAGUGAAUCĠÄCAGCCGACĊ

(SEQ ID NO: 50)
GGCACCACCACUGACCUGGGACAGUGAAUĊGACAGCCGACĊ

(SEQ ID NO: 51)
GGCACCACCACUGACCUGGGACAGUGAAUĊGACAGCCGACĊ

(SEQ ID NO: 52)
GGCACCACCACUGACCUGGGACAGUGAAÜCGACAGCCGACĊ

(SEQ ID NO: 53)
GGCACCACCACUGACCUGGGACAGUGAÄUCGACAGCCGACĊ

(SEQ ID NO: 54)
GGCACCACCACUGACCUGGGACAGUGÄAUCGACAGCCGACĊ

(SEQ ID NO: 55)
GGCACCACCACUGACCUGGGACAGUĠAAUCGACAGCCGACĊ

(SEQ ID NO: 56)
GGCACCACCACUGACCUGGGACAĊÜGAAUCGACAGCCGACĊ

(SEQ ID NO: 57)
GGCACCACCACUGACCUGGGACAĠUGAAUCGACAGCCGACĊ

(SEQ ID NO: 58)
GGCACCACCACUGACCUGGGACÄGUGAAUCGACAGCCGACĊ

(SEQ ID NO: 59)
GGCACCACCACUGACCUGGGAĊAGUGAAUCGACAGCCGACĊ

(SEQ ID NO: 60)
GGCACCACCACUGACCUGGÄCAGUGAAUCGACAGCCGACĊ

(SEQ ID NO: 61)
GGCACCACCACUGACCUGĠACAGUGAAUCGACAGCCGACĊ

(SEQ ID NO: 62)
GGCACCACCACUGACCUĠGACAGUGAAUCGACAGCCGACĊ

(SEQ ID NO: 63)
GGCACCACCACUGACCÜGGACAGUGAAUCGACAGCCGACĊ

(SEQ ID NO: 64)
GGCACCACCACUGACCÜGGACAGUGAAUCGACAGCCGACĊ

(SEQ ID NO: 65)
GGCACCACCACUGAĊUGGACAGUGAAUCGACAGCCGACĊ

(SEQ ID NO: 66)
GGCACCACCACUGAĊCUGGGACAGUGAAUCGACAGCCGACĊ

(SEQ ID NO: 67)
GGCACCACCACUGÄCCUGGGACAGUGAAUCGACAGCCGACĊ

(SEQ ID NO: 68)
GGCACCACCACUĠACCUGGGACAGUGAAUCGACAGCCGACĊ

(SEQ ID NO: 69)
GGCACCACCACÜGACCUGGGACAGUGAAUCGACAGCCGACĊ

(SEQ ID NO: 70)
GGCACCACCAĊUGACCUGGGACAGUGAAUCGACAGCCGACĊ

(SEQ ID NO: 71)
GGCACCACĊÄCUGACCUGGGACAGUGAAUCGACAGCCGACĊ

(SEQ ID NO: 72)
GGCACCAĊCACUGACCUGGGACAGUGAAUCGACAGCCGACĊ

(SEQ ID NO: 73)
GGCACCAĊCACUGACCUGGGACAGUGAAUCGACAGCCGACĊ

(SEQ ID NO: 74)
GGCACĊÄCCACUGACCUGGGACAGUGAAUCGACAGCCGACĊ

(SEQ ID NO: 75)
GGCACĊACCACUGACCUGGGACAGUGAAUCGACAGCCGACĊ

(SEQ ID NO: 76)
GGCAĊCACCACUGACCUGGGACAGUGAAUCGACAGCCGACĊ

(SEQ ID NO: 77)
GGĊÄCCACCACUGACCUGGGACAGUGAAUCGACAGCCGACĊ

(SEQ ID NO: 78)
GGĊACCACCACUGACCUGGGACAGUGAAUCGACAGCCGACĊ

-continued (SEQ ID NO: 79)
GĜCACCACCACUGACCUGGGACAGUGAAUCGACAGCCGACĈ

(SEQ ID NO: 80)
GGCACCACCACUGACCUGGGACAGUGAAUCGACAGCCGÃĈĈ

(SEQ ID NO: 81)
GGCACCACCACUGACCUGGGACAGUGAAUCGACAGĈĈĜACC (SEQ ID NO: 82)
GGCACCACCACUGACCUGGGACAGUGAAUCGĈÃĜCCGACC (SEQ ID NO: 83)
GGCACCACCACUGACCUGGGACAGUGAAUĈĜÃCAGCCGACC (SEQ ID NO: 84)
GGCACCACCACUGACCUGGGACAGUGÃÃŨCGACAGCCGACC (SEQ ID NO: 85)
GGCACCACCACUGACCUGGGACAĜŨĜAAUCGACAGCCGACC (SEQ ID NO: 86)
GGCACCACCACUGACCUGGGÃĈÃGUGAAUCGACAGCCGACC (SEQ ID NO: 87)
GGCACCACCACUGACCUĜĜĜACAGUGAAUCGACAGCCGACC (SEQ ID NO: 88)
GGCACCACCACUGAĈĈŨGGGACAGUGAAUCGACAGCCGACC (SEQ ID NO: 89)
GGCACCACCACŨĜÃCCUGGGACAGUGAAUCGACAGCCGACC (SEQ ID NO: 90)
GGCACCACĈÃĈUGACCUGGGACAGUGAAUCGACAGCCGACC (SEQ ID NO: 91)
GGCACĈÃĈCACUGACCUGGGACAGUGAAUCGACAGCCGACC (SEQ ID NO: 92)
GGĈÃĈCACCACUGACCUGGGACAGUGAAUCGACAGCCGACC (SEQ ID NO: 93)
GĜCACCACCACUGACCUGGGACAGUGAAUCGACAGCCGÃCĈ

(SEQ ID NO: 94)
GĜCACCACCACUGACCUGGGACAGUGAAUCGACAGCCĜACĈ

(SEQ ID NO: 95)
GĜCACCACCACUGACCUGGGACAGUGAAUCGACAGCĈGACĈ

(SEQ ID NO: 96)
GĜCACCACCACUGACCUGGGACAGUGAAUCGACAGĈCGACĈ

(SEQ ID NO: 97)
GĜCACCACCACUGACCUGGGACAGUGAAUCGACAĜCCGACĈ

(SEQ ID NO: 98)
GĜCACCACCACUGACCUGGGACAGUGAAUCGACÃGCCGACĈ

(SEQ ID NO: 99)
GĜCACCACCACUGACCUGGGACAGUGAAUCGĈAGCCGACĈ

(SEQ ID NO: 100)
GĜCACCACCACUGACCUGGGACAGUGAAUCGÃCAGCCGACĈ

(SEQ ID NO: 101)
GĜCACCACCACUGACCUGGGACAGUGAAUCĜACAGCCGACĈ

(SEQ ID NO: 102)
GĜCACCACCACUGACCUGGGACAGUGAAUĈGACAGCCGACĈ

(SEQ ID NO: 103)
GĜCACCACCACUGACCUGGGACAGUGAAŨCGACAGCCGACĈ

(SEQ ID NO: 104)
GĜCACCACCACUGACCUGGGACAGUGAÃUCGACAGCCGACĈ

(SEQ ID NO: 105)
GĜCACCACCACUGACCUGGGACAGUGÃAUCGACAGCCGACĈ

(SEQ ID NO: 106)
GĜCACCACCACUGACCUGGGACAGUĜAAUCGACAGCCGACĈ

(SEQ ID NO: 107)
GĜCACCACCACUGACCUGGGACAGŨGAAUCGACAGCCGACĈ

(SEQ ID NO: 108)
GĜCACCACCACUGACCUGGGACAĜUGAAUCGACAGCCGACĈ

(SEQ ID NO: 109)
GĜCACCACCACUGACCUGGGACÃGUGAAUCGACAGCCGACĈ

(SEQ ID NO: 110)
GĜCACCACCACUGACCUGGGAĈAGUGAAUCGACAGCCGACĈ

(SEQ ID NO: 111)
GĜCACCACCACUGACCUGGGÃCAGUGAAUCGACAGCCGACĈ

(SEQ ID NO: 112)
GĜCACCACCACUGACCUGGĜACAGUGAAUCGACAGCCGACĈ

(SEQ ID NO: 113)
GĜCACCACCACUGACCUGĜGACAGUGAAUCGACAGCCGACĈ

(SEQ ID NO: 114)
GĜCACCACCACUGACCUĜGGACAGUGAAUCGACAGCCGACĈ

(SEQ ID NO: 115)
GĜCACCACCACUGACCŨGGGACAGUGAAUCGACAGCCGACĈ

(SEQ ID NO: 116)
GĜCACCACCACUGACĈUGGGACAGUGAAUCGACAGCCGACĈ

(SEQ ID NO: 117)
GĜCACCACCACUGAĈCUGGGACAGUGAAUCGACAGCCGACĈ

(SEQ ID NO: 118)
GĜCACCACCACUGÃCCUGGGACAGUGAAUCGACAGCCGACĈ

(SEQ ID NO: 119)
GĜCACCACCACUĜACCUGGGACAGUGAAUCGACAGCCGACĈ

(SEQ ID NO: 120)
GĜCACCACCACŨGACCUGGGACAGUGAAUCGACAGCCGACĈ

(SEQ ID NO: 121)
GĜCACCACCAĈUGACCUGGGACAGUGAAUCGACAGCCGACĈ

(SEQ ID NO: 122)
GĜCACCACCÃCUGACCUGGGACAGUGAAUCGACAGCCGACĈ

(SEQ ID NO: 123)
GĜCACCACĈACUGACCUGGGACAGUGAAUCGACAGCCGACĈ

(SEQ ID NO: 124)
GĜCACCAĈCACUGACCUGGGACAGUGAAUCGACAGCCGACĈ

(SEQ ID NO: 125)
GĜCACCÃCCACUGACCUGGGACAGUGAAUCGACAGCCGACĈ

(SEQ ID NO: 126)
GĜCACĈACCACUGACCUGGGACAGUGAAUCGACAGCCGACĈ

(SEQ ID NO: 127)
GĜCAĈCACCACUGACCUGGGACAGUGAAUCGACAGCCGACĈ

(SEQ ID NO: 128)
GĜCÃCCACCACUGACCUGGGACAGUGAAUCGACAGCCGACĈ

(SEQ ID NO: 129)
GĜĈACCACCACUGACCUGGGACAGUGAAUCGACAGCCGACĈ

-continued (SEQ ID NO: 130)
GCACCACCACUGACCUGGGACAGUGAAUCGACAGCCGACC

Example 16: mUNA Oligomer Expressing Erythropoietin (EPO)

In this example, the structures of mUNA molecules for use in expressing human Erythropoietin (EPO) are shown.

Erythropoietin is available as a commercial drug and is indicated for anemia resulting from chronic kidney disease, inflammatory bowel disease including Crohn's disease and ulcer colitis, and myelodysplasia from the treatment of cancer with chemotherapy or radiation.

The base sequences shown below are the portion of the mUNA molecule that may correspond in functionality to the open reading frame of the native mRNA of human Erythropoietin. The complete mUNA molecule comprises a 5' cap (m7GpppGm), and a 5'-UTR upstream of the sequence below, and a 3' UTR and polyA tail (SEQ ID Nos:4 to 12) downstream of the sequence below, each of which corresponds to the structure of the native mRNA of human Erythropoietin.

Human Erythropoietin is accession NM_000799.2.

(SEQ ID NO: 131)
AUGGGGUGCACGAAUGUCCUGCCUGGCUGUGGCUUCUCCUGUCCCUGCUGUCGCUCCC
UCUGGGCCUCCCAGUCCUGGGCGCCCCACCACGCCUCAUCUGUGACAGCCGAGUCCUGG
AGAGGUACCUCUUGGAGGCCAAGGAGGCCGAGAAUAUCACGACGGGCUGUGCUGAACAC
UGCAGCUUGAAUGAGAAUAUCACUGUCCCAGACACCAAAGUUAAUUUCUAUGCCUGGAA
GAGGAUGGAGGUCGGGCAGCAGGCCGUAGAAGUCUGGCAGGGCCUGGCCCUGCUGUCGG
AAGCUGUCCUGCGGGGCCAGGCCCUGUUGGUCAACUCUUCCCAGCCGUGGGAGCCCCUG
CAGCUGCAUGUGGAUAAAGCCGUCAGUGGCCUUCGCAGCCUCACCACUCUGCUUCGGGC
UCUGGGAGCCCAGAAGGAAGCCAUCUCCCCUCCAGAUGCGGCCUCAGCUGCUCCACUCC
GAACAAUCACUGCUGACACUUUCCGCAAACUCUUCCGAGUCUACUCCAAUUUCCUCCGG
GGAAAGCUGAAGCUGUACACAGGGGAGGCCUGCAGGACAGGGGACAGAUGA (SEQ ID NO: 132)
AUGGGGUGCACGAAUGUCCUGCCUGCUGUGGCUUCUCCUGUCCCUGCUGUCGCUCCC
UCUGGGCCUCCCAGUCCUGGGCGCCCCACCACGCCUCAUCUGUGACAGCCGAGUCCUGG
AGAGGUACCUCUUGGAGGCCAAGGAGGCCGAGAAUAUCACGACGGGCUGUGCUGAACAC
UGCAGCUUGAAUGAGAAUAUCACUGUCCCAGACACCAAAGUUAAUUUCUAUGCCUGGAA
GAGGAUGGAGGUCGGGCAGCAGGCCGUAGAAGUCUGGCAGGGCCUGGCCCUGCUGUCGG
AAGCUGUCCUGCGGGGCCAGGCCCUGUUGGUCAACUCUUCCCAGCCGUGGGAGCCCCUG
CAGCUGCAUGUGGAUAAAGCCGUCAGUGGCCUUCGCAGCCUCACCACUCUGCUUCGGGC
UCUGGGAGCCCAGAAGGAAGCCAUCUCCCCUCCAGAUGCGGCCUCAGCUGCUCCACUCC
GAACAAUCACUGCUGACACUUUCCGCAAACUCUUCCGAGUCUACUCCAAUUUCCUCCGG
GGAAAGCUGAAGCUGUACACAGGGGAGGCCUGCAGGACAGGGGACAGAUGA (SEQ ID NO: 133)
AUGGGGUGCACGAAUGUCCUGCCUGGCUGUGGCUUCUCCUGUCCCUGCUGUCGCUCCC
UCUGGGCCUCCCAGUCCUGGGCGCCCCACCACGCCUCAUCUGUGACAGCCGAGUCCUGG
AGAGGUACCUCUUGGAGGCCAAGGAGGCCGAGAAUAUCACGACGGGCUGUGCUGAACAC
UGCAGCUUGAAUGAGAAUAUCACUGUCCCAGACACCAAAGUUAAUUUCUAUGCCUGGAA
GAGGAUGGAGGUCGGGCAGCAGGCCGUAGAAGUCUGGCAGGGCCUGGCCCUGCUGUCGG
AAGCUGUCCUGCGGGGCCAGGCCCUGUUGGUCAACUCUUCCCAGCCGUGGGAGCCCCUG
CAGCUGCAUGUGGAUAAAGCCGUCAGUGGCCUUCGCAGCCUCACCACUCUGCUUCGGGC
UCUGGGAGCCCAGAAGGAAGCCAUCUCCCCUCCAGAUGCGGCCUCAGCUGCUCCACUCC
GAACAAUCACUGCUGACACUUUCCGCAAACUCUUCCGAGUCUACUCCAAUUUCCUCCGG
GGAAAGCUGAAGCUGUACACAGGGGAGGCCUGCAGGACAGGGGACAGAUGA

Example 17: mUNA Oligomer Expressing Ornithine Transcarbamylase

In this example, the structures of mUNA molecules for use in expressing human Ornithine transcarbamylase are shown.

Ornithine transcarbamylase is associated with Ornithine transcarbamylase deficiency.

The base sequences shown below are the portion of the mUNA molecule that may correspond in functionality to the open reading frame of the native mRNA of human Ornithine transcarbamylase. The complete mUNA molecule comprises a 5' cap (m7GpppGm), and a 5'-UTR upstream of the sequence below, and a 3' UTR and polyA tail (SEQ ID Nos:4 to 12) downstream of the sequence below, each of which corresponds to the structure of the native mRNA of human Ornithine transcarbamylase.

Human Ornithine transcarbamylase is accession NM_000531.5.

(SEQ ID NO: 134)

```
AUGCUGUUUAAUCUGAGGAUCCUGUUUAAACAAUGCAGCUUUUAGAAAUGGUCACAACU
UCAUGGUUCGAAAUUUUCGGUGUGGACAACCACUACAAAAUAAAGUGCAGCUGAAGGGC
CGUGACCUUCUCACUCUAAAAAACUUUACCGGAGAAGAAAUUAAAUAUAUGCUAUGGCU
AUCAGCAGAUCUGAAAUUUAGGAUAAAACAGAAAGGAGAGUAUUUGCCUUUAUUGCAAG
GGAAGUCCUUAGGCAUGAUUUUUGAGAAAAGAAGUACUCGAACAAGAUUGUCUACAGAA
ACAGGCUUUGCACUUCUGGGAGGACAUCCUUGUUUUCUUACCACACAAGAUAUUCAUUU
GGGUGUGAAUGAAAGUCUCACGGACACGGCCCGUGUAUUGUCUAGCAUGGCAGAUGCAG
UAUUGGCUCGAGUGUAUAAACAAUCAGAUUUGGACACCCUGGCUAAAGAAGCAUCCAUC
CCAAUUAUCAAUGGGCUGUCAGAUUUGUACCAUCCUAUCCAGAUCCUGGCUGAUUACCU
CACGCUCCAGGAACACUAUAGCUCUCUGAAAGGUCUUACCCUCAGCUGGAUCGGGGAUG
GGAACAAUAUCCUGCACUCCAUCAUGAUGAGCGCAGCGAAAUUCGGAAUGCACCUUCAG
GCAGCUACUCCAAAGGGUUAUGAGCCGGAUGCUAGUGUAACCAAGUUGGCAGAGCAGUA
UGCCAAAGAGAAUGGUACCAAGCUGUUGCUGACAAAUGAUCCAUUGGAAGCAGCGCAUG
GAGGCAAUGUAUUAAUUACAGACACUUGGAUAAGCAUGGACAAGAAGAGGAGAAGAAA
AAGCGGCUCCAGGCUUUCCAAGGUUACCAGGUUACAAUGAAGACUGCUAAACUUGCUGC
CUCUGACUGGACAUUUUUACACUGCUUGCCCAGAAAGCCAGAAGAAGUGGAUCAUGAAG
UCUUUUAUUCUCCUCGAUCACUAGUGUUCCCAGAGGCAGAAAACAGAAAGUGGACAAUC
AUGGCUGUCAUGGUGUCCCUGCUGACAGAUUACUCACCUCAGCUCCAGAAGCCUAAAUU
UUGA
```

(SEQ ID NO: 135)

```
AUGCUGUUUAAUCUGAGGAUCCUGUUAAACAAUGCAGCUUUUAGAAAUGGUCACAACUU
CAUGGUUCGAAAUUUUCGGUGUGGACAACCACUACAAAAUAAAGUGCAGCUGAAGGGCC
GUGACCUUCUCACUCUAAAAAACUUUACCGGAGAAGAAAUUAAAUAUAUGCUAUGGCUA
UCAGCAGAUCUGAAAUUUAGGAUAAAACAGAAAGGAGAGUAUUUGCCUUUAUUGCAAGG
GAAGUCCUUAGGCAUGAUUUUUGAGAAAAGAAGUACUCGAACAAGAUUGUCUACAGAAA
CAGGCUUUGCACUUCUGGGAGGACAUCCUUGUUUUCUUACCACACAAGAUAUUCAUUUG
GGUGUGAAUGAAAGUCUCACGGACACGGCCCGUGUAUUGUCUAGCAUGGCAGAUGCAGU
AUUGGCUCGAGUGUAUAAACAAUCAGAUUUGGACACCCUGGCUAAAGAAGCAUCCAUCC
CAAUUAUCAAUGGGCUGUCAGAUUUGUACCAUCCUAUCCAGAUCCUGGCUGAUUACCUC
ACGCUCCAGGAACACUAUAGCUCUCUGAAAGGUCUUACCCUCAGCUGGAUCGGGGAUGG
GAACAAUAUCCUGCACUCCAUCAUGAUGAGCGCAGCGAAAUUCGGAAUGCACCUUCAGG
CAGCUACUCCAAAGGGUUAUGAGCCGGAUGCUAGUGUAACCAAGUUGGCAGAGCAGUAU
GCCAAAGAGAAUGGUACCAAGCUGUUGCUGACAAAUGAUCCAUUGGAAGCAGCGCAUGG
```

-continued

AGGCAAUGUAUUAAUUACAGACACUUGGAUAAGCAUGGGACAAGAAGAGGAGAAGAAAA

AGCGGCUCCAGGCUUUCCAAGGUUACCAGGUUACAAUGAAGACUGCUAAAGUUGCUGCC

UCUGACUGGACAUUUUUACACUGCUUGCCCAGAAAGCCAGAAGAAGUGGAUGAUGAAGU

CUUUUAUUCUCCUCGAUCACUAGUGUUCCCAGAGGCAGAAAACAGAAAGUGGACAAUCA

UGGCUGUCAUGGUGUCCCUGCUGACAGAUUACUCACCUCAGCUCCAGAAGCCUAAAUŬŬ

ŬGA (SEQ ID NO: 136)

AŬGCUGŬŬŬAAŬCŬGAGGAŬCCŬGŬŬAAACAAŬGCAGCŬŬŬAGAAAŬGGŬCACAACŬŬ

CAŬGGŬŬCGAAAŬŬŬCGGŬGŬGGACAACCACŬACAAAAŬAAAŬGCAGCŬGAAGGGCC

GŬGACCŬŬCŬCACŬCŬAAAAAACŬŬŬACCGGAGAAGAAAŬŬAAAŬAŬAŬGCŬAŬGGCŬA

ŬCAGCAGAŬCŬGAAAŬŬŬAGGAŬAAAACAGAAAGGAGAGŬAŬŬŬGCCŬŬŬAŬŬGCAAGG

GAAGŬCCŬŬAGGCAŬGAŬŬŬŬŬGAGAAAAGAAGŬACŬCGAACAAGAŬŬGŬCŬACAGAAA

CAGGCŬŬŬGCACŬŬCŬGGGAGGACAŬCCŬŬGŬŬŬCŬŬACCACACAAGAŬAŬŬCAŬŬŬG

GGŬGŬGAAŬGAAAGŬCŬCACGGACACGGCCCGŬGŬAŬŬGŬCŬAGCAŬGGCAGAŬGCAGŬ

AŬŬGGCŬCGAGŬGŬAŬAAACAAŬCAGAŬŬŬGGACACCCŬGGCŬAAAGAAGCAŬCCAŬCC

CAAŬŬAŬCAAŬGGGCŬGŬCAGAŬŬŬGŬACCAŬCCŬAŬCCAGAŬCCŬGGCŬGAŬŬACCŬC

ACGCŬCCAGGAACAŬAŬAGCŬCŬCŬGAAAGGŬCŬŬACCCŬCAGCŬGGAŬCGGGGAŬGG

GAACAAŬAŬCCŬGCACŬCCAŬCAŬGAŬGAGCGCAGCGAAAŬŬCGGAAŬGCACCŬŬCAGG

CAGCŬACŬCCAAAGGGŬŬAŬGAGCCGGAŬGCŬAGŬGŬAACCAAGŬŬGGCAGAGCAGŬAŬ

GCCAAAGAGAAŬGGŬACCAAGCŬGŬŬGCŬGACAAAŬGAŬCCAŬŬGGAAGCAGCGCAŬGG

AGGCAAŬGŬAŬŬAAŬŬACAGACACŬŬGGAŬAAGCAŬGGGACAAGAAGAGGAGAAGAAAA

AGCGGCŬCCAGGCŬŬŬCCAAGGŬŬACCAGGŬŬACAAŬGAAGACŬGCŬAAAGŬŬGCŬGCC

ŬCŬGACŬGGACAŬŬŬŬŬACACŬGCŬŬGCCCAGAAAGCCAGAAGAAGŬGGAŬGAŬGAAGŬ

CŬŬŬŬAŬŬCŬCCŬCGAŬCACŬAGŬGŬŬCCCAGAGGCAGAAAACAGAAAGŬGGACAAŬCA

ŬGGCŬGŬCAŬGGŬGŬCCCŬGCŬGACAGAŬŬACŬCACCŬCAGCŬCCAGAAGCCŬAAAŬŬŬ

ŬGA

Example 18: mUNA Oligomer Expressing Beta-Globin

In this example, the structures of mUNA molecules for use in expressing human beta-globin are shown.

Beta-globin may be associated with sickle-cell disease, beta thalassemia, and genetic resistance to malaria.

The base sequences shown below are the portion of the mUNA molecule that may correspond in functionality to the 3'-UTR of the native mRNA of human beta-globin. The complete mUNA molecule comprises a 5' cap (m7GpppGm), 5'-UTR, and coding region (CDS) for human beta-globin upstream of the sequence below, and a polyA tail (SEQ ID Nos:4 to 12) downstream of the sequence below, each of which corresponds to the structure of the native mRNA of human beta-globin.

Human beta-globin is accession NM_000518.4.

(SEQ ID NO: 137)

GĈUCGCUUUCUUGCUGUCCAAUUUCUAUUAAAGGUUCCUUUGUUCCCUAAGUCCAACUA

CUAAACUGGGGGAUAUUAUGAAGGGCCUUGAGCAUCUGGAUUCUGCCUAAUAAAAAACA

UUUAUUUUCAUUGCÃA (SEQ ID NO: 138)

GĈĈCGCUUUCUUGCUGUCCAAUUUCUAUUAAAGGUUCCUUUGUUCCCUAAGUCCAACUA

CUAAACUGGGGGAUAUUAUGAAGGGCCUUGAGCAUCUGGAUUCUGCCUAAUAAAAAACA

UUUAUUUUCAUUĜĈAA (SEQ ID NO: 139)
GCUCGCUUCUUGCUGUCCAAUUUCUAUUAAAGGUUCCUUUGUUCCCUAAGUCCAACUA

CUAAACUGGGGAUAUUAUGAAGGGCCUUGAGCAUCUGGAUUCUGCCUAAUAAAAAACA

UUUAUUUUCAUUGCAA (SEQ ID NO: 140)
GCUCGCUUCUUGCUGUCCAAUUUCUAUUAAAGGUUCCUUUGUUCCCUAAGUCCAACUA

CUAAACUGGGGAUAUUAUGAAGGGCCUUGAGCAUCUGGAUUCUGCCUAAUAAAAAACA

UUUAUUUUCAUUGCAA (SEQ ID NO: 141)
GCUCGCUUUCUGCUGUCAAUUUCUAUUAAAGGUUCCUUUGUUCCCUAAGUCCAACUA

CUAAACUGGGGAUAUUAUGAAGGGCCUUGAGCAUCUGGAUUCUGCCUAAUAAAAAACA

UUUAUUUUCAUUGCAA

Example 19: mUNA Oligomer Translation Enhancer Based on Xenopus Beta-Globin 3'UTR In this example, the structures of mUNA molecules for use in enhancing translational efficiency are shown.

The base sequences shown below are the portion of the mUNA molecule that may correspond in functionality to the 3'-UTR of Xenopus beta-globin. The complete mUNA molecule comprises a 5' cap (m7GpppGm), 5'-UTR, and coding region (CDS) upstream of the sequence below, and a polyA tail (SEQ ID Nos:4 to 12) downstream of the sequence below, each of which corresponds to the structure of a native human mRNA. Thus, a UNA oligomer incorporating the oligomer fragment below can have enhanced translational efficiency.

Xenopus beta-globin is accession NM_001096347.1.

(SEQ ID NO: 142)
CUAGUGACUGACUAGGAUCUGGUUACCACUAAACCAGCCUCAAGAACACC

CGAAUGGAGUCUCUAAGCUACAUAAUACCAACUUACACUUACAAAAUGUU

GUCCCCAAAAUGUAGCCAUUCGUAUCUGCUCCUAAUAAAAAGAAAGUUU

CUUCACAU (SEQ ID NO: 143)
CUAGUGACUGACUAGGAUCUGGUUACCACUAAACCAGCCUCAAGAACACC

CGAAUGGAGUCUCUAAGCUACAUAAUACCAACUUACACUUACAAAAUGUU

GUCCCCAAAAUGUAGCCAUUCGUAUCUGCUCCUAAUAAAAAGAAAGUUU

CUUCACAU (SEQ ID NO: 144)
CUAGUGACUGACUAGGAUCUGGUUACCACUAAACCAGCCUCAAGAACACC

CGAAUGGAGUCUCUAAGCUACAUAAUACCAACUUACACUUACAAAAUGUU

GUCCCCAAAAUGUAGCCAUUCGUAUCUGCUCCUAAUAAAAAGAAAGUUU

CUUCACAU (SEQ ID NO: 145)
CUAGUGACUGACUAGGAUCUGGUUACCACUAAACCAGCCUCAAGAACACC

CGAAUGGAGUCUCUAAGCUACAUAAUACCAACUUACACUUACAAAAUGUU

GUCCCCAAAAUGUAGCCAUUCGUAUCUGCUCCUAAUAAAAAGAAAGUUU

CUUCACAU (SEQ ID NO: 146)
CUAGUGACUGACUAGGAUCUGGUUACCACUAAACCAGCUCAAGAACACCCGAAUGGAG

UCUCUAAGCUACAUAAUACCACUUACACUUACAAAAUGUUGUCCCCCAAAAUGUAGCC

AUUCGUAUCUGCUCCUAAUAAAAAGAAAGUUUCUUCACAU

Example 20: mUNA Oligomer Expressing Thrombopoietin

In this example, the structures of mUNA molecules for use in expressing human Thrombopoietin are shown.

Thrombopoietin is associated with liver and kidney disease.

The base sequences shown below are the portion of the mUNA molecule that may correspond in functionality to the open reading frame of the native mRNA of human Thrombopoietin. The complete mUNA molecule comprises a 5' cap (m7GpppGm), and a 5'-UTR upstream of the sequence below, and a 3' UTR and polyA tail (SEQ ID Nos:4 to 12) downstream of the sequence below, each of which corresponds to the structure of the native mRNA of human Thrombopoietin.

Human Thrombopoietin is accession NM_000460.3.

(SEQ ID NO: 147)
AUGGAGCUGACUGAAUUGCUCCUCGUGGUCAUGCUUCUCCUAACUGCAAG
GCUAACGCUGUCCAGCCCGGCUCCUCCUGCUUGUGACCUCCAGUCCUCA
GUAAACUGCUUCGUGACUCCCAUGUCCUUCACAGCAGACUGAGCCAGUGC
CCAGAGGUUCACCCUUUGCCUACACCUGUCCUGCUGCCUGCUGUGGACUU
UAGCUUGGGAGAAUGGAAAACCCAGAUGGAGGAGACCAAGGCACAGGACA
UUCUGGGAGCAGUGACCCUUCUGCUGGAGGGAGUGAUGGCAGCACGGGA
CAACUGGACCCACUUGCCUCUCAUCCUCCUGGGGCAGCUUUCUGGACA
GGUCCGUCUCCUCUUGGGGCCCUGCAGAGCCUCCUUGGAACCCAGCUUC
CUCCACAGGGCAGGACCACAGCUCACAAGGAUCCCAAUGCCAUCUUCCUG
AGCUUCCAACACCUGCUCCAGGAAAGGUGCGUUUCCUGAUGCUUGUAGG
AGGGUCCACCCUCUGCGUCAGGCGGGCCCCACCCACCACAGCUGUCCCCA
GCAGAACCUCUCUAGUCCUCACACUGAACGAGCUCCCAAACAGGACUUC
UGGAUUGUUGGAGACAAACUUCACUGCCUCAGCCAGAACUACUGGCUCUGG
GCUUCUGAAGUGGCAGCAGGGAUUCAGAGCCAAGAUUCCUGGUCUGCUGA
ACCAAACCUCCAGGUCCCUGGACCAAAUCCCCGGAUACCUGAACAGGAUA
CACGAACUCUUGAAUGGAACUCGUGGACUCUUUCCUGGACCCUCACGCAG
GACCCUAGGAGCCCCGGACAUUUCCUCAGGAACAUCAGACACAGGCUCCC
CUGCCACCCAACCUCCAGCCUGGAUAUUCUCCUUCCCCAACCCAUCCUCCU
ACUGGACAGUAUACGCUCUUCCCUCUUCCACCCACCUUGCCCACCCCUGU
GGUCCAGCUCCACCCCCUGCUUCCUGACCCUUCUGCUCCAACGCCCACCC
CUACCAGCCCUCUUCUAAACACAUCCUACACCCACUCCCAGAAUCUGUCU
UCAGGAAGGGUAA (SEQ ID NO: 148)
AUGGAGCUGACUGAAUUGCUCCUCGUGGUCAUGCUUCUCCUAACUGCAAG
GCUAACGCUGUCCAGCCCGGCUCCUCCUGCUUGUGACCUCCGAGUCCUCA
GUAAACUGCUUCGUGACUCCCAUGUCCUUCACAGCAGACUGAGCCAGUGC
CCAGAGGUUCACCCUUUGCCUACACCUGUCCUGCUGCCUGCUGUGGACUU
UAGCUUGGGAGAAUGGAAAACCCAGAUGGAGGAGACCAAGGCACAGGACA
UUCUGGGAGCAGUGACCCUUCUGCUGGAGGGAGUGAUGGCAGCACGGGA
CAACUGGGACCCACUUGCCUCUCAUCCCUCCUGGGGCAGCUUUCUGGACA
GGUCCGUCUCCUCCUUGGGGCCCUGCAGAGCCUCCUUGGAACCCAGCUUC
CUCCACAGGGCAGGACCACAGCUCACAAGGAUCCCAAUGCCAUCUUCCUG
AGCUUCCAACACCUGCUCCGAGGAAAGGUGCGUUUCCUGAUGCUUGUAGG
AGGGUCCACCCUCUGCGUCAGGCGGGCCCCACCCACCACAGCUGUCCCCA
GCAGAACCUCUCUAGUCCUCACACUGAACGAGCUCCCAAACAGGACUUCU
GGAUUGUUGGAGACAAACUUCACUGCCUCAGCCAGAACUACUGGCUCUGG
GCUUCUGAAGUGGCAGCAGGGAUUCAGAGCCAAGAUUCCUGGUCUGCUGA
ACCAAACCUCCAGGUCCCUGGACCAAAUCCCCGGAUACCUGAACAGGAUA
CACGAACUCUUGAAUGGAACUCGUGGACUCUUUCCUGGACCCUCACGCAG
GACCCUAGGAGCCCCGGACAUUUCCUCAGGAACAUCAGACACAGGCUCCC
UGCCACCCAACCUCCAGCCUGGAUAUUCUCCUUCCCCAACCCAUCCUCCU
ACUGGACAGUAUACGCUCUUCCCUCUUCCACCCACCUUGCCCACCCCUGU
GGUCCAGCUCCACCCCUGCUUCCUGACCCUUCUGCUCCAACGCCCACCC
CUACCAGCCCUCUUCUAAACACAUCCUACACCCACUCCCAGAAUCUGUCU
CAGGAAGGGUAA (SEQ ID NO: 149)
AUGGAGCUGACUGAAUUGCUCCUCGUGGUCAUGCUUCUCCUAACUGCAAG
GCUAACGCUGUCCAGCCCGGCUCCUCCUGCUUGUGACCUCCGAGUCCUCA
GUAAACUGCUUCGUGACUCCCAUGUCCUUCACAGCAGACUGAGCCAGUGC
CCAGAGGUUCACCCUUUGCCUACACCUGUCCUGCUGCCUGCUGUGGACUU
UAGCUUGGGAGAAUGGAAAACCCAGAUGGAGGAGACCAAGGCACAGGACA
UUCUGGGAGCAGUGACCCUUCUGCUGGAGGGAGUGAUGGCAGCACGGGA
CAACUGGGACCCACUUGCCUCUCAUCCCUCCUGGGGCAGCUUUCUGGACA
GGUCCGUCUCCUCCUUGGGGCCCUGCAGAGCCUCCUUGGAACCCAGCUUC
CUCCACAGGGCAGGACCACAGCUCACAAGGAUCCCAAUGCCAUCUUCCUG
AGCUUCCAACACCUGCUCCGAGGAAAGGUGCGUUUCCUGAUGCUUGUAGG
AGGGUCCACCCUCUGCGUCAGGCGGGCCCCACCCACCACAGCUGUCCCCA
GCAGAACCUCUCUAGUCCUCACACUGAACGAGCUCCCAAACAGGACUUCU
GGAUUGUUGGAGACAAACUUCACUGCCUCAGCCAGAACUACUGGCUCUGG
GCUUCUGAAGUGGCAGCAGGGAUUCAGAGCCAAGAUUCCUGGUCUGCUGA
ACCAAACCUCCAGGUCCCUGGACCAAAUCCCCGGAUACCUGAACAGGAUA
CACGAACUCUUGAAUGGAACUCGUGGACUCUUUCCUGGACCCUCACGCAG
GACCCUAGGAGCCCCGGACAUUUCCUCAGGAACAUCAGACACAGGCUCCC
UGCCACCCAACCUCCAGCCUGGAUAUUCUCCUUCCCCAACCCAUCCUCCU
ACUGGACAGUAUACGCUCUUCCCUCUUCCACCCACCUUGCCCACCCCUGU
GGUCCAGCUCCACCCCUGCUUCCUGACCCUUCUGCUCCAACGCCCACCC
CUACCAGCCCUCUUCUAAACACAUCCUACACCCACUCCCAGAAUCUGUCU
CAGGAAGGGUAA

Example 21: mUNA Oligomer Expressing Human Amylo-Alpha-1, 6-Glucosidase, 4-Alpha-Glucanotransferase (AGL)

In this example, the structures of mUNA molecules for use in expressing human amylo-alpha-1, 6-glucosidase, 4-alpha-glucanotransferase (AGL) are shown.

AGL is associated with glycogen storage disease.

The base sequences shown below are the portion of the mUNA molecule that may correspond in functionality to the open reading frame of the native mRNA of human AGL. The complete mUNA molecule comprises a 5' cap (m7GpppGm), and a 5'-UTR upstream of the sequence below, and a 3' UTR and polyA tail (SEQ ID Nos:4 to 12) downstream of the sequence below, each of which corresponds to the structure of the native mRNA of human AGL.

Human AGL is accession NM_000642.2.

(SEQ ID NO: 150)
AUGGACACAGUAAACAGAUUCGAAUUUUACUUCUGAACGAAAUGGAGAA
ACUGGAAAAGACCCUCUUCAGACUUGAACAAGGGUAUGAGCUACAGUUCC
GAUUAGGCCCAACUUUACAGGGAAAAGCAGUUACCGUGUAUACAAAUUAC
CCAUUUCCUGGAGAAACAUUUAAUAGAGAAAAAUUCCGUUCUCUGGAUUG
GGAAAAUCCAACAGAAAGAGAAGAUGAUUCUGAUAAAUACUGUAAACUUA
AUCUGCAACAAUCUGGUUCAUUUCAGUAUUAUUUCCUUCAAGGAAAUGAG
AAAAGUGGUGGAGGUUACAUAGUUGUGGACCCCAUUUUACGUGUUGGUGC
UGAUAAUCAUGUGCUACCCUUGGACUGUGUUACUCUUCAGACAUUUUUAG
CUAAGUGUUUGGGACCUUUUGAUGAAUGGGAAAGCAGACUUAGGGUUGCA
AAAGAAUCAGGCUACAACAUGAUUCAUUUUACCCCAUUGCAGACUCUUGG
ACUAUCUAGGUCAUGCUACUCCCUUGCCAAUCAGUUAGAAUUAAAUCCUG
ACUUUUCAAGACCUAAUAGAAAGUAUACCUGGAAUGAUGUUGGACAGCUA
GUGGAAAAAUUAAAAAAGGAAUGGAAUGUUAUUUGUAUUACUGAUGUUGU
CUACAAUCAUACUGCUGCUAAUAGUAAAUGGAUCCAGGAACAUCCAGAAU
GUGCCUAUAAUCUUGUGAAUUCUCCACACUUAAAACCUGCCUGGGUCUUA
GACAGAGCACUUUGGCGUUUCUCCUGUGAUGUUGCAGAAGGGAAAUACAA
AGAAAAGGGAAUACCUGCUUUGAUUGAAAAUGAUCACCAUAUGAAUUCCA
UCCGAAAAAUAAUUUGGAGGAUAUUUUUCCAAAGCUUAAACUCUGGGAA
UUUUUCCAAGUAGAUGUCAACAAAGCGGUUGAGCAAUUUAGAAGACUUCU
UACACAAGAAAAUAGGCGAGUAACCAAGUCUGAUCCAAACCAACACCUUA
CGAUUAUUCAAGAUCCUGAAUACAGACGGUUUGGCUGUACUGUAGAUAUG
AACAUUGCACUAACGACUUUCAUACCACAUGACAAGGGGCCAGCAGCAAU
UGAAGAAUGCUGUAAUGGUUUCAUAAAGAAUGGAGGAAUUAAAUUCAG
AGAAGCAUCGACUCAUUAACUAUCAUCAGGAACAGGCAGUUAAUUGCCUU
UUGGGAAAUGUGUUUUAUGAACGACUGGCUGGCCAUGGUCCAAAACUAGG
ACCUGUCACUAGAAAGCAUCCUUUAGUUACCAGGUAUUUUACUUUCCCAU
UUGAAGAGAUAGACUUCUCCAUGGAAGAAUCUAUGAUUCAUCUGCCAAAU
AAAGCUUGUUUUCUGAUGGCACACAAUGGAUGGGUAAUGGGAGAUGAUCC
UCUUCGAAACUUUGCUGAACCGGGUUCAGAAGUUUACCUAAGGAGAGAAC
UUAUUUGCUGGGGAGACAGUGUUAAAUUACGCUAUGGGAAUAAACCAGAG
GACUGUCCUUAUCUCUGGGCACACAUGAAAAAAUACACUGAAAUAACUGC
AACUUAUUUCCAGGGAGUACGUCUUGAUAACUGCCACUCAACACCUCUUC
ACGUAGCUGAGUACAUGUUGGAUGCUGCUAGGAAUUUGCAACCCAAUUUA
UAUGUAGUAGCUGAACUGUUCACAGGAAGUGAAGAUCUGGACAAUGUCUU
UGUUACUAGACUGGGCAUUAGUUCCUUAAUAAGAGAGGCAAUGAGUGCAU
AUAAUAGUCAUGAAGAGGGCAGAUUAGUUUACCGAUAUGGAGGAGAACCU
GUUGGAUCCUUUGUUCAGCCCUGUUUGAGGCCUUUAAUGCCAGCUAUUGC
ACAUGCCCUGUUUAUGGAUAUUACGCAUGAUAAUGAGUGUCCUAUUGUGC
AUAGAUCAGCGUAUGAUGCUCUUCCAAGUACUACAAUUGUUUCUAUGGCA
UGUUGUGCUAGUGGAAGUACAAGAGGCUAUGAUGAAUUAGUGCCUCAUCA
GAUUUCAGUGGUUUCUGAAGAACGGUUUUACACUAAGUGGAAUCCUGAAG
CAUUGCCUUCAAACACAGGUGAAGUUAAUUUCCAAAGCGGCAUUAUUGCA
GCCAGGUGUGCUAUCAGUAAACUUCAUCAGGAGCUUGGAGCCAAGGGUUU
UAUUCAGGUGUAUGUGGAUCAAGUUGAUGAAGACAUAGUGGCAGUAACAA
GACACUCACCUAGCAUCCAUCAGUCUGUUGUGGCUGUAUCUAGAACUGCU
UUCAGGAAUCCCAAGACUUCAUUUUACAGCAAGGAAGUGCCUCAAAUGUG
CAUCCCUGGCAAAAUUGAAGAAGUAGUUCUUGAAGCUAGAACUAUUGAGA
GAAACACGAAACCUUAUAGGAAGGAUGAGAAUUCAAUCAAUGGAACACCA
GAUAUCACAGUAGAAAUUAGAGAACAUAUUCAGCUUAAUGAAAGUAAAAU
UGUUAAACAAGCUGGAGUUGCCACAAAAGGGCCCAAUGAAUAUAUUCAAG
AAAUAGAAUUUGAAAACUUGUCUCCAGGAAGUGUUAUUAUAUUCAGAGUU
AGUCUUGAUCCACAUGCACAAGUCGCUGUUGGAAUUCUUCGAAAUCAUCU
GACACAAUUCAGUCCUCACUUUAAAUCUGGCAGCCUAGCUGUUGACAAUG
CAGAUCCUAUAUUAAAAAUUCCUUUUGCUUCUCUUGCCUCCAGAUUAACU
UUGGCUGAGCUAAAUCAGAUCCUUUACCGAUGUGAAUCAGAAGAAAAGGA
AGAUGGUGGAGGGUGCUAUGACAUACCAAACUGGUCAGCCCUUAAAUAUG
CAGGUCUUCAAGGUUUAAUGUCUGUAUUGGCAGAAAUAAGACCAAAGAAU
GACUUGGGGCAUCCUUUUUGUAAUAAUUUGAGAUCUGGAGAUUGGAUGAU
UGACUAUGUCAGUAACCGGCUUAUUUCACGAUCAGGAACUAUUGCUGAAG
UUGGUAAAUGGUUGCAGGCUAUGUUCUUCUACCUGAAGCAGAUCCCACGU
UACCUUAUCCCAUGUUACUUUGAUGCUAUAUUAAUUGGUGCAUAUACCAC
UCUUCGGAUACAGCAUGGAAGCAGAUGUCAAGCUUUGUUCAGAAUGGUU
CAACCUUUGUGAAACACCUUUCAUUGGGUUCAGUUCAACUGUGUGGAGUA
GGAAAAUUCCCUUCCCUGCCAAUUCUUUCACCUGCCCUAAUGGAUGUACC
UUAUAGGUUAAAUGAGAUCACAAAAGAAAGGAGCAAUGUUGUGUUUCUC
UAGCUGCAGGCUUACCUCAUUUUUCUUCUGGUAUUUUCCGCUGCUGGGA
AGGGAUACUUUUAUUGCACUUAGAGGUAUACUGCUGAUUACUGGACGCUA
UGUAGAAGCCAGGAAUAUUAUUUAGCAUUUGCGGGUACCCUGAGGCAUG
GUCUCAUUCCUAAUCUACUGGGUGAAGGAAUUUAUGCCAGAUACAAUUGU

-continued

CGGGAUGCUGUGUGGUGGUGGCUGCAGUGUAUCCAGGAUUACUGUAAAAU
GGUUCCAAAUGGUCUAGACAUUCUCAAGUGCCCAGUUUCCAGAAUGUAUC
CUACAGAUGAUUCUGCUCCUUUGCCUGCUGGCACACUGGAUCAGCCAUUG
UUUGAAGUCAUACAGGAAGCAAUGCAAAAACACAUGCAGGGCAUACAGUU
CCGAGAAAGGAAUGCUGGUCCCCAGAUAGAUCGAAACAUGAAGGACGAAG
GUUUAAUAUAACUGCAGGAGUUGAUGAAGAAACAGGAUUUGUUUAUGGA
GGAAAUCGUUUCAAUUGUGGCACAUGGAUGGAUAAAAUGGGAGAAAGUGA
CAGAGCUAGAAACAGAGGAAUCCCAGCCACACCAAGAGAUGGGUCUGCUG
UGGAAAUUGUGGGCCUGAGUAAAUCUGCUGUUCGCUGGUUGCUGGAAUUA
UCCAAAAAAAUAUUUUCCCUUAUCAUGAAGUCACAGUAAAAAGACAUGG
AAAGGCUAUAAAGGUCUCAUAUGAUGAGUGGAACAGAAAAAUACAAGACA
ACUUUGAAAAGCUAUUUCAUGUUUCCGAAGACCCUUCAGAUUUAAAUGAA
AAGCAUCCAAAUCUGGUUCACAAACGUGGCAUAUACAAAGAUAGUUAUGG
AGCUUCAAGUCCUUGGUGUGACUAUCAGCUCAGGCCUAAUUUUACCAUAG
CAAUGGUUGUGGCCCCUGAGCUCUUUACUACAGAAAAGCAUGGAAAGCU
UUGGAGAUUGCAGAAAAAAAUUGCUUGGUCCCCUUGGCAUGAAAACUUU
AGAUCCAGAUGAUAUGGUUUACUGUGGAAUUUAUGACAAUGCAUUAGACA
AUGACAACUACAAUCUUGCUAAAGGUUUCAAUUAUCACCAAGGACCUGAG
UGGCUGUGGCCUAUGGGUAUUUCUUCGUGCAAAAUUAUAUUUUUCCAG
AUUGAUGGGCCCGGAGACUACUGCAAAGACUAUAGUUUUGGUUAAAAAUG
UUCUUUCCCGACAUUAUGUUCAUCUUGAGAGAUCCCCUUGGAAAGGACUU
CCAGAACUGACCAAUGAGAAUGCCCAGUACUGUCCUUUCAGCUGUGAAAC
ACAAGCCUGGUCAAUUGCUACUAUUCUUGAGACACUUUAUGAUUU<span>AUA</span>G (SEQ ID NO: 151)
AUGGGACACAGUAAACAGAUUCGAAUUUUACUUCUGAACGAAAUGGAGAA
ACUGGAAAAGACCCUCUUCAGACUUGAACAAGGGUAUGAGCUACAGUUCC
GAUUAGGCCCAACUUUACAGGGAAAAGCAGUUACCGUGUAUACAAAUUAC
CCAUUUCCUGGAGAAACAUUUAAUAGAGAAAAAUUCCGUUCUCUGGAUUG
GGAAAAUCCAACAGAAAGAGAAGAUGAUUCUGAUAAAUACUGUAAACUUA
AUCUGCAACAAUCUGGUUCAUUUCAGUAUUAUUUCCUUCAAGGAAAUGAG
AAAAGUGGUGGAGGUUACAUAGUUGUGGACCCCAUUUUACGUGUUGGUGC
UGAUAAUCAUGUGCUACCCUUGGACUGUGUUACUCUUCAGACAUUUUUAG
CUAAGUGUUUGGGACCUUUUGAUGAAUGGGAAAGCAGACUUAGGGUUGCA
AAAGAAUCAGGCUACAACAUGAUUCAUUUUACCCCAUUGCAGACUCUUGG
ACUAUCUAGGUCAUGCUACUCCCUUGCCAAUCAGUUAGAAUUAAAUCCUG
ACUUUUCAAGACCUAAUAGAAAGUAUACCUGGAAUGAUGUUGGACAGCUA
GUGGAAAAUUAAAAAAGGAAUGGAAUGUUAUUUGUAUUACUGAUGUUGU
CUACAAUCAUACUGCUGCUAAUAGUAAAUGGAUCCAGGAACAUCCAGAAU
GUGCCUAUAAUCUUGUGAAUUCUCCACACUUAAAACCUGCCUGGGUCUUA
GACAGAGCACUUUGGCGUUUCUCCUGUGAUGUUGCAGAAGGGAAAUACAA
AGAAAAGGGAAUACCUGCUUUGAUUGAAAAUGAUCACCAUAUGAAUUCCA -continued UCCGAAAAAUAAUUUGGGAGGAUAUUUUUCCAAAGCUUAAACUCUGGGAA
UUUUUCCAAGUAGAUGUCAACAAAGCGGUUGAGCAAUUUAGAAGACUUCU
UACACAAGAAAAUAGGCGAGUAACCAAGUCUGAUCCAAACCAACACCUUA
CGAUUAUUCAAGAUCCUGAAUACAGACGGUUUGGCUGUACUGUAGAUAUG
AACAUUGCACUAACGACUUUCAUACCACAUGACAAGGGGCCAGCAGCAAU
UGAAGAAUGCUGUAAUUGGUUUCAUAAAAGAAUGGAGGAAUUAAAUUCAG
AGAAGCAUCGACUCAUUAACUAUCAUCAGGAACAGGCAGUUAAUUGCCUU
UUGGGAAAUGUGUUUUAUGAACGACUGGCUGGCCAUGGUCCAAAACUAGG
ACCUGUACUAGAAAGCAUCCUUUAGUUACCAGGUAUUUUACUUUCCCAU
UUGAAGAGAUAGACUUCUCCAUGGAAGAAUCUAUGAUUCAUCUGCCAAAU
AAAGCUUGUUUUCUGAUGGCACACAAUGGAUGGGUAAUGGGAGAUGAUCC
UCUUCGAAACUUUGCUGAACCGGGUUCAGAAGUUUACCUAAGGAGAGAAC
UUAUUUGCUGGGGAGACAGUGUUUAAAUUACGCUAUGGGGAAUAAACCAGAG
GACUGUCCUUAUCUCUGGGCACACAUGAAAAAAUACACUGAAAUAACUGC
AACUUAUUUCCAGGGAGUACGUCUUGAUAACUGCCACUCAACACCUCUUC
ACGUAGCUGAGUACAUGUUGGAUGCUGCUAGGAAUUUGCAACCCAAUUUA
UAUGUAGUAGCUGAACUGUUCACAGGAAGUGAAGAUCUGGACAAUGUCUU
UGUUACUAGACUGGGCAUUAGUUCCUUAAUAAGAGAGGCAAUGAGUGCAU
AUAAUAGUCAUGAAGAGGGCAGAUUAGUUUACCGAUAUGGAGGAGAACCU
GUUGGAUCCUUUGUUCAGCCCUGUUUGAGGCCUUUAAUGCCAGCUAUUGC
ACAUGCCCUGUUUAUGGAUAUUACGCAUGAUAAUGAGUGUCCUAUUGUGC
AUAGAUCAGCGUAUGAUGCUCUUCCAAGUACUACAAUUGUUUCUAUGGCA
UGUUGUCUAGUGGAAGUACAAGAGGCUAUGAUGAAUUAGUGCCUCAUCA
GAUUUCAGUGGUUUCUGAAGAACGGUUUUACACUAAGUGGAAUCCUGAAG
CAUUGCCUUCAAACACAGGUGAAGUUAAUUUCCAAAGCGGCAUUAUUGCA
GCCAGGUGUGCUAUCAGUAAACUUCAUCAGGAGCUUGGAGCCAAGGGUUU
UAUUCAGGUGUAUGUGGAUCAAGUUGAUGAAGACAUAGUGGCAGUAACAA
GACACUCACCUAGCAUCCAUCAGUCUGUUGUGGCUGUAUCUAGAACUGCU
UUCAGGAAUCCAAGACUUCAUUUUACAGCAAGGAAGUGCCUCAAAUGUG
CAUCCCUGGCAAAAUUGAAGAAGUAGUUCUUGAAGCUAGAACUAUUGAGA
GAAACACGAAACCUUAUAGGAAGGAUGAGAAUUCAAUCAAUGGAACACCA
GAUAUCACAGUAGAAAUUAGAGAACAUAUUCAGCUUAAUGAAAGUAAAAU
UGUUAAACAAGCUGGAGUUGCACAAAAGGGCCCAAUGAAUAUAUUCAAG
AAAUAGAAUUUGAAAACUUGUCUCCAGGAAGUGUUAUUAUUCAGAGUUU
AGUCUUGAUCCACAUGCACAAGUCGCUGUUUGAAUUCUUCGAAAUCAUCU
GACACAAUUCAGUCCUCACUUUAAAUCUGGCAGCCUAGCUGUUGACAAUG
CAGAUCCUAUAUUAAAAAUUCCUUUUGCUUCUCUUGCCUCCAGAUUAACU
UUGGCUGAGCUAAAUCAGAUCCUUUACCGAUGUGAAUCAGAAGAAAGGA
AGAUGGUGGAGGGUUGCUAUGACAUACCAAACUGGUCAGCCCUUAAAUAUG
CAGGUCUUCAAGGUUUAAUGUCUGUAUUGGCAGAAAAUAAGACCAAAGAAU
GACUUGGGGCAUCCUUUUUGUAAUAAUUUGAGAUCUGGAGAUUGGAUGAU -continued

UGACUAUGUCAGUAACCGGCUUAUUUCACGAUCAGGAACUAUUGCUGAAG

UUGGUAAAUGGUUGCAGGCUAUGUUCUUCUACCUGAAGCAGAUCCCACGU

UACCUUAUCCCAUGUUACUUUGAUGCUAUAUUAAUUGGUGCAUAUACCAC

UCUUCUGGAUACAGCAUGGAAGCAGAUGUCAAGCUUUGUUCAGAAUGGUU

CAACCUUUGUGAAACACCUUUCAUUGGGUUCAGUUCAACUGUGUGGAGUA

GGAAAAUUCCCUUCCCUGCCAAUUCUUUCACCUGCCCUAAUGGAUGUACC

UUAUAGGUUAAAUGAGAUCACAAAAGAAAAGGAGCAAUGUUGUGUUUCUC

UAGCUGCAGGCUUACCUCAUUUUUCUUCUGGUAUUUUCCGCUGCUGGGGA

AGGGAUACUUUUAUUGCACUUAGAGGUAUACUGCUGAUUACUGGACGCUA

UGUAGAAGCCAGGAAUAUUAUUUUAGCAUUUGCGGGUACCCUGAGGCAUG

GUCUCAUUCCUAAUCUACUGGGUGAAGGAAUUUAUGCCAGAUACAAUUGU

CGGGAUGCUGUGUGGUGGUGGCUGCAGUGUAUCCAGGAUUACUGUAAAAU

GGUUCCAAAUGGUCUAGACAUUCUCAAGUGCCCAGUUUCCAGAAUGUAUC

CUACAGAUGAUUCUGCUCCUUUGCCUGCUGGCACACUGGAUCAGCCAUUG

UUUGAAGUCAUACAGGAAGCAAUGCAAAAACACAUGCAGGGCAUACAGUU

CCGAGAAAGGAAUGCUGGUCCCCAGAUAGAUCGAAACAUGAAGGACGAAG

GUUUUAAUAUAACUGCAGGAGUUGAUGAAGAAACAGGAUUUGUUUAUGGA

GGAAAUCGUUUCAAUUGUGGCACAUGGAUGGAUAAAAUGGGAGAAAGUGA

CAGAGCUAGAAACAGAGGAAUCCCAGCCACACCAAGAGAUGGGUCUGCUG

UGGAAAUUGUGGGCCUGAGUAAAUCUGCUGUUCGCUGGUUGCUGGAAUUA

UCCAAAAAAAUAUUUUCCCUUAUCAUGAAGUCACAGUAAAAGACAUGG

AAAGGCUAUAAAGGUCUCAUAUGAUGAGUGGAACAGAAAAAUACAAGACA

ACUUUGAAAAGCUAUUUCAUGUUUCCGAAGACCCUUCAGAUUUAAAUGAA

AAGCAUCCAAAUCUGGUUCACAAACGUGGCAUAUACAAAGAUAGUUAUGG

AGCUUCAAGUCCUUGGUGUGACUAUCAGCUCAGGCCUAAUUUUACCAUAG

CAAUGGUUGUGGCCCCUGAGCUCUUUACUACAGAAAAAGCAUGGAAAGCU

UUGGAGAUUGCAGAAAAAAAAUUGCUUGGUCCCCUUGGCAUGAAAACUUU

AGAUCCAGAUGAUAUGGUUUACUGUGGAAUUUAUGACAAUGCAUUAGACA

AUGACAACUACAAUCUUGCUAAAGGUUUCAAUUAUCACCAAGGACCUGAG

UGGCUGUGGCCUAUUGGGUAUUUUCUUCGUGCAAAAUUAUAUUUUUCCAG

AUUGAUGGGCCCGGAGACUACUGCAAAGACUAUAGUUUUGGUUAAAAAUG

UUCUUUCCCGACAUUAUGUUCAUCUUGAGAGAUCCCCUUGGAAGGACUU

CCAGAACUGACCAAUGAGAAUGCCCAGUACUGUCCUUUCAGCUGUGAAAC

ACAAGCCUGGUCAAUUGCUACUAUUCUUGAGACACUUUAUGAUUUAUAG

Example 22: mUNA Oligomer Expressing Human Protein S (Alpha) (PROS1)

In this example, the structures of mUNA molecules for use in expressing human protein S (alpha) (PROS1) are shown.

Human protein S (alpha) is associated with Protein S deficiency, thrombosis, and arterial occlusive disease.

The base sequences shown below are the portion of the mUNA molecule that may correspond in functionality to the open reading frame of the native mRNA of human protein S (alpha). The complete mUNA molecule comprises a 5' cap (m7GpppGm), and a 5'-UTR upstream of the sequence below, and a 3' UTR and polyA tail (SEQ ID Nos:4 to 12) downstream of the sequence below, each of which corresponds to the structure of the native mRNA of human protein S (alpha).

Human protein S (alpha) is accession NM_001314077.1.

(SEQ ID NO: 152)

AUGAGGGUCCUGGGUGGGCGCUGCGGGGCGCUGCUGGCGUGUCUCCUCCU

AGUGCUUCCCGUCUCAGAGGCAAACUUUUGUUUAUAUUUUAGAAAUGAUU

UUAUAUACAACCGUGCAUGCAUUUCUGUAUUGGUCGGCUUAUCUGGAUGC

AAUUUUUUCUAUUCUAUAUGCUUUUUGUCAAAGCAACAGGCUUCACAAGU

CCUGGUUAGGAAGCGUCGUGCAAAUUCUUUACUUGAAGAAACCAAACAGG

GUAAUCUUGAAAGAGAAUGCAUCGAAGAACUGUGCAAUAAAGAAGAAGCC

AGGGAGGUCUUUGAAAAUGACCCGGAAACGGAUUAUUUUUAUCCAAAAUA

CUUAGUUUGUCUUCGCUCUUUUCAAACUGGGUUAUUCACUGCUGCACGUC

AGUCAACUAAUGCUUAUCCUGACCUAAGAAGCUGUGUCAAUGCCAUUCCA

GACCAGUGUAGUCCUCUGCCAUGCAAUGAAGAUGGAUAUAUGAGCUGCAA

AGAUGGAAAAGCUUCUUUUUACUUGCACUUGUAAACCAGGUUGGCAAGGAG

AAAAGUGUGAAUUGACAUAAAUGAAUGCAAAGAUCCCUCAAAUAUAAAU

GGAGGUUGCAGUCAAAUUUGUGAUAAUACACCUGGAAGUUACCACUGUUC

CUGUAAAAAUGGUUUUGUUAUGCUUUCAAAUAAGAAAGAUUGUAAAGAUG

UGGAUGAAUGCUCUUUGAAGCCAAGCAUUUGUGGCACAGCUGUGUGCAAG

AACAUCCCAGGAGAUUUUGAAUGUGAAUGCCCCGAAGGCUACAGAUAUAA

UCUCAAAUCAAAGUCUUGUGAAGAUAUAGAUGAAUGCUCUGAGAACAUGU

GUGCUCAGCUUUGUGUCAAUUACCCUGGAGGUUACACUUGCUAUUGUGAU

GGGAAGAAAGGAUUCAAACUUGCCCAAGAUCAGAAGAGUUGUGAGGUUGU

UUCAGUGUGCCUUCCCUUGAACCUUGACACAAAGUAUGAAUUACUUUACU

UGGCGGAGCAGUUUGCAGGGGUUGUUUUAUAUUUAAAAUUUCGUUUGCCA

GAAAUCAGCAGAUUUUCAGCAGAAUUUGAUUUCCGGACAUAUGAUUCAGA

AGGCGUGAUACUGUACGCAGAAUCUAUCGAUCACUCAGCGUGGCUCCUGA

UUGCACUUCGUGGUGGAAAGAUUGAAGUUCAGCUUAAGAAUGAACAUACA

UCCAAAAUCACAACUGGAGGUGAUGUUAUUAAUAAUGGUCUAUGGAAUAU

GGUGUCUGUGGAAGAAUUAGAACAUAGUAUUAGCAUUAAAAUAGCUAAAG

AAGCUGUGAUGGAUAUAAAUAAACCUGGACCCCUUUUUAAGCCGGAAAAU

GGAUUGCUGGAAACCAAAGUAUACUUUGCAGGAUUCCCUCGGAAAGUGGA

AAGUGAACUCAUUAAACCGAUUAACCCUCGUCUAGAUGGAUGUAUACGAA

GCUGGAAUUUGAUGAAGCAAGGAGCUUCUGGAAUAAAGGAAAUUAUUCAA

GAAAAACAAAAUAAGCAUUGCCUGGUUACUGUGGGAGAAGGGCUCCUACUA

UCCUGGUUCUGGAAUUGCUCAAUUUCACAUAGAUUAUAAUAAUGUAUCCA

GUGCUGAGGGUUGGCAUGUAAAUGUGACCUUGAAUAUUCGUCCAUCCACG

GGCACUGGUGUUAUGCUUGCCUUGGUUUCUGGUAACAACACAGUGCCCUU

UGCUGUGUCCUUGGUGGACUCCACCUCUGAAAAAAUCACAGGAUAUUCUGU

-continued

UAUCUGUUGAAAAUACUGUAAUAUAUCGGAUACAGGCCCUAAGUCUAUGU

UCCGAUCAACAAUCUCAUCUGGAAUUUAGAGUCAACAGAAACAAUCUGGA

GUUGUCGACACCACUUAAAAUAGAAACCAUCUCCCAUGAAGACCUUCAAA

GACAACUUGCCGUCUUGGACAAAGCAAUGAAAGCAAAAGUGGCCACAUAC

CUGGGUGGCCUUCCAGAUGUUCCAUUCAGUGCCACACCAGUGAAUGCCUU

UUAUAAUGGCUGCAUGGAAGUGAAUAUUAAUGGUGUACAGUUGGAUCUGG

AUGAAGCCAUUUCUAAACAUAAUGAUAUUAGAGCUCACUCAUGUCCAUCA

GUUUGGAAAAAGACAAAGAAUUCUŪŪĀA (SEQ ID NO: 153)
AUGAGGGUCCUGGGUGGGCGCUGCGGGGCGCUGCUGGCGUGUCUCCUCCU

AGUGCUUCCCGUCUCAGAGGCAAACUUUUGUUUAUAUUUUAGAAAUGAUU

UUAUAUACAACCGUGCAUGCAUUUCUGUAUUGGUCGGCUUAUCUGGAUGC

AAUUUUUUCUAUUCUAUAUGCUUUUUGUCAAAGCAACAGGCUUCACAAGU

CCUGGUUAGGAAGCGUCGUGCAAAUUCUUUACUUGAAGAAACCAAACAGG

GUAAUCUUGAAAGAGAAUGCAUCGAAGAACUGUGCAAUAAAGAAGAAGCC

AGGGAGGUCUUUGAAAAUGACCCGGAAACGGAUUAUUUUUAUCCAAAAUA

CUUAGUUUGUCUUCGCUCUUUUCAAACUGGGUUAUUCACUGCUGCACGUC

AGUCAACUAAUGCUUAUCCUGACCUAAGAAGCUGUGUCAAUGCCAUUCCA

GACCAGUGUAGUCCUCUGCCAUGCAAUGAAGAUGGAUAUAUGAGCUGCAA

AGAUGGAAAAGCUUCUUUUACUUGCACUUGUAAACCAGGUUGGCAAGGAG

AAAAGUGUGAAUUUGACAUAAAUGAAUGCAAAGAUCCCUCAAAUAUAAAU

GGAGGUUGCAGUCAAAUUUGUGAUAAUACACCUGGAAGUUACCACUGUUC

CUGUAAAAUGGUUUUGUUAUGCUUUCAAAUAAGAAAGAUUGUAAAGAUG

UGGAUGAAUGCUCUUUGAAGCCAAGCAUUUGUGGCACAGCUGUGUGCAAG

AACAUCCCAGGAGAUUUGAAUGUGAAUGCCCCGAAGGCUACAGAUAUAA

UCUCAAAUCAAAGUCUUGUGAAGAUAUAGAUGAAUGCUCUGAGAACAUGU

GUGCUCAGCUUUGUGUCAAUUACCCUGGAGGUUACACUUGCUAUUGUGAU

GGGAAGAAAGGAUUCAAACUUGCCCAAGAUCAGAAGAGUUGUGAGGUUGU

UUCAGUGUGCCUUCCCUUGAACCUUGACACAAAGUAUGAAUUACUUUACU

UGGCGGAGCAGUUUGCAGGGGUUGUUUUAUAUUUAAAAUUUCGUUUGCCA

GAAAUCAGCAGAUUUUCAGCAGAAUUUGAUUUCCGGACAUAUGAUUCAGA

AGGCGUGAUACUGUACGCAGAAUCUAUCGAUCACUCAGCUGGCUCCUGA

UUGCACUUCGUGGUGGAAAGAUUGAAGUUCAGCUUAAGAAUGAACAUACA

UCCAAAAUCACAACUGGAGGUGAUGUUAUUAAUAAUGGUCUAUGGAAUAU

GGUGUCUGUGGAAGAAUUAGAACAUAGUAUUAGCAUUAAAAUAGCUAAAG

AAGCUGUGAUGGAUAUAAAUAAACCUGGACCCCUUUUUAAGCCGAAAAU

GGAUUGCUGGAAACCAAAGUAUACUUUGCAGGAUUCCCUCGGAAAGUGGA

AAGUGAACUCAUUAAACCGAUUAACCCUCGUCUAGAUGGAUGUAUACGAA

GCUGGAAUUUGAUGAAGCAAGGAGCUUCUGGAAUAAAGGAAAUUAUUCAA

GAAAAACAAAAUAAGCAUUGCCUGGUUACUGUGGGAGAAGGGCUCCUACUA

UCCUGGUUCUGGAAUUGCUCAAUUUCACAUAGAUUAUAAUAAUGUAUCCA

GUGCUGAGGGUUGGCAUGUAAAUGUGACCUUGAAUAUUCGUCCAUCCACG

GGCACUGGUGUUAUGCUUGCCUUGGUUUCUGGUAACAACACAGUGCCCUU

UGCUGUGUCCUUGGUGGACUCCACCUCUGAAAAAUCACAGGAUAUUCUGU

UAUCUGUUGAAAAUACUGUAAUAUAUCGGAUACAGGCCCUAAGUCUAUGU

UCCGAUCAACAAUCUCAUCUGGAAUUUAGAGUCAACAGAAACAAUCUGGA

GUUGUCGACACCACUUAAAAUAGAAACCAUCUCCCAUGAAGACCUUCAAA

GACAACUUGCCGUCUUGGACAAAGCAAUGAAAGCAAAAGUGGCCACAUAC

CUGGGUGGCCUUCCAGAUGUUCCAUUCAGUGCCACACCAGUGAAUGCCUU

UUAUAAUGGCUGCAUGGAAGUGAAUAUUAAUGGUGUACAGUUGGAUCUGG

AUGAAGCCAUUUCUAAACAUAAUGAUAUUAGAGCUCACUCAUGUCCAUCA

GUUUGGAAAAAGACAAAGAAUUCUUAA

Example 23: mUNA Oligomer Expressing Human Pyruvate Kinase, Liver and RBC (PKLR)

In this example, the structures of mUNA molecules for use in expressing human pyruvate kinase, liver and RBC (PKLR) are shown.

Human pyruvate kinase, liver and RBC (PKLR) is associated with chronic hereditary nonspherocytic hemolytic anemia.

The base sequences shown below are the portion of the mUNA molecule that may correspond in functionality to the open reading frame of the native mRNA of human pyruvate kinase, liver and RBC (PKLR). The complete mUNA molecule comprises a 5' cap (m7GpppGm), and a 5'-UTR upstream of the sequence below, and a 3' UTR and polyA tail (SEQ ID Nos:4 to 12) downstream of the sequence below, each of which corresponds to the structure of the native mRNA of human pyruvate kinase, liver and RBC (PKLR).

Human pyruvate kinase, liver and RBC (PKLR) is accession NM_000298.5.

(SEQ ID NO: 154)
AŪĜŪCGAUCCAGGAGAACAUAUCAUCCCUGCAGCUUCGGUCAUGGGUCUC

UAAGUCCCAAAGAGACUUAGCAAAGUCCAUCCUGAUUGGGGCUCCAGGAG

GGCCAGCGGGGUAUCUGCGGCGGGCCAGUGUGGCCCAACUGACCCAGGAG

CUGGGCACUGCCUUCUUCCAGCAGCAGCAGCUGCCAGCUGCUAUGGCAGA

CACCUUCCUGGAACACCUCUGCCUACUGGACAUUGACUCCGAGCCCGUGG

CUGCUCGCAGUACCAGCAUCAUUGCCACCAUCGGGCCAGCAUCUCGCUCC

GUGGAGCGCCUCAAGGAGAUGAUCAAGGCCGGGAUGAACAUUGCGCGACU

CAACUUCUCCCACGGCUCCCACGAGUACCAUGCUGAGUCCAUCGCCAACG

UCCGGGAGGCGGUGGAGAGCUUUGCAGGUUCCCCACUCAGCUACCGGCCC

GUGGCCAUCGCCCUGGACACCAAGGGACCGGAGAUCCGCACUGGGAUCCU

GCAGGGGGUCCAGAGUCGGAAGUGGAGCUGGUGAAGGGCUCCCAGGUGC

UGGUGACUGUGGACCCCGCGUUCCGGACGCGGGGGAACGCGAACACCGUG

UGGGUGGACUACCCCAAUAUUGUCCGGGUCGUGCCGGUGGGGGCCGCAU

CUACAUUGACGACGGGCUCAUCUCCCUAGUGGUCCAGAAAAAUCGGCCCAG

```
AGGGACUGGUGACCCAAGUGGAGAACGGCGGCGUCCUGGGCAGCCGGAAG

GGCGUGAACUUGCCAGGGGCCCAGGUGGACUUGCCCGGGCUGUCCGAGCA

GGACGUCCGAGACCUGCGCUUCGGGGUGGAGCAUGGGGUGGACAUCGUCU

UUGCCUCCUUUGUGCGGAAAGCCAGCGACGUGGCUGCCGUCAGGGCUGCU

CUGGGUCCGGAAGGACACGGCAUCAAGAUCAUCAGCAAAAUUGAGAACCA

CGAAGGCGUGAAGAGGUUUGAUGAAAUCCUGGAGGUGAGCGACGGCAUCA

UGGUGGCACGGGGGACCUAGGCAUCGAGAUCCCAGCAGAGAAGGUUUUC

CUGGCUCAGAAGAUGAUGAUUGGGCGCUGCAACUUGGCGGGCAAGCCUGU

UGUCUGUGCCACACAGAUGCUGGAGAGCAUGAUUACCAAGCCCCGGCCAA

CGAGGGCAGAGACAAGCGAUGUCGCCAAUGCUGUGCUGGAUGGGCUGAC

UGCAUCAUGCUGUCAGGGGAGACUGCCAAGGGCAACUUCCCUGUGGAAGC

GGUGAAGAUGCAGCAUGCGAUUGCCCGGGAGGCAGAGGCCGCAGUGUACC

ACCGGCAGCUGUUUGAGGAGCUACGUCGGGCAGCGCCACUAAGCCGUGAU

CCCACUGAGGUCACCGCCAUUGGUGCUGUGGAGGCUGCCUUCAAGUGCUG

UGCUGCUGCCAUCAUUGUGCUGACCACAACUGGCCGCUCAGCCCAGCUUC

UGUCUCGGUACCGACCUCGGGCAGCAGUCAUUGCUGUCACCCGCUCUGCC

CAGGCUGCCCGCCAGGUCCACUUAUGCCGAGGAGUCUUCCCCUUGCUUUA

CCGUGAACCUCCAGAAGCCAUCUGGGCAGAUGAUGUAGAUCGCCGGGUGC

AAUUUGGCAUUGAAAGUGGAAAGCUCCGUGGCUUCCUCCGUGUUGGAGAC

CUGGUGAUUGUGGUGACAGGCUGGCGACCUGGCUCCGGCUACACCAACAU

CAUGCGGGUGCUAAGCAUAUCCUGA
                        (SEQ ID NO: 155)
AUGUCGAUCCAGGAGAACAUAUCAUCCCUGCAGCUUCGGUCAUGGGUCUC

UAAGUCCCAAAGAGACUUAGCAAAGUCCAUCCUGAUUGGGGCUCCAGGAG

GGCCAGCGGGGUAUCUGCGGCGGGCCAGUGUGGCCCAACUGACCCAGGAG

CUGGGCACUGCCUUCUUCCAGCAGCAGCAGCUGCCAGCUGCUAUGGCAGA

CACCUUCCUGGAACACCUCUGCCUACUGGACAUUGACUCCGAGCCCGUGG

CUGCUCGCAGUACCAGCAUCAUUGCCACCAUCGGGCCAGCAUCUCGCUCC

GUGGAGCGCCUCAAGGAGAUGAUCAAGGCCGGGAUGAACAUUGCGCGACU

CAACUUCUCCCACGGCUCCCACGAGUACCAUGCUGAGUCCAUCGCCAACG

UCCGGGAGGCGGUGGAGAGCUUUGCAGGUUCCCCACUCAGCUACCGGCCC

GUGGCCAUCGCCCUGGACACCAAGGGACCGGAGAUCCGCACUGGGAUCCU

GCAGGGGGGUCCAGAGUCGGAAGUGGAGCUGGUGAAGGGCUCCCAGGUGC

UGGUGACUGUGGACCCCGCGUUCCGGACGCGGGGAACGCGAACACCGUG

UGGGUGGACUACCCCAAUAUUGUCCGGGUCGUGCCGGUGGGGGCCGCAU

CUACAUUGACGACGGGCUCAUCUCCCUAGUGGUCCAGAAAAUCGGCCAG

AGGGACUGGUGACCCAAGUGGAGAACGGCGGCGUCCUGGGCAGCCGGAAG

GGCGUGAACUUGCCAGGGGCCCAGGUGGACUUGCCCGGGCUGUCCGAGCA

GGACGUCCGAGACCUGCGCUUCGGGGUGGAGCAUGGGGUGGACAUCGUCU

UUGCCUCCUUUGUGCGGAAAGCCAGCGACGUGGCUGCCGUCAGGGCUGCU

CUGGGUCCGGAAGGACACGGCAUCAAGAUCAUCAGCAAAAUUGAGAACCA

CGAAGGCGUGAAGAGGUUUGAUGAAAUCCUGGAGGUGAGCGACGGCAUCA

UGGUGGCACGGGGGACCUAGGCAUCGAGAUCCCAGCAGAGAAGGUUUUC

CUGGCUCAGAAGAUGAUGAUUGGGCGCUGCAACUUGGCGGGCAAGCCUGU

UGUCUGUGCCACACAGAUGCUGGAGAGCAUGAUUACCAAGCCCCGGCCAA

CGAGGGCAGAGACAAGCGAUGUCGCCAAUGCUGUGCUGGAUGGGCUGAC

UGCAUCAUGCUGUCAGGGGAGACUGCCAAGGGCAACUUCCCUGUGGAAGC

GGUGAAGAUGCAGCAUGCGAUUGCCCGGGAGGCAGAGGCCGCAGUGUACC

ACCGGCAGCUGUUUGAGGAGCUACGUCGGGCAGCGCCACUAAGCCGUGAU

CCCACUGAGGUCACCGCCAUUGGUGCUGUGGAGGCUGCCUUCAAGUGCUG

UGCUGCUGCCAUCAUUGUGCUGACCACAACUGGCCGCUCAGCCCAGCUUC

UGUCUCGGUACCGACCUCGGGCAGCAGUCAUUGCUGUCACCCGCUCUGCC

CAGGCUGCCCGCCAGGUCCACUUAUGCCGAGGAGUCUUCCCCUUGCUUUA

CCGUGAACCUCCAGAAGCCAUCUGGGCAGAUGAUGUAGAUCGCCGGGUGC

AAUUUGGCAUUGAAAGUGGAAAGCUCCGUGGCUUCCUCCGUGUUGGAGAC

CUGGUGAUUGUGGUGACAGGCUGGCGACCUGGCUCCGGCUACACCAACAU

CAUGCGGGUGCUAAGCAUAUCCUGA
```

Example 24: mUNA Oligomer Expressing Human Phenylalanine Hydroxylase

In this example, the structures of mUNA molecules for use in expressing human phenylalanine hydroxylase are shown.

Human phenylalanine hydroxylase is associated with phenylketonuria.

The base sequences shown below are the portion of the mUNA molecule that may correspond in functionality to the open reading frame of the native mRNA of human phenylalanine hydroxylase. The complete mUNA molecule comprises a 5' cap (m7GpppGm), and a 5'-UTR upstream of the sequence below, and a 3' UTR and polyA tail (SEQ ID NOs:4 to 12) downstream of the sequence below, each of which corresponds to the structure of the native mRNA of human phenylalanine hydroxylase.

Human phenylalanine hydroxylase is accession NM_000277.1.

```
                                    (SEQ ID NO: 156)
AUGUCCACUGCGGUCCUGGAAAACCCAGGCUUGGGCAGGAAACUCUCUGA

CUUUGGACAGGAAACAAGCUAUAUUGAAGACAACUGCAAUCAAAAUGGUG

CCAUAUCACUGAUCUUCUCACUCAAAGAAGAAGUUGGUGCAUUGGCCAAA

GUAUUGCGCUUAUUUGAGGAGAAUGAUGUAAACCUGACCCACAUUGAAUC

UAGACCUUCUCGUUUAAAGAAAGAUGAGUAUGAAUUUUUCACCCAUUUGG

AUAAACGUAGCCUGCCUGCUCUGACAAACAUCAUCAAGAUCUUGAGGCAU

GACAUUGGUGCCACUGUCCAUGAGCUUUCACGAGAUAAGAAGAAAGACAC

AGUGCCCUGGUUCCCAAGAACCAUUCAAGAGCUGGACAGAUUUGCCAAUC

AGAUUCUCAGCUAUGGAGCGGAACUGGAUGCUGACCACCCUGGUUUUAAA

GAUCCUGUGUACCGUGCAAGACGGAAGCAGUUUGCUGACAUUGCCUACAA
```

-continued
CUACCGCCAUGGGCAGCCCAUCCCUCGAGUGGAAUACAUGGAGGAAGAAA
AGAAAACAUGGGGCACAGUGUUCAAGACUCUGAAGUCCUUGUAUAAACC
CAUGCUUGCUAUGAGUACAAUCACAUUUUUCCACUUCUUGAAAAGUACUG
UGGCUUCCAUGAAGAUAACAUUCCCCAGCUGGAAGACGUUUCUCAAUUCC
UGCAGACUUGCACUGGUUUCCGCCUCCGACCUGUGGCUGGCCUGCUUUCC
UCUCGGGAUUUCUUGGGUGGCCUGGCCUUCCGAGUCUUCCACUGCACACA
GUACAUCAGACAUGGAUCCAAGCCCAUGUAUACCCCGAACCUGACAUCU
GCCAUGAGCUGUUGGGACAUGUGCCCUUGUUUUCAGAUCGCAGCUUUGCC
CAGUUUUCCCAGGAAAUUGGCCUUGCCUCUCUGGGUGCACCUGAUGAAUA
CAUUGAAAAGCUCGCCACAAUUUACUGGUUUACUGUGGAGUUUGGGCUCU
GCAAACAAGGAGACUCCAUAAAGGCAUAUGGUGCUGGGCUCCUGUCAUCC
UUUGGUGAAUUACAGUACUGCUUAUCAGAGAAGCCAAAGCUUCUCCCCCU
GGAGCUGGAGAAGACAGCCAUCCAAAAUUACACUGUCACGGAGUUCCAGC
CCCUGUAUUACGUGGCAGAGAGUUUUAAUGAUGCCAAGGAGAAAGUAAGG
AACUUUGCUGCCACAAUACCUCGGCCCUUCUCAGUUCGCUACGACCCAUA
CACCCAAAGGAUUGAGGUCUUGGACAAUACCCAGCAGCUUAAGAUUUGG
CUGAUUCCAUUAACAGUGAAAUUGGAAUCCUUUGCAGUGCCCUCCAGAAA
AUAAAGÜAA (SEQ ID NO: 157)
AUĜUCCACUGCGGUCCUGGAÃAACCCAGGCUUGGGCAGÂAACUCUCUGA
CUUUGGÃCAGGAAACAAGCUAUAUŨGAAGACAACUGCAAUCAÃAAUGGUG
CCAUAUCACUĜAUCUUCUCACUCAAAGAÃGAAGUUGGUGCAUUGGCĈAAA
GUAUUGCGCUUAUUŨGAGGAGAAUGAUGUAAAĈCUGACCCACAUUGAAUC
ŨAGACCUUCUCGUUUAAAĜAAAGAUGAGUAUGAAUUŨUUCACCCAUUUGG
AUAAÃCGUAGCCUGCCUGCUCUĜACAAACAUCAUCAAGAUĈUUGAGGCAU
GACAUUGĜUGCCACUGUCCAUGAGCUŨUCACGAGAUAAGAAGAAÃGACAC
AGUGCCCUGGUUĈCAAGAACCAUUCAAGAĜCUGGACAGAUUUGCCAAŨC
AGAUUCUCAGCUAUGÃGCGGAACUGGAUGCUGAĈCACCCUGGUUUUAAA
GAŨCCUGUGUACCGUGCAAGÃCGGAAGCAGUUUGCUGAĈAUUGCCUACAA
CUACCĜCCAUGGGCAGCCCAUCCĈUCGAGUGGAAUACAUGGAĜGAAGAAA
AGAAAACAUĜGGCACAGUGUUCAAGAĈUCUGAAGUCCUUGUAUAÃACC
CAUGCUUGCUAUGAĜUACAAUCACAUUUUUCCÃCUUCUUGAAAAGUACUG
ŨGGCUUCCAUGAAGAUAAĈAUUCCCCAGCUGGAAGAĈGUUUCUCAAUUCC
UGCAĜACUUGCACUGGUUUCCĈCUCCGACCUGUGGCUGĈCUGCUUUCC
UCUCGGGAŨUUCUUGGGUGGCCUGGĈUUCCGAGUCUUCCACUĜCACACA
GUACAUCAGACAŨGGAUCCAAGCCCAUGUAŨACCCCGAACCUGACAUĈU
GCCAUGAGCUGUUGGĜACAUGUGCCCUUGUUUUĈAGAUCGCAGCUUUGCC
CAĜUUUUCCCAGGAAAUUGĈCUUGCCUCUCUGGGUGCÃCCUGAUGAAUA
CAUUGAÃAAGCUCGCCACAAUUUAĈUGGUUUACUGUGGAGUUŨGGGCUCU
GCAAACAAGĜAGACUCCAUAAAGGCAUAŨGGUGCUGGGCUCCUGUĈAUCC -continued
UUUGGUGAAUUACAĜUACUGCUUAUCAGAGAAĜCCAAAGCUUCUCCCCCU
ĜGAGCUGGAGAAGACAGCĈAUCCAAAAUUACACUGUĈACGGAGUUCCAGC
CCCUĜUAUUACGUGGCAGAGAĈUUUUAAUGAUGCCAAGGAĜGAAAGUAAG
GAACUUUGĈUGCCACAAUACCUCGGĈCUUCUCAGUUCGCUACĜACCCAU
ACACCCAAAGGAŨUGAGGUCUUGGACAAUAĈCCAGCAGCUUAAGAUUŨG
GCUGAUUCCAUUAACAĜUGAAAUUGGAAUCCUUUĜCAGUGCCCUCCAGAA
AAŨAAAGUÃA (SEQ ID NO: 158)
AUGUCCACUGCGGUCCUGGAAAACCCAGGCUUGGGCAGGAAACUCUCUGA
CUUUGGACAGGAAACAAGCUAUAUUGAAGACAACUGCAAUCAAAAUGGUG
CCAUAUCACUGAUCUUCUCACUCAAAGAAGAAGUUGGUGCAUUGGCCAAA
GUAUUGCGCUUAUUUGAGGAGAAUGAUGUAAACCUGACCCACAUUGAAUC
UAGACCUUCUCGUUUAAAGAAAGAUGAGUAUGAAUUUUUCACCCAUUUGG
AUAAACGUAGCCUGCCUGCUCUGACAAACAUCAUCAAGAUCUUGAGGCAU
GACAUUGGUGCCACUGUCCAUGAGCUUUCACGAGAUAAGAAGAAAGACAC
AGUGCCCUGGUUCCCAAGAACCAUUCAAGAGCUGGACAGAUUUGCCAAUC
AGAUUCUCAGCUAUGGAGCGGAACUGGAUGCUGACCACCCUGGUUUUAAA
GAUCCUGUGUACCGUGCAAGACGGAAGCAGUUUGCUGACAUUGCCUACAA
CUACCGCCAUGGGCAGCCCAUCCCUCGAGUGGAAUACAUGGAGGAAGAAA
AGAAAACAUGGGGCACAGUGUUCAAGACUCUGAAGUCCUUGUAUAAACC
CAUGCUUGCUAUGAGUACAAUCACAUUUUUCCACUUCUUGAAAAGUACUG
UGGCUUCCAUGAAGAUAACAUUCCCCAGCUGGAAGACGUUUCUCAAUUCC
UGCAGACUUGCACUGGUUUCCGCCUCCGACCUGUGGCUGGCCUGCUUUCC
UCUCGGGAUUUCUUGGGUGGCCUGGCCUUCCGAGUCUUCCACUGCACACA
GUACAUCAGACAUGGAUCCAAGCCCAUGUAUACCCCGAACCUGACAUCU
GCCAUGAGCUGUUGGGACAUGUGCCCUUGUUUUCAGAUCGCAGCUUUGCC
CAGUUUUCCCAGGAAAUUGGCCUUGCCUCUCUGGGUGCACCUGAUGAAUA
CAUUGAAAAGCUCGCCACAAUUUACUGGUUUACUGUGGAGUUUGGGCUCU
GCAAACAAGGAGACUCCAUAAAGGCAUAUGGUGCUGGGCUCCUGUCAUCC
UUUGGUGAAUUACAGUACUGCUUAUCAGAGAAGCCAAAGCUUCUCCCCCU
GGAGCUGGAGAAGACAGCCAUCCAAAAUUACACUGUCACGGAGUUCCAGC
CCCUGUAUUACGUGGCAGAGAGUUUUAAUGAUGCCAAGGAGAAAGUAAGG
AACUUUGCUGCCACAAUACCUCGGCCCUUCUCAGUUCGCUACGACCCAUA
CACCCAAAGGAUUGAGGUCUUGGACAAUACCCAGCAGCUUAAGAUUUGG
CUGAUUCCAUUAACAGUGAAAUUGGAAUCCUUUGCAGUGCCCUCCAGAAA
AUAAAGUAA

Example 25: mUNA Oligomer Translation Enhancer Based on TEV 5'UTR

In this example, the structures of mUNA molecules for enhancing translational efficiency are shown.

The 5'-UTR of tobacco etch virus (TEV) is as follows:

(SEQ ID NO: 159)
UCAACACAACAUAUACAAAAACAAACGAAUCUCAAGCAAUCAAGCAUUCU

ACUUCUAUUCAGCAAUUUAAAUCAUUUCUUUUAAAGCAAAAGCAAUUUUC

UGAAAAUUUUCACCAUUUACGAACGAUAGCC

The base sequences shown below are the portion of the mUNA molecule that may correspond in functionality to the 5'-UTR of tobacco etch virus (TEV). The complete mUNA molecule comprises a 5' cap upstream of the sequence below (m7GpppGm), and a coding region (CDS) of a protein of interest, a 3'-UTR, and a polyA tail (SEQ ID Nos:4 to 12) downstream of the sequence below, each of which corresponds to the structure of any native human mRNA. Thus, a UNA oligomer incorporating the oligomer fragment below can have enhanced translational efficiency.

The translation enhancer is placed upstream of the AUG translation start site, and the enhancer region is not translated into the therapeutic protein.

(SEQ ID NO: 160)
UĊAAĊÃCAAĊAUAŨACAAÃAACÃAAĊGAAUĊUCAÃGCAÃUCAÃGCAŨUCU

ÃCUUĊUAUŨGCAĠCAAŨUUAÃAUĊÃUUUĊUUUŨAAAĠCAAÃAGĊÃAUUŨU

CUĠAAAÃUUUŨCACĊAUUŨACĠÃACĠÃUAGĊC (SEQ ID NO: 161)
UĊAACACAACAUAUACAAAACAAACGAAUCUĊAAGCAAUCAAGCAUUCUA

CUUCUAUUGCAĠCAAUUUAAAUCAUUUCUUUUAAAGCAAAAĠCAAUUUUC

UGAAAAUUUUCACCAUUUACGAACGAUAGCĊC (SEQ ID NO: 162)
UĊÃÃCACAACAUAUACAAAACAAACGAAUCUCAAGCAAUCAAGCAUUCUA

CUUCUAUUGCAGCAAUUUAAAUCAUUUCUUUUAAAGCAAAAGCAAUUUUC

UGAAAAUUUUCACCAUUUACGAACGAUÃĠĊc (SEQ ID NO: 163)
ŨCAACACAACAŨAŨACAAAACAAACGAAŨCŨCAAGCAAŨCAAGCAŨŨCŨA

CŨŨCŨAŨŨGCAGCAAŨŨŨAAAŨCAŨŨŨCŨŨŨŨAAAGCAAAAGCAAŨŨŨŨC

ŨGAAAAŨŨŨŨCACCAŨŨŨACGAACGAŨAGCC (SEQ ID NO: 164)
ŨCÃÃCÃCÃÃCÃŨÃŨACÃÃÃACÃÃÃCGÃÃUCŨCÃÃGCÃÃUCÃÃGCÃŨŨC

ŨACŨŨCŨAŨŨGCÃGCÃAŨŨŨÃÃAŨCÃŨŨŨCŨŨŨŨÃÃAGCÃÃÃAGCÃÃ

ŨŨŨŨCŨGÃÃÃAŨŨŨŨCÃCCÃŨŨŨACGÃÃCGÃŨAGCC

Example 26: Messenger RNA Containing UNA Monomers

An nGFP transcript having a polyA tail of 30 monomers in length is ligated to a donor polyÃ tail of 30 UNA Monomers in length to give an UNA-nGFP mRNA product having a polyA$_{30}$Ã$_{30}$ tail of 60 monomers in length. The UNA-nGFP has an increased lifetime and markedly increased translational activity in fibroblasts.

Example 27: Messenger RNA Containing UNA Monomers and Encoding HIV-1 Antigen An mRNA encoding HIV-1 gag antigen having a polyA tail of 30 monomers in length is ligated to a donor polyÃ tail of 20 UNA Monomers in length to give an UNA-HIV-1 gag antigen mRNA product having a polyA$_{30}$Ã$_{20}$ tail of 50 monomers in length. The UNA-HIV-1 gag antigen mRNA has an increased lifetime and markedly increased translational activity in fibroblasts.

Example 28: Messenger RNA Containing UNA Monomers and Encoding Lung Cancer Antigens An mRNA encoding antigens overexpressed in lung cancers having a polyA tail of 30 monomers in length is ligated to a donor polyÃ tail of 10 UNA Monomers in length to give an UNA-mRNA product having a polyA$_{30}$Ã$_{10}$ tail of 40 monomers in length. The UNA-mRNA has an increased lifetime and markedly increased translational activity in fibroblasts.

Example 29: Messenger RNA Containing UNA Monomers and Encoding Malarial *P. falciparum* Reticulocyte-Binding Protein Homologue 5 (PfRH5)

An mRNA encoding malarial *P. falciparum* reticulocyte-binding protein homologue 5 (PfRH5) having a polyA tail of 30 monomers in length is ligated to a donor polyÃ tail of 10 UNA Monomers in length to give an UNA-mRNA product having a polyA$_{30}$Ã$_{10}$ tail of 40 monomers in length. The UNA-mRNA has an increased lifetime and markedly increased translational activity in fibroblasts. The UNA-mRNA is found to induce an antibody response in an animal model.

Example 30: Messenger RNA Containing UNA Monomers and Encoding Malarial *Plasmodium falciparum* PfSEA-1

An mRNA encoding malarial *Plasmodium falciparum* PfSEA-1, a 244 KD malaria antigen expressed in schizont-infected RBCS, having a polyA tail of 30 monomers in length is ligated to a donor polyÃ tail of 10 UNA Monomers in length to give an UNA-mRNA product having a polyA$_{30}$Ã$_{10}$ tail of 40 monomers in length. The UNA-mRNA has an increased lifetime and markedly increased translational activity in fibroblasts. The UNA-mRNA is found to induce an antibody response in an animal model.

Example 31: Splint-Mediated Ligation

Figure 7:
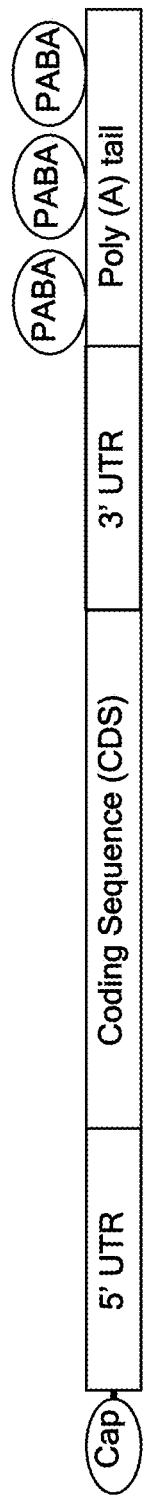
FIG. 7.

FIG. 7 shows the primary structure of a functional mRNA transcript in the cytoplasm. The mRNA includes a 5' methylguanosine cap, a protein coding sequence flanked by untranslated regions (UTRs), and a polyadenosine (polyA) tail bound by polyA binding proteins (PABPs).

Figure 8:
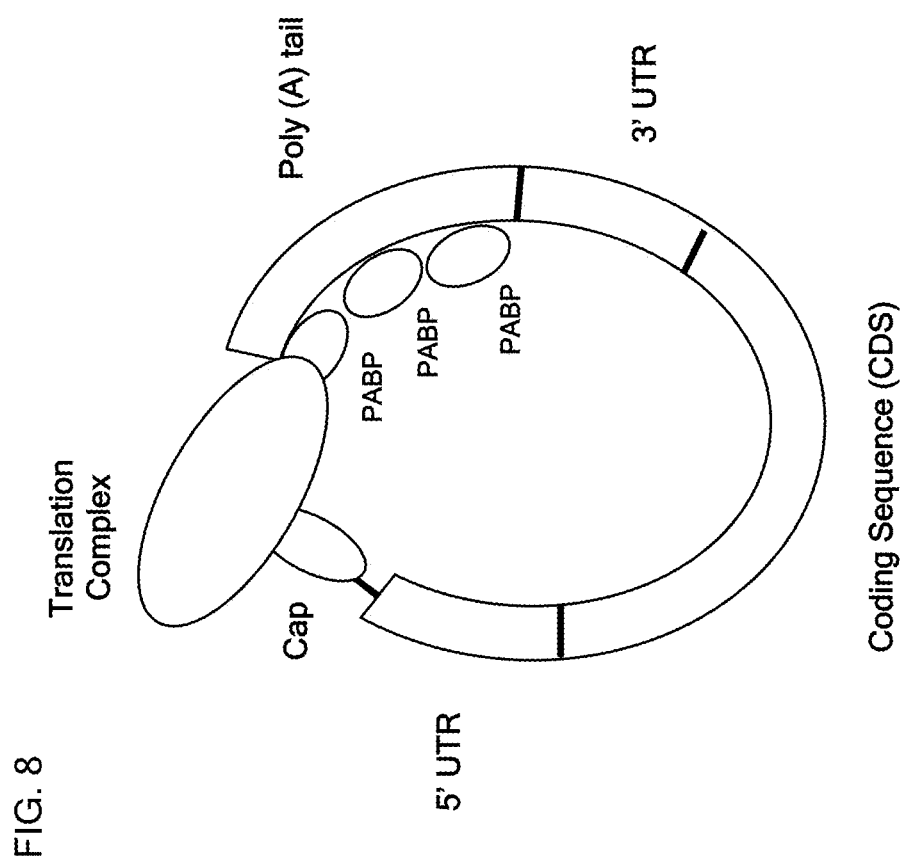
FIG. 8.

FIG. 8 shows the 5' cap and PABPs cooperatively interacting with proteins involved in translation to facilitate the recruitment and recycling of ribosome complexes.

DNA splint oligomers were made for splint-mediated ligation of a donor oligomer to an acceptor RNA. As shown in the scheme of FIG. 8, a short mRNA acceptor oligomer and a 5'-monophosphate-bearing polyA donor oligomer can be ligated in the presence of a DNA splint oligomer.

Figure 9:
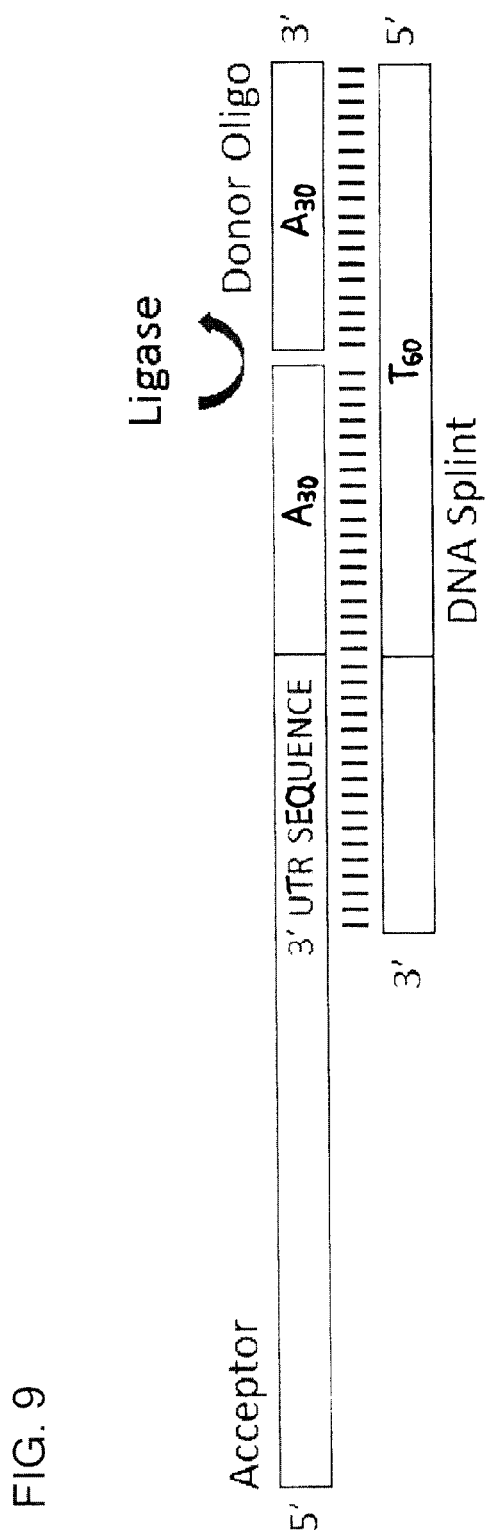
FIG. 9.

FIG. 9 shows the splint-mediated ligation scheme, in which an acceptor RNA with a 30-monomer stub polyA tail (A(30)) was ligated to a 30-monomer donor oligomer (A(30)). The splint-mediated ligation used a DNA oligomer splint which was complementary to the 3' UTR sequence upstream of the stub polyA tail, and included a 60-monomer oligo(dT) 5' heel (T(60)) to splint the ligation. The anchoring region of the splint was complementary to the UTR sequence to ensure that a 5' dT$_{30}$ overhang was presented upon hybridization to the acceptor. This brings the donor oligomer into juxtaposition with the 3' terminus of the stub tail, dramatically improving the kinetics of ligation.

Figure 10:
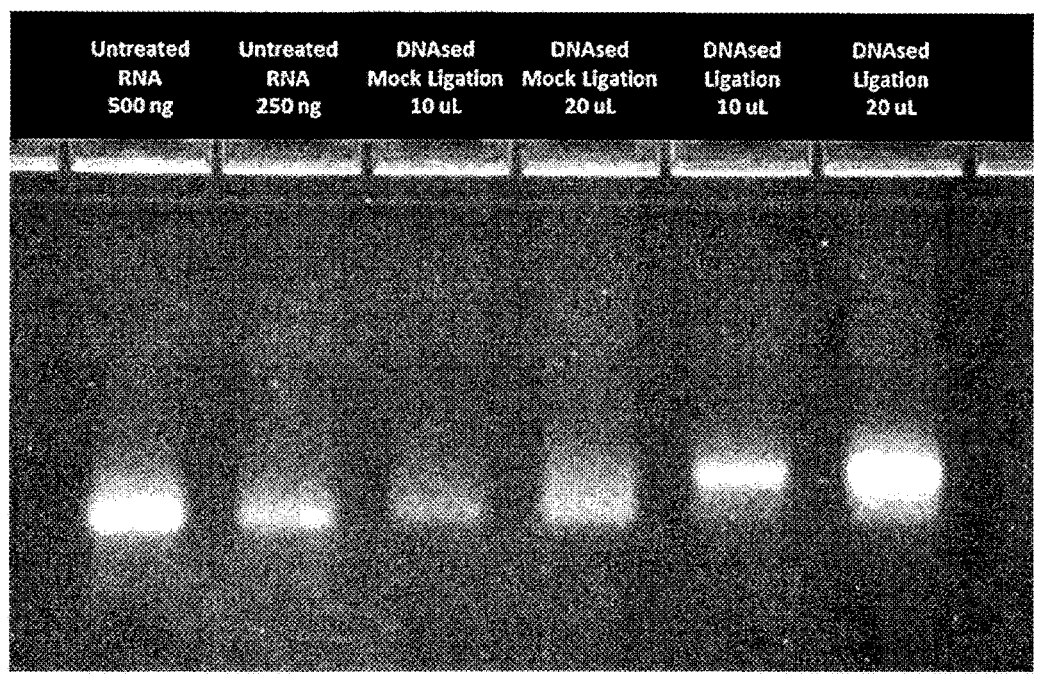
FIG. 10.

FIG. 10 shows the results of ligation using 2 ug of a 120-monomer acceptor with an A$_{30}$ stub tail that was ligated to a 5'-phosphorylated A$_{30}$ RNA donor oligomer using T4 RNA Ligase 2. The reaction was incubated overnight at 37° C. The ligation and a mock reaction done without enzyme were purified, treated with DNAse I for 1 hour to degrade and detach the splint oligomers, and re-purified in a volume of 30 uL. The ligation efficiency was nearly 100%. The absence of a size shift in the mock-reaction prep shows that the acceptor and donor were truly ligated and not simply held together by undigested splint oligomers.

Figure 11:
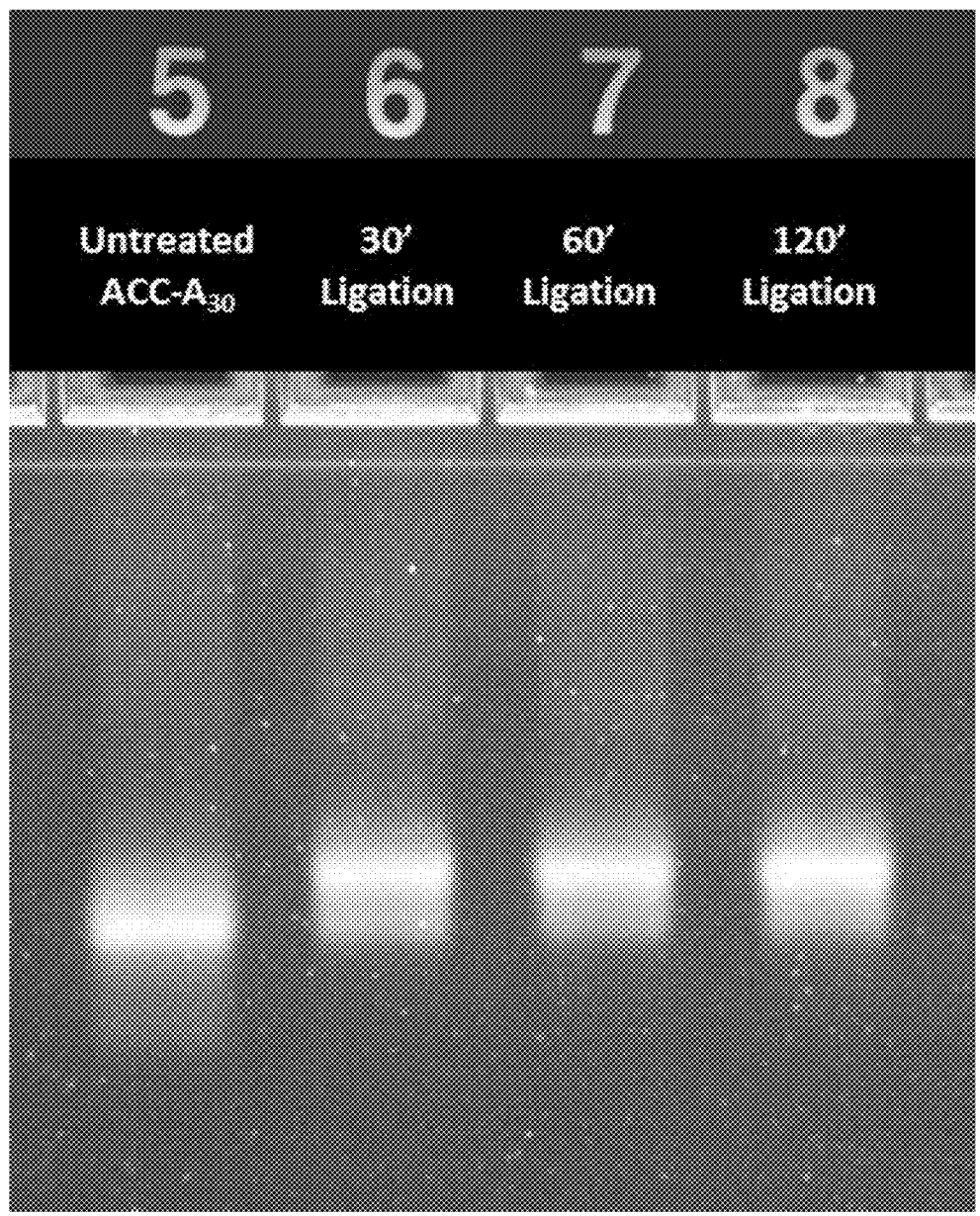
FIG. 11.

Following the same protocol with a short incubation period, high efficiency ligation of the short acceptor mRNA proceeded to nearly 100% completion. FIG. 11 shows the results of splint-mediated ligation using an acceptor RNA with a 30-monomer stub polyA tail (A(30)). The ligation reactions were performed with three different donor oligomer species: A(30), A(60), and A(120). Based on the gel shifts, the ligations attained nearly 100% efficiency.

Example 32: Splint-Mediated Ligation

A protocol used for a 100 ul splint-mediated ligation reaction included the following materials, reagents, and steps.
100 pmol UNA-PolyA UNA Oligomer donor.
100 pmol TAIL-60 splint oligomer.
50 pmol purified RNA acceptor.
10 uL T4 RNA Ligase 2 10× Buffer.
2 uL T4 RNA Ligase 2.
Nuclease-free Water to 100 uL.
Mix and incubate for 1-2 hours at 37 degrees, then purify the RNA in a total of ~90 uL RNAse-free water.
Add 10 uL 10× DNase buffer to eluent and 2 ul DNase I, mix and incubate for 1 hour at 37 degrees to digest splint DNA.
Repurify the RNA using RNeasy spin columns, eluting in water or TE pH 7.0.
Reagents.
NEB M0239 T4 RNA Ligase 2.
NEB M0303 DNase I (RNase-free).
Qiagen 74104RNeasy Mini Kit.
TAIL-60 splint oligomer sequence:

```
                                      (SEQ ID NO: 165)
       CTTCCTACTCAGGCTTTATTCAAAGACCA.
```

Notes:
(a) The splint oligomer sequence includes an anchor that is specific to the 3' UTR used for making mRNA.

(b) This protocol requires an mRNA transcript with a pre-incorporated 30-nt polyA tail.

Example 33: Splint-Mediated Ligation

Figure 12:
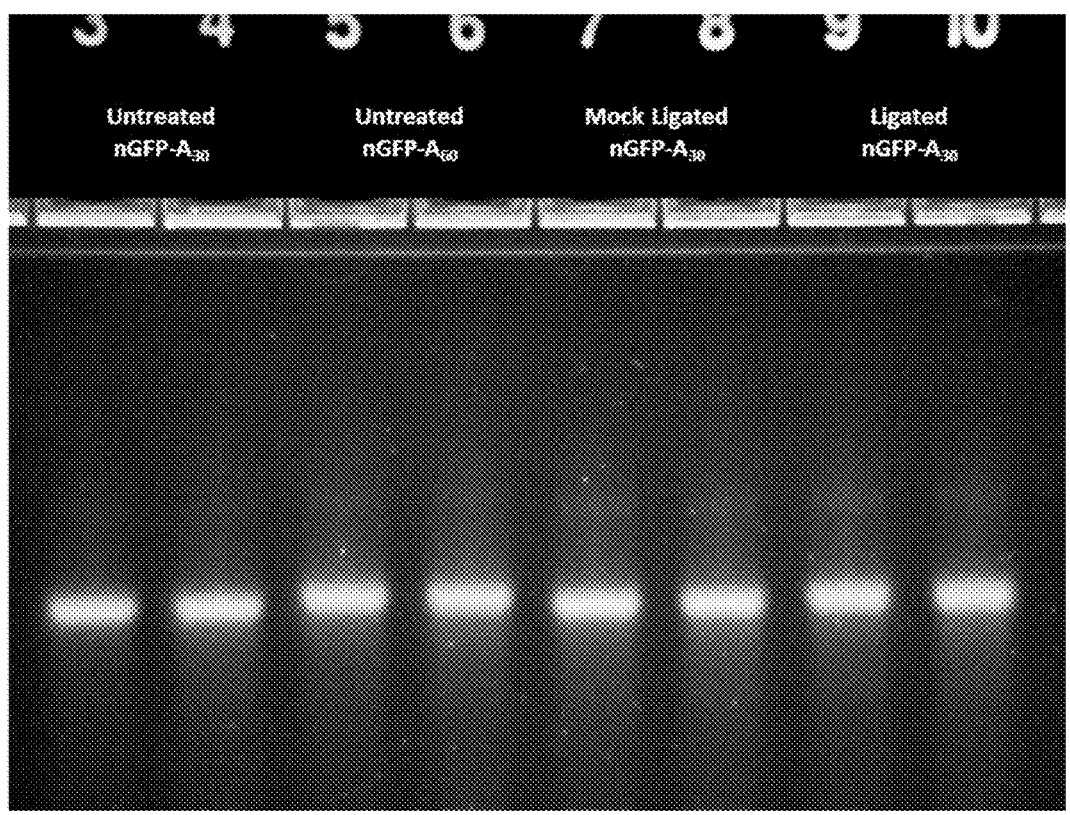
FIG. 12.

A full-length synthetic mRNA acceptor and a 5'-monophosphate-bearing polyA donor were ligated in the presence of a DNA splint oligomer. On ligating a 30-monomer length tail to a ~1 Kb nGFP transcript, a size shift was apparent on a 2% agarose gel, providing a direct indication that bulk ligation was achieved. FIG. 12 shows the results of one-hour splint-mediated ligations that were performed on nGFP-A$_{30}$ transcripts. The resulting ligation products were compared to untreated transcripts and native nGFP-A$_{60}$ IVT products. The native nGFP-A$_{60}$ and the ligated products were up-shifted on the gel relative to the untreated nGFP-A$_{30}$ transcripts and mock-ligated material.

Example 34: Splint-Mediated Ligation

A UNA-PolyA UNA Oligomer donor was made having the following structure:

```
                                      (SEQ ID NO: 166)
 5'-(rAp)-AAAAAAAAAAAAAAAAAAAAAAAAAAAAAA-(3' C3

Spacer), wherein 5'-(rAp) is 5' Phosphorylation and A is UNA-A.
```

Example 35: Translatable RNA Molecules

An nGFP transcript with a polyA tail of 30-monomers in length (untreated A$_{30}$ mRNA) was ligated to a donor polyA tail of 30-monomers in length to give an mRNA product having a polyA tail of 60-monomers in length (A$_{60}$-bearing ligation product) by splint-mediated ligation.

Figure 13:
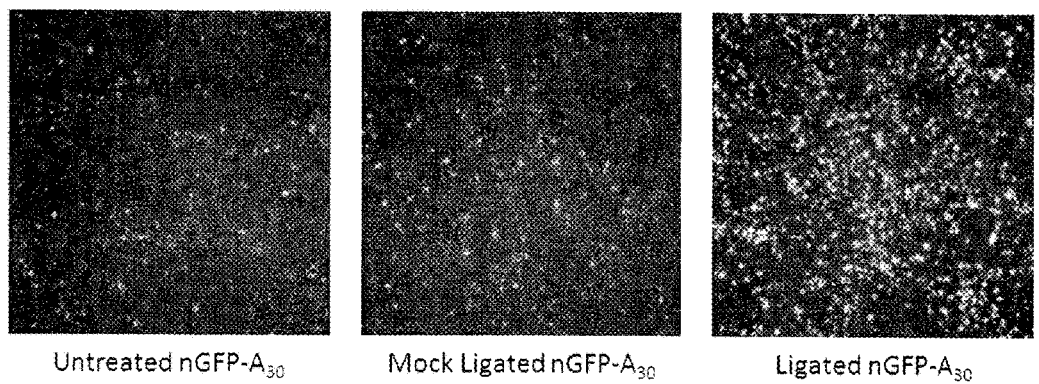
FIG. 13.

FIG. 13 shows increased lifetime and translational activity for the nGFP-A$_{60}$ ligation product. As shown in FIG. 13, nuclearized transcripts were transfected into fibroblasts for comparison of nGFP-A$_{30}$, mock-ligated nGFP-A$_{30}$, and an nGFP-A$_{60}$ ligation product (FIG. 13, left to right). The significantly higher fluorescence signal observed for the nGFP-A$_{60}$ ligation product shows that it has markedly increased translational activity.

Example 36: Cohesive End Ligation

A wild-type T4 RNA ligase was used to ligate a donor 5' phosphorylated oligomer to a short IVT transcript. Short synthetic RNAs were generated by IVT, and the outcome of ligation reactions was evaluated on high-resolution 4% agarose gels. The increase in transcript size from ligation of a synthetic oligomer 30 monomers in length to a full-sized mRNA of 1-2 Kb is too small to clearly visualize on a gel. Thus, short synthetic RNAs of 100-180 monomers were generated by IVT. The 3' terminal sequence of these short synthetic RNAs was identical to that in the 3' UTRs of synthetic mRNAs.

Example 37: Cohesive End Ligation with Pre-Adenylated Donor

A synthetic oligomer having an adenylated 5' end was prepared. The adenylated 5' end, normally formed as a catalytic intermediate by the ligase, pre-activated the synthetic oligomer for ligation. Use of the pre-adenylated synthetic oligomer obviated the need for ATP in the reactions, and allowed the use of a mutant ligase that was active exclusively on adenylated substrates. Pre-adenylation of the synthetic oligomer increased ligation efficiency and minimized side-product formation.

A KQ mutant variant of T4 RNA Ligase 2 was used to ligate a pre-adenylated donor oligomer to a short IVT transcript.

Figure 14:
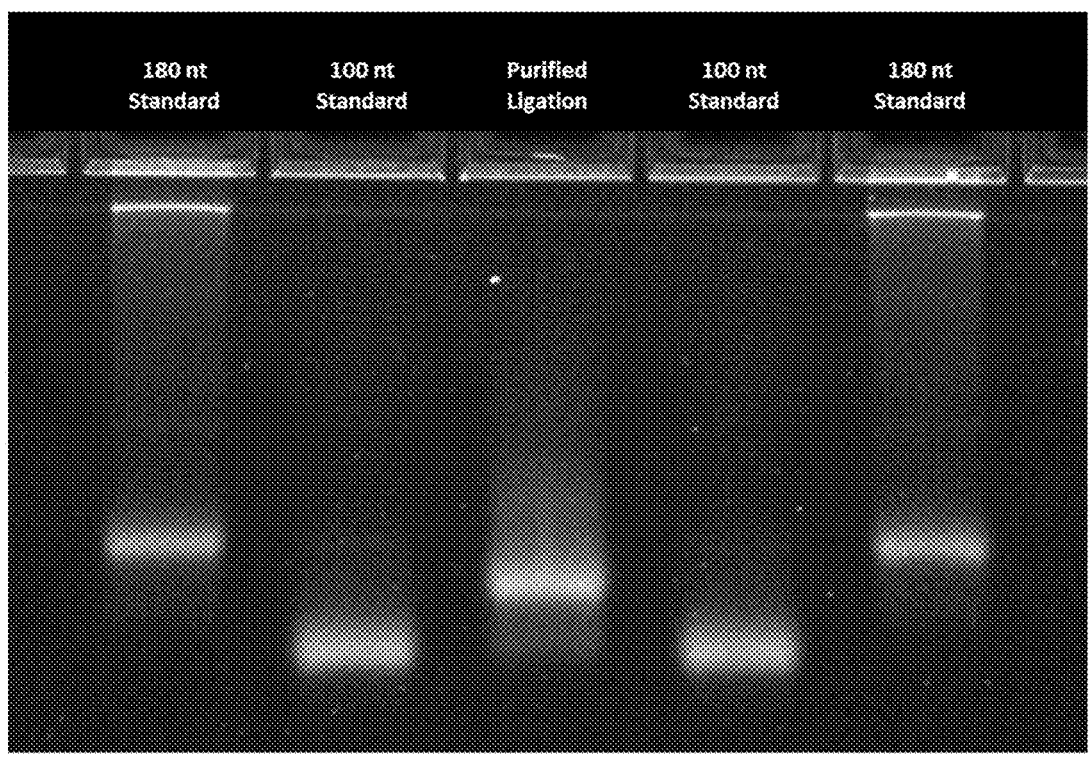
FIG. 14.

FIG. 14 shows the results of a ligation performed with a 100-monomer acceptor RNA that was treated for 3 hours at room temperature with T4 RNA Ligase 2 (truncated KQ mutant) using a 10 uM concentration of a polyA tail 30-monomer donor oligomer. 15% PEG 8000 was included in the reaction as a volume excluder to promote efficient ligation. The ligation reaction showed that a high molecular weight product was formed, having a size in between the 100-monomer acceptor RNA and a 180-monomer RNA transcript included as a size standard. These results show that the ligation reaction produced a predominant product having high molecular weight with nearly 100% ligation of the donor to the acceptor. Additional experiments performed with concentrations of the polyA tail at 10 uM, 20 uM, and 40 uM showed that at least half of the acceptor RNA was ligated in all cases.

All publications, patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A messenger unlocked nucleic acid (mUNA) molecule, comprising: one or more unlocked nucleic acid (UNA) monomers, each independently having a structure of the formula:

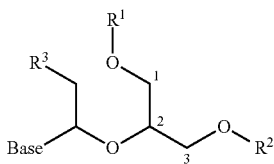

wherein $R^1$ and $R^2$ are each independently H or a phosphodiester linkage,

Base is a nucleobase selected from the group consisting of uracil, thymine, cytosine, 5-methylcytosine, adenine, guanine, inosine, pseudouracil, 1-methylpseudouracil, and 5-methoxyuracil, and $R^3$ is selected from the group consisting of —$OR^4$, $SR^4$, —$N(R^4)_2$, —$NH(C=O)R^4$, morpholino, piperazin-1-yl, or 4-alkanoyl-piperazin-1-yl;

wherein each $R^4$ is independently selected from the group consisting of H, alkyl, a cholesterol, a lipid molecule, a polyamine, an amino acid, and a polypeptide; and nucleic acid monomers wherein the mUNA molecule is translatable to express a polypeptide or protein.

2. The molecule of claim 1, wherein the molecule comprises from 200 to 12,000 monomers.

3. The molecule of claim 1, wherein the molecule comprises from 1 to 100 UNA monomers.

4. The molecule of claim 1, wherein the molecule comprises one or more modified nucleic acid nucleotides, or one or more chemically-modified nucleic acid nucleotides.

5. The molecule of claim 1, wherein the molecule comprises a 5' cap, a 5' untranslated region of monomers, a coding region of monomers, a 3' untranslated region of monomers, and a tail region of monomers.

6. The molecule of claim 5, wherein the molecule comprises a translation enhancer in a 5' or 3' untranslated region.

7. The molecule of claim 1, wherein the molecule is translatable in vivo or in vitro.

8. The molecule of claim 1, wherein a translation product of the molecule is an active peptide or protein.

9. The molecule of claim 1, wherein a translation product of the molecule is human EPO, human Factor IX, or human alpha-1-antitrypsin.

10. The molecule of claim 1, wherein the molecule exhibits at least 2-fold increased translation efficiency in vivo as compared to a native mRNA that encodes the same translation product.

11. The molecule of claim 1, wherein the molecule comprises a sequence selected from SEQ ID NOs:1-164.

12. A composition comprising a mUNA molecule of claim 1 and a pharmaceutically acceptable carrier.

13. A vaccine or immunization composition comprising a mUNA molecule of claim 1.

14. The composition of claim 12, wherein the carrier is a nanoparticle or liposome.

15. A method for producing a polypeptide or protein in vivo, the method comprising administering to a mammal a composition of claim 12.

16. The method of claim 15, wherein the polypeptide or protein is deficient in a disease or condition described in Table 1.

17. The method of claim 15, wherein the protein is human EPO, human Factor IX, or human alpha-1-antitrypsin.

18. The molecule of claim 4, wherein the one or more modified nucleic acid nucleotides is selected from the group consisting of 2'-O-methyl ribonucleotides; 2'-O-methyl purine nucleotides; 2'-deoxy-2'-fluoro ribonucleotides; 2'-deoxy-2'-fluoro pyrimidine nucleotides; 2'-deoxy ribonucleotides; 2'-deoxy purine nucleotides; 5-C-methyl-nucleotides; inverted deoxyabasic monomer residues; 3'-end stabilized nucleotides; 3'-glyceryl nucleotides; 3'-inverted abasic nucleotides; 3'-inverted thymidine; locked nucleic acid nucleotides (LNA); 2'-O,4'-C-methylene-(D-ribofuranosyl) nucleotides; 2'-methoxyethoxy (MOE) nucleotides; 2'-methyl-thio-ethyl; 2'-deoxy-2'-fluoro nucleotides; 2'-O-methyl nucleotides; 2',4'-constrained 2'-O-Methoxyethyl (cMOE); 2'-O-Ethyl (cEt) Modified DNAs; 2'-amino nucleotides; 2'-O-amino nucleotides; 2'-C-allyl nucleotides; 2'-O-allyl nucleotides; $N^6$-methyladenosine nucleotides; nucleotide monomers with modified bases including 5-(3-amino)propyluridine, 5-(2-mercapto)ethyluridine, 5-bromouridine, 8-bromoguanosine, or 7-deazaadenosine; 2'-O-aminopropyl substituted nucleotides; and nucleotide monomers in which the 2'-OH group is replaced with a 2'-R, a 2'-OR, a 2'-halogen, a 2'-SR, or a 2'-amino, wherein R is H, alkyl, alkenyl, or alkynyl.

19. The molecule of claim 4, wherein the one or more modified nucleic acid nucleotides is selected from the group consisting of pseudouridine (psi-uridine), 1-methylpseudouridine, 5-methylcytosine, and 5-methoxyuridine.

* * * * *

SEQUENCE LISTING

```
<160> NUMBER OF SEQ ID NOS: 166

<210> SEQ ID NO 1
<211> LENGTH: 1750
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5' cap (m7GpppGm)
<220> FEATURE:
<221> NAME/KEY: modified_base
<222> LOCATION: (1747)..(1748)
<223> OTHER INFORMATION: UNA monomer

<400> SEQUENCE: 1
gggaaacaua agucaacaca acauauacaa aacaaacgaa ucucaagcaa ucaagcauuc      60
uacuucuauu gcagcaauuu aaaucauuuc uuuuaaagca aaagcaauuu ucugaaaauu     120
uucaccauuu acgaacgaua gccauggccc agcgcgugaa caugaucaug gcagaaucac     180
caggccucau caccaucugc cuuuuaggau aucuacucag ugcugaaugu acaguuuuuc     240
uugaucauga aaacgccaac aaaauucuga aucggccaaa gagguauaau ucagguaaau     300
uggaagaguu uguucaaggg aaccuugaga gagaauguau ggaagaaaag uguaguuuug     360
aagaagcacg agaaguuuuu gaaaacacug aaagaacaac ugaauuuugg aagcaguaug     420
uugauggaga ucagugugag uccaauccau guuuaaaugg cggcaguugc aaggaugaca     480
uuaauuccua ugaauguugg ugucccuuug gauuugaagg aaagaacugu gaauuagaug     540
uaacauguaa cauuaagaau ggcagaugcg agcaguuuug uaaaaauagu gcugauaaca     600
aggugguuug cuccuguacu gagggauauc gacuugcaga aaaccagaag uccugugaac     660
cagcagugcc auuuccaugu ggaagaguuu cuguuucaca aacuucuaag cucacccgug     720
cugagacugu uuuccugau guggacuaug uaaauucuac ugaagcugaa accauuuugg     780
auaacaucac ucaaagcacc caaucauuua augacuucac ucgggguuguu gguggagaag     840
```

```
augccaaacc aggucaauuc ccuuggcagg uuguuuugaa ugguaaaguu gaugcauucu    900
guggaggcuc uaucguuaau gaaaaaugga uuguaacugc ugcccacugu guugaaacug    960
guguuaaaau uacaguuguc gcaggugaac auaauauuga ggagacagaa cauacagagc   1020
aaaagcgaaa ugugauucga auuauuccuc accacaacua caaugcagcu auuaauaagu   1080
acaaccauga cauugcccuu cuggaacugg acgaacccuu agugcuaaac agcuacguua   1140
caccuauuug cauugcugac aaggaauaca cgaacaucuu ccucaaauuu ggaucuggcu   1200
auguaagugg cugggaaga gucuuccaca aagggagauc agcuuuaguu cuucaguacc    1260
uuagaguucc acuuguugac cgagccacau gucuucgauc uacaaaguuc accaucuaua   1320
acaacauguu cugugcuggc uuccaugaag gagguagaga uucaugucaa ggagauagug   1380 ggggaccccca uguuacugaa gugaagggga ccaguuucuu aacuggaauu auuagcuggg  1440
gugaagagug ugcaaugaaa ggcaaauaug gaauauauac caagguaucc cgguaugca   1500 acuggauuaa ggaaaaaaca aagcucacuu gacuagugca ugacuaggau cugguuacca   1560
cuaaaccagc cucaagaaca cccgaaugga gucucuaagc uacauaauac caacuuacac   1620
uuacaaaaug uugucccca aaauguagcc auucguaucu gcuccuaaua aaagaaagu    1680 uucuucacau aaaaaaaaaa aaaaaaaaaa aaaaaaaaaa aaaaaaaaaa aaaaaaaaaa   1740
aaaaaaaaaa                                                         1750

<210> SEQ ID NO 2
<211> LENGTH: 943
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5' cap (m7GpppGm)
<220> FEATURE:
<221> NAME/KEY: modified_base
<222> LOCATION: (940)..(941)
<223> OTHER INFORMATION: UNA monomer

<400> SEQUENCE: 2
gggaaacaua agucaacaca acauauacaa aacaaacgaa ucucaagcaa ucaagcauuc     60
uacuucuauu gcagcaauuu aaaucauuuc uuuuaaagca aaagcaauuu ucugaaaauu    120
uucaccauuu acgaacgaua gccauggggg ugcacgaaug uccugccugg cuguggcuuc    180
uccugucccu gcugucgcuc ccucugggcc uccaguccu gggcgcccca ccacgccuca    240
ucugugacag ccgaguccug gagagguacc ucuuggaggc caaggaggcc gagaauauca    300
cgacgggcug ugcugaacac ugcagcuuga augagaauau cacugucccca gacaccaaag   360 uuaauuucua ugccuggaag aggauggagg ucgggcagca ggccguagaa gucuggcagg    420
gccuggcccu gcugucggaa gcugccugc ggggccaggc ccuguugguc aacucuucc     480 agccguggga gccccugcag cugcaugugg auaaagccgu caguggccuu cgcagccuca    540
ccacucugcu ucgggcucug ggagcccaga aggaagccau cucccucca gaugcggccu     600 cagcugcucc acuccgaaca aucacugcug acacuuuccg caaacucuuc cgagucuacu    660
ccaauuuccu ccggggaaag cugaagcugu acacagggga ggccugcagg caggggaca    720 gaugacuagu gacugacuag gaucugguua ccacuaaacc agccucaaga cacccgaau    780 ggagucucua agcuacauaa uaccaacuua cacuuacaaa auguugcccc caaaaaugua   840
gccauucgua ucugcuccua auaaaagaa aguuucuuca cauaaaaaaa aaaaaaaaaa    900
```
aaaaaaaaaa aaaaaaaaaa aaaaaaaaaa aaaaaaaaaa aaa    943

<210> SEQ ID NO 3
<211> LENGTH: 940
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' cap (m7GpppGm)
<220> FEATURE:
<221> NAME/KEY: modified_base
<222> LOCATION: (939)..(940)
<223> OTHER INFORMATION: a, c, t, g, unknown or other

<400> SEQUENCE: 3
gggaaacaua agucaacaca acauauacaa aacaaacgaa ucucaagcaa ucaagcauuc    60
uacuucuauu gcagcaauuu aaaucauuuc uuuuaaagca aaagcaauuu ucugaaaauu   120
uucaccauuu acgaacgaua gccauggggg ugcccgaacg ucccacccug cugcuuuuac   180
ucuccuugcu acugauuccu cugggccucc caguccucug ugcuccccca cgccucaucu   240
gcgacagucg aguucuggag agguacaucu uagaggccaa ggaggcagaa aaugucacga   300
uggguugugc agaaggcccc agacugagug aaaauauuac agucccagau accaaaguca   360
acuucuaugc uuggaaaaga auggaggugg aagaacaggc cauagaaguu uggcaaggcc   420
ugucccugcu cucagaagcc auccugcagg cccaggcccu gcuagccaau uccucccagc   480
caccagagac ccuucagcuu cauauagaca aagccaucag uggucuacgu agccucacuu   540
cacugcuucg gguacuggga gcucagaagg aauugaugc gccuccagau accaccccac   600
cugcuccacu ccgaacacuc acagugggaua cuuucgcaa gcucuuccgg gucuacgcca   660
acuuccuccg ggggaaacug aagcuguaca cgggagaggu cugcaggaga ggggacaggt   720
gacuagugac ugacuaggau cugguuacca cuaaaccagc cucaagaaca cccgaaugga   780
gucucuaagc uacauaauac caacuuacac uuacaaaaug uugucccca aaauguagcc   840
auucguaucu gcuccuaaua aaaagaaagu uucuucacau aaaaaaaaaa aaaaaaaaaa   900
aaaaaaaaaa aaaaaaaaaa aaaaaaaaaa aaaaaaaaaa                        940

<210> SEQ ID NO 4
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (57)..(58)
<223> OTHER INFORMATION: UNA monomer

<400> SEQUENCE: 4
aaaaaaaaaa aaaaaaaaaa aaaaaaaaaa aaaaaaaaaa aaaaaaaaaa aaaaaaaaaa    60

<210> SEQ ID NO 5
<211> LENGTH: 60
<212> TYPE: RNA
<213> ORGANISM: Artificial Sequence
<220> FEATURE:
<223> OTHER INFORMATION: Description of Artificial Sequence: Synthetic

```
        oligonucleotide
<220> FEATURE:
<221> NAME/KEY: modified_base
<222> LOCATION: (55)..(56)
<223> OTHER INFORMATION: UNA monomer

<400> SEQUENCE: 5
aaaaaaaaaa aaaaaaaaaa aaaaaaaaaa aaaaaaaaaa aaaaaaaaaa aaaaaaaaaa      60

<210> SEQ ID NO 6
<211> LENGTH: 60
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (53)..(54)
<223> OTHER INFORMATION: UNA monomer

<400> SEQUENCE: 6
aaaaaaaaaa aaaaaaaaaa aaaaaaaaaa aaaaaaaaaa aaaaaaaaaa aaaaaaaaaa      60

<210> SEQ ID NO 7
<211> LENGTH: 60
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (51)..(52)
<223> OTHER INFORMATION: UNA monomer

<400> SEQUENCE: 7
aaaaaaaaaa aaaaaaaaaa aaaaaaaaaa aaaaaaaaaa aaaaaaaaaa aaaaaaaaaa      60

<210> SEQ ID NO 8
<211> LENGTH: 60
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (49)..(50)
<223> OTHER INFORMATION: UNA monomer

<400> SEQUENCE: 8
aaaaaaaaaa aaaaaaaaaa aaaaaaaaaa aaaaaaaaaa aaaaaaaaaa aaaaaaaaaa      60

<210> SEQ ID NO 9
<211> LENGTH: 60
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (47)..(48)
<223> OTHER INFORMATION: UNA monomer

<400> SEQUENCE: 9
aaaaaaaaaa aaaaaaaaaa aaaaaaaaaa aaaaaaaaaa aaaaaaaaaa aaaaaaaaaa      60
```

```
<210> SEQ ID NO 10
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (45)..(46)
<223> OTHER INFORMATION: UNA monomer

<400> SEQUENCE: 10
aaaaaaaaaa aaaaaaaaaa aaaaaaaaaa aaaaaaaaaa aaaaaaaaaa aaaaaaaaaa      60

<210> SEQ ID NO 11
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: UNA monomer

<400> SEQUENCE: 11
aaaaaaaaaa aaaaaaaaaa aaaaaaaaaa aaaaaaaaaa aaaaaaaaaa aaaaaaaaaa      60

<210> SEQ ID NO 12
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)..(42)
<223> OTHER INFORMATION: UNA monomer

<400> SEQUENCE: 12
aaaaaaaaaa aaaaaaaaaa aaaaaaaaaa aaaaaaaaaa aaaaaaaaaa aaaaaaaaaa      60

<210> SEQ ID NO 13
<211> LENGTH: 1618
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5' cap (m7GpppGm)
<220> FEATURE:
<221> NAME/KEY: modified_base
<222> LOCATION: (1613)..(1614)
<223> OTHER INFORMATION: UNA monomer

<400> SEQUENCE: 13
gggaaacaua agucaacaca acauauacaa aacaaacgaa ucucaagcaa ucaagcauuc      60
uacuucuauu gcagcaauuu aaaucauuuc uuuuaaagca aaagcaauuu ucugaaaauu     120
uucaccauuu acgaacgaua gccaugccgu cuucugucuc guggggcauc cuccugcugg     180
caggccugug cugccugguc ccugucuccc uggcugagga uccccaggga gaugcugccc     240
agaagacaga uacaucccac caugaucagg aucacccaac cuucaacaag aucaccccca     300
accuggcuga guucgccuuc agccuauacc gccagcuggc acaccagucc aacagcacca     360
```

| | |
|---|---|
| auaucuucuu cuccccagug agcaucgcua cagccuuugc aaugcucucc cuggggacca | 420 |
| aggcugacac ucacgaugaa auccuggagg gccugaauuu caaccucacg gagauuccgg | 480 |
| aggcucagau ccaugaaggc uuccaggaac uccuccguac ccucaaccag ccagacagcc | 540 |
| agcuccagcu gaccaccggc aauggccugu uccucagcga gggccugaag cuaguggaua | 600 |
| aguuuuugga ggauguuaaa aaguuguacc acucagaagc cuucacuguc aacuucgggg | 660 |
| acaccgaaga ggccaagaaa cagaucaacg auuacgugga gaagggguacu caagggaaaa | 720 |
| uugugauuu ggucaaggag cuugacagag acacaguuuu ugcucuggug aauuacaucu | 780 |
| ucuuuaaagg caaaugggag agacccuuug aagucaagga caccgaggaa gaggacuucc | 840 |
| acguggacca ggugaccacc gugaaggugc cuaugaugaa gcguuuaggc auguuuaaca | 900 |
| uccagcacug uaagaagcug uccagcuggg ugcugcugau gaaauaccug ggcaaugcca | 960 |
| ccgccaucuu cuuccugccu gaugagggga aacuacagca ccuggaaaau gaacucaccc | 1020 |
| acgauaucau caccaaguuc cuggaaaaug aagacagaag gucugccagc uuacauuuac | 1080 |
| ccaaacuguc cauuacugga accaugaucu ugaagagcgu ccuggucaa cugggcauca | 1140 |
| cuaaggucuu cagcaauggg gcugaccucu ccggggucac agaggaggca ccccugaagc | 1200 |
| ucuccaaggc cgugcauaag gcugugcuga ccaucgacga gaaagggacu gaagcugcug | 1260 |
| gggccauguu uuuagaggcc auacccaugu cuauccccc cgaggucaag uucaacaaac | 1320 |
| ccuuugucuu cuuaaugauu gaacaaaaua ccaagucucc ccucuucaug ggaaaagugg | 1380 |
| ugaaucccac ccaaaaauaa cuagugacug acuaggaucu gguuaccacu aaaccagccu | 1440 |
| caagaacacc cgaauggagu cucuaagcua cauaauacca acuuacacuu acaaaauguu | 1500 |
| gucccccaaa auguagccau ucguaucgc uccuaauaaa aagaaaguuu cuucacauaa | 1560 |
| aaaaaaaaaa aaaaaaaaaa aaaaaaaaaa aaaaaaaaaa aaaaaaaaaa aaaaaaaa | 1618 |

```
<210> SEQ ID NO 14
<211> LENGTH: 943
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5' cap (m7GpppGm)
<220> FEATURE:
<221> NAME/KEY: modified_base
<222> LOCATION: (938)..(939)
<223> OTHER INFORMATION: UNA monomer

<400> SEQUENCE: 14
```

| | |
|---|---|
| gggaaacaua agucaacaca acauauacaa aacaaacgaa ucucaagcaa ucaagcauuc | 60 |
| uacuucuauu gcagcaauuu aaaucauuuc uuuuaaagca aaagcaauuu ucugaaaauu | 120 |
| uucaccauuu acgaacgaua gccauggggg ugcacgaaug uccugccugg cuguggcuuc | 180 |
| uccugucccu gcugucgcuc ccucgggcc uccagccu gggcgcccca ccacgccuca | 240 |
| ucugugacag ccgaguccug gagagguacc ucuuggaggc caaggaggcc gagaauauca | 300 |
| cgacgggcug ugcugaacac ugcagccuuga augagaauau cacugucccca gacaccaaag | 360 |
| uuaauuucua ugccuggaag aggauggagg ucggcagca ggccguagaa ucugcagg | 420 |
| gccuggcccu gcugucggaa gcuguccugc ggggccaggc ccguuggguc aacucuuccc | 480 |
| agccguggga gccccugcag cugcauguqg auaaagccgu cagugccuu cgcagccuca | 540 |
| ccacucugcu ucgggcucug ggagcccaga aggaagccau cuccccucca gaugcggccu | 600 |

-continued

```
cagcugcucc acuccgaaca aucacugcug acacuuuccg caaacucuuc cgagucuacu    660
ccaauuuccu ccggggaaag cugaagcugu acacagggga ggccugcagg acagggaca     720 gaugacuagu gacugacuag gaucugguua ccacuaaacc agccucaaga acacccgaau    780
ggagucucua agcuacauaa uaccaacuua cacuuacaaa auguugcccc ccaaaaugua    840
gccauucgua ucugcuccua auaaaaagaa aguuucuuca cauaaaaaaa aaaaaaaaaa    900 aaaaaaaaa  aaaaaaaaaa aaaaaaaaaa aaaaaaaaaa aaa                     943

<210> SEQ ID NO 15
<211> LENGTH: 1386
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: UNA monomer
<220> FEATURE:
<221> NAME/KEY: modified_base
<222> LOCATION: (33)..(33)
<223> OTHER INFORMATION: UNA monomer
<220> FEATURE:
<221> NAME/KEY: modified_base
<222> LOCATION: (63)..(63)
<223> OTHER INFORMATION: UNA monomer
<220> FEATURE:
<221> NAME/KEY: modified_base
<222> LOCATION: (93)..(93)
<223> OTHER INFORMATION: UNA monomer
<220> FEATURE:
<221> NAME/KEY: modified_base
<222> LOCATION: (123)..(123)
<223> OTHER INFORMATION: UNA monomer
<220> FEATURE:
<221> NAME/KEY: modified_base
<222> LOCATION: (153)..(153)
<223> OTHER INFORMATION: UNA monomer
<220> FEATURE:
<221> NAME/KEY: modified_base
<222> LOCATION: (183)..(183)
<223> OTHER INFORMATION: UNA monomer
<220> FEATURE:
<221> NAME/KEY: modified_base
<222> LOCATION: (213)..(213)
<223> OTHER INFORMATION: UNA monomer
<220> FEATURE:
<221> NAME/KEY: modified_base
<222> LOCATION: (243)..(243)
<223> OTHER INFORMATION: UNA monomer
<220> FEATURE:
<221> NAME/KEY: modified_base
<222> LOCATION: (273)..(273)
<223> OTHER INFORMATION: UNA monomer
<220> FEATURE:
<221> NAME/KEY: modified_base
<222> LOCATION: (303)..(303)
<223> OTHER INFORMATION: UNA monomer
<220> FEATURE:
<221> NAME/KEY: modified_base
<222> LOCATION: (333)..(333)
<223> OTHER INFORMATION: UNA monomer
<220> FEATURE:
<221> NAME/KEY: modified_base
<222> LOCATION: (363)..(363)
<223> OTHER INFORMATION: UNA monomer
<220> FEATURE:
<221> NAME/KEY: modified_base
<222> LOCATION: (393)..(393)
<223> OTHER INFORMATION: UNA monomer
<220> FEATURE:
<221> NAME/KEY: modified_base
<222> LOCATION: (423)..(423)
```

```
<223> OTHER INFORMATION: UNA monomer
<220> FEATURE:
<221> NAME/KEY: modified_base
<222> LOCATION: (453)..(453)
<223> OTHER INFORMATION: UNA monomer
<220> FEATURE:
<221> NAME/KEY: modified_base
<222> LOCATION: (483)..(483)
<223> OTHER INFORMATION: UNA monomer
<220> FEATURE:
<221> NAME/KEY: modified_base
<222> LOCATION: (513)..(513)
<223> OTHER INFORMATION: UNA monomer
<220> FEATURE:
<221> NAME/KEY: modified_base
<222> LOCATION: (543)..(543)
<223> OTHER INFORMATION: UNA monomer
<220> FEATURE:
<221> NAME/KEY: modified_base
<222> LOCATION: (573)..(573)
<223> OTHER INFORMATION: UNA monomer
<220> FEATURE:
<221> NAME/KEY: modified_base
<222> LOCATION: (603)..(603)
<223> OTHER INFORMATION: UNA monomer
<220> FEATURE:
<221> NAME/KEY: modified_base
<222> LOCATION: (633)..(633)
<223> OTHER INFORMATION: UNA monomer
<220> FEATURE:
<221> NAME/KEY: modified_base
<222> LOCATION: (663)..(663)
<223> OTHER INFORMATION: UNA monomer
<220> FEATURE:
<221> NAME/KEY: modified_base
<222> LOCATION: (693)..(693)
<223> OTHER INFORMATION: UNA monomer
<220> FEATURE:
<221> NAME/KEY: modified_base
<222> LOCATION: (723)..(723)
<223> OTHER INFORMATION: UNA monomer
<220> FEATURE:
<221> NAME/KEY: modified_base
<222> LOCATION: (753)..(753)
<223> OTHER INFORMATION: UNA monomer
<220> FEATURE:
<221> NAME/KEY: modified_base
<222> LOCATION: (783)..(783)
<223> OTHER INFORMATION: UNA monomer
<220> FEATURE:
<221> NAME/KEY: modified_base
<222> LOCATION: (813)..(813)
<223> OTHER INFORMATION: UNA monomer
<220> FEATURE:
<221> NAME/KEY: modified_base
<222> LOCATION: (843)..(843)
<223> OTHER INFORMATION: UNA monomer
<220> FEATURE:
<221> NAME/KEY: modified_base
<222> LOCATION: (873)..(873)
<223> OTHER INFORMATION: UNA monomer
<220> FEATURE:
<221> NAME/KEY: modified_base
<222> LOCATION: (903)..(903)
<223> OTHER INFORMATION: UNA monomer
<220> FEATURE:
<221> NAME/KEY: modified_base
<222> LOCATION: (933)..(933)
<223> OTHER INFORMATION: UNA monomer
<220> FEATURE:
<221> NAME/KEY: modified_base
<222> LOCATION: (963)..(963)
<223> OTHER INFORMATION: UNA monomer
<220> FEATURE:
<221> NAME/KEY: modified_base
<222> LOCATION: (993)..(993)
<223> OTHER INFORMATION: UNA monomer
<220> FEATURE:
<221> NAME/KEY: modified_base
```

```
<222> LOCATION: (1023)..(1023)
<223> OTHER INFORMATION: UNA monomer
<220> FEATURE:
<221> NAME/KEY: modified_base
<222> LOCATION: (1053)..(1053)
<223> OTHER INFORMATION: UNA monomer
<220> FEATURE:
<221> NAME/KEY: modified_base
<222> LOCATION: (1083)..(1083)
<223> OTHER INFORMATION: UNA monomer
<220> FEATURE:
<221> NAME/KEY: modified_base
<222> LOCATION: (1113)..(1113)
<223> OTHER INFORMATION: UNA monomer
<220> FEATURE:
<221> NAME/KEY: modified_base
<222> LOCATION: (1143)..(1143)
<223> OTHER INFORMATION: UNA monomer
<220> FEATURE:
<221> NAME/KEY: modified_base
<222> LOCATION: (1173)..(1173)
<223> OTHER INFORMATION: UNA monomer
<220> FEATURE:
<221> NAME/KEY: modified_base
<222> LOCATION: (1203)..(1203)
<223> OTHER INFORMATION: UNA monomer
<220> FEATURE:
<221> NAME/KEY: modified_base
<222> LOCATION: (1233)..(1233)
<223> OTHER INFORMATION: UNA monomer
<220> FEATURE:
<221> NAME/KEY: modified_base
<222> LOCATION: (1263)..(1263)
<223> OTHER INFORMATION: UNA monomer
<220> FEATURE:
<221> NAME/KEY: modified_base
<222> LOCATION: (1293)..(1293)
<223> OTHER INFORMATION: UNA monomer
<220> FEATURE:
<221> NAME/KEY: modified_base
<222> LOCATION: (1323)..(1323)
<223> OTHER INFORMATION: UNA monomer
<220> FEATURE:
<221> NAME/KEY: modified_base
<222> LOCATION: (1353)..(1353)
<223> OTHER INFORMATION: UNA monomer
<220> FEATURE:
<221> NAME/KEY: modified_base
<222> LOCATION: (1383)..(1383)
<223> OTHER INFORMATION: UNA monomer

<400> SEQUENCE: 15
augcagcgcg ugaacaugau cauggcagaa ucaccaggcc ucaucaccau cugccuuuua      60
ggauaucuac ucagugcuga auguacaguu uuucuugauc augaaaacgc caacaaaauu     120
cugaaucggc caaagaggua uaauucaggu aaauuggaag aguuuguuca agggaaccuu     180
gagagagaau guauggaaga aaaguguagu uuugaagaag cacgagaagu uuugaaaac      240 acugaaagaa caacugaauu uuggaagcag uauguugaug gagaucagug ugaguccaau     300
ccauguuuaa auggcggcag uugcaaggau gacauuaauu ccaugaaaug uugguguccc     360
uuuggauuug aaggaaagaa cuguaauua gaugaaacau guaacauuaa gaauggcaga     420
ugcgagcagu uuuguaaaaa uagugcugau aacaagguggg uuugcuccug uacugaggga     480
uaucgacuug cagaaaacca gaaguccugu gaaccagcag ugccauuucc auguggaaga     540
guuucuguuu cacaaacuuc uaagcucacc cgucugagaa cuguuuuccc ugauguggac     600
uauguaaauu cuacugaagc ugaaaccauu uggauaaca ucacucaaag cacccaauca     660
uuuaaugacu ucacucgggu uguuggugga gaagaugcca aaccagguca auucccuugg     720
cagguuguuu ugaauggua aaguugaugca uucuguggag gcucuaucgu uaaugaaaa     780
```

| | |
|---|---:|
| uggauuguaa cugcugccca cuguguugaa acugguguua aaauuacagu gucgcaggu | 840 |
| gaacauaaua uugaggagac agaacauaca gagcaaaagc gaaaugugau ucgaauuauu | 900 |
| ccucaccaca acuacaaugc agcuauuaau aaguacaacc augacauugc ccuucuggaa | 960 |
| cuggacgaac ccuuagugcu aaacagcuac guuacaccua uuugcauugc ugacaaggaa | 1020 |
| uacacgaaca ucuuccucaa auuuggaucu ggcuauguaa guggcugggg aagagucuuc | 1080 |
| cacaaaggga gaucagcuuu aguucuucag uaccuuagag uuccacugu ugaccgagcc | 1140 |
| acaugucuuc gaucuacaaa guucaccauc uauaacaaca guucugugc uggcuuccau | 1200 |
| gaaggaggua gagauucaug ucaaggagau aguggggac cccauguuac ugaaguggaa | 1260 |
| gggaccaguu ucuuaacugg aauuauuagc uggggugaag agugugcaau gaaaggcaaa | 1320 |
| uauggaauau auaccaaggu aucccgguau gucaacugga uuaaggaaaa aacaaagcuc | 1380 |
| acuuaa | 1386 |

<210> SEQ ID NO 16
<211> LENGTH: 1386
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (2)..(4)
<223> OTHER INFORMATION: UNA monomer
<220> FEATURE:
<221> NAME/KEY: modified_base
<222> LOCATION: (1383)..(1385)
<223> OTHER INFORMATION: UNA monomer

<400> SEQUENCE: 16

| | |
|---|---:|
| augcagcgcg ugaacaugau cauggcagaa ucaccaggcc ucaucaccau cugccuuuua | 60 |
| ggauaucuac ucagugcuga auguacaguu uuucuugauc augaaaacgc caacaaaauu | 120 |
| cugaaucggc caaagaggua uaauucaggu aaauuggaag aguuuguuca agggaaccuu | 180 |
| gagagagaau guauggaaga aaagugnuagu uuugaagaag cacgagaagu uuuugaaaac | 240 |
| acugaaagaa caacugaauu uuggaagcag uauguugaug gagaucagug ugaguccaau | 300 |
| ccauguuuaa auggcggcag uugcaaggau gacauuaauu ccuaugaaug uuggugnuccc | 360 |
| uuuggauuug aaggaaagaa cugugaauua gauguaacau guaacauuaa gaauggcaga | 420 |
| ugcgagcagu uuuguaaaaa uagugcugau aacaaggugg uuugcuccug uacugaggga | 480 |
| uaucgacuug cagaaaacca gaaguccugu gaaccagcag ugccauuucc augugagaaa | 540 |
| guuucuguuu cacaaacuuc uaagcucacc cgugcugaga cuguuuuucc ugaugnuggac | 600 |
| uauguaaauu cuacugaagc ugaaaccauu uggauaaca ucacucaaag cacccaauca | 660 |
| uuuaaugacu ucacucgggu uguggugga gaagaugcca aaccagguca auucccuugg | 720 |
| caguugnuuu ugaaugguaa agugaugnca uucuguggag gcucuaucgu uaaugaaaaa | 780 |
| uggauuguaa cugcugccca cuguguugaa acugguguua aaauuacagu gucgcaggu | 840 |
| gaacauaaua uugaggagac agaacauaca gagcaaaagc gaaaugugau ucgaauuauu | 900 |
| ccucaccaca acuacaaugc agcuauuaau aaguacaacc augacauugc ccuucuggaa | 960 |
| cuggacgaac ccuuagugcu aaacagcuac guuacaccua uuugcauugc ugacaaggaa | 1020 |
| uacacgaaca ucuuccucaa auuuggaucu ggcuauguaa guggcugggg aagagucuuc | 1080 |
| cacaaaggga gaucagcuuu aguucuucag uaccuuagag uuccacugu ugaccgagcc | 1140 |

```
acaugucuuc gaucuacaaa guucaccauc uauaacaaca uguucugugc uggcuuccau    1200
gaaggaggua gagauucaug ucaaggagau aguggggggac cccauguuac ugaaguggaa    1260
gggaccaguu ucuuaacugg aauuauuagc uggggugaag agugugcaau gaaaggcaaa    1320
uauggaauau auaccaaggu aucccgguau gucaacugga uuaaggaaaa aacaaagcuc    1380
acuuaa                                                                1386

<210> SEQ ID NO 17
<211> LENGTH: 1386
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (11)..(11)
<223> OTHER INFORMATION: UNA monomer
<220> FEATURE:
<221> NAME/KEY: modified_base
<222> LOCATION: (17)..(17)
<223> OTHER INFORMATION: UNA monomer
<220> FEATURE:
<221> NAME/KEY: modified_base
<222> LOCATION: (20)..(20)
<223> OTHER INFORMATION: UNA monomer
<220> FEATURE:
<221> NAME/KEY: modified_base
<222> LOCATION: (23)..(23)
<223> OTHER INFORMATION: UNA monomer
<220> FEATURE:
<221> NAME/KEY: modified_base
<222> LOCATION: (31)..(31)
<223> OTHER INFORMATION: UNA monomer
<220> FEATURE:
<221> NAME/KEY: modified_base
<222> LOCATION: (41)..(41)
<223> OTHER INFORMATION: UNA monomer
<220> FEATURE:
<221> NAME/KEY: modified_base
<222> LOCATION: (44)..(44)
<223> OTHER INFORMATION: UNA monomer
<220> FEATURE:
<221> NAME/KEY: modified_base
<222> LOCATION: (50)..(50)
<223> OTHER INFORMATION: UNA monomer
<220> FEATURE:
<221> NAME/KEY: modified_base
<222> LOCATION: (52)..(52)
<223> OTHER INFORMATION: UNA monomer
<220> FEATURE:
<221> NAME/KEY: modified_base
<222> LOCATION: (56)..(59)
<223> OTHER INFORMATION: UNA monomer
<220> FEATURE:
<221> NAME/KEY: modified_base
<222> LOCATION: (64)..(64)
<223> OTHER INFORMATION: UNA monomer
<220> FEATURE:
<221> NAME/KEY: modified_base
<222> LOCATION: (66)..(66)
<223> OTHER INFORMATION: UNA monomer
<220> FEATURE:
<221> NAME/KEY: modified_base
<222> LOCATION: (68)..(68)
<223> OTHER INFORMATION: UNA monomer
<220> FEATURE:
<221> NAME/KEY: modified_base
<222> LOCATION: (71)..(71)
<223> OTHER INFORMATION: UNA monomer
<220> FEATURE:
```

```
<221> NAME/KEY: modified_base
<222> LOCATION: (75)..(75)
<223> OTHER INFORMATION: UNA monomer
<220> FEATURE:
<221> NAME/KEY: modified_base
<222> LOCATION: (78)..(78)
<223> OTHER INFORMATION: UNA monomer
<220> FEATURE:
<221> NAME/KEY: modified_base
<222> LOCATION: (82)..(82)
<223> OTHER INFORMATION: UNA monomer
<220> FEATURE:
<221> NAME/KEY: modified_base
<222> LOCATION: (84)..(84)
<223> OTHER INFORMATION: UNA monomer
<220> FEATURE:
<221> NAME/KEY: modified_base
<222> LOCATION: (89)..(93)
<223> OTHER INFORMATION: UNA monomer
<220> FEATURE:
<221> NAME/KEY: modified_base
<222> LOCATION: (95)..(96)
<223> OTHER INFORMATION: UNA monomer
<220> FEATURE:
<221> NAME/KEY: modified_base
<222> LOCATION: (99)..(99)
<223> OTHER INFORMATION: UNA monomer
<220> FEATURE:
<221> NAME/KEY: modified_base
<222> LOCATION: (102)..(102)
<223> OTHER INFORMATION: UNA monomer
<220> FEATURE:
<221> NAME/KEY: modified_base
<222> LOCATION: (119)..(120)
<223> OTHER INFORMATION: UNA monomer
<220> FEATURE:
<221> NAME/KEY: modified_base
<222> LOCATION: (122)..(122)
<223> OTHER INFORMATION: UNA monomer
<220> FEATURE:
<221> NAME/KEY: modified_base
<222> LOCATION: (126)..(126)
<223> OTHER INFORMATION: UNA monomer
<220> FEATURE:
<221> NAME/KEY: modified_base
<222> LOCATION: (139)..(139)
<223> OTHER INFORMATION: UNA monomer
<220> FEATURE:
<221> NAME/KEY: modified_base
<222> LOCATION: (141)..(141)
<223> OTHER INFORMATION: UNA monomer
<220> FEATURE:
<221> NAME/KEY: modified_base
<222> LOCATION: (144)..(145)
<223> OTHER INFORMATION: UNA monomer
<220> FEATURE:
<221> NAME/KEY: modified_base
<222> LOCATION: (150)..(150)
<223> OTHER INFORMATION: UNA monomer
<220> FEATURE:
<221> NAME/KEY: modified_base
<222> LOCATION: (154)..(155)
<223> OTHER INFORMATION: UNA monomer
<220> FEATURE:
<221> NAME/KEY: modified_base
<222> LOCATION: (163)..(165)
<223> OTHER INFORMATION: UNA monomer
<220> FEATURE:
<221> NAME/KEY: modified_base
<222> LOCATION: (167)..(168)
<223> OTHER INFORMATION: UNA monomer
<220> FEATURE:
<221> NAME/KEY: modified_base
<222> LOCATION: (179)..(180)
<223> OTHER INFORMATION: UNA monomer
<220> FEATURE:
<221> NAME/KEY: modified_base
<222> LOCATION: (190)..(190)
<223> OTHER INFORMATION: UNA monomer
```

```
<220> FEATURE:
<221> NAME/KEY: modified_base
<222> LOCATION: (192)..(192)
<223> OTHER INFORMATION: UNA monomer
<220> FEATURE:
<221> NAME/KEY: modified_base
<222> LOCATION: (194)..(194)
<223> OTHER INFORMATION: UNA monomer
<220> FEATURE:
<221> NAME/KEY: modified_base
<222> LOCATION: (205)..(205)
<223> OTHER INFORMATION: UNA monomer
<220> FEATURE:
<221> NAME/KEY: modified_base
<222> LOCATION: (207)..(207)
<223> OTHER INFORMATION: UNA monomer
<220> FEATURE:
<221> NAME/KEY: modified_base
<222> LOCATION: (210)..(213)
<223> OTHER INFORMATION: UNA monomer
<220> FEATURE:
<221> NAME/KEY: modified_base
<222> LOCATION: (230)..(234)
<223> OTHER INFORMATION: UNA monomer
<220> FEATURE:
<221> NAME/KEY: modified_base
<222> LOCATION: (243)..(243)
<223> OTHER INFORMATION: UNA monomer
<220> FEATURE:
<221> NAME/KEY: modified_base
<222> LOCATION: (255)..(255)
<223> OTHER INFORMATION: UNA monomer
<220> FEATURE:
<221> NAME/KEY: modified_base
<222> LOCATION: (259)..(262)
<223> OTHER INFORMATION: UNA monomer
<220> FEATURE:
<221> NAME/KEY: modified_base
<222> LOCATION: (271)..(271)
<223> OTHER INFORMATION: UNA monomer
<220> FEATURE:
<221> NAME/KEY: modified_base
<222> LOCATION: (273)..(273)
<223> OTHER INFORMATION: UNA monomer
<220> FEATURE:
<221> NAME/KEY: modified_base
<222> LOCATION: (275)..(276)
<223> OTHER INFORMATION: UNA monomer
<220> FEATURE:
<221> NAME/KEY: modified_base
<222> LOCATION: (279)..(279)
<223> OTHER INFORMATION: UNA monomer
<220> FEATURE:
<221> NAME/KEY: modified_base
<222> LOCATION: (285)..(285)
<223> OTHER INFORMATION: UNA monomer
<220> FEATURE:
<221> NAME/KEY: modified_base
<222> LOCATION: (289)..(289)
<223> OTHER INFORMATION: UNA monomer
<220> FEATURE:
<221> NAME/KEY: modified_base
<222> LOCATION: (291)..(291)
<223> OTHER INFORMATION: UNA monomer
<220> FEATURE:
<221> NAME/KEY: modified_base
<222> LOCATION: (295)..(295)
<223> OTHER INFORMATION: UNA monomer
<220> FEATURE:
<221> NAME/KEY: modified_base
<222> LOCATION: (300)..(300)
<223> OTHER INFORMATION: UNA monomer
<220> FEATURE:
<221> NAME/KEY: modified_base
<222> LOCATION: (304)..(304)
<223> OTHER INFORMATION: UNA monomer
<220> FEATURE:
<221> NAME/KEY: modified_base
<222> LOCATION: (306)..(308)
```

```
<223> OTHER INFORMATION: UNA monomer
<220> FEATURE:
<221> NAME/KEY: modified_base
<222> LOCATION: (312)..(312)
<223> OTHER INFORMATION: UNA monomer
<220> FEATURE:
<221> NAME/KEY: modified_base
<222> LOCATION: (321)..(322)
<223> OTHER INFORMATION: UNA monomer
<220> FEATURE:
<221> NAME/KEY: modified_base
<222> LOCATION: (330)..(330)
<223> OTHER INFORMATION: UNA monomer
<220> FEATURE:
<221> NAME/KEY: modified_base
<222> LOCATION: (335)..(336)
<223> OTHER INFORMATION: UNA monomer
<220> FEATURE:
<221> NAME/KEY: modified_base
<222> LOCATION: (339)..(340)
<223> OTHER INFORMATION: UNA monomer
<220> FEATURE:
<221> NAME/KEY: modified_base
<222> LOCATION: (343)..(343)
<223> OTHER INFORMATION: UNA monomer
<220> FEATURE:
<221> NAME/KEY: modified_base
<222> LOCATION: (345)..(345)
<223> OTHER INFORMATION: UNA monomer
<220> FEATURE:
<221> NAME/KEY: modified_base
<222> LOCATION: (349)..(349)
<223> OTHER INFORMATION: UNA monomer
<220> FEATURE:
<221> NAME/KEY: modified_base
<222> LOCATION: (351)..(352)
<223> OTHER INFORMATION: UNA monomer
<220> FEATURE:
<221> NAME/KEY: modified_base
<222> LOCATION: (355)..(355)
<223> OTHER INFORMATION: UNA monomer
<220> FEATURE:
<221> NAME/KEY: modified_base
<222> LOCATION: (357)..(357)
<223> OTHER INFORMATION: UNA monomer
<220> FEATURE:
<221> NAME/KEY: modified_base
<222> LOCATION: (361)..(363)
<223> OTHER INFORMATION: UNA monomer
<220> FEATURE:
<221> NAME/KEY: modified_base
<222> LOCATION: (367)..(369)
<223> OTHER INFORMATION: UNA monomer
<220> FEATURE:
<221> NAME/KEY: modified_base
<222> LOCATION: (382)..(382)
<223> OTHER INFORMATION: UNA monomer
<220> FEATURE:
<221> NAME/KEY: modified_base
<222> LOCATION: (384)..(384)
<223> OTHER INFORMATION: UNA monomer
<220> FEATURE:
<221> NAME/KEY: modified_base
<222> LOCATION: (388)..(389)
<223> OTHER INFORMATION: UNA monomer
<220> FEATURE:
<221> NAME/KEY: modified_base
<222> LOCATION: (393)..(393)
<223> OTHER INFORMATION: UNA monomer
<220> FEATURE:
<221> NAME/KEY: modified_base
<222> LOCATION: (395)..(395)
<223> OTHER INFORMATION: UNA monomer
<220> FEATURE:
<221> NAME/KEY: modified_base
<222> LOCATION: (400)..(400)
<223> OTHER INFORMATION: UNA monomer
<220> FEATURE:
<221> NAME/KEY: modified_base
```

```
<222> LOCATION: (402)..(402)
<223> OTHER INFORMATION: UNA monomer
<220> FEATURE:
<221> NAME/KEY: modified_base
<222> LOCATION: (407)..(408)
<223> OTHER INFORMATION: UNA monomer
<220> FEATURE:
<221> NAME/KEY: modified_base
<222> LOCATION: (414)..(414)
<223> OTHER INFORMATION: UNA monomer
<220> FEATURE:
<221> NAME/KEY: modified_base
<222> LOCATION: (421)..(421)
<223> OTHER INFORMATION: UNA monomer
<220> FEATURE:
<221> NAME/KEY: modified_base
<222> LOCATION: (430)..(433)
<223> OTHER INFORMATION: UNA monomer
<220> FEATURE:
<221> NAME/KEY: modified_base
<222> LOCATION: (435)..(435)
<223> OTHER INFORMATION: UNA monomer
<220> FEATURE:
<221> NAME/KEY: modified_base
<222> LOCATION: (441)..(441)
<223> OTHER INFORMATION: UNA monomer
<220> FEATURE:
<221> NAME/KEY: modified_base
<222> LOCATION: (444)..(444)
<223> OTHER INFORMATION: UNA monomer
<220> FEATURE:
<221> NAME/KEY: modified_base
<222> LOCATION: (447)..(447)
<223> OTHER INFORMATION: UNA monomer
<220> FEATURE:
<221> NAME/KEY: modified_base
<222> LOCATION: (450)..(450)
<223> OTHER INFORMATION: UNA monomer
<220> FEATURE:
<221> NAME/KEY: modified_base
<222> LOCATION: (458)..(458)
<223> OTHER INFORMATION: UNA monomer
<220> FEATURE:
<221> NAME/KEY: modified_base
<222> LOCATION: (461)..(463)
<223> OTHER INFORMATION: UNA monomer
<220> FEATURE:
<221> NAME/KEY: modified_base
<222> LOCATION: (466)..(466)
<223> OTHER INFORMATION: UNA monomer
<220> FEATURE:
<221> NAME/KEY: modified_base
<222> LOCATION: (469)..(469)
<223> OTHER INFORMATION: UNA monomer
<220> FEATURE:
<221> NAME/KEY: modified_base
<222> LOCATION: (471)..(471)
<223> OTHER INFORMATION: UNA monomer
<220> FEATURE:
<221> NAME/KEY: modified_base
<222> LOCATION: (474)..(474)
<223> OTHER INFORMATION: UNA monomer
<220> FEATURE:
<221> NAME/KEY: modified_base
<222> LOCATION: (481)..(481)
<223> OTHER INFORMATION: UNA monomer
<220> FEATURE:
<221> NAME/KEY: modified_base
<222> LOCATION: (483)..(483)
<223> OTHER INFORMATION: UNA monomer
<220> FEATURE:
<221> NAME/KEY: modified_base
<222> LOCATION: (488)..(489)
<223> OTHER INFORMATION: UNA monomer
<220> FEATURE:
<221> NAME/KEY: modified_base
<222> LOCATION: (505)..(505)
<223> OTHER INFORMATION: UNA monomer
<220> FEATURE:
```

```
<221> NAME/KEY: modified_base
<222> LOCATION: (508)..(508)
<223> OTHER INFORMATION: UNA monomer
<220> FEATURE:
<221> NAME/KEY: modified_base
<222> LOCATION: (510)..(510)
<223> OTHER INFORMATION: UNA monomer
<220> FEATURE:
<221> NAME/KEY: modified_base
<222> LOCATION: (521)..(521)
<223> OTHER INFORMATION: UNA monomer
<220> FEATURE:
<221> NAME/KEY: modified_base
<222> LOCATION: (526)..(528)
<223> OTHER INFORMATION: UNA monomer
<220> FEATURE:
<221> NAME/KEY: modified_base
<222> LOCATION: (532)..(532)
<223> OTHER INFORMATION: UNA monomer
<220> FEATURE:
<221> NAME/KEY: modified_base
<222> LOCATION: (534)..(534)
<223> OTHER INFORMATION: UNA monomer
<220> FEATURE:
<221> NAME/KEY: modified_base
<222> LOCATION: (542)..(544)
<223> OTHER INFORMATION: UNA monomer
<220> FEATURE:
<221> NAME/KEY: modified_base
<222> LOCATION: (546)..(546)
<223> OTHER INFORMATION: UNA monomer
<220> FEATURE:
<221> NAME/KEY: modified_base
<222> LOCATION: (548)..(550)
<223> OTHER INFORMATION: UNA monomer
<220> FEATURE:
<221> NAME/KEY: modified_base
<222> LOCATION: (558)..(559)
<223> OTHER INFORMATION: UNA monomer
<220> FEATURE:
<221> NAME/KEY: modified_base
<222> LOCATION: (561)..(561)
<223> OTHER INFORMATION: UNA monomer
<220> FEATURE:
<221> NAME/KEY: modified_base
<222> LOCATION: (566)..(566)
<223> OTHER INFORMATION: UNA monomer
<220> FEATURE:
<221> NAME/KEY: modified_base
<222> LOCATION: (573)..(573)
<223> OTHER INFORMATION: UNA monomer
<220> FEATURE:
<221> NAME/KEY: modified_base
<222> LOCATION: (576)..(576)
<223> OTHER INFORMATION: UNA monomer
<220> FEATURE:
<221> NAME/KEY: modified_base
<222> LOCATION: (582)..(582)
<223> OTHER INFORMATION: UNA monomer
<220> FEATURE:
<221> NAME/KEY: modified_base
<222> LOCATION: (584)..(588)
<223> OTHER INFORMATION: UNA monomer
<220> FEATURE:
<221> NAME/KEY: modified_base
<222> LOCATION: (591)..(591)
<223> OTHER INFORMATION: UNA monomer
<220> FEATURE:
<221> NAME/KEY: modified_base
<222> LOCATION: (594)..(594)
<223> OTHER INFORMATION: UNA monomer
<220> FEATURE:
<221> NAME/KEY: modified_base
<222> LOCATION: (596)..(596)
<223> OTHER INFORMATION: UNA monomer
<220> FEATURE:
<221> NAME/KEY: modified_base
<222> LOCATION: (601)..(601)
<223> OTHER INFORMATION: UNA monomer
```

-continued

```
<220> FEATURE:
<221> NAME/KEY: modified_base
<222> LOCATION: (603)..(603)
<223> OTHER INFORMATION: UNA monomer
<220> FEATURE:
<221> NAME/KEY: modified_base
<222> LOCATION: (605)..(605)
<223> OTHER INFORMATION: UNA monomer
<220> FEATURE:
<221> NAME/KEY: modified_base
<222> LOCATION: (609)..(610)
<223> OTHER INFORMATION: UNA monomer
<220> FEATURE:
<221> NAME/KEY: modified_base
<222> LOCATION: (612)..(612)
<223> OTHER INFORMATION: UNA monomer
<220> FEATURE:
<221> NAME/KEY: modified_base
<222> LOCATION: (615)..(615)
<223> OTHER INFORMATION: UNA monomer
<220> FEATURE:
<221> NAME/KEY: modified_base
<222> LOCATION: (621)..(621)
<223> OTHER INFORMATION: UNA monomer
<220> FEATURE:
<221> NAME/KEY: modified_base
<222> LOCATION: (629)..(632)
<223> OTHER INFORMATION: UNA monomer
<220> FEATURE:
<221> NAME/KEY: modified_base
<222> LOCATION: (636)..(636)
<223> OTHER INFORMATION: UNA monomer
<220> FEATURE:
<221> NAME/KEY: modified_base
<222> LOCATION: (641)..(641)
<223> OTHER INFORMATION: UNA monomer
<220> FEATURE:
<221> NAME/KEY: modified_base
<222> LOCATION: (645)..(645)
<223> OTHER INFORMATION: UNA monomer
<220> FEATURE:
<221> NAME/KEY: modified_base
<222> LOCATION: (658)..(658)
<223> OTHER INFORMATION: UNA monomer
<220> FEATURE:
<221> NAME/KEY: modified_base
<222> LOCATION: (661)..(663)
<223> OTHER INFORMATION: UNA monomer
<220> FEATURE:
<221> NAME/KEY: modified_base
<222> LOCATION: (666)..(666)
<223> OTHER INFORMATION: UNA monomer
<220> FEATURE:
<221> NAME/KEY: modified_base
<222> LOCATION: (670)..(671)
<223> OTHER INFORMATION: UNA monomer
<220> FEATURE:
<221> NAME/KEY: modified_base
<222> LOCATION: (675)..(675)
<223> OTHER INFORMATION: UNA monomer
<220> FEATURE:
<221> NAME/KEY: modified_base
<222> LOCATION: (680)..(681)
<223> OTHER INFORMATION: UNA monomer
<220> FEATURE:
<221> NAME/KEY: modified_base
<222> LOCATION: (683)..(684)
<223> OTHER INFORMATION: UNA monomer
<220> FEATURE:
<221> NAME/KEY: modified_base
<222> LOCATION: (687)..(687)
<223> OTHER INFORMATION: UNA monomer
<220> FEATURE:
<221> NAME/KEY: modified_base
<222> LOCATION: (696)..(696)
<223> OTHER INFORMATION: UNA monomer
<220> FEATURE:
<221> NAME/KEY: modified_base
<222> LOCATION: (708)..(708)
```

```
<223> OTHER INFORMATION: UNA monomer
<220> FEATURE:
<221> NAME/KEY: modified_base
<222> LOCATION: (712)..(713)
<223> OTHER INFORMATION: UNA monomer
<220> FEATURE:
<221> NAME/KEY: modified_base
<222> LOCATION: (717)..(718)
<223> OTHER INFORMATION: UNA monomer
<220> FEATURE:
<221> NAME/KEY: modified_base
<222> LOCATION: (725)..(726)
<223> OTHER INFORMATION: UNA monomer
<220> FEATURE:
<221> NAME/KEY: modified_base
<222> LOCATION: (728)..(731)
<223> OTHER INFORMATION: UNA monomer
<220> FEATURE:
<221> NAME/KEY: modified_base
<222> LOCATION: (735)..(735)
<223> OTHER INFORMATION: UNA monomer
<220> FEATURE:
<221> NAME/KEY: modified_base
<222> LOCATION: (738)..(738)
<223> OTHER INFORMATION: UNA monomer
<220> FEATURE:
<221> NAME/KEY: modified_base
<222> LOCATION: (743)..(744)
<223> OTHER INFORMATION: UNA monomer
<220> FEATURE:
<221> NAME/KEY: modified_base
<222> LOCATION: (747)..(747)
<223> OTHER INFORMATION: UNA monomer
<220> FEATURE:
<221> NAME/KEY: modified_base
<222> LOCATION: (751)..(752)
<223> OTHER INFORMATION: UNA monomer
<220> FEATURE:
<221> NAME/KEY: modified_base
<222> LOCATION: (754)..(754)
<223> OTHER INFORMATION: UNA monomer
<220> FEATURE:
<221> NAME/KEY: modified_base
<222> LOCATION: (756)..(756)
<223> OTHER INFORMATION: UNA monomer
<220> FEATURE:
<221> NAME/KEY: modified_base
<222> LOCATION: (763)..(763)
<223> OTHER INFORMATION: UNA monomer
<220> FEATURE:
<221> NAME/KEY: modified_base
<222> LOCATION: (765)..(765)
<223> OTHER INFORMATION: UNA monomer
<220> FEATURE:
<221> NAME/KEY: modified_base
<222> LOCATION: (767)..(767)
<223> OTHER INFORMATION: UNA monomer
<220> FEATURE:
<221> NAME/KEY: modified_base
<222> LOCATION: (770)..(771)
<223> OTHER INFORMATION: UNA monomer
<220> FEATURE:
<221> NAME/KEY: modified_base
<222> LOCATION: (774)..(774)
<223> OTHER INFORMATION: UNA monomer
<220> FEATURE:
<221> NAME/KEY: modified_base
<222> LOCATION: (781)..(781)
<223> OTHER INFORMATION: UNA monomer
<220> FEATURE:
<221> NAME/KEY: modified_base
<222> LOCATION: (785)..(786)
<223> OTHER INFORMATION: UNA monomer
<220> FEATURE:
<221> NAME/KEY: modified_base
<222> LOCATION: (788)..(788)
<223> OTHER INFORMATION: UNA monomer
<220> FEATURE:
<221> NAME/KEY: modified_base
```

```
<222> LOCATION: (792)..(792)
<223> OTHER INFORMATION: UNA monomer
<220> FEATURE:
<221> NAME/KEY: modified_base
<222> LOCATION: (795)..(795)
<223> OTHER INFORMATION: UNA monomer
<220> FEATURE:
<221> NAME/KEY: modified_base
<222> LOCATION: (802)..(802)
<223> OTHER INFORMATION: UNA monomer
<220> FEATURE:
<221> NAME/KEY: modified_base
<222> LOCATION: (804)..(804)
<223> OTHER INFORMATION: UNA monomer
<220> FEATURE:
<221> NAME/KEY: modified_base
<222> LOCATION: (806)..(807)
<223> OTHER INFORMATION: UNA monomer
<220> FEATURE:
<221> NAME/KEY: modified_base
<222> LOCATION: (813)..(813)
<223> OTHER INFORMATION: UNA monomer
<220> FEATURE:
<221> NAME/KEY: modified_base
<222> LOCATION: (816)..(816)
<223> OTHER INFORMATION: UNA monomer
<220> FEATURE:
<221> NAME/KEY: modified_base
<222> LOCATION: (818)..(819)
<223> OTHER INFORMATION: UNA monomer
<220> FEATURE:
<221> NAME/KEY: modified_base
<222> LOCATION: (824)..(825)
<223> OTHER INFORMATION: UNA monomer
<220> FEATURE:
<221> NAME/KEY: modified_base
<222> LOCATION: (830)..(831)
<223> OTHER INFORMATION: UNA monomer
<220> FEATURE:
<221> NAME/KEY: modified_base
<222> LOCATION: (833)..(833)
<223> OTHER INFORMATION: UNA monomer
<220> FEATURE:
<221> NAME/KEY: modified_base
<222> LOCATION: (840)..(840)
<223> OTHER INFORMATION: UNA monomer
<220> FEATURE:
<221> NAME/KEY: modified_base
<222> LOCATION: (846)..(846)
<223> OTHER INFORMATION: UNA monomer
<220> FEATURE:
<221> NAME/KEY: modified_base
<222> LOCATION: (849)..(849)
<223> OTHER INFORMATION: UNA monomer
<220> FEATURE:
<221> NAME/KEY: modified_base
<222> LOCATION: (851)..(852)
<223> OTHER INFORMATION: UNA monomer
<220> FEATURE:
<221> NAME/KEY: modified_base
<222> LOCATION: (867)..(867)
<223> OTHER INFORMATION: UNA monomer
<220> FEATURE:
<221> NAME/KEY: modified_base
<222> LOCATION: (885)..(885)
<223> OTHER INFORMATION: UNA monomer
<220> FEATURE:
<221> NAME/KEY: modified_base
<222> LOCATION: (887)..(887)
<223> OTHER INFORMATION: UNA monomer
<220> FEATURE:
<221> NAME/KEY: modified_base
<222> LOCATION: (890)..(891)
<223> OTHER INFORMATION: UNA monomer
<220> FEATURE:
<221> NAME/KEY: modified_base
<222> LOCATION: (896)..(897)
<223> OTHER INFORMATION: UNA monomer
<220> FEATURE:
```

```
<221> NAME/KEY: modified_base
<222> LOCATION: (899)..(900)
<223> OTHER INFORMATION: UNA monomer
<220> FEATURE:
<221> NAME/KEY: modified_base
<222> LOCATION: (903)..(903)
<223> OTHER INFORMATION: UNA monomer
<220> FEATURE:
<221> NAME/KEY: modified_base
<222> LOCATION: (913)..(913)
<223> OTHER INFORMATION: UNA monomer
<220> FEATURE:
<221> NAME/KEY: modified_base
<222> LOCATION: (918)..(918)
<223> OTHER INFORMATION: UNA monomer
<220> FEATURE:
<221> NAME/KEY: modified_base
<222> LOCATION: (924)..(924)
<223> OTHER INFORMATION: UNA monomer
<220> FEATURE:
<221> NAME/KEY: modified_base
<222> LOCATION: (926)..(927)
<223> OTHER INFORMATION: UNA monomer
<220> FEATURE:
<221> NAME/KEY: modified_base
<222> LOCATION: (930)..(930)
<223> OTHER INFORMATION: UNA monomer
<220> FEATURE:
<221> NAME/KEY: modified_base
<222> LOCATION: (934)..(934)
<223> OTHER INFORMATION: UNA monomer
<220> FEATURE:
<221> NAME/KEY: modified_base
<222> LOCATION: (942)..(942)
<223> OTHER INFORMATION: UNA monomer
<220> FEATURE:
<221> NAME/KEY: modified_base
<222> LOCATION: (947)..(948)
<223> OTHER INFORMATION: UNA monomer
<220> FEATURE:
<221> NAME/KEY: modified_base
<222> LOCATION: (953)..(954)
<223> OTHER INFORMATION: UNA monomer
<220> FEATURE:
<221> NAME/KEY: modified_base
<222> LOCATION: (956)..(956)
<223> OTHER INFORMATION: UNA monomer
<220> FEATURE:
<221> NAME/KEY: modified_base
<222> LOCATION: (962)..(962)
<223> OTHER INFORMATION: UNA monomer
<220> FEATURE:
<221> NAME/KEY: modified_base
<222> LOCATION: (973)..(974)
<223> OTHER INFORMATION: UNA monomer
<220> FEATURE:
<221> NAME/KEY: modified_base
<222> LOCATION: (977)..(977)
<223> OTHER INFORMATION: UNA monomer
<220> FEATURE:
<221> NAME/KEY: modified_base
<222> LOCATION: (980)..(980)
<223> OTHER INFORMATION: UNA monomer
<220> FEATURE:
<221> NAME/KEY: modified_base
<222> LOCATION: (988)..(988)
<223> OTHER INFORMATION: UNA monomer
<220> FEATURE:
<221> NAME/KEY: modified_base
<222> LOCATION: (992)..(993)
<223> OTHER INFORMATION: UNA monomer
<220> FEATURE:
<221> NAME/KEY: modified_base
<222> LOCATION: (999)..(999)
<223> OTHER INFORMATION: UNA monomer
<220> FEATURE:
<221> NAME/KEY: modified_base
<222> LOCATION: (1001)..(1003)
<223> OTHER INFORMATION: UNA monomer
```

-continued

```
<220> FEATURE:
<221> NAME/KEY: modified_base
<222> LOCATION: (1007)..(1008)
<223> OTHER INFORMATION: UNA monomer
<220> FEATURE:
<221> NAME/KEY: modified_base
<222> LOCATION: (1011)..(1011)
<223> OTHER INFORMATION: UNA monomer
<220> FEATURE:
<221> NAME/KEY: modified_base
<222> LOCATION: (1021)..(1021)
<223> OTHER INFORMATION: UNA monomer
<220> FEATURE:
<221> NAME/KEY: modified_base
<222> LOCATION: (1031)..(1031)
<223> OTHER INFORMATION: UNA monomer
<220> FEATURE:
<221> NAME/KEY: modified_base
<222> LOCATION: (1033)..(1034)
<223> OTHER INFORMATION: UNA monomer
<220> FEATURE:
<221> NAME/KEY: modified_base
<222> LOCATION: (1037)..(1037)
<223> OTHER INFORMATION: UNA monomer
<220> FEATURE:
<221> NAME/KEY: modified_base
<222> LOCATION: (1042)..(1044)
<223> OTHER INFORMATION: UNA monomer
<220> FEATURE:
<221> NAME/KEY: modified_base
<222> LOCATION: (1048)..(1048)
<223> OTHER INFORMATION: UNA monomer
<220> FEATURE:
<221> NAME/KEY: modified_base
<222> LOCATION: (1050)..(1050)
<223> OTHER INFORMATION: UNA monomer
<220> FEATURE:
<221> NAME/KEY: modified_base
<222> LOCATION: (1054)..(1054)
<223> OTHER INFORMATION: UNA monomer
<220> FEATURE:
<221> NAME/KEY: modified_base
<222> LOCATION: (1056)..(1056)
<223> OTHER INFORMATION: UNA monomer
<220> FEATURE:
<221> NAME/KEY: modified_base
<222> LOCATION: (1058)..(1058)
<223> OTHER INFORMATION: UNA monomer
<220> FEATURE:
<221> NAME/KEY: modified_base
<222> LOCATION: (1062)..(1062)
<223> OTHER INFORMATION: UNA monomer
<220> FEATURE:
<221> NAME/KEY: modified_base
<222> LOCATION: (1066)..(1066)
<223> OTHER INFORMATION: UNA monomer
<220> FEATURE:
<221> NAME/KEY: modified_base
<222> LOCATION: (1076)..(1076)
<223> OTHER INFORMATION: UNA monomer
<220> FEATURE:
<221> NAME/KEY: modified_base
<222> LOCATION: (1078)..(1079)
<223> OTHER INFORMATION: UNA monomer
<220> FEATURE:
<221> NAME/KEY: modified_base
<222> LOCATION: (1093)..(1093)
<223> OTHER INFORMATION: UNA monomer
<220> FEATURE:
<221> NAME/KEY: modified_base
<222> LOCATION: (1098)..(1100)
<223> OTHER INFORMATION: UNA monomer
<220> FEATURE:
<221> NAME/KEY: modified_base
<222> LOCATION: (1103)..(1104)
<223> OTHER INFORMATION: UNA monomer
<220> FEATURE:
<221> NAME/KEY: modified_base
<222> LOCATION: (1106)..(1107)
```

```
<223> OTHER INFORMATION: UNA monomer
<220> FEATURE:
<221> NAME/KEY: modified_base
<222> LOCATION: (1111)..(1111)
<223> OTHER INFORMATION: UNA monomer
<220> FEATURE:
<221> NAME/KEY: modified_base
<222> LOCATION: (1115)..(1116)
<223> OTHER INFORMATION: UNA monomer
<220> FEATURE:
<221> NAME/KEY: modified_base
<222> LOCATION: (1121)..(1122)
<223> OTHER INFORMATION: UNA monomer
<220> FEATURE:
<221> NAME/KEY: modified_base
<222> LOCATION: (1127)..(1128)
<223> OTHER INFORMATION: UNA monomer
<220> FEATURE:
<221> NAME/KEY: modified_base
<222> LOCATION: (1130)..(1131)
<223> OTHER INFORMATION: UNA monomer
<220> FEATURE:
<221> NAME/KEY: modified_base
<222> LOCATION: (1144)..(1144)
<223> OTHER INFORMATION: UNA monomer
<220> FEATURE:
<221> NAME/KEY: modified_base
<222> LOCATION: (1146)..(1146)
<223> OTHER INFORMATION: UNA monomer
<220> FEATURE:
<221> NAME/KEY: modified_base
<222> LOCATION: (1148)..(1149)
<223> OTHER INFORMATION: UNA monomer
<220> FEATURE:
<221> NAME/KEY: modified_base
<222> LOCATION: (1153)..(1153)
<223> OTHER INFORMATION: UNA monomer
<220> FEATURE:
<221> NAME/KEY: modified_base
<222> LOCATION: (1155)..(1155)
<223> OTHER INFORMATION: UNA monomer
<220> FEATURE:
<221> NAME/KEY: modified_base
<222> LOCATION: (1162)..(1163)
<223> OTHER INFORMATION: UNA monomer
<220> FEATURE:
<221> NAME/KEY: modified_base
<222> LOCATION: (1169)..(1169)
<223> OTHER INFORMATION: UNA monomer
<220> FEATURE:
<221> NAME/KEY: modified_base
<222> LOCATION: (1171)..(1171)
<223> OTHER INFORMATION: UNA monomer
<220> FEATURE:
<221> NAME/KEY: modified_base
<222> LOCATION: (1173)..(1173)
<223> OTHER INFORMATION: UNA monomer
<220> FEATURE:
<221> NAME/KEY: modified_base
<222> LOCATION: (1181)..(1181)
<223> OTHER INFORMATION: UNA monomer
<220> FEATURE:
<221> NAME/KEY: modified_base
<222> LOCATION: (1183)..(1184)
<223> OTHER INFORMATION: UNA monomer
<220> FEATURE:
<221> NAME/KEY: modified_base
<222> LOCATION: (1186)..(1186)
<223> OTHER INFORMATION: UNA monomer
<220> FEATURE:
<221> NAME/KEY: modified_base
<222> LOCATION: (1188)..(1188)
<223> OTHER INFORMATION: UNA monomer
<220> FEATURE:
<221> NAME/KEY: modified_base
<222> LOCATION: (1191)..(1191)
<223> OTHER INFORMATION: UNA monomer
<220> FEATURE:
<221> NAME/KEY: modified_base
```

-continued

```
<222> LOCATION: (1195)..(1196)
<223> OTHER INFORMATION: UNA monomer
<220> FEATURE:
<221> NAME/KEY: modified_base
<222> LOCATION: (1200)..(1200)
<223> OTHER INFORMATION: UNA monomer
<220> FEATURE:
<221> NAME/KEY: modified_base
<222> LOCATION: (1209)..(1209)
<223> OTHER INFORMATION: UNA monomer
<220> FEATURE:
<221> NAME/KEY: modified_base
<222> LOCATION: (1215)..(1216)
<223> OTHER INFORMATION: UNA monomer
<220> FEATURE:
<221> NAME/KEY: modified_base
<222> LOCATION: (1219)..(1219)
<223> OTHER INFORMATION: UNA monomer
<220> FEATURE:
<221> NAME/KEY: modified_base
<222> LOCATION: (1221)..(1221)
<223> OTHER INFORMATION: UNA monomer
<220> FEATURE:
<221> NAME/KEY: modified_base
<222> LOCATION: (1230)..(1230)
<223> OTHER INFORMATION: UNA monomer
<220> FEATURE:
<221> NAME/KEY: modified_base
<222> LOCATION: (1233)..(1233)
<223> OTHER INFORMATION: UNA monomer
<220> FEATURE:
<221> NAME/KEY: modified_base
<222> LOCATION: (1245)..(1245)
<223> OTHER INFORMATION: UNA monomer
<220> FEATURE:
<221> NAME/KEY: modified_base
<222> LOCATION: (1247)..(1248)
<223> OTHER INFORMATION: UNA monomer
<220> FEATURE:
<221> NAME/KEY: modified_base
<222> LOCATION: (1251)..(1251)
<223> OTHER INFORMATION: UNA monomer
<220> FEATURE:
<221> NAME/KEY: modified_base
<222> LOCATION: (1256)..(1256)
<223> OTHER INFORMATION: UNA monomer
<220> FEATURE:
<221> NAME/KEY: modified_base
<222> LOCATION: (1269)..(1271)
<223> OTHER INFORMATION: UNA monomer
<220> FEATURE:
<221> NAME/KEY: modified_base
<222> LOCATION: (1273)..(1274)
<223> OTHER INFORMATION: UNA monomer
<220> FEATURE:
<221> NAME/KEY: modified_base
<222> LOCATION: (1278)..(1278)
<223> OTHER INFORMATION: UNA monomer
<220> FEATURE:
<221> NAME/KEY: modified_base
<222> LOCATION: (1283)..(1284)
<223> OTHER INFORMATION: UNA monomer
<220> FEATURE:
<221> NAME/KEY: modified_base
<222> LOCATION: (1286)..(1287)
<223> OTHER INFORMATION: UNA monomer
<220> FEATURE:
<221> NAME/KEY: modified_base
<222> LOCATION: (1291)..(1291)
<223> OTHER INFORMATION: UNA monomer
<220> FEATURE:
<221> NAME/KEY: modified_base
<222> LOCATION: (1296)..(1296)
<223> OTHER INFORMATION: UNA monomer
<220> FEATURE:
<221> NAME/KEY: modified_base
<222> LOCATION: (1303)..(1303)
<223> OTHER INFORMATION: UNA monomer
<220> FEATURE:
```

```
<221> NAME/KEY: modified_base
<222> LOCATION: (1305)..(1305)
<223> OTHER INFORMATION: UNA monomer
<220> FEATURE:
<221> NAME/KEY: modified_base
<222> LOCATION: (1310)..(1310)
<223> OTHER INFORMATION: UNA monomer
<220> FEATURE:
<221> NAME/KEY: modified_base
<222> LOCATION: (1321)..(1321)
<223> OTHER INFORMATION: UNA monomer
<220> FEATURE:
<221> NAME/KEY: modified_base
<222> LOCATION: (1323)..(1323)
<223> OTHER INFORMATION: UNA monomer
<220> FEATURE:
<221> NAME/KEY: modified_base
<222> LOCATION: (1328)..(1328)
<223> OTHER INFORMATION: UNA monomer
<220> FEATURE:
<221> NAME/KEY: modified_base
<222> LOCATION: (1330)..(1330)
<223> OTHER INFORMATION: UNA monomer
<220> FEATURE:
<221> NAME/KEY: modified_base
<222> LOCATION: (1332)..(1332)
<223> OTHER INFORMATION: UNA monomer
<220> FEATURE:
<221> NAME/KEY: modified_base
<222> LOCATION: (1340)..(1340)
<223> OTHER INFORMATION: UNA monomer
<220> FEATURE:
<221> NAME/KEY: modified_base
<222> LOCATION: (1342)..(1342)
<223> OTHER INFORMATION: UNA monomer
<220> FEATURE:
<221> NAME/KEY: modified_base
<222> LOCATION: (1348)..(1348)
<223> OTHER INFORMATION: UNA monomer
<220> FEATURE:
<221> NAME/KEY: modified_base
<222> LOCATION: (1350)..(1350)
<223> OTHER INFORMATION: UNA monomer
<220> FEATURE:
<221> NAME/KEY: modified_base
<222> LOCATION: (1352)..(1352)
<223> OTHER INFORMATION: UNA monomer
<220> FEATURE:
<221> NAME/KEY: modified_base
<222> LOCATION: (1357)..(1357)
<223> OTHER INFORMATION: UNA monomer
<220> FEATURE:
<221> NAME/KEY: modified_base
<222> LOCATION: (1361)..(1362)
<223> OTHER INFORMATION: UNA monomer
<220> FEATURE:
<221> NAME/KEY: modified_base
<222> LOCATION: (1379)..(1379)
<223> OTHER INFORMATION: UNA monomer
<220> FEATURE:
<221> NAME/KEY: modified_base
<222> LOCATION: (1383)..(1384)
<223> OTHER INFORMATION: UNA monomer

<400> SEQUENCE: 17
augcagcgcg ugaacaugau cauggcagaa ucaccaggcc ucaucaccau cugccuuuua      60
ggauaucuac ucagugcuga auguacaguu uuucuugauc augaaaacgc caacaaaauu     120
cugaaucggc caaagaggua uaauucaggu aaauuggaag aguuuguuca agggaaccuu     180
gagagagaau guauggaaga aaaguguagu uuugaagaag cacgagaagu uuugaaaac      240 acugaaagaa caacugaauu uuggaagcag uauguugaug gagaucagug ugaguccaau     300
ccauguuuaa auggcggcag uugcaaggau gacauuaauu ccuaugaaug uuggugoccc     360 uuuggauuug aaggaaagaa cugugaauua gauguaacau guaacauuaa gaauggcaga     420
```

-continued

```
ugcgagcagu uuuguaaaaa uagugcugau aacaaggugg uuugcuccug uacugaggga      480
uaucgacuug cagaaaacca gaagccugu gaaccagcag ugccauuucc auguggaaga       540
guuucuguuu cacaaacuuc uaagcucacc cgugcugaga cuguuuucc ugaugusgac       600 uauguaaauu cuacugaagc ugaaaccauu uggauaaca ucacucaaag cacccaauca      660
uuuaaugacu ucacucgggu uguuggugga gaagaugcca aaccagguca auucccuugg     720
cagguuguuu ugaaugguaa aguugaugca uucugugag gcucuaucgu uaaugaaaaa      780
uggauuguaa cugcugccca cuguguugaa acuggugua aaauuacagu gucgcaggu       840 gaacauaaua uugaggagac agaacauaca gagcaaaagc gaaaugugau ucgaauuauu     900
ccucaccaca acuacaaugc agcuauuaau aaguacaacc augacauugc ccuucuggaa    960
cuggacgaac ccuuagugcu aaacagcuac guuacaccua uuugcauugc ugacaaggaa    1020
uacacgaaca ucuuccucaa auuuggaucu ggcuauguaa guggcugggg aagagucuuc    1080
cacaaaggga gaucagcuuu aguucuucag uaccuuagag uuccacugu ugaccgagcc     1140 acaugucuuc gaucuacaaa guucaccauc uauaacaaca uguucuguga uggcuuccau    1200
gaaggaggua gagauucaug ucaaggagau aguggggac cccauguuac ugaaguggaa     1260
gggaccaguu ucuuaacugg aauuauuagc ugggguggaag agugugcaau gaaaggcaaa   1320
uauggaauau auaccaaggu aucccggguau gucaacugga uuaaggaaaa aacaaagcuc   1380
acuuaa                                                               1386

<210> SEQ ID NO 18
<211> LENGTH: 1257
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: UNA monomer
<220> FEATURE:
<221> NAME/KEY: modified_base
<222> LOCATION: (33)..(33)
<223> OTHER INFORMATION: UNA monomer
<220> FEATURE:
<221> NAME/KEY: modified_base
<222> LOCATION: (63)..(63)
<223> OTHER INFORMATION: UNA monomer
<220> FEATURE:
<221> NAME/KEY: modified_base
<222> LOCATION: (93)..(93)
<223> OTHER INFORMATION: UNA monomer
<220> FEATURE:
<221> NAME/KEY: modified_base
<222> LOCATION: (123)..(123)
<223> OTHER INFORMATION: UNA monomer
<220> FEATURE:
<221> NAME/KEY: modified_base
<222> LOCATION: (153)..(153)
<223> OTHER INFORMATION: UNA monomer
<220> FEATURE:
<221> NAME/KEY: modified_base
<222> LOCATION: (183)..(183)
<223> OTHER INFORMATION: UNA monomer
<220> FEATURE:
<221> NAME/KEY: modified_base
<222> LOCATION: (213)..(213)
<223> OTHER INFORMATION: UNA monomer
<220> FEATURE:
<221> NAME/KEY: modified_base
<222> LOCATION: (243)..(243)
<223> OTHER INFORMATION: UNA monomer
```

-continued

```
<220> FEATURE:
<221> NAME/KEY: modified_base
<222> LOCATION: (273)..(273)
<223> OTHER INFORMATION: UNA monomer
<220> FEATURE:
<221> NAME/KEY: modified_base
<222> LOCATION: (303)..(303)
<223> OTHER INFORMATION: UNA monomer
<220> FEATURE:
<221> NAME/KEY: modified_base
<222> LOCATION: (333)..(333)
<223> OTHER INFORMATION: UNA monomer
<220> FEATURE:
<221> NAME/KEY: modified_base
<222> LOCATION: (363)..(363)
<223> OTHER INFORMATION: UNA monomer
<220> FEATURE:
<221> NAME/KEY: modified_base
<222> LOCATION: (393)..(393)
<223> OTHER INFORMATION: UNA monomer
<220> FEATURE:
<221> NAME/KEY: modified_base
<222> LOCATION: (423)..(423)
<223> OTHER INFORMATION: UNA monomer
<220> FEATURE:
<221> NAME/KEY: modified_base
<222> LOCATION: (453)..(453)
<223> OTHER INFORMATION: UNA monomer
<220> FEATURE:
<221> NAME/KEY: modified_base
<222> LOCATION: (483)..(483)
<223> OTHER INFORMATION: UNA monomer
<220> FEATURE:
<221> NAME/KEY: modified_base
<222> LOCATION: (513)..(513)
<223> OTHER INFORMATION: UNA monomer
<220> FEATURE:
<221> NAME/KEY: modified_base
<222> LOCATION: (543)..(543)
<223> OTHER INFORMATION: UNA monomer
<220> FEATURE:
<221> NAME/KEY: modified_base
<222> LOCATION: (573)..(573)
<223> OTHER INFORMATION: UNA monomer
<220> FEATURE:
<221> NAME/KEY: modified_base
<222> LOCATION: (603)..(603)
<223> OTHER INFORMATION: UNA monomer
<220> FEATURE:
<221> NAME/KEY: modified_base
<222> LOCATION: (633)..(633)
<223> OTHER INFORMATION: UNA monomer
<220> FEATURE:
<221> NAME/KEY: modified_base
<222> LOCATION: (663)..(663)
<223> OTHER INFORMATION: UNA monomer
<220> FEATURE:
<221> NAME/KEY: modified_base
<222> LOCATION: (693)..(693)
<223> OTHER INFORMATION: UNA monomer
<220> FEATURE:
<221> NAME/KEY: modified_base
<222> LOCATION: (723)..(723)
<223> OTHER INFORMATION: UNA monomer
<220> FEATURE:
<221> NAME/KEY: modified_base
<222> LOCATION: (753)..(753)
<223> OTHER INFORMATION: UNA monomer
<220> FEATURE:
<221> NAME/KEY: modified_base
<222> LOCATION: (783)..(783)
<223> OTHER INFORMATION: UNA monomer
<220> FEATURE:
<221> NAME/KEY: modified_base
<222> LOCATION: (813)..(813)
<223> OTHER INFORMATION: UNA monomer
<220> FEATURE:
<221> NAME/KEY: modified_base
<222> LOCATION: (843)..(843)
```

```
<223> OTHER INFORMATION: UNA monomer
<220> FEATURE:
<221> NAME/KEY: modified_base
<222> LOCATION: (873)..(873)
<223> OTHER INFORMATION: UNA monomer
<220> FEATURE:
<221> NAME/KEY: modified_base
<222> LOCATION: (903)..(903)
<223> OTHER INFORMATION: UNA monomer
<220> FEATURE:
<221> NAME/KEY: modified_base
<222> LOCATION: (933)..(933)
<223> OTHER INFORMATION: UNA monomer
<220> FEATURE:
<221> NAME/KEY: modified_base
<222> LOCATION: (963)..(963)
<223> OTHER INFORMATION: UNA monomer
<220> FEATURE:
<221> NAME/KEY: modified_base
<222> LOCATION: (993)..(993)
<223> OTHER INFORMATION: UNA monomer
<220> FEATURE:
<221> NAME/KEY: modified_base
<222> LOCATION: (1023)..(1023)
<223> OTHER INFORMATION: UNA monomer
<220> FEATURE:
<221> NAME/KEY: modified_base
<222> LOCATION: (1053)..(1053)
<223> OTHER INFORMATION: UNA monomer
<220> FEATURE:
<221> NAME/KEY: modified_base
<222> LOCATION: (1083)..(1083)
<223> OTHER INFORMATION: UNA monomer
<220> FEATURE:
<221> NAME/KEY: modified_base
<222> LOCATION: (1113)..(1113)
<223> OTHER INFORMATION: UNA monomer
<220> FEATURE:
<221> NAME/KEY: modified_base
<222> LOCATION: (1143)..(1143)
<223> OTHER INFORMATION: UNA monomer
<220> FEATURE:
<221> NAME/KEY: modified_base
<222> LOCATION: (1173)..(1173)
<223> OTHER INFORMATION: UNA monomer
<220> FEATURE:
<221> NAME/KEY: modified_base
<222> LOCATION: (1203)..(1203)
<223> OTHER INFORMATION: UNA monomer
<220> FEATURE:
<221> NAME/KEY: modified_base
<222> LOCATION: (1233)..(1233)
<223> OTHER INFORMATION: UNA monomer
<220> FEATURE:
<221> NAME/KEY: modified_base
<222> LOCATION: (1256)..(1256)
<223> OTHER INFORMATION: UNA monomer

<400> SEQUENCE: 18
augccgucuu cugucucgug gggcauccuc cugcuggcag gccugugcug ccuggucccu      60
gucucccugg cugaggaucc ccagggagau gcugcccaga agacagauac aucccaccau     120
gaucaggauc acccaaccuu caacaagauc accccccaacc uggcugaguu cgccuucagc    180
cuauaccgcc agcuggcaca ccaguccaac agcaccaaua ucuucuucuc cccagugagc     240
aucgcuacag ccuuugcaau gcucucccug ggaccaagg cugacacuca cgaugaaauc      300
cuggagggcc ugaauuucaa ccucacggag auuccggagg cucagauccca ugaaggcuuc    360 caggaacucc uccguacccu caaccagcca gacagccagc uccagcugac caccggcaau    420
ggccuguucc ucagcgaggg ccugaagcua guggauaagu uuuggaggga uguuaaaaag    480
uuguaccacu cagaagccuu cacgucaac uucggggaca ccgaagaggc caagaaacag      540
aucaacgauu acguggagaa gguacucaa gggaaaauug uggauuuggu caaggagcuu     600
```

```
gacagagaca caguuuuugc ucuggugaau uacaucuucu uuaaaggcaa augggagaga    660
cccuuugaag ucaaggacac cgaggaagag gacuuccacg uggaccaggu gaccaccgug    720
aaggugccua ugaugaagcg uuuaggcaug uuuaacaucc agcacuguaa gaagcugucc    780 agcuggugc ugcugaugaa auaccugggc aaugccaccg ccaucuucuu ccugccugau     840
gaggggaaac uacagcaccu ggaaaaugaa cucacccacg auaucaucac caaguuccug    900
gaaaaugaag acagaagguc ugccagcuua cauuuaccca aacugccau uacuggaacc    960 uaugaucuga agagcguccu gggucaacug ggcaucacua aggucuucag caaugggcu    1020 gaccucuccg gggucacaga ggaggcaccc cugaagcucu ccaaggccgu gcauaaggcu   1080
gugcugacca ucgacgagaa agggacugaa gcugcugggg ccauguuuuu agaggccaua   1140
cccaugucua uccccccga ggucaaguuc aacaaacccu uugucuucuu aaugauugaa    1200
caaaauacca agucucccu cuucauggga aagugguga aucccaccca aaaauaa        1257
```

<210> SEQ ID NO 19
<211> LENGTH: 1257
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(4)
<223> OTHER INFORMATION: UNA monomer
<220> FEATURE:
<221> NAME/KEY: modified_base
<222> LOCATION: (1254)..(1256)
<223> OTHER INFORMATION: UNA monomer

<400> SEQUENCE: 19

```
augccgucuu cugucucgug gggcauccuc cugcuggcag gccugugcug ccuggucccu     60
gucucccugg cugaggaucc ccagggagau gcugcccaga agacagauac auccaccau    120 gaucaggauc acccaaccuu caacaagauc accccaacc uggcugaguu cgccuucagc    180
cuauaccgcc agcuggcaca ccaguccaac agcaccauua ucuucuucuc cccagugagc    240
aucgcuacag ccuuugcaau gcucucccug gggaccaagg cugacacuca cgaugaaauc    300
cuggagggcc ugaauuucaa ccucacggag auuccgaggg cucagaucca ugaaggcuuc    360
caggaacucc uccguacccu caaccagcca gacagccagc uccagcugac caccggcaau    420
ggccuguucc ucagcgaggg ccugaagcua guggauaagu uuuuggagga guuuaaaaag    480
uuguaccacu cagaagccuu cacgucaacc uucggggaca ccgaagaggc caagaaacag    540
aucaacgauu acguggagaa ggguacucaa gggaaaauug uggauuuggu caaggagcuu    600
gacagagaca caguuuugc ucuggugaau uacaucuucu uuaaaggcaa augggagaga    660
cccuuugaag ucaaggacac cgaggaagag gacuuccacg uggaccaggu gaccaccgug    720
aaggugccua ugaugaagcg uuuaggcaug uuuaacaucc agcacuguaa gaagcugucc    780 agcuggugc ugcugaugaa auaccugggc aaugccaccg ccaucuucuu ccugccugau     840
gaggggaaac uacagcaccu ggaaaaugaa cucacccacg auaucaucac caaguuccug    900
gaaaaugaag acagaagguc ugccagcuua cauuuaccca aacugccau uacuggaacc    960 uaugaucuga agagcguccu gggucaacug ggcaucacua aggucuucag caaugggcu    1020 gaccucuccg gggucacaga ggaggcaccc cugaagcucu ccaaggccgu gcauaaggcu   1080
gugcugacca ucgacgagaa agggacugaa gcugcugggg ccauguuuuu agaggccaua   1140
```

```
cccaugucua uccccccga ggucaaguuc aacaaacccu uugucuucuu aaugauugaa    1200
caaaauacca agucuccccu cuucauggga aaagugguga aucccaccca aaaauaa      1257
```

```
<210> SEQ ID NO 20
<211> LENGTH: 1257
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (7)..(7)
<223> OTHER INFORMATION: UNA monomer
<220> FEATURE:
<221> NAME/KEY: modified_base
<222> LOCATION: (9)..(10)
<223> OTHER INFORMATION: UNA monomer
<220> FEATURE:
<221> NAME/KEY: modified_base
<222> LOCATION: (12)..(12)
<223> OTHER INFORMATION: UNA monomer
<220> FEATURE:
<221> NAME/KEY: modified_base
<222> LOCATION: (14)..(14)
<223> OTHER INFORMATION: UNA monomer
<220> FEATURE:
<221> NAME/KEY: modified_base
<222> LOCATION: (16)..(16)
<223> OTHER INFORMATION: UNA monomer
<220> FEATURE:
<221> NAME/KEY: modified_base
<222> LOCATION: (19)..(19)
<223> OTHER INFORMATION: UNA monomer
<220> FEATURE:
<221> NAME/KEY: modified_base
<222> LOCATION: (26)..(26)
<223> OTHER INFORMATION: UNA monomer
<220> FEATURE:
<221> NAME/KEY: modified_base
<222> LOCATION: (29)..(29)
<223> OTHER INFORMATION: UNA monomer
<220> FEATURE:
<221> NAME/KEY: modified_base
<222> LOCATION: (32)..(32)
<223> OTHER INFORMATION: UNA monomer
<220> FEATURE:
<221> NAME/KEY: modified_base
<222> LOCATION: (35)..(35)
<223> OTHER INFORMATION: UNA monomer
<220> FEATURE:
<221> NAME/KEY: modified_base
<222> LOCATION: (44)..(44)
<223> OTHER INFORMATION: UNA monomer
<220> FEATURE:
<221> NAME/KEY: modified_base
<222> LOCATION: (46)..(46)
<223> OTHER INFORMATION: UNA monomer
<220> FEATURE:
<221> NAME/KEY: modified_base
<222> LOCATION: (49)..(49)
<223> OTHER INFORMATION: UNA monomer
<220> FEATURE:
<221> NAME/KEY: modified_base
<222> LOCATION: (53)..(53)
<223> OTHER INFORMATION: UNA monomer
<220> FEATURE:
<221> NAME/KEY: modified_base
<222> LOCATION: (56)..(56)
<223> OTHER INFORMATION: UNA monomer
<220> FEATURE:
<221> NAME/KEY: modified_base
```

```
<222> LOCATION: (60)..(60)
<223> OTHER INFORMATION: UNA monomer
<220> FEATURE:
<221> NAME/KEY: modified_base
<222> LOCATION: (62)..(62)
<223> OTHER INFORMATION: UNA monomer
<220> FEATURE:
<221> NAME/KEY: modified_base
<222> LOCATION: (64)..(64)
<223> OTHER INFORMATION: UNA monomer
<220> FEATURE:
<221> NAME/KEY: modified_base
<222> LOCATION: (68)..(68)
<223> OTHER INFORMATION: UNA monomer
<220> FEATURE:
<221> NAME/KEY: modified_base
<222> LOCATION: (72)..(72)
<223> OTHER INFORMATION: UNA monomer
<220> FEATURE:
<221> NAME/KEY: modified_base
<222> LOCATION: (78)..(78)
<223> OTHER INFORMATION: UNA monomer
<220> FEATURE:
<221> NAME/KEY: modified_base
<222> LOCATION: (90)..(90)
<223> OTHER INFORMATION: UNA monomer
<220> FEATURE:
<221> NAME/KEY: modified_base
<222> LOCATION: (93)..(93)
<223> OTHER INFORMATION: UNA monomer
<220> FEATURE:
<221> NAME/KEY: modified_base
<222> LOCATION: (108)..(108)
<223> OTHER INFORMATION: UNA monomer
<220> FEATURE:
<221> NAME/KEY: modified_base
<222> LOCATION: (112)..(112)
<223> OTHER INFORMATION: UNA monomer
<220> FEATURE:
<221> NAME/KEY: modified_base
<222> LOCATION: (120)..(120)
<223> OTHER INFORMATION: UNA monomer
<220> FEATURE:
<221> NAME/KEY: modified_base
<222> LOCATION: (123)..(123)
<223> OTHER INFORMATION: UNA monomer
<220> FEATURE:
<221> NAME/KEY: modified_base
<222> LOCATION: (129)..(129)
<223> OTHER INFORMATION: UNA monomer
<220> FEATURE:
<221> NAME/KEY: modified_base
<222> LOCATION: (139)..(140)
<223> OTHER INFORMATION: UNA monomer
<220> FEATURE:
<221> NAME/KEY: modified_base
<222> LOCATION: (149)..(149)
<223> OTHER INFORMATION: UNA monomer
<220> FEATURE:
<221> NAME/KEY: modified_base
<222> LOCATION: (161)..(161)
<223> OTHER INFORMATION: UNA monomer
<220> FEATURE:
<221> NAME/KEY: modified_base
<222> LOCATION: (165)..(165)
<223> OTHER INFORMATION: UNA monomer
<220> FEATURE:
<221> NAME/KEY: modified_base
<222> LOCATION: (169)..(170)
<223> OTHER INFORMATION: UNA monomer
<220> FEATURE:
<221> NAME/KEY: modified_base
<222> LOCATION: (175)..(176)
<223> OTHER INFORMATION: UNA monomer
<220> FEATURE:
<221> NAME/KEY: modified_base
<222> LOCATION: (182)..(182)
<223> OTHER INFORMATION: UNA monomer
<220> FEATURE:
```

```
<221> NAME/KEY: modified_base
<222> LOCATION: (184)..(184)
<223> OTHER INFORMATION: UNA monomer
<220> FEATURE:
<221> NAME/KEY: modified_base
<222> LOCATION: (194)..(194)
<223> OTHER INFORMATION: UNA monomer
<220> FEATURE:
<221> NAME/KEY: modified_base
<222> LOCATION: (205)..(205)
<223> OTHER INFORMATION: UNA monomer
<220> FEATURE:
<221> NAME/KEY: modified_base
<222> LOCATION: (219)..(219)
<223> OTHER INFORMATION: UNA monomer
<220> FEATURE:
<221> NAME/KEY: modified_base
<222> LOCATION: (221)..(221)
<223> OTHER INFORMATION: UNA monomer
<220> FEATURE:
<221> NAME/KEY: modified_base
<222> LOCATION: (223)..(224)
<223> OTHER INFORMATION: UNA monomer
<220> FEATURE:
<221> NAME/KEY: modified_base
<222> LOCATION: (226)..(227)
<223> OTHER INFORMATION: UNA monomer
<220> FEATURE:
<221> NAME/KEY: modified_base
<222> LOCATION: (229)..(229)
<223> OTHER INFORMATION: UNA monomer
<220> FEATURE:
<221> NAME/KEY: modified_base
<222> LOCATION: (236)..(236)
<223> OTHER INFORMATION: UNA monomer
<220> FEATURE:
<221> NAME/KEY: modified_base
<222> LOCATION: (242)..(242)
<223> OTHER INFORMATION: UNA monomer
<220> FEATURE:
<221> NAME/KEY: modified_base
<222> LOCATION: (246)..(246)
<223> OTHER INFORMATION: UNA monomer
<220> FEATURE:
<221> NAME/KEY: modified_base
<222> LOCATION: (253)..(255)
<223> OTHER INFORMATION: UNA monomer
<220> FEATURE:
<221> NAME/KEY: modified_base
<222> LOCATION: (260)..(260)
<223> OTHER INFORMATION: UNA monomer
<220> FEATURE:
<221> NAME/KEY: modified_base
<222> LOCATION: (263)..(263)
<223> OTHER INFORMATION: UNA monomer
<220> FEATURE:
<221> NAME/KEY: modified_base
<222> LOCATION: (265)..(265)
<223> OTHER INFORMATION: UNA monomer
<220> FEATURE:
<221> NAME/KEY: modified_base
<222> LOCATION: (269)..(269)
<223> OTHER INFORMATION: UNA monomer
<220> FEATURE:
<221> NAME/KEY: modified_base
<222> LOCATION: (282)..(282)
<223> OTHER INFORMATION: UNA monomer
<220> FEATURE:
<221> NAME/KEY: modified_base
<222> LOCATION: (288)..(288)
<223> OTHER INFORMATION: UNA monomer
<220> FEATURE:
<221> NAME/KEY: modified_base
<222> LOCATION: (294)..(294)
<223> OTHER INFORMATION: UNA monomer
<220> FEATURE:
<221> NAME/KEY: modified_base
<222> LOCATION: (299)..(299)
<223> OTHER INFORMATION: UNA monomer
```

```
-continued

<220> FEATURE:
<221> NAME/KEY: modified_base
<222> LOCATION: (302)..(302)
<223> OTHER INFORMATION: UNA monomer
<220> FEATURE:
<221> NAME/KEY: modified_base
<222> LOCATION: (311)..(311)
<223> OTHER INFORMATION: UNA monomer
<220> FEATURE:
<221> NAME/KEY: modified_base
<222> LOCATION: (315)..(317)
<223> OTHER INFORMATION: UNA monomer
<220> FEATURE:
<221> NAME/KEY: modified_base
<222> LOCATION: (323)..(323)
<223> OTHER INFORMATION: UNA monomer
<220> FEATURE:
<221> NAME/KEY: modified_base
<222> LOCATION: (332)..(333)
<223> OTHER INFORMATION: UNA monomer
<220> FEATURE:
<221> NAME/KEY: modified_base
<222> LOCATION: (342)..(342)
<223> OTHER INFORMATION: UNA monomer
<220> FEATURE:
<221> NAME/KEY: modified_base
<222> LOCATION: (347)..(347)
<223> OTHER INFORMATION: UNA monomer
<220> FEATURE:
<221> NAME/KEY: modified_base
<222> LOCATION: (351)..(351)
<223> OTHER INFORMATION: UNA monomer
<220> FEATURE:
<221> NAME/KEY: modified_base
<222> LOCATION: (358)..(359)
<223> OTHER INFORMATION: UNA monomer
<220> FEATURE:
<221> NAME/KEY: modified_base
<222> LOCATION: (368)..(368)
<223> OTHER INFORMATION: UNA monomer
<220> FEATURE:
<221> NAME/KEY: modified_base
<222> LOCATION: (371)..(371)
<223> OTHER INFORMATION: UNA monomer
<220> FEATURE:
<221> NAME/KEY: modified_base
<222> LOCATION: (375)..(375)
<223> OTHER INFORMATION: UNA monomer
<220> FEATURE:
<221> NAME/KEY: modified_base
<222> LOCATION: (380)..(380)
<223> OTHER INFORMATION: UNA monomer
<220> FEATURE:
<221> NAME/KEY: modified_base
<222> LOCATION: (401)..(401)
<223> OTHER INFORMATION: UNA monomer
<220> FEATURE:
<221> NAME/KEY: modified_base
<222> LOCATION: (407)..(407)
<223> OTHER INFORMATION: UNA monomer
<220> FEATURE:
<221> NAME/KEY: modified_base
<222> LOCATION: (420)..(420)
<223> OTHER INFORMATION: UNA monomer
<220> FEATURE:
<221> NAME/KEY: modified_base
<222> LOCATION: (425)..(425)
<223> OTHER INFORMATION: UNA monomer
<220> FEATURE:
<221> NAME/KEY: modified_base
<222> LOCATION: (427)..(428)
<223> OTHER INFORMATION: UNA monomer
<220> FEATURE:
<221> NAME/KEY: modified_base
<222> LOCATION: (431)..(431)
<223> OTHER INFORMATION: UNA monomer
<220> FEATURE:
<221> NAME/KEY: modified_base
<222> LOCATION: (443)..(443)
```

```
<223> OTHER INFORMATION: UNA monomer
<220> FEATURE:
<221> NAME/KEY: modified_base
<222> LOCATION: (449)..(449)
<223> OTHER INFORMATION: UNA monomer
<220> FEATURE:
<221> NAME/KEY: modified_base
<222> LOCATION: (452)..(452)
<223> OTHER INFORMATION: UNA monomer
<220> FEATURE:
<221> NAME/KEY: modified_base
<222> LOCATION: (456)..(456)
<223> OTHER INFORMATION: UNA monomer
<220> FEATURE:
<221> NAME/KEY: modified_base
<222> LOCATION: (460)..(464)
<223> OTHER INFORMATION: UNA monomer
<220> FEATURE:
<221> NAME/KEY: modified_base
<222> LOCATION: (471)..(471)
<223> OTHER INFORMATION: UNA monomer
<220> FEATURE:
<221> NAME/KEY: modified_base
<222> LOCATION: (473)..(474)
<223> OTHER INFORMATION: UNA monomer
<220> FEATURE:
<221> NAME/KEY: modified_base
<222> LOCATION: (481)..(482)
<223> OTHER INFORMATION: UNA monomer
<220> FEATURE:
<221> NAME/KEY: modified_base
<222> LOCATION: (484)..(484)
<223> OTHER INFORMATION: UNA monomer
<220> FEATURE:
<221> NAME/KEY: modified_base
<222> LOCATION: (490)..(490)
<223> OTHER INFORMATION: UNA monomer
<220> FEATURE:
<221> NAME/KEY: modified_base
<222> LOCATION: (499)..(500)
<223> OTHER INFORMATION: UNA monomer
<220> FEATURE:
<221> NAME/KEY: modified_base
<222> LOCATION: (504)..(504)
<223> OTHER INFORMATION: UNA monomer
<220> FEATURE:
<221> NAME/KEY: modified_base
<222> LOCATION: (506)..(506)
<223> OTHER INFORMATION: UNA monomer
<220> FEATURE:
<221> NAME/KEY: modified_base
<222> LOCATION: (511)..(512)
<223> OTHER INFORMATION: UNA monomer
<220> FEATURE:
<221> NAME/KEY: modified_base
<222> LOCATION: (542)..(542)
<223> OTHER INFORMATION: UNA monomer
<220> FEATURE:
<221> NAME/KEY: modified_base
<222> LOCATION: (549)..(550)
<223> OTHER INFORMATION: UNA monomer
<220> FEATURE:
<221> NAME/KEY: modified_base
<222> LOCATION: (554)..(554)
<223> OTHER INFORMATION: UNA monomer
<220> FEATURE:
<221> NAME/KEY: modified_base
<222> LOCATION: (564)..(564)
<223> OTHER INFORMATION: UNA monomer
<220> FEATURE:
<221> NAME/KEY: modified_base
<222> LOCATION: (567)..(567)
<223> OTHER INFORMATION: UNA monomer
<220> FEATURE:
<221> NAME/KEY: modified_base
<222> LOCATION: (578)..(579)
<223> OTHER INFORMATION: UNA monomer
<220> FEATURE:
<221> NAME/KEY: modified_base
```

```
<222> LOCATION: (581)..(581)
<223> OTHER INFORMATION: UNA monomer
<220> FEATURE:
<221> NAME/KEY: modified_base
<222> LOCATION: (585)..(587)
<223> OTHER INFORMATION: UNA monomer
<220> FEATURE:
<221> NAME/KEY: modified_base
<222> LOCATION: (590)..(590)
<223> OTHER INFORMATION: UNA monomer
<220> FEATURE:
<221> NAME/KEY: modified_base
<222> LOCATION: (599)..(600)
<223> OTHER INFORMATION: UNA monomer
<220> FEATURE:
<221> NAME/KEY: modified_base
<222> LOCATION: (614)..(618)
<223> OTHER INFORMATION: UNA monomer
<220> FEATURE:
<221> NAME/KEY: modified_base
<222> LOCATION: (621)..(621)
<223> OTHER INFORMATION: UNA monomer
<220> FEATURE:
<221> NAME/KEY: modified_base
<222> LOCATION: (623)..(623)
<223> OTHER INFORMATION: UNA monomer
<220> FEATURE:
<221> NAME/KEY: modified_base
<222> LOCATION: (626)..(626)
<223> OTHER INFORMATION: UNA monomer
<220> FEATURE:
<221> NAME/KEY: modified_base
<222> LOCATION: (630)..(631)
<223> OTHER INFORMATION: UNA monomer
<220> FEATURE:
<221> NAME/KEY: modified_base
<222> LOCATION: (635)..(635)
<223> OTHER INFORMATION: UNA monomer
<220> FEATURE:
<221> NAME/KEY: modified_base
<222> LOCATION: (637)..(638)
<223> OTHER INFORMATION: UNA monomer
<220> FEATURE:
<221> NAME/KEY: modified_base
<222> LOCATION: (640)..(642)
<223> OTHER INFORMATION: UNA monomer
<220> FEATURE:
<221> NAME/KEY: modified_base
<222> LOCATION: (652)..(652)
<223> OTHER INFORMATION: UNA monomer
<220> FEATURE:
<221> NAME/KEY: modified_base
<222> LOCATION: (664)..(666)
<223> OTHER INFORMATION: UNA monomer
<220> FEATURE:
<221> NAME/KEY: modified_base
<222> LOCATION: (671)..(671)
<223> OTHER INFORMATION: UNA monomer
<220> FEATURE:
<221> NAME/KEY: modified_base
<222> LOCATION: (694)..(695)
<223> OTHER INFORMATION: UNA monomer
<220> FEATURE:
<221> NAME/KEY: modified_base
<222> LOCATION: (701)..(701)
<223> OTHER INFORMATION: UNA monomer
<220> FEATURE:
<221> NAME/KEY: modified_base
<222> LOCATION: (710)..(710)
<223> OTHER INFORMATION: UNA monomer
<220> FEATURE:
<221> NAME/KEY: modified_base
<222> LOCATION: (719)..(719)
<223> OTHER INFORMATION: UNA monomer
<220> FEATURE:
<221> NAME/KEY: modified_base
<222> LOCATION: (725)..(725)
<223> OTHER INFORMATION: UNA monomer
<220> FEATURE:
```

```
<221> NAME/KEY: modified_base
<222> LOCATION: (729)..(729)
<223> OTHER INFORMATION: UNA monomer
<220> FEATURE:
<221> NAME/KEY: modified_base
<222> LOCATION: (731)..(731)
<223> OTHER INFORMATION: UNA monomer
<220> FEATURE:
<221> NAME/KEY: modified_base
<222> LOCATION: (734)..(734)
<223> OTHER INFORMATION: UNA monomer
<220> FEATURE:
<221> NAME/KEY: modified_base
<222> LOCATION: (741)..(743)
<223> OTHER INFORMATION: UNA monomer
<220> FEATURE:
<221> NAME/KEY: modified_base
<222> LOCATION: (749)..(749)
<223> OTHER INFORMATION: UNA monomer
<220> FEATURE:
<221> NAME/KEY: modified_base
<222> LOCATION: (751)..(753)
<223> OTHER INFORMATION: UNA monomer
<220> FEATURE:
<221> NAME/KEY: modified_base
<222> LOCATION: (758)..(758)
<223> OTHER INFORMATION: UNA monomer
<220> FEATURE:
<221> NAME/KEY: modified_base
<222> LOCATION: (766)..(766)
<223> OTHER INFORMATION: UNA monomer
<220> FEATURE:
<221> NAME/KEY: modified_base
<222> LOCATION: (768)..(768)
<223> OTHER INFORMATION: UNA monomer
<220> FEATURE:
<221> NAME/KEY: modified_base
<222> LOCATION: (776)..(776)
<223> OTHER INFORMATION: UNA monomer
<220> FEATURE:
<221> NAME/KEY: modified_base
<222> LOCATION: (778)..(778)
<223> OTHER INFORMATION: UNA monomer
<220> FEATURE:
<221> NAME/KEY: modified_base
<222> LOCATION: (784)..(784)
<223> OTHER INFORMATION: UNA monomer
<220> FEATURE:
<221> NAME/KEY: modified_base
<222> LOCATION: (788)..(788)
<223> OTHER INFORMATION: UNA monomer
<220> FEATURE:
<221> NAME/KEY: modified_base
<222> LOCATION: (791)..(791)
<223> OTHER INFORMATION: UNA monomer
<220> FEATURE:
<221> NAME/KEY: modified_base
<222> LOCATION: (794)..(794)
<223> OTHER INFORMATION: UNA monomer
<220> FEATURE:
<221> NAME/KEY: modified_base
<222> LOCATION: (797)..(797)
<223> OTHER INFORMATION: UNA monomer
<220> FEATURE:
<221> NAME/KEY: modified_base
<222> LOCATION: (802)..(802)
<223> OTHER INFORMATION: UNA monomer
<220> FEATURE:
<221> NAME/KEY: modified_base
<222> LOCATION: (806)..(806)
<223> OTHER INFORMATION: UNA monomer
<220> FEATURE:
<221> NAME/KEY: modified_base
<222> LOCATION: (813)..(813)
<223> OTHER INFORMATION: UNA monomer
<220> FEATURE:
<221> NAME/KEY: modified_base
<222> LOCATION: (824)..(824)
<223> OTHER INFORMATION: UNA monomer
```

```
-continued

<220> FEATURE:
<221> NAME/KEY: modified_base
<222> LOCATION: (826)..(827)
<223> OTHER INFORMATION: UNA monomer
<220> FEATURE:
<221> NAME/KEY: modified_base
<222> LOCATION: (829)..(830)
<223> OTHER INFORMATION: UNA monomer
<220> FEATURE:
<221> NAME/KEY: modified_base
<222> LOCATION: (833)..(833)
<223> OTHER INFORMATION: UNA monomer
<220> FEATURE:
<221> NAME/KEY: modified_base
<222> LOCATION: (837)..(837)
<223> OTHER INFORMATION: UNA monomer
<220> FEATURE:
<221> NAME/KEY: modified_base
<222> LOCATION: (840)..(840)
<223> OTHER INFORMATION: UNA monomer
<220> FEATURE:
<221> NAME/KEY: modified_base
<222> LOCATION: (851)..(851)
<223> OTHER INFORMATION: UNA monomer
<220> FEATURE:
<221> NAME/KEY: modified_base
<222> LOCATION: (860)..(860)
<223> OTHER INFORMATION: UNA monomer
<220> FEATURE:
<221> NAME/KEY: modified_base
<222> LOCATION: (867)..(867)
<223> OTHER INFORMATION: UNA monomer
<220> FEATURE:
<221> NAME/KEY: modified_base
<222> LOCATION: (872)..(872)
<223> OTHER INFORMATION: UNA monomer
<220> FEATURE:
<221> NAME/KEY: modified_base
<222> LOCATION: (882)..(882)
<223> OTHER INFORMATION: UNA monomer
<220> FEATURE:
<221> NAME/KEY: modified_base
<222> LOCATION: (884)..(884)
<223> OTHER INFORMATION: UNA monomer
<220> FEATURE:
<221> NAME/KEY: modified_base
<222> LOCATION: (887)..(887)
<223> OTHER INFORMATION: UNA monomer
<220> FEATURE:
<221> NAME/KEY: modified_base
<222> LOCATION: (895)..(896)
<223> OTHER INFORMATION: UNA monomer
<220> FEATURE:
<221> NAME/KEY: modified_base
<222> LOCATION: (899)..(899)
<223> OTHER INFORMATION: UNA monomer
<220> FEATURE:
<221> NAME/KEY: modified_base
<222> LOCATION: (906)..(906)
<223> OTHER INFORMATION: UNA monomer
<220> FEATURE:
<221> NAME/KEY: modified_base
<222> LOCATION: (919)..(919)
<223> OTHER INFORMATION: UNA monomer
<220> FEATURE:
<221> NAME/KEY: modified_base
<222> LOCATION: (921)..(921)
<223> OTHER INFORMATION: UNA monomer
<220> FEATURE:
<221> NAME/KEY: modified_base
<222> LOCATION: (928)..(929)
<223> OTHER INFORMATION: UNA monomer
<220> FEATURE:
<221> NAME/KEY: modified_base
<222> LOCATION: (933)..(935)
<223> OTHER INFORMATION: UNA monomer
<220> FEATURE:
<221> NAME/KEY: modified_base
<222> LOCATION: (944)..(944)
```

```
<223> OTHER INFORMATION: UNA monomer
<220> FEATURE:
<221> NAME/KEY: modified_base
<222> LOCATION: (946)..(946)
<223> OTHER INFORMATION: UNA monomer
<220> FEATURE:
<221> NAME/KEY: modified_base
<222> LOCATION: (950)..(951)
<223> OTHER INFORMATION: UNA monomer
<220> FEATURE:
<221> NAME/KEY: modified_base
<222> LOCATION: (954)..(954)
<223> OTHER INFORMATION: UNA monomer
<220> FEATURE:
<221> NAME/KEY: modified_base
<222> LOCATION: (961)..(961)
<223> OTHER INFORMATION: UNA monomer
<220> FEATURE:
<221> NAME/KEY: modified_base
<222> LOCATION: (963)..(963)
<223> OTHER INFORMATION: UNA monomer
<220> FEATURE:
<221> NAME/KEY: modified_base
<222> LOCATION: (966)..(966)
<223> OTHER INFORMATION: UNA monomer
<220> FEATURE:
<221> NAME/KEY: modified_base
<222> LOCATION: (968)..(968)
<223> OTHER INFORMATION: UNA monomer
<220> FEATURE:
<221> NAME/KEY: modified_base
<222> LOCATION: (977)..(977)
<223> OTHER INFORMATION: UNA monomer
<220> FEATURE:
<221> NAME/KEY: modified_base
<222> LOCATION: (980)..(980)
<223> OTHER INFORMATION: UNA monomer
<220> FEATURE:
<221> NAME/KEY: modified_base
<222> LOCATION: (984)..(984)
<223> OTHER INFORMATION: UNA monomer
<220> FEATURE:
<221> NAME/KEY: modified_base
<222> LOCATION: (989)..(989)
<223> OTHER INFORMATION: UNA monomer
<220> FEATURE:
<221> NAME/KEY: modified_base
<222> LOCATION: (995)..(995)
<223> OTHER INFORMATION: UNA monomer
<220> FEATURE:
<221> NAME/KEY: modified_base
<222> LOCATION: (999)..(999)
<223> OTHER INFORMATION: UNA monomer
<220> FEATURE:
<221> NAME/KEY: modified_base
<222> LOCATION: (1004)..(1004)
<223> OTHER INFORMATION: UNA monomer
<220> FEATURE:
<221> NAME/KEY: modified_base
<222> LOCATION: (1006)..(1007)
<223> OTHER INFORMATION: UNA monomer
<220> FEATURE:
<221> NAME/KEY: modified_base
<222> LOCATION: (1014)..(1014)
<223> OTHER INFORMATION: UNA monomer
<220> FEATURE:
<221> NAME/KEY: modified_base
<222> LOCATION: (1020)..(1020)
<223> OTHER INFORMATION: UNA monomer
<220> FEATURE:
<221> NAME/KEY: modified_base
<222> LOCATION: (1025)..(1025)
<223> OTHER INFORMATION: UNA monomer
<220> FEATURE:
<221> NAME/KEY: modified_base
<222> LOCATION: (1027)..(1027)
<223> OTHER INFORMATION: UNA monomer
<220> FEATURE:
<221> NAME/KEY: modified_base
```

```
<222> LOCATION: (1034)..(1034)
<223> OTHER INFORMATION: UNA monomer
<220> FEATURE:
<221> NAME/KEY: modified_base
<222> LOCATION: (1052)..(1052)
<223> OTHER INFORMATION: UNA monomer
<220> FEATURE:
<221> NAME/KEY: modified_base
<222> LOCATION: (1058)..(1058)
<223> OTHER INFORMATION: UNA monomer
<220> FEATURE:
<221> NAME/KEY: modified_base
<222> LOCATION: (1060)..(1060)
<223> OTHER INFORMATION: UNA monomer
<220> FEATURE:
<221> NAME/KEY: modified_base
<222> LOCATION: (1070)..(1070)
<223> OTHER INFORMATION: UNA monomer
<220> FEATURE:
<221> NAME/KEY: modified_base
<222> LOCATION: (1074)..(1074)
<223> OTHER INFORMATION: UNA monomer
<220> FEATURE:
<221> NAME/KEY: modified_base
<222> LOCATION: (1080)..(1080)
<223> OTHER INFORMATION: UNA monomer
<220> FEATURE:
<221> NAME/KEY: modified_base
<222> LOCATION: (1082)..(1082)
<223> OTHER INFORMATION: UNA monomer
<220> FEATURE:
<221> NAME/KEY: modified_base
<222> LOCATION: (1085)..(1085)
<223> OTHER INFORMATION: UNA monomer
<220> FEATURE:
<221> NAME/KEY: modified_base
<222> LOCATION: (1091)..(1091)
<223> OTHER INFORMATION: UNA monomer
<220> FEATURE:
<221> NAME/KEY: modified_base
<222> LOCATION: (1107)..(1107)
<223> OTHER INFORMATION: UNA monomer
<220> FEATURE:
<221> NAME/KEY: modified_base
<222> LOCATION: (1113)..(1113)
<223> OTHER INFORMATION: UNA monomer
<220> FEATURE:
<221> NAME/KEY: modified_base
<222> LOCATION: (1116)..(1116)
<223> OTHER INFORMATION: UNA monomer
<220> FEATURE:
<221> NAME/KEY: modified_base
<222> LOCATION: (1124)..(1124)
<223> OTHER INFORMATION: UNA monomer
<220> FEATURE:
<221> NAME/KEY: modified_base
<222> LOCATION: (1126)..(1130)
<223> OTHER INFORMATION: UNA monomer
<220> FEATURE:
<221> NAME/KEY: modified_base
<222> LOCATION: (1139)..(1139)
<223> OTHER INFORMATION: UNA monomer
<220> FEATURE:
<221> NAME/KEY: modified_base
<222> LOCATION: (1145)..(1145)
<223> OTHER INFORMATION: UNA monomer
<220> FEATURE:
<221> NAME/KEY: modified_base
<222> LOCATION: (1147)..(1147)
<223> OTHER INFORMATION: UNA monomer
<220> FEATURE:
<221> NAME/KEY: modified_base
<222> LOCATION: (1149)..(1149)
<223> OTHER INFORMATION: UNA monomer
<220> FEATURE:
<221> NAME/KEY: modified_base
<222> LOCATION: (1151)..(1151)
<223> OTHER INFORMATION: UNA monomer
<220> FEATURE:
```

```
<221> NAME/KEY: modified_base
<222> LOCATION: (1163)..(1163)
<223> OTHER INFORMATION: UNA monomer
<220> FEATURE:
<221> NAME/KEY: modified_base
<222> LOCATION: (1168)..(1169)
<223> OTHER INFORMATION: UNA monomer
<220> FEATURE:
<221> NAME/KEY: modified_base
<222> LOCATION: (1180)..(1182)
<223> OTHER INFORMATION: UNA monomer
<220> FEATURE:
<221> NAME/KEY: modified_base
<222> LOCATION: (1184)..(1184)
<223> OTHER INFORMATION: UNA monomer
<220> FEATURE:
<221> NAME/KEY: modified_base
<222> LOCATION: (1186)..(1187)
<223> OTHER INFORMATION: UNA monomer
<220> FEATURE:
<221> NAME/KEY: modified_base
<222> LOCATION: (1189)..(1190)
<223> OTHER INFORMATION: UNA monomer
<220> FEATURE:
<221> NAME/KEY: modified_base
<222> LOCATION: (1193)..(1193)
<223> OTHER INFORMATION: UNA monomer
<220> FEATURE:
<221> NAME/KEY: modified_base
<222> LOCATION: (1196)..(1197)
<223> OTHER INFORMATION: UNA monomer
<220> FEATURE:
<221> NAME/KEY: modified_base
<222> LOCATION: (1206)..(1206)
<223> OTHER INFORMATION: UNA monomer
<220> FEATURE:
<221> NAME/KEY: modified_base
<222> LOCATION: (1213)..(1213)
<223> OTHER INFORMATION: UNA monomer
<220> FEATURE:
<221> NAME/KEY: modified_base
<222> LOCATION: (1215)..(1215)
<223> OTHER INFORMATION: UNA monomer
<220> FEATURE:
<221> NAME/KEY: modified_base
<222> LOCATION: (1220)..(1220)
<223> OTHER INFORMATION: UNA monomer
<220> FEATURE:
<221> NAME/KEY: modified_base
<222> LOCATION: (1222)..(1223)
<223> OTHER INFORMATION: UNA monomer
<220> FEATURE:
<221> NAME/KEY: modified_base
<222> LOCATION: (1226)..(1226)
<223> OTHER INFORMATION: UNA monomer
<220> FEATURE:
<221> NAME/KEY: modified_base
<222> LOCATION: (1235)..(1235)
<223> OTHER INFORMATION: UNA monomer
<220> FEATURE:
<221> NAME/KEY: modified_base
<222> LOCATION: (1238)..(1238)
<223> OTHER INFORMATION: UNA monomer
<220> FEATURE:
<221> NAME/KEY: modified_base
<222> LOCATION: (1242)..(1242)
<223> OTHER INFORMATION: UNA monomer
<220> FEATURE:
<221> NAME/KEY: modified_base
<222> LOCATION: (1255)..(1255)
<223> OTHER INFORMATION: UNA monomer

<400> SEQUENCE: 20
augccgucuu cugucucgug gggcauccuc cugcuggcag gccugugcug ccuggucccu    60 gucuccugg cugaggaucc ccagggagau gcugcccaga agacagauac aucccaccau   120
gaucaggauc acccaaccuu caacaagauc accccccaacc uggcugaguu cgccuucagc   180
```

```
cuauaccgcc agcuggcaca ccaguccaac agcaccaaua ucuucuucuc cccagugagc      240
aucgcuacag ccuuugcaau gcucucccug gggaccaagg cugacacuca cgaugaaauc      300
cuggagggcc ugaauuucaa ccucacggag auuccggagg cucagauccca ugaaggcuuc     360 caggaacucc uccguacccu caaccagcca gacagccagc uccagcugac caccggcaau      420
ggccuguucc ucagcgaggg ccugaagcua guggauaagu uuuggagga uguuaaaaag       480 uuguaccacu cagaagccuu cacgucaac uucggggaca ccgaagaggc caagaaacag       540
aucaacgauu acguggagaa gguacucaa ggaaauug uggauuggu caaggagcuu         600 gacagagaca caguuuugc ucggugaau uacaucuucu uuaaggcaa augggagaga         660 cccuuugaag ucaaggacac cgaggaagag gacuuccacg uggaccaggu gaccaccgug      720
aaggugccua ugaugaagcg uuuaggcaug uuuaacaucc agcacuguaa gaagcugucc      780
agcugggugc ugcugaugaa auaccugggc aaugccaccg ccaucuucuu ccugccugau      840
gaggggaaac uacagcaccu ggaaaaugaa cucacccacg auaucaucac caaguuccug      900
gaaaaugaag acagaagguc ugccagcuua cauuuaccca aacugccau acuggaacc       960 uaugaucuga agagcguccu gggucaacug ggcaucacua aggucuucag caaugggcu     1020 gaccucuccg ggucacaga ggaggcaccc cugaagcucu ccaaggccgu gcauaaggcu     1080
gugcugacca ucgacgagaa agggacugaa gcugcugggg ccauguuuuu agaggccaua     1140
cccaugucua uccccccga ggucaaguuc aacaaacccu uugucuucuu aaugauugaa     1200
caaaauacca agucucccu cuucauggga aaaguggua aucccaccca aaaauaa          1257

<210> SEQ ID NO 21
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ggcaccacca cugaccuggg acagugaauc gacagccgac c                      41

<210> SEQ ID NO 22
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(41)
<223> OTHER INFORMATION: UNA monomer

<400> SEQUENCE: 22
ggcaccacca cugaccuggg acagugaauc gacagccgac c                      41

<210> SEQ ID NO 23
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: UNA monomer
```

-continued

<400> SEQUENCE: 23
ggcaccacca cugaccuggg acagugaauc gacagccgac c                41

<210> SEQ ID NO 24
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (36)..(37)
<223> OTHER INFORMATION: UNA monomer

<400> SEQUENCE: 24
ggcaccacca cugaccuggg acagugaauc gacagccgac c                41

<210> SEQ ID NO 25
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(35)
<223> OTHER INFORMATION: UNA monomer

<400> SEQUENCE: 25
ggcaccacca cugaccuggg acagugaauc gacagccgac c                41

<210> SEQ ID NO 26
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(33)
<223> OTHER INFORMATION: UNA monomer

<400> SEQUENCE: 26
ggcaccacca cugaccuggg acagugaauc gacagccgac c                41

<210> SEQ ID NO 27
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (30)..(31)
<223> OTHER INFORMATION: UNA monomer

<400> SEQUENCE: 27
ggcaccacca cugaccuggg acagugaauc gacagccgac c                41

<210> SEQ ID NO 28
<211> LENGTH: 41
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (28)..(29)
<223> OTHER INFORMATION: UNA monomer

<400> SEQUENCE: 28
ggcaccacca cugaccuggg acagugaauc gacagccgac c                 41

<210> SEQ ID NO 29
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(27)
<223> OTHER INFORMATION: UNA monomer

<400> SEQUENCE: 29
ggcaccacca cugaccuggg acagugaauc gacagccgac c                 41

<210> SEQ ID NO 30
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(25)
<223> OTHER INFORMATION: UNA monomer

<400> SEQUENCE: 30
ggcaccacca cugaccuggg acagugaauc gacagccgac c                 41

<210> SEQ ID NO 31
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(23)
<223> OTHER INFORMATION: UNA monomer

<400> SEQUENCE: 31
ggcaccacca cugaccuggg acagugaauc gacagccgac c                 41

<210> SEQ ID NO 32
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: UNA monomer

<400> SEQUENCE: 32
ggcaccacca cugaccuggg acagugaauc gacagccgac c                 41
```

<210> SEQ ID NO 33
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(19)
<223> OTHER INFORMATION: UNA monomer

<400> SEQUENCE: 33
ggcaccacca cugaccuggg acagugaauc gacagccgac c                           41

<210> SEQ ID NO 34
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(17)
<223> OTHER INFORMATION: UNA monomer

<400> SEQUENCE: 34
ggcaccacca cugaccuggg acagugaauc gacagccgac c                           41

<210> SEQ ID NO 35
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(15)
<223> OTHER INFORMATION: UNA monomer

<400> SEQUENCE: 35
ggcaccacca cugaccuggg acagugaauc gacagccgac c                           41

<210> SEQ ID NO 36
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(13)
<223> OTHER INFORMATION: UNA monomer

<400> SEQUENCE: 36
ggcaccacca cugaccuggg acagugaauc gacagccgac c                           41

<210> SEQ ID NO 37
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(11)

```
<223> OTHER INFORMATION: UNA monomer

<400> SEQUENCE: 37
ggcaccacca cugaccuggg acagugaauc gacagccgac c         41

<210> SEQ ID NO 38
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(9)
<223> OTHER INFORMATION: UNA monomer

<400> SEQUENCE: 38
ggcaccacca cugaccuggg acagugaauc gacagccgac c         41

<210> SEQ ID NO 39
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(7)
<223> OTHER INFORMATION: UNA monomer

<400> SEQUENCE: 39
ggcaccacca cugaccuggg acagugaauc gacagccgac c         41

<210> SEQ ID NO 40
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: UNA monomer

<400> SEQUENCE: 40
ggcaccacca cugaccuggg acagugaauc gacagccgac c         41

<210> SEQ ID NO 41
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: UNA monomer

<400> SEQUENCE: 41
ggcaccacca cugaccuggg acagugaauc gacagccgac c         41

<210> SEQ ID NO 42
<211> LENGTH: 41
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 42
ggcaccacca cugaccuggg acagugaauc gacagccgac c          41

<210> SEQ ID NO 43
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(38)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 43
ggcaccacca cugaccuggg acagugaauc gacagccgac c          41

<210> SEQ ID NO 44
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(37)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 44
ggcaccacca cugaccuggg acagugaauc gacagccgac c          41

<210> SEQ ID NO 45
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (36)..(36)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 45
ggcaccacca cugaccuggg acagugaauc gacagccgac c          41
```

<210> SEQ ID NO 46
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(35)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 46
ggcaccacca cugaccuggg acagugaauc gacagccgac c                 41

<210> SEQ ID NO 47
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(34)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 47
ggcaccacca cugaccuggg acagugaauc gacagccgac c                 41

<210> SEQ ID NO 48
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (33)..(33)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 48
ggcaccacca cugaccuggg acagugaauc gacagccgac c                 41

<210> SEQ ID NO 49
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 49
ggcaccacca cugaccuggg acagugaauc gacagccgac c          41

<210> SEQ ID NO 50
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 50
ggcaccacca cugaccuggg acagugaauc gacagccgac c          41

<210> SEQ ID NO 51
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (30)..(30)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 51
ggcaccacca cugaccuggg acagugaauc gacagccgac c          41

<210> SEQ ID NO 52
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(29)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 52
ggcaccacca cugaccuggg acagugaauc gacagccgac c          41

<210> SEQ ID NO 53
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(28)

<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 53
ggcaccacca cugaccuggg acagugaauc gacagccgac c                          41

<210> SEQ ID NO 54
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(27)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 54
ggcaccacca cugaccuggg acagugaauc gacagccgac c                          41

<210> SEQ ID NO 55
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 55
ggcaccacca cugaccuggg acagugaauc gacagccgac c                          41

<210> SEQ ID NO 56
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(25)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 56
ggcaccacca cugaccuggg acagugaauc gacagccgac c                          41

<210> SEQ ID NO 57
<211> LENGTH: 41
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (24)..(24)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 57
ggcaccacca cugaccuggg acagugaauc gacagccgac c                              41

<210> SEQ ID NO 58
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 58
ggcaccacca cugaccuggg acagugaauc gacagccgac c                              41

<210> SEQ ID NO 59
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 59
ggcaccacca cugaccuggg acagugaauc gacagccgac c                              41

<210> SEQ ID NO 60
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 60
ggcaccacca cugaccuggg acagugaauc gacagccgac c                              41
```

```
<210> SEQ ID NO 61
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 61
ggcaccacca cugaccuggg acagugaauc gacagccgac c                          41

<210> SEQ ID NO 62
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 62
ggcaccacca cugaccuggg acagugaauc gacagccgac c                          41

<210> SEQ ID NO 63
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 63
ggcaccacca cugaccuggg acagugaauc gacagccgac c                          41

<210> SEQ ID NO 64
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: UNA monomer
<220> FEATURE:
<221> NAME/KEY: modified_base
<222> LOCATION: (41)..(41)
<223> OTHER INFORMATION: UNA monomer
```

<400> SEQUENCE: 64
ggcaccacca cugaccuggg acagugaauc gacagccgac c                          41

<210> SEQ ID NO 65
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 65
ggcaccacca cugaccuggg acagugaauc gacagccgac c                          41

<210> SEQ ID NO 66
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 66
ggcaccacca cugaccuggg acagugaauc gacagccgac c                          41

<210> SEQ ID NO 67
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 67
ggcaccacca cugaccuggg acagugaauc gacagccgac c                          41

<210> SEQ ID NO 68
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: UNA monomer

```
<220> FEATURE:
<221> NAME/KEY: modified_base
<222> LOCATION: (41)..(41)
<223> OTHER INFORMATION: UNA monomer

<400> SEQUENCE: 68
ggcaccacca cugaccuggg acagugaauc gacagccgac c          41

<210> SEQ ID NO 69
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 69
ggcaccacca cugaccuggg acagugaauc gacagccgac c          41

<210> SEQ ID NO 70
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 70
ggcaccacca cugaccuggg acagugaauc gacagccgac c          41

<210> SEQ ID NO 71
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 71
ggcaccacca cugaccuggg acagugaauc gacagccgac c          41

<210> SEQ ID NO 72
<211> LENGTH: 41
<212> TYPE: RNA
<213> ORGANISM: Artificial Sequence
<220> FEATURE:
<223> OTHER INFORMATION: Description of Artificial Sequence: Synthetic
```

-continued

```
        oligonucleotide
<220> FEATURE:
<221> NAME/KEY: modified_base
<222> LOCATION: (9)..(9)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 72
ggcaccacca cugaccuggg acagugaauc gacagccgac c                         41

<210> SEQ ID NO 73
<211> LENGTH: 41
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (8)..(8)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 73
ggcaccacca cugaccuggg acagugaauc gacagccgac c                         41

<210> SEQ ID NO 74
<211> LENGTH: 41
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (7)..(7)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 74
ggcaccacca cugaccuggg acagugaauc gacagccgac c                         41

<210> SEQ ID NO 75
<211> LENGTH: 41
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (6)..(6)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 75
ggcaccacca cugaccuggg acagugaauc gacagccgac c                         41

<210> SEQ ID NO 76
```

```
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 76
ggcaccacca cugaccuggg acagugaauc gacagccgac c                              41

<210> SEQ ID NO 77
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 77
ggcaccacca cugaccuggg acagugaauc gacagccgac c                              41

<210> SEQ ID NO 78
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 78
ggcaccacca cugaccuggg acagugaauc gacagccgac c                              41

<210> SEQ ID NO 79
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 79
```
ggcaccacca cugaccuggg acagugaauc gacagccgac c                         41

<210> SEQ ID NO 80
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(41)
<223> OTHER INFORMATION: UNA monomer

<400> SEQUENCE: 80
ggcaccacca cugaccuggg acagugaauc gacagccgac c                         41

<210> SEQ ID NO 81
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (36)..(38)
<223> OTHER INFORMATION: UNA monomer

<400> SEQUENCE: 81
ggcaccacca cugaccuggg acagugaauc gacagccgac c                         41

<210> SEQ ID NO 82
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (33)..(35)
<223> OTHER INFORMATION: UNA monomer

<400> SEQUENCE: 82
ggcaccacca cugaccuggg acagugaauc gacagccgac c                         41

<210> SEQ ID NO 83
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (30)..(32)
<223> OTHER INFORMATION: UNA monomer

<400> SEQUENCE: 83
ggcaccacca cugaccuggg acagugaauc gacagccgac c                         41

<210> SEQ ID NO 84
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (27)..(29)
<223> OTHER INFORMATION: UNA monomer

<400> SEQUENCE: 84
ggcaccacca cugaccuggg acagugaauc gacagccgac c           41

<210> SEQ ID NO 85
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(26)
<223> OTHER INFORMATION: UNA monomer

<400> SEQUENCE: 85
ggcaccacca cugaccuggg acagugaauc gacagccgac c           41

<210> SEQ ID NO 86
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(23)
<223> OTHER INFORMATION: UNA monomer

<400> SEQUENCE: 86
ggcaccacca cugaccuggg acagugaauc gacagccgac c           41

<210> SEQ ID NO 87
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(20)
<223> OTHER INFORMATION: UNA monomer

<400> SEQUENCE: 87
ggcaccacca cugaccuggg acagugaauc gacagccgac c           41

<210> SEQ ID NO 88
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(17)
<223> OTHER INFORMATION: UNA monomer

<400> SEQUENCE: 88
ggcaccacca cugaccuggg acagugaauc gacagccgac c           41

<210> SEQ ID NO 89
```

```
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(14)
<223> OTHER INFORMATION: UNA monomer

<400> SEQUENCE: 89
ggcaccacca cugaccuggg acagugaauc gacagccgac c                           41

<210> SEQ ID NO 90
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(11)
<223> OTHER INFORMATION: UNA monomer

<400> SEQUENCE: 90
ggcaccacca cugaccuggg acagugaauc gacagccgac c                           41

<210> SEQ ID NO 91
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(8)
<223> OTHER INFORMATION: UNA monomer

<400> SEQUENCE: 91
ggcaccacca cugaccuggg acagugaauc gacagccgac c                           41

<210> SEQ ID NO 92
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(5)
<223> OTHER INFORMATION: UNA monomer

<400> SEQUENCE: 92
ggcaccacca cugaccuggg acagugaauc gacagccgac c                           41

<210> SEQ ID NO 93
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
```

```
<221> NAME/KEY: modified_base
<222> LOCATION: (39)..(39)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 93
ggcaccacca cugaccuggg acagugaauc gacagccgac c                      41

<210> SEQ ID NO 94
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (38)..(38)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 94
ggcaccacca cugaccuggg acagugaauc gacagccgac c                      41

<210> SEQ ID NO 95
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (37)..(37)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 95
ggcaccacca cugaccuggg acagugaauc gacagccgac c                      41

<210> SEQ ID NO 96
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (36)..(36)
<223> OTHER INFORMATION: UNA monomer
<220> FEATURE:
```

```
<221> NAME/KEY: modified_base
<222> LOCATION: (41)..(41)
<223> OTHER INFORMATION: UNA monomer

<400> SEQUENCE: 96
ggcaccacca cugaccuggg acagugaauc gacagccgac c        41

<210> SEQ ID NO 97
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (35)..(35)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 97
ggcaccacca cugaccuggg acagugaauc gacagccgac c        41

<210> SEQ ID NO 98
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (34)..(34)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 98
ggcaccacca cugaccuggg acagugaauc gacagccgac c        41

<210> SEQ ID NO 99
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (33)..(33)
<223> OTHER INFORMATION: UNA monomer
<220> FEATURE:
<221> NAME/KEY: modified_base
<222> LOCATION: (41)..(41)
<223> OTHER INFORMATION: UNA monomer
```

```
-continued

<400> SEQUENCE: 99
ggcaccacca cugaccuggg acagugaauc gacagccgac c                              41

<210> SEQ ID NO 100
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (32)..(32)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 100
ggcaccacca cugaccuggg acagugaauc gacagccgac c                              41

<210> SEQ ID NO 101
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (31)..(31)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 101
ggcaccacca cugaccuggg acagugaauc gacagccgac c                              41

<210> SEQ ID NO 102
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (30)..(30)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 102
ggcaccacca cugaccuggg acagugaauc gacagccgac c                              41
```

```
<210> SEQ ID NO 103
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (29)..(29)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 103
ggcaccacca cugaccuggg acagugaauc gacagccgac c                              41

<210> SEQ ID NO 104
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (28)..(28)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 104
ggcaccacca cugaccuggg acagugaauc gacagccgac c                              41

<210> SEQ ID NO 105
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (27)..(27)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 105
ggcaccacca cugaccuggg acagugaauc gacagccgac c                              41

<210> SEQ ID NO 106
<211> LENGTH: 41
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (26)..(26)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 106
ggcaccacca cugaccuggg acagugaauc gacagccgac c                   41

<210> SEQ ID NO 107
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (25)..(25)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 107
ggcaccacca cugaccuggg acagugaauc gacagccgac c                   41

<210> SEQ ID NO 108
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (24)..(24)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 108
ggcaccacca cugaccuggg acagugaauc gacagccgac c                   41

<210> SEQ ID NO 109
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (23)..(23)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 109
ggcaccacca cugaccuggg acagugaauc gacagccgac c        41

<210> SEQ ID NO 110
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (22)..(22)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 110
ggcaccacca cugaccuggg acagugaauc gacagccgac c        41

<210> SEQ ID NO 111
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (21)..(21)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 111
ggcaccacca cugaccuggg acagugaauc gacagccgac c        41

<210> SEQ ID NO 112
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
```

```
<220> FEATURE:
<221> NAME/KEY: modified_base
<222> LOCATION: (20)..(20)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 112
ggcaccacca cugaccuggg acagugaauc gacagccgac c                           41

<210> SEQ ID NO 113
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (19)..(19)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 113
ggcaccacca cugaccuggg acagugaauc gacagccgac c                           41

<210> SEQ ID NO 114
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (18)..(18)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 114
ggcaccacca cugaccuggg acagugaauc gacagccgac c                           41

<210> SEQ ID NO 115
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (17)..(17)
<223> OTHER INFORMATION: UNA monomer
```

```
<220> FEATURE:
<221> NAME/KEY: modified_base
<222> LOCATION: (41)..(41)
<223> OTHER INFORMATION: UNA monomer

<400> SEQUENCE: 115
ggcaccacca cugaccuggg acagugaauc gacagccgac c                          41

<210> SEQ ID NO 116
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (16)..(16)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 116
ggcaccacca cugaccuggg acagugaauc gacagccgac c                          41

<210> SEQ ID NO 117
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (15)..(15)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 117
ggcaccacca cugaccuggg acagugaauc gacagccgac c                          41

<210> SEQ ID NO 118
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (14)..(14)
<223> OTHER INFORMATION: UNA monomer
<220> FEATURE:
<221> NAME/KEY: modified_base
<222> LOCATION: (41)..(41)
<223> OTHER INFORMATION: UNA monomer
```

<400> SEQUENCE: 118
ggcaccacca cugaccuggg acagugaauc gacagccgac c                41

<210> SEQ ID NO 119
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (13)..(13)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 119
ggcaccacca cugaccuggg acagugaauc gacagccgac c                41

<210> SEQ ID NO 120
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (12)..(12)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 120
ggcaccacca cugaccuggg acagugaauc gacagccgac c                41

<210> SEQ ID NO 121
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (11)..(11)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 121
ggcaccacca cugaccuggg acagugaauc gacagccgac c                41

```
<210> SEQ ID NO 122
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (10)..(10)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 122
ggcaccacca cugaccuggg acagugaauc gacagccgac c                              41

<210> SEQ ID NO 123
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (9)..(9)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 123
ggcaccacca cugaccuggg acagugaauc gacagccgac c                              41

<210> SEQ ID NO 124
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (8)..(8)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 124
ggcaccacca cugaccuggg acagugaauc gacagccgac c                              41

<210> SEQ ID NO 125
<211> LENGTH: 41
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (7)..(7)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 125
ggcaccacca cugaccuggg acagugaauc gacagccgac c         41

<210> SEQ ID NO 126
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (6)..(6)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 126
ggcaccacca cugaccuggg acagugaauc gacagccgac c         41

<210> SEQ ID NO 127
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (5)..(5)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 127
ggcaccacca cugaccuggg acagugaauc gacagccgac c         41

<210> SEQ ID NO 128
<211> LENGTH: 41
<212> TYPE: RNA
<213> ORGANISM: Artificial Sequence
<220> FEATURE:
<223> OTHER INFORMATION: Description of Artificial Sequence: Synthetic
```

```
                              oligonucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (4)..(4)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 128
ggcaccacca cugaccuggg acagugaauc gacagccgac c                        41

<210> SEQ ID NO 129
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 129
ggcaccacca cugaccuggg acagugaauc gacagccgac c                        41

<210> SEQ ID NO 130
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: UNA monomer
<220> FEATURE:
<221> NAME/KEY: modified_base
<222> LOCATION: (41)..(41)
<223> OTHER INFORMATION: UNA monomer

<400> SEQUENCE: 130
ggcaccacca cugaccuggg acagugaauc gacagccgac c                        41

<210> SEQ ID NO 131
<211> LENGTH: 582
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(4)
<223> OTHER INFORMATION: UNA monomer
<220> FEATURE:
<221> NAME/KEY: modified_base
<222> LOCATION: (579)..(581)
<223> OTHER INFORMATION: UNA monomer

<400> SEQUENCE: 131
```

```
auggggguge acgaaugucc ugccuggcug uggcuucucc ugucccugcu gucgcucccu    60
cugggccucc caguccuggg cgccccacca cgccucaucu gugacagccg aguccuggag   120
agguaccucu uggaggccaa ggaggccgag aauaucacga cgggcugugc ugaacacugc   180
agcuugaaug agaauaucac ugucccagac accaaaguua auuucuaugc cuggaagagg   240
auggaggucg ggcagcaggc cguagaaguc uggcagggcc uggcccugcu gucggaagcu   300
guccugcggg gccaggcccu guuggucaac ucuucccagc cguggaagcc ccugcagcug   360 caugggaua aagccgucag uggccuucgc agccucacca cucugcuucg ggcucuggga    420
gcccagaagg aagccaucuc cccuccagau gcggccucag cugcuccacu ccgaacaauc   480
acugcugaca cuuccgcaa acucuuccga gucuaccucca auuccuccg gggaaagcug    540 aagcuguaca caggggaggc cugcaggaca ggggacagau ga                     582
```

```
<210> SEQ ID NO 132
<211> LENGTH: 582
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: UNA monomer
<220> FEATURE:
<221> NAME/KEY: modified_base
<222> LOCATION: (15)..(15)
<223> OTHER INFORMATION: UNA monomer
<220> FEATURE:
<221> NAME/KEY: modified_base
<222> LOCATION: (27)..(27)
<223> OTHER INFORMATION: UNA monomer
<220> FEATURE:
<221> NAME/KEY: modified_base
<222> LOCATION: (39)..(39)
<223> OTHER INFORMATION: UNA monomer
<220> FEATURE:
<221> NAME/KEY: modified_base
<222> LOCATION: (51)..(51)
<223> OTHER INFORMATION: UNA monomer
<220> FEATURE:
<221> NAME/KEY: modified_base
<222> LOCATION: (63)..(63)
<223> OTHER INFORMATION: UNA monomer
<220> FEATURE:
<221> NAME/KEY: modified_base
<222> LOCATION: (75)..(75)
<223> OTHER INFORMATION: UNA monomer
<220> FEATURE:
<221> NAME/KEY: modified_base
<222> LOCATION: (87)..(87)
<223> OTHER INFORMATION: UNA monomer
<220> FEATURE:
<221> NAME/KEY: modified_base
<222> LOCATION: (99)..(99)
<223> OTHER INFORMATION: UNA monomer
<220> FEATURE:
<221> NAME/KEY: modified_base
<222> LOCATION: (111)..(111)
<223> OTHER INFORMATION: UNA monomer
<220> FEATURE:
<221> NAME/KEY: modified_base
<222> LOCATION: (123)..(123)
<223> OTHER INFORMATION: UNA monomer
<220> FEATURE:
<221> NAME/KEY: modified_base
<222> LOCATION: (135)..(135)
<223> OTHER INFORMATION: UNA monomer
<220> FEATURE:
<221> NAME/KEY: modified_base
<222> LOCATION: (147)..(147)
```

```
<223> OTHER INFORMATION: UNA monomer
<220> FEATURE:
<221> NAME/KEY: modified_base
<222> LOCATION: (159)..(159)
<223> OTHER INFORMATION: UNA monomer
<220> FEATURE:
<221> NAME/KEY: modified_base
<222> LOCATION: (171)..(171)
<223> OTHER INFORMATION: UNA monomer
<220> FEATURE:
<221> NAME/KEY: modified_base
<222> LOCATION: (183)..(183)
<223> OTHER INFORMATION: UNA monomer
<220> FEATURE:
<221> NAME/KEY: modified_base
<222> LOCATION: (195)..(195)
<223> OTHER INFORMATION: UNA monomer
<220> FEATURE:
<221> NAME/KEY: modified_base
<222> LOCATION: (207)..(207)
<223> OTHER INFORMATION: UNA monomer
<220> FEATURE:
<221> NAME/KEY: modified_base
<222> LOCATION: (219)..(219)
<223> OTHER INFORMATION: UNA monomer
<220> FEATURE:
<221> NAME/KEY: modified_base
<222> LOCATION: (231)..(231)
<223> OTHER INFORMATION: UNA monomer
<220> FEATURE:
<221> NAME/KEY: modified_base
<222> LOCATION: (243)..(243)
<223> OTHER INFORMATION: UNA monomer
<220> FEATURE:
<221> NAME/KEY: modified_base
<222> LOCATION: (255)..(255)
<223> OTHER INFORMATION: UNA monomer
<220> FEATURE:
<221> NAME/KEY: modified_base
<222> LOCATION: (267)..(267)
<223> OTHER INFORMATION: UNA monomer
<220> FEATURE:
<221> NAME/KEY: modified_base
<222> LOCATION: (279)..(279)
<223> OTHER INFORMATION: UNA monomer
<220> FEATURE:
<221> NAME/KEY: modified_base
<222> LOCATION: (291)..(291)
<223> OTHER INFORMATION: UNA monomer
<220> FEATURE:
<221> NAME/KEY: modified_base
<222> LOCATION: (303)..(303)
<223> OTHER INFORMATION: UNA monomer
<220> FEATURE:
<221> NAME/KEY: modified_base
<222> LOCATION: (315)..(315)
<223> OTHER INFORMATION: UNA monomer
<220> FEATURE:
<221> NAME/KEY: modified_base
<222> LOCATION: (327)..(327)
<223> OTHER INFORMATION: UNA monomer
<220> FEATURE:
<221> NAME/KEY: modified_base
<222> LOCATION: (339)..(339)
<223> OTHER INFORMATION: UNA monomer
<220> FEATURE:
<221> NAME/KEY: modified_base
<222> LOCATION: (351)..(351)
<223> OTHER INFORMATION: UNA monomer
<220> FEATURE:
<221> NAME/KEY: modified_base
<222> LOCATION: (363)..(363)
<223> OTHER INFORMATION: UNA monomer
<220> FEATURE:
<221> NAME/KEY: modified_base
<222> LOCATION: (375)..(375)
<223> OTHER INFORMATION: UNA monomer
<220> FEATURE:
<221> NAME/KEY: modified_base
```

-continued

```
<222> LOCATION: (387)..(387)
<223> OTHER INFORMATION: UNA monomer
<220> FEATURE:
<221> NAME/KEY: modified_base
<222> LOCATION: (399)..(399)
<223> OTHER INFORMATION: UNA monomer
<220> FEATURE:
<221> NAME/KEY: modified_base
<222> LOCATION: (411)..(411)
<223> OTHER INFORMATION: UNA monomer
<220> FEATURE:
<221> NAME/KEY: modified_base
<222> LOCATION: (423)..(423)
<223> OTHER INFORMATION: UNA monomer
<220> FEATURE:
<221> NAME/KEY: modified_base
<222> LOCATION: (435)..(435)
<223> OTHER INFORMATION: UNA monomer
<220> FEATURE:
<221> NAME/KEY: modified_base
<222> LOCATION: (447)..(447)
<223> OTHER INFORMATION: UNA monomer
<220> FEATURE:
<221> NAME/KEY: modified_base
<222> LOCATION: (459)..(459)
<223> OTHER INFORMATION: UNA monomer
<220> FEATURE:
<221> NAME/KEY: modified_base
<222> LOCATION: (471)..(471)
<223> OTHER INFORMATION: UNA monomer
<220> FEATURE:
<221> NAME/KEY: modified_base
<222> LOCATION: (483)..(483)
<223> OTHER INFORMATION: UNA monomer
<220> FEATURE:
<221> NAME/KEY: modified_base
<222> LOCATION: (495)..(495)
<223> OTHER INFORMATION: UNA monomer
<220> FEATURE:
<221> NAME/KEY: modified_base
<222> LOCATION: (507)..(507)
<223> OTHER INFORMATION: UNA monomer
<220> FEATURE:
<221> NAME/KEY: modified_base
<222> LOCATION: (519)..(519)
<223> OTHER INFORMATION: UNA monomer
<220> FEATURE:
<221> NAME/KEY: modified_base
<222> LOCATION: (531)..(531)
<223> OTHER INFORMATION: UNA monomer
<220> FEATURE:
<221> NAME/KEY: modified_base
<222> LOCATION: (543)..(543)
<223> OTHER INFORMATION: UNA monomer
<220> FEATURE:
<221> NAME/KEY: modified_base
<222> LOCATION: (555)..(555)
<223> OTHER INFORMATION: UNA monomer
<220> FEATURE:
<221> NAME/KEY: modified_base
<222> LOCATION: (567)..(567)
<223> OTHER INFORMATION: UNA monomer
<220> FEATURE:
<221> NAME/KEY: modified_base
<222> LOCATION: (579)..(579)
<223> OTHER INFORMATION: UNA monomer

<400> SEQUENCE: 132 auggggugc acgaaugucc ugccuggcug uggcuucucc uguccccugcu gucgcucccu      60 cugggccucc caguccuggg cgccccacca cgccucaucu gugacagccg aguccuggag     120
agguaccucu uggaggccaa ggaggccgag aauaucacga cgggcugugc ugaacacugc     180
agcuugaaug agaauaucac ugucccagac accaaaguua auuucuaugc cuggaagagg     240
auggaggucg ggcagcaggc cguagaaguc uggcagggcc uggcccugcu gucggaagcu     300
```

```
guccugcggg gccaggcccu guuggucaac ucuucccagc cgugggagcc ccugcagcug    360 caugggaua aagccgucag uggccuucgc agccucacca cucugcuucg ggcucuggga    420
gcccagaagg aagccaucuc cccuccagau gcggccucag cugcuccacu ccgaacaauc    480
acugcugaca cuuuccgcaa acucuuccga gucuacucca auuccucccg gggaaagcug    540
aagcuguaca caggggaggc cugcaggaca ggggacagau ga                      582
```

```
<210> SEQ ID NO 133
<211> LENGTH: 582
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (8)..(8)
<223> OTHER INFORMATION: UNA monomer
<220> FEATURE:
<221> NAME/KEY: modified_base
<222> LOCATION: (16)..(16)
<223> OTHER INFORMATION: UNA monomer
<220> FEATURE:
<221> NAME/KEY: modified_base
<222> LOCATION: (18)..(18)
<223> OTHER INFORMATION: UNA monomer
<220> FEATURE:
<221> NAME/KEY: modified_base
<222> LOCATION: (21)..(21)
<223> OTHER INFORMATION: UNA monomer
<220> FEATURE:
<221> NAME/KEY: modified_base
<222> LOCATION: (25)..(25)
<223> OTHER INFORMATION: UNA monomer
<220> FEATURE:
<221> NAME/KEY: modified_base
<222> LOCATION: (29)..(29)
<223> OTHER INFORMATION: UNA monomer
<220> FEATURE:
<221> NAME/KEY: modified_base
<222> LOCATION: (31)..(31)
<223> OTHER INFORMATION: UNA monomer
<220> FEATURE:
<221> NAME/KEY: modified_base
<222> LOCATION: (35)..(36)
<223> OTHER INFORMATION: UNA monomer
<220> FEATURE:
<221> NAME/KEY: modified_base
<222> LOCATION: (38)..(38)
<223> OTHER INFORMATION: UNA monomer
<220> FEATURE:
<221> NAME/KEY: modified_base
<222> LOCATION: (41)..(41)
<223> OTHER INFORMATION: UNA monomer
<220> FEATURE:
<221> NAME/KEY: modified_base
<222> LOCATION: (43)..(43)
<223> OTHER INFORMATION: UNA monomer
<220> FEATURE:
<221> NAME/KEY: modified_base
<222> LOCATION: (47)..(47)
<223> OTHER INFORMATION: UNA monomer
<220> FEATURE:
<221> NAME/KEY: modified_base
<222> LOCATION: (50)..(50)
<223> OTHER INFORMATION: UNA monomer
<220> FEATURE:
<221> NAME/KEY: modified_base
<222> LOCATION: (52)..(52)
<223> OTHER INFORMATION: UNA monomer
<220> FEATURE:
```

```
<221> NAME/KEY: modified_base
<222> LOCATION: (56)..(56)
<223> OTHER INFORMATION: UNA monomer
<220> FEATURE:
<221> NAME/KEY: modified_base
<222> LOCATION: (60)..(60)
<223> OTHER INFORMATION: UNA monomer
<220> FEATURE:
<221> NAME/KEY: modified_base
<222> LOCATION: (62)..(62)
<223> OTHER INFORMATION: UNA monomer
<220> FEATURE:
<221> NAME/KEY: modified_base
<222> LOCATION: (68)..(68)
<223> OTHER INFORMATION: UNA monomer
<220> FEATURE:
<221> NAME/KEY: modified_base
<222> LOCATION: (74)..(74)
<223> OTHER INFORMATION: UNA monomer
<220> FEATURE:
<221> NAME/KEY: modified_base
<222> LOCATION: (77)..(77)
<223> OTHER INFORMATION: UNA monomer
<220> FEATURE:
<221> NAME/KEY: modified_base
<222> LOCATION: (95)..(95)
<223> OTHER INFORMATION: UNA monomer
<220> FEATURE:
<221> NAME/KEY: modified_base
<222> LOCATION: (98)..(98)
<223> OTHER INFORMATION: UNA monomer
<220> FEATURE:
<221> NAME/KEY: modified_base
<222> LOCATION: (100)..(100)
<223> OTHER INFORMATION: UNA monomer
<220> FEATURE:
<221> NAME/KEY: modified_base
<222> LOCATION: (102)..(102)
<223> OTHER INFORMATION: UNA monomer
<220> FEATURE:
<221> NAME/KEY: modified_base
<222> LOCATION: (113)..(113)
<223> OTHER INFORMATION: UNA monomer
<220> FEATURE:
<221> NAME/KEY: modified_base
<222> LOCATION: (116)..(116)
<223> OTHER INFORMATION: UNA monomer
<220> FEATURE:
<221> NAME/KEY: modified_base
<222> LOCATION: (124)..(124)
<223> OTHER INFORMATION: UNA monomer
<220> FEATURE:
<221> NAME/KEY: modified_base
<222> LOCATION: (128)..(128)
<223> OTHER INFORMATION: UNA monomer
<220> FEATURE:
<221> NAME/KEY: modified_base
<222> LOCATION: (130)..(131)
<223> OTHER INFORMATION: UNA monomer
<220> FEATURE:
<221> NAME/KEY: modified_base
<222> LOCATION: (153)..(153)
<223> OTHER INFORMATION: UNA monomer
<220> FEATURE:
<221> NAME/KEY: modified_base
<222> LOCATION: (155)..(155)
<223> OTHER INFORMATION: UNA monomer
<220> FEATURE:
<221> NAME/KEY: modified_base
<222> LOCATION: (166)..(166)
<223> OTHER INFORMATION: UNA monomer
<220> FEATURE:
<221> NAME/KEY: modified_base
<222> LOCATION: (168)..(168)
<223> OTHER INFORMATION: UNA monomer
<220> FEATURE:
<221> NAME/KEY: modified_base
<222> LOCATION: (171)..(171)
<223> OTHER INFORMATION: UNA monomer
```

-continued

```
<220> FEATURE:
<221> NAME/KEY: modified_base
<222> LOCATION: (178)..(178)
<223> OTHER INFORMATION: UNA monomer
<220> FEATURE:
<221> NAME/KEY: modified_base
<222> LOCATION: (184)..(185)
<223> OTHER INFORMATION: UNA monomer
<220> FEATURE:
<221> NAME/KEY: modified_base
<222> LOCATION: (189)..(189)
<223> OTHER INFORMATION: UNA monomer
<220> FEATURE:
<221> NAME/KEY: modified_base
<222> LOCATION: (195)..(195)
<223> OTHER INFORMATION: UNA monomer
<220> FEATURE:
<221> NAME/KEY: modified_base
<222> LOCATION: (197)..(197)
<223> OTHER INFORMATION: UNA monomer
<220> FEATURE:
<221> NAME/KEY: modified_base
<222> LOCATION: (201)..(201)
<223> OTHER INFORMATION: UNA monomer
<220> FEATURE:
<221> NAME/KEY: modified_base
<222> LOCATION: (203)..(203)
<223> OTHER INFORMATION: UNA monomer
<220> FEATURE:
<221> NAME/KEY: modified_base
<222> LOCATION: (218)..(219)
<223> OTHER INFORMATION: UNA monomer
<220> FEATURE:
<221> NAME/KEY: modified_base
<222> LOCATION: (222)..(224)
<223> OTHER INFORMATION: UNA monomer
<220> FEATURE:
<221> NAME/KEY: modified_base
<222> LOCATION: (226)..(226)
<223> OTHER INFORMATION: UNA monomer
<220> FEATURE:
<221> NAME/KEY: modified_base
<222> LOCATION: (228)..(228)
<223> OTHER INFORMATION: UNA monomer
<220> FEATURE:
<221> NAME/KEY: modified_base
<222> LOCATION: (232)..(232)
<223> OTHER INFORMATION: UNA monomer
<220> FEATURE:
<221> NAME/KEY: modified_base
<222> LOCATION: (242)..(242)
<223> OTHER INFORMATION: UNA monomer
<220> FEATURE:
<221> NAME/KEY: modified_base
<222> LOCATION: (248)..(248)
<223> OTHER INFORMATION: UNA monomer
<220> FEATURE:
<221> NAME/KEY: modified_base
<222> LOCATION: (263)..(263)
<223> OTHER INFORMATION: UNA monomer
<220> FEATURE:
<221> NAME/KEY: modified_base
<222> LOCATION: (269)..(269)
<223> OTHER INFORMATION: UNA monomer
<220> FEATURE:
<221> NAME/KEY: modified_base
<222> LOCATION: (271)..(271)
<223> OTHER INFORMATION: UNA monomer
<220> FEATURE:
<221> NAME/KEY: modified_base
<222> LOCATION: (281)..(281)
<223> OTHER INFORMATION: UNA monomer
<220> FEATURE:
<221> NAME/KEY: modified_base
<222> LOCATION: (287)..(287)
<223> OTHER INFORMATION: UNA monomer
<220> FEATURE:
<221> NAME/KEY: modified_base
<222> LOCATION: (290)..(290)
```

```
<223> OTHER INFORMATION: UNA monomer
<220> FEATURE:
<221> NAME/KEY: modified_base
<222> LOCATION: (292)..(292)
<223> OTHER INFORMATION: UNA monomer
<220> FEATURE:
<221> NAME/KEY: modified_base
<222> LOCATION: (300)..(300)
<223> OTHER INFORMATION: UNA monomer
<220> FEATURE:
<221> NAME/KEY: modified_base
<222> LOCATION: (302)..(302)
<223> OTHER INFORMATION: UNA monomer
<220> FEATURE:
<221> NAME/KEY: modified_base
<222> LOCATION: (305)..(305)
<223> OTHER INFORMATION: UNA monomer
<220> FEATURE:
<221> NAME/KEY: modified_base
<222> LOCATION: (320)..(320)
<223> OTHER INFORMATION: UNA monomer
<220> FEATURE:
<221> NAME/KEY: modified_base
<222> LOCATION: (322)..(323)
<223> OTHER INFORMATION: UNA monomer
<220> FEATURE:
<221> NAME/KEY: modified_base
<222> LOCATION: (326)..(326)
<223> OTHER INFORMATION: UNA monomer
<220> FEATURE:
<221> NAME/KEY: modified_base
<222> LOCATION: (331)..(331)
<223> OTHER INFORMATION: UNA monomer
<220> FEATURE:
<221> NAME/KEY: modified_base
<222> LOCATION: (333)..(334)
<223> OTHER INFORMATION: UNA monomer
<220> FEATURE:
<221> NAME/KEY: modified_base
<222> LOCATION: (343)..(343)
<223> OTHER INFORMATION: UNA monomer
<220> FEATURE:
<221> NAME/KEY: modified_base
<222> LOCATION: (353)..(353)
<223> OTHER INFORMATION: UNA monomer
<220> FEATURE:
<221> NAME/KEY: modified_base
<222> LOCATION: (359)..(359)
<223> OTHER INFORMATION: UNA monomer
<220> FEATURE:
<221> NAME/KEY: modified_base
<222> LOCATION: (363)..(363)
<223> OTHER INFORMATION: UNA monomer
<220> FEATURE:
<221> NAME/KEY: modified_base
<222> LOCATION: (365)..(365)
<223> OTHER INFORMATION: UNA monomer
<220> FEATURE:
<221> NAME/KEY: modified_base
<222> LOCATION: (369)..(369)
<223> OTHER INFORMATION: UNA monomer
<220> FEATURE:
<221> NAME/KEY: modified_base
<222> LOCATION: (377)..(377)
<223> OTHER INFORMATION: UNA monomer
<220> FEATURE:
<221> NAME/KEY: modified_base
<222> LOCATION: (381)..(381)
<223> OTHER INFORMATION: UNA monomer
<220> FEATURE:
<221> NAME/KEY: modified_base
<222> LOCATION: (386)..(387)
<223> OTHER INFORMATION: UNA monomer
<220> FEATURE:
<221> NAME/KEY: modified_base
<222> LOCATION: (395)..(395)
<223> OTHER INFORMATION: UNA monomer
<220> FEATURE:
<221> NAME/KEY: modified_base
```

```
<222> LOCATION: (402)..(402)
<223> OTHER INFORMATION: UNA monomer
<220> FEATURE:
<221> NAME/KEY: modified_base
<222> LOCATION: (404)..(404)
<223> OTHER INFORMATION: UNA monomer
<220> FEATURE:
<221> NAME/KEY: modified_base
<222> LOCATION: (407)..(408)
<223> OTHER INFORMATION: UNA monomer
<220> FEATURE:
<221> NAME/KEY: modified_base
<222> LOCATION: (414)..(414)
<223> OTHER INFORMATION: UNA monomer
<220> FEATURE:
<221> NAME/KEY: modified_base
<222> LOCATION: (416)..(416)
<223> OTHER INFORMATION: UNA monomer
<220> FEATURE:
<221> NAME/KEY: modified_base
<222> LOCATION: (437)..(437)
<223> OTHER INFORMATION: UNA monomer
<220> FEATURE:
<221> NAME/KEY: modified_base
<222> LOCATION: (439)..(439)
<223> OTHER INFORMATION: UNA monomer
<220> FEATURE:
<221> NAME/KEY: modified_base
<222> LOCATION: (444)..(444)
<223> OTHER INFORMATION: UNA monomer
<220> FEATURE:
<221> NAME/KEY: modified_base
<222> LOCATION: (450)..(450)
<223> OTHER INFORMATION: UNA monomer
<220> FEATURE:
<221> NAME/KEY: modified_base
<222> LOCATION: (457)..(457)
<223> OTHER INFORMATION: UNA monomer
<220> FEATURE:
<221> NAME/KEY: modified_base
<222> LOCATION: (462)..(462)
<223> OTHER INFORMATION: UNA monomer
<220> FEATURE:
<221> NAME/KEY: modified_base
<222> LOCATION: (465)..(465)
<223> OTHER INFORMATION: UNA monomer
<220> FEATURE:
<221> NAME/KEY: modified_base
<222> LOCATION: (470)..(470)
<223> OTHER INFORMATION: UNA monomer
<220> FEATURE:
<221> NAME/KEY: modified_base
<222> LOCATION: (479)..(479)
<223> OTHER INFORMATION: UNA monomer
<220> FEATURE:
<221> NAME/KEY: modified_base
<222> LOCATION: (483)..(483)
<223> OTHER INFORMATION: UNA monomer
<220> FEATURE:
<221> NAME/KEY: modified_base
<222> LOCATION: (486)..(486)
<223> OTHER INFORMATION: UNA monomer
<220> FEATURE:
<221> NAME/KEY: modified_base
<222> LOCATION: (492)..(494)
<223> OTHER INFORMATION: UNA monomer
<220> FEATURE:
<221> NAME/KEY: modified_base
<222> LOCATION: (503)..(503)
<223> OTHER INFORMATION: UNA monomer
<220> FEATURE:
<221> NAME/KEY: modified_base
<222> LOCATION: (505)..(506)
<223> OTHER INFORMATION: UNA monomer
<220> FEATURE:
<221> NAME/KEY: modified_base
<222> LOCATION: (512)..(512)
<223> OTHER INFORMATION: UNA monomer
<220> FEATURE:
```

-continued

```
<221> NAME/KEY: modified_base
<222> LOCATION: (514)..(514)
<223> OTHER INFORMATION: UNA monomer
<220> FEATURE:
<221> NAME/KEY: modified_base
<222> LOCATION: (517)..(517)
<223> OTHER INFORMATION: UNA monomer
<220> FEATURE:
<221> NAME/KEY: modified_base
<222> LOCATION: (522)..(524)
<223> OTHER INFORMATION: UNA monomer
<220> FEATURE:
<221> NAME/KEY: modified_base
<222> LOCATION: (527)..(527)
<223> OTHER INFORMATION: UNA monomer
<220> FEATURE:
<221> NAME/KEY: modified_base
<222> LOCATION: (539)..(539)
<223> OTHER INFORMATION: UNA monomer
<220> FEATURE:
<221> NAME/KEY: modified_base
<222> LOCATION: (545)..(545)
<223> OTHER INFORMATION: UNA monomer
<220> FEATURE:
<221> NAME/KEY: modified_base
<222> LOCATION: (547)..(547)
<223> OTHER INFORMATION: UNA monomer
<220> FEATURE:
<221> NAME/KEY: modified_base
<222> LOCATION: (562)..(562)
<223> OTHER INFORMATION: UNA monomer
<220> FEATURE:
<221> NAME/KEY: modified_base
<222> LOCATION: (580)..(580)
<223> OTHER INFORMATION: UNA monomer

<400> SEQUENCE: 133 auggggugc acgaaugucc ugccuggcug uggcuucucc ugucccugcu gucgcucccu      60
cugggccucc caguccuggg cgccccacca cgccucaucu gugacagccg aguccuggag    120
agguaccucu uggaggccaa ggaggccgag aauaucacga cgggcugugc ugaacacugc    180
agcuugaaug agaauaucac ugucccagac accaaaguua auuucuaugc cuggaagagg    240
auggaggucg ggcagcaggc cguagaaguc uggcagggcc uggcccugcu gucggaagcu    300
guccugcggg gccaggcccu guuggucaac ucuucccagc cguggagcc ccugcagcug     360 caugugguaua aagccgucag uggccuucgc agccucacca cucugcuucg ggcucuggga   420
gcccagaagg aagccaucuc ccccccagau gcggccucag cugcuccacu ccgaacaauc    480
acugcugaca cuuuccgcaa acucuuccga gucuacucca auuccuccg gggaaagcug     540 aagcuguaca caggggaggc cugcaggaca ggggacagau ga                       582

<210> SEQ ID NO 134
<211> LENGTH: 1066
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: UNA monomer
<220> FEATURE:
<221> NAME/KEY: modified_base
<222> LOCATION: (15)..(15)
<223> OTHER INFORMATION: UNA monomer
<220> FEATURE:
<221> NAME/KEY: modified_base
<222> LOCATION: (27)..(27)
<223> OTHER INFORMATION: UNA monomer
<220> FEATURE:
```

```
<221> NAME/KEY: modified_base
<222> LOCATION: (39)..(39)
<223> OTHER INFORMATION: UNA monomer
<220> FEATURE:
<221> NAME/KEY: modified_base
<222> LOCATION: (51)..(51)
<223> OTHER INFORMATION: UNA monomer
<220> FEATURE:
<221> NAME/KEY: modified_base
<222> LOCATION: (63)..(63)
<223> OTHER INFORMATION: UNA monomer
<220> FEATURE:
<221> NAME/KEY: modified_base
<222> LOCATION: (75)..(75)
<223> OTHER INFORMATION: UNA monomer
<220> FEATURE:
<221> NAME/KEY: modified_base
<222> LOCATION: (87)..(87)
<223> OTHER INFORMATION: UNA monomer
<220> FEATURE:
<221> NAME/KEY: modified_base
<222> LOCATION: (99)..(99)
<223> OTHER INFORMATION: UNA monomer
<220> FEATURE:
<221> NAME/KEY: modified_base
<222> LOCATION: (111)..(111)
<223> OTHER INFORMATION: UNA monomer
<220> FEATURE:
<221> NAME/KEY: modified_base
<222> LOCATION: (123)..(123)
<223> OTHER INFORMATION: UNA monomer
<220> FEATURE:
<221> NAME/KEY: modified_base
<222> LOCATION: (135)..(135)
<223> OTHER INFORMATION: UNA monomer
<220> FEATURE:
<221> NAME/KEY: modified_base
<222> LOCATION: (147)..(147)
<223> OTHER INFORMATION: UNA monomer
<220> FEATURE:
<221> NAME/KEY: modified_base
<222> LOCATION: (159)..(159)
<223> OTHER INFORMATION: UNA monomer
<220> FEATURE:
<221> NAME/KEY: modified_base
<222> LOCATION: (171)..(171)
<223> OTHER INFORMATION: UNA monomer
<220> FEATURE:
<221> NAME/KEY: modified_base
<222> LOCATION: (183)..(183)
<223> OTHER INFORMATION: UNA monomer
<220> FEATURE:
<221> NAME/KEY: modified_base
<222> LOCATION: (195)..(195)
<223> OTHER INFORMATION: UNA monomer
<220> FEATURE:
<221> NAME/KEY: modified_base
<222> LOCATION: (207)..(207)
<223> OTHER INFORMATION: UNA monomer
<220> FEATURE:
<221> NAME/KEY: modified_base
<222> LOCATION: (219)..(219)
<223> OTHER INFORMATION: UNA monomer
<220> FEATURE:
<221> NAME/KEY: modified_base
<222> LOCATION: (231)..(231)
<223> OTHER INFORMATION: UNA monomer
<220> FEATURE:
<221> NAME/KEY: modified_base
<222> LOCATION: (243)..(243)
<223> OTHER INFORMATION: UNA monomer
<220> FEATURE:
<221> NAME/KEY: modified_base
<222> LOCATION: (255)..(255)
<223> OTHER INFORMATION: UNA monomer
<220> FEATURE:
<221> NAME/KEY: modified_base
<222> LOCATION: (267)..(267)
<223> OTHER INFORMATION: UNA monomer
```

```
<220> FEATURE:
<221> NAME/KEY: modified_base
<222> LOCATION: (279)..(279)
<223> OTHER INFORMATION: UNA monomer
<220> FEATURE:
<221> NAME/KEY: modified_base
<222> LOCATION: (291)..(291)
<223> OTHER INFORMATION: UNA monomer
<220> FEATURE:
<221> NAME/KEY: modified_base
<222> LOCATION: (303)..(303)
<223> OTHER INFORMATION: UNA monomer
<220> FEATURE:
<221> NAME/KEY: modified_base
<222> LOCATION: (315)..(315)
<223> OTHER INFORMATION: UNA monomer
<220> FEATURE:
<221> NAME/KEY: modified_base
<222> LOCATION: (327)..(327)
<223> OTHER INFORMATION: UNA monomer
<220> FEATURE:
<221> NAME/KEY: modified_base
<222> LOCATION: (339)..(339)
<223> OTHER INFORMATION: UNA monomer
<220> FEATURE:
<221> NAME/KEY: modified_base
<222> LOCATION: (351)..(351)
<223> OTHER INFORMATION: UNA monomer
<220> FEATURE:
<221> NAME/KEY: modified_base
<222> LOCATION: (363)..(363)
<223> OTHER INFORMATION: UNA monomer
<220> FEATURE:
<221> NAME/KEY: modified_base
<222> LOCATION: (375)..(375)
<223> OTHER INFORMATION: UNA monomer
<220> FEATURE:
<221> NAME/KEY: modified_base
<222> LOCATION: (387)..(387)
<223> OTHER INFORMATION: UNA monomer
<220> FEATURE:
<221> NAME/KEY: modified_base
<222> LOCATION: (399)..(399)
<223> OTHER INFORMATION: UNA monomer
<220> FEATURE:
<221> NAME/KEY: modified_base
<222> LOCATION: (411)..(411)
<223> OTHER INFORMATION: UNA monomer
<220> FEATURE:
<221> NAME/KEY: modified_base
<222> LOCATION: (423)..(423)
<223> OTHER INFORMATION: UNA monomer
<220> FEATURE:
<221> NAME/KEY: modified_base
<222> LOCATION: (435)..(435)
<223> OTHER INFORMATION: UNA monomer
<220> FEATURE:
<221> NAME/KEY: modified_base
<222> LOCATION: (447)..(447)
<223> OTHER INFORMATION: UNA monomer
<220> FEATURE:
<221> NAME/KEY: modified_base
<222> LOCATION: (459)..(459)
<223> OTHER INFORMATION: UNA monomer
<220> FEATURE:
<221> NAME/KEY: modified_base
<222> LOCATION: (471)..(471)
<223> OTHER INFORMATION: UNA monomer
<220> FEATURE:
<221> NAME/KEY: modified_base
<222> LOCATION: (483)..(483)
<223> OTHER INFORMATION: UNA monomer
<220> FEATURE:
<221> NAME/KEY: modified_base
<222> LOCATION: (495)..(495)
<223> OTHER INFORMATION: UNA monomer
<220> FEATURE:
<221> NAME/KEY: modified_base
<222> LOCATION: (507)..(507)
```

```
<223> OTHER INFORMATION: UNA monomer
<220> FEATURE:
<221> NAME/KEY: modified_base
<222> LOCATION: (519)..(519)
<223> OTHER INFORMATION: UNA monomer
<220> FEATURE:
<221> NAME/KEY: modified_base
<222> LOCATION: (531)..(531)
<223> OTHER INFORMATION: UNA monomer
<220> FEATURE:
<221> NAME/KEY: modified_base
<222> LOCATION: (543)..(543)
<223> OTHER INFORMATION: UNA monomer
<220> FEATURE:
<221> NAME/KEY: modified_base
<222> LOCATION: (555)..(555)
<223> OTHER INFORMATION: UNA monomer
<220> FEATURE:
<221> NAME/KEY: modified_base
<222> LOCATION: (567)..(567)
<223> OTHER INFORMATION: UNA monomer
<220> FEATURE:
<221> NAME/KEY: modified_base
<222> LOCATION: (579)..(579)
<223> OTHER INFORMATION: UNA monomer
<220> FEATURE:
<221> NAME/KEY: modified_base
<222> LOCATION: (591)..(591)
<223> OTHER INFORMATION: UNA monomer
<220> FEATURE:
<221> NAME/KEY: modified_base
<222> LOCATION: (603)..(603)
<223> OTHER INFORMATION: UNA monomer
<220> FEATURE:
<221> NAME/KEY: modified_base
<222> LOCATION: (615)..(615)
<223> OTHER INFORMATION: UNA monomer
<220> FEATURE:
<221> NAME/KEY: modified_base
<222> LOCATION: (627)..(627)
<223> OTHER INFORMATION: UNA monomer
<220> FEATURE:
<221> NAME/KEY: modified_base
<222> LOCATION: (639)..(639)
<223> OTHER INFORMATION: UNA monomer
<220> FEATURE:
<221> NAME/KEY: modified_base
<222> LOCATION: (651)..(651)
<223> OTHER INFORMATION: UNA monomer
<220> FEATURE:
<221> NAME/KEY: modified_base
<222> LOCATION: (663)..(663)
<223> OTHER INFORMATION: UNA monomer
<220> FEATURE:
<221> NAME/KEY: modified_base
<222> LOCATION: (675)..(675)
<223> OTHER INFORMATION: UNA monomer
<220> FEATURE:
<221> NAME/KEY: modified_base
<222> LOCATION: (687)..(687)
<223> OTHER INFORMATION: UNA monomer
<220> FEATURE:
<221> NAME/KEY: modified_base
<222> LOCATION: (699)..(699)
<223> OTHER INFORMATION: UNA monomer
<220> FEATURE:
<221> NAME/KEY: modified_base
<222> LOCATION: (711)..(711)
<223> OTHER INFORMATION: UNA monomer
<220> FEATURE:
<221> NAME/KEY: modified_base
<222> LOCATION: (723)..(723)
<223> OTHER INFORMATION: UNA monomer
<220> FEATURE:
<221> NAME/KEY: modified_base
<222> LOCATION: (735)..(735)
<223> OTHER INFORMATION: UNA monomer
<220> FEATURE:
<221> NAME/KEY: modified_base
```

```
<222> LOCATION: (747)..(747)
<223> OTHER INFORMATION: UNA monomer
<220> FEATURE:
<221> NAME/KEY: modified_base
<222> LOCATION: (759)..(759)
<223> OTHER INFORMATION: UNA monomer
<220> FEATURE:
<221> NAME/KEY: modified_base
<222> LOCATION: (771)..(771)
<223> OTHER INFORMATION: UNA monomer
<220> FEATURE:
<221> NAME/KEY: modified_base
<222> LOCATION: (783)..(783)
<223> OTHER INFORMATION: UNA monomer
<220> FEATURE:
<221> NAME/KEY: modified_base
<222> LOCATION: (795)..(795)
<223> OTHER INFORMATION: UNA monomer
<220> FEATURE:
<221> NAME/KEY: modified_base
<222> LOCATION: (807)..(807)
<223> OTHER INFORMATION: UNA monomer
<220> FEATURE:
<221> NAME/KEY: modified_base
<222> LOCATION: (819)..(819)
<223> OTHER INFORMATION: UNA monomer
<220> FEATURE:
<221> NAME/KEY: modified_base
<222> LOCATION: (831)..(831)
<223> OTHER INFORMATION: UNA monomer
<220> FEATURE:
<221> NAME/KEY: modified_base
<222> LOCATION: (843)..(843)
<223> OTHER INFORMATION: UNA monomer
<220> FEATURE:
<221> NAME/KEY: modified_base
<222> LOCATION: (855)..(855)
<223> OTHER INFORMATION: UNA monomer
<220> FEATURE:
<221> NAME/KEY: modified_base
<222> LOCATION: (867)..(867)
<223> OTHER INFORMATION: UNA monomer
<220> FEATURE:
<221> NAME/KEY: modified_base
<222> LOCATION: (879)..(879)
<223> OTHER INFORMATION: UNA monomer
<220> FEATURE:
<221> NAME/KEY: modified_base
<222> LOCATION: (891)..(891)
<223> OTHER INFORMATION: UNA monomer
<220> FEATURE:
<221> NAME/KEY: modified_base
<222> LOCATION: (903)..(903)
<223> OTHER INFORMATION: UNA monomer
<220> FEATURE:
<221> NAME/KEY: modified_base
<222> LOCATION: (915)..(915)
<223> OTHER INFORMATION: UNA monomer
<220> FEATURE:
<221> NAME/KEY: modified_base
<222> LOCATION: (927)..(927)
<223> OTHER INFORMATION: UNA monomer
<220> FEATURE:
<221> NAME/KEY: modified_base
<222> LOCATION: (939)..(939)
<223> OTHER INFORMATION: UNA monomer
<220> FEATURE:
<221> NAME/KEY: modified_base
<222> LOCATION: (951)..(951)
<223> OTHER INFORMATION: UNA monomer
<220> FEATURE:
<221> NAME/KEY: modified_base
<222> LOCATION: (963)..(963)
<223> OTHER INFORMATION: UNA monomer
<220> FEATURE:
<221> NAME/KEY: modified_base
<222> LOCATION: (975)..(975)
<223> OTHER INFORMATION: UNA monomer
<220> FEATURE:
```

```
<221> NAME/KEY: modified_base
<222> LOCATION: (987)..(987)
<223> OTHER INFORMATION: UNA monomer
<220> FEATURE:
<221> NAME/KEY: modified_base
<222> LOCATION: (999)..(999)
<223> OTHER INFORMATION: UNA monomer
<220> FEATURE:
<221> NAME/KEY: modified_base
<222> LOCATION: (1011)..(1011)
<223> OTHER INFORMATION: UNA monomer
<220> FEATURE:
<221> NAME/KEY: modified_base
<222> LOCATION: (1023)..(1023)
<223> OTHER INFORMATION: UNA monomer
<220> FEATURE:
<221> NAME/KEY: modified_base
<222> LOCATION: (1035)..(1035)
<223> OTHER INFORMATION: UNA monomer
<220> FEATURE:
<221> NAME/KEY: modified_base
<222> LOCATION: (1047)..(1047)
<223> OTHER INFORMATION: UNA monomer
<220> FEATURE:
<221> NAME/KEY: modified_base
<222> LOCATION: (1059)..(1059)
<223> OTHER INFORMATION: UNA monomer
<220> FEATURE:
<221> NAME/KEY: modified_base
<222> LOCATION: (1065)..(1065)
<223> OTHER INFORMATION: UNA monomer

<400> SEQUENCE: 134
augcuguuua aucugaggau ccuguuuaaa caaugcagcu uuuagaaaug gucacaacuu      60
caugguucga aauuuucggu guggacaacc acuacaaaau aaagugcagc ugaagggccg     120
ugaccuucuc acucuaaaaa acuuuaccgg agaagaaauu aaauauaugc uauggcuauc     180
agcagaucgc aaauuuagga uaaaacagaa aggagaguau uugccuuuau ugcaagggaa     240
guccuuaggc augauuuuug agaaaagaag uacucgaaca agauugucua cagaaacagg     300
cuuugcacuu cugggaggac auccuuguuu ucuuaccaca caagauauuc auuugggugu     360
gaaugaaagu cucacggaca cggcccgugu auugucuagc auggcagaug caguauuggc     420
ucgaguguau aaacaaucag auuuggacac ccuggcuaaa gaagcaucca ucccaauuau     480
caaugggcug ucagauuugu accauccuau ccagauccug gcugauuacc ucacgcucca     540
ggaacacuau agcucucuga aaggucuuac cccucagcugg aucggggaug ggaacaauau     600
ccugcacucc aucaugauga gcgcagcgaa auucggaaug caccuucagg cagcuacucc     660
aaagggguuau gagccggaug cuaguguaac caaguuggca gagcaguaug ccaaagagaa     720
ugguaccaag cuguugcuga caaaugaucc auuggaagca gcgcauggag gcaauguauu     780
aauuacagac acuuggauaa gcaugggaca agaagaggag aagaaaaagc ggcuccaggc     840
uuuccaaggu uaccagguua caaugaagac ugcuaaaguu gcugccucug acuggacauu     900
uuuacacugc uugcccagaa agccagaaga aguggaugau gaagucuuuu auucccucg     960
aucacuagug uucccagagg cagaaaacag aaaguggaca aucauggcug ucaugguguc    1020
ccugcugaca gauuacucac cucagcucca gaagccuaaa uuuuga                   1066

<210> SEQ ID NO 135
<211> LENGTH: 1065
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
```

```
<221> NAME/KEY: modified_base
<222> LOCATION: (2)..(4)
<223> OTHER INFORMATION: UNA monomer
<220> FEATURE:
<221> NAME/KEY: modified_base
<222> LOCATION: (1062)..(1064)
<223> OTHER INFORMATION: UNA monomer

<400> SEQUENCE: 135
augcuguuua aucugaggau ccuguuaaac aaugcagcuu uuagaaaugg ucacaacuuc      60
augguucgaa auuuucggug uggacaacca cuacaaaaua aagugcagcu gaagggccgu     120
gaccuucuca cucuaaaaaa cuuuaccgga gaagaaauua aauauaugcu augucuauca     180
gcagaucuga aauuuaggau aaaacagaaa ggagaguauu ugccuuuauu gcaagggaag     240
uccuuaggca ugauuuuuga gaaagaagu acucgaacaa gauugucuac agaaacaggc      300
uuugcacuuc ugggaggaca uccuuguuuu cuuaccacac aagauauuca uuugggugug     360
aaugaaaguc ucacggacac ggcccgugua uugucuagca uggcagaugc aguauuggcu     420
cgaguguaua aacaaucaga uuuggacacc cuggcuaaag aagcauccau cccaauuauc     480
aaugggcugu cagauuugua ccauccuauc cagauccugg cugauuaccu cacgcuccag     540
gaacacuaua gcucucugaa aggucuuacc cucagcugga ucggggaugg gaacaauauc     600
cugcacucca ucaugaugag cgcagcgaaa uucggaaugc accuucaggc agcuacucca     660
aagguuaug agccggaugc uaguguaacc aaguggcag agcaguaugc caaagagaau       720
gguaccaagc uguugcugac aaaugauccacc uuggaagcag cgcauggagg caauguauua    780
```

```
<221> NAME/KEY: modified_base
<222> LOCATION: (23)..(23)
<223> OTHER INFORMATION: UNA monomer
<220> FEATURE:
<221> NAME/KEY: modified_base
<222> LOCATION: (25)..(26)
<223> OTHER INFORMATION: UNA monomer
<220> FEATURE:
<221> NAME/KEY: modified_base
<222> LOCATION: (33)..(33)
<223> OTHER INFORMATION: UNA monomer
<220> FEATURE:
<221> NAME/KEY: modified_base
<222> LOCATION: (39)..(42)
<223> OTHER INFORMATION: UNA monomer
<220> FEATURE:
<221> NAME/KEY: modified_base
<222> LOCATION: (48)..(48)
<223> OTHER INFORMATION: UNA monomer
<220> FEATURE:
<221> NAME/KEY: modified_base
<222> LOCATION: (51)..(51)
<223> OTHER INFORMATION: UNA monomer
<220> FEATURE:
<221> NAME/KEY: modified_base
<222> LOCATION: (58)..(59)
<223> OTHER INFORMATION: UNA monomer
<220> FEATURE:
<221> NAME/KEY: modified_base
<222> LOCATION: (62)..(62)
<223> OTHER INFORMATION: UNA monomer
<220> FEATURE:
<221> NAME/KEY: modified_base
<222> LOCATION: (65)..(66)
<223> OTHER INFORMATION: UNA monomer
<220> FEATURE:
<221> NAME/KEY: modified_base
<222> LOCATION: (72)..(75)
<223> OTHER INFORMATION: UNA monomer
<220> FEATURE:
<221> NAME/KEY: modified_base
<222> LOCATION: (79)..(79)
<223> OTHER INFORMATION: UNA monomer
<220> FEATURE:
<221> NAME/KEY: modified_base
<222> LOCATION: (81)..(81)
<223> OTHER INFORMATION: UNA monomer
<220> FEATURE:
<221> NAME/KEY: modified_base
<222> LOCATION: (92)..(92)
<223> OTHER INFORMATION: UNA monomer
<220> FEATURE:
<221> NAME/KEY: modified_base
<222> LOCATION: (99)..(99)
<223> OTHER INFORMATION: UNA monomer
<220> FEATURE:
<221> NAME/KEY: modified_base
<222> LOCATION: (104)..(104)
<223> OTHER INFORMATION: UNA monomer
<220> FEATURE:
<221> NAME/KEY: modified_base
<222> LOCATION: (110)..(110)
<223> OTHER INFORMATION: UNA monomer
<220> FEATURE:
<221> NAME/KEY: modified_base
<222> LOCATION: (120)..(120)
<223> OTHER INFORMATION: UNA monomer
<220> FEATURE:
<221> NAME/KEY: modified_base
<222> LOCATION: (125)..(126)
<223> OTHER INFORMATION: UNA monomer
<220> FEATURE:
<221> NAME/KEY: modified_base
<222> LOCATION: (128)..(128)
<223> OTHER INFORMATION: UNA monomer
<220> FEATURE:
<221> NAME/KEY: modified_base
<222> LOCATION: (132)..(132)
<223> OTHER INFORMATION: UNA monomer
```

```
<220> FEATURE:
<221> NAME/KEY: modified_base
<222> LOCATION: (134)..(134)
<223> OTHER INFORMATION: UNA monomer
<220> FEATURE:
<221> NAME/KEY: modified_base
<222> LOCATION: (142)..(144)
<223> OTHER INFORMATION: UNA monomer
<220> FEATURE:
<221> NAME/KEY: modified_base
<222> LOCATION: (158)..(159)
<223> OTHER INFORMATION: UNA monomer
<220> FEATURE:
<221> NAME/KEY: modified_base
<222> LOCATION: (163)..(163)
<223> OTHER INFORMATION: UNA monomer
<220> FEATURE:
<221> NAME/KEY: modified_base
<222> LOCATION: (165)..(165)
<223> OTHER INFORMATION: UNA monomer
<220> FEATURE:
<221> NAME/KEY: modified_base
<222> LOCATION: (167)..(167)
<223> OTHER INFORMATION: UNA monomer
<220> FEATURE:
<221> NAME/KEY: modified_base
<222> LOCATION: (170)..(170)
<223> OTHER INFORMATION: UNA monomer
<220> FEATURE:
<221> NAME/KEY: modified_base
<222> LOCATION: (172)..(172)
<223> OTHER INFORMATION: UNA monomer
<220> FEATURE:
<221> NAME/KEY: modified_base
<222> LOCATION: (176)..(176)
<223> OTHER INFORMATION: UNA monomer
<220> FEATURE:
<221> NAME/KEY: modified_base
<222> LOCATION: (178)..(178)
<223> OTHER INFORMATION: UNA monomer
<220> FEATURE:
<221> NAME/KEY: modified_base
<222> LOCATION: (186)..(186)
<223> OTHER INFORMATION: UNA monomer
<220> FEATURE:
<221> NAME/KEY: modified_base
<222> LOCATION: (188)..(188)
<223> OTHER INFORMATION: UNA monomer
<220> FEATURE:
<221> NAME/KEY: modified_base
<222> LOCATION: (193)..(195)
<223> OTHER INFORMATION: UNA monomer
<220> FEATURE:
<221> NAME/KEY: modified_base
<222> LOCATION: (200)..(200)
<223> OTHER INFORMATION: UNA monomer
<220> FEATURE:
<221> NAME/KEY: modified_base
<222> LOCATION: (217)..(217)
<223> OTHER INFORMATION: UNA monomer
<220> FEATURE:
<221> NAME/KEY: modified_base
<222> LOCATION: (219)..(221)
<223> OTHER INFORMATION: UNA monomer
<220> FEATURE:
<221> NAME/KEY: modified_base
<222> LOCATION: (225)..(227)
<223> OTHER INFORMATION: UNA monomer
<220> FEATURE:
<221> NAME/KEY: modified_base
<222> LOCATION: (229)..(230)
<223> OTHER INFORMATION: UNA monomer
<220> FEATURE:
<221> NAME/KEY: modified_base
<222> LOCATION: (241)..(241)
<223> OTHER INFORMATION: UNA monomer
<220> FEATURE:
<221> NAME/KEY: modified_base
<222> LOCATION: (244)..(245)
```

```
<223> OTHER INFORMATION: UNA monomer
<220> FEATURE:
<221> NAME/KEY: modified_base
<222> LOCATION: (251)..(251)
<223> OTHER INFORMATION: UNA monomer
<220> FEATURE:
<221> NAME/KEY: modified_base
<222> LOCATION: (254)..(258)
<223> OTHER INFORMATION: UNA monomer
<220> FEATURE:
<221> NAME/KEY: modified_base
<222> LOCATION: (270)..(270)
<223> OTHER INFORMATION: UNA monomer
<220> FEATURE:
<221> NAME/KEY: modified_base
<222> LOCATION: (273)..(273)
<223> OTHER INFORMATION: UNA monomer
<220> FEATURE:
<221> NAME/KEY: modified_base
<222> LOCATION: (283)..(284)
<223> OTHER INFORMATION: UNA monomer
<220> FEATURE:
<221> NAME/KEY: modified_base
<222> LOCATION: (286)..(286)
<223> OTHER INFORMATION: UNA monomer
<220> FEATURE:
<221> NAME/KEY: modified_base
<222> LOCATION: (288)..(288)
<223> OTHER INFORMATION: UNA monomer
<220> FEATURE:
<221> NAME/KEY: modified_base
<222> LOCATION: (301)..(303)
<223> OTHER INFORMATION: UNA monomer
<220> FEATURE:
<221> NAME/KEY: modified_base
<222> LOCATION: (308)..(309)
<223> OTHER INFORMATION: UNA monomer
<220> FEATURE:
<221> NAME/KEY: modified_base
<222> LOCATION: (311)..(311)
<223> OTHER INFORMATION: UNA monomer
<220> FEATURE:
<221> NAME/KEY: modified_base
<222> LOCATION: (321)..(321)
<223> OTHER INFORMATION: UNA monomer
<220> FEATURE:
<221> NAME/KEY: modified_base
<222> LOCATION: (324)..(325)
<223> OTHER INFORMATION: UNA monomer
<220> FEATURE:
<221> NAME/KEY: modified_base
<222> LOCATION: (327)..(330)
<223> OTHER INFORMATION: UNA monomer
<220> FEATURE:
<221> NAME/KEY: modified_base
<222> LOCATION: (332)..(333)
<223> OTHER INFORMATION: UNA monomer
<220> FEATURE:
<221> NAME/KEY: modified_base
<222> LOCATION: (345)..(345)
<223> OTHER INFORMATION: UNA monomer
<220> FEATURE:
<221> NAME/KEY: modified_base
<222> LOCATION: (347)..(348)
<223> OTHER INFORMATION: UNA monomer
<220> FEATURE:
<221> NAME/KEY: modified_base
<222> LOCATION: (351)..(353)
<223> OTHER INFORMATION: UNA monomer
<220> FEATURE:
<221> NAME/KEY: modified_base
<222> LOCATION: (357)..(357)
<223> OTHER INFORMATION: UNA monomer
<220> FEATURE:
<221> NAME/KEY: modified_base
<222> LOCATION: (359)..(359)
<223> OTHER INFORMATION: UNA monomer
<220> FEATURE:
<221> NAME/KEY: modified_base
```

```
<222> LOCATION: (363)..(363)
<223> OTHER INFORMATION: UNA monomer
<220> FEATURE:
<221> NAME/KEY: modified_base
<222> LOCATION: (369)..(369)
<223> OTHER INFORMATION: UNA monomer
<220> FEATURE:
<221> NAME/KEY: modified_base
<222> LOCATION: (371)..(371)
<223> OTHER INFORMATION: UNA monomer
<220> FEATURE:
<221> NAME/KEY: modified_base
<222> LOCATION: (387)..(387)
<223> OTHER INFORMATION: UNA monomer
<220> FEATURE:
<221> NAME/KEY: modified_base
<222> LOCATION: (389)..(389)
<223> OTHER INFORMATION: UNA monomer
<220> FEATURE:
<221> NAME/KEY: modified_base
<222> LOCATION: (391)..(392)
<223> OTHER INFORMATION: UNA monomer
<220> FEATURE:
<221> NAME/KEY: modified_base
<222> LOCATION: (394)..(394)
<223> OTHER INFORMATION: UNA monomer
<220> FEATURE:
<221> NAME/KEY: modified_base
<222> LOCATION: (396)..(396)
<223> OTHER INFORMATION: UNA monomer
<220> FEATURE:
<221> NAME/KEY: modified_base
<222> LOCATION: (401)..(401)
<223> OTHER INFORMATION: UNA monomer
<220> FEATURE:
<221> NAME/KEY: modified_base
<222> LOCATION: (408)..(408)
<223> OTHER INFORMATION: UNA monomer
<220> FEATURE:
<221> NAME/KEY: modified_base
<222> LOCATION: (413)..(413)
<223> OTHER INFORMATION: UNA monomer
<220> FEATURE:
<221> NAME/KEY: modified_base
<222> LOCATION: (415)..(416)
<223> OTHER INFORMATION: UNA monomer
<220> FEATURE:
<221> NAME/KEY: modified_base
<222> LOCATION: (420)..(420)
<223> OTHER INFORMATION: UNA monomer
<220> FEATURE:
<221> NAME/KEY: modified_base
<222> LOCATION: (425)..(425)
<223> OTHER INFORMATION: UNA monomer
<220> FEATURE:
<221> NAME/KEY: modified_base
<222> LOCATION: (427)..(427)
<223> OTHER INFORMATION: UNA monomer
<220> FEATURE:
<221> NAME/KEY: modified_base
<222> LOCATION: (429)..(429)
<223> OTHER INFORMATION: UNA monomer
<220> FEATURE:
<221> NAME/KEY: modified_base
<222> LOCATION: (436)..(436)
<223> OTHER INFORMATION: UNA monomer
<220> FEATURE:
<221> NAME/KEY: modified_base
<222> LOCATION: (441)..(443)
<223> OTHER INFORMATION: UNA monomer
<220> FEATURE:
<221> NAME/KEY: modified_base
<222> LOCATION: (452)..(452)
<223> OTHER INFORMATION: UNA monomer
<220> FEATURE:
<221> NAME/KEY: modified_base
<222> LOCATION: (456)..(456)
<223> OTHER INFORMATION: UNA monomer
<220> FEATURE:
```

```
-continued

<221> NAME/KEY: modified_base
<222> LOCATION: (466)..(466)
<223> OTHER INFORMATION: UNA monomer
<220> FEATURE:
<221> NAME/KEY: modified_base
<222> LOCATION: (470)..(470)
<223> OTHER INFORMATION: UNA monomer
<220> FEATURE:
<221> NAME/KEY: modified_base
<222> LOCATION: (476)..(477)
<223> OTHER INFORMATION: UNA monomer
<220> FEATURE:
<221> NAME/KEY: modified_base
<222> LOCATION: (479)..(479)
<223> OTHER INFORMATION: UNA monomer
<220> FEATURE:
<221> NAME/KEY: modified_base
<222> LOCATION: (483)..(483)
<223> OTHER INFORMATION: UNA monomer
<220> FEATURE:
<221> NAME/KEY: modified_base
<222> LOCATION: (488)..(488)
<223> OTHER INFORMATION: UNA monomer
<220> FEATURE:
<221> NAME/KEY: modified_base
<222> LOCATION: (490)..(490)
<223> OTHER INFORMATION: UNA monomer
<220> FEATURE:
<221> NAME/KEY: modified_base
<222> LOCATION: (495)..(497)
<223> OTHER INFORMATION: UNA monomer
<220> FEATURE:
<221> NAME/KEY: modified_base
<222> LOCATION: (499)..(499)
<223> OTHER INFORMATION: UNA monomer
<220> FEATURE:
<221> NAME/KEY: modified_base
<222> LOCATION: (504)..(504)
<223> OTHER INFORMATION: UNA monomer
<220> FEATURE:
<221> NAME/KEY: modified_base
<222> LOCATION: (507)..(507)
<223> OTHER INFORMATION: UNA monomer
<220> FEATURE:
<221> NAME/KEY: modified_base
<222> LOCATION: (509)..(509)
<223> OTHER INFORMATION: UNA monomer
<220> FEATURE:
<221> NAME/KEY: modified_base
<222> LOCATION: (515)..(515)
<223> OTHER INFORMATION: UNA monomer
<220> FEATURE:
<221> NAME/KEY: modified_base
<222> LOCATION: (518)..(518)
<223> OTHER INFORMATION: UNA monomer
<220> FEATURE:
<221> NAME/KEY: modified_base
<222> LOCATION: (522)..(522)
<223> OTHER INFORMATION: UNA monomer
<220> FEATURE:
<221> NAME/KEY: modified_base
<222> LOCATION: (525)..(526)
<223> OTHER INFORMATION: UNA monomer
<220> FEATURE:
<221> NAME/KEY: modified_base
<222> LOCATION: (530)..(530)
<223> OTHER INFORMATION: UNA monomer
<220> FEATURE:
<221> NAME/KEY: modified_base
<222> LOCATION: (536)..(536)
<223> OTHER INFORMATION: UNA monomer
<220> FEATURE:
<221> NAME/KEY: modified_base
<222> LOCATION: (547)..(547)
<223> OTHER INFORMATION: UNA monomer
<220> FEATURE:
<221> NAME/KEY: modified_base
<222> LOCATION: (549)..(549)
<223> OTHER INFORMATION: UNA monomer
```

```
<220> FEATURE:
<221> NAME/KEY: modified_base
<222> LOCATION: (553)..(553)
<223> OTHER INFORMATION: UNA monomer
<220> FEATURE:
<221> NAME/KEY: modified_base
<222> LOCATION: (555)..(555)
<223> OTHER INFORMATION: UNA monomer
<220> FEATURE:
<221> NAME/KEY: modified_base
<222> LOCATION: (557)..(557)
<223> OTHER INFORMATION: UNA monomer
<220> FEATURE:
<221> NAME/KEY: modified_base
<222> LOCATION: (564)..(564)
<223> OTHER INFORMATION: UNA monomer
<220> FEATURE:
<221> NAME/KEY: modified_base
<222> LOCATION: (566)..(567)
<223> OTHER INFORMATION: UNA monomer
<220> FEATURE:
<221> NAME/KEY: modified_base
<222> LOCATION: (572)..(572)
<223> OTHER INFORMATION: UNA monomer
<220> FEATURE:
<221> NAME/KEY: modified_base
<222> LOCATION: (577)..(577)
<223> OTHER INFORMATION: UNA monomer
<220> FEATURE:
<221> NAME/KEY: modified_base
<222> LOCATION: (581)..(581)
<223> OTHER INFORMATION: UNA monomer
<220> FEATURE:
<221> NAME/KEY: modified_base
<222> LOCATION: (588)..(588)
<223> OTHER INFORMATION: UNA monomer
<220> FEATURE:
<221> NAME/KEY: modified_base
<222> LOCATION: (597)..(597)
<223> OTHER INFORMATION: UNA monomer
<220> FEATURE:
<221> NAME/KEY: modified_base
<222> LOCATION: (599)..(599)
<223> OTHER INFORMATION: UNA monomer
<220> FEATURE:
<221> NAME/KEY: modified_base
<222> LOCATION: (602)..(602)
<223> OTHER INFORMATION: UNA monomer
<220> FEATURE:
<221> NAME/KEY: modified_base
<222> LOCATION: (607)..(607)
<223> OTHER INFORMATION: UNA monomer
<220> FEATURE:
<221> NAME/KEY: modified_base
<222> LOCATION: (611)..(611)
<223> OTHER INFORMATION: UNA monomer
<220> FEATURE:
<221> NAME/KEY: modified_base
<222> LOCATION: (614)..(614)
<223> OTHER INFORMATION: UNA monomer
<220> FEATURE:
<221> NAME/KEY: modified_base
<222> LOCATION: (617)..(617)
<223> OTHER INFORMATION: UNA monomer
<220> FEATURE:
<221> NAME/KEY: modified_base
<222> LOCATION: (631)..(632)
<223> OTHER INFORMATION: UNA monomer
<220> FEATURE:
<221> NAME/KEY: modified_base
<222> LOCATION: (638)..(638)
<223> OTHER INFORMATION: UNA monomer
<220> FEATURE:
<221> NAME/KEY: modified_base
<222> LOCATION: (644)..(645)
<223> OTHER INFORMATION: UNA monomer
<220> FEATURE:
<221> NAME/KEY: modified_base
<222> LOCATION: (654)..(654)
```

```
<223> OTHER INFORMATION: UNA monomer
<220> FEATURE:
<221> NAME/KEY: modified_base
<222> LOCATION: (657)..(657)
<223> OTHER INFORMATION: UNA monomer
<220> FEATURE:
<221> NAME/KEY: modified_base
<222> LOCATION: (666)..(667)
<223> OTHER INFORMATION: UNA monomer
<220> FEATURE:
<221> NAME/KEY: modified_base
<222> LOCATION: (669)..(669)
<223> OTHER INFORMATION: UNA monomer
<220> FEATURE:
<221> NAME/KEY: modified_base
<222> LOCATION: (678)..(678)
<223> OTHER INFORMATION: UNA monomer
<220> FEATURE:
<221> NAME/KEY: modified_base
<222> LOCATION: (681)..(681)
<223> OTHER INFORMATION: UNA monomer
<220> FEATURE:
<221> NAME/KEY: modified_base
<222> LOCATION: (684)..(684)
<223> OTHER INFORMATION: UNA monomer
<220> FEATURE:
<221> NAME/KEY: modified_base
<222> LOCATION: (686)..(686)
<223> OTHER INFORMATION: UNA monomer
<220> FEATURE:
<221> NAME/KEY: modified_base
<222> LOCATION: (694)..(695)
<223> OTHER INFORMATION: UNA monomer
<220> FEATURE:
<221> NAME/KEY: modified_base
<222> LOCATION: (706)..(706)
<223> OTHER INFORMATION: UNA monomer
<220> FEATURE:
<221> NAME/KEY: modified_base
<222> LOCATION: (708)..(708)
<223> OTHER INFORMATION: UNA monomer
<220> FEATURE:
<221> NAME/KEY: modified_base
<222> LOCATION: (720)..(720)
<223> OTHER INFORMATION: UNA monomer
<220> FEATURE:
<221> NAME/KEY: modified_base
<222> LOCATION: (723)..(723)
<223> OTHER INFORMATION: UNA monomer
<220> FEATURE:
<221> NAME/KEY: modified_base
<222> LOCATION: (731)..(731)
<223> OTHER INFORMATION: UNA monomer
<220> FEATURE:
<221> NAME/KEY: modified_base
<222> LOCATION: (733)..(734)
<223> OTHER INFORMATION: UNA monomer
<220> FEATURE:
<221> NAME/KEY: modified_base
<222> LOCATION: (737)..(737)
<223> OTHER INFORMATION: UNA monomer
<220> FEATURE:
<221> NAME/KEY: modified_base
<222> LOCATION: (744)..(744)
<223> OTHER INFORMATION: UNA monomer
<220> FEATURE:
<221> NAME/KEY: modified_base
<222> LOCATION: (747)..(747)
<223> OTHER INFORMATION: UNA monomer
<220> FEATURE:
<221> NAME/KEY: modified_base
<222> LOCATION: (751)..(752)
<223> OTHER INFORMATION: UNA monomer
<220> FEATURE:
<221> NAME/KEY: modified_base
<222> LOCATION: (765)..(765)
<223> OTHER INFORMATION: UNA monomer
<220> FEATURE:
<221> NAME/KEY: modified_base
```

```
<222> LOCATION: (774)..(774)
<223> OTHER INFORMATION: UNA monomer
<220> FEATURE:
<221> NAME/KEY: modified_base
<222> LOCATION: (776)..(776)
<223> OTHER INFORMATION: UNA monomer
<220> FEATURE:
<221> NAME/KEY: modified_base
<222> LOCATION: (778)..(779)
<223> OTHER INFORMATION: UNA monomer
<220> FEATURE:
<221> NAME/KEY: modified_base
<222> LOCATION: (782)..(783)
<223> OTHER INFORMATION: UNA monomer
<220> FEATURE:
<221> NAME/KEY: modified_base
<222> LOCATION: (792)..(793)
<223> OTHER INFORMATION: UNA monomer
<220> FEATURE:
<221> NAME/KEY: modified_base
<222> LOCATION: (797)..(797)
<223> OTHER INFORMATION: UNA monomer
<220> FEATURE:
<221> NAME/KEY: modified_base
<222> LOCATION: (803)..(803)
<223> OTHER INFORMATION: UNA monomer
<220> FEATURE:
<221> NAME/KEY: modified_base
<222> LOCATION: (833)..(833)
<223> OTHER INFORMATION: UNA monomer
<220> FEATURE:
<221> NAME/KEY: modified_base
<222> LOCATION: (840)..(842)
<223> OTHER INFORMATION: UNA monomer
<220> FEATURE:
<221> NAME/KEY: modified_base
<222> LOCATION: (849)..(850)
<223> OTHER INFORMATION: UNA monomer
<220> FEATURE:
<221> NAME/KEY: modified_base
<222> LOCATION: (857)..(858)
<223> OTHER INFORMATION: UNA monomer
<220> FEATURE:
<221> NAME/KEY: modified_base
<222> LOCATION: (863)..(863)
<223> OTHER INFORMATION: UNA monomer
<220> FEATURE:
<221> NAME/KEY: modified_base
<222> LOCATION: (870)..(870)
<223> OTHER INFORMATION: UNA monomer
<220> FEATURE:
<221> NAME/KEY: modified_base
<222> LOCATION: (873)..(873)
<223> OTHER INFORMATION: UNA monomer
<220> FEATURE:
<221> NAME/KEY: modified_base
<222> LOCATION: (878)..(879)
<223> OTHER INFORMATION: UNA monomer
<220> FEATURE:
<221> NAME/KEY: modified_base
<222> LOCATION: (882)..(882)
<223> OTHER INFORMATION: UNA monomer
<220> FEATURE:
<221> NAME/KEY: modified_base
<222> LOCATION: (886)..(886)
<223> OTHER INFORMATION: UNA monomer
<220> FEATURE:
<221> NAME/KEY: modified_base
<222> LOCATION: (888)..(888)
<223> OTHER INFORMATION: UNA monomer
<220> FEATURE:
<221> NAME/KEY: modified_base
<222> LOCATION: (892)..(892)
<223> OTHER INFORMATION: UNA monomer
<220> FEATURE:
<221> NAME/KEY: modified_base
<222> LOCATION: (898)..(902)
<223> OTHER INFORMATION: UNA monomer
<220> FEATURE:
```

```
<221> NAME/KEY: modified_base
<222> LOCATION: (907)..(907)
<223> OTHER INFORMATION: UNA monomer
<220> FEATURE:
<221> NAME/KEY: modified_base
<222> LOCATION: (910)..(911)
<223> OTHER INFORMATION: UNA monomer
<220> FEATURE:
<221> NAME/KEY: modified_base
<222> LOCATION: (932)..(932)
<223> OTHER INFORMATION: UNA monomer
<220> FEATURE:
<221> NAME/KEY: modified_base
<222> LOCATION: (936)..(936)
<223> OTHER INFORMATION: UNA monomer
<220> FEATURE:
<221> NAME/KEY: modified_base
<222> LOCATION: (939)..(939)
<223> OTHER INFORMATION: UNA monomer
<220> FEATURE:
<221> NAME/KEY: modified_base
<222> LOCATION: (944)..(944)
<223> OTHER INFORMATION: UNA monomer
<220> FEATURE:
<221> NAME/KEY: modified_base
<222> LOCATION: (946)..(949)
<223> OTHER INFORMATION: UNA monomer
<220> FEATURE:
<221> NAME/KEY: modified_base
<222> LOCATION: (951)..(952)
<223> OTHER INFORMATION: UNA monomer
<220> FEATURE:
<221> NAME/KEY: modified_base
<222> LOCATION: (954)..(954)
<223> OTHER INFORMATION: UNA monomer
<220> FEATURE:
<221> NAME/KEY: modified_base
<222> LOCATION: (957)..(957)
<223> OTHER INFORMATION: UNA monomer
<220> FEATURE:
<221> NAME/KEY: modified_base
<222> LOCATION: (961)..(961)
<223> OTHER INFORMATION: UNA monomer
<220> FEATURE:
<221> NAME/KEY: modified_base
<222> LOCATION: (965)..(965)
<223> OTHER INFORMATION: UNA monomer
<220> FEATURE:
<221> NAME/KEY: modified_base
<222> LOCATION: (968)..(968)
<223> OTHER INFORMATION: UNA monomer
<220> FEATURE:
<221> NAME/KEY: modified_base
<222> LOCATION: (970)..(971)
<223> OTHER INFORMATION: UNA monomer
<220> FEATURE:
<221> NAME/KEY: modified_base
<222> LOCATION: (994)..(994)
<223> OTHER INFORMATION: UNA monomer
<220> FEATURE:
<221> NAME/KEY: modified_base
<222> LOCATION: (1001)..(1001)
<223> OTHER INFORMATION: UNA monomer
<220> FEATURE:
<221> NAME/KEY: modified_base
<222> LOCATION: (1004)..(1004)
<223> OTHER INFORMATION: UNA monomer
<220> FEATURE:
<221> NAME/KEY: modified_base
<222> LOCATION: (1008)..(1008)
<223> OTHER INFORMATION: UNA monomer
<220> FEATURE:
<221> NAME/KEY: modified_base
<222> LOCATION: (1010)..(1010)
<223> OTHER INFORMATION: UNA monomer
<220> FEATURE:
<221> NAME/KEY: modified_base
<222> LOCATION: (1013)..(1013)
<223> OTHER INFORMATION: UNA monomer
```

```
<220> FEATURE:
<221> NAME/KEY: modified_base
<222> LOCATION: (1016)..(1016)
<223> OTHER INFORMATION: UNA monomer
<220> FEATURE:
<221> NAME/KEY: modified_base
<222> LOCATION: (1018)..(1018)
<223> OTHER INFORMATION: UNA monomer
<220> FEATURE:
<221> NAME/KEY: modified_base
<222> LOCATION: (1022)..(1022)
<223> OTHER INFORMATION: UNA monomer
<220> FEATURE:
<221> NAME/KEY: modified_base
<222> LOCATION: (1025)..(1025)
<223> OTHER INFORMATION: UNA monomer
<220> FEATURE:
<221> NAME/KEY: modified_base
<222> LOCATION: (1032)..(1033)
<223> OTHER INFORMATION: UNA monomer
<220> FEATURE:
<221> NAME/KEY: modified_base
<222> LOCATION: (1036)..(1036)
<223> OTHER INFORMATION: UNA monomer
<220> FEATURE:
<221> NAME/KEY: modified_base
<222> LOCATION: (1041)..(1041)
<223> OTHER INFORMATION: UNA monomer
<220> FEATURE:
<221> NAME/KEY: modified_base
<222> LOCATION: (1046)..(1046)
<223> OTHER INFORMATION: UNA monomer
<220> FEATURE:
<221> NAME/KEY: modified_base
<222> LOCATION: (1056)..(1056)
<223> OTHER INFORMATION: UNA monomer
<220> FEATURE:
<221> NAME/KEY: modified_base
<222> LOCATION: (1060)..(1063)
<223> OTHER INFORMATION: UNA monomer

<400> SEQUENCE: 136
augcuguuua aucugaggau ccuguuaaac aaugcagcuu uuagaaaugg ucacaacuuc      60
augguucgaa auuuucggug uggacaacca cuacaaaaua aagugcagcu gaagggccgu     120
gaccuucuca cucuaaaaaa cuuuaccgga gaagaaauua aauauaugcu auggcuauca     180
gcagaucuga aauuuaggau aaaacagaaa ggagaguauu ugccuuuauu gcaagggaag     240
uccuuaggca ugauuuuuga gaaaagaagu acucgaacaa gauugcuuac agaaacaggc     300
uuugcacuuc ugggaggaca uccuuguuuu cuuaccacac aagauauuca uuggguguug     360
aaugaaaguc ucacggacac ggcccgugua uugucuagca uggcagaugc aguauuggcu     420
cgaguguaua aacaaucaga uuuggacacc cuggcuaaag aagcauccau cccaauuauc     480
aaugggcugu cagauuugua ccauccuauc cagauccugg cugauuaccu cacgcuccag     540
gaacacuaua gcucucugaa agguucuacc cucagcugga ucggggaugg gaacaauauc     600
cugcacucca ucaugaugag cgcagcgaaa uucggaaugc accuucaggc agcuacucca     660
aagguuuaug agccggaugc uaguguaacc aaguugcag agcaguaugc caaagagaau     720
gguaccaagc uguugcugac aaaugauccca uuggaagcag cgcauggagg caauguauua     780
auuacagaca cuuggauaag cauggacaa gaagaggaga gaaaaagcg gcuccaggcu     840
uccaagguu accagguac aaugaagacu gcuaaaguug cugccucuga cuggacauuu     900
uuacacugcu ugcccagaaa gccagaagaa guggaugaug aagucuuuua uucuccucga     960
ucacuagugu ucccagaggc agaaaacaga aaguggacaa ucauggcugu cauggugucc    1020
cugcugacag auuacucacc ucagcuccag aagccuaaau uuuga                    1065
```

```
<210> SEQ ID NO 137
<211> LENGTH: 134
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (133)..(133)
<223> OTHER INFORMATION: UNA monomer

<400> SEQUENCE: 137
gcucgcuuuc uugcugucca auuucuauua aagguuccuu uguucccuaa guccaacuac      60
uaaacugggg gauauuauga agggccuuga gcaucuggau ucugccuaau aaaaaacauu    120
uauuuucauu gcaa                                                      134

<210> SEQ ID NO 138
<211> LENGTH: 134
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(4)
<223> OTHER INFORMATION: UNA monomer
<220> FEATURE:
<221> NAME/KEY: modified_base
<222> LOCATION: (131)..(133)
<223> OTHER INFORMATION: UNA monomer

<400> SEQUENCE: 138
gcucgcuuuc uugcugucca auuucuauua aagguuccuu uguucccuaa guccaacuac      60
uaaacugggg gauauuauga agggccuuga gcaucuggau ucugccuaau aaaaaacauu    120
uauuuucauu gcaa                                                      134

<210> SEQ ID NO 139
<211> LENGTH: 134
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (8)..(8)
<223> OTHER INFORMATION: UNA monomer
<220> FEATURE:
<221> NAME/KEY: modified_base
<222> LOCATION: (14)..(14)
<223> OTHER INFORMATION: UNA monomer
<220> FEATURE:
<221> NAME/KEY: modified_base
<222> LOCATION: (20)..(20)
<223> OTHER INFORMATION: UNA monomer
<220> FEATURE:
<221> NAME/KEY: modified_base
<222> LOCATION: (26)..(26)
<223> OTHER INFORMATION: UNA monomer
<220> FEATURE:
```

```
<221> NAME/KEY: modified_base
<222> LOCATION: (32)..(32)
<223> OTHER INFORMATION: UNA monomer
<220> FEATURE:
<221> NAME/KEY: modified_base
<222> LOCATION: (38)..(38)
<223> OTHER INFORMATION: UNA monomer
<220> FEATURE:
<221> NAME/KEY: modified_base
<222> LOCATION: (44)..(44)
<223> OTHER INFORMATION: UNA monomer
<220> FEATURE:
<221> NAME/KEY: modified_base
<222> LOCATION: (50)..(50)
<223> OTHER INFORMATION: UNA monomer
<220> FEATURE:
<221> NAME/KEY: modified_base
<222> LOCATION: (56)..(56)
<223> OTHER INFORMATION: UNA monomer
<220> FEATURE:
<221> NAME/KEY: modified_base
<222> LOCATION: (62)..(62)
<223> OTHER INFORMATION: UNA monomer
<220> FEATURE:
<221> NAME/KEY: modified_base
<222> LOCATION: (68)..(68)
<223> OTHER INFORMATION: UNA monomer
<220> FEATURE:
<221> NAME/KEY: modified_base
<222> LOCATION: (74)..(74)
<223> OTHER INFORMATION: UNA monomer
<220> FEATURE:
<221> NAME/KEY: modified_base
<222> LOCATION: (80)..(80)
<223> OTHER INFORMATION: UNA monomer
<220> FEATURE:
<221> NAME/KEY: modified_base
<222> LOCATION: (86)..(86)
<223> OTHER INFORMATION: UNA monomer
<220> FEATURE:
<221> NAME/KEY: modified_base
<222> LOCATION: (92)..(92)
<223> OTHER INFORMATION: UNA monomer
<220> FEATURE:
<221> NAME/KEY: modified_base
<222> LOCATION: (98)..(98)
<223> OTHER INFORMATION: UNA monomer
<220> FEATURE:
<221> NAME/KEY: modified_base
<222> LOCATION: (104)..(104)
<223> OTHER INFORMATION: UNA monomer
<220> FEATURE:
<221> NAME/KEY: modified_base
<222> LOCATION: (110)..(110)
<223> OTHER INFORMATION: UNA monomer
<220> FEATURE:
<221> NAME/KEY: modified_base
<222> LOCATION: (116)..(116)
<223> OTHER INFORMATION: UNA monomer
<220> FEATURE:
<221> NAME/KEY: modified_base
<222> LOCATION: (122)..(122)
<223> OTHER INFORMATION: UNA monomer
<220> FEATURE:
<221> NAME/KEY: modified_base
<222> LOCATION: (128)..(128)
<223> OTHER INFORMATION: UNA monomer
<220> FEATURE:
<221> NAME/KEY: modified_base
<222> LOCATION: (133)..(133)
<223> OTHER INFORMATION: UNA monomer

<400> SEQUENCE: 139
gcucgcuuuc uugcugucca auuucuauua aagguuccuu uguucccuaa guccaacuac    60
uaaacugggg gauauuauga agggccuuga gcaucuggau ucugccuaau aaaaaacauu   120
uauuuucauu gcaa                                                    134
```

```
<210> SEQ ID NO 140
<211> LENGTH: 134
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(3)
<223> OTHER INFORMATION: UNA monomer
<220> FEATURE:
<221> NAME/KEY: modified_base
<222> LOCATION: (8)..(9)
<223> OTHER INFORMATION: UNA monomer
<220> FEATURE:
<221> NAME/KEY: modified_base
<222> LOCATION: (14)..(15)
<223> OTHER INFORMATION: UNA monomer
<220> FEATURE:
<221> NAME/KEY: modified_base
<222> LOCATION: (20)..(21)
<223> OTHER INFORMATION: UNA monomer
<220> FEATURE:
<221> NAME/KEY: modified_base
<222> LOCATION: (26)..(27)
<223> OTHER INFORMATION: UNA monomer
<220> FEATURE:
<221> NAME/KEY: modified_base
<222> LOCATION: (32)..(33)
<223> OTHER INFORMATION: UNA monomer
<220> FEATURE:
<221> NAME/KEY: modified_base
<222> LOCATION: (38)..(39)
<223> OTHER INFORMATION: UNA monomer
<220> FEATURE:
<221> NAME/KEY: modified_base
<222> LOCATION: (44)..(45)
<223> OTHER INFORMATION: UNA monomer
<220> FEATURE:
<221> NAME/KEY: modified_base
<222> LOCATION: (50)..(51)
<223> OTHER INFORMATION: UNA monomer
<220> FEATURE:
<221> NAME/KEY: modified_base
<222> LOCATION: (56)..(57)
<223> OTHER INFORMATION: UNA monomer
<220> FEATURE:
<221> NAME/KEY: modified_base
<222> LOCATION: (62)..(63)
<223> OTHER INFORMATION: UNA monomer
<220> FEATURE:
<221> NAME/KEY: modified_base
<222> LOCATION: (68)..(69)
<223> OTHER INFORMATION: UNA monomer
<220> FEATURE:
<221> NAME/KEY: modified_base
<222> LOCATION: (74)..(75)
<223> OTHER INFORMATION: UNA monomer
<220> FEATURE:
<221> NAME/KEY: modified_base
<222> LOCATION: (80)..(81)
<223> OTHER INFORMATION: UNA monomer
<220> FEATURE:
<221> NAME/KEY: modified_base
<222> LOCATION: (86)..(87)
<223> OTHER INFORMATION: UNA monomer
<220> FEATURE:
<221> NAME/KEY: modified_base
<222> LOCATION: (92)..(93)
<223> OTHER INFORMATION: UNA monomer
<220> FEATURE:
<221> NAME/KEY: modified_base
<222> LOCATION: (98)..(99)
<223> OTHER INFORMATION: UNA monomer
<220> FEATURE:
<221> NAME/KEY: modified_base
```

```
<222> LOCATION: (104)..(105)
<223> OTHER INFORMATION: UNA monomer
<220> FEATURE:
<221> NAME/KEY: modified_base
<222> LOCATION: (110)..(111)
<223> OTHER INFORMATION: UNA monomer
<220> FEATURE:
<221> NAME/KEY: modified_base
<222> LOCATION: (116)..(117)
<223> OTHER INFORMATION: UNA monomer
<220> FEATURE:
<221> NAME/KEY: modified_base
<222> LOCATION: (122)..(123)
<223> OTHER INFORMATION: UNA monomer
<220> FEATURE:
<221> NAME/KEY: modified_base
<222> LOCATION: (128)..(129)
<223> OTHER INFORMATION: UNA monomer
<220> FEATURE:
<221> NAME/KEY: modified_base
<222> LOCATION: (133)..(133)
<223> OTHER INFORMATION: UNA monomer

<400> SEQUENCE: 140
gcucgcuuuc uugcugucca auuucuauua aagguuccuu uguucccuaa guccaacuac      60
uaaacugggg gauauuauga agggccuuga gcaucuggau ucugccuaau aaaaaacauu    120
uauuuucauu gcaa                                                      134

<210> SEQ ID NO 141
<211> LENGTH: 134
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(134)
<223> OTHER INFORMATION: UNA monomer

<400> SEQUENCE: 141
gcucgcuuuc uugcugucca auuucuauua aagguuccuu uguucccuaa guccaacuac      60
uaaacugggg gauauuauga agggccuuga gcaucuggau ucugccuaau aaaaaacauu    120
uauuuucauu gcaa                                                      134

<210> SEQ ID NO 142
<211> LENGTH: 158
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (157)..(157)
<223> OTHER INFORMATION: UNA monomer

<400> SEQUENCE: 142
cuagugacug acuaggaucu gguuaccacu aaaccagccu caagaacacc cgaauggagu      60
cucuaagcua cauaauacca acuuacacuu acaaaauguu gucccccaaa auguagccau    120
ucguaucugc uccuaauaaa aagaaaguuu cuucacau                             158

<210> SEQ ID NO 143
```

```
<211> LENGTH: 158
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(4)
<223> OTHER INFORMATION: UNA monomer
<220> FEATURE:
<221> NAME/KEY: modified_base
<222> LOCATION: (155)..(157)
<223> OTHER INFORMATION: UNA monomer

<400> SEQUENCE: 143
cuagugacug acuaggaucu gguuaccacu aaaccagccu caagaacacc cgaauggagu     60
cucuaagcua cauaauacca acuuacacuu acaaaauguu gucccccaaa auguagccau   120
ucguaucugc uccaauaaaa aagaaaguuu cuucacau                            158

<210> SEQ ID NO 144
<211> LENGTH: 158
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (8)..(8)
<223> OTHER INFORMATION: UNA monomer
<220> FEATURE:
<221> NAME/KEY: modified_base
<222> LOCATION: (14)..(14)
<223> OTHER INFORMATION: UNA monomer
<220> FEATURE:
<221> NAME/KEY: modified_base
<222> LOCATION: (20)..(20)
<223> OTHER INFORMATION: UNA monomer
<220> FEATURE:
<221> NAME/KEY: modified_base
<222> LOCATION: (26)..(26)
<223> OTHER INFORMATION: UNA monomer
<220> FEATURE:
<221> NAME/KEY: modified_base
<222> LOCATION: (32)..(32)
<223> OTHER INFORMATION: UNA monomer
<220> FEATURE:
<221> NAME/KEY: modified_base
<222> LOCATION: (38)..(38)
<223> OTHER INFORMATION: UNA monomer
<220> FEATURE:
<221> NAME/KEY: modified_base
<222> LOCATION: (44)..(44)
<223> OTHER INFORMATION: UNA monomer
<220> FEATURE:
<221> NAME/KEY: modified_base
<222> LOCATION: (50)..(50)
<223> OTHER INFORMATION: UNA monomer
<220> FEATURE:
<221> NAME/KEY: modified_base
<222> LOCATION: (56)..(56)
<223> OTHER INFORMATION: UNA monomer
<220> FEATURE:
<221> NAME/KEY: modified_base
<222> LOCATION: (62)..(62)
<223> OTHER INFORMATION: UNA monomer
<220> FEATURE:
<221> NAME/KEY: modified_base
<222> LOCATION: (68)..(68)
<223> OTHER INFORMATION: UNA monomer
```

```
<220> FEATURE:
<221> NAME/KEY: modified_base
<222> LOCATION: (74)..(74)
<223> OTHER INFORMATION: UNA monomer
<220> FEATURE:
<221> NAME/KEY: modified_base
<222> LOCATION: (80)..(80)
<223> OTHER INFORMATION: UNA monomer
<220> FEATURE:
<221> NAME/KEY: modified_base
<222> LOCATION: (86)..(86)
<223> OTHER INFORMATION: UNA monomer
<220> FEATURE:
<221> NAME/KEY: modified_base
<222> LOCATION: (92)..(92)
<223> OTHER INFORMATION: UNA monomer
<220> FEATURE:
<221> NAME/KEY: modified_base
<222> LOCATION: (98)..(98)
<223> OTHER INFORMATION: UNA monomer
<220> FEATURE:
<221> NAME/KEY: modified_base
<222> LOCATION: (104)..(104)
<223> OTHER INFORMATION: UNA monomer
<220> FEATURE:
<221> NAME/KEY: modified_base
<222> LOCATION: (110)..(110)
<223> OTHER INFORMATION: UNA monomer
<220> FEATURE:
<221> NAME/KEY: modified_base
<222> LOCATION: (116)..(116)
<223> OTHER INFORMATION: UNA monomer
<220> FEATURE:
<221> NAME/KEY: modified_base
<222> LOCATION: (122)..(122)
<223> OTHER INFORMATION: UNA monomer
<220> FEATURE:
<221> NAME/KEY: modified_base
<222> LOCATION: (128)..(128)
<223> OTHER INFORMATION: UNA monomer
<220> FEATURE:
<221> NAME/KEY: modified_base
<222> LOCATION: (134)..(134)
<223> OTHER INFORMATION: UNA monomer
<220> FEATURE:
<221> NAME/KEY: modified_base
<222> LOCATION: (140)..(140)
<223> OTHER INFORMATION: UNA monomer
<220> FEATURE:
<221> NAME/KEY: modified_base
<222> LOCATION: (146)..(146)
<223> OTHER INFORMATION: UNA monomer
<220> FEATURE:
<221> NAME/KEY: modified_base
<222> LOCATION: (152)..(152)
<223> OTHER INFORMATION: UNA monomer
<220> FEATURE:
<221> NAME/KEY: modified_base
<222> LOCATION: (157)..(157)
<223> OTHER INFORMATION: UNA monomer

<400> SEQUENCE: 144
cuagugacug acuaggaucu gguuaccacu aaaccagccu caagaacacc cgaauggagu      60
cucuaagcua cauaauacca acuuacacuu acaaaauguu gucccccaaa auguagccau     120
ucguaucugc uccuaauaaa aagaaaguuu cuucacau                             158

<210> SEQ ID NO 145
<211> LENGTH: 158
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
```

```
<222> LOCATION: (2)..(3)
<223> OTHER INFORMATION: UNA monomer
<220> FEATURE:
<221> NAME/KEY: modified_base
<222> LOCATION: (8)..(9)
<223> OTHER INFORMATION: UNA monomer
<220> FEATURE:
<221> NAME/KEY: modified_base
<222> LOCATION: (14)..(15)
<223> OTHER INFORMATION: UNA monomer
<220> FEATURE:
<221> NAME/KEY: modified_base
<222> LOCATION: (20)..(21)
<223> OTHER INFORMATION: UNA monomer
<220> FEATURE:
<221> NAME/KEY: modified_base
<222> LOCATION: (26)..(27)
<223> OTHER INFORMATION: UNA monomer
<220> FEATURE:
<221> NAME/KEY: modified_base
<222> LOCATION: (32)..(33)
<223> OTHER INFORMATION: UNA monomer
<220> FEATURE:
<221> NAME/KEY: modified_base
<222> LOCATION: (38)..(39)
<223> OTHER INFORMATION: UNA monomer
<220> FEATURE:
<221> NAME/KEY: modified_base
<222> LOCATION: (44)..(45)
<223> OTHER INFORMATION: UNA monomer
<220> FEATURE:
<221> NAME/KEY: modified_base
<222> LOCATION: (50)..(51)
<223> OTHER INFORMATION: UNA monomer
<220> FEATURE:
<221> NAME/KEY: modified_base
<222> LOCATION: (56)..(57)
<223> OTHER INFORMATION: UNA monomer
<220> FEATURE:
<221> NAME/KEY: modified_base
<222> LOCATION: (62)..(63)
<223> OTHER INFORMATION: UNA monomer
<220> FEATURE:
<221> NAME/KEY: modified_base
<222> LOCATION: (68)..(69)
<223> OTHER INFORMATION: UNA monomer
<220> FEATURE:
<221> NAME/KEY: modified_base
<222> LOCATION: (74)..(75)
<223> OTHER INFORMATION: UNA monomer
<220> FEATURE:
<221> NAME/KEY: modified_base
<222> LOCATION: (80)..(81)
<223> OTHER INFORMATION: UNA monomer
<220> FEATURE:
<221> NAME/KEY: modified_base
<222> LOCATION: (86)..(87)
<223> OTHER INFORMATION: UNA monomer
<220> FEATURE:
<221> NAME/KEY: modified_base
<222> LOCATION: (92)..(93)
<223> OTHER INFORMATION: UNA monomer
<220> FEATURE:
<221> NAME/KEY: modified_base
<222> LOCATION: (98)..(99)
<223> OTHER INFORMATION: UNA monomer
<220> FEATURE:
<221> NAME/KEY: modified_base
<222> LOCATION: (104)..(105)
<223> OTHER INFORMATION: UNA monomer
<220> FEATURE:
<221> NAME/KEY: modified_base
<222> LOCATION: (110)..(111)
<223> OTHER INFORMATION: UNA monomer
<220> FEATURE:
<221> NAME/KEY: modified_base
<222> LOCATION: (116)..(117)
<223> OTHER INFORMATION: UNA monomer
<220> FEATURE:
```

```
<221> NAME/KEY: modified_base
<222> LOCATION: (122)..(123)
<223> OTHER INFORMATION: UNA monomer
<220> FEATURE:
<221> NAME/KEY: modified_base
<222> LOCATION: (128)..(129)
<223> OTHER INFORMATION: UNA monomer
<220> FEATURE:
<221> NAME/KEY: modified_base
<222> LOCATION: (134)..(135)
<223> OTHER INFORMATION: UNA monomer
<220> FEATURE:
<221> NAME/KEY: modified_base
<222> LOCATION: (140)..(141)
<223> OTHER INFORMATION: UNA monomer
<220> FEATURE:
<221> NAME/KEY: modified_base
<222> LOCATION: (146)..(147)
<223> OTHER INFORMATION: UNA monomer
<220> FEATURE:
<221> NAME/KEY: modified_base
<222> LOCATION: (152)..(153)
<223> OTHER INFORMATION: UNA monomer
<220> FEATURE:
<221> NAME/KEY: modified_base
<222> LOCATION: (157)..(157)
<223> OTHER INFORMATION: UNA monomer

<400> SEQUENCE: 145
cuagugacug acuaggaucu gguuaccacu aaaccagccu caagaacacc cgaauggagu      60
cucuaagcua cauaauacca acuuacacuu acaaaauguu gucccccaaa auguagccau     120
ucguaucugc uccuaauaaa aagaaaguuu cuucacau                             158

<210> SEQ ID NO 146
<211> LENGTH: 158
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(158)
<223> OTHER INFORMATION: UNA monomer

<400> SEQUENCE: 146
cuagugacug acuaggaucu gguuaccacu aaaccagccu caagaacacc cgaauggagu      60
cucuaagcua cauaauacca acuuacacuu acaaaauguu gucccccaaa auguagccau     120
ucguaucugc uccuaauaaa aagaaaguuu cuucacau                             158

<210> SEQ ID NO 147
<211> LENGTH: 1063
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: UNA monomer
<220> FEATURE:
<221> NAME/KEY: modified_base
<222> LOCATION: (21)..(21)
<223> OTHER INFORMATION: UNA monomer
<220> FEATURE:
<221> NAME/KEY: modified_base
<222> LOCATION: (39)..(39)
<223> OTHER INFORMATION: UNA monomer
<220> FEATURE:
<221> NAME/KEY: modified_base
```

```
<222> LOCATION: (57)..(57)
<223> OTHER INFORMATION: UNA monomer
<220> FEATURE:
<221> NAME/KEY: modified_base
<222> LOCATION: (75)..(75)
<223> OTHER INFORMATION: UNA monomer
<220> FEATURE:
<221> NAME/KEY: modified_base
<222> LOCATION: (93)..(93)
<223> OTHER INFORMATION: UNA monomer
<220> FEATURE:
<221> NAME/KEY: modified_base
<222> LOCATION: (111)..(111)
<223> OTHER INFORMATION: UNA monomer
<220> FEATURE:
<221> NAME/KEY: modified_base
<222> LOCATION: (129)..(129)
<223> OTHER INFORMATION: UNA monomer
<220> FEATURE:
<221> NAME/KEY: modified_base
<222> LOCATION: (147)..(147)
<223> OTHER INFORMATION: UNA monomer
<220> FEATURE:
<221> NAME/KEY: modified_base
<222> LOCATION: (165)..(165)
<223> OTHER INFORMATION: UNA monomer
<220> FEATURE:
<221> NAME/KEY: modified_base
<222> LOCATION: (183)..(183)
<223> OTHER INFORMATION: UNA monomer
<220> FEATURE:
<221> NAME/KEY: modified_base
<222> LOCATION: (201)..(201)
<223> OTHER INFORMATION: UNA monomer
<220> FEATURE:
<221> NAME/KEY: modified_base
<222> LOCATION: (218)..(218)
<223> OTHER INFORMATION: UNA monomer
<220> FEATURE:
<221> NAME/KEY: modified_base
<222> LOCATION: (236)..(236)
<223> OTHER INFORMATION: UNA monomer
<220> FEATURE:
<221> NAME/KEY: modified_base
<222> LOCATION: (254)..(254)
<223> OTHER INFORMATION: UNA monomer
<220> FEATURE:
<221> NAME/KEY: modified_base
<222> LOCATION: (272)..(272)
<223> OTHER INFORMATION: UNA monomer
<220> FEATURE:
<221> NAME/KEY: modified_base
<222> LOCATION: (290)..(290)
<223> OTHER INFORMATION: UNA monomer
<220> FEATURE:
<221> NAME/KEY: modified_base
<222> LOCATION: (308)..(308)
<223> OTHER INFORMATION: UNA monomer
<220> FEATURE:
<221> NAME/KEY: modified_base
<222> LOCATION: (327)..(327)
<223> OTHER INFORMATION: UNA monomer
<220> FEATURE:
<221> NAME/KEY: modified_base
<222> LOCATION: (345)..(345)
<223> OTHER INFORMATION: UNA monomer
<220> FEATURE:
<221> NAME/KEY: modified_base
<222> LOCATION: (363)..(363)
<223> OTHER INFORMATION: UNA monomer
<220> FEATURE:
<221> NAME/KEY: modified_base
<222> LOCATION: (381)..(381)
<223> OTHER INFORMATION: UNA monomer
<220> FEATURE:
<221> NAME/KEY: modified_base
<222> LOCATION: (399)..(399)
<223> OTHER INFORMATION: UNA monomer
<220> FEATURE:
```

```
<221> NAME/KEY: modified_base
<222> LOCATION: (417)..(417)
<223> OTHER INFORMATION: UNA monomer
<220> FEATURE:
<221> NAME/KEY: modified_base
<222> LOCATION: (453)..(453)
<223> OTHER INFORMATION: UNA monomer
<220> FEATURE:
<221> NAME/KEY: modified_base
<222> LOCATION: (471)..(471)
<223> OTHER INFORMATION: UNA monomer
<220> FEATURE:
<221> NAME/KEY: modified_base
<222> LOCATION: (490)..(490)
<223> OTHER INFORMATION: UNA monomer
<220> FEATURE:
<221> NAME/KEY: modified_base
<222> LOCATION: (508)..(508)
<223> OTHER INFORMATION: UNA monomer
<220> FEATURE:
<221> NAME/KEY: modified_base
<222> LOCATION: (527)..(527)
<223> OTHER INFORMATION: UNA monomer
<220> FEATURE:
<221> NAME/KEY: modified_base
<222> LOCATION: (545)..(545)
<223> OTHER INFORMATION: UNA monomer
<220> FEATURE:
<221> NAME/KEY: modified_base
<222> LOCATION: (563)..(563)
<223> OTHER INFORMATION: UNA monomer
<220> FEATURE:
<221> NAME/KEY: modified_base
<222> LOCATION: (581)..(581)
<223> OTHER INFORMATION: UNA monomer
<220> FEATURE:
<221> NAME/KEY: modified_base
<222> LOCATION: (599)..(599)
<223> OTHER INFORMATION: UNA monomer
<220> FEATURE:
<221> NAME/KEY: modified_base
<222> LOCATION: (617)..(617)
<223> OTHER INFORMATION: UNA monomer
<220> FEATURE:
<221> NAME/KEY: modified_base
<222> LOCATION: (635)..(635)
<223> OTHER INFORMATION: UNA monomer
<220> FEATURE:
<221> NAME/KEY: modified_base
<222> LOCATION: (653)..(653)
<223> OTHER INFORMATION: UNA monomer
<220> FEATURE:
<221> NAME/KEY: modified_base
<222> LOCATION: (671)..(671)
<223> OTHER INFORMATION: UNA monomer
<220> FEATURE:
<221> NAME/KEY: modified_base
<222> LOCATION: (689)..(689)
<223> OTHER INFORMATION: UNA monomer
<220> FEATURE:
<221> NAME/KEY: modified_base
<222> LOCATION: (707)..(707)
<223> OTHER INFORMATION: UNA monomer
<220> FEATURE:
<221> NAME/KEY: modified_base
<222> LOCATION: (725)..(725)
<223> OTHER INFORMATION: UNA monomer
<220> FEATURE:
<221> NAME/KEY: modified_base
<222> LOCATION: (743)..(743)
<223> OTHER INFORMATION: UNA monomer
<220> FEATURE:
<221> NAME/KEY: modified_base
<222> LOCATION: (761)..(761)
<223> OTHER INFORMATION: UNA monomer
<220> FEATURE:
<221> NAME/KEY: modified_base
<222> LOCATION: (779)..(779)
<223> OTHER INFORMATION: UNA monomer
```

```
<220> FEATURE:
<221> NAME/KEY: modified_base
<222> LOCATION: (797)..(797)
<223> OTHER INFORMATION: UNA monomer
<220> FEATURE:
<221> NAME/KEY: modified_base
<222> LOCATION: (815)..(815)
<223> OTHER INFORMATION: UNA monomer
<220> FEATURE:
<221> NAME/KEY: modified_base
<222> LOCATION: (833)..(833)
<223> OTHER INFORMATION: UNA monomer
<220> FEATURE:
<221> NAME/KEY: modified_base
<222> LOCATION: (851)..(851)
<223> OTHER INFORMATION: UNA monomer
<220> FEATURE:
<221> NAME/KEY: modified_base
<222> LOCATION: (869)..(869)
<223> OTHER INFORMATION: UNA monomer
<220> FEATURE:
<221> NAME/KEY: modified_base
<222> LOCATION: (887)..(887)
<223> OTHER INFORMATION: UNA monomer
<220> FEATURE:
<221> NAME/KEY: modified_base
<222> LOCATION: (905)..(905)
<223> OTHER INFORMATION: UNA monomer
<220> FEATURE:
<221> NAME/KEY: modified_base
<222> LOCATION: (923)..(923)
<223> OTHER INFORMATION: UNA monomer
<220> FEATURE:
<221> NAME/KEY: modified_base
<222> LOCATION: (941)..(941)
<223> OTHER INFORMATION: UNA monomer
<220> FEATURE:
<221> NAME/KEY: modified_base
<222> LOCATION: (959)..(959)
<223> OTHER INFORMATION: UNA monomer
<220> FEATURE:
<221> NAME/KEY: modified_base
<222> LOCATION: (977)..(977)
<223> OTHER INFORMATION: UNA monomer
<220> FEATURE:
<221> NAME/KEY: modified_base
<222> LOCATION: (995)..(995)
<223> OTHER INFORMATION: UNA monomer
<220> FEATURE:
<221> NAME/KEY: modified_base
<222> LOCATION: (1013)..(1013)
<223> OTHER INFORMATION: UNA monomer
<220> FEATURE:
<221> NAME/KEY: modified_base
<222> LOCATION: (1031)..(1031)
<223> OTHER INFORMATION: UNA monomer
<220> FEATURE:
<221> NAME/KEY: modified_base
<222> LOCATION: (1049)..(1049)
<223> OTHER INFORMATION: UNA monomer
<220> FEATURE:
<221> NAME/KEY: modified_base
<222> LOCATION: (1062)..(1062)
<223> OTHER INFORMATION: UNA monomer

<400> SEQUENCE: 147
auggagcuga cugaauugcu ccucgugguc augcuucucc uaacugcaag gcuaacgcug      60
uccagcccgg cuccuccugc uugugaccuc cgagccuca guaaacugcu ucgugacucc     120
cauguccuuc acagcagacu gagccagugc ccagagguuc acccuuugcc uacaccguc      180 cugcugccug cuguggacuu uagcuuggga gaauggaaaa cccagaugga ggagaccaag     240
gcacaggaca uucugggagc agugacccuu cugcuggagg gagugauggc agcacgggga     300
caacugggac ccacuugccu ucaucccuc cugggggcagc uuucuggaca ggucgucuc     360
```

| | |
|---|---|
| cuccuugggg cccugcagag ccuccuugga acccagcuuc cuccacaggg caggaccaca | 420 |
| gcucacaagg aucccaaugc caucuuccug agcuuccaac accugcuccg aggaaaggug | 480 |
| cguuuccuga ugcuuguagg agguccacc cucugcguca ggcggggccc cacccaccac | 540 |
| agcugucccc agcagaaccu cucuagcccu cacacugaac gagcucccaa acaggacuuc | 600 |
| uggauuguug gagacaaacu ucacugccuc agccagaacu acuggcucug ggcuucugaa | 660 |
| guggcagcag ggauucagag ccaagauucc uggucugcug aaccaaaccu ccaggucccu | 720 |
| ggaccaaauc cccggauacc ugaacaggau acacgaacuc uugaauggaa cucguggacu | 780 |
| cuuuccugga cccucacgca ggacccuagg agccccggac auuuccucag gaacaucaga | 840 |
| cacaggcucc cugccacca accuccagcc uggauauucu ccuuccccaa cccauccucc | 900 |
| uacuggacag uauacgcucu ucccucuucc acccaccuug cccacccccug uggccagcu | 960 |
| ccaccccug cuuccugacc cuucugcccc aacgcccacc ccuaccagcc ucuucuaaa | 1020 |
| cacauccuac acccacuccc agaaucuguc ucaggaaggg uaa | 1063 |

```
<210> SEQ ID NO 148
<211> LENGTH: 1062
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(4)
<223> OTHER INFORMATION: UNA monomer
<220> FEATURE:
<221> NAME/KEY: modified_base
<222> LOCATION: (1059)..(1061)
<223> OTHER INFORMATION: UNA monomer

<400> SEQUENCE: 148
```

| | |
|---|---|
| auggagcuga cugaauugcu ccucgugguc augcuucucc uaacugcaag gcuaacgcug | 60 |
| uccagcccgg cuccuccugc uugugaccuc cgaguccuca guaaacugcu ucugacucc | 120 |
| caugccuuc acagcagacu gagccagugc ccagagguuc acccuuugcc uacaccugu | 180 |
| cugcugccug cuguggacuu uagcuuggga gaauggaaaa cccagaugga ggagaccaag | 240 |
| gcacaggaca uucugggagc agugacccuu cugcuggagg gagugauggc agcacgggga | 300 |
| caacugggac ccacugccu cucaucccuc cuggggcagc uuucuggaca gguccgucuc | 360 |
| cuccuugggg cccugcagag ccuccuugga acccagcuuc cuccacaggg caggaccaca | 420 |
| gcucacaagg aucccaaugc caucuuccug agcuuccaac accugcuccg aggaaaggug | 480 |
| cguuuccuga ugcuuguagg agguccacc cucugcguca ggcggggccc acccaccaca | 540 |
| gcugucccca gcagaaccuc ucuagccuc acacugaacg agcucccaaa caggacuucu | 600 |
| ggauuguugg agacaaacuu cacugccuca gccagaacua cuggcucugg gcuucugaag | 660 |
| uggcagcagg gauucagagc caagauuccu ggucugcuga accaaaccuc caggucccug | 720 |
| gaccaaaucc ccggauaccu gaacaggaua cacgaacucu ugaauggaac ucguggacuc | 780 |
| uuuccuggac ccucacgcag gacccuagga gccccggaca uuuccucagg aacaucagac | 840 |
| acaggcuccc ugccacccaa ccuccagccu ggauauucuc cuuccccaac ccauccuccu | 900 |
| acuggacagu auacgcucuu cccucuucca cccaccuugc cacccccugu gguccagcuc | 960 |
| cacccccugc uuccugaccc uucugcucca acgcccaccc uaccagcccu cuucuaaac | 1020 |
| acauccuaca cccacucca gaaucugucu caggaagggu aa | 1062 |

-continued

```
<210> SEQ ID NO 149
<211> LENGTH: 1062
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (8)..(8)
<223> OTHER INFORMATION: UNA monomer
<220> FEATURE:
<221> NAME/KEY: modified_base
<222> LOCATION: (12)..(12)
<223> OTHER INFORMATION: UNA monomer
<220> FEATURE:
<221> NAME/KEY: modified_base
<222> LOCATION: (16)..(17)
<223> OTHER INFORMATION: UNA monomer
<220> FEATURE:
<221> NAME/KEY: modified_base
<222> LOCATION: (20)..(20)
<223> OTHER INFORMATION: UNA monomer
<220> FEATURE:
<221> NAME/KEY: modified_base
<222> LOCATION: (23)..(23)
<223> OTHER INFORMATION: UNA monomer
<220> FEATURE:
<221> NAME/KEY: modified_base
<222> LOCATION: (26)..(26)
<223> OTHER INFORMATION: UNA monomer
<220> FEATURE:
<221> NAME/KEY: modified_base
<222> LOCATION: (29)..(29)
<223> OTHER INFORMATION: UNA monomer
<220> FEATURE:
<221> NAME/KEY: modified_base
<222> LOCATION: (32)..(32)
<223> OTHER INFORMATION: UNA monomer
<220> FEATURE:
<221> NAME/KEY: modified_base
<222> LOCATION: (35)..(36)
<223> OTHER INFORMATION: UNA monomer
<220> FEATURE:
<221> NAME/KEY: modified_base
<222> LOCATION: (38)..(38)
<223> OTHER INFORMATION: UNA monomer
<220> FEATURE:
<221> NAME/KEY: modified_base
<222> LOCATION: (41)..(41)
<223> OTHER INFORMATION: UNA monomer
<220> FEATURE:
<221> NAME/KEY: modified_base
<222> LOCATION: (45)..(45)
<223> OTHER INFORMATION: UNA monomer
<220> FEATURE:
<221> NAME/KEY: modified_base
<222> LOCATION: (53)..(53)
<223> OTHER INFORMATION: UNA monomer
<220> FEATURE:
<221> NAME/KEY: modified_base
<222> LOCATION: (59)..(59)
<223> OTHER INFORMATION: UNA monomer
<220> FEATURE:
<221> NAME/KEY: modified_base
<222> LOCATION: (61)..(61)
<223> OTHER INFORMATION: UNA monomer
<220> FEATURE:
<221> NAME/KEY: modified_base
<222> LOCATION: (72)..(72)
<223> OTHER INFORMATION: UNA monomer
<220> FEATURE:
<221> NAME/KEY: modified_base
<222> LOCATION: (75)..(75)
```

```
<223> OTHER INFORMATION: UNA monomer
<220> FEATURE:
<221> NAME/KEY: modified_base
<222> LOCATION: (78)..(78)
<223> OTHER INFORMATION: UNA monomer
<220> FEATURE:
<221> NAME/KEY: modified_base
<222> LOCATION: (81)..(82)
<223> OTHER INFORMATION: UNA monomer
<220> FEATURE:
<221> NAME/KEY: modified_base
<222> LOCATION: (84)..(84)
<223> OTHER INFORMATION: UNA monomer
<220> FEATURE:
<221> NAME/KEY: modified_base
<222> LOCATION: (89)..(89)
<223> OTHER INFORMATION: UNA monomer
<220> FEATURE:
<221> NAME/KEY: modified_base
<222> LOCATION: (95)..(95)
<223> OTHER INFORMATION: UNA monomer
<220> FEATURE:
<221> NAME/KEY: modified_base
<222> LOCATION: (98)..(98)
<223> OTHER INFORMATION: UNA monomer
<220> FEATURE:
<221> NAME/KEY: modified_base
<222> LOCATION: (102)..(102)
<223> OTHER INFORMATION: UNA monomer
<220> FEATURE:
<221> NAME/KEY: modified_base
<222> LOCATION: (107)..(107)
<223> OTHER INFORMATION: UNA monomer
<220> FEATURE:
<221> NAME/KEY: modified_base
<222> LOCATION: (110)..(111)
<223> OTHER INFORMATION: UNA monomer
<220> FEATURE:
<221> NAME/KEY: modified_base
<222> LOCATION: (114)..(114)
<223> OTHER INFORMATION: UNA monomer
<220> FEATURE:
<221> NAME/KEY: modified_base
<222> LOCATION: (118)..(118)
<223> OTHER INFORMATION: UNA monomer
<220> FEATURE:
<221> NAME/KEY: modified_base
<222> LOCATION: (123)..(123)
<223> OTHER INFORMATION: UNA monomer
<220> FEATURE:
<221> NAME/KEY: modified_base
<222> LOCATION: (125)..(125)
<223> OTHER INFORMATION: UNA monomer
<220> FEATURE:
<221> NAME/KEY: modified_base
<222> LOCATION: (128)..(129)
<223> OTHER INFORMATION: UNA monomer
<220> FEATURE:
<221> NAME/KEY: modified_base
<222> LOCATION: (140)..(140)
<223> OTHER INFORMATION: UNA monomer
<220> FEATURE:
<221> NAME/KEY: modified_base
<222> LOCATION: (148)..(148)
<223> OTHER INFORMATION: UNA monomer
<220> FEATURE:
<221> NAME/KEY: modified_base
<222> LOCATION: (158)..(159)
<223> OTHER INFORMATION: UNA monomer
<220> FEATURE:
<221> NAME/KEY: modified_base
<222> LOCATION: (165)..(167)
<223> OTHER INFORMATION: UNA monomer
<220> FEATURE:
<221> NAME/KEY: modified_base
<222> LOCATION: (171)..(171)
<223> OTHER INFORMATION: UNA monomer
<220> FEATURE:
<221> NAME/KEY: modified_base
```

```
<222> LOCATION: (177)..(177)
<223> OTHER INFORMATION: UNA monomer
<220> FEATURE:
<221> NAME/KEY: modified_base
<222> LOCATION: (179)..(179)
<223> OTHER INFORMATION: UNA monomer
<220> FEATURE:
<221> NAME/KEY: modified_base
<222> LOCATION: (182)..(182)
<223> OTHER INFORMATION: UNA monomer
<220> FEATURE:
<221> NAME/KEY: modified_base
<222> LOCATION: (185)..(185)
<223> OTHER INFORMATION: UNA monomer
<220> FEATURE:
<221> NAME/KEY: modified_base
<222> LOCATION: (189)..(189)
<223> OTHER INFORMATION: UNA monomer
<220> FEATURE:
<221> NAME/KEY: modified_base
<222> LOCATION: (192)..(192)
<223> OTHER INFORMATION: UNA monomer
<220> FEATURE:
<221> NAME/KEY: modified_base
<222> LOCATION: (194)..(194)
<223> OTHER INFORMATION: UNA monomer
<220> FEATURE:
<221> NAME/KEY: modified_base
<222> LOCATION: (199)..(201)
<223> OTHER INFORMATION: UNA monomer
<220> FEATURE:
<221> NAME/KEY: modified_base
<222> LOCATION: (205)..(206)
<223> OTHER INFORMATION: UNA monomer
<220> FEATURE:
<221> NAME/KEY: modified_base
<222> LOCATION: (214)..(214)
<223> OTHER INFORMATION: UNA monomer
<220> FEATURE:
<221> NAME/KEY: modified_base
<222> LOCATION: (227)..(227)
<223> OTHER INFORMATION: UNA monomer
<220> FEATURE:
<221> NAME/KEY: modified_base
<222> LOCATION: (251)..(252)
<223> OTHER INFORMATION: UNA monomer
<220> FEATURE:
<221> NAME/KEY: modified_base
<222> LOCATION: (254)..(254)
<223> OTHER INFORMATION: UNA monomer
<220> FEATURE:
<221> NAME/KEY: modified_base
<222> LOCATION: (263)..(263)
<223> OTHER INFORMATION: UNA monomer
<220> FEATURE:
<221> NAME/KEY: modified_base
<222> LOCATION: (269)..(270)
<223> OTHER INFORMATION: UNA monomer
<220> FEATURE:
<221> NAME/KEY: modified_base
<222> LOCATION: (272)..(272)
<223> OTHER INFORMATION: UNA monomer
<220> FEATURE:
<221> NAME/KEY: modified_base
<222> LOCATION: (275)..(275)
<223> OTHER INFORMATION: UNA monomer
<220> FEATURE:
<221> NAME/KEY: modified_base
<222> LOCATION: (284)..(284)
<223> OTHER INFORMATION: UNA monomer
<220> FEATURE:
<221> NAME/KEY: modified_base
<222> LOCATION: (287)..(287)
<223> OTHER INFORMATION: UNA monomer
<220> FEATURE:
<221> NAME/KEY: modified_base
<222> LOCATION: (305)..(305)
<223> OTHER INFORMATION: UNA monomer
<220> FEATURE:
```

-continued

```
<221> NAME/KEY: modified_base
<222> LOCATION: (315)..(316)
<223> OTHER INFORMATION: UNA monomer
<220> FEATURE:
<221> NAME/KEY: modified_base
<222> LOCATION: (320)..(320)
<223> OTHER INFORMATION: UNA monomer
<220> FEATURE:
<221> NAME/KEY: modified_base
<222> LOCATION: (322)..(322)
<223> OTHER INFORMATION: UNA monomer
<220> FEATURE:
<221> NAME/KEY: modified_base
<222> LOCATION: (325)..(325)
<223> OTHER INFORMATION: UNA monomer
<220> FEATURE:
<221> NAME/KEY: modified_base
<222> LOCATION: (329)..(329)
<223> OTHER INFORMATION: UNA monomer
<220> FEATURE:
<221> NAME/KEY: modified_base
<222> LOCATION: (332)..(332)
<223> OTHER INFORMATION: UNA monomer
<220> FEATURE:
<221> NAME/KEY: modified_base
<222> LOCATION: (341)..(343)
<223> OTHER INFORMATION: UNA monomer
<220> FEATURE:
<221> NAME/KEY: modified_base
<222> LOCATION: (345)..(345)
<223> OTHER INFORMATION: UNA monomer
<220> FEATURE:
<221> NAME/KEY: modified_base
<222> LOCATION: (353)..(353)
<223> OTHER INFORMATION: UNA monomer
<220> FEATURE:
<221> NAME/KEY: modified_base
<222> LOCATION: (357)..(357)
<223> OTHER INFORMATION: UNA monomer
<220> FEATURE:
<221> NAME/KEY: modified_base
<222> LOCATION: (359)..(359)
<223> OTHER INFORMATION: UNA monomer
<220> FEATURE:
<221> NAME/KEY: modified_base
<222> LOCATION: (362)..(362)
<223> OTHER INFORMATION: UNA monomer
<220> FEATURE:
<221> NAME/KEY: modified_base
<222> LOCATION: (365)..(366)
<223> OTHER INFORMATION: UNA monomer
<220> FEATURE:
<221> NAME/KEY: modified_base
<222> LOCATION: (374)..(374)
<223> OTHER INFORMATION: UNA monomer
<220> FEATURE:
<221> NAME/KEY: modified_base
<222> LOCATION: (383)..(383)
<223> OTHER INFORMATION: UNA monomer
<220> FEATURE:
<221> NAME/KEY: modified_base
<222> LOCATION: (386)..(387)
<223> OTHER INFORMATION: UNA monomer
<220> FEATURE:
<221> NAME/KEY: modified_base
<222> LOCATION: (398)..(399)
<223> OTHER INFORMATION: UNA monomer
<220> FEATURE:
<221> NAME/KEY: modified_base
<222> LOCATION: (402)..(402)
<223> OTHER INFORMATION: UNA monomer
<220> FEATURE:
<221> NAME/KEY: modified_base
<222> LOCATION: (423)..(423)
<223> OTHER INFORMATION: UNA monomer
<220> FEATURE:
<221> NAME/KEY: modified_base
<222> LOCATION: (432)..(432)
<223> OTHER INFORMATION: UNA monomer
```

-continued

```
<220> FEATURE:
<221> NAME/KEY: modified_base
<222> LOCATION: (438)..(438)
<223> OTHER INFORMATION: UNA monomer
<220> FEATURE:
<221> NAME/KEY: modified_base
<222> LOCATION: (443)..(443)
<223> OTHER INFORMATION: UNA monomer
<220> FEATURE:
<221> NAME/KEY: modified_base
<222> LOCATION: (445)..(446)
<223> OTHER INFORMATION: UNA monomer
<220> FEATURE:
<221> NAME/KEY: modified_base
<222> LOCATION: (449)..(449)
<223> OTHER INFORMATION: UNA monomer
<220> FEATURE:
<221> NAME/KEY: modified_base
<222> LOCATION: (454)..(455)
<223> OTHER INFORMATION: UNA monomer
<220> FEATURE:
<221> NAME/KEY: modified_base
<222> LOCATION: (464)..(464)
<223> OTHER INFORMATION: UNA monomer
<220> FEATURE:
<221> NAME/KEY: modified_base
<222> LOCATION: (467)..(467)
<223> OTHER INFORMATION: UNA monomer
<220> FEATURE:
<221> NAME/KEY: modified_base
<222> LOCATION: (479)..(479)
<223> OTHER INFORMATION: UNA monomer
<220> FEATURE:
<221> NAME/KEY: modified_base
<222> LOCATION: (483)..(485)
<223> OTHER INFORMATION: UNA monomer
<220> FEATURE:
<221> NAME/KEY: modified_base
<222> LOCATION: (488)..(488)
<223> OTHER INFORMATION: UNA monomer
<220> FEATURE:
<221> NAME/KEY: modified_base
<222> LOCATION: (491)..(491)
<223> OTHER INFORMATION: UNA monomer
<220> FEATURE:
<221> NAME/KEY: modified_base
<222> LOCATION: (494)..(495)
<223> OTHER INFORMATION: UNA monomer
<220> FEATURE:
<221> NAME/KEY: modified_base
<222> LOCATION: (497)..(497)
<223> OTHER INFORMATION: UNA monomer
<220> FEATURE:
<221> NAME/KEY: modified_base
<222> LOCATION: (505)..(505)
<223> OTHER INFORMATION: UNA monomer
<220> FEATURE:
<221> NAME/KEY: modified_base
<222> LOCATION: (512)..(512)
<223> OTHER INFORMATION: UNA monomer
<220> FEATURE:
<221> NAME/KEY: modified_base
<222> LOCATION: (514)..(514)
<223> OTHER INFORMATION: UNA monomer
<220> FEATURE:
<221> NAME/KEY: modified_base
<222> LOCATION: (518)..(518)
<223> OTHER INFORMATION: UNA monomer
<220> FEATURE:
<221> NAME/KEY: modified_base
<222> LOCATION: (543)..(543)
<223> OTHER INFORMATION: UNA monomer
<220> FEATURE:
<221> NAME/KEY: modified_base
<222> LOCATION: (545)..(545)
<223> OTHER INFORMATION: UNA monomer
<220> FEATURE:
<221> NAME/KEY: modified_base
<222> LOCATION: (559)..(559)
```

```
<223> OTHER INFORMATION: UNA monomer
<220> FEATURE:
<221> NAME/KEY: modified_base
<222> LOCATION: (561)..(561)
<223> OTHER INFORMATION: UNA monomer
<220> FEATURE:
<221> NAME/KEY: modified_base
<222> LOCATION: (563)..(563)
<223> OTHER INFORMATION: UNA monomer
<220> FEATURE:
<221> NAME/KEY: modified_base
<222> LOCATION: (566)..(566)
<223> OTHER INFORMATION: UNA monomer
<220> FEATURE:
<221> NAME/KEY: modified_base
<222> LOCATION: (569)..(569)
<223> OTHER INFORMATION: UNA monomer
<220> FEATURE:
<221> NAME/KEY: modified_base
<222> LOCATION: (575)..(575)
<223> OTHER INFORMATION: UNA monomer
<220> FEATURE:
<221> NAME/KEY: modified_base
<222> LOCATION: (584)..(584)
<223> OTHER INFORMATION: UNA monomer
<220> FEATURE:
<221> NAME/KEY: modified_base
<222> LOCATION: (597)..(598)
<223> OTHER INFORMATION: UNA monomer
<220> FEATURE:
<221> NAME/KEY: modified_base
<222> LOCATION: (600)..(600)
<223> OTHER INFORMATION: UNA monomer
<220> FEATURE:
<221> NAME/KEY: modified_base
<222> LOCATION: (604)..(605)
<223> OTHER INFORMATION: UNA monomer
<220> FEATURE:
<221> NAME/KEY: modified_base
<222> LOCATION: (607)..(608)
<223> OTHER INFORMATION: UNA monomer
<220> FEATURE:
<221> NAME/KEY: modified_base
<222> LOCATION: (619)..(620)
<223> OTHER INFORMATION: UNA monomer
<220> FEATURE:
<221> NAME/KEY: modified_base
<222> LOCATION: (624)..(624)
<223> OTHER INFORMATION: UNA monomer
<220> FEATURE:
<221> NAME/KEY: modified_base
<222> LOCATION: (628)..(628)
<223> OTHER INFORMATION: UNA monomer
<220> FEATURE:
<221> NAME/KEY: modified_base
<222> LOCATION: (639)..(639)
<223> OTHER INFORMATION: UNA monomer
<220> FEATURE:
<221> NAME/KEY: modified_base
<222> LOCATION: (642)..(642)
<223> OTHER INFORMATION: UNA monomer
<220> FEATURE:
<221> NAME/KEY: modified_base
<222> LOCATION: (646)..(646)
<223> OTHER INFORMATION: UNA monomer
<220> FEATURE:
<221> NAME/KEY: modified_base
<222> LOCATION: (648)..(648)
<223> OTHER INFORMATION: UNA monomer
<220> FEATURE:
<221> NAME/KEY: modified_base
<222> LOCATION: (653)..(654)
<223> OTHER INFORMATION: UNA monomer
<220> FEATURE:
<221> NAME/KEY: modified_base
<222> LOCATION: (656)..(656)
<223> OTHER INFORMATION: UNA monomer
<220> FEATURE:
<221> NAME/KEY: modified_base
```

```
<222> LOCATION: (661)..(661)
<223> OTHER INFORMATION: UNA monomer
<220> FEATURE:
<221> NAME/KEY: modified_base
<222> LOCATION: (673)..(674)
<223> OTHER INFORMATION: UNA monomer
<220> FEATURE:
<221> NAME/KEY: modified_base
<222> LOCATION: (686)..(687)
<223> OTHER INFORMATION: UNA monomer
<220> FEATURE:
<221> NAME/KEY: modified_base
<222> LOCATION: (690)..(690)
<223> OTHER INFORMATION: UNA monomer
<220> FEATURE:
<221> NAME/KEY: modified_base
<222> LOCATION: (693)..(693)
<223> OTHER INFORMATION: UNA monomer
<220> FEATURE:
<221> NAME/KEY: modified_base
<222> LOCATION: (695)..(695)
<223> OTHER INFORMATION: UNA monomer
<220> FEATURE:
<221> NAME/KEY: modified_base
<222> LOCATION: (698)..(698)
<223> OTHER INFORMATION: UNA monomer
<220> FEATURE:
<221> NAME/KEY: modified_base
<222> LOCATION: (709)..(709)
<223> OTHER INFORMATION: UNA monomer
<220> FEATURE:
<221> NAME/KEY: modified_base
<222> LOCATION: (715)..(715)
<223> OTHER INFORMATION: UNA monomer
<220> FEATURE:
<221> NAME/KEY: modified_base
<222> LOCATION: (719)..(719)
<223> OTHER INFORMATION: UNA monomer
<220> FEATURE:
<221> NAME/KEY: modified_base
<222> LOCATION: (728)..(728)
<223> OTHER INFORMATION: UNA monomer
<220> FEATURE:
<221> NAME/KEY: modified_base
<222> LOCATION: (736)..(736)
<223> OTHER INFORMATION: UNA monomer
<220> FEATURE:
<221> NAME/KEY: modified_base
<222> LOCATION: (740)..(740)
<223> OTHER INFORMATION: UNA monomer
<220> FEATURE:
<221> NAME/KEY: modified_base
<222> LOCATION: (749)..(749)
<223> OTHER INFORMATION: UNA monomer
<220> FEATURE:
<221> NAME/KEY: modified_base
<222> LOCATION: (758)..(758)
<223> OTHER INFORMATION: UNA monomer
<220> FEATURE:
<221> NAME/KEY: modified_base
<222> LOCATION: (760)..(761)
<223> OTHER INFORMATION: UNA monomer
<220> FEATURE:
<221> NAME/KEY: modified_base
<222> LOCATION: (765)..(765)
<223> OTHER INFORMATION: UNA monomer
<220> FEATURE:
<221> NAME/KEY: modified_base
<222> LOCATION: (771)..(771)
<223> OTHER INFORMATION: UNA monomer
<220> FEATURE:
<221> NAME/KEY: modified_base
<222> LOCATION: (774)..(774)
<223> OTHER INFORMATION: UNA monomer
<220> FEATURE:
<221> NAME/KEY: modified_base
<222> LOCATION: (779)..(779)
<223> OTHER INFORMATION: UNA monomer
<220> FEATURE:
```

```
<221> NAME/KEY: modified_base
<222> LOCATION: (781)..(783)
<223> OTHER INFORMATION: UNA monomer
<220> FEATURE:
<221> NAME/KEY: modified_base
<222> LOCATION: (786)..(786)
<223> OTHER INFORMATION: UNA monomer
<220> FEATURE:
<221> NAME/KEY: modified_base
<222> LOCATION: (793)..(793)
<223> OTHER INFORMATION: UNA monomer
<220> FEATURE:
<221> NAME/KEY: modified_base
<222> LOCATION: (806)..(806)
<223> OTHER INFORMATION: UNA monomer
<220> FEATURE:
<221> NAME/KEY: modified_base
<222> LOCATION: (821)..(823)
<223> OTHER INFORMATION: UNA monomer
<220> FEATURE:
<221> NAME/KEY: modified_base
<222> LOCATION: (826)..(826)
<223> OTHER INFORMATION: UNA monomer
<220> FEATURE:
<221> NAME/KEY: modified_base
<222> LOCATION: (835)..(835)
<223> OTHER INFORMATION: UNA monomer
<220> FEATURE:
<221> NAME/KEY: modified_base
<222> LOCATION: (847)..(847)
<223> OTHER INFORMATION: UNA monomer
<220> FEATURE:
<221> NAME/KEY: modified_base
<222> LOCATION: (851)..(851)
<223> OTHER INFORMATION: UNA monomer
<220> FEATURE:
<221> NAME/KEY: modified_base
<222> LOCATION: (863)..(863)
<223> OTHER INFORMATION: UNA monomer
<220> FEATURE:
<221> NAME/KEY: modified_base
<222> LOCATION: (870)..(870)
<223> OTHER INFORMATION: UNA monomer
<220> FEATURE:
<221> NAME/KEY: modified_base
<222> LOCATION: (874)..(874)
<223> OTHER INFORMATION: UNA monomer
<220> FEATURE:
<221> NAME/KEY: modified_base
<222> LOCATION: (876)..(877)
<223> OTHER INFORMATION: UNA monomer
<220> FEATURE:
<221> NAME/KEY: modified_base
<222> LOCATION: (879)..(879)
<223> OTHER INFORMATION: UNA monomer
<220> FEATURE:
<221> NAME/KEY: modified_base
<222> LOCATION: (882)..(883)
<223> OTHER INFORMATION: UNA monomer
<220> FEATURE:
<221> NAME/KEY: modified_base
<222> LOCATION: (894)..(894)
<223> OTHER INFORMATION: UNA monomer
<220> FEATURE:
<221> NAME/KEY: modified_base
<222> LOCATION: (897)..(897)
<223> OTHER INFORMATION: UNA monomer
<220> FEATURE:
<221> NAME/KEY: modified_base
<222> LOCATION: (900)..(900)
<223> OTHER INFORMATION: UNA monomer
<220> FEATURE:
<221> NAME/KEY: modified_base
<222> LOCATION: (903)..(903)
<223> OTHER INFORMATION: UNA monomer
<220> FEATURE:
<221> NAME/KEY: modified_base
<222> LOCATION: (910)..(910)
<223> OTHER INFORMATION: UNA monomer
```

-continued

```
<220> FEATURE:
<221> NAME/KEY: modified_base
<222> LOCATION: (912)..(912)
<223> OTHER INFORMATION: UNA monomer
<220> FEATURE:
<221> NAME/KEY: modified_base
<222> LOCATION: (917)..(917)
<223> OTHER INFORMATION: UNA monomer
<220> FEATURE:
<221> NAME/KEY: modified_base
<222> LOCATION: (919)..(920)
<223> OTHER INFORMATION: UNA monomer
<220> FEATURE:
<221> NAME/KEY: modified_base
<222> LOCATION: (924)..(924)
<223> OTHER INFORMATION: UNA monomer
<220> FEATURE:
<221> NAME/KEY: modified_base
<222> LOCATION: (926)..(927)
<223> OTHER INFORMATION: UNA monomer
<220> FEATURE:
<221> NAME/KEY: modified_base
<222> LOCATION: (937)..(938)
<223> OTHER INFORMATION: UNA monomer
<220> FEATURE:
<221> NAME/KEY: modified_base
<222> LOCATION: (948)..(948)
<223> OTHER INFORMATION: UNA monomer
<220> FEATURE:
<221> NAME/KEY: modified_base
<222> LOCATION: (950)..(950)
<223> OTHER INFORMATION: UNA monomer
<220> FEATURE:
<221> NAME/KEY: modified_base
<222> LOCATION: (953)..(953)
<223> OTHER INFORMATION: UNA monomer
<220> FEATURE:
<221> NAME/KEY: modified_base
<222> LOCATION: (959)..(959)
<223> OTHER INFORMATION: UNA monomer
<220> FEATURE:
<221> NAME/KEY: modified_base
<222> LOCATION: (968)..(968)
<223> OTHER INFORMATION: UNA monomer
<220> FEATURE:
<221> NAME/KEY: modified_base
<222> LOCATION: (971)..(972)
<223> OTHER INFORMATION: UNA monomer
<220> FEATURE:
<221> NAME/KEY: modified_base
<222> LOCATION: (975)..(975)
<223> OTHER INFORMATION: UNA monomer
<220> FEATURE:
<221> NAME/KEY: modified_base
<222> LOCATION: (981)..(982)
<223> OTHER INFORMATION: UNA monomer
<220> FEATURE:
<221> NAME/KEY: modified_base
<222> LOCATION: (984)..(984)
<223> OTHER INFORMATION: UNA monomer
<220> FEATURE:
<221> NAME/KEY: modified_base
<222> LOCATION: (987)..(987)
<223> OTHER INFORMATION: UNA monomer
<220> FEATURE:
<221> NAME/KEY: modified_base
<222> LOCATION: (1002)..(1002)
<223> OTHER INFORMATION: UNA monomer
<220> FEATURE:
<221> NAME/KEY: modified_base
<222> LOCATION: (1011)..(1011)
<223> OTHER INFORMATION: UNA monomer
<220> FEATURE:
<221> NAME/KEY: modified_base
<222> LOCATION: (1013)..(1014)
<223> OTHER INFORMATION: UNA monomer
<220> FEATURE:
<221> NAME/KEY: modified_base
<222> LOCATION: (1016)..(1016)
```

```
<223> OTHER INFORMATION: UNA monomer
<220> FEATURE:
<221> NAME/KEY: modified_base
<222> LOCATION: (1024)..(1024)
<223> OTHER INFORMATION: UNA monomer
<220> FEATURE:
<221> NAME/KEY: modified_base
<222> LOCATION: (1027)..(1027)
<223> OTHER INFORMATION: UNA monomer
<220> FEATURE:
<221> NAME/KEY: modified_base
<222> LOCATION: (1036)..(1036)
<223> OTHER INFORMATION: UNA monomer
<220> FEATURE:
<221> NAME/KEY: modified_base
<222> LOCATION: (1044)..(1044)
<223> OTHER INFORMATION: UNA monomer
<220> FEATURE:
<221> NAME/KEY: modified_base
<222> LOCATION: (1046)..(1046)
<223> OTHER INFORMATION: UNA monomer
<220> FEATURE:
<221> NAME/KEY: modified_base
<222> LOCATION: (1048)..(1048)
<223> OTHER INFORMATION: UNA monomer
<220> FEATURE:
<221> NAME/KEY: modified_base
<222> LOCATION: (1050)..(1050)
<223> OTHER INFORMATION: UNA monomer
<220> FEATURE:
<221> NAME/KEY: modified_base
<222> LOCATION: (1060)..(1060)
<223> OTHER INFORMATION: UNA monomer

<400> SEQUENCE: 149
auggagcuga cugaauugcu ccucgugguc augcuucucc uaacugcaag gcuaacgcug      60
uccagcccgg cuccuccugc uugugaccuc cgagccucua guaaacugcu ucgugacucc     120
cauguccuuc acagcagacu gagccagugc cagagguuc  acccuuugcc uacaccuguc     180
cugcugccug cuguggacuu uagcuuggga gaauggaaaa cccagaugga ggagaccaag     240
gcacaggaca uucugggagc agugacccuu cugcuggagg gagugauggc agcacgggga     300
caacugggac ccacuugccu cucaucccuc cuggggcagc uuucuggaca gguccgucuc     360
cuccuugggg cccugcagag ccuccuugga acccagcuuc cuccacaggg caggaccaca     420
gcucacaagg aucccaaugc caucuuccug agcuuccaac accugcuccg aggaaaggug     480
cguuuccuga ugcuuguagg agggucacc  cucugcguca ggcgggcccc acccaccaca     540
gcugucccca gcagaaccuc ucuaguccuc acacugaacg agcucccaaa caggacuucu     600
ggauuguugg agacaaacuu cacugccuca gccagaacua cuggcucugg gcuucugaag     660
uggcagcagg gauucagagc caagauuccu ggucugcuga accaaaccuc caggucccug     720
gaccaaauuc ccggauaccu gaacaggaua cacgaacucu ugaauggaac ucguggacuc     780
uuuccuggac ccuacgcag  gacccuagga gccccggaca uuccucagg  aacaucagac     840
acaggcuccc ugccacccaa ccuccagccu ggauauucuc cuuccccaac ccauccuccu     900
acuggacagu auacgcucuu cccucuucca cccaccuugc ccaccccugu gguccagcuc     960
cacccccugc uuccugaccc uucugcucca acgcccaccc cuaccagccc ucuucuaaac    1020
acauccuaca cccacucccca gaaucugucu caggaagggu aa                      1062

<210> SEQ ID NO 150
<211> LENGTH: 4599
<212> TYPE: RNA
<213> ORGANISM: Artificial Sequence
<220> FEATURE:
<223> OTHER INFORMATION: Description of Artificial Sequence: Synthetic
```

```
        polynucleotide
<220> FEATURE:
<221> NAME/KEY: modified_base
<222> LOCATION: (2)..(4)
<223> OTHER INFORMATION: UNA monomer
<220> FEATURE:
<221> NAME/KEY: modified_base
<222> LOCATION: (4596)..(4598)
<223> OTHER INFORMATION: UNA monomer

<400> SEQUENCE: 150
augggacaca guaaacagau ucgaauuuua cuucugaacg aaauggagaa acuggaaaag      60
acccucuuca gacuugaaca aggguaugag cuacaguucc gauuaggccc aacuuuacag     120
ggaaaagcag uuaccgugua acaaauuac ccauuuccug gagaaacauu uaauagagaa      180
aaauuccguu cucuggauug ggaaaaucca acagaaagag aagaugauuc ugauaaauac     240
uguaaacuua aucugcaaca aucugguuca uuucaguauu auuccuuca aggaaaugag      300 aaaaguggug gagguuacau aguuguggac cccauuuuac guguuggcgc ugauaaucau     360
gugcuacccu uggacugugu uacucuucag acauuuuuag cuaaguguuu gggaccuuuu     420
gaugaauggg aaagcagacu uagggguugca aagaaucag gcuacaacau gauucauuuu      480
accccauugc agacucuugg acuaucuagg ucaugcuacu cccuugccaa ucaguuagaa     540
uuaaauccug acuuuucaag accaauaga aaguauaccu ggaaugaugu uggacagcua      600
guggaaaaau uaaaaagga auggaauguu auuuguauua cugauguugu cuacaaucau     660
acugcugcua auaguaaaug gauccaggaa cauccagaau gugccuauaa ucuugugaau     720
ucuccacacu uaaaaccugc cugggucuua gacagagcac uuuggcguuu ucccugugau     780
guugcagaag ggaaauacaa agaaaaggga auaccugcuu gauugaaaa ugaucaccau      840 augaauucca uccgaaaaau aauuuggag gauauuuuc caaagcuuaa acucugggaa       900
uuuuuccaag uagaugucaa caaagcgguu gagcaauuua gaagacuucu uacacaagaa     960
aauaggcgag uaaccaaguc ugauccaaac caacaccuua cgauuauuca agauccgaa     1020 uacagacggu uggcuguac uguagauaug aacauugcac uaacgacuuu cauaccacau      1080 gacaagggc cagcagcaau ugaagaaugc uguaauuggu ucauaaaag aauggaggaa      1140 uuaaauucag agaagcaucg acucauuaac uaucaucagg aacaggcagu uaauugccuu     1200
uugggaaaug uguuuuauga acgacuggcu ggccauggu caaaacuagg accgucacu      1260 agaaagcauc cuuuaguuac cagguauuuu acuuucccau uugaagagau agacuucucc     1320
auggaagaau cuaugauuca ucugccaaau aaagcuuguu uucugauggc acacaaugga     1380
uggguaaugg gagaugaucc ucuucgaaac uuugcugaac cgguucaga aguuaccua      1440 aggagagaac uuauuugcug gggagacagu guuaaauuac gcuaugggaa uaaaccagag    1500
gacuguccuu aucucugggc acacaugaaa aaauacacug aaauaacugc aacuuauuuc     1560
cagggaguac gucuugauaa cugccacuca acaccucuuc acguagcuga guacauguug    1620
gaugcugcua ggaauuugca acccaauuua uguaguag cugaacuguu cacaggaagu     1680
gaagaucugg acaaugucuu uguuacuaga cugggcauua guccuuaau aagagaggca     1740 augagugcau auaauaguca ugaagaggc agauuaguuu accgauaugg aggagaaccu    1800
guuggauccu uuguucagcc cuguugagg ccuuaaaugc cagcuauugc acaugcccug     1860
uuuauggaua uuacgcauga uaaugagugu ccuauugugc auagaucagc guaugaugcu   1920
cuuccaagua cuacaauugu uucuauggca uguugugcua guggaaguac aagaggcuau    1980
gaugaauuag ugccucauca gauuucagug guuucugaag aacgguuuua cacuaagugg    2040
```

-continued

```
aauccugaag cauugccuuc aaacacaggu gaaguuaauu uccaaagcgg cauuauugca    2100
gccaggugug cuaucaguaa acuucaucag gagcuuggag ccaaggguuu auucaggug    2160 uauguggauc aaguugauga agacauagug gcaguaacaa gacacucacc uagcauccau    2220
cagucuguug uggcuguauc uagaacugcu uucaggaauc ccaagacuuc auuuuacagc    2280
aaggaagugc cucaaaugug caucccuggc aaaauugaag aaguaguucu ugaagcuaga    2340
acuauugaga gaaacacgaa accuuauagg aaggaugaga auucaaucaa uggaacacca    2400
gauaucacag uagaaauuag agaacauauu cagcuuaaug aaaguaaaau uguuaaacaa    2460
gcuggaguug ccacaaaagg gcccaaugaa uauauucaag aaaugaauu ugaaaacuug    2520 ucuccaggaa guguuauuau auucagaguu agucuugauc cacaugcaca agucgcuguu    2580
ggaauucuuc gaaaucaucu gacacaauuc agccucacu uuaaaucugg cagccuagcu    2640
guugacaaug cagauccuau auuaaaaauu ccuuuugcuu cucuugccuc cagauuaacu    2700
uuggcugagc uaaaucagau ccuuuaccga ugugaaucag aagaaaagga agaugguga    2760 gggugcuaug acauaccaaa cuggucagcc cuuaaauaug caggucuuca agguuuaaug    2820
ucuguauugg cagaaauaag accaaagaau gacuuggggc auccuuuuug uaauaauuug    2880
agaucuggag auuggaugau ugacuaugc aguaaccggc uuauucacg aucaggaacu    2940 auugcugaag uugguaaaug guugcaggcu auguucuucu accugaagca gaucccacgu    3000
uaccuuaucc caguguacuu ugaugcuaua uuaauggug cauauaccac ucuucuggau    3060
acagcaugga agcagaugc aagcuuuguu cagaauggu caaccuuugu gaaacaccuu    3120 ucauggguu caguucaacu guuggagua ggaaaauucc cuucccugcc aauucuuuca    3180
ccugcccuaa uggauguacc uuauagguua aaugagauca caaagaaaa ggagcaaugu    3240 uguguuucuc uagcugcagg cuuaccucau uuucuucug guauuuuccg cugcugggga    3300
agggauacuu uuauugcacu uagagguaua cugcugauua cuggacgcua uguagaagcc    3360
aggaauauua uuuuagcauu ugcggguacc cugaggcaug gucucauuc uaaucuacug    3420 ggugaaggaa uuuaugccag auacaauugc cgggaugcug ugguggugug gcugcagugu    3480
auccaggauu acuguaaaau gguuccaaau ggucuagaca uucucaagug cccaguuucc    3540
agaauguauc cuacagauga uucugcuccu ugccugcug gcacacugga ucagccauug    3600
uuugaaguca uacaggaagc aaugcaaaaa cacaugcagg gcauacaguu ccgagaaagg    3660
aaugcugguc cccagauaga ucgaaacaug aaggacgaag guuuaauau aacugcagga    3720 guugaugaag aaacaggauu uguuuaugga ggaaaucguu caauugugg cacauggaug    3780 gauaaaaugg gagaaaguga cagagcuaga aacagaggaa ucccagccac accaagagau    3840
gggucugcug uggaaauugu gggccugagu aaaucgcug uucgcugguu gcuggaauua    3900
uccaaaaaaa auauuuuccc uuaucaugaa gucacaguaa aagacaugg aaaggcuaua    3960 aaggucucau augaugagug gaacagaaaa auacaagaca acuuugaaaa gcauuucau    4020 guuuccgaag acccuucaga uuuaaugaa aagcauccaa aucugguuca caaacgugc    4080 auauacaaag auaguuaugg agcuucaagu ccuggugugu acaucagcu caggccuaau    4140 uuuaccauag caaugguugu ggccccgag cucuuacua cagaaaaagc augaaagcu    4200 uggagauug cagaaaaaaa auugcuuggu ccccuuggca ugaaaacuuu agauccagau    4260
gauaugguuu acuguggaau uuaugacaau gcauugaaca augacaacua caacuuugcu    4320
aaagguuuca auuaucacca aggaccugag uggcuguggg cuauuggguua uuucuucgu    4380
```

```
gcaaaauuau auuuuuccag auugaugggc ccggagacua cugcaaagac uauaguuuug      4440
guuaaaaaug uucuuucccg acauuauguu caucuugaga gaucccccuug gaaaggacuu    4500 ccagaacuga ccaaugagaa ugcccaguac uguccuuuca gcugugaaac acaagccugg     4560
ucaauugcua cuauucuuga gacacuuuau gauuuauag                            4599
```

```
<210> SEQ ID NO 151
<211> LENGTH: 4599
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (12)..(12)
<223> OTHER INFORMATION: UNA monomer
<220> FEATURE:
<221> NAME/KEY: modified_base
<222> LOCATION: (20)..(21)
<223> OTHER INFORMATION: UNA monomer
<220> FEATURE:
<221> NAME/KEY: modified_base
<222> LOCATION: (26)..(29)
<223> OTHER INFORMATION: UNA monomer
<220> FEATURE:
<221> NAME/KEY: modified_base
<222> LOCATION: (32)..(33)
<223> OTHER INFORMATION: UNA monomer
<220> FEATURE:
<221> NAME/KEY: modified_base
<222> LOCATION: (35)..(35)
<223> OTHER INFORMATION: UNA monomer
<220> FEATURE:
<221> NAME/KEY: modified_base
<222> LOCATION: (44)..(44)
<223> OTHER INFORMATION: UNA monomer
<220> FEATURE:
<221> NAME/KEY: modified_base
<222> LOCATION: (53)..(53)
<223> OTHER INFORMATION: UNA monomer
<220> FEATURE:
<221> NAME/KEY: modified_base
<222> LOCATION: (65)..(65)
<223> OTHER INFORMATION: UNA monomer
<220> FEATURE:
<221> NAME/KEY: modified_base
<222> LOCATION: (67)..(68)
<223> OTHER INFORMATION: UNA monomer
<220> FEATURE:
<221> NAME/KEY: modified_base
<222> LOCATION: (74)..(75)
<223> OTHER INFORMATION: UNA monomer
<220> FEATURE:
<221> NAME/KEY: modified_base
<222> LOCATION: (85)..(85)
<223> OTHER INFORMATION: UNA monomer
<220> FEATURE:
<221> NAME/KEY: modified_base
<222> LOCATION: (87)..(87)
<223> OTHER INFORMATION: UNA monomer
<220> FEATURE:
<221> NAME/KEY: modified_base
<222> LOCATION: (92)..(92)
<223> OTHER INFORMATION: UNA monomer
<220> FEATURE:
<221> NAME/KEY: modified_base
<222> LOCATION: (97)..(98)
<223> OTHER INFORMATION: UNA monomer
<220> FEATURE:
<221> NAME/KEY: modified_base
<222> LOCATION: (103)..(104)
```

```
<223> OTHER INFORMATION: UNA monomer
<220> FEATURE:
<221> NAME/KEY: modified_base
<222> LOCATION: (114)..(116)
<223> OTHER INFORMATION: UNA monomer
<220> FEATURE:
<221> NAME/KEY: modified_base
<222> LOCATION: (131)..(132)
<223> OTHER INFORMATION: UNA monomer
<220> FEATURE:
<221> NAME/KEY: modified_base
<222> LOCATION: (137)..(137)
<223> OTHER INFORMATION: UNA monomer
<220> FEATURE:
<221> NAME/KEY: modified_base
<222> LOCATION: (139)..(139)
<223> OTHER INFORMATION: UNA monomer
<220> FEATURE:
<221> NAME/KEY: modified_base
<222> LOCATION: (141)..(141)
<223> OTHER INFORMATION: UNA monomer
<220> FEATURE:
<221> NAME/KEY: modified_base
<222> LOCATION: (147)..(148)
<223> OTHER INFORMATION: UNA monomer
<220> FEATURE:
<221> NAME/KEY: modified_base
<222> LOCATION: (154)..(156)
<223> OTHER INFORMATION: UNA monomer
<220> FEATURE:
<221> NAME/KEY: modified_base
<222> LOCATION: (159)..(159)
<223> OTHER INFORMATION: UNA monomer
<220> FEATURE:
<221> NAME/KEY: modified_base
<222> LOCATION: (169)..(171)
<223> OTHER INFORMATION: UNA monomer
<220> FEATURE:
<221> NAME/KEY: modified_base
<222> LOCATION: (174)..(174)
<223> OTHER INFORMATION: UNA monomer
<220> FEATURE:
<221> NAME/KEY: modified_base
<222> LOCATION: (184)..(185)
<223> OTHER INFORMATION: UNA monomer
<220> FEATURE:
<221> NAME/KEY: modified_base
<222> LOCATION: (189)..(190)
<223> OTHER INFORMATION: UNA monomer
<220> FEATURE:
<221> NAME/KEY: modified_base
<222> LOCATION: (192)..(192)
<223> OTHER INFORMATION: UNA monomer
<220> FEATURE:
<221> NAME/KEY: modified_base
<222> LOCATION: (194)..(194)
<223> OTHER INFORMATION: UNA monomer
<220> FEATURE:
<221> NAME/KEY: modified_base
<222> LOCATION: (198)..(199)
<223> OTHER INFORMATION: UNA monomer
<220> FEATURE:
<221> NAME/KEY: modified_base
<222> LOCATION: (207)..(207)
<223> OTHER INFORMATION: UNA monomer
<220> FEATURE:
<221> NAME/KEY: modified_base
<222> LOCATION: (225)..(225)
<223> OTHER INFORMATION: UNA monomer
<220> FEATURE:
<221> NAME/KEY: modified_base
<222> LOCATION: (228)..(229)
<223> OTHER INFORMATION: UNA monomer
<220> FEATURE:
<221> NAME/KEY: modified_base
<222> LOCATION: (231)..(231)
<223> OTHER INFORMATION: UNA monomer
<220> FEATURE:
<221> NAME/KEY: modified_base
```

```
<222> LOCATION: (234)..(234)
<223> OTHER INFORMATION: UNA monomer
<220> FEATURE:
<221> NAME/KEY: modified_base
<222> LOCATION: (238)..(238)
<223> OTHER INFORMATION: UNA monomer
<220> FEATURE:
<221> NAME/KEY: modified_base
<222> LOCATION: (241)..(241)
<223> OTHER INFORMATION: UNA monomer
<220> FEATURE:
<221> NAME/KEY: modified_base
<222> LOCATION: (243)..(243)
<223> OTHER INFORMATION: UNA monomer
<220> FEATURE:
<221> NAME/KEY: modified_base
<222> LOCATION: (248)..(249)
<223> OTHER INFORMATION: UNA monomer
<220> FEATURE:
<221> NAME/KEY: modified_base
<222> LOCATION: (252)..(252)
<223> OTHER INFORMATION: UNA monomer
<220> FEATURE:
<221> NAME/KEY: modified_base
<222> LOCATION: (254)..(254)
<223> OTHER INFORMATION: UNA monomer
<220> FEATURE:
<221> NAME/KEY: modified_base
<222> LOCATION: (262)..(262)
<223> OTHER INFORMATION: UNA monomer
<220> FEATURE:
<221> NAME/KEY: modified_base
<222> LOCATION: (264)..(264)
<223> OTHER INFORMATION: UNA monomer
<220> FEATURE:
<221> NAME/KEY: modified_base
<222> LOCATION: (267)..(268)
<223> OTHER INFORMATION: UNA monomer
<220> FEATURE:
<221> NAME/KEY: modified_base
<222> LOCATION: (271)..(273)
<223> OTHER INFORMATION: UNA monomer
<220> FEATURE:
<221> NAME/KEY: modified_base
<222> LOCATION: (277)..(277)
<223> OTHER INFORMATION: UNA monomer
<220> FEATURE:
<221> NAME/KEY: modified_base
<222> LOCATION: (279)..(280)
<223> OTHER INFORMATION: UNA monomer
<220> FEATURE:
<221> NAME/KEY: modified_base
<222> LOCATION: (282)..(284)
<223> OTHER INFORMATION: UNA monomer
<220> FEATURE:
<221> NAME/KEY: modified_base
<222> LOCATION: (287)..(288)
<223> OTHER INFORMATION: UNA monomer
<220> FEATURE:
<221> NAME/KEY: modified_base
<222> LOCATION: (297)..(297)
<223> OTHER INFORMATION: UNA monomer
<220> FEATURE:
<221> NAME/KEY: modified_base
<222> LOCATION: (306)..(306)
<223> OTHER INFORMATION: UNA monomer
<220> FEATURE:
<221> NAME/KEY: modified_base
<222> LOCATION: (309)..(309)
<223> OTHER INFORMATION: UNA monomer
<220> FEATURE:
<221> NAME/KEY: modified_base
<222> LOCATION: (315)..(316)
<223> OTHER INFORMATION: UNA monomer
<220> FEATURE:
<221> NAME/KEY: modified_base
<222> LOCATION: (320)..(320)
<223> OTHER INFORMATION: UNA monomer
<220> FEATURE:
```

```
<221> NAME/KEY: modified_base
<222> LOCATION: (323)..(324)
<223> OTHER INFORMATION: UNA monomer
<220> FEATURE:
<221> NAME/KEY: modified_base
<222> LOCATION: (326)..(326)
<223> OTHER INFORMATION: UNA monomer
<220> FEATURE:
<221> NAME/KEY: modified_base
<222> LOCATION: (335)..(338)
<223> OTHER INFORMATION: UNA monomer
<220> FEATURE:
<221> NAME/KEY: modified_base
<222> LOCATION: (342)..(342)
<223> OTHER INFORMATION: UNA monomer
<220> FEATURE:
<221> NAME/KEY: modified_base
<222> LOCATION: (344)..(345)
<223> OTHER INFORMATION: UNA monomer
<220> FEATURE:
<221> NAME/KEY: modified_base
<222> LOCATION: (348)..(348)
<223> OTHER INFORMATION: UNA monomer
<220> FEATURE:
<221> NAME/KEY: modified_base
<222> LOCATION: (351)..(351)
<223> OTHER INFORMATION: UNA monomer
<220> FEATURE:
<221> NAME/KEY: modified_base
<222> LOCATION: (354)..(354)
<223> OTHER INFORMATION: UNA monomer
<220> FEATURE:
<221> NAME/KEY: modified_base
<222> LOCATION: (357)..(357)
<223> OTHER INFORMATION: UNA monomer
<220> FEATURE:
<221> NAME/KEY: modified_base
<222> LOCATION: (360)..(360)
<223> OTHER INFORMATION: UNA monomer
<220> FEATURE:
<221> NAME/KEY: modified_base
<222> LOCATION: (362)..(362)
<223> OTHER INFORMATION: UNA monomer
<220> FEATURE:
<221> NAME/KEY: modified_base
<222> LOCATION: (365)..(365)
<223> OTHER INFORMATION: UNA monomer
<220> FEATURE:
<221> NAME/KEY: modified_base
<222> LOCATION: (370)..(371)
<223> OTHER INFORMATION: UNA monomer
<220> FEATURE:
<221> NAME/KEY: modified_base
<222> LOCATION: (376)..(376)
<223> OTHER INFORMATION: UNA monomer
<220> FEATURE:
<221> NAME/KEY: modified_base
<222> LOCATION: (378)..(378)
<223> OTHER INFORMATION: UNA monomer
<220> FEATURE:
<221> NAME/KEY: modified_base
<222> LOCATION: (380)..(381)
<223> OTHER INFORMATION: UNA monomer
<220> FEATURE:
<221> NAME/KEY: modified_base
<222> LOCATION: (384)..(384)
<223> OTHER INFORMATION: UNA monomer
<220> FEATURE:
<221> NAME/KEY: modified_base
<222> LOCATION: (386)..(387)
<223> OTHER INFORMATION: UNA monomer
<220> FEATURE:
<221> NAME/KEY: modified_base
<222> LOCATION: (394)..(398)
<223> OTHER INFORMATION: UNA monomer
<220> FEATURE:
<221> NAME/KEY: modified_base
<222> LOCATION: (402)..(402)
<223> OTHER INFORMATION: UNA monomer
```

```
<220> FEATURE:
<221> NAME/KEY: modified_base
<222> LOCATION: (406)..(406)
<223> OTHER INFORMATION: UNA monomer
<220> FEATURE:
<221> NAME/KEY: modified_base
<222> LOCATION: (408)..(410)
<223> OTHER INFORMATION: UNA monomer
<220> FEATURE:
<221> NAME/KEY: modified_base
<222> LOCATION: (417)..(420)
<223> OTHER INFORMATION: UNA monomer
<220> FEATURE:
<221> NAME/KEY: modified_base
<222> LOCATION: (423)..(423)
<223> OTHER INFORMATION: UNA monomer
<220> FEATURE:
<221> NAME/KEY: modified_base
<222> LOCATION: (427)..(427)
<223> OTHER INFORMATION: UNA monomer
<220> FEATURE:
<221> NAME/KEY: modified_base
<222> LOCATION: (440)..(441)
<223> OTHER INFORMATION: UNA monomer
<220> FEATURE:
<221> NAME/KEY: modified_base
<222> LOCATION: (446)..(447)
<223> OTHER INFORMATION: UNA monomer
<220> FEATURE:
<221> NAME/KEY: modified_base
<222> LOCATION: (457)..(457)
<223> OTHER INFORMATION: UNA monomer
<220> FEATURE:
<221> NAME/KEY: modified_base
<222> LOCATION: (463)..(463)
<223> OTHER INFORMATION: UNA monomer
<220> FEATURE:
<221> NAME/KEY: modified_base
<222> LOCATION: (470)..(470)
<223> OTHER INFORMATION: UNA monomer
<220> FEATURE:
<221> NAME/KEY: modified_base
<222> LOCATION: (473)..(474)
<223> OTHER INFORMATION: UNA monomer
<220> FEATURE:
<221> NAME/KEY: modified_base
<222> LOCATION: (477)..(480)
<223> OTHER INFORMATION: UNA monomer
<220> FEATURE:
<221> NAME/KEY: modified_base
<222> LOCATION: (487)..(488)
<223> OTHER INFORMATION: UNA monomer
<220> FEATURE:
<221> NAME/KEY: modified_base
<222> LOCATION: (495)..(495)
<223> OTHER INFORMATION: UNA monomer
<220> FEATURE:
<221> NAME/KEY: modified_base
<222> LOCATION: (497)..(498)
<223> OTHER INFORMATION: UNA monomer
<220> FEATURE:
<221> NAME/KEY: modified_base
<222> LOCATION: (503)..(503)
<223> OTHER INFORMATION: UNA monomer
<220> FEATURE:
<221> NAME/KEY: modified_base
<222> LOCATION: (505)..(505)
<223> OTHER INFORMATION: UNA monomer
<220> FEATURE:
<221> NAME/KEY: modified_base
<222> LOCATION: (507)..(507)
<223> OTHER INFORMATION: UNA monomer
<220> FEATURE:
<221> NAME/KEY: modified_base
<222> LOCATION: (511)..(511)
<223> OTHER INFORMATION: UNA monomer
<220> FEATURE:
<221> NAME/KEY: modified_base
<222> LOCATION: (514)..(514)
```

```
<223> OTHER INFORMATION: UNA monomer
<220> FEATURE:
<221> NAME/KEY: modified_base
<222> LOCATION: (517)..(517)
<223> OTHER INFORMATION: UNA monomer
<220> FEATURE:
<221> NAME/KEY: modified_base
<222> LOCATION: (520)..(520)
<223> OTHER INFORMATION: UNA monomer
<220> FEATURE:
<221> NAME/KEY: modified_base
<222> LOCATION: (524)..(525)
<223> OTHER INFORMATION: UNA monomer
<220> FEATURE:
<221> NAME/KEY: modified_base
<222> LOCATION: (531)..(531)
<223> OTHER INFORMATION: UNA monomer
<220> FEATURE:
<221> NAME/KEY: modified_base
<222> LOCATION: (535)..(536)
<223> OTHER INFORMATION: UNA monomer
<220> FEATURE:
<221> NAME/KEY: modified_base
<222> LOCATION: (541)..(542)
<223> OTHER INFORMATION: UNA monomer
<220> FEATURE:
<221> NAME/KEY: modified_base
<222> LOCATION: (546)..(546)
<223> OTHER INFORMATION: UNA monomer
<220> FEATURE:
<221> NAME/KEY: modified_base
<222> LOCATION: (549)..(549)
<223> OTHER INFORMATION: UNA monomer
<220> FEATURE:
<221> NAME/KEY: modified_base
<222> LOCATION: (553)..(556)
<223> OTHER INFORMATION: UNA monomer
<220> FEATURE:
<221> NAME/KEY: modified_base
<222> LOCATION: (564)..(564)
<223> OTHER INFORMATION: UNA monomer
<220> FEATURE:
<221> NAME/KEY: modified_base
<222> LOCATION: (567)..(567)
<223> OTHER INFORMATION: UNA monomer
<220> FEATURE:
<221> NAME/KEY: modified_base
<222> LOCATION: (574)..(574)
<223> OTHER INFORMATION: UNA monomer
<220> FEATURE:
<221> NAME/KEY: modified_base
<222> LOCATION: (576)..(576)
<223> OTHER INFORMATION: UNA monomer
<220> FEATURE:
<221> NAME/KEY: modified_base
<222> LOCATION: (580)..(580)
<223> OTHER INFORMATION: UNA monomer
<220> FEATURE:
<221> NAME/KEY: modified_base
<222> LOCATION: (585)..(585)
<223> OTHER INFORMATION: UNA monomer
<220> FEATURE:
<221> NAME/KEY: modified_base
<222> LOCATION: (588)..(588)
<223> OTHER INFORMATION: UNA monomer
<220> FEATURE:
<221> NAME/KEY: modified_base
<222> LOCATION: (590)..(591)
<223> OTHER INFORMATION: UNA monomer
<220> FEATURE:
<221> NAME/KEY: modified_base
<222> LOCATION: (599)..(599)
<223> OTHER INFORMATION: UNA monomer
<220> FEATURE:
<221> NAME/KEY: modified_base
<222> LOCATION: (602)..(602)
<223> OTHER INFORMATION: UNA monomer
<220> FEATURE:
<221> NAME/KEY: modified_base
```

```
<222> LOCATION: (610)..(611)
<223> OTHER INFORMATION: UNA monomer
<220> FEATURE:
<221> NAME/KEY: modified_base
<222> LOCATION: (622)..(622)
<223> OTHER INFORMATION: UNA monomer
<220> FEATURE:
<221> NAME/KEY: modified_base
<222> LOCATION: (627)..(627)
<223> OTHER INFORMATION: UNA monomer
<220> FEATURE:
<221> NAME/KEY: modified_base
<222> LOCATION: (629)..(630)
<223> OTHER INFORMATION: UNA monomer
<220> FEATURE:
<221> NAME/KEY: modified_base
<222> LOCATION: (632)..(634)
<223> OTHER INFORMATION: UNA monomer
<220> FEATURE:
<221> NAME/KEY: modified_base
<222> LOCATION: (636)..(636)
<223> OTHER INFORMATION: UNA monomer
<220> FEATURE:
<221> NAME/KEY: modified_base
<222> LOCATION: (638)..(639)
<223> OTHER INFORMATION: UNA monomer
<220> FEATURE:
<221> NAME/KEY: modified_base
<222> LOCATION: (642)..(642)
<223> OTHER INFORMATION: UNA monomer
<220> FEATURE:
<221> NAME/KEY: modified_base
<222> LOCATION: (645)..(645)
<223> OTHER INFORMATION: UNA monomer
<220> FEATURE:
<221> NAME/KEY: modified_base
<222> LOCATION: (647)..(648)
<223> OTHER INFORMATION: UNA monomer
<220> FEATURE:
<221> NAME/KEY: modified_base
<222> LOCATION: (650)..(650)
<223> OTHER INFORMATION: UNA monomer
<220> FEATURE:
<221> NAME/KEY: modified_base
<222> LOCATION: (652)..(652)
<223> OTHER INFORMATION: UNA monomer
<220> FEATURE:
<221> NAME/KEY: modified_base
<222> LOCATION: (657)..(657)
<223> OTHER INFORMATION: UNA monomer
<220> FEATURE:
<221> NAME/KEY: modified_base
<222> LOCATION: (660)..(660)
<223> OTHER INFORMATION: UNA monomer
<220> FEATURE:
<221> NAME/KEY: modified_base
<222> LOCATION: (663)..(663)
<223> OTHER INFORMATION: UNA monomer
<220> FEATURE:
<221> NAME/KEY: modified_base
<222> LOCATION: (666)..(666)
<223> OTHER INFORMATION: UNA monomer
<220> FEATURE:
<221> NAME/KEY: modified_base
<222> LOCATION: (669)..(669)
<223> OTHER INFORMATION: UNA monomer
<220> FEATURE:
<221> NAME/KEY: modified_base
<222> LOCATION: (672)..(672)
<223> OTHER INFORMATION: UNA monomer
<220> FEATURE:
<221> NAME/KEY: modified_base
<222> LOCATION: (675)..(675)
<223> OTHER INFORMATION: UNA monomer
<220> FEATURE:
<221> NAME/KEY: modified_base
<222> LOCATION: (679)..(679)
<223> OTHER INFORMATION: UNA monomer
<220> FEATURE:
```

-continued

```
<221> NAME/KEY: modified_base
<222> LOCATION: (683)..(683)
<223> OTHER INFORMATION: UNA monomer
<220> FEATURE:
<221> NAME/KEY: modified_base
<222> LOCATION: (693)..(693)
<223> OTHER INFORMATION: UNA monomer
<220> FEATURE:
<221> NAME/KEY: modified_base
<222> LOCATION: (700)..(700)
<223> OTHER INFORMATION: UNA monomer
<220> FEATURE:
<221> NAME/KEY: modified_base
<222> LOCATION: (702)..(702)
<223> OTHER INFORMATION: UNA monomer
<220> FEATURE:
<221> NAME/KEY: modified_base
<222> LOCATION: (706)..(706)
<223> OTHER INFORMATION: UNA monomer
<220> FEATURE:
<221> NAME/KEY: modified_base
<222> LOCATION: (708)..(708)
<223> OTHER INFORMATION: UNA monomer
<220> FEATURE:
<221> NAME/KEY: modified_base
<222> LOCATION: (711)..(711)
<223> OTHER INFORMATION: UNA monomer
<220> FEATURE:
<221> NAME/KEY: modified_base
<222> LOCATION: (713)..(714)
<223> OTHER INFORMATION: UNA monomer
<220> FEATURE:
<221> NAME/KEY: modified_base
<222> LOCATION: (716)..(716)
<223> OTHER INFORMATION: UNA monomer
<220> FEATURE:
<221> NAME/KEY: modified_base
<222> LOCATION: (720)..(721)
<223> OTHER INFORMATION: UNA monomer
<220> FEATURE:
<221> NAME/KEY: modified_base
<222> LOCATION: (723)..(723)
<223> OTHER INFORMATION: UNA monomer
<220> FEATURE:
<221> NAME/KEY: modified_base
<222> LOCATION: (730)..(731)
<223> OTHER INFORMATION: UNA monomer
<220> FEATURE:
<221> NAME/KEY: modified_base
<222> LOCATION: (738)..(738)
<223> OTHER INFORMATION: UNA monomer
<220> FEATURE:
<221> NAME/KEY: modified_base
<222> LOCATION: (742)..(742)
<223> OTHER INFORMATION: UNA monomer
<220> FEATURE:
<221> NAME/KEY: modified_base
<222> LOCATION: (746)..(746)
<223> OTHER INFORMATION: UNA monomer
<220> FEATURE:
<221> NAME/KEY: modified_base
<222> LOCATION: (748)..(749)
<223> OTHER INFORMATION: UNA monomer
<220> FEATURE:
<221> NAME/KEY: modified_base
<222> LOCATION: (761)..(763)
<223> OTHER INFORMATION: UNA monomer
<220> FEATURE:
<221> NAME/KEY: modified_base
<222> LOCATION: (768)..(770)
<223> OTHER INFORMATION: UNA monomer
<220> FEATURE:
<221> NAME/KEY: modified_base
<222> LOCATION: (772)..(772)
<223> OTHER INFORMATION: UNA monomer
<220> FEATURE:
<221> NAME/KEY: modified_base
<222> LOCATION: (775)..(775)
<223> OTHER INFORMATION: UNA monomer
```

-continued

```
<220> FEATURE:
<221> NAME/KEY: modified_base
<222> LOCATION: (777)..(777)
<223> OTHER INFORMATION: UNA monomer
<220> FEATURE:
<221> NAME/KEY: modified_base
<222> LOCATION: (780)..(780)
<223> OTHER INFORMATION: UNA monomer
<220> FEATURE:
<221> NAME/KEY: modified_base
<222> LOCATION: (782)..(783)
<223> OTHER INFORMATION: UNA monomer
<220> FEATURE:
<221> NAME/KEY: modified_base
<222> LOCATION: (796)..(796)
<223> OTHER INFORMATION: UNA monomer
<220> FEATURE:
<221> NAME/KEY: modified_base
<222> LOCATION: (812)..(812)
<223> OTHER INFORMATION: UNA monomer
<220> FEATURE:
<221> NAME/KEY: modified_base
<222> LOCATION: (816)..(816)
<223> OTHER INFORMATION: UNA monomer
<220> FEATURE:
<221> NAME/KEY: modified_base
<222> LOCATION: (819)..(821)
<223> OTHER INFORMATION: UNA monomer
<220> FEATURE:
<221> NAME/KEY: modified_base
<222> LOCATION: (824)..(825)
<223> OTHER INFORMATION: UNA monomer
<220> FEATURE:
<221> NAME/KEY: modified_base
<222> LOCATION: (831)..(831)
<223> OTHER INFORMATION: UNA monomer
<220> FEATURE:
<221> NAME/KEY: modified_base
<222> LOCATION: (834)..(834)
<223> OTHER INFORMATION: UNA monomer
<220> FEATURE:
<221> NAME/KEY: modified_base
<222> LOCATION: (840)..(840)
<223> OTHER INFORMATION: UNA monomer
<220> FEATURE:
<221> NAME/KEY: modified_base
<222> LOCATION: (842)..(842)
<223> OTHER INFORMATION: UNA monomer
<220> FEATURE:
<221> NAME/KEY: modified_base
<222> LOCATION: (846)..(847)
<223> OTHER INFORMATION: UNA monomer
<220> FEATURE:
<221> NAME/KEY: modified_base
<222> LOCATION: (851)..(851)
<223> OTHER INFORMATION: UNA monomer
<220> FEATURE:
<221> NAME/KEY: modified_base
<222> LOCATION: (860)..(860)
<223> OTHER INFORMATION: UNA monomer
<220> FEATURE:
<221> NAME/KEY: modified_base
<222> LOCATION: (863)..(865)
<223> OTHER INFORMATION: UNA monomer
<220> FEATURE:
<221> NAME/KEY: modified_base
<222> LOCATION: (873)..(873)
<223> OTHER INFORMATION: UNA monomer
<220> FEATURE:
<221> NAME/KEY: modified_base
<222> LOCATION: (875)..(879)
<223> OTHER INFORMATION: UNA monomer
<220> FEATURE:
<221> NAME/KEY: modified_base
<222> LOCATION: (887)..(888)
<223> OTHER INFORMATION: UNA monomer
<220> FEATURE:
<221> NAME/KEY: modified_base
<222> LOCATION: (893)..(893)
```

```
<223> OTHER INFORMATION: UNA monomer
<220> FEATURE:
<221> NAME/KEY: modified_base
<222> LOCATION: (895)..(895)
<223> OTHER INFORMATION: UNA monomer
<220> FEATURE:
<221> NAME/KEY: modified_base
<222> LOCATION: (901)..(905)
<223> OTHER INFORMATION: UNA monomer
<220> FEATURE:
<221> NAME/KEY: modified_base
<222> LOCATION: (911)..(911)
<223> OTHER INFORMATION: UNA monomer
<220> FEATURE:
<221> NAME/KEY: modified_base
<222> LOCATION: (915)..(915)
<223> OTHER INFORMATION: UNA monomer
<220> FEATURE:
<221> NAME/KEY: modified_base
<222> LOCATION: (917)..(917)
<223> OTHER INFORMATION: UNA monomer
<220> FEATURE:
<221> NAME/KEY: modified_base
<222> LOCATION: (929)..(930)
<223> OTHER INFORMATION: UNA monomer
<220> FEATURE:
<221> NAME/KEY: modified_base
<222> LOCATION: (937)..(939)
<223> OTHER INFORMATION: UNA monomer
<220> FEATURE:
<221> NAME/KEY: modified_base
<222> LOCATION: (947)..(948)
<223> OTHER INFORMATION: UNA monomer
<220> FEATURE:
<221> NAME/KEY: modified_base
<222> LOCATION: (950)..(951)
<223> OTHER INFORMATION: UNA monomer
<220> FEATURE:
<221> NAME/KEY: modified_base
<222> LOCATION: (963)..(963)
<223> OTHER INFORMATION: UNA monomer
<220> FEATURE:
<221> NAME/KEY: modified_base
<222> LOCATION: (971)..(971)
<223> OTHER INFORMATION: UNA monomer
<220> FEATURE:
<221> NAME/KEY: modified_base
<222> LOCATION: (979)..(979)
<223> OTHER INFORMATION: UNA monomer
<220> FEATURE:
<221> NAME/KEY: modified_base
<222> LOCATION: (981)..(981)
<223> OTHER INFORMATION: UNA monomer
<220> FEATURE:
<221> NAME/KEY: modified_base
<222> LOCATION: (984)..(984)
<223> OTHER INFORMATION: UNA monomer
<220> FEATURE:
<221> NAME/KEY: modified_base
<222> LOCATION: (998)..(999)
<223> OTHER INFORMATION: UNA monomer
<220> FEATURE:
<221> NAME/KEY: modified_base
<222> LOCATION: (1004)..(1005)
<223> OTHER INFORMATION: UNA monomer
<220> FEATURE:
<221> NAME/KEY: modified_base
<222> LOCATION: (1007)..(1008)
<223> OTHER INFORMATION: UNA monomer
<220> FEATURE:
<221> NAME/KEY: modified_base
<222> LOCATION: (1014)..(1014)
<223> OTHER INFORMATION: UNA monomer
<220> FEATURE:
<221> NAME/KEY: modified_base
<222> LOCATION: (1017)..(1017)
<223> OTHER INFORMATION: UNA monomer
<220> FEATURE:
<221> NAME/KEY: modified_base
```

-continued

```
<222> LOCATION: (1021)..(1021)
<223> OTHER INFORMATION: UNA monomer
<220> FEATURE:
<221> NAME/KEY: modified_base
<222> LOCATION: (1030)..(1032)
<223> OTHER INFORMATION: UNA monomer
<220> FEATURE:
<221> NAME/KEY: modified_base
<222> LOCATION: (1036)..(1036)
<223> OTHER INFORMATION: UNA monomer
<220> FEATURE:
<221> NAME/KEY: modified_base
<222> LOCATION: (1038)..(1038)
<223> OTHER INFORMATION: UNA monomer
<220> FEATURE:
<221> NAME/KEY: modified_base
<222> LOCATION: (1041)..(1041)
<223> OTHER INFORMATION: UNA monomer
<220> FEATURE:
<221> NAME/KEY: modified_base
<222> LOCATION: (1043)..(1043)
<223> OTHER INFORMATION: UNA monomer
<220> FEATURE:
<221> NAME/KEY: modified_base
<222> LOCATION: (1047)..(1047)
<223> OTHER INFORMATION: UNA monomer
<220> FEATURE:
<221> NAME/KEY: modified_base
<222> LOCATION: (1049)..(1049)
<223> OTHER INFORMATION: UNA monomer
<220> FEATURE:
<221> NAME/KEY: modified_base
<222> LOCATION: (1055)..(1056)
<223> OTHER INFORMATION: UNA monomer
<220> FEATURE:
<221> NAME/KEY: modified_base
<222> LOCATION: (1061)..(1061)
<223> OTHER INFORMATION: UNA monomer
<220> FEATURE:
<221> NAME/KEY: modified_base
<222> LOCATION: (1068)..(1070)
<223> OTHER INFORMATION: UNA monomer
<220> FEATURE:
<221> NAME/KEY: modified_base
<222> LOCATION: (1073)..(1073)
<223> OTHER INFORMATION: UNA monomer
<220> FEATURE:
<221> NAME/KEY: modified_base
<222> LOCATION: (1080)..(1080)
<223> OTHER INFORMATION: UNA monomer
<220> FEATURE:
<221> NAME/KEY: modified_base
<222> LOCATION: (1100)..(1101)
<223> OTHER INFORMATION: UNA monomer
<220> FEATURE:
<221> NAME/KEY: modified_base
<222> LOCATION: (1108)..(1108)
<223> OTHER INFORMATION: UNA monomer
<220> FEATURE:
<221> NAME/KEY: modified_base
<222> LOCATION: (1111)..(1111)
<223> OTHER INFORMATION: UNA monomer
<220> FEATURE:
<221> NAME/KEY: modified_base
<222> LOCATION: (1113)..(1113)
<223> OTHER INFORMATION: UNA monomer
<220> FEATURE:
<221> NAME/KEY: modified_base
<222> LOCATION: (1116)..(1117)
<223> OTHER INFORMATION: UNA monomer
<220> FEATURE:
<221> NAME/KEY: modified_base
<222> LOCATION: (1120)..(1122)
<223> OTHER INFORMATION: UNA monomer
<220> FEATURE:
<221> NAME/KEY: modified_base
<222> LOCATION: (1125)..(1125)
<223> OTHER INFORMATION: UNA monomer
<220> FEATURE:
```

-continued

```
<221> NAME/KEY: modified_base
<222> LOCATION: (1133)..(1133)
<223> OTHER INFORMATION: UNA monomer
<220> FEATURE:
<221> NAME/KEY: modified_base
<222> LOCATION: (1141)..(1142)
<223> OTHER INFORMATION: UNA monomer
<220> FEATURE:
<221> NAME/KEY: modified_base
<222> LOCATION: (1146)..(1147)
<223> OTHER INFORMATION: UNA monomer
<220> FEATURE:
<221> NAME/KEY: modified_base
<222> LOCATION: (1158)..(1158)
<223> OTHER INFORMATION: UNA monomer
<220> FEATURE:
<221> NAME/KEY: modified_base
<222> LOCATION: (1163)..(1163)
<223> OTHER INFORMATION: UNA monomer
<220> FEATURE:
<221> NAME/KEY: modified_base
<222> LOCATION: (1166)..(1167)
<223> OTHER INFORMATION: UNA monomer
<220> FEATURE:
<221> NAME/KEY: modified_base
<222> LOCATION: (1171)..(1171)
<223> OTHER INFORMATION: UNA monomer
<220> FEATURE:
<221> NAME/KEY: modified_base
<222> LOCATION: (1173)..(1173)
<223> OTHER INFORMATION: UNA monomer
<220> FEATURE:
<221> NAME/KEY: modified_base
<222> LOCATION: (1176)..(1176)
<223> OTHER INFORMATION: UNA monomer
<220> FEATURE:
<221> NAME/KEY: modified_base
<222> LOCATION: (1190)..(1191)
<223> OTHER INFORMATION: UNA monomer
<220> FEATURE:
<221> NAME/KEY: modified_base
<222> LOCATION: (1194)..(1195)
<223> OTHER INFORMATION: UNA monomer
<220> FEATURE:
<221> NAME/KEY: modified_base
<222> LOCATION: (1199)..(1202)
<223> OTHER INFORMATION: UNA monomer
<220> FEATURE:
<221> NAME/KEY: modified_base
<222> LOCATION: (1209)..(1209)
<223> OTHER INFORMATION: UNA monomer
<220> FEATURE:
<221> NAME/KEY: modified_base
<222> LOCATION: (1211)..(1211)
<223> OTHER INFORMATION: UNA monomer
<220> FEATURE:
<221> NAME/KEY: modified_base
<222> LOCATION: (1213)..(1216)
<223> OTHER INFORMATION: UNA monomer
<220> FEATURE:
<221> NAME/KEY: modified_base
<222> LOCATION: (1218)..(1218)
<223> OTHER INFORMATION: UNA monomer
<220> FEATURE:
<221> NAME/KEY: modified_base
<222> LOCATION: (1226)..(1226)
<223> OTHER INFORMATION: UNA monomer
<220> FEATURE:
<221> NAME/KEY: modified_base
<222> LOCATION: (1230)..(1230)
<223> OTHER INFORMATION: UNA monomer
<220> FEATURE:
<221> NAME/KEY: modified_base
<222> LOCATION: (1236)..(1236)
<223> OTHER INFORMATION: UNA monomer
<220> FEATURE:
<221> NAME/KEY: modified_base
<222> LOCATION: (1239)..(1239)
<223> OTHER INFORMATION: UNA monomer
```

```
-continued

<220> FEATURE:
<221> NAME/KEY: modified_base
<222> LOCATION: (1247)..(1247)
<223> OTHER INFORMATION: UNA monomer
<220> FEATURE:
<221> NAME/KEY: modified_base
<222> LOCATION: (1254)..(1254)
<223> OTHER INFORMATION: UNA monomer
<220> FEATURE:
<221> NAME/KEY: modified_base
<222> LOCATION: (1256)..(1256)
<223> OTHER INFORMATION: UNA monomer
<220> FEATURE:
<221> NAME/KEY: modified_base
<222> LOCATION: (1260)..(1260)
<223> OTHER INFORMATION: UNA monomer
<220> FEATURE:
<221> NAME/KEY: modified_base
<222> LOCATION: (1269)..(1269)
<223> OTHER INFORMATION: UNA monomer
<220> FEATURE:
<221> NAME/KEY: modified_base
<222> LOCATION: (1272)..(1274)
<223> OTHER INFORMATION: UNA monomer
<220> FEATURE:
<221> NAME/KEY: modified_base
<222> LOCATION: (1277)..(1278)
<223> OTHER INFORMATION: UNA monomer
<220> FEATURE:
<221> NAME/KEY: modified_base
<222> LOCATION: (1285)..(1285)
<223> OTHER INFORMATION: UNA monomer
<220> FEATURE:
<221> NAME/KEY: modified_base
<222> LOCATION: (1287)..(1290)
<223> OTHER INFORMATION: UNA monomer
<220> FEATURE:
<221> NAME/KEY: modified_base
<222> LOCATION: (1293)..(1295)
<223> OTHER INFORMATION: UNA monomer
<220> FEATURE:
<221> NAME/KEY: modified_base
<222> LOCATION: (1300)..(1302)
<223> OTHER INFORMATION: UNA monomer
<220> FEATURE:
<221> NAME/KEY: modified_base
<222> LOCATION: (1310)..(1310)
<223> OTHER INFORMATION: UNA monomer
<220> FEATURE:
<221> NAME/KEY: modified_base
<222> LOCATION: (1315)..(1316)
<223> OTHER INFORMATION: UNA monomer
<220> FEATURE:
<221> NAME/KEY: modified_base
<222> LOCATION: (1318)..(1318)
<223> OTHER INFORMATION: UNA monomer
<220> FEATURE:
<221> NAME/KEY: modified_base
<222> LOCATION: (1322)..(1322)
<223> OTHER INFORMATION: UNA monomer
<220> FEATURE:
<221> NAME/KEY: modified_base
<222> LOCATION: (1330)..(1330)
<223> OTHER INFORMATION: UNA monomer
<220> FEATURE:
<221> NAME/KEY: modified_base
<222> LOCATION: (1332)..(1332)
<223> OTHER INFORMATION: UNA monomer
<220> FEATURE:
<221> NAME/KEY: modified_base
<222> LOCATION: (1334)..(1334)
<223> OTHER INFORMATION: UNA monomer
<220> FEATURE:
<221> NAME/KEY: modified_base
<222> LOCATION: (1337)..(1338)
<223> OTHER INFORMATION: UNA monomer
<220> FEATURE:
<221> NAME/KEY: modified_base
<222> LOCATION: (1341)..(1341)
```

```
<223> OTHER INFORMATION: UNA monomer
<220> FEATURE:
<221> NAME/KEY: modified_base
<222> LOCATION: (1343)..(1343)
<223> OTHER INFORMATION: UNA monomer
<220> FEATURE:
<221> NAME/KEY: modified_base
<222> LOCATION: (1350)..(1350)
<223> OTHER INFORMATION: UNA monomer
<220> FEATURE:
<221> NAME/KEY: modified_base
<222> LOCATION: (1356)..(1357)
<223> OTHER INFORMATION: UNA monomer
<220> FEATURE:
<221> NAME/KEY: modified_base
<222> LOCATION: (1359)..(1362)
<223> OTHER INFORMATION: UNA monomer
<220> FEATURE:
<221> NAME/KEY: modified_base
<222> LOCATION: (1364)..(1364)
<223> OTHER INFORMATION: UNA monomer
<220> FEATURE:
<221> NAME/KEY: modified_base
<222> LOCATION: (1367)..(1367)
<223> OTHER INFORMATION: UNA monomer
<220> FEATURE:
<221> NAME/KEY: modified_base
<222> LOCATION: (1377)..(1377)
<223> OTHER INFORMATION: UNA monomer
<220> FEATURE:
<221> NAME/KEY: modified_base
<222> LOCATION: (1381)..(1381)
<223> OTHER INFORMATION: UNA monomer
<220> FEATURE:
<221> NAME/KEY: modified_base
<222> LOCATION: (1385)..(1385)
<223> OTHER INFORMATION: UNA monomer
<220> FEATURE:
<221> NAME/KEY: modified_base
<222> LOCATION: (1388)..(1388)
<223> OTHER INFORMATION: UNA monomer
<220> FEATURE:
<221> NAME/KEY: modified_base
<222> LOCATION: (1395)..(1395)
<223> OTHER INFORMATION: UNA monomer
<220> FEATURE:
<221> NAME/KEY: modified_base
<222> LOCATION: (1398)..(1398)
<223> OTHER INFORMATION: UNA monomer
<220> FEATURE:
<221> NAME/KEY: modified_base
<222> LOCATION: (1401)..(1401)
<223> OTHER INFORMATION: UNA monomer
<220> FEATURE:
<221> NAME/KEY: modified_base
<222> LOCATION: (1403)..(1404)
<223> OTHER INFORMATION: UNA monomer
<220> FEATURE:
<221> NAME/KEY: modified_base
<222> LOCATION: (1411)..(1413)
<223> OTHER INFORMATION: UNA monomer
<220> FEATURE:
<221> NAME/KEY: modified_base
<222> LOCATION: (1416)..(1416)
<223> OTHER INFORMATION: UNA monomer
<220> FEATURE:
<221> NAME/KEY: modified_base
<222> LOCATION: (1425)..(1426)
<223> OTHER INFORMATION: UNA monomer
<220> FEATURE:
<221> NAME/KEY: modified_base
<222> LOCATION: (1433)..(1435)
<223> OTHER INFORMATION: UNA monomer
<220> FEATURE:
<221> NAME/KEY: modified_base
<222> LOCATION: (1439)..(1439)
<223> OTHER INFORMATION: UNA monomer
<220> FEATURE:
<221> NAME/KEY: modified_base
```

```
<222> LOCATION: (1451)..(1452)
<223> OTHER INFORMATION: UNA monomer
<220> FEATURE:
<221> NAME/KEY: modified_base
<222> LOCATION: (1454)..(1456)
<223> OTHER INFORMATION: UNA monomer
<220> FEATURE:
<221> NAME/KEY: modified_base
<222> LOCATION: (1459)..(1459)
<223> OTHER INFORMATION: UNA monomer
<220> FEATURE:
<221> NAME/KEY: modified_base
<222> LOCATION: (1470)..(1470)
<223> OTHER INFORMATION: UNA monomer
<220> FEATURE:
<221> NAME/KEY: modified_base
<222> LOCATION: (1472)..(1473)
<223> OTHER INFORMATION: UNA monomer
<220> FEATURE:
<221> NAME/KEY: modified_base
<222> LOCATION: (1477)..(1478)
<223> OTHER INFORMATION: UNA monomer
<220> FEATURE:
<221> NAME/KEY: modified_base
<222> LOCATION: (1483)..(1483)
<223> OTHER INFORMATION: UNA monomer
<220> FEATURE:
<221> NAME/KEY: modified_base
<222> LOCATION: (1485)..(1485)
<223> OTHER INFORMATION: UNA monomer
<220> FEATURE:
<221> NAME/KEY: modified_base
<222> LOCATION: (1491)..(1491)
<223> OTHER INFORMATION: UNA monomer
<220> FEATURE:
<221> NAME/KEY: modified_base
<222> LOCATION: (1504)..(1504)
<223> OTHER INFORMATION: UNA monomer
<220> FEATURE:
<221> NAME/KEY: modified_base
<222> LOCATION: (1506)..(1506)
<223> OTHER INFORMATION: UNA monomer
<220> FEATURE:
<221> NAME/KEY: modified_base
<222> LOCATION: (1509)..(1510)
<223> OTHER INFORMATION: UNA monomer
<220> FEATURE:
<221> NAME/KEY: modified_base
<222> LOCATION: (1512)..(1512)
<223> OTHER INFORMATION: UNA monomer
<220> FEATURE:
<221> NAME/KEY: modified_base
<222> LOCATION: (1514)..(1514)
<223> OTHER INFORMATION: UNA monomer
<220> FEATURE:
<221> NAME/KEY: modified_base
<222> LOCATION: (1516)..(1516)
<223> OTHER INFORMATION: UNA monomer
<220> FEATURE:
<221> NAME/KEY: modified_base
<222> LOCATION: (1526)..(1526)
<223> OTHER INFORMATION: UNA monomer
<220> FEATURE:
<221> NAME/KEY: modified_base
<222> LOCATION: (1534)..(1534)
<223> OTHER INFORMATION: UNA monomer
<220> FEATURE:
<221> NAME/KEY: modified_base
<222> LOCATION: (1539)..(1539)
<223> OTHER INFORMATION: UNA monomer
<220> FEATURE:
<221> NAME/KEY: modified_base
<222> LOCATION: (1544)..(1544)
<223> OTHER INFORMATION: UNA monomer
<220> FEATURE:
<221> NAME/KEY: modified_base
<222> LOCATION: (1548)..(1548)
<223> OTHER INFORMATION: UNA monomer
<220> FEATURE:
```

-continued

```
<221> NAME/KEY: modified_base
<222> LOCATION: (1554)..(1555)
<223> OTHER INFORMATION: UNA monomer
<220> FEATURE:
<221> NAME/KEY: modified_base
<222> LOCATION: (1557)..(1559)
<223> OTHER INFORMATION: UNA monomer
<220> FEATURE:
<221> NAME/KEY: modified_base
<222> LOCATION: (1568)..(1568)
<223> OTHER INFORMATION: UNA monomer
<220> FEATURE:
<221> NAME/KEY: modified_base
<222> LOCATION: (1572)..(1572)
<223> OTHER INFORMATION: UNA monomer
<220> FEATURE:
<221> NAME/KEY: modified_base
<222> LOCATION: (1574)..(1575)
<223> OTHER INFORMATION: UNA monomer
<220> FEATURE:
<221> NAME/KEY: modified_base
<222> LOCATION: (1578)..(1578)
<223> OTHER INFORMATION: UNA monomer
<220> FEATURE:
<221> NAME/KEY: modified_base
<222> LOCATION: (1582)..(1582)
<223> OTHER INFORMATION: UNA monomer
<220> FEATURE:
<221> NAME/KEY: modified_base
<222> LOCATION: (1588)..(1588)
<223> OTHER INFORMATION: UNA monomer
<220> FEATURE:
<221> NAME/KEY: modified_base
<222> LOCATION: (1596)..(1596)
<223> OTHER INFORMATION: UNA monomer
<220> FEATURE:
<221> NAME/KEY: modified_base
<222> LOCATION: (1598)..(1599)
<223> OTHER INFORMATION: UNA monomer
<220> FEATURE:
<221> NAME/KEY: modified_base
<222> LOCATION: (1604)..(1604)
<223> OTHER INFORMATION: UNA monomer
<220> FEATURE:
<221> NAME/KEY: modified_base
<222> LOCATION: (1608)..(1608)
<223> OTHER INFORMATION: UNA monomer
<220> FEATURE:
<221> NAME/KEY: modified_base
<222> LOCATION: (1612)..(1612)
<223> OTHER INFORMATION: UNA monomer
<220> FEATURE:
<221> NAME/KEY: modified_base
<222> LOCATION: (1616)..(1616)
<223> OTHER INFORMATION: UNA monomer
<220> FEATURE:
<221> NAME/KEY: modified_base
<222> LOCATION: (1618)..(1619)
<223> OTHER INFORMATION: UNA monomer
<220> FEATURE:
<221> NAME/KEY: modified_base
<222> LOCATION: (1623)..(1623)
<223> OTHER INFORMATION: UNA monomer
<220> FEATURE:
<221> NAME/KEY: modified_base
<222> LOCATION: (1626)..(1626)
<223> OTHER INFORMATION: UNA monomer
<220> FEATURE:
<221> NAME/KEY: modified_base
<222> LOCATION: (1629)..(1629)
<223> OTHER INFORMATION: UNA monomer
<220> FEATURE:
<221> NAME/KEY: modified_base
<222> LOCATION: (1635)..(1637)
<223> OTHER INFORMATION: UNA monomer
<220> FEATURE:
<221> NAME/KEY: modified_base
<222> LOCATION: (1647)..(1649)
<223> OTHER INFORMATION: UNA monomer
```

-continued

```
<220> FEATURE:
<221> NAME/KEY: modified_base
<222> LOCATION: (1651)..(1651)
<223> OTHER INFORMATION: UNA monomer
<220> FEATURE:
<221> NAME/KEY: modified_base
<222> LOCATION: (1653)..(1653)
<223> OTHER INFORMATION: UNA monomer
<220> FEATURE:
<221> NAME/KEY: modified_base
<222> LOCATION: (1655)..(1655)
<223> OTHER INFORMATION: UNA monomer
<220> FEATURE:
<221> NAME/KEY: modified_base
<222> LOCATION: (1658)..(1658)
<223> OTHER INFORMATION: UNA monomer
<220> FEATURE:
<221> NAME/KEY: modified_base
<222> LOCATION: (1662)..(1662)
<223> OTHER INFORMATION: UNA monomer
<220> FEATURE:
<221> NAME/KEY: modified_base
<222> LOCATION: (1667)..(1667)
<223> OTHER INFORMATION: UNA monomer
<220> FEATURE:
<221> NAME/KEY: modified_base
<222> LOCATION: (1669)..(1670)
<223> OTHER INFORMATION: UNA monomer
<220> FEATURE:
<221> NAME/KEY: modified_base
<222> LOCATION: (1680)..(1680)
<223> OTHER INFORMATION: UNA monomer
<220> FEATURE:
<221> NAME/KEY: modified_base
<222> LOCATION: (1686)..(1686)
<223> OTHER INFORMATION: UNA monomer
<220> FEATURE:
<221> NAME/KEY: modified_base
<222> LOCATION: (1688)..(1688)
<223> OTHER INFORMATION: UNA monomer
<220> FEATURE:
<221> NAME/KEY: modified_base
<222> LOCATION: (1695)..(1695)
<223> OTHER INFORMATION: UNA monomer
<220> FEATURE:
<221> NAME/KEY: modified_base
<222> LOCATION: (1697)..(1697)
<223> OTHER INFORMATION: UNA monomer
<220> FEATURE:
<221> NAME/KEY: modified_base
<222> LOCATION: (1699)..(1701)
<223> OTHER INFORMATION: UNA monomer
<220> FEATURE:
<221> NAME/KEY: modified_base
<222> LOCATION: (1703)..(1704)
<223> OTHER INFORMATION: UNA monomer
<220> FEATURE:
<221> NAME/KEY: modified_base
<222> LOCATION: (1707)..(1707)
<223> OTHER INFORMATION: UNA monomer
<220> FEATURE:
<221> NAME/KEY: modified_base
<222> LOCATION: (1712)..(1712)
<223> OTHER INFORMATION: UNA monomer
<220> FEATURE:
<221> NAME/KEY: modified_base
<222> LOCATION: (1718)..(1719)
<223> OTHER INFORMATION: UNA monomer
<220> FEATURE:
<221> NAME/KEY: modified_base
<222> LOCATION: (1722)..(1723)
<223> OTHER INFORMATION: UNA monomer
<220> FEATURE:
<221> NAME/KEY: modified_base
<222> LOCATION: (1726)..(1727)
<223> OTHER INFORMATION: UNA monomer
<220> FEATURE:
<221> NAME/KEY: modified_base
<222> LOCATION: (1730)..(1730)
```

```
<223> OTHER INFORMATION: UNA monomer
<220> FEATURE:
<221> NAME/KEY: modified_base
<222> LOCATION: (1742)..(1742)
<223> OTHER INFORMATION: UNA monomer
<220> FEATURE:
<221> NAME/KEY: modified_base
<222> LOCATION: (1746)..(1746)
<223> OTHER INFORMATION: UNA monomer
<220> FEATURE:
<221> NAME/KEY: modified_base
<222> LOCATION: (1750)..(1750)
<223> OTHER INFORMATION: UNA monomer
<220> FEATURE:
<221> NAME/KEY: modified_base
<222> LOCATION: (1752)..(1752)
<223> OTHER INFORMATION: UNA monomer
<220> FEATURE:
<221> NAME/KEY: modified_base
<222> LOCATION: (1755)..(1755)
<223> OTHER INFORMATION: UNA monomer
<220> FEATURE:
<221> NAME/KEY: modified_base
<222> LOCATION: (1758)..(1758)
<223> OTHER INFORMATION: UNA monomer
<220> FEATURE:
<221> NAME/KEY: modified_base
<222> LOCATION: (1761)..(1761)
<223> OTHER INFORMATION: UNA monomer
<220> FEATURE:
<221> NAME/KEY: modified_base
<222> LOCATION: (1774)..(1775)
<223> OTHER INFORMATION: UNA monomer
<220> FEATURE:
<221> NAME/KEY: modified_base
<222> LOCATION: (1778)..(1780)
<223> OTHER INFORMATION: UNA monomer
<220> FEATURE:
<221> NAME/KEY: modified_base
<222> LOCATION: (1786)..(1786)
<223> OTHER INFORMATION: UNA monomer
<220> FEATURE:
<221> NAME/KEY: modified_base
<222> LOCATION: (1788)..(1788)
<223> OTHER INFORMATION: UNA monomer
<220> FEATURE:
<221> NAME/KEY: modified_base
<222> LOCATION: (1800)..(1800)
<223> OTHER INFORMATION: UNA monomer
<220> FEATURE:
<221> NAME/KEY: modified_base
<222> LOCATION: (1802)..(1803)
<223> OTHER INFORMATION: UNA monomer
<220> FEATURE:
<221> NAME/KEY: modified_base
<222> LOCATION: (1807)..(1807)
<223> OTHER INFORMATION: UNA monomer
<220> FEATURE:
<221> NAME/KEY: modified_base
<222> LOCATION: (1810)..(1812)
<223> OTHER INFORMATION: UNA monomer
<220> FEATURE:
<221> NAME/KEY: modified_base
<222> LOCATION: (1814)..(1815)
<223> OTHER INFORMATION: UNA monomer
<220> FEATURE:
<221> NAME/KEY: modified_base
<222> LOCATION: (1822)..(1822)
<223> OTHER INFORMATION: UNA monomer
<220> FEATURE:
<221> NAME/KEY: modified_base
<222> LOCATION: (1824)..(1826)
<223> OTHER INFORMATION: UNA monomer
<220> FEATURE:
<221> NAME/KEY: modified_base
<222> LOCATION: (1833)..(1835)
<223> OTHER INFORMATION: UNA monomer
<220> FEATURE:
<221> NAME/KEY: modified_base
```

```
<222> LOCATION: (1838)..(1838)
<223> OTHER INFORMATION: UNA monomer
<220> FEATURE:
<221> NAME/KEY: modified_base
<222> LOCATION: (1845)..(1845)
<223> OTHER INFORMATION: UNA monomer
<220> FEATURE:
<221> NAME/KEY: modified_base
<222> LOCATION: (1847)..(1848)
<223> OTHER INFORMATION: UNA monomer
<220> FEATURE:
<221> NAME/KEY: modified_base
<222> LOCATION: (1854)..(1854)
<223> OTHER INFORMATION: UNA monomer
<220> FEATURE:
<221> NAME/KEY: modified_base
<222> LOCATION: (1859)..(1859)
<223> OTHER INFORMATION: UNA monomer
<220> FEATURE:
<221> NAME/KEY: modified_base
<222> LOCATION: (1861)..(1863)
<223> OTHER INFORMATION: UNA monomer
<220> FEATURE:
<221> NAME/KEY: modified_base
<222> LOCATION: (1865)..(1865)
<223> OTHER INFORMATION: UNA monomer
<220> FEATURE:
<221> NAME/KEY: modified_base
<222> LOCATION: (1869)..(1869)
<223> OTHER INFORMATION: UNA monomer
<220> FEATURE:
<221> NAME/KEY: modified_base
<222> LOCATION: (1871)..(1872)
<223> OTHER INFORMATION: UNA monomer
<220> FEATURE:
<221> NAME/KEY: modified_base
<222> LOCATION: (1878)..(1878)
<223> OTHER INFORMATION: UNA monomer
<220> FEATURE:
<221> NAME/KEY: modified_base
<222> LOCATION: (1881)..(1881)
<223> OTHER INFORMATION: UNA monomer
<220> FEATURE:
<221> NAME/KEY: modified_base
<222> LOCATION: (1884)..(1884)
<223> OTHER INFORMATION: UNA monomer
<220> FEATURE:
<221> NAME/KEY: modified_base
<222> LOCATION: (1888)..(1888)
<223> OTHER INFORMATION: UNA monomer
<220> FEATURE:
<221> NAME/KEY: modified_base
<222> LOCATION: (1890)..(1890)
<223> OTHER INFORMATION: UNA monomer
<220> FEATURE:
<221> NAME/KEY: modified_base
<222> LOCATION: (1893)..(1893)
<223> OTHER INFORMATION: UNA monomer
<220> FEATURE:
<221> NAME/KEY: modified_base
<222> LOCATION: (1895)..(1896)
<223> OTHER INFORMATION: UNA monomer
<220> FEATURE:
<221> NAME/KEY: modified_base
<222> LOCATION: (1898)..(1898)
<223> OTHER INFORMATION: UNA monomer
<220> FEATURE:
<221> NAME/KEY: modified_base
<222> LOCATION: (1902)..(1902)
<223> OTHER INFORMATION: UNA monomer
<220> FEATURE:
<221> NAME/KEY: modified_base
<222> LOCATION: (1906)..(1906)
<223> OTHER INFORMATION: UNA monomer
<220> FEATURE:
<221> NAME/KEY: modified_base
<222> LOCATION: (1912)..(1912)
<223> OTHER INFORMATION: UNA monomer
<220> FEATURE:
```

```
<221> NAME/KEY: modified_base
<222> LOCATION: (1914)..(1914)
<223> OTHER INFORMATION: UNA monomer
<220> FEATURE:
<221> NAME/KEY: modified_base
<222> LOCATION: (1917)..(1917)
<223> OTHER INFORMATION: UNA monomer
<220> FEATURE:
<221> NAME/KEY: modified_base
<222> LOCATION: (1920)..(1920)
<223> OTHER INFORMATION: UNA monomer
<220> FEATURE:
<221> NAME/KEY: modified_base
<222> LOCATION: (1922)..(1923)
<223> OTHER INFORMATION: UNA monomer
<220> FEATURE:
<221> NAME/KEY: modified_base
<222> LOCATION: (1929)..(1929)
<223> OTHER INFORMATION: UNA monomer
<220> FEATURE:
<221> NAME/KEY: modified_base
<222> LOCATION: (1932)..(1932)
<223> OTHER INFORMATION: UNA monomer
<220> FEATURE:
<221> NAME/KEY: modified_base
<222> LOCATION: (1937)..(1938)
<223> OTHER INFORMATION: UNA monomer
<220> FEATURE:
<221> NAME/KEY: modified_base
<222> LOCATION: (1940)..(1942)
<223> OTHER INFORMATION: UNA monomer
<220> FEATURE:
<221> NAME/KEY: modified_base
<222> LOCATION: (1944)..(1944)
<223> OTHER INFORMATION: UNA monomer
<220> FEATURE:
<221> NAME/KEY: modified_base
<222> LOCATION: (1946)..(1946)
<223> OTHER INFORMATION: UNA monomer
<220> FEATURE:
<221> NAME/KEY: modified_base
<222> LOCATION: (1951)..(1951)
<223> OTHER INFORMATION: UNA monomer
<220> FEATURE:
<221> NAME/KEY: modified_base
<222> LOCATION: (1953)..(1954)
<223> OTHER INFORMATION: UNA monomer
<220> FEATURE:
<221> NAME/KEY: modified_base
<222> LOCATION: (1956)..(1956)
<223> OTHER INFORMATION: UNA monomer
<220> FEATURE:
<221> NAME/KEY: modified_base
<222> LOCATION: (1959)..(1959)
<223> OTHER INFORMATION: UNA monomer
<220> FEATURE:
<221> NAME/KEY: modified_base
<222> LOCATION: (1962)..(1962)
<223> OTHER INFORMATION: UNA monomer
<220> FEATURE:
<221> NAME/KEY: modified_base
<222> LOCATION: (1968)..(1968)
<223> OTHER INFORMATION: UNA monomer
<220> FEATURE:
<221> NAME/KEY: modified_base
<222> LOCATION: (1978)..(1978)
<223> OTHER INFORMATION: UNA monomer
<220> FEATURE:
<221> NAME/KEY: modified_base
<222> LOCATION: (1980)..(1980)
<223> OTHER INFORMATION: UNA monomer
<220> FEATURE:
<221> NAME/KEY: modified_base
<222> LOCATION: (1983)..(1983)
<223> OTHER INFORMATION: UNA monomer
<220> FEATURE:
<221> NAME/KEY: modified_base
<222> LOCATION: (1987)..(1988)
<223> OTHER INFORMATION: UNA monomer
```

-continued

```
<220> FEATURE:
<221> NAME/KEY: modified_base
<222> LOCATION: (1991)..(1991)
<223> OTHER INFORMATION: UNA monomer
<220> FEATURE:
<221> NAME/KEY: modified_base
<222> LOCATION: (1995)..(1995)
<223> OTHER INFORMATION: UNA monomer
<220> FEATURE:
<221> NAME/KEY: modified_base
<222> LOCATION: (1998)..(1998)
<223> OTHER INFORMATION: UNA monomer
<220> FEATURE:
<221> NAME/KEY: modified_base
<222> LOCATION: (2003)..(2005)
<223> OTHER INFORMATION: UNA monomer
<220> FEATURE:
<221> NAME/KEY: modified_base
<222> LOCATION: (2009)..(2009)
<223> OTHER INFORMATION: UNA monomer
<220> FEATURE:
<221> NAME/KEY: modified_base
<222> LOCATION: (2012)..(2014)
<223> OTHER INFORMATION: UNA monomer
<220> FEATURE:
<221> NAME/KEY: modified_base
<222> LOCATION: (2016)..(2016)
<223> OTHER INFORMATION: UNA monomer
<220> FEATURE:
<221> NAME/KEY: modified_base
<222> LOCATION: (2026)..(2029)
<223> OTHER INFORMATION: UNA monomer
<220> FEATURE:
<221> NAME/KEY: modified_base
<222> LOCATION: (2034)..(2034)
<223> OTHER INFORMATION: UNA monomer
<220> FEATURE:
<221> NAME/KEY: modified_base
<222> LOCATION: (2038)..(2038)
<223> OTHER INFORMATION: UNA monomer
<220> FEATURE:
<221> NAME/KEY: modified_base
<222> LOCATION: (2043)..(2043)
<223> OTHER INFORMATION: UNA monomer
<220> FEATURE:
<221> NAME/KEY: modified_base
<222> LOCATION: (2046)..(2046)
<223> OTHER INFORMATION: UNA monomer
<220> FEATURE:
<221> NAME/KEY: modified_base
<222> LOCATION: (2053)..(2054)
<223> OTHER INFORMATION: UNA monomer
<220> FEATURE:
<221> NAME/KEY: modified_base
<222> LOCATION: (2058)..(2059)
<223> OTHER INFORMATION: UNA monomer
<220> FEATURE:
<221> NAME/KEY: modified_base
<222> LOCATION: (2070)..(2070)
<223> OTHER INFORMATION: UNA monomer
<220> FEATURE:
<221> NAME/KEY: modified_base
<222> LOCATION: (2075)..(2076)
<223> OTHER INFORMATION: UNA monomer
<220> FEATURE:
<221> NAME/KEY: modified_base
<222> LOCATION: (2079)..(2081)
<223> OTHER INFORMATION: UNA monomer
<220> FEATURE:
<221> NAME/KEY: modified_base
<222> LOCATION: (2093)..(2094)
<223> OTHER INFORMATION: UNA monomer
<220> FEATURE:
<221> NAME/KEY: modified_base
<222> LOCATION: (2096)..(2097)
<223> OTHER INFORMATION: UNA monomer
<220> FEATURE:
<221> NAME/KEY: modified_base
<222> LOCATION: (2107)..(2107)
```

```
<223> OTHER INFORMATION: UNA monomer
<220> FEATURE:
<221> NAME/KEY: modified_base
<222> LOCATION: (2109)..(2109)
<223> OTHER INFORMATION: UNA monomer
<220> FEATURE:
<221> NAME/KEY: modified_base
<222> LOCATION: (2112)..(2112)
<223> OTHER INFORMATION: UNA monomer
<220> FEATURE:
<221> NAME/KEY: modified_base
<222> LOCATION: (2114)..(2114)
<223> OTHER INFORMATION: UNA monomer
<220> FEATURE:
<221> NAME/KEY: modified_base
<222> LOCATION: (2118)..(2118)
<223> OTHER INFORMATION: UNA monomer
<220> FEATURE:
<221> NAME/KEY: modified_base
<222> LOCATION: (2123)..(2124)
<223> OTHER INFORMATION: UNA monomer
<220> FEATURE:
<221> NAME/KEY: modified_base
<222> LOCATION: (2127)..(2127)
<223> OTHER INFORMATION: UNA monomer
<220> FEATURE:
<221> NAME/KEY: modified_base
<222> LOCATION: (2135)..(2136)
<223> OTHER INFORMATION: UNA monomer
<220> FEATURE:
<221> NAME/KEY: modified_base
<222> LOCATION: (2148)..(2151)
<223> OTHER INFORMATION: UNA monomer
<220> FEATURE:
<221> NAME/KEY: modified_base
<222> LOCATION: (2153)..(2154)
<223> OTHER INFORMATION: UNA monomer
<220> FEATURE:
<221> NAME/KEY: modified_base
<222> LOCATION: (2159)..(2159)
<223> OTHER INFORMATION: UNA monomer
<220> FEATURE:
<221> NAME/KEY: modified_base
<222> LOCATION: (2161)..(2161)
<223> OTHER INFORMATION: UNA monomer
<220> FEATURE:
<221> NAME/KEY: modified_base
<222> LOCATION: (2163)..(2163)
<223> OTHER INFORMATION: UNA monomer
<220> FEATURE:
<221> NAME/KEY: modified_base
<222> LOCATION: (2165)..(2165)
<223> OTHER INFORMATION: UNA monomer
<220> FEATURE:
<221> NAME/KEY: modified_base
<222> LOCATION: (2169)..(2169)
<223> OTHER INFORMATION: UNA monomer
<220> FEATURE:
<221> NAME/KEY: modified_base
<222> LOCATION: (2174)..(2175)
<223> OTHER INFORMATION: UNA monomer
<220> FEATURE:
<221> NAME/KEY: modified_base
<222> LOCATION: (2178)..(2178)
<223> OTHER INFORMATION: UNA monomer
<220> FEATURE:
<221> NAME/KEY: modified_base
<222> LOCATION: (2186)..(2186)
<223> OTHER INFORMATION: UNA monomer
<220> FEATURE:
<221> NAME/KEY: modified_base
<222> LOCATION: (2189)..(2189)
<223> OTHER INFORMATION: UNA monomer
<220> FEATURE:
<221> NAME/KEY: modified_base
<222> LOCATION: (2195)..(2195)
<223> OTHER INFORMATION: UNA monomer
<220> FEATURE:
<221> NAME/KEY: modified_base
```

-continued

```
<222> LOCATION: (2206)..(2206)
<223> OTHER INFORMATION: UNA monomer
<220> FEATURE:
<221> NAME/KEY: modified_base
<222> LOCATION: (2211)..(2211)
<223> OTHER INFORMATION: UNA monomer
<220> FEATURE:
<221> NAME/KEY: modified_base
<222> LOCATION: (2216)..(2216)
<223> OTHER INFORMATION: UNA monomer
<220> FEATURE:
<221> NAME/KEY: modified_base
<222> LOCATION: (2220)..(2220)
<223> OTHER INFORMATION: UNA monomer
<220> FEATURE:
<221> NAME/KEY: modified_base
<222> LOCATION: (2224)..(2224)
<223> OTHER INFORMATION: UNA monomer
<220> FEATURE:
<221> NAME/KEY: modified_base
<222> LOCATION: (2226)..(2226)
<223> OTHER INFORMATION: UNA monomer
<220> FEATURE:
<221> NAME/KEY: modified_base
<222> LOCATION: (2228)..(2229)
<223> OTHER INFORMATION: UNA monomer
<220> FEATURE:
<221> NAME/KEY: modified_base
<222> LOCATION: (2231)..(2231)
<223> OTHER INFORMATION: UNA monomer
<220> FEATURE:
<221> NAME/KEY: modified_base
<222> LOCATION: (2235)..(2235)
<223> OTHER INFORMATION: UNA monomer
<220> FEATURE:
<221> NAME/KEY: modified_base
<222> LOCATION: (2237)..(2237)
<223> OTHER INFORMATION: UNA monomer
<220> FEATURE:
<221> NAME/KEY: modified_base
<222> LOCATION: (2239)..(2239)
<223> OTHER INFORMATION: UNA monomer
<220> FEATURE:
<221> NAME/KEY: modified_base
<222> LOCATION: (2241)..(2241)
<223> OTHER INFORMATION: UNA monomer
<220> FEATURE:
<221> NAME/KEY: modified_base
<222> LOCATION: (2247)..(2247)
<223> OTHER INFORMATION: UNA monomer
<220> FEATURE:
<221> NAME/KEY: modified_base
<222> LOCATION: (2250)..(2252)
<223> OTHER INFORMATION: UNA monomer
<220> FEATURE:
<221> NAME/KEY: modified_base
<222> LOCATION: (2259)..(2259)
<223> OTHER INFORMATION: UNA monomer
<220> FEATURE:
<221> NAME/KEY: modified_base
<222> LOCATION: (2268)..(2269)
<223> OTHER INFORMATION: UNA monomer
<220> FEATURE:
<221> NAME/KEY: modified_base
<222> LOCATION: (2272)..(2275)
<223> OTHER INFORMATION: UNA monomer
<220> FEATURE:
<221> NAME/KEY: modified_base
<222> LOCATION: (2288)..(2288)
<223> OTHER INFORMATION: UNA monomer
<220> FEATURE:
<221> NAME/KEY: modified_base
<222> LOCATION: (2292)..(2292)
<223> OTHER INFORMATION: UNA monomer
<220> FEATURE:
<221> NAME/KEY: modified_base
<222> LOCATION: (2297)..(2297)
<223> OTHER INFORMATION: UNA monomer
<220> FEATURE:
```

-continued

```
<221> NAME/KEY: modified_base
<222> LOCATION: (2299)..(2299)
<223> OTHER INFORMATION: UNA monomer
<220> FEATURE:
<221> NAME/KEY: modified_base
<222> LOCATION: (2303)..(2303)
<223> OTHER INFORMATION: UNA monomer
<220> FEATURE:
<221> NAME/KEY: modified_base
<222> LOCATION: (2307)..(2307)
<223> OTHER INFORMATION: UNA monomer
<220> FEATURE:
<221> NAME/KEY: modified_base
<222> LOCATION: (2315)..(2316)
<223> OTHER INFORMATION: UNA monomer
<220> FEATURE:
<221> NAME/KEY: modified_base
<222> LOCATION: (2324)..(2324)
<223> OTHER INFORMATION: UNA monomer
<220> FEATURE:
<221> NAME/KEY: modified_base
<222> LOCATION: (2327)..(2328)
<223> OTHER INFORMATION: UNA monomer
<220> FEATURE:
<221> NAME/KEY: modified_base
<222> LOCATION: (2330)..(2331)
<223> OTHER INFORMATION: UNA monomer
<220> FEATURE:
<221> NAME/KEY: modified_base
<222> LOCATION: (2337)..(2337)
<223> OTHER INFORMATION: UNA monomer
<220> FEATURE:
<221> NAME/KEY: modified_base
<222> LOCATION: (2343)..(2343)
<223> OTHER INFORMATION: UNA monomer
<220> FEATURE:
<221> NAME/KEY: modified_base
<222> LOCATION: (2345)..(2346)
<223> OTHER INFORMATION: UNA monomer
<220> FEATURE:
<221> NAME/KEY: modified_base
<222> LOCATION: (2364)..(2365)
<223> OTHER INFORMATION: UNA monomer
<220> FEATURE:
<221> NAME/KEY: modified_base
<222> LOCATION: (2367)..(2367)
<223> OTHER INFORMATION: UNA monomer
<220> FEATURE:
<221> NAME/KEY: modified_base
<222> LOCATION: (2376)..(2376)
<223> OTHER INFORMATION: UNA monomer
<220> FEATURE:
<221> NAME/KEY: modified_base
<222> LOCATION: (2382)..(2383)
<223> OTHER INFORMATION: UNA monomer
<220> FEATURE:
<221> NAME/KEY: modified_base
<222> LOCATION: (2387)..(2387)
<223> OTHER INFORMATION: UNA monomer
<220> FEATURE:
<221> NAME/KEY: modified_base
<222> LOCATION: (2391)..(2391)
<223> OTHER INFORMATION: UNA monomer
<220> FEATURE:
<221> NAME/KEY: modified_base
<222> LOCATION: (2403)..(2403)
<223> OTHER INFORMATION: UNA monomer
<220> FEATURE:
<221> NAME/KEY: modified_base
<222> LOCATION: (2405)..(2405)
<223> OTHER INFORMATION: UNA monomer
<220> FEATURE:
<221> NAME/KEY: modified_base
<222> LOCATION: (2411)..(2411)
<223> OTHER INFORMATION: UNA monomer
<220> FEATURE:
<221> NAME/KEY: modified_base
<222> LOCATION: (2417)..(2418)
<223> OTHER INFORMATION: UNA monomer
```

-continued

```
<220> FEATURE:
<221> NAME/KEY: modified_base
<222> LOCATION: (2427)..(2427)
<223> OTHER INFORMATION: UNA monomer
<220> FEATURE:
<221> NAME/KEY: modified_base
<222> LOCATION: (2429)..(2430)
<223> OTHER INFORMATION: UNA monomer
<220> FEATURE:
<221> NAME/KEY: modified_base
<222> LOCATION: (2435)..(2436)
<223> OTHER INFORMATION: UNA monomer
<220> FEATURE:
<221> NAME/KEY: modified_base
<222> LOCATION: (2439)..(2439)
<223> OTHER INFORMATION: UNA monomer
<220> FEATURE:
<221> NAME/KEY: modified_base
<222> LOCATION: (2445)..(2445)
<223> OTHER INFORMATION: UNA monomer
<220> FEATURE:
<221> NAME/KEY: modified_base
<222> LOCATION: (2450)..(2451)
<223> OTHER INFORMATION: UNA monomer
<220> FEATURE:
<221> NAME/KEY: modified_base
<222> LOCATION: (2453)..(2454)
<223> OTHER INFORMATION: UNA monomer
<220> FEATURE:
<221> NAME/KEY: modified_base
<222> LOCATION: (2463)..(2463)
<223> OTHER INFORMATION: UNA monomer
<220> FEATURE:
<221> NAME/KEY: modified_base
<222> LOCATION: (2468)..(2469)
<223> OTHER INFORMATION: UNA monomer
<220> FEATURE:
<221> NAME/KEY: modified_base
<222> LOCATION: (2487)..(2487)
<223> OTHER INFORMATION: UNA monomer
<220> FEATURE:
<221> NAME/KEY: modified_base
<222> LOCATION: (2491)..(2491)
<223> OTHER INFORMATION: UNA monomer
<220> FEATURE:
<221> NAME/KEY: modified_base
<222> LOCATION: (2493)..(2493)
<223> OTHER INFORMATION: UNA monomer
<220> FEATURE:
<221> NAME/KEY: modified_base
<222> LOCATION: (2495)..(2496)
<223> OTHER INFORMATION: UNA monomer
<220> FEATURE:
<221> NAME/KEY: modified_base
<222> LOCATION: (2504)..(2504)
<223> OTHER INFORMATION: UNA monomer
<220> FEATURE:
<221> NAME/KEY: modified_base
<222> LOCATION: (2509)..(2511)
<223> OTHER INFORMATION: UNA monomer
<220> FEATURE:
<221> NAME/KEY: modified_base
<222> LOCATION: (2518)..(2519)
<223> OTHER INFORMATION: UNA monomer
<220> FEATURE:
<221> NAME/KEY: modified_base
<222> LOCATION: (2521)..(2521)
<223> OTHER INFORMATION: UNA monomer
<220> FEATURE:
<221> NAME/KEY: modified_base
<222> LOCATION: (2523)..(2523)
<223> OTHER INFORMATION: UNA monomer
<220> FEATURE:
<221> NAME/KEY: modified_base
<222> LOCATION: (2532)..(2532)
<223> OTHER INFORMATION: UNA monomer
<220> FEATURE:
<221> NAME/KEY: modified_base
<222> LOCATION: (2534)..(2535)
```

```
<223> OTHER INFORMATION: UNA monomer
<220> FEATURE:
<221> NAME/KEY: modified_base
<222> LOCATION: (2537)..(2538)
<223> OTHER INFORMATION: UNA monomer
<220> FEATURE:
<221> NAME/KEY: modified_base
<222> LOCATION: (2540)..(2540)
<223> OTHER INFORMATION: UNA monomer
<220> FEATURE:
<221> NAME/KEY: modified_base
<222> LOCATION: (2542)..(2543)
<223> OTHER INFORMATION: UNA monomer
<220> FEATURE:
<221> NAME/KEY: modified_base
<222> LOCATION: (2549)..(2550)
<223> OTHER INFORMATION: UNA monomer
<220> FEATURE:
<221> NAME/KEY: modified_base
<222> LOCATION: (2553)..(2553)
<223> OTHER INFORMATION: UNA monomer
<220> FEATURE:
<221> NAME/KEY: modified_base
<222> LOCATION: (2555)..(2556)
<223> OTHER INFORMATION: UNA monomer
<220> FEATURE:
<221> NAME/KEY: modified_base
<222> LOCATION: (2559)..(2559)
<223> OTHER INFORMATION: UNA monomer
<220> FEATURE:
<221> NAME/KEY: modified_base
<222> LOCATION: (2565)..(2565)
<223> OTHER INFORMATION: UNA monomer
<220> FEATURE:
<221> NAME/KEY: modified_base
<222> LOCATION: (2573)..(2573)
<223> OTHER INFORMATION: UNA monomer
<220> FEATURE:
<221> NAME/KEY: modified_base
<222> LOCATION: (2577)..(2577)
<223> OTHER INFORMATION: UNA monomer
<220> FEATURE:
<221> NAME/KEY: modified_base
<222> LOCATION: (2579)..(2580)
<223> OTHER INFORMATION: UNA monomer
<220> FEATURE:
<221> NAME/KEY: modified_base
<222> LOCATION: (2585)..(2586)
<223> OTHER INFORMATION: UNA monomer
<220> FEATURE:
<221> NAME/KEY: modified_base
<222> LOCATION: (2588)..(2589)
<223> OTHER INFORMATION: UNA monomer
<220> FEATURE:
<221> NAME/KEY: modified_base
<222> LOCATION: (2595)..(2595)
<223> OTHER INFORMATION: UNA monomer
<220> FEATURE:
<221> NAME/KEY: modified_base
<222> LOCATION: (2598)..(2598)
<223> OTHER INFORMATION: UNA monomer
<220> FEATURE:
<221> NAME/KEY: modified_base
<222> LOCATION: (2600)..(2600)
<223> OTHER INFORMATION: UNA monomer
<220> FEATURE:
<221> NAME/KEY: modified_base
<222> LOCATION: (2608)..(2609)
<223> OTHER INFORMATION: UNA monomer
<220> FEATURE:
<221> NAME/KEY: modified_base
<222> LOCATION: (2613)..(2613)
<223> OTHER INFORMATION: UNA monomer
<220> FEATURE:
<221> NAME/KEY: modified_base
<222> LOCATION: (2616)..(2616)
<223> OTHER INFORMATION: UNA monomer
<220> FEATURE:
<221> NAME/KEY: modified_base
```

-continued

```
<222> LOCATION: (2620)..(2622)
<223> OTHER INFORMATION: UNA monomer
<220> FEATURE:
<221> NAME/KEY: modified_base
<222> LOCATION: (2626)..(2626)
<223> OTHER INFORMATION: UNA monomer
<220> FEATURE:
<221> NAME/KEY: modified_base
<222> LOCATION: (2628)..(2628)
<223> OTHER INFORMATION: UNA monomer
<220> FEATURE:
<221> NAME/KEY: modified_base
<222> LOCATION: (2636)..(2636)
<223> OTHER INFORMATION: UNA monomer
<220> FEATURE:
<221> NAME/KEY: modified_base
<222> LOCATION: (2640)..(2640)
<223> OTHER INFORMATION: UNA monomer
<220> FEATURE:
<221> NAME/KEY: modified_base
<222> LOCATION: (2642)..(2643)
<223> OTHER INFORMATION: UNA monomer
<220> FEATURE:
<221> NAME/KEY: modified_base
<222> LOCATION: (2649)..(2649)
<223> OTHER INFORMATION: UNA monomer
<220> FEATURE:
<221> NAME/KEY: modified_base
<222> LOCATION: (2655)..(2655)
<223> OTHER INFORMATION: UNA monomer
<220> FEATURE:
<221> NAME/KEY: modified_base
<222> LOCATION: (2658)..(2658)
<223> OTHER INFORMATION: UNA monomer
<220> FEATURE:
<221> NAME/KEY: modified_base
<222> LOCATION: (2660)..(2660)
<223> OTHER INFORMATION: UNA monomer
<220> FEATURE:
<221> NAME/KEY: modified_base
<222> LOCATION: (2662)..(2663)
<223> OTHER INFORMATION: UNA monomer
<220> FEATURE:
<221> NAME/KEY: modified_base
<222> LOCATION: (2669)..(2670)
<223> OTHER INFORMATION: UNA monomer
<220> FEATURE:
<221> NAME/KEY: modified_base
<222> LOCATION: (2673)..(2676)
<223> OTHER INFORMATION: UNA monomer
<220> FEATURE:
<221> NAME/KEY: modified_base
<222> LOCATION: (2679)..(2680)
<223> OTHER INFORMATION: UNA monomer
<220> FEATURE:
<221> NAME/KEY: modified_base
<222> LOCATION: (2682)..(2682)
<223> OTHER INFORMATION: UNA monomer
<220> FEATURE:
<221> NAME/KEY: modified_base
<222> LOCATION: (2684)..(2685)
<223> OTHER INFORMATION: UNA monomer
<220> FEATURE:
<221> NAME/KEY: modified_base
<222> LOCATION: (2689)..(2689)
<223> OTHER INFORMATION: UNA monomer
<220> FEATURE:
<221> NAME/KEY: modified_base
<222> LOCATION: (2695)..(2696)
<223> OTHER INFORMATION: UNA monomer
<220> FEATURE:
<221> NAME/KEY: modified_base
<222> LOCATION: (2700)..(2702)
<223> OTHER INFORMATION: UNA monomer
<220> FEATURE:
<221> NAME/KEY: modified_base
<222> LOCATION: (2706)..(2706)
<223> OTHER INFORMATION: UNA monomer
<220> FEATURE:
```

-continued

```
<221> NAME/KEY: modified_base
<222> LOCATION: (2711)..(2711)
<223> OTHER INFORMATION: UNA monomer
<220> FEATURE:
<221> NAME/KEY: modified_base
<222> LOCATION: (2715)..(2715)
<223> OTHER INFORMATION: UNA monomer
<220> FEATURE:
<221> NAME/KEY: modified_base
<222> LOCATION: (2720)..(2720)
<223> OTHER INFORMATION: UNA monomer
<220> FEATURE:
<221> NAME/KEY: modified_base
<222> LOCATION: (2723)..(2725)
<223> OTHER INFORMATION: UNA monomer
<220> FEATURE:
<221> NAME/KEY: modified_base
<222> LOCATION: (2731)..(2731)
<223> OTHER INFORMATION: UNA monomer
<220> FEATURE:
<221> NAME/KEY: modified_base
<222> LOCATION: (2733)..(2733)
<223> OTHER INFORMATION: UNA monomer
<220> FEATURE:
<221> NAME/KEY: modified_base
<222> LOCATION: (2737)..(2737)
<223> OTHER INFORMATION: UNA monomer
<220> FEATURE:
<221> NAME/KEY: modified_base
<222> LOCATION: (2754)..(2754)
<223> OTHER INFORMATION: UNA monomer
<220> FEATURE:
<221> NAME/KEY: modified_base
<222> LOCATION: (2757)..(2757)
<223> OTHER INFORMATION: UNA monomer
<220> FEATURE:
<221> NAME/KEY: modified_base
<222> LOCATION: (2764)..(2764)
<223> OTHER INFORMATION: UNA monomer
<220> FEATURE:
<221> NAME/KEY: modified_base
<222> LOCATION: (2767)..(2767)
<223> OTHER INFORMATION: UNA monomer
<220> FEATURE:
<221> NAME/KEY: modified_base
<222> LOCATION: (2769)..(2769)
<223> OTHER INFORMATION: UNA monomer
<220> FEATURE:
<221> NAME/KEY: modified_base
<222> LOCATION: (2774)..(2774)
<223> OTHER INFORMATION: UNA monomer
<220> FEATURE:
<221> NAME/KEY: modified_base
<222> LOCATION: (2782)..(2782)
<223> OTHER INFORMATION: UNA monomer
<220> FEATURE:
<221> NAME/KEY: modified_base
<222> LOCATION: (2785)..(2785)
<223> OTHER INFORMATION: UNA monomer
<220> FEATURE:
<221> NAME/KEY: modified_base
<222> LOCATION: (2792)..(2793)
<223> OTHER INFORMATION: UNA monomer
<220> FEATURE:
<221> NAME/KEY: modified_base
<222> LOCATION: (2797)..(2797)
<223> OTHER INFORMATION: UNA monomer
<220> FEATURE:
<221> NAME/KEY: modified_base
<222> LOCATION: (2799)..(2799)
<223> OTHER INFORMATION: UNA monomer
<220> FEATURE:
<221> NAME/KEY: modified_base
<222> LOCATION: (2805)..(2805)
<223> OTHER INFORMATION: UNA monomer
<220> FEATURE:
<221> NAME/KEY: modified_base
<222> LOCATION: (2807)..(2808)
<223> OTHER INFORMATION: UNA monomer
```

-continued

```
<220> FEATURE:
<221> NAME/KEY: modified_base
<222> LOCATION: (2814)..(2816)
<223> OTHER INFORMATION: UNA monomer
<220> FEATURE:
<221> NAME/KEY: modified_base
<222> LOCATION: (2819)..(2819)
<223> OTHER INFORMATION: UNA monomer
<220> FEATURE:
<221> NAME/KEY: modified_base
<222> LOCATION: (2821)..(2821)
<223> OTHER INFORMATION: UNA monomer
<220> FEATURE:
<221> NAME/KEY: modified_base
<222> LOCATION: (2823)..(2823)
<223> OTHER INFORMATION: UNA monomer
<220> FEATURE:
<221> NAME/KEY: modified_base
<222> LOCATION: (2825)..(2825)
<223> OTHER INFORMATION: UNA monomer
<220> FEATURE:
<221> NAME/KEY: modified_base
<222> LOCATION: (2827)..(2828)
<223> OTHER INFORMATION: UNA monomer
<220> FEATURE:
<221> NAME/KEY: modified_base
<222> LOCATION: (2837)..(2837)
<223> OTHER INFORMATION: UNA monomer
<220> FEATURE:
<221> NAME/KEY: modified_base
<222> LOCATION: (2850)..(2850)
<223> OTHER INFORMATION: UNA monomer
<220> FEATURE:
<221> NAME/KEY: modified_base
<222> LOCATION: (2854)..(2855)
<223> OTHER INFORMATION: UNA monomer
<220> FEATURE:
<221> NAME/KEY: modified_base
<222> LOCATION: (2862)..(2862)
<223> OTHER INFORMATION: UNA monomer
<220> FEATURE:
<221> NAME/KEY: modified_base
<222> LOCATION: (2865)..(2869)
<223> OTHER INFORMATION: UNA monomer
<220> FEATURE:
<221> NAME/KEY: modified_base
<222> LOCATION: (2871)..(2871)
<223> OTHER INFORMATION: UNA monomer
<220> FEATURE:
<221> NAME/KEY: modified_base
<222> LOCATION: (2874)..(2874)
<223> OTHER INFORMATION: UNA monomer
<220> FEATURE:
<221> NAME/KEY: modified_base
<222> LOCATION: (2877)..(2879)
<223> OTHER INFORMATION: UNA monomer
<220> FEATURE:
<221> NAME/KEY: modified_base
<222> LOCATION: (2884)..(2884)
<223> OTHER INFORMATION: UNA monomer
<220> FEATURE:
<221> NAME/KEY: modified_base
<222> LOCATION: (2886)..(2886)
<223> OTHER INFORMATION: UNA monomer
<220> FEATURE:
<221> NAME/KEY: modified_base
<222> LOCATION: (2892)..(2893)
<223> OTHER INFORMATION: UNA monomer
<220> FEATURE:
<221> NAME/KEY: modified_base
<222> LOCATION: (2897)..(2897)
<223> OTHER INFORMATION: UNA monomer
<220> FEATURE:
<221> NAME/KEY: modified_base
<222> LOCATION: (2900)..(2901)
<223> OTHER INFORMATION: UNA monomer
<220> FEATURE:
<221> NAME/KEY: modified_base
<222> LOCATION: (2905)..(2905)
```

```
<223> OTHER INFORMATION: UNA monomer
<220> FEATURE:
<221> NAME/KEY: modified_base
<222> LOCATION: (2907)..(2907)
<223> OTHER INFORMATION: UNA monomer
<220> FEATURE:
<221> NAME/KEY: modified_base
<222> LOCATION: (2909)..(2909)
<223> OTHER INFORMATION: UNA monomer
<220> FEATURE:
<221> NAME/KEY: modified_base
<222> LOCATION: (2913)..(2913)
<223> OTHER INFORMATION: UNA monomer
<220> FEATURE:
<221> NAME/KEY: modified_base
<222> LOCATION: (2921)..(2922)
<223> OTHER INFORMATION: UNA monomer
<220> FEATURE:
<221> NAME/KEY: modified_base
<222> LOCATION: (2924)..(2926)
<223> OTHER INFORMATION: UNA monomer
<220> FEATURE:
<221> NAME/KEY: modified_base
<222> LOCATION: (2932)..(2932)
<223> OTHER INFORMATION: UNA monomer
<220> FEATURE:
<221> NAME/KEY: modified_base
<222> LOCATION: (2940)..(2940)
<223> OTHER INFORMATION: UNA monomer
<220> FEATURE:
<221> NAME/KEY: modified_base
<222> LOCATION: (2942)..(2943)
<223> OTHER INFORMATION: UNA monomer
<220> FEATURE:
<221> NAME/KEY: modified_base
<222> LOCATION: (2946)..(2946)
<223> OTHER INFORMATION: UNA monomer
<220> FEATURE:
<221> NAME/KEY: modified_base
<222> LOCATION: (2951)..(2952)
<223> OTHER INFORMATION: UNA monomer
<220> FEATURE:
<221> NAME/KEY: modified_base
<222> LOCATION: (2955)..(2955)
<223> OTHER INFORMATION: UNA monomer
<220> FEATURE:
<221> NAME/KEY: modified_base
<222> LOCATION: (2959)..(2959)
<223> OTHER INFORMATION: UNA monomer
<220> FEATURE:
<221> NAME/KEY: modified_base
<222> LOCATION: (2962)..(2963)
<223> OTHER INFORMATION: UNA monomer
<220> FEATURE:
<221> NAME/KEY: modified_base
<222> LOCATION: (2970)..(2970)
<223> OTHER INFORMATION: UNA monomer
<220> FEATURE:
<221> NAME/KEY: modified_base
<222> LOCATION: (2972)..(2972)
<223> OTHER INFORMATION: UNA monomer
<220> FEATURE:
<221> NAME/KEY: modified_base
<222> LOCATION: (2974)..(2975)
<223> OTHER INFORMATION: UNA monomer
<220> FEATURE:
<221> NAME/KEY: modified_base
<222> LOCATION: (2977)..(2978)
<223> OTHER INFORMATION: UNA monomer
<220> FEATURE:
<221> NAME/KEY: modified_base
<222> LOCATION: (2980)..(2980)
<223> OTHER INFORMATION: UNA monomer
<220> FEATURE:
<221> NAME/KEY: modified_base
<222> LOCATION: (2984)..(2984)
<223> OTHER INFORMATION: UNA monomer
<220> FEATURE:
<221> NAME/KEY: modified_base
```

-continued

```
<222> LOCATION: (2993)..(2993)
<223> OTHER INFORMATION: UNA monomer
<220> FEATURE:
<221> NAME/KEY: modified_base
<222> LOCATION: (3000)..(3001)
<223> OTHER INFORMATION: UNA monomer
<220> FEATURE:
<221> NAME/KEY: modified_base
<222> LOCATION: (3005)..(3006)
<223> OTHER INFORMATION: UNA monomer
<220> FEATURE:
<221> NAME/KEY: modified_base
<222> LOCATION: (3008)..(3008)
<223> OTHER INFORMATION: UNA monomer
<220> FEATURE:
<221> NAME/KEY: modified_base
<222> LOCATION: (3013)..(3013)
<223> OTHER INFORMATION: UNA monomer
<220> FEATURE:
<221> NAME/KEY: modified_base
<222> LOCATION: (3015)..(3016)
<223> OTHER INFORMATION: UNA monomer
<220> FEATURE:
<221> NAME/KEY: modified_base
<222> LOCATION: (3019)..(3021)
<223> OTHER INFORMATION: UNA monomer
<220> FEATURE:
<221> NAME/KEY: modified_base
<222> LOCATION: (3024)..(3024)
<223> OTHER INFORMATION: UNA monomer
<220> FEATURE:
<221> NAME/KEY: modified_base
<222> LOCATION: (3027)..(3027)
<223> OTHER INFORMATION: UNA monomer
<220> FEATURE:
<221> NAME/KEY: modified_base
<222> LOCATION: (3029)..(3029)
<223> OTHER INFORMATION: UNA monomer
<220> FEATURE:
<221> NAME/KEY: modified_base
<222> LOCATION: (3031)..(3032)
<223> OTHER INFORMATION: UNA monomer
<220> FEATURE:
<221> NAME/KEY: modified_base
<222> LOCATION: (3035)..(3036)
<223> OTHER INFORMATION: UNA monomer
<220> FEATURE:
<221> NAME/KEY: modified_base
<222> LOCATION: (3039)..(3039)
<223> OTHER INFORMATION: UNA monomer
<220> FEATURE:
<221> NAME/KEY: modified_base
<222> LOCATION: (3043)..(3043)
<223> OTHER INFORMATION: UNA monomer
<220> FEATURE:
<221> NAME/KEY: modified_base
<222> LOCATION: (3045)..(3045)
<223> OTHER INFORMATION: UNA monomer
<220> FEATURE:
<221> NAME/KEY: modified_base
<222> LOCATION: (3051)..(3051)
<223> OTHER INFORMATION: UNA monomer
<220> FEATURE:
<221> NAME/KEY: modified_base
<222> LOCATION: (3053)..(3054)
<223> OTHER INFORMATION: UNA monomer
<220> FEATURE:
<221> NAME/KEY: modified_base
<222> LOCATION: (3056)..(3056)
<223> OTHER INFORMATION: UNA monomer
<220> FEATURE:
<221> NAME/KEY: modified_base
<222> LOCATION: (3060)..(3060)
<223> OTHER INFORMATION: UNA monomer
<220> FEATURE:
<221> NAME/KEY: modified_base
<222> LOCATION: (3067)..(3067)
<223> OTHER INFORMATION: UNA monomer
<220> FEATURE:
```

```
<221> NAME/KEY: modified_base
<222> LOCATION: (3077)..(3077)
<223> OTHER INFORMATION: UNA monomer
<220> FEATURE:
<221> NAME/KEY: modified_base
<222> LOCATION: (3079)..(3079)
<223> OTHER INFORMATION: UNA monomer
<220> FEATURE:
<221> NAME/KEY: modified_base
<222> LOCATION: (3085)..(3087)
<223> OTHER INFORMATION: UNA monomer
<220> FEATURE:
<221> NAME/KEY: modified_base
<222> LOCATION: (3089)..(3090)
<223> OTHER INFORMATION: UNA monomer
<220> FEATURE:
<221> NAME/KEY: modified_base
<222> LOCATION: (3096)..(3096)
<223> OTHER INFORMATION: UNA monomer
<220> FEATURE:
<221> NAME/KEY: modified_base
<222> LOCATION: (3099)..(3100)
<223> OTHER INFORMATION: UNA monomer
<220> FEATURE:
<221> NAME/KEY: modified_base
<222> LOCATION: (3106)..(3108)
<223> OTHER INFORMATION: UNA monomer
<220> FEATURE:
<221> NAME/KEY: modified_base
<222> LOCATION: (3110)..(3110)
<223> OTHER INFORMATION: UNA monomer
<220> FEATURE:
<221> NAME/KEY: modified_base
<222> LOCATION: (3119)..(3121)
<223> OTHER INFORMATION: UNA monomer
<220> FEATURE:
<221> NAME/KEY: modified_base
<222> LOCATION: (3124)..(3125)
<223> OTHER INFORMATION: UNA monomer
<220> FEATURE:
<221> NAME/KEY: modified_base
<222> LOCATION: (3129)..(3130)
<223> OTHER INFORMATION: UNA monomer
<220> FEATURE:
<221> NAME/KEY: modified_base
<222> LOCATION: (3134)..(3135)
<223> OTHER INFORMATION: UNA monomer
<220> FEATURE:
<221> NAME/KEY: modified_base
<222> LOCATION: (3140)..(3140)
<223> OTHER INFORMATION: UNA monomer
<220> FEATURE:
<221> NAME/KEY: modified_base
<222> LOCATION: (3142)..(3142)
<223> OTHER INFORMATION: UNA monomer
<220> FEATURE:
<221> NAME/KEY: modified_base
<222> LOCATION: (3144)..(3144)
<223> OTHER INFORMATION: UNA monomer
<220> FEATURE:
<221> NAME/KEY: modified_base
<222> LOCATION: (3149)..(3149)
<223> OTHER INFORMATION: UNA monomer
<220> FEATURE:
<221> NAME/KEY: modified_base
<222> LOCATION: (3157)..(3158)
<223> OTHER INFORMATION: UNA monomer
<220> FEATURE:
<221> NAME/KEY: modified_base
<222> LOCATION: (3162)..(3163)
<223> OTHER INFORMATION: UNA monomer
<220> FEATURE:
<221> NAME/KEY: modified_base
<222> LOCATION: (3167)..(3167)
<223> OTHER INFORMATION: UNA monomer
<220> FEATURE:
<221> NAME/KEY: modified_base
<222> LOCATION: (3173)..(3174)
<223> OTHER INFORMATION: UNA monomer
```

```
-continued

<220> FEATURE:
<221> NAME/KEY: modified_base
<222> LOCATION: (3176)..(3178)
<223> OTHER INFORMATION: UNA monomer
<220> FEATURE:
<221> NAME/KEY: modified_base
<222> LOCATION: (3183)..(3183)
<223> OTHER INFORMATION: UNA monomer
<220> FEATURE:
<221> NAME/KEY: modified_base
<222> LOCATION: (3188)..(3188)
<223> OTHER INFORMATION: UNA monomer
<220> FEATURE:
<221> NAME/KEY: modified_base
<222> LOCATION: (3191)..(3191)
<223> OTHER INFORMATION: UNA monomer
<220> FEATURE:
<221> NAME/KEY: modified_base
<222> LOCATION: (3195)..(3195)
<223> OTHER INFORMATION: UNA monomer
<220> FEATURE:
<221> NAME/KEY: modified_base
<222> LOCATION: (3197)..(3197)
<223> OTHER INFORMATION: UNA monomer
<220> FEATURE:
<221> NAME/KEY: modified_base
<222> LOCATION: (3201)..(3202)
<223> OTHER INFORMATION: UNA monomer
<220> FEATURE:
<221> NAME/KEY: modified_base
<222> LOCATION: (3204)..(3204)
<223> OTHER INFORMATION: UNA monomer
<220> FEATURE:
<221> NAME/KEY: modified_base
<222> LOCATION: (3208)..(3209)
<223> OTHER INFORMATION: UNA monomer
<220> FEATURE:
<221> NAME/KEY: modified_base
<222> LOCATION: (3213)..(3213)
<223> OTHER INFORMATION: UNA monomer
<220> FEATURE:
<221> NAME/KEY: modified_base
<222> LOCATION: (3218)..(3218)
<223> OTHER INFORMATION: UNA monomer
<220> FEATURE:
<221> NAME/KEY: modified_base
<222> LOCATION: (3238)..(3238)
<223> OTHER INFORMATION: UNA monomer
<220> FEATURE:
<221> NAME/KEY: modified_base
<222> LOCATION: (3240)..(3241)
<223> OTHER INFORMATION: UNA monomer
<220> FEATURE:
<221> NAME/KEY: modified_base
<222> LOCATION: (3243)..(3243)
<223> OTHER INFORMATION: UNA monomer
<220> FEATURE:
<221> NAME/KEY: modified_base
<222> LOCATION: (3245)..(3247)
<223> OTHER INFORMATION: UNA monomer
<220> FEATURE:
<221> NAME/KEY: modified_base
<222> LOCATION: (3249)..(3249)
<223> OTHER INFORMATION: UNA monomer
<220> FEATURE:
<221> NAME/KEY: modified_base
<222> LOCATION: (3251)..(3251)
<223> OTHER INFORMATION: UNA monomer
<220> FEATURE:
<221> NAME/KEY: modified_base
<222> LOCATION: (3255)..(3255)
<223> OTHER INFORMATION: UNA monomer
<220> FEATURE:
<221> NAME/KEY: modified_base
<222> LOCATION: (3262)..(3263)
<223> OTHER INFORMATION: UNA monomer
<220> FEATURE:
<221> NAME/KEY: modified_base
<222> LOCATION: (3267)..(3267)
```

```
<223> OTHER INFORMATION: UNA monomer
<220> FEATURE:
<221> NAME/KEY: modified_base
<222> LOCATION: (3270)..(3274)
<223> OTHER INFORMATION: UNA monomer
<220> FEATURE:
<221> NAME/KEY: modified_base
<222> LOCATION: (3276)..(3277)
<223> OTHER INFORMATION: UNA monomer
<220> FEATURE:
<221> NAME/KEY: modified_base
<222> LOCATION: (3279)..(3279)
<223> OTHER INFORMATION: UNA monomer
<220> FEATURE:
<221> NAME/KEY: modified_base
<222> LOCATION: (3282)..(3282)
<223> OTHER INFORMATION: UNA monomer
<220> FEATURE:
<221> NAME/KEY: modified_base
<222> LOCATION: (3284)..(3287)
<223> OTHER INFORMATION: UNA monomer
<220> FEATURE:
<221> NAME/KEY: modified_base
<222> LOCATION: (3292)..(3292)
<223> OTHER INFORMATION: UNA monomer
<220> FEATURE:
<221> NAME/KEY: modified_base
<222> LOCATION: (3295)..(3295)
<223> OTHER INFORMATION: UNA monomer
<220> FEATURE:
<221> NAME/KEY: modified_base
<222> LOCATION: (3306)..(3306)
<223> OTHER INFORMATION: UNA monomer
<220> FEATURE:
<221> NAME/KEY: modified_base
<222> LOCATION: (3309)..(3312)
<223> OTHER INFORMATION: UNA monomer
<220> FEATURE:
<221> NAME/KEY: modified_base
<222> LOCATION: (3314)..(3315)
<223> OTHER INFORMATION: UNA monomer
<220> FEATURE:
<221> NAME/KEY: modified_base
<222> LOCATION: (3320)..(3321)
<223> OTHER INFORMATION: UNA monomer
<220> FEATURE:
<221> NAME/KEY: modified_base
<222> LOCATION: (3327)..(3327)
<223> OTHER INFORMATION: UNA monomer
<220> FEATURE:
<221> NAME/KEY: modified_base
<222> LOCATION: (3329)..(3329)
<223> OTHER INFORMATION: UNA monomer
<220> FEATURE:
<221> NAME/KEY: modified_base
<222> LOCATION: (3332)..(3332)
<223> OTHER INFORMATION: UNA monomer
<220> FEATURE:
<221> NAME/KEY: modified_base
<222> LOCATION: (3335)..(3335)
<223> OTHER INFORMATION: UNA monomer
<220> FEATURE:
<221> NAME/KEY: modified_base
<222> LOCATION: (3338)..(3339)
<223> OTHER INFORMATION: UNA monomer
<220> FEATURE:
<221> NAME/KEY: modified_base
<222> LOCATION: (3342)..(3342)
<223> OTHER INFORMATION: UNA monomer
<220> FEATURE:
<221> NAME/KEY: modified_base
<222> LOCATION: (3349)..(3349)
<223> OTHER INFORMATION: UNA monomer
<220> FEATURE:
<221> NAME/KEY: modified_base
<222> LOCATION: (3351)..(3351)
<223> OTHER INFORMATION: UNA monomer
<220> FEATURE:
<221> NAME/KEY: modified_base
```

```
<222> LOCATION: (3353)..(3353)
<223> OTHER INFORMATION: UNA monomer
<220> FEATURE:
<221> NAME/KEY: modified_base
<222> LOCATION: (3366)..(3366)
<223> OTHER INFORMATION: UNA monomer
<220> FEATURE:
<221> NAME/KEY: modified_base
<222> LOCATION: (3368)..(3369)
<223> OTHER INFORMATION: UNA monomer
<220> FEATURE:
<221> NAME/KEY: modified_base
<222> LOCATION: (3371)..(3374)
<223> OTHER INFORMATION: UNA monomer
<220> FEATURE:
<221> NAME/KEY: modified_base
<222> LOCATION: (3379)..(3381)
<223> OTHER INFORMATION: UNA monomer
<220> FEATURE:
<221> NAME/KEY: modified_base
<222> LOCATION: (3387)..(3387)
<223> OTHER INFORMATION: UNA monomer
<220> FEATURE:
<221> NAME/KEY: modified_base
<222> LOCATION: (3392)..(3392)
<223> OTHER INFORMATION: UNA monomer
<220> FEATURE:
<221> NAME/KEY: modified_base
<222> LOCATION: (3399)..(3399)
<223> OTHER INFORMATION: UNA monomer
<220> FEATURE:
<221> NAME/KEY: modified_base
<222> LOCATION: (3402)..(3402)
<223> OTHER INFORMATION: UNA monomer
<220> FEATURE:
<221> NAME/KEY: modified_base
<222> LOCATION: (3404)..(3404)
<223> OTHER INFORMATION: UNA monomer
<220> FEATURE:
<221> NAME/KEY: modified_base
<222> LOCATION: (3407)..(3408)
<223> OTHER INFORMATION: UNA monomer
<220> FEATURE:
<221> NAME/KEY: modified_base
<222> LOCATION: (3411)..(3411)
<223> OTHER INFORMATION: UNA monomer
<220> FEATURE:
<221> NAME/KEY: modified_base
<222> LOCATION: (3414)..(3414)
<223> OTHER INFORMATION: UNA monomer
<220> FEATURE:
<221> NAME/KEY: modified_base
<222> LOCATION: (3416)..(3416)
<223> OTHER INFORMATION: UNA monomer
<220> FEATURE:
<221> NAME/KEY: modified_base
<222> LOCATION: (3419)..(3419)
<223> OTHER INFORMATION: UNA monomer
<220> FEATURE:
<221> NAME/KEY: modified_base
<222> LOCATION: (3423)..(3423)
<223> OTHER INFORMATION: UNA monomer
<220> FEATURE:
<221> NAME/KEY: modified_base
<222> LOCATION: (3431)..(3433)
<223> OTHER INFORMATION: UNA monomer
<220> FEATURE:
<221> NAME/KEY: modified_base
<222> LOCATION: (3435)..(3435)
<223> OTHER INFORMATION: UNA monomer
<220> FEATURE:
<221> NAME/KEY: modified_base
<222> LOCATION: (3442)..(3442)
<223> OTHER INFORMATION: UNA monomer
<220> FEATURE:
<221> NAME/KEY: modified_base
<222> LOCATION: (3447)..(3448)
<223> OTHER INFORMATION: UNA monomer
<220> FEATURE:
```

-continued

```
<221> NAME/KEY: modified_base
<222> LOCATION: (3450)..(3450)
<223> OTHER INFORMATION: UNA monomer
<220> FEATURE:
<221> NAME/KEY: modified_base
<222> LOCATION: (3456)..(3456)
<223> OTHER INFORMATION: UNA monomer
<220> FEATURE:
<221> NAME/KEY: modified_base
<222> LOCATION: (3459)..(3459)
<223> OTHER INFORMATION: UNA monomer
<220> FEATURE:
<221> NAME/KEY: modified_base
<222> LOCATION: (3461)..(3461)
<223> OTHER INFORMATION: UNA monomer
<220> FEATURE:
<221> NAME/KEY: modified_base
<222> LOCATION: (3463)..(3463)
<223> OTHER INFORMATION: UNA monomer
<220> FEATURE:
<221> NAME/KEY: modified_base
<222> LOCATION: (3466)..(3466)
<223> OTHER INFORMATION: UNA monomer
<220> FEATURE:
<221> NAME/KEY: modified_base
<222> LOCATION: (3469)..(3469)
<223> OTHER INFORMATION: UNA monomer
<220> FEATURE:
<221> NAME/KEY: modified_base
<222> LOCATION: (3473)..(3473)
<223> OTHER INFORMATION: UNA monomer
<220> FEATURE:
<221> NAME/KEY: modified_base
<222> LOCATION: (3478)..(3478)
<223> OTHER INFORMATION: UNA monomer
<220> FEATURE:
<221> NAME/KEY: modified_base
<222> LOCATION: (3480)..(3480)
<223> OTHER INFORMATION: UNA monomer
<220> FEATURE:
<221> NAME/KEY: modified_base
<222> LOCATION: (3482)..(3482)
<223> OTHER INFORMATION: UNA monomer
<220> FEATURE:
<221> NAME/KEY: modified_base
<222> LOCATION: (3489)..(3490)
<223> OTHER INFORMATION: UNA monomer
<220> FEATURE:
<221> NAME/KEY: modified_base
<222> LOCATION: (3493)..(3493)
<223> OTHER INFORMATION: UNA monomer
<220> FEATURE:
<221> NAME/KEY: modified_base
<222> LOCATION: (3495)..(3495)
<223> OTHER INFORMATION: UNA monomer
<220> FEATURE:
<221> NAME/KEY: modified_base
<222> LOCATION: (3500)..(3500)
<223> OTHER INFORMATION: UNA monomer
<220> FEATURE:
<221> NAME/KEY: modified_base
<222> LOCATION: (3503)..(3504)
<223> OTHER INFORMATION: UNA monomer
<220> FEATURE:
<221> NAME/KEY: modified_base
<222> LOCATION: (3510)..(3510)
<223> OTHER INFORMATION: UNA monomer
<220> FEATURE:
<221> NAME/KEY: modified_base
<222> LOCATION: (3513)..(3513)
<223> OTHER INFORMATION: UNA monomer
<220> FEATURE:
<221> NAME/KEY: modified_base
<222> LOCATION: (3515)..(3515)
<223> OTHER INFORMATION: UNA monomer
<220> FEATURE:
<221> NAME/KEY: modified_base
<222> LOCATION: (3521)..(3522)
<223> OTHER INFORMATION: UNA monomer
```

-continued

```
<220> FEATURE:
<221> NAME/KEY: modified_base
<222> LOCATION: (3524)..(3524)
<223> OTHER INFORMATION: UNA monomer
<220> FEATURE:
<221> NAME/KEY: modified_base
<222> LOCATION: (3529)..(3529)
<223> OTHER INFORMATION: UNA monomer
<220> FEATURE:
<221> NAME/KEY: modified_base
<222> LOCATION: (3536)..(3538)
<223> OTHER INFORMATION: UNA monomer
<220> FEATURE:
<221> NAME/KEY: modified_base
<222> LOCATION: (3545)..(3545)
<223> OTHER INFORMATION: UNA monomer
<220> FEATURE:
<221> NAME/KEY: modified_base
<222> LOCATION: (3547)..(3547)
<223> OTHER INFORMATION: UNA monomer
<220> FEATURE:
<221> NAME/KEY: modified_base
<222> LOCATION: (3549)..(3549)
<223> OTHER INFORMATION: UNA monomer
<220> FEATURE:
<221> NAME/KEY: modified_base
<222> LOCATION: (3552)..(3552)
<223> OTHER INFORMATION: UNA monomer
<220> FEATURE:
<221> NAME/KEY: modified_base
<222> LOCATION: (3558)..(3558)
<223> OTHER INFORMATION: UNA monomer
<220> FEATURE:
<221> NAME/KEY: modified_base
<222> LOCATION: (3561)..(3562)
<223> OTHER INFORMATION: UNA monomer
<220> FEATURE:
<221> NAME/KEY: modified_base
<222> LOCATION: (3564)..(3564)
<223> OTHER INFORMATION: UNA monomer
<220> FEATURE:
<221> NAME/KEY: modified_base
<222> LOCATION: (3567)..(3567)
<223> OTHER INFORMATION: UNA monomer
<220> FEATURE:
<221> NAME/KEY: modified_base
<222> LOCATION: (3570)..(3572)
<223> OTHER INFORMATION: UNA monomer
<220> FEATURE:
<221> NAME/KEY: modified_base
<222> LOCATION: (3576)..(3576)
<223> OTHER INFORMATION: UNA monomer
<220> FEATURE:
<221> NAME/KEY: modified_base
<222> LOCATION: (3579)..(3579)
<223> OTHER INFORMATION: UNA monomer
<220> FEATURE:
<221> NAME/KEY: modified_base
<222> LOCATION: (3587)..(3587)
<223> OTHER INFORMATION: UNA monomer
<220> FEATURE:
<221> NAME/KEY: modified_base
<222> LOCATION: (3591)..(3591)
<223> OTHER INFORMATION: UNA monomer
<220> FEATURE:
<221> NAME/KEY: modified_base
<222> LOCATION: (3598)..(3599)
<223> OTHER INFORMATION: UNA monomer
<220> FEATURE:
<221> NAME/KEY: modified_base
<222> LOCATION: (3601)..(3603)
<223> OTHER INFORMATION: UNA monomer
<220> FEATURE:
<221> NAME/KEY: modified_base
<222> LOCATION: (3608)..(3608)
<223> OTHER INFORMATION: UNA monomer
<220> FEATURE:
<221> NAME/KEY: modified_base
<222> LOCATION: (3611)..(3611)
```

```
<223> OTHER INFORMATION: UNA monomer
<220> FEATURE:
<221> NAME/KEY: modified_base
<222> LOCATION: (3623)..(3623)
<223> OTHER INFORMATION: UNA monomer
<220> FEATURE:
<221> NAME/KEY: modified_base
<222> LOCATION: (3635)..(3635)
<223> OTHER INFORMATION: UNA monomer
<220> FEATURE:
<221> NAME/KEY: modified_base
<222> LOCATION: (3644)..(3644)
<223> OTHER INFORMATION: UNA monomer
<220> FEATURE:
<221> NAME/KEY: modified_base
<222> LOCATION: (3649)..(3650)
<223> OTHER INFORMATION: UNA monomer
<220> FEATURE:
<221> NAME/KEY: modified_base
<222> LOCATION: (3663)..(3663)
<223> OTHER INFORMATION: UNA monomer
<220> FEATURE:
<221> NAME/KEY: modified_base
<222> LOCATION: (3666)..(3666)
<223> OTHER INFORMATION: UNA monomer
<220> FEATURE:
<221> NAME/KEY: modified_base
<222> LOCATION: (3669)..(3669)
<223> OTHER INFORMATION: UNA monomer
<220> FEATURE:
<221> NAME/KEY: modified_base
<222> LOCATION: (3677)..(3677)
<223> OTHER INFORMATION: UNA monomer
<220> FEATURE:
<221> NAME/KEY: modified_base
<222> LOCATION: (3681)..(3681)
<223> OTHER INFORMATION: UNA monomer
<220> FEATURE:
<221> NAME/KEY: modified_base
<222> LOCATION: (3689)..(3689)
<223> OTHER INFORMATION: UNA monomer
<220> FEATURE:
<221> NAME/KEY: modified_base
<222> LOCATION: (3702)..(3705)
<223> OTHER INFORMATION: UNA monomer
<220> FEATURE:
<221> NAME/KEY: modified_base
<222> LOCATION: (3708)..(3708)
<223> OTHER INFORMATION: UNA monomer
<220> FEATURE:
<221> NAME/KEY: modified_base
<222> LOCATION: (3710)..(3710)
<223> OTHER INFORMATION: UNA monomer
<220> FEATURE:
<221> NAME/KEY: modified_base
<222> LOCATION: (3714)..(3714)
<223> OTHER INFORMATION: UNA monomer
<220> FEATURE:
<221> NAME/KEY: modified_base
<222> LOCATION: (3722)..(3723)
<223> OTHER INFORMATION: UNA monomer
<220> FEATURE:
<221> NAME/KEY: modified_base
<222> LOCATION: (3726)..(3726)
<223> OTHER INFORMATION: UNA monomer
<220> FEATURE:
<221> NAME/KEY: modified_base
<222> LOCATION: (3739)..(3741)
<223> OTHER INFORMATION: UNA monomer
<220> FEATURE:
<221> NAME/KEY: modified_base
<222> LOCATION: (3743)..(3745)
<223> OTHER INFORMATION: UNA monomer
<220> FEATURE:
<221> NAME/KEY: modified_base
<222> LOCATION: (3747)..(3747)
<223> OTHER INFORMATION: UNA monomer
<220> FEATURE:
<221> NAME/KEY: modified_base
```

```
<222> LOCATION: (3756)..(3756)
<223> OTHER INFORMATION: UNA monomer
<220> FEATURE:
<221> NAME/KEY: modified_base
<222> LOCATION: (3759)..(3761)
<223> OTHER INFORMATION: UNA monomer
<220> FEATURE:
<221> NAME/KEY: modified_base
<222> LOCATION: (3765)..(3766)
<223> OTHER INFORMATION: UNA monomer
<220> FEATURE:
<221> NAME/KEY: modified_base
<222> LOCATION: (3768)..(3768)
<223> OTHER INFORMATION: UNA monomer
<220> FEATURE:
<221> NAME/KEY: modified_base
<222> LOCATION: (3775)..(3775)
<223> OTHER INFORMATION: UNA monomer
<220> FEATURE:
<221> NAME/KEY: modified_base
<222> LOCATION: (3779)..(3779)
<223> OTHER INFORMATION: UNA monomer
<220> FEATURE:
<221> NAME/KEY: modified_base
<222> LOCATION: (3783)..(3783)
<223> OTHER INFORMATION: UNA monomer
<220> FEATURE:
<221> NAME/KEY: modified_base
<222> LOCATION: (3788)..(3788)
<223> OTHER INFORMATION: UNA monomer
<220> FEATURE:
<221> NAME/KEY: modified_base
<222> LOCATION: (3798)..(3798)
<223> OTHER INFORMATION: UNA monomer
<220> FEATURE:
<221> NAME/KEY: modified_base
<222> LOCATION: (3807)..(3807)
<223> OTHER INFORMATION: UNA monomer
<220> FEATURE:
<221> NAME/KEY: modified_base
<222> LOCATION: (3821)..(3821)
<223> OTHER INFORMATION: UNA monomer
<220> FEATURE:
<221> NAME/KEY: modified_base
<222> LOCATION: (3840)..(3840)
<223> OTHER INFORMATION: UNA monomer
<220> FEATURE:
<221> NAME/KEY: modified_base
<222> LOCATION: (3844)..(3844)
<223> OTHER INFORMATION: UNA monomer
<220> FEATURE:
<221> NAME/KEY: modified_base
<222> LOCATION: (3846)..(3846)
<223> OTHER INFORMATION: UNA monomer
<220> FEATURE:
<221> NAME/KEY: modified_base
<222> LOCATION: (3849)..(3849)
<223> OTHER INFORMATION: UNA monomer
<220> FEATURE:
<221> NAME/KEY: modified_base
<222> LOCATION: (3851)..(3851)
<223> OTHER INFORMATION: UNA monomer
<220> FEATURE:
<221> NAME/KEY: modified_base
<222> LOCATION: (3857)..(3858)
<223> OTHER INFORMATION: UNA monomer
<220> FEATURE:
<221> NAME/KEY: modified_base
<222> LOCATION: (3860)..(3860)
<223> OTHER INFORMATION: UNA monomer
<220> FEATURE:
<221> NAME/KEY: modified_base
<222> LOCATION: (3866)..(3866)
<223> OTHER INFORMATION: UNA monomer
<220> FEATURE:
<221> NAME/KEY: modified_base
<222> LOCATION: (3870)..(3870)
<223> OTHER INFORMATION: UNA monomer
<220> FEATURE:
```

-continued

```
<221> NAME/KEY: modified_base
<222> LOCATION: (3874)..(3874)
<223> OTHER INFORMATION: UNA monomer
<220> FEATURE:
<221> NAME/KEY: modified_base
<222> LOCATION: (3876)..(3876)
<223> OTHER INFORMATION: UNA monomer
<220> FEATURE:
<221> NAME/KEY: modified_base
<222> LOCATION: (3879)..(3879)
<223> OTHER INFORMATION: UNA monomer
<220> FEATURE:
<221> NAME/KEY: modified_base
<222> LOCATION: (3881)..(3882)
<223> OTHER INFORMATION: UNA monomer
<220> FEATURE:
<221> NAME/KEY: modified_base
<222> LOCATION: (3886)..(3886)
<223> OTHER INFORMATION: UNA monomer
<220> FEATURE:
<221> NAME/KEY: modified_base
<222> LOCATION: (3889)..(3890)
<223> OTHER INFORMATION: UNA monomer
<220> FEATURE:
<221> NAME/KEY: modified_base
<222> LOCATION: (3893)..(3893)
<223> OTHER INFORMATION: UNA monomer
<220> FEATURE:
<221> NAME/KEY: modified_base
<222> LOCATION: (3898)..(3899)
<223> OTHER INFORMATION: UNA monomer
<220> FEATURE:
<221> NAME/KEY: modified_base
<222> LOCATION: (3901)..(3901)
<223> OTHER INFORMATION: UNA monomer
<220> FEATURE:
<221> NAME/KEY: modified_base
<222> LOCATION: (3912)..(3912)
<223> OTHER INFORMATION: UNA monomer
<220> FEATURE:
<221> NAME/KEY: modified_base
<222> LOCATION: (3914)..(3917)
<223> OTHER INFORMATION: UNA monomer
<220> FEATURE:
<221> NAME/KEY: modified_base
<222> LOCATION: (3921)..(3922)
<223> OTHER INFORMATION: UNA monomer
<220> FEATURE:
<221> NAME/KEY: modified_base
<222> LOCATION: (3924)..(3924)
<223> OTHER INFORMATION: UNA monomer
<220> FEATURE:
<221> NAME/KEY: modified_base
<222> LOCATION: (3927)..(3927)
<223> OTHER INFORMATION: UNA monomer
<220> FEATURE:
<221> NAME/KEY: modified_base
<222> LOCATION: (3932)..(3932)
<223> OTHER INFORMATION: UNA monomer
<220> FEATURE:
<221> NAME/KEY: modified_base
<222> LOCATION: (3938)..(3938)
<223> OTHER INFORMATION: UNA monomer
<220> FEATURE:
<221> NAME/KEY: modified_base
<222> LOCATION: (3948)..(3948)
<223> OTHER INFORMATION: UNA monomer
<220> FEATURE:
<221> NAME/KEY: modified_base
<222> LOCATION: (3957)..(3957)
<223> OTHER INFORMATION: UNA monomer
<220> FEATURE:
<221> NAME/KEY: modified_base
<222> LOCATION: (3959)..(3959)
<223> OTHER INFORMATION: UNA monomer
<220> FEATURE:
<221> NAME/KEY: modified_base
<222> LOCATION: (3965)..(3965)
<223> OTHER INFORMATION: UNA monomer
```

-continued

```
<220> FEATURE:
<221> NAME/KEY: modified_base
<222> LOCATION: (3967)..(3967)
<223> OTHER INFORMATION: UNA monomer
<220> FEATURE:
<221> NAME/KEY: modified_base
<222> LOCATION: (3970)..(3970)
<223> OTHER INFORMATION: UNA monomer
<220> FEATURE:
<221> NAME/KEY: modified_base
<222> LOCATION: (3972)..(3972)
<223> OTHER INFORMATION: UNA monomer
<220> FEATURE:
<221> NAME/KEY: modified_base
<222> LOCATION: (3975)..(3975)
<223> OTHER INFORMATION: UNA monomer
<220> FEATURE:
<221> NAME/KEY: modified_base
<222> LOCATION: (3979)..(3979)
<223> OTHER INFORMATION: UNA monomer
<220> FEATURE:
<221> NAME/KEY: modified_base
<222> LOCATION: (3992)..(3992)
<223> OTHER INFORMATION: UNA monomer
<220> FEATURE:
<221> NAME/KEY: modified_base
<222> LOCATION: (4003)..(4005)
<223> OTHER INFORMATION: UNA monomer
<220> FEATURE:
<221> NAME/KEY: modified_base
<222> LOCATION: (4013)..(4013)
<223> OTHER INFORMATION: UNA monomer
<220> FEATURE:
<221> NAME/KEY: modified_base
<222> LOCATION: (4015)..(4017)
<223> OTHER INFORMATION: UNA monomer
<220> FEATURE:
<221> NAME/KEY: modified_base
<222> LOCATION: (4020)..(4020)
<223> OTHER INFORMATION: UNA monomer
<220> FEATURE:
<221> NAME/KEY: modified_base
<222> LOCATION: (4022)..(4024)
<223> OTHER INFORMATION: UNA monomer
<220> FEATURE:
<221> NAME/KEY: modified_base
<222> LOCATION: (4035)..(4036)
<223> OTHER INFORMATION: UNA monomer
<220> FEATURE:
<221> NAME/KEY: modified_base
<222> LOCATION: (4041)..(4043)
<223> OTHER INFORMATION: UNA monomer
<220> FEATURE:
<221> NAME/KEY: modified_base
<222> LOCATION: (4047)..(4047)
<223> OTHER INFORMATION: UNA monomer
<220> FEATURE:
<221> NAME/KEY: modified_base
<222> LOCATION: (4056)..(4056)
<223> OTHER INFORMATION: UNA monomer
<220> FEATURE:
<221> NAME/KEY: modified_base
<222> LOCATION: (4062)..(4062)
<223> OTHER INFORMATION: UNA monomer
<220> FEATURE:
<221> NAME/KEY: modified_base
<222> LOCATION: (4064)..(4064)
<223> OTHER INFORMATION: UNA monomer
<220> FEATURE:
<221> NAME/KEY: modified_base
<222> LOCATION: (4067)..(4068)
<223> OTHER INFORMATION: UNA monomer
<220> FEATURE:
<221> NAME/KEY: modified_base
<222> LOCATION: (4077)..(4077)
<223> OTHER INFORMATION: UNA monomer
<220> FEATURE:
<221> NAME/KEY: modified_base
<222> LOCATION: (4082)..(4082)
```

```
<223> OTHER INFORMATION: UNA monomer
<220> FEATURE:
<221> NAME/KEY: modified_base
<222> LOCATION: (4084)..(4084)
<223> OTHER INFORMATION: UNA monomer
<220> FEATURE:
<221> NAME/KEY: modified_base
<222> LOCATION: (4092)..(4092)
<223> OTHER INFORMATION: UNA monomer
<220> FEATURE:
<221> NAME/KEY: modified_base
<222> LOCATION: (4095)..(4096)
<223> OTHER INFORMATION: UNA monomer
<220> FEATURE:
<221> NAME/KEY: modified_base
<222> LOCATION: (4098)..(4098)
<223> OTHER INFORMATION: UNA monomer
<220> FEATURE:
<221> NAME/KEY: modified_base
<222> LOCATION: (4104)..(4105)
<223> OTHER INFORMATION: UNA monomer
<220> FEATURE:
<221> NAME/KEY: modified_base
<222> LOCATION: (4110)..(4110)
<223> OTHER INFORMATION: UNA monomer
<220> FEATURE:
<221> NAME/KEY: modified_base
<222> LOCATION: (4113)..(4114)
<223> OTHER INFORMATION: UNA monomer
<220> FEATURE:
<221> NAME/KEY: modified_base
<222> LOCATION: (4117)..(4117)
<223> OTHER INFORMATION: UNA monomer
<220> FEATURE:
<221> NAME/KEY: modified_base
<222> LOCATION: (4119)..(4119)
<223> OTHER INFORMATION: UNA monomer
<220> FEATURE:
<221> NAME/KEY: modified_base
<222> LOCATION: (4123)..(4123)
<223> OTHER INFORMATION: UNA monomer
<220> FEATURE:
<221> NAME/KEY: modified_base
<222> LOCATION: (4125)..(4125)
<223> OTHER INFORMATION: UNA monomer
<220> FEATURE:
<221> NAME/KEY: modified_base
<222> LOCATION: (4130)..(4130)
<223> OTHER INFORMATION: UNA monomer
<220> FEATURE:
<221> NAME/KEY: modified_base
<222> LOCATION: (4137)..(4137)
<223> OTHER INFORMATION: UNA monomer
<220> FEATURE:
<221> NAME/KEY: modified_base
<222> LOCATION: (4140)..(4143)
<223> OTHER INFORMATION: UNA monomer
<220> FEATURE:
<221> NAME/KEY: modified_base
<222> LOCATION: (4148)..(4148)
<223> OTHER INFORMATION: UNA monomer
<220> FEATURE:
<221> NAME/KEY: modified_base
<222> LOCATION: (4154)..(4154)
<223> OTHER INFORMATION: UNA monomer
<220> FEATURE:
<221> NAME/KEY: modified_base
<222> LOCATION: (4157)..(4158)
<223> OTHER INFORMATION: UNA monomer
<220> FEATURE:
<221> NAME/KEY: modified_base
<222> LOCATION: (4160)..(4160)
<223> OTHER INFORMATION: UNA monomer
<220> FEATURE:
<221> NAME/KEY: modified_base
<222> LOCATION: (4167)..(4167)
<223> OTHER INFORMATION: UNA monomer
<220> FEATURE:
<221> NAME/KEY: modified_base
```

```
<222> LOCATION: (4172)..(4172)
<223> OTHER INFORMATION: UNA monomer
<220> FEATURE:
<221> NAME/KEY: modified_base
<222> LOCATION: (4174)..(4176)
<223> OTHER INFORMATION: UNA monomer
<220> FEATURE:
<221> NAME/KEY: modified_base
<222> LOCATION: (4179)..(4179)
<223> OTHER INFORMATION: UNA monomer
<220> FEATURE:
<221> NAME/KEY: modified_base
<222> LOCATION: (4192)..(4192)
<223> OTHER INFORMATION: UNA monomer
<220> FEATURE:
<221> NAME/KEY: modified_base
<222> LOCATION: (4200)..(4202)
<223> OTHER INFORMATION: UNA monomer
<220> FEATURE:
<221> NAME/KEY: modified_base
<222> LOCATION: (4208)..(4209)
<223> OTHER INFORMATION: UNA monomer
<220> FEATURE:
<221> NAME/KEY: modified_base
<222> LOCATION: (4222)..(4223)
<223> OTHER INFORMATION: UNA monomer
<220> FEATURE:
<221> NAME/KEY: modified_base
<222> LOCATION: (4226)..(4227)
<223> OTHER INFORMATION: UNA monomer
<220> FEATURE:
<221> NAME/KEY: modified_base
<222> LOCATION: (4230)..(4230)
<223> OTHER INFORMATION: UNA monomer
<220> FEATURE:
<221> NAME/KEY: modified_base
<222> LOCATION: (4235)..(4236)
<223> OTHER INFORMATION: UNA monomer
<220> FEATURE:
<221> NAME/KEY: modified_base
<222> LOCATION: (4241)..(4241)
<223> OTHER INFORMATION: UNA monomer
<220> FEATURE:
<221> NAME/KEY: modified_base
<222> LOCATION: (4248)..(4250)
<223> OTHER INFORMATION: UNA monomer
<220> FEATURE:
<221> NAME/KEY: modified_base
<222> LOCATION: (4254)..(4254)
<223> OTHER INFORMATION: UNA monomer
<220> FEATURE:
<221> NAME/KEY: modified_base
<222> LOCATION: (4260)..(4260)
<223> OTHER INFORMATION: UNA monomer
<220> FEATURE:
<221> NAME/KEY: modified_base
<222> LOCATION: (4263)..(4263)
<223> OTHER INFORMATION: UNA monomer
<220> FEATURE:
<221> NAME/KEY: modified_base
<222> LOCATION: (4265)..(4265)
<223> OTHER INFORMATION: UNA monomer
<220> FEATURE:
<221> NAME/KEY: modified_base
<222> LOCATION: (4268)..(4270)
<223> OTHER INFORMATION: UNA monomer
<220> FEATURE:
<221> NAME/KEY: modified_base
<222> LOCATION: (4273)..(4273)
<223> OTHER INFORMATION: UNA monomer
<220> FEATURE:
<221> NAME/KEY: modified_base
<222> LOCATION: (4275)..(4275)
<223> OTHER INFORMATION: UNA monomer
<220> FEATURE:
<221> NAME/KEY: modified_base
<222> LOCATION: (4280)..(4282)
<223> OTHER INFORMATION: UNA monomer
<220> FEATURE:
```

-continued

```
<221> NAME/KEY: modified_base
<222> LOCATION: (4284)..(4284)
<223> OTHER INFORMATION: UNA monomer
<220> FEATURE:
<221> NAME/KEY: modified_base
<222> LOCATION: (4290)..(4290)
<223> OTHER INFORMATION: UNA monomer
<220> FEATURE:
<221> NAME/KEY: modified_base
<222> LOCATION: (4294)..(4295)
<223> OTHER INFORMATION: UNA monomer
<220> FEATURE:
<221> NAME/KEY: modified_base
<222> LOCATION: (4302)..(4302)
<223> OTHER INFORMATION: UNA monomer
<220> FEATURE:
<221> NAME/KEY: modified_base
<222> LOCATION: (4309)..(4309)
<223> OTHER INFORMATION: UNA monomer
<220> FEATURE:
<221> NAME/KEY: modified_base
<222> LOCATION: (4314)..(4314)
<223> OTHER INFORMATION: UNA monomer
<220> FEATURE:
<221> NAME/KEY: modified_base
<222> LOCATION: (4316)..(4317)
<223> OTHER INFORMATION: UNA monomer
<220> FEATURE:
<221> NAME/KEY: modified_base
<222> LOCATION: (4320)..(4320)
<223> OTHER INFORMATION: UNA monomer
<220> FEATURE:
<221> NAME/KEY: modified_base
<222> LOCATION: (4326)..(4328)
<223> OTHER INFORMATION: UNA monomer
<220> FEATURE:
<221> NAME/KEY: modified_base
<222> LOCATION: (4332)..(4333)
<223> OTHER INFORMATION: UNA monomer
<220> FEATURE:
<221> NAME/KEY: modified_base
<222> LOCATION: (4335)..(4335)
<223> OTHER INFORMATION: UNA monomer
<220> FEATURE:
<221> NAME/KEY: modified_base
<222> LOCATION: (4347)..(4347)
<223> OTHER INFORMATION: UNA monomer
<220> FEATURE:
<221> NAME/KEY: modified_base
<222> LOCATION: (4351)..(4351)
<223> OTHER INFORMATION: UNA monomer
<220> FEATURE:
<221> NAME/KEY: modified_base
<222> LOCATION: (4355)..(4355)
<223> OTHER INFORMATION: UNA monomer
<220> FEATURE:
<221> NAME/KEY: modified_base
<222> LOCATION: (4357)..(4357)
<223> OTHER INFORMATION: UNA monomer
<220> FEATURE:
<221> NAME/KEY: modified_base
<222> LOCATION: (4362)..(4362)
<223> OTHER INFORMATION: UNA monomer
<220> FEATURE:
<221> NAME/KEY: modified_base
<222> LOCATION: (4364)..(4365)
<223> OTHER INFORMATION: UNA monomer
<220> FEATURE:
<221> NAME/KEY: modified_base
<222> LOCATION: (4369)..(4369)
<223> OTHER INFORMATION: UNA monomer
<220> FEATURE:
<221> NAME/KEY: modified_base
<222> LOCATION: (4371)..(4374)
<223> OTHER INFORMATION: UNA monomer
<220> FEATURE:
<221> NAME/KEY: modified_base
<222> LOCATION: (4376)..(4377)
<223> OTHER INFORMATION: UNA monomer
```

```
<220> FEATURE:
<221> NAME/KEY: modified_base
<222> LOCATION: (4380)..(4380)
<223> OTHER INFORMATION: UNA monomer
<220> FEATURE:
<221> NAME/KEY: modified_base
<222> LOCATION: (4387)..(4388)
<223> OTHER INFORMATION: UNA monomer
<220> FEATURE:
<221> NAME/KEY: modified_base
<222> LOCATION: (4390)..(4390)
<223> OTHER INFORMATION: UNA monomer
<220> FEATURE:
<221> NAME/KEY: modified_base
<222> LOCATION: (4392)..(4396)
<223> OTHER INFORMATION: UNA monomer
<220> FEATURE:
<221> NAME/KEY: modified_base
<222> LOCATION: (4402)..(4403)
<223> OTHER INFORMATION: UNA monomer
<220> FEATURE:
<221> NAME/KEY: modified_base
<222> LOCATION: (4406)..(4406)
<223> OTHER INFORMATION: UNA monomer
<220> FEATURE:
<221> NAME/KEY: modified_base
<222> LOCATION: (4419)..(4419)
<223> OTHER INFORMATION: UNA monomer
<220> FEATURE:
<221> NAME/KEY: modified_base
<222> LOCATION: (4422)..(4422)
<223> OTHER INFORMATION: UNA monomer
<220> FEATURE:
<221> NAME/KEY: modified_base
<222> LOCATION: (4431)..(4431)
<223> OTHER INFORMATION: UNA monomer
<220> FEATURE:
<221> NAME/KEY: modified_base
<222> LOCATION: (4433)..(4433)
<223> OTHER INFORMATION: UNA monomer
<220> FEATURE:
<221> NAME/KEY: modified_base
<222> LOCATION: (4436)..(4439)
<223> OTHER INFORMATION: UNA monomer
<220> FEATURE:
<221> NAME/KEY: modified_base
<222> LOCATION: (4442)..(4443)
<223> OTHER INFORMATION: UNA monomer
<220> FEATURE:
<221> NAME/KEY: modified_base
<222> LOCATION: (4449)..(4449)
<223> OTHER INFORMATION: UNA monomer
<220> FEATURE:
<221> NAME/KEY: modified_base
<222> LOCATION: (4451)..(4452)
<223> OTHER INFORMATION: UNA monomer
<220> FEATURE:
<221> NAME/KEY: modified_base
<222> LOCATION: (4454)..(4456)
<223> OTHER INFORMATION: UNA monomer
<220> FEATURE:
<221> NAME/KEY: modified_base
<222> LOCATION: (4464)..(4465)
<223> OTHER INFORMATION: UNA monomer
<220> FEATURE:
<221> NAME/KEY: modified_base
<222> LOCATION: (4467)..(4467)
<223> OTHER INFORMATION: UNA monomer
<220> FEATURE:
<221> NAME/KEY: modified_base
<222> LOCATION: (4469)..(4470)
<223> OTHER INFORMATION: UNA monomer
<220> FEATURE:
<221> NAME/KEY: modified_base
<222> LOCATION: (4473)..(4473)
<223> OTHER INFORMATION: UNA monomer
<220> FEATURE:
<221> NAME/KEY: modified_base
<222> LOCATION: (4475)..(4476)
```

```
<223> OTHER INFORMATION: UNA monomer
<220> FEATURE:
<221> NAME/KEY: modified_base
<222> LOCATION: (4483)..(4483)
<223> OTHER INFORMATION: UNA monomer
<220> FEATURE:
<221> NAME/KEY: modified_base
<222> LOCATION: (4488)..(4489)
<223> OTHER INFORMATION: UNA monomer
<220> FEATURE:
<221> NAME/KEY: modified_base
<222> LOCATION: (4499)..(4500)
<223> OTHER INFORMATION: UNA monomer
<220> FEATURE:
<221> NAME/KEY: modified_base
<222> LOCATION: (4508)..(4508)
<223> OTHER INFORMATION: UNA monomer
<220> FEATURE:
<221> NAME/KEY: modified_base
<222> LOCATION: (4515)..(4515)
<223> OTHER INFORMATION: UNA monomer
<220> FEATURE:
<221> NAME/KEY: modified_base
<222> LOCATION: (4521)..(4521)
<223> OTHER INFORMATION: UNA monomer
<220> FEATURE:
<221> NAME/KEY: modified_base
<222> LOCATION: (4528)..(4528)
<223> OTHER INFORMATION: UNA monomer
<220> FEATURE:
<221> NAME/KEY: modified_base
<222> LOCATION: (4531)..(4531)
<223> OTHER INFORMATION: UNA monomer
<220> FEATURE:
<221> NAME/KEY: modified_base
<222> LOCATION: (4533)..(4533)
<223> OTHER INFORMATION: UNA monomer
<220> FEATURE:
<221> NAME/KEY: modified_base
<222> LOCATION: (4536)..(4538)
<223> OTHER INFORMATION: UNA monomer
<220> FEATURE:
<221> NAME/KEY: modified_base
<222> LOCATION: (4543)..(4543)
<223> OTHER INFORMATION: UNA monomer
<220> FEATURE:
<221> NAME/KEY: modified_base
<222> LOCATION: (4545)..(4545)
<223> OTHER INFORMATION: UNA monomer
<220> FEATURE:
<221> NAME/KEY: modified_base
<222> LOCATION: (4558)..(4558)
<223> OTHER INFORMATION: UNA monomer
<220> FEATURE:
<221> NAME/KEY: modified_base
<222> LOCATION: (4561)..(4561)
<223> OTHER INFORMATION: UNA monomer
<220> FEATURE:
<221> NAME/KEY: modified_base
<222> LOCATION: (4565)..(4566)
<223> OTHER INFORMATION: UNA monomer
<220> FEATURE:
<221> NAME/KEY: modified_base
<222> LOCATION: (4569)..(4569)
<223> OTHER INFORMATION: UNA monomer
<220> FEATURE:
<221> NAME/KEY: modified_base
<222> LOCATION: (4572)..(4572)
<223> OTHER INFORMATION: UNA monomer
<220> FEATURE:
<221> NAME/KEY: modified_base
<222> LOCATION: (4574)..(4575)
<223> OTHER INFORMATION: UNA monomer
<220> FEATURE:
<221> NAME/KEY: modified_base
<222> LOCATION: (4577)..(4578)
<223> OTHER INFORMATION: UNA monomer
<220> FEATURE:
<221> NAME/KEY: modified_base
```

```
<222> LOCATION: (4586)..(4588)
<223> OTHER INFORMATION: UNA monomer
<220> FEATURE:
<221> NAME/KEY: modified_base
<222> LOCATION: (4590)..(4590)
<223> OTHER INFORMATION: UNA monomer
<220> FEATURE:
<221> NAME/KEY: modified_base
<222> LOCATION: (4593)..(4595)
<223> OTHER INFORMATION: UNA monomer
<220> FEATURE:
<221> NAME/KEY: modified_base
<222> LOCATION: (4597)..(4597)
<223> OTHER INFORMATION: UNA monomer

<400> SEQUENCE: 151
augggacaca guaaacagau ucgaauuuua cuucugaacg aaauggagaa acuggaaaag      60
acccucuuca gacuugaaca agggauagag cuacaguucc gauuaggccc aacuuuacag     120
ggaaaagcag uuaccgugua acaaauuac ccauuccug gagaaacauu aauagagaa        180 aaauuccguu cucuggauug ggaaaauccaa acagaaagag aagaugauuc ugauaaauac    240
uguaaacuua aucugcaaca aucugguuca uuucaguauu auuccuuca aggaaaugag     300 aaaaguggug gagguuacau aguuuggac cccauuuuac guguuggugc ugauaaucau     360
gugcuacccu uggacugugu uacucuucag acauuuuag cuaaguguuu gggaccuuuu    420
gaugaauggg aaagcagacu uagggguugca aagaaucag gcuacaacau gauucauuuu   480
accccauugc agacucuugg acuaucuagg ucaugcuacu cccuugccaa ucaguuagaa   540
uuaaauccug acuuuucaag accaauaga aaguauaccu ggaaugaugu uggacagcua   600
guggaaaaau uaaaaaagga auggaauguu auuuguauua cugauguugu cuacaaucau 660
acugcugcua auaguaaaug gauccaggaa caucccagaau gugccuauaa ucuugugaau 720
ucuccacacu uaaaaccugc cugggucuua gacagagcac uuuggcguuu cuccugugau 780
guugcagaag ggaaauacaa agaaaggga auaccgcccu ugauugaaaa ugaucaccau 840
augaauucca uccgaaaaau aauuugggag gauauuuuc caaagcuuaa acucugggaa 900 uuuucuucaag uagaugucaa caaagcgguu gagcaauuua gaagacuucu acacaagaa 960 aauaggcgag uaccaaguc ugauccaaac caacaccuua cgauauauca agauccgaa 1020 uacagacggu uugcuguac uguaagauaug aacauugcac uaacgacuuu cauaccacau 1080
gacaaggggc cagcagcaau ugaagaaugc uguaauuggu ucauaaaag aauggaggaa 1140 uuaaauucag agaagcaucg acucauuaac uaucaucagg aacaggcagu uaauugccuu 1200
uugggaaaug uguuuaugua acgacuggcu ggccauggguc caaaacuagg accgucacu 1260 agaaagcauc cuuuaguauac cagguauuuu acuuucccau uugaagagau agacuucucc 1320
auggaagaau cuaugauuca ucuccauugcccaaau aaagcuuguu uucugauggc acacaaugga 1380
uggguaaugg gagaugauccc ucuucgaaac uuugcugaac ggguucaga aguuaccua  1440 aggagagaac uuauuugcug gggagacagu guuaaauuac gcuauggaau uaaaccagag 1500
gacuguccuu aucucugggc acacaugaaa aaauacacug aaauaacugc aacuauuuuc 1560
cagggaguac gucuugauaa cugccacuca acaccucuuc acguagcuga guacauguug 1620
gaugcugcua ggaauuugca acccaauuua uauguagag cugaacuguu cacaggaagu 1680 gaagaucug acaaugucuu uguuacuaga cugggcauua guuccuuaau aagagaggca 1740
augagugcau auaauaguca ugaagagggc agauuaguuu accgauaugg aggagaaccu 1800 guuggaucu uuguucagcc cuguuugagg ccuuuaaugc cagcuauugc acaugcccug 1860
```

```
uuuauggaua uuacgcauga uaaugagugu ccuauugugc auagaucagc guaugaugcu    1920
cuuccaagua cuacaauugu uucuauggca uguugugcua ugggaaguac aagaggcuau    1980
gaugaauuag ugccucauca gauuucagug guuucugaag aacgguuuua cacuaagugg    2040
aauccugaag cauugccuuc aaacacaggu gaaguuaauu ccaaagcgg cauuauugca     2100 gccaggugug cuaucaguaa acuucaucag gagcuuggag ccaagggu u uauucaggug    2160 uaugggauc aaguugauga agacauagug gcaguaacaa gacacucacc uagcauccau     2220
cagucuguug uggcuguauc uagaacugcu ucaggaauc ccaagacuuc auuuuacagc     2280
aaggaagugc cucaaauguᵍ caucccuggc aaaauugaag aaguaguucu ugaagcuaga    2340
acuauugaga gaaacacgaa accuuauagg aaggaugaga auucaaucaa uggaacacca    2400
gauaucacag uagaaauuag agaacauauu cagcuuaaug aaaguaaaau uguuaaacaa    2460
gcuggaguug ccacaaaagg gcccaaugaa uauuucaag aaauagaauu ugaaaacuug     2520
ucuccaggaa guguuauuau auucagaguu agucuugauc cacaugcaca agucgcuguu    2580
ggaauucuuc gaaaucaucu gacacaauuc agcccucacu uuaaaucugg cagccuagcu    2640
guugacaaug cagauccuau auuaaaaauu ccuuugccuu cucuugccuc cagauuaacu    2700
uuggcugagc uaaaucagau ccuuuaccga ugugaaucag aagaaaagga agauggugga    2760
gggugcuaug acauaccaaa cuggucagcc cuuaaauaug caggucuuca agguuuaaug    2820
ucuguauugg cagaaauaag accaagaau gacuugggc auccuuuuug uaauaauuug     2880
agaucuggag auuggaugau ugacuaugu aguaaccggc uuauuucacg aucaggaacu    2940
auugcugaag uggugaaaug guugcaggcu auguucuucu accugaagca gaucccacgu    3000
uaccuuaucc caugᵍᵘacuu ugaugcuaua uuaauggug cauauaccac ucuucggau     3060 acagcaugga agcagaugᵘс aagcuuugu cagaauggu uuaaccuuugu gaaacaccuu    3120 ucauggguu caguucaacu guguggagua ggaaaauucc cuucccugcc aauucuuuca    3180
ccugcccuaa uggauguacc uuauagguua aaugagauca caaaagaaaa ggagcaaugu    3240
uguguuucuc uagcugcagg cuuaccucau uuuucuucug guauuucg cugcuᵍᵍᵍa     3300 agggauacuu uuauugcacu uagaggᵘᵃᵘᵃ cugcugauua cuggacgcua uguagaagcc    3360
aggaauauua uuuuagcauu ugcgggᵘᵃcc cugaggcaug gucucauucc uaaucuacug    3420
ggugaaggaa uuuaugccag auacaauugu cgggaugcug uguggugᵍᵘᵍ gcugcagugu    3480 auccaggauu acuguaaaau gguccaaaau ggucuagaca uucucaagug cccaguuucc    3540
agaauguauc cuacagauga uucugcuccu uugccugcug gcacacugga ucagccauug    3600
uuugaaguca uacaggaagc aaugcaaaaa cacaugcagg gcauacaguu ccgagaaagg    3660
aaugcugguc cccagauaga ucgaaacaug aaggacgaag guuuaauau aacugcagga    3720 guugaugaag aaacaggauu uguuuaugga ggaaaucguu caauugᵘgg cacauggaug    3780 gauaaaaugg gagaaaguga cagagcuaga acagaggaa ucccagccac accaagagau    3840
gggucugcug uggaauugu gggccugagu aaaucugcug uucgcgguu gcuggaauua    3900 uccaaaaaaa auauuuuccc uuaucaugaa gucacaguaa aaagacaugg aaaggcuaua    3960
aaggucucau augaugagug gaacagaaaa auacaagaca cuuugaaaaa gcuauuucau    4020 guuccgaag acccuucaga uuuaaaugaa aagcauccaa aucugguuca caacguggc    4080 auauacaaag auaguauᵍg agcuucagu ccuggugug acauacagcu caggccuaau     4140
uuuaccauag caauggᵘugu ggccccgag cucuuuacua cagaaaaagc auggaaagcu    4200
uuggagauug cagaaaaaaa auugcuuggu ccccuuggca ugaaaacuuu agauccagau    4260
```

-continued

| | |
|---|---|
| gauaugguuu acugugggaau uuaugacaau gcauuagaca augacaacua caaucuugcu | 4320 |
| aaagguuuca auuaucacca aggaccugag uggcugugge cuauugggua uuucuucgu | 4380 |
| gcaaaauuau auuuuccag auugaugggc ccggagacua cugcaaagac uauaguuug | 4440 |
| guuaaaaug uucuucccg acauuauguu caucuugaga gaucccuug gaaggacuu | 4500 |
| ccagaacuga ccaaugagaa ugcccaguac uguccuuuca gcugugaaac acaagccugg | 4560 |
| ucaaugcua cuauucuuga gacacuuuau gauuuauag | 4599 |

<210> SEQ ID NO 152
<211> LENGTH: 2128
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(4)
<223> OTHER INFORMATION: UNA monomer
<220> FEATURE:
<221> NAME/KEY: modified_base
<222> LOCATION: (2125)..(2127)
<223> OTHER INFORMATION: UNA monomer

<400> SEQUENCE: 152

| | |
|---|---|
| augagggucc uggguggcg cugcggggcg cugcuggcgu gucuccuccu agugcuuccc | 60 |
| gucucagagg caaacuuuug uuuauauuuu agaaugauu uuauauacaa ccgugcaugc | 120 |
| auucuguau uggucggcuu aucuggaugc aauuuuucu auucuauaug cuuuuuguca | 180 |
| aagcaacagg cuucacaagu ccugguuagg aagcgucgug caaauucuuu acuugaagaa | 240 |
| accaaacagg guaaucuuga aagagaaugc aucgaagaac ugugcaauaa agaagaagcc | 300 |
| agggaggucu uugaaaauga cccggaaacg gauuauuuu auccaaaaua cuuaguuugu | 360 |
| cuucgcucuu uucaaacugg guauucacu gcugcacguc agucaacuaa ugcuuauccu | 420 |
| gaccuaagaa gcugugucaa ugccauucca gaccaguguua guccucugcc augcaaugaa | 480 |
| gauggauaua ugagcugcaa agauggaaaa gcuucuuuua cuugcacuug uaaaccaggu | 540 |
| uggcaaggag aaaaguguga auuugacaua aaugaaugca aagaucccuc aaauauaaau | 600 |
| ggagguugca gucaaauuug ugauaauaca ccuggaaguu accacuguuc cuguaaaaau | 660 |
| gguuuuguua ugcuuucaaa uaagaaagau uguaagaug uggaugaaug cucuuugaag | 720 |
| ccaagcauuu guggcacagc ugugugcaag aacaucccag gagauuuuga augugaaugc | 780 |
| cccgaaggcu acagauauaa ucucaaauca aagucuugug aagauauaga ugaaugcucu | 840 |
| gagaacaugu gugcucagcu uugugucaau uacccuggag guuacacuug cuauugugau | 900 |
| gggaagaaag gauucaaacu ugcccaagau cagaagaguu gugaggugu ucagugugc | 960 |
| cuucccuuga accuugacac aaaguaugaa uuacuuuacu uggcggagca guuugcaggg | 1020 |
| guuguuuau auuuaaaauu ucguuugcca gaaaucagca gauuuucagc agaauuugau | 1080 |
| uuccggacau augauucaga aggcgugaua cuguacgcag aaucuaucga ucacucagcg | 1140 |
| uggcuccuga uugcacuucg ugguggaaag auugaaguuc agcuuaagaa ugaacauaca | 1200 |
| uccaaaauca caacuggagg ugauguuauu aauaaugguc uauggaauau ggugucugug | 1260 |
| gaagaauuag aacauagau uagcauuaaa uagcuaaag aagcugugau ggauauaaau | 1320 |
| aaaccuggac cccuuuuuaa gccggaaaau ggauugcugg aaaccaaagu auacuuugca | 1380 |
| ggauucccuc ggaaagugga aaguagaacuc auuaaaccga uuaacccucg ucuagaugga | 1440 |

```
uguauacgaa gcuggaauuu gaugaagcaa ggagcuucug gaauaaagga aauuauucaa    1500
gaaaaacaaa auaagcauug ccugguuacu guggagaagg gcuccuacua uccugguucu    1560
ggaauugcuc aauuucacau agauuauaau aauguaucca gugcugaggg uuggcaugua    1620
aaugugaccu ugaauauucg uccauccacg ggcacuggug uuaugcuugc cuugguuucu    1680
gguaacaaca cagugcccuu ugcuguguuc uuggugggacu ccaccucuga aaaaucacag    1740
gauauucugu uaucuguuga aaauacugua auauaucgga uacaggcccu aagucuaugu    1800
uccgaucaac aaucucaucu ggaauuuaga gucaacagaa acaaucugga guugucgaca    1860
ccacuuaaaa uagaaaccau cucccaugaa gaccuucaaa gacaacuugc cgucuuggac    1920
aaagcaauga aagcaaaagu ggccacauac cuggguggcc uuccagaugu uccauucagu    1980
gccacaccag ugaaugccuu uuauaauggc ugcauggaag ugaauauuaa uggguacag     2040 uuggaucugg augaagccau uucuaaacau aaugauauua gagcucacuc auguccauca    2100
guuuggaaaa agacaaagaa uucuuuaa                                       2128
```

<210> SEQ ID NO 153
<211> LENGTH: 2127
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (8)..(8)
<223> OTHER INFORMATION: UNA monomer
<220> FEATURE:
<221> NAME/KEY: modified_base
<222> LOCATION: (11)..(11)
<223> OTHER INFORMATION: UNA monomer
<220> FEATURE:
<221> NAME/KEY: modified_base
<222> LOCATION: (15)..(15)
<223> OTHER INFORMATION: UNA monomer
<220> FEATURE:
<221> NAME/KEY: modified_base
<222> LOCATION: (22)..(22)
<223> OTHER INFORMATION: UNA monomer
<220> FEATURE:
<221> NAME/KEY: modified_base
<222> LOCATION: (32)..(32)
<223> OTHER INFORMATION: UNA monomer
<220> FEATURE:
<221> NAME/KEY: modified_base
<222> LOCATION: (35)..(35)
<223> OTHER INFORMATION: UNA monomer
<220> FEATURE:
<221> NAME/KEY: modified_base
<222> LOCATION: (40)..(40)
<223> OTHER INFORMATION: UNA monomer
<220> FEATURE:
<221> NAME/KEY: modified_base
<222> LOCATION: (42)..(42)
<223> OTHER INFORMATION: UNA monomer
<220> FEATURE:
<221> NAME/KEY: modified_base
<222> LOCATION: (44)..(44)
<223> OTHER INFORMATION: UNA monomer
<220> FEATURE:
<221> NAME/KEY: modified_base
<222> LOCATION: (47)..(47)
<223> OTHER INFORMATION: UNA monomer
<220> FEATURE:
<221> NAME/KEY: modified_base

```
<222> LOCATION: (50)..(50)
<223> OTHER INFORMATION: UNA monomer
<220> FEATURE:
<221> NAME/KEY: modified_base
<222> LOCATION: (53)..(53)
<223> OTHER INFORMATION: UNA monomer
<220> FEATURE:
<221> NAME/KEY: modified_base
<222> LOCATION: (56)..(57)
<223> OTHER INFORMATION: UNA monomer
<220> FEATURE:
<221> NAME/KEY: modified_base
<222> LOCATION: (62)..(62)
<223> OTHER INFORMATION: UNA monomer
<220> FEATURE:
<221> NAME/KEY: modified_base
<222> LOCATION: (64)..(64)
<223> OTHER INFORMATION: UNA monomer
<220> FEATURE:
<221> NAME/KEY: modified_base
<222> LOCATION: (76)..(79)
<223> OTHER INFORMATION: UNA monomer
<220> FEATURE:
<221> NAME/KEY: modified_base
<222> LOCATION: (81)..(83)
<223> OTHER INFORMATION: UNA monomer
<220> FEATURE:
<221> NAME/KEY: modified_base
<222> LOCATION: (85)..(85)
<223> OTHER INFORMATION: UNA monomer
<220> FEATURE:
<221> NAME/KEY: modified_base
<222> LOCATION: (87)..(90)
<223> OTHER INFORMATION: UNA monomer
<220> FEATURE:
<221> NAME/KEY: modified_base
<222> LOCATION: (96)..(96)
<223> OTHER INFORMATION: UNA monomer
<220> FEATURE:
<221> NAME/KEY: modified_base
<222> LOCATION: (99)..(102)
<223> OTHER INFORMATION: UNA monomer
<220> FEATURE:
<221> NAME/KEY: modified_base
<222> LOCATION: (104)..(104)
<223> OTHER INFORMATION: UNA monomer
<220> FEATURE:
<221> NAME/KEY: modified_base
<222> LOCATION: (106)..(106)
<223> OTHER INFORMATION: UNA monomer
<220> FEATURE:
<221> NAME/KEY: modified_base
<222> LOCATION: (114)..(114)
<223> OTHER INFORMATION: UNA monomer
<220> FEATURE:
<221> NAME/KEY: modified_base
<222> LOCATION: (118)..(118)
<223> OTHER INFORMATION: UNA monomer
<220> FEATURE:
<221> NAME/KEY: modified_base
<222> LOCATION: (122)..(124)
<223> OTHER INFORMATION: UNA monomer
<220> FEATURE:
<221> NAME/KEY: modified_base
<222> LOCATION: (126)..(126)
<223> OTHER INFORMATION: UNA monomer
<220> FEATURE:
<221> NAME/KEY: modified_base
<222> LOCATION: (128)..(128)
<223> OTHER INFORMATION: UNA monomer
<220> FEATURE:
<221> NAME/KEY: modified_base
<222> LOCATION: (130)..(131)
<223> OTHER INFORMATION: UNA monomer
<220> FEATURE:
<221> NAME/KEY: modified_base
<222> LOCATION: (134)..(134)
<223> OTHER INFORMATION: UNA monomer
<220> FEATURE:
```

```
<221> NAME/KEY: modified_base
<222> LOCATION: (139)..(140)
<223> OTHER INFORMATION: UNA monomer
<220> FEATURE:
<221> NAME/KEY: modified_base
<222> LOCATION: (142)..(142)
<223> OTHER INFORMATION: UNA monomer
<220> FEATURE:
<221> NAME/KEY: modified_base
<222> LOCATION: (144)..(144)
<223> OTHER INFORMATION: UNA monomer
<220> FEATURE:
<221> NAME/KEY: modified_base
<222> LOCATION: (148)..(148)
<223> OTHER INFORMATION: UNA monomer
<220> FEATURE:
<221> NAME/KEY: modified_base
<222> LOCATION: (153)..(158)
<223> OTHER INFORMATION: UNA monomer
<220> FEATURE:
<221> NAME/KEY: modified_base
<222> LOCATION: (160)..(160)
<223> OTHER INFORMATION: UNA monomer
<220> FEATURE:
<221> NAME/KEY: modified_base
<222> LOCATION: (162)..(163)
<223> OTHER INFORMATION: UNA monomer
<220> FEATURE:
<221> NAME/KEY: modified_base
<222> LOCATION: (165)..(165)
<223> OTHER INFORMATION: UNA monomer
<220> FEATURE:
<221> NAME/KEY: modified_base
<222> LOCATION: (167)..(167)
<223> OTHER INFORMATION: UNA monomer
<220> FEATURE:
<221> NAME/KEY: modified_base
<222> LOCATION: (169)..(169)
<223> OTHER INFORMATION: UNA monomer
<220> FEATURE:
<221> NAME/KEY: modified_base
<222> LOCATION: (172)..(176)
<223> OTHER INFORMATION: UNA monomer
<220> FEATURE:
<221> NAME/KEY: modified_base
<222> LOCATION: (178)..(178)
<223> OTHER INFORMATION: UNA monomer
<220> FEATURE:
<221> NAME/KEY: modified_base
<222> LOCATION: (192)..(193)
<223> OTHER INFORMATION: UNA monomer
<220> FEATURE:
<221> NAME/KEY: modified_base
<222> LOCATION: (200)..(200)
<223> OTHER INFORMATION: UNA monomer
<220> FEATURE:
<221> NAME/KEY: modified_base
<222> LOCATION: (203)..(203)
<223> OTHER INFORMATION: UNA monomer
<220> FEATURE:
<221> NAME/KEY: modified_base
<222> LOCATION: (206)..(207)
<223> OTHER INFORMATION: UNA monomer
<220> FEATURE:
<221> NAME/KEY: modified_base
<222> LOCATION: (216)..(216)
<223> OTHER INFORMATION: UNA monomer
<220> FEATURE:
<221> NAME/KEY: modified_base
<222> LOCATION: (219)..(219)
<223> OTHER INFORMATION: UNA monomer
<220> FEATURE:
<221> NAME/KEY: modified_base
<222> LOCATION: (225)..(226)
<223> OTHER INFORMATION: UNA monomer
<220> FEATURE:
<221> NAME/KEY: modified_base
<222> LOCATION: (228)..(230)
<223> OTHER INFORMATION: UNA monomer
```

-continued

```
<220> FEATURE:
<221> NAME/KEY: modified_base
<222> LOCATION: (233)..(234)
<223> OTHER INFORMATION: UNA monomer
<220> FEATURE:
<221> NAME/KEY: modified_base
<222> LOCATION: (252)..(252)
<223> OTHER INFORMATION: UNA monomer
<220> FEATURE:
<221> NAME/KEY: modified_base
<222> LOCATION: (255)..(255)
<223> OTHER INFORMATION: UNA monomer
<220> FEATURE:
<221> NAME/KEY: modified_base
<222> LOCATION: (257)..(258)
<223> OTHER INFORMATION: UNA monomer
<220> FEATURE:
<221> NAME/KEY: modified_base
<222> LOCATION: (268)..(268)
<223> OTHER INFORMATION: UNA monomer
<220> FEATURE:
<221> NAME/KEY: modified_base
<222> LOCATION: (272)..(272)
<223> OTHER INFORMATION: UNA monomer
<220> FEATURE:
<221> NAME/KEY: modified_base
<222> LOCATION: (281)..(281)
<223> OTHER INFORMATION: UNA monomer
<220> FEATURE:
<221> NAME/KEY: modified_base
<222> LOCATION: (283)..(283)
<223> OTHER INFORMATION: UNA monomer
<220> FEATURE:
<221> NAME/KEY: modified_base
<222> LOCATION: (288)..(288)
<223> OTHER INFORMATION: UNA monomer
<220> FEATURE:
<221> NAME/KEY: modified_base
<222> LOCATION: (308)..(308)
<223> OTHER INFORMATION: UNA monomer
<220> FEATURE:
<221> NAME/KEY: modified_base
<222> LOCATION: (310)..(312)
<223> OTHER INFORMATION: UNA monomer
<220> FEATURE:
<221> NAME/KEY: modified_base
<222> LOCATION: (318)..(318)
<223> OTHER INFORMATION: UNA monomer
<220> FEATURE:
<221> NAME/KEY: modified_base
<222> LOCATION: (333)..(334)
<223> OTHER INFORMATION: UNA monomer
<220> FEATURE:
<221> NAME/KEY: modified_base
<222> LOCATION: (336)..(340)
<223> OTHER INFORMATION: UNA monomer
<220> FEATURE:
<221> NAME/KEY: modified_base
<222> LOCATION: (342)..(342)
<223> OTHER INFORMATION: UNA monomer
<220> FEATURE:
<221> NAME/KEY: modified_base
<222> LOCATION: (349)..(349)
<223> OTHER INFORMATION: UNA monomer
<220> FEATURE:
<221> NAME/KEY: modified_base
<222> LOCATION: (352)..(353)
<223> OTHER INFORMATION: UNA monomer
<220> FEATURE:
<221> NAME/KEY: modified_base
<222> LOCATION: (356)..(358)
<223> OTHER INFORMATION: UNA monomer
<220> FEATURE:
<221> NAME/KEY: modified_base
<222> LOCATION: (360)..(360)
<223> OTHER INFORMATION: UNA monomer
<220> FEATURE:
<221> NAME/KEY: modified_base
<222> LOCATION: (362)..(363)
```

```
<223> OTHER INFORMATION: UNA monomer
<220> FEATURE:
<221> NAME/KEY: modified_base
<222> LOCATION: (367)..(367)
<223> OTHER INFORMATION: UNA monomer
<220> FEATURE:
<221> NAME/KEY: modified_base
<222> LOCATION: (369)..(372)
<223> OTHER INFORMATION: UNA monomer
<220> FEATURE:
<221> NAME/KEY: modified_base
<222> LOCATION: (378)..(378)
<223> OTHER INFORMATION: UNA monomer
<220> FEATURE:
<221> NAME/KEY: modified_base
<222> LOCATION: (382)..(383)
<223> OTHER INFORMATION: UNA monomer
<220> FEATURE:
<221> NAME/KEY: modified_base
<222> LOCATION: (385)..(386)
<223> OTHER INFORMATION: UNA monomer
<220> FEATURE:
<221> NAME/KEY: modified_base
<222> LOCATION: (390)..(390)
<223> OTHER INFORMATION: UNA monomer
<220> FEATURE:
<221> NAME/KEY: modified_base
<222> LOCATION: (393)..(393)
<223> OTHER INFORMATION: UNA monomer
<220> FEATURE:
<221> NAME/KEY: modified_base
<222> LOCATION: (399)..(399)
<223> OTHER INFORMATION: UNA monomer
<220> FEATURE:
<221> NAME/KEY: modified_base
<222> LOCATION: (403)..(403)
<223> OTHER INFORMATION: UNA monomer
<220> FEATURE:
<221> NAME/KEY: modified_base
<222> LOCATION: (408)..(408)
<223> OTHER INFORMATION: UNA monomer
<220> FEATURE:
<221> NAME/KEY: modified_base
<222> LOCATION: (411)..(411)
<223> OTHER INFORMATION: UNA monomer
<220> FEATURE:
<221> NAME/KEY: modified_base
<222> LOCATION: (414)..(415)
<223> OTHER INFORMATION: UNA monomer
<220> FEATURE:
<221> NAME/KEY: modified_base
<222> LOCATION: (417)..(417)
<223> OTHER INFORMATION: UNA monomer
<220> FEATURE:
<221> NAME/KEY: modified_base
<222> LOCATION: (420)..(420)
<223> OTHER INFORMATION: UNA monomer
<220> FEATURE:
<221> NAME/KEY: modified_base
<222> LOCATION: (425)..(425)
<223> OTHER INFORMATION: UNA monomer
<220> FEATURE:
<221> NAME/KEY: modified_base
<222> LOCATION: (433)..(433)
<223> OTHER INFORMATION: UNA monomer
<220> FEATURE:
<221> NAME/KEY: modified_base
<222> LOCATION: (435)..(435)
<223> OTHER INFORMATION: UNA monomer
<220> FEATURE:
<221> NAME/KEY: modified_base
<222> LOCATION: (437)..(437)
<223> OTHER INFORMATION: UNA monomer
<220> FEATURE:
<221> NAME/KEY: modified_base
<222> LOCATION: (441)..(441)
<223> OTHER INFORMATION: UNA monomer
<220> FEATURE:
<221> NAME/KEY: modified_base
```

-continued

```
<222> LOCATION: (446)..(447)
<223> OTHER INFORMATION: UNA monomer
<220> FEATURE:
<221> NAME/KEY: modified_base
<222> LOCATION: (457)..(457)
<223> OTHER INFORMATION: UNA monomer
<220> FEATURE:
<221> NAME/KEY: modified_base
<222> LOCATION: (459)..(459)
<223> OTHER INFORMATION: UNA monomer
<220> FEATURE:
<221> NAME/KEY: modified_base
<222> LOCATION: (462)..(462)
<223> OTHER INFORMATION: UNA monomer
<220> FEATURE:
<221> NAME/KEY: modified_base
<222> LOCATION: (465)..(465)
<223> OTHER INFORMATION: UNA monomer
<220> FEATURE:
<221> NAME/KEY: modified_base
<222> LOCATION: (467)..(467)
<223> OTHER INFORMATION: UNA monomer
<220> FEATURE:
<221> NAME/KEY: modified_base
<222> LOCATION: (472)..(472)
<223> OTHER INFORMATION: UNA monomer
<220> FEATURE:
<221> NAME/KEY: modified_base
<222> LOCATION: (477)..(477)
<223> OTHER INFORMATION: UNA monomer
<220> FEATURE:
<221> NAME/KEY: modified_base
<222> LOCATION: (483)..(483)
<223> OTHER INFORMATION: UNA monomer
<220> FEATURE:
<221> NAME/KEY: modified_base
<222> LOCATION: (487)..(487)
<223> OTHER INFORMATION: UNA monomer
<220> FEATURE:
<221> NAME/KEY: modified_base
<222> LOCATION: (489)..(489)
<223> OTHER INFORMATION: UNA monomer
<220> FEATURE:
<221> NAME/KEY: modified_base
<222> LOCATION: (491)..(491)
<223> OTHER INFORMATION: UNA monomer
<220> FEATURE:
<221> NAME/KEY: modified_base
<222> LOCATION: (496)..(496)
<223> OTHER INFORMATION: UNA monomer
<220> FEATURE:
<221> NAME/KEY: modified_base
<222> LOCATION: (504)..(504)
<223> OTHER INFORMATION: UNA monomer
<220> FEATURE:
<221> NAME/KEY: modified_base
<222> LOCATION: (513)..(514)
<223> OTHER INFORMATION: UNA monomer
<220> FEATURE:
<221> NAME/KEY: modified_base
<222> LOCATION: (516)..(519)
<223> OTHER INFORMATION: UNA monomer
<220> FEATURE:
<221> NAME/KEY: modified_base
<222> LOCATION: (522)..(523)
<223> OTHER INFORMATION: UNA monomer
<220> FEATURE:
<221> NAME/KEY: modified_base
<222> LOCATION: (528)..(529)
<223> OTHER INFORMATION: UNA monomer
<220> FEATURE:
<221> NAME/KEY: modified_base
<222> LOCATION: (531)..(531)
<223> OTHER INFORMATION: UNA monomer
<220> FEATURE:
<221> NAME/KEY: modified_base
<222> LOCATION: (540)..(541)
<223> OTHER INFORMATION: UNA monomer
<220> FEATURE:
```

```
<221> NAME/KEY: modified_base
<222> LOCATION: (556)..(556)
<223> OTHER INFORMATION: UNA monomer
<220> FEATURE:
<221> NAME/KEY: modified_base
<222> LOCATION: (558)..(558)
<223> OTHER INFORMATION: UNA monomer
<220> FEATURE:
<221> NAME/KEY: modified_base
<222> LOCATION: (562)..(564)
<223> OTHER INFORMATION: UNA monomer
<220> FEATURE:
<221> NAME/KEY: modified_base
<222> LOCATION: (569)..(569)
<223> OTHER INFORMATION: UNA monomer
<220> FEATURE:
<221> NAME/KEY: modified_base
<222> LOCATION: (573)..(573)
<223> OTHER INFORMATION: UNA monomer
<220> FEATURE:
<221> NAME/KEY: modified_base
<222> LOCATION: (577)..(577)
<223> OTHER INFORMATION: UNA monomer
<220> FEATURE:
<221> NAME/KEY: modified_base
<222> LOCATION: (585)..(585)
<223> OTHER INFORMATION: UNA monomer
<220> FEATURE:
<221> NAME/KEY: modified_base
<222> LOCATION: (589)..(589)
<223> OTHER INFORMATION: UNA monomer
<220> FEATURE:
<221> NAME/KEY: modified_base
<222> LOCATION: (594)..(594)
<223> OTHER INFORMATION: UNA monomer
<220> FEATURE:
<221> NAME/KEY: modified_base
<222> LOCATION: (596)..(596)
<223> OTHER INFORMATION: UNA monomer
<220> FEATURE:
<221> NAME/KEY: modified_base
<222> LOCATION: (600)..(600)
<223> OTHER INFORMATION: UNA monomer
<220> FEATURE:
<221> NAME/KEY: modified_base
<222> LOCATION: (606)..(607)
<223> OTHER INFORMATION: UNA monomer
<220> FEATURE:
<221> NAME/KEY: modified_base
<222> LOCATION: (612)..(612)
<223> OTHER INFORMATION: UNA monomer
<220> FEATURE:
<221> NAME/KEY: modified_base
<222> LOCATION: (617)..(619)
<223> OTHER INFORMATION: UNA monomer
<220> FEATURE:
<221> NAME/KEY: modified_base
<222> LOCATION: (621)..(621)
<223> OTHER INFORMATION: UNA monomer
<220> FEATURE:
<221> NAME/KEY: modified_base
<222> LOCATION: (624)..(624)
<223> OTHER INFORMATION: UNA monomer
<220> FEATURE:
<221> NAME/KEY: modified_base
<222> LOCATION: (627)..(627)
<223> OTHER INFORMATION: UNA monomer
<220> FEATURE:
<221> NAME/KEY: modified_base
<222> LOCATION: (633)..(633)
<223> OTHER INFORMATION: UNA monomer
<220> FEATURE:
<221> NAME/KEY: modified_base
<222> LOCATION: (639)..(640)
<223> OTHER INFORMATION: UNA monomer
<220> FEATURE:
<221> NAME/KEY: modified_base
<222> LOCATION: (646)..(646)
<223> OTHER INFORMATION: UNA monomer
```

-continued

```
<220> FEATURE:
<221> NAME/KEY: modified_base
<222> LOCATION: (648)..(649)
<223> OTHER INFORMATION: UNA monomer
<220> FEATURE:
<221> NAME/KEY: modified_base
<222> LOCATION: (652)..(652)
<223> OTHER INFORMATION: UNA monomer
<220> FEATURE:
<221> NAME/KEY: modified_base
<222> LOCATION: (654)..(654)
<223> OTHER INFORMATION: UNA monomer
<220> FEATURE:
<221> NAME/KEY: modified_base
<222> LOCATION: (660)..(660)
<223> OTHER INFORMATION: UNA monomer
<220> FEATURE:
<221> NAME/KEY: modified_base
<222> LOCATION: (663)..(666)
<223> OTHER INFORMATION: UNA monomer
<220> FEATURE:
<221> NAME/KEY: modified_base
<222> LOCATION: (668)..(669)
<223> OTHER INFORMATION: UNA monomer
<220> FEATURE:
<221> NAME/KEY: modified_base
<222> LOCATION: (671)..(671)
<223> OTHER INFORMATION: UNA monomer
<220> FEATURE:
<221> NAME/KEY: modified_base
<222> LOCATION: (674)..(676)
<223> OTHER INFORMATION: UNA monomer
<220> FEATURE:
<221> NAME/KEY: modified_base
<222> LOCATION: (681)..(681)
<223> OTHER INFORMATION: UNA monomer
<220> FEATURE:
<221> NAME/KEY: modified_base
<222> LOCATION: (690)..(691)
<223> OTHER INFORMATION: UNA monomer
<220> FEATURE:
<221> NAME/KEY: modified_base
<222> LOCATION: (693)..(693)
<223> OTHER INFORMATION: UNA monomer
<220> FEATURE:
<221> NAME/KEY: modified_base
<222> LOCATION: (699)..(699)
<223> OTHER INFORMATION: UNA monomer
<220> FEATURE:
<221> NAME/KEY: modified_base
<222> LOCATION: (701)..(701)
<223> OTHER INFORMATION: UNA monomer
<220> FEATURE:
<221> NAME/KEY: modified_base
<222> LOCATION: (705)..(705)
<223> OTHER INFORMATION: UNA monomer
<220> FEATURE:
<221> NAME/KEY: modified_base
<222> LOCATION: (709)..(709)
<223> OTHER INFORMATION: UNA monomer
<220> FEATURE:
<221> NAME/KEY: modified_base
<222> LOCATION: (712)..(712)
<223> OTHER INFORMATION: UNA monomer
<220> FEATURE:
<221> NAME/KEY: modified_base
<222> LOCATION: (714)..(716)
<223> OTHER INFORMATION: UNA monomer
<220> FEATURE:
<221> NAME/KEY: modified_base
<222> LOCATION: (728)..(730)
<223> OTHER INFORMATION: UNA monomer
<220> FEATURE:
<221> NAME/KEY: modified_base
<222> LOCATION: (732)..(732)
<223> OTHER INFORMATION: UNA monomer
<220> FEATURE:
<221> NAME/KEY: modified_base
<222> LOCATION: (741)..(741)
```

```
<223> OTHER INFORMATION: UNA monomer
<220> FEATURE:
<221> NAME/KEY: modified_base
<222> LOCATION: (743)..(743)
<223> OTHER INFORMATION: UNA monomer
<220> FEATURE:
<221> NAME/KEY: modified_base
<222> LOCATION: (745)..(745)
<223> OTHER INFORMATION: UNA monomer
<220> FEATURE:
<221> NAME/KEY: modified_base
<222> LOCATION: (755)..(755)
<223> OTHER INFORMATION: UNA monomer
<220> FEATURE:
<221> NAME/KEY: modified_base
<222> LOCATION: (765)..(768)
<223> OTHER INFORMATION: UNA monomer
<220> FEATURE:
<221> NAME/KEY: modified_base
<222> LOCATION: (772)..(772)
<223> OTHER INFORMATION: UNA monomer
<220> FEATURE:
<221> NAME/KEY: modified_base
<222> LOCATION: (774)..(774)
<223> OTHER INFORMATION: UNA monomer
<220> FEATURE:
<221> NAME/KEY: modified_base
<222> LOCATION: (778)..(778)
<223> OTHER INFORMATION: UNA monomer
<220> FEATURE:
<221> NAME/KEY: modified_base
<222> LOCATION: (790)..(790)
<223> OTHER INFORMATION: UNA monomer
<220> FEATURE:
<221> NAME/KEY: modified_base
<222> LOCATION: (796)..(796)
<223> OTHER INFORMATION: UNA monomer
<220> FEATURE:
<221> NAME/KEY: modified_base
<222> LOCATION: (798)..(798)
<223> OTHER INFORMATION: UNA monomer
<220> FEATURE:
<221> NAME/KEY: modified_base
<222> LOCATION: (801)..(801)
<223> OTHER INFORMATION: UNA monomer
<220> FEATURE:
<221> NAME/KEY: modified_base
<222> LOCATION: (803)..(803)
<223> OTHER INFORMATION: UNA monomer
<220> FEATURE:
<221> NAME/KEY: modified_base
<222> LOCATION: (808)..(808)
<223> OTHER INFORMATION: UNA monomer
<220> FEATURE:
<221> NAME/KEY: modified_base
<222> LOCATION: (814)..(814)
<223> OTHER INFORMATION: UNA monomer
<220> FEATURE:
<221> NAME/KEY: modified_base
<222> LOCATION: (816)..(817)
<223> OTHER INFORMATION: UNA monomer
<220> FEATURE:
<221> NAME/KEY: modified_base
<222> LOCATION: (819)..(819)
<223> OTHER INFORMATION: UNA monomer
<220> FEATURE:
<221> NAME/KEY: modified_base
<222> LOCATION: (825)..(825)
<223> OTHER INFORMATION: UNA monomer
<220> FEATURE:
<221> NAME/KEY: modified_base
<222> LOCATION: (827)..(827)
<223> OTHER INFORMATION: UNA monomer
<220> FEATURE:
<221> NAME/KEY: modified_base
<222> LOCATION: (831)..(831)
<223> OTHER INFORMATION: UNA monomer
<220> FEATURE:
<221> NAME/KEY: modified_base
```

```
<222> LOCATION: (835)..(835)
<223> OTHER INFORMATION: UNA monomer
<220> FEATURE:
<221> NAME/KEY: modified_base
<222> LOCATION: (838)..(838)
<223> OTHER INFORMATION: UNA monomer
<220> FEATURE:
<221> NAME/KEY: modified_base
<222> LOCATION: (840)..(840)
<223> OTHER INFORMATION: UNA monomer
<220> FEATURE:
<221> NAME/KEY: modified_base
<222> LOCATION: (848)..(848)
<223> OTHER INFORMATION: UNA monomer
<220> FEATURE:
<221> NAME/KEY: modified_base
<222> LOCATION: (850)..(850)
<223> OTHER INFORMATION: UNA monomer
<220> FEATURE:
<221> NAME/KEY: modified_base
<222> LOCATION: (852)..(852)
<223> OTHER INFORMATION: UNA monomer
<220> FEATURE:
<221> NAME/KEY: modified_base
<222> LOCATION: (855)..(855)
<223> OTHER INFORMATION: UNA monomer
<220> FEATURE:
<221> NAME/KEY: modified_base
<222> LOCATION: (860)..(862)
<223> OTHER INFORMATION: UNA monomer
<220> FEATURE:
<221> NAME/KEY: modified_base
<222> LOCATION: (864)..(864)
<223> OTHER INFORMATION: UNA monomer
<220> FEATURE:
<221> NAME/KEY: modified_base
<222> LOCATION: (866)..(866)
<223> OTHER INFORMATION: UNA monomer
<220> FEATURE:
<221> NAME/KEY: modified_base
<222> LOCATION: (870)..(871)
<223> OTHER INFORMATION: UNA monomer
<220> FEATURE:
<221> NAME/KEY: modified_base
<222> LOCATION: (876)..(876)
<223> OTHER INFORMATION: UNA monomer
<220> FEATURE:
<221> NAME/KEY: modified_base
<222> LOCATION: (882)..(883)
<223> OTHER INFORMATION: UNA monomer
<220> FEATURE:
<221> NAME/KEY: modified_base
<222> LOCATION: (888)..(889)
<223> OTHER INFORMATION: UNA monomer
<220> FEATURE:
<221> NAME/KEY: modified_base
<222> LOCATION: (892)..(892)
<223> OTHER INFORMATION: UNA monomer
<220> FEATURE:
<221> NAME/KEY: modified_base
<222> LOCATION: (894)..(895)
<223> OTHER INFORMATION: UNA monomer
<220> FEATURE:
<221> NAME/KEY: modified_base
<222> LOCATION: (897)..(897)
<223> OTHER INFORMATION: UNA monomer
<220> FEATURE:
<221> NAME/KEY: modified_base
<222> LOCATION: (900)..(900)
<223> OTHER INFORMATION: UNA monomer
<220> FEATURE:
<221> NAME/KEY: modified_base
<222> LOCATION: (913)..(914)
<223> OTHER INFORMATION: UNA monomer
<220> FEATURE:
<221> NAME/KEY: modified_base
<222> LOCATION: (920)..(921)
<223> OTHER INFORMATION: UNA monomer
<220> FEATURE:
```

```
<221> NAME/KEY: modified_base
<222> LOCATION: (930)..(930)
<223> OTHER INFORMATION: UNA monomer
<220> FEATURE:
<221> NAME/KEY: modified_base
<222> LOCATION: (939)..(940)
<223> OTHER INFORMATION: UNA monomer
<220> FEATURE:
<221> NAME/KEY: modified_base
<222> LOCATION: (942)..(942)
<223> OTHER INFORMATION: UNA monomer
<220> FEATURE:
<221> NAME/KEY: modified_base
<222> LOCATION: (947)..(948)
<223> OTHER INFORMATION: UNA monomer
<220> FEATURE:
<221> NAME/KEY: modified_base
<222> LOCATION: (950)..(952)
<223> OTHER INFORMATION: UNA monomer
<220> FEATURE:
<221> NAME/KEY: modified_base
<222> LOCATION: (956)..(956)
<223> OTHER INFORMATION: UNA monomer
<220> FEATURE:
<221> NAME/KEY: modified_base
<222> LOCATION: (958)..(958)
<223> OTHER INFORMATION: UNA monomer
<220> FEATURE:
<221> NAME/KEY: modified_base
<222> LOCATION: (962)..(963)
<223> OTHER INFORMATION: UNA monomer
<220> FEATURE:
<221> NAME/KEY: modified_base
<222> LOCATION: (967)..(968)
<223> OTHER INFORMATION: UNA monomer
<220> FEATURE:
<221> NAME/KEY: modified_base
<222> LOCATION: (974)..(975)
<223> OTHER INFORMATION: UNA monomer
<220> FEATURE:
<221> NAME/KEY: modified_base
<222> LOCATION: (985)..(985)
<223> OTHER INFORMATION: UNA monomer
<220> FEATURE:
<221> NAME/KEY: modified_base
<222> LOCATION: (987)..(987)
<223> OTHER INFORMATION: UNA monomer
<220> FEATURE:
<221> NAME/KEY: modified_base
<222> LOCATION: (991)..(992)
<223> OTHER INFORMATION: UNA monomer
<220> FEATURE:
<221> NAME/KEY: modified_base
<222> LOCATION: (995)..(997)
<223> OTHER INFORMATION: UNA monomer
<220> FEATURE:
<221> NAME/KEY: modified_base
<222> LOCATION: (1000)..(1001)
<223> OTHER INFORMATION: UNA monomer
<220> FEATURE:
<221> NAME/KEY: modified_base
<222> LOCATION: (1012)..(1014)
<223> OTHER INFORMATION: UNA monomer
<220> FEATURE:
<221> NAME/KEY: modified_base
<222> LOCATION: (1022)..(1023)
<223> OTHER INFORMATION: UNA monomer
<220> FEATURE:
<221> NAME/KEY: modified_base
<222> LOCATION: (1025)..(1028)
<223> OTHER INFORMATION: UNA monomer
<220> FEATURE:
<221> NAME/KEY: modified_base
<222> LOCATION: (1030)..(1030)
<223> OTHER INFORMATION: UNA monomer
<220> FEATURE:
<221> NAME/KEY: modified_base
<222> LOCATION: (1032)..(1034)
<223> OTHER INFORMATION: UNA monomer
```

-continued

```
<220> FEATURE:
<221> NAME/KEY: modified_base
<222> LOCATION: (1039)..(1041)
<223> OTHER INFORMATION: UNA monomer
<220> FEATURE:
<221> NAME/KEY: modified_base
<222> LOCATION: (1044)..(1046)
<223> OTHER INFORMATION: UNA monomer
<220> FEATURE:
<221> NAME/KEY: modified_base
<222> LOCATION: (1055)..(1055)
<223> OTHER INFORMATION: UNA monomer
<220> FEATURE:
<221> NAME/KEY: modified_base
<222> LOCATION: (1063)..(1066)
<223> OTHER INFORMATION: UNA monomer
<220> FEATURE:
<221> NAME/KEY: modified_base
<222> LOCATION: (1075)..(1077)
<223> OTHER INFORMATION: UNA monomer
<220> FEATURE:
<221> NAME/KEY: modified_base
<222> LOCATION: (1080)..(1082)
<223> OTHER INFORMATION: UNA monomer
<220> FEATURE:
<221> NAME/KEY: modified_base
<222> LOCATION: (1090)..(1090)
<223> OTHER INFORMATION: UNA monomer
<220> FEATURE:
<221> NAME/KEY: modified_base
<222> LOCATION: (1092)..(1092)
<223> OTHER INFORMATION: UNA monomer
<220> FEATURE:
<221> NAME/KEY: modified_base
<222> LOCATION: (1095)..(1096)
<223> OTHER INFORMATION: UNA monomer
<220> FEATURE:
<221> NAME/KEY: modified_base
<222> LOCATION: (1106)..(1106)
<223> OTHER INFORMATION: UNA monomer
<220> FEATURE:
<221> NAME/KEY: modified_base
<222> LOCATION: (1109)..(1109)
<223> OTHER INFORMATION: UNA monomer
<220> FEATURE:
<221> NAME/KEY: modified_base
<222> LOCATION: (1112)..(1112)
<223> OTHER INFORMATION: UNA monomer
<220> FEATURE:
<221> NAME/KEY: modified_base
<222> LOCATION: (1114)..(1114)
<223> OTHER INFORMATION: UNA monomer
<220> FEATURE:
<221> NAME/KEY: modified_base
<222> LOCATION: (1123)..(1123)
<223> OTHER INFORMATION: UNA monomer
<220> FEATURE:
<221> NAME/KEY: modified_base
<222> LOCATION: (1125)..(1125)
<223> OTHER INFORMATION: UNA monomer
<220> FEATURE:
<221> NAME/KEY: modified_base
<222> LOCATION: (1127)..(1127)
<223> OTHER INFORMATION: UNA monomer
<220> FEATURE:
<221> NAME/KEY: modified_base
<222> LOCATION: (1131)..(1131)
<223> OTHER INFORMATION: UNA monomer
<220> FEATURE:
<221> NAME/KEY: modified_base
<222> LOCATION: (1135)..(1135)
<223> OTHER INFORMATION: UNA monomer
<220> FEATURE:
<221> NAME/KEY: modified_base
<222> LOCATION: (1141)..(1141)
<223> OTHER INFORMATION: UNA monomer
<220> FEATURE:
<221> NAME/KEY: modified_base
<222> LOCATION: (1145)..(1145)
```

```
<223> OTHER INFORMATION: UNA monomer
<220> FEATURE:
<221> NAME/KEY: modified_base
<222> LOCATION: (1148)..(1148)
<223> OTHER INFORMATION: UNA monomer
<220> FEATURE:
<221> NAME/KEY: modified_base
<222> LOCATION: (1151)..(1152)
<223> OTHER INFORMATION: UNA monomer
<220> FEATURE:
<221> NAME/KEY: modified_base
<222> LOCATION: (1157)..(1158)
<223> OTHER INFORMATION: UNA monomer
<220> FEATURE:
<221> NAME/KEY: modified_base
<222> LOCATION: (1161)..(1161)
<223> OTHER INFORMATION: UNA monomer
<220> FEATURE:
<221> NAME/KEY: modified_base
<222> LOCATION: (1164)..(1164)
<223> OTHER INFORMATION: UNA monomer
<220> FEATURE:
<221> NAME/KEY: modified_base
<222> LOCATION: (1172)..(1173)
<223> OTHER INFORMATION: UNA monomer
<220> FEATURE:
<221> NAME/KEY: modified_base
<222> LOCATION: (1178)..(1179)
<223> OTHER INFORMATION: UNA monomer
<220> FEATURE:
<221> NAME/KEY: modified_base
<222> LOCATION: (1184)..(1185)
<223> OTHER INFORMATION: UNA monomer
<220> FEATURE:
<221> NAME/KEY: modified_base
<222> LOCATION: (1191)..(1191)
<223> OTHER INFORMATION: UNA monomer
<220> FEATURE:
<221> NAME/KEY: modified_base
<222> LOCATION: (1197)..(1197)
<223> OTHER INFORMATION: UNA monomer
<220> FEATURE:
<221> NAME/KEY: modified_base
<222> LOCATION: (1201)..(1201)
<223> OTHER INFORMATION: UNA monomer
<220> FEATURE:
<221> NAME/KEY: modified_base
<222> LOCATION: (1208)..(1208)
<223> OTHER INFORMATION: UNA monomer
<220> FEATURE:
<221> NAME/KEY: modified_base
<222> LOCATION: (1215)..(1215)
<223> OTHER INFORMATION: UNA monomer
<220> FEATURE:
<221> NAME/KEY: modified_base
<222> LOCATION: (1221)..(1221)
<223> OTHER INFORMATION: UNA monomer
<220> FEATURE:
<221> NAME/KEY: modified_base
<222> LOCATION: (1224)..(1224)
<223> OTHER INFORMATION: UNA monomer
<220> FEATURE:
<221> NAME/KEY: modified_base
<222> LOCATION: (1226)..(1227)
<223> OTHER INFORMATION: UNA monomer
<220> FEATURE:
<221> NAME/KEY: modified_base
<222> LOCATION: (1229)..(1230)
<223> OTHER INFORMATION: UNA monomer
<220> FEATURE:
<221> NAME/KEY: modified_base
<222> LOCATION: (1233)..(1233)
<223> OTHER INFORMATION: UNA monomer
<220> FEATURE:
<221> NAME/KEY: modified_base
<222> LOCATION: (1236)..(1236)
<223> OTHER INFORMATION: UNA monomer
<220> FEATURE:
<221> NAME/KEY: modified_base
```

```
<222> LOCATION: (1239)..(1239)
<223> OTHER INFORMATION: UNA monomer
<220> FEATURE:
<221> NAME/KEY: modified_base
<222> LOCATION: (1241)..(1241)
<223> OTHER INFORMATION: UNA monomer
<220> FEATURE:
<221> NAME/KEY: modified_base
<222> LOCATION: (1243)..(1243)
<223> OTHER INFORMATION: UNA monomer
<220> FEATURE:
<221> NAME/KEY: modified_base
<222> LOCATION: (1248)..(1248)
<223> OTHER INFORMATION: UNA monomer
<220> FEATURE:
<221> NAME/KEY: modified_base
<222> LOCATION: (1250)..(1250)
<223> OTHER INFORMATION: UNA monomer
<220> FEATURE:
<221> NAME/KEY: modified_base
<222> LOCATION: (1253)..(1253)
<223> OTHER INFORMATION: UNA monomer
<220> FEATURE:
<221> NAME/KEY: modified_base
<222> LOCATION: (1255)..(1255)
<223> OTHER INFORMATION: UNA monomer
<220> FEATURE:
<221> NAME/KEY: modified_base
<222> LOCATION: (1257)..(1257)
<223> OTHER INFORMATION: UNA monomer
<220> FEATURE:
<221> NAME/KEY: modified_base
<222> LOCATION: (1259)..(1259)
<223> OTHER INFORMATION: UNA monomer
<220> FEATURE:
<221> NAME/KEY: modified_base
<222> LOCATION: (1267)..(1268)
<223> OTHER INFORMATION: UNA monomer
<220> FEATURE:
<221> NAME/KEY: modified_base
<222> LOCATION: (1275)..(1275)
<223> OTHER INFORMATION: UNA monomer
<220> FEATURE:
<221> NAME/KEY: modified_base
<222> LOCATION: (1278)..(1278)
<223> OTHER INFORMATION: UNA monomer
<220> FEATURE:
<221> NAME/KEY: modified_base
<222> LOCATION: (1280)..(1281)
<223> OTHER INFORMATION: UNA monomer
<220> FEATURE:
<221> NAME/KEY: modified_base
<222> LOCATION: (1286)..(1287)
<223> OTHER INFORMATION: UNA monomer
<220> FEATURE:
<221> NAME/KEY: modified_base
<222> LOCATION: (1292)..(1292)
<223> OTHER INFORMATION: UNA monomer
<220> FEATURE:
<221> NAME/KEY: modified_base
<222> LOCATION: (1296)..(1296)
<223> OTHER INFORMATION: UNA monomer
<220> FEATURE:
<221> NAME/KEY: modified_base
<222> LOCATION: (1305)..(1305)
<223> OTHER INFORMATION: UNA monomer
<220> FEATURE:
<221> NAME/KEY: modified_base
<222> LOCATION: (1307)..(1307)
<223> OTHER INFORMATION: UNA monomer
<220> FEATURE:
<221> NAME/KEY: modified_base
<222> LOCATION: (1310)..(1310)
<223> OTHER INFORMATION: UNA monomer
<220> FEATURE:
<221> NAME/KEY: modified_base
<222> LOCATION: (1314)..(1314)
<223> OTHER INFORMATION: UNA monomer
<220> FEATURE:
```

```
<221> NAME/KEY: modified_base
<222> LOCATION: (1316)..(1316)
<223> OTHER INFORMATION: UNA monomer
<220> FEATURE:
<221> NAME/KEY: modified_base
<222> LOCATION: (1320)..(1320)
<223> OTHER INFORMATION: UNA monomer
<220> FEATURE:
<221> NAME/KEY: modified_base
<222> LOCATION: (1326)..(1326)
<223> OTHER INFORMATION: UNA monomer
<220> FEATURE:
<221> NAME/KEY: modified_base
<222> LOCATION: (1334)..(1338)
<223> OTHER INFORMATION: UNA monomer
<220> FEATURE:
<221> NAME/KEY: modified_base
<222> LOCATION: (1350)..(1350)
<223> OTHER INFORMATION: UNA monomer
<220> FEATURE:
<221> NAME/KEY: modified_base
<222> LOCATION: (1354)..(1355)
<223> OTHER INFORMATION: UNA monomer
<220> FEATURE:
<221> NAME/KEY: modified_base
<222> LOCATION: (1358)..(1358)
<223> OTHER INFORMATION: UNA monomer
<220> FEATURE:
<221> NAME/KEY: modified_base
<222> LOCATION: (1370)..(1370)
<223> OTHER INFORMATION: UNA monomer
<220> FEATURE:
<221> NAME/KEY: modified_base
<222> LOCATION: (1372)..(1372)
<223> OTHER INFORMATION: UNA monomer
<220> FEATURE:
<221> NAME/KEY: modified_base
<222> LOCATION: (1375)..(1377)
<223> OTHER INFORMATION: UNA monomer
<220> FEATURE:
<221> NAME/KEY: modified_base
<222> LOCATION: (1384)..(1385)
<223> OTHER INFORMATION: UNA monomer
<220> FEATURE:
<221> NAME/KEY: modified_base
<222> LOCATION: (1389)..(1389)
<223> OTHER INFORMATION: UNA monomer
<220> FEATURE:
<221> NAME/KEY: modified_base
<222> LOCATION: (1397)..(1397)
<223> OTHER INFORMATION: UNA monomer
<220> FEATURE:
<221> NAME/KEY: modified_base
<222> LOCATION: (1404)..(1404)
<223> OTHER INFORMATION: UNA monomer
<220> FEATURE:
<221> NAME/KEY: modified_base
<222> LOCATION: (1409)..(1409)
<223> OTHER INFORMATION: UNA monomer
<220> FEATURE:
<221> NAME/KEY: modified_base
<222> LOCATION: (1412)..(1413)
<223> OTHER INFORMATION: UNA monomer
<220> FEATURE:
<221> NAME/KEY: modified_base
<222> LOCATION: (1421)..(1422)
<223> OTHER INFORMATION: UNA monomer
<220> FEATURE:
<221> NAME/KEY: modified_base
<222> LOCATION: (1428)..(1428)
<223> OTHER INFORMATION: UNA monomer
<220> FEATURE:
<221> NAME/KEY: modified_base
<222> LOCATION: (1431)..(1431)
<223> OTHER INFORMATION: UNA monomer
<220> FEATURE:
<221> NAME/KEY: modified_base
<222> LOCATION: (1433)..(1433)
<223> OTHER INFORMATION: UNA monomer
```

-continued

```
<220> FEATURE:
<221> NAME/KEY: modified_base
<222> LOCATION: (1437)..(1437)
<223> OTHER INFORMATION: UNA monomer
<220> FEATURE:
<221> NAME/KEY: modified_base
<222> LOCATION: (1441)..(1441)
<223> OTHER INFORMATION: UNA monomer
<220> FEATURE:
<221> NAME/KEY: modified_base
<222> LOCATION: (1443)..(1443)
<223> OTHER INFORMATION: UNA monomer
<220> FEATURE:
<221> NAME/KEY: modified_base
<222> LOCATION: (1445)..(1445)
<223> OTHER INFORMATION: UNA monomer
<220> FEATURE:
<221> NAME/KEY: modified_base
<222> LOCATION: (1453)..(1453)
<223> OTHER INFORMATION: UNA monomer
<220> FEATURE:
<221> NAME/KEY: modified_base
<222> LOCATION: (1458)..(1460)
<223> OTHER INFORMATION: UNA monomer
<220> FEATURE:
<221> NAME/KEY: modified_base
<222> LOCATION: (1463)..(1463)
<223> OTHER INFORMATION: UNA monomer
<220> FEATURE:
<221> NAME/KEY: modified_base
<222> LOCATION: (1476)..(1477)
<223> OTHER INFORMATION: UNA monomer
<220> FEATURE:
<221> NAME/KEY: modified_base
<222> LOCATION: (1479)..(1479)
<223> OTHER INFORMATION: UNA monomer
<220> FEATURE:
<221> NAME/KEY: modified_base
<222> LOCATION: (1484)..(1484)
<223> OTHER INFORMATION: UNA monomer
<220> FEATURE:
<221> NAME/KEY: modified_base
<222> LOCATION: (1493)..(1494)
<223> OTHER INFORMATION: UNA monomer
<220> FEATURE:
<221> NAME/KEY: modified_base
<222> LOCATION: (1496)..(1497)
<223> OTHER INFORMATION: UNA monomer
<220> FEATURE:
<221> NAME/KEY: modified_base
<222> LOCATION: (1512)..(1512)
<223> OTHER INFORMATION: UNA monomer
<220> FEATURE:
<221> NAME/KEY: modified_base
<222> LOCATION: (1518)..(1519)
<223> OTHER INFORMATION: UNA monomer
<220> FEATURE:
<221> NAME/KEY: modified_base
<222> LOCATION: (1523)..(1523)
<223> OTHER INFORMATION: UNA monomer
<220> FEATURE:
<221> NAME/KEY: modified_base
<222> LOCATION: (1526)..(1527)
<223> OTHER INFORMATION: UNA monomer
<220> FEATURE:
<221> NAME/KEY: modified_base
<222> LOCATION: (1530)..(1530)
<223> OTHER INFORMATION: UNA monomer
<220> FEATURE:
<221> NAME/KEY: modified_base
<222> LOCATION: (1532)..(1532)
<223> OTHER INFORMATION: UNA monomer
<220> FEATURE:
<221> NAME/KEY: modified_base
<222> LOCATION: (1543)..(1543)
<223> OTHER INFORMATION: UNA monomer
<220> FEATURE:
<221> NAME/KEY: modified_base
<222> LOCATION: (1546)..(1546)
```

```
<223> OTHER INFORMATION: UNA monomer
<220> FEATURE:
<221> NAME/KEY: modified_base
<222> LOCATION: (1549)..(1549)
<223> OTHER INFORMATION: UNA monomer
<220> FEATURE:
<221> NAME/KEY: modified_base
<222> LOCATION: (1551)..(1551)
<223> OTHER INFORMATION: UNA monomer
<220> FEATURE:
<221> NAME/KEY: modified_base
<222> LOCATION: (1554)..(1554)
<223> OTHER INFORMATION: UNA monomer
<220> FEATURE:
<221> NAME/KEY: modified_base
<222> LOCATION: (1557)..(1558)
<223> OTHER INFORMATION: UNA monomer
<220> FEATURE:
<221> NAME/KEY: modified_base
<222> LOCATION: (1560)..(1560)
<223> OTHER INFORMATION: UNA monomer
<220> FEATURE:
<221> NAME/KEY: modified_base
<222> LOCATION: (1565)..(1566)
<223> OTHER INFORMATION: UNA monomer
<220> FEATURE:
<221> NAME/KEY: modified_base
<222> LOCATION: (1569)..(1569)
<223> OTHER INFORMATION: UNA monomer
<220> FEATURE:
<221> NAME/KEY: modified_base
<222> LOCATION: (1573)..(1575)
<223> OTHER INFORMATION: UNA monomer
<220> FEATURE:
<221> NAME/KEY: modified_base
<222> LOCATION: (1580)..(1580)
<223> OTHER INFORMATION: UNA monomer
<220> FEATURE:
<221> NAME/KEY: modified_base
<222> LOCATION: (1584)..(1585)
<223> OTHER INFORMATION: UNA monomer
<220> FEATURE:
<221> NAME/KEY: modified_base
<222> LOCATION: (1587)..(1587)
<223> OTHER INFORMATION: UNA monomer
<220> FEATURE:
<221> NAME/KEY: modified_base
<222> LOCATION: (1590)..(1590)
<223> OTHER INFORMATION: UNA monomer
<220> FEATURE:
<221> NAME/KEY: modified_base
<222> LOCATION: (1593)..(1593)
<223> OTHER INFORMATION: UNA monomer
<220> FEATURE:
<221> NAME/KEY: modified_base
<222> LOCATION: (1595)..(1595)
<223> OTHER INFORMATION: UNA monomer
<220> FEATURE:
<221> NAME/KEY: modified_base
<222> LOCATION: (1597)..(1597)
<223> OTHER INFORMATION: UNA monomer
<220> FEATURE:
<221> NAME/KEY: modified_base
<222> LOCATION: (1602)..(1602)
<223> OTHER INFORMATION: UNA monomer
<220> FEATURE:
<221> NAME/KEY: modified_base
<222> LOCATION: (1605)..(1605)
<223> OTHER INFORMATION: UNA monomer
<220> FEATURE:
<221> NAME/KEY: modified_base
<222> LOCATION: (1611)..(1612)
<223> OTHER INFORMATION: UNA monomer
<220> FEATURE:
<221> NAME/KEY: modified_base
<222> LOCATION: (1617)..(1617)
<223> OTHER INFORMATION: UNA monomer
<220> FEATURE:
<221> NAME/KEY: modified_base
```

-continued

```
<222> LOCATION: (1619)..(1619)
<223> OTHER INFORMATION: UNA monomer
<220> FEATURE:
<221> NAME/KEY: modified_base
<222> LOCATION: (1623)..(1623)
<223> OTHER INFORMATION: UNA monomer
<220> FEATURE:
<221> NAME/KEY: modified_base
<222> LOCATION: (1625)..(1625)
<223> OTHER INFORMATION: UNA monomer
<220> FEATURE:
<221> NAME/KEY: modified_base
<222> LOCATION: (1630)..(1631)
<223> OTHER INFORMATION: UNA monomer
<220> FEATURE:
<221> NAME/KEY: modified_base
<222> LOCATION: (1635)..(1635)
<223> OTHER INFORMATION: UNA monomer
<220> FEATURE:
<221> NAME/KEY: modified_base
<222> LOCATION: (1637)..(1638)
<223> OTHER INFORMATION: UNA monomer
<220> FEATURE:
<221> NAME/KEY: modified_base
<222> LOCATION: (1641)..(1641)
<223> OTHER INFORMATION: UNA monomer
<220> FEATURE:
<221> NAME/KEY: modified_base
<222> LOCATION: (1645)..(1645)
<223> OTHER INFORMATION: UNA monomer
<220> FEATURE:
<221> NAME/KEY: modified_base
<222> LOCATION: (1656)..(1656)
<223> OTHER INFORMATION: UNA monomer
<220> FEATURE:
<221> NAME/KEY: modified_base
<222> LOCATION: (1659)..(1659)
<223> OTHER INFORMATION: UNA monomer
<220> FEATURE:
<221> NAME/KEY: modified_base
<222> LOCATION: (1661)..(1662)
<223> OTHER INFORMATION: UNA monomer
<220> FEATURE:
<221> NAME/KEY: modified_base
<222> LOCATION: (1664)..(1664)
<223> OTHER INFORMATION: UNA monomer
<220> FEATURE:
<221> NAME/KEY: modified_base
<222> LOCATION: (1667)..(1668)
<223> OTHER INFORMATION: UNA monomer
<220> FEATURE:
<221> NAME/KEY: modified_base
<222> LOCATION: (1672)..(1673)
<223> OTHER INFORMATION: UNA monomer
<220> FEATURE:
<221> NAME/KEY: modified_base
<222> LOCATION: (1676)..(1678)
<223> OTHER INFORMATION: UNA monomer
<220> FEATURE:
<221> NAME/KEY: modified_base
<222> LOCATION: (1680)..(1680)
<223> OTHER INFORMATION: UNA monomer
<220> FEATURE:
<221> NAME/KEY: modified_base
<222> LOCATION: (1683)..(1683)
<223> OTHER INFORMATION: UNA monomer
<220> FEATURE:
<221> NAME/KEY: modified_base
<222> LOCATION: (1694)..(1694)
<223> OTHER INFORMATION: UNA monomer
<220> FEATURE:
<221> NAME/KEY: modified_base
<222> LOCATION: (1699)..(1701)
<223> OTHER INFORMATION: UNA monomer
<220> FEATURE:
<221> NAME/KEY: modified_base
<222> LOCATION: (1704)..(1704)
<223> OTHER INFORMATION: UNA monomer
<220> FEATURE:
```

-continued

```
<221> NAME/KEY: modified_base
<222> LOCATION: (1706)..(1706)
<223> OTHER INFORMATION: UNA monomer
<220> FEATURE:
<221> NAME/KEY: modified_base
<222> LOCATION: (1708)..(1708)
<223> OTHER INFORMATION: UNA monomer
<220> FEATURE:
<221> NAME/KEY: modified_base
<222> LOCATION: (1711)..(1712)
<223> OTHER INFORMATION: UNA monomer
<220> FEATURE:
<221> NAME/KEY: modified_base
<222> LOCATION: (1715)..(1715)
<223> OTHER INFORMATION: UNA monomer
<220> FEATURE:
<221> NAME/KEY: modified_base
<222> LOCATION: (1720)..(1720)
<223> OTHER INFORMATION: UNA monomer
<220> FEATURE:
<221> NAME/KEY: modified_base
<222> LOCATION: (1726)..(1726)
<223> OTHER INFORMATION: UNA monomer
<220> FEATURE:
<221> NAME/KEY: modified_base
<222> LOCATION: (1728)..(1728)
<223> OTHER INFORMATION: UNA monomer
<220> FEATURE:
<221> NAME/KEY: modified_base
<222> LOCATION: (1735)..(1735)
<223> OTHER INFORMATION: UNA monomer
<220> FEATURE:
<221> NAME/KEY: modified_base
<222> LOCATION: (1743)..(1743)
<223> OTHER INFORMATION: UNA monomer
<220> FEATURE:
<221> NAME/KEY: modified_base
<222> LOCATION: (1745)..(1746)
<223> OTHER INFORMATION: UNA monomer
<220> FEATURE:
<221> NAME/KEY: modified_base
<222> LOCATION: (1748)..(1748)
<223> OTHER INFORMATION: UNA monomer
<220> FEATURE:
<221> NAME/KEY: modified_base
<222> LOCATION: (1750)..(1751)
<223> OTHER INFORMATION: UNA monomer
<220> FEATURE:
<221> NAME/KEY: modified_base
<222> LOCATION: (1753)..(1753)
<223> OTHER INFORMATION: UNA monomer
<220> FEATURE:
<221> NAME/KEY: modified_base
<222> LOCATION: (1755)..(1755)
<223> OTHER INFORMATION: UNA monomer
<220> FEATURE:
<221> NAME/KEY: modified_base
<222> LOCATION: (1757)..(1758)
<223> OTHER INFORMATION: UNA monomer
<220> FEATURE:
<221> NAME/KEY: modified_base
<222> LOCATION: (1764)..(1764)
<223> OTHER INFORMATION: UNA monomer
<220> FEATURE:
<221> NAME/KEY: modified_base
<222> LOCATION: (1767)..(1767)
<223> OTHER INFORMATION: UNA monomer
<220> FEATURE:
<221> NAME/KEY: modified_base
<222> LOCATION: (1769)..(1769)
<223> OTHER INFORMATION: UNA monomer
<220> FEATURE:
<221> NAME/KEY: modified_base
<222> LOCATION: (1772)..(1772)
<223> OTHER INFORMATION: UNA monomer
<220> FEATURE:
<221> NAME/KEY: modified_base
<222> LOCATION: (1774)..(1774)
<223> OTHER INFORMATION: UNA monomer
```

```
-continued

<220> FEATURE:
<221> NAME/KEY: modified_base
<222> LOCATION: (1776)..(1776)
<223> OTHER INFORMATION: UNA monomer
<220> FEATURE:
<221> NAME/KEY: modified_base
<222> LOCATION: (1781)..(1781)
<223> OTHER INFORMATION: UNA monomer
<220> FEATURE:
<221> NAME/KEY: modified_base
<222> LOCATION: (1790)..(1790)
<223> OTHER INFORMATION: UNA monomer
<220> FEATURE:
<221> NAME/KEY: modified_base
<222> LOCATION: (1794)..(1794)
<223> OTHER INFORMATION: UNA monomer
<220> FEATURE:
<221> NAME/KEY: modified_base
<222> LOCATION: (1796)..(1796)
<223> OTHER INFORMATION: UNA monomer
<220> FEATURE:
<221> NAME/KEY: modified_base
<222> LOCATION: (1798)..(1798)
<223> OTHER INFORMATION: UNA monomer
<220> FEATURE:
<221> NAME/KEY: modified_base
<222> LOCATION: (1800)..(1801)
<223> OTHER INFORMATION: UNA monomer
<220> FEATURE:
<221> NAME/KEY: modified_base
<222> LOCATION: (1806)..(1806)
<223> OTHER INFORMATION: UNA monomer
<220> FEATURE:
<221> NAME/KEY: modified_base
<222> LOCATION: (1813)..(1813)
<223> OTHER INFORMATION: UNA monomer
<220> FEATURE:
<221> NAME/KEY: modified_base
<222> LOCATION: (1815)..(1815)
<223> OTHER INFORMATION: UNA monomer
<220> FEATURE:
<221> NAME/KEY: modified_base
<222> LOCATION: (1818)..(1818)
<223> OTHER INFORMATION: UNA monomer
<220> FEATURE:
<221> NAME/KEY: modified_base
<222> LOCATION: (1820)..(1820)
<223> OTHER INFORMATION: UNA monomer
<220> FEATURE:
<221> NAME/KEY: modified_base
<222> LOCATION: (1825)..(1827)
<223> OTHER INFORMATION: UNA monomer
<220> FEATURE:
<221> NAME/KEY: modified_base
<222> LOCATION: (1832)..(1832)
<223> OTHER INFORMATION: UNA monomer
<220> FEATURE:
<221> NAME/KEY: modified_base
<222> LOCATION: (1845)..(1845)
<223> OTHER INFORMATION: UNA monomer
<220> FEATURE:
<221> NAME/KEY: modified_base
<222> LOCATION: (1847)..(1847)
<223> OTHER INFORMATION: UNA monomer
<220> FEATURE:
<221> NAME/KEY: modified_base
<222> LOCATION: (1852)..(1853)
<223> OTHER INFORMATION: UNA monomer
<220> FEATURE:
<221> NAME/KEY: modified_base
<222> LOCATION: (1855)..(1855)
<223> OTHER INFORMATION: UNA monomer
<220> FEATURE:
<221> NAME/KEY: modified_base
<222> LOCATION: (1865)..(1866)
<223> OTHER INFORMATION: UNA monomer
<220> FEATURE:
<221> NAME/KEY: modified_base
<222> LOCATION: (1871)..(1871)
```

```
<223> OTHER INFORMATION: UNA monomer
<220> FEATURE:
<221> NAME/KEY: modified_base
<222> LOCATION: (1880)..(1880)
<223> OTHER INFORMATION: UNA monomer
<220> FEATURE:
<221> NAME/KEY: modified_base
<222> LOCATION: (1882)..(1882)
<223> OTHER INFORMATION: UNA monomer
<220> FEATURE:
<221> NAME/KEY: modified_base
<222> LOCATION: (1887)..(1887)
<223> OTHER INFORMATION: UNA monomer
<220> FEATURE:
<221> NAME/KEY: modified_base
<222> LOCATION: (1895)..(1896)
<223> OTHER INFORMATION: UNA monomer
<220> FEATURE:
<221> NAME/KEY: modified_base
<222> LOCATION: (1907)..(1908)
<223> OTHER INFORMATION: UNA monomer
<220> FEATURE:
<221> NAME/KEY: modified_base
<222> LOCATION: (1913)..(1913)
<223> OTHER INFORMATION: UNA monomer
<220> FEATURE:
<221> NAME/KEY: modified_base
<222> LOCATION: (1915)..(1916)
<223> OTHER INFORMATION: UNA monomer
<220> FEATURE:
<221> NAME/KEY: modified_base
<222> LOCATION: (1928)..(1928)
<223> OTHER INFORMATION: UNA monomer
<220> FEATURE:
<221> NAME/KEY: modified_base
<222> LOCATION: (1940)..(1940)
<223> OTHER INFORMATION: UNA monomer
<220> FEATURE:
<221> NAME/KEY: modified_base
<222> LOCATION: (1948)..(1948)
<223> OTHER INFORMATION: UNA monomer
<220> FEATURE:
<221> NAME/KEY: modified_base
<222> LOCATION: (1952)..(1952)
<223> OTHER INFORMATION: UNA monomer
<220> FEATURE:
<221> NAME/KEY: modified_base
<222> LOCATION: (1956)..(1956)
<223> OTHER INFORMATION: UNA monomer
<220> FEATURE:
<221> NAME/KEY: modified_base
<222> LOCATION: (1961)..(1962)
<223> OTHER INFORMATION: UNA monomer
<220> FEATURE:
<221> NAME/KEY: modified_base
<222> LOCATION: (1968)..(1968)
<223> OTHER INFORMATION: UNA monomer
<220> FEATURE:
<221> NAME/KEY: modified_base
<222> LOCATION: (1970)..(1971)
<223> OTHER INFORMATION: UNA monomer
<220> FEATURE:
<221> NAME/KEY: modified_base
<222> LOCATION: (1975)..(1976)
<223> OTHER INFORMATION: UNA monomer
<220> FEATURE:
<221> NAME/KEY: modified_base
<222> LOCATION: (1980)..(1980)
<223> OTHER INFORMATION: UNA monomer
<220> FEATURE:
<221> NAME/KEY: modified_base
<222> LOCATION: (1991)..(1991)
<223> OTHER INFORMATION: UNA monomer
<220> FEATURE:
<221> NAME/KEY: modified_base
<222> LOCATION: (1995)..(1995)
<223> OTHER INFORMATION: UNA monomer
<220> FEATURE:
<221> NAME/KEY: modified_base
```

```
<222> LOCATION: (1999)..(2002)
<223> OTHER INFORMATION: UNA monomer
<220> FEATURE:
<221> NAME/KEY: modified_base
<222> LOCATION: (2004)..(2004)
<223> OTHER INFORMATION: UNA monomer
<220> FEATURE:
<221> NAME/KEY: modified_base
<222> LOCATION: (2007)..(2007)
<223> OTHER INFORMATION: UNA monomer
<220> FEATURE:
<221> NAME/KEY: modified_base
<222> LOCATION: (2011)..(2011)
<223> OTHER INFORMATION: UNA monomer
<220> FEATURE:
<221> NAME/KEY: modified_base
<222> LOCATION: (2015)..(2015)
<223> OTHER INFORMATION: UNA monomer
<220> FEATURE:
<221> NAME/KEY: modified_base
<222> LOCATION: (2021)..(2021)
<223> OTHER INFORMATION: UNA monomer
<220> FEATURE:
<221> NAME/KEY: modified_base
<222> LOCATION: (2025)..(2025)
<223> OTHER INFORMATION: UNA monomer
<220> FEATURE:
<221> NAME/KEY: modified_base
<222> LOCATION: (2027)..(2028)
<223> OTHER INFORMATION: UNA monomer
<220> FEATURE:
<221> NAME/KEY: modified_base
<222> LOCATION: (2031)..(2031)
<223> OTHER INFORMATION: UNA monomer
<220> FEATURE:
<221> NAME/KEY: modified_base
<222> LOCATION: (2034)..(2034)
<223> OTHER INFORMATION: UNA monomer
<220> FEATURE:
<221> NAME/KEY: modified_base
<222> LOCATION: (2036)..(2036)
<223> OTHER INFORMATION: UNA monomer
<220> FEATURE:
<221> NAME/KEY: modified_base
<222> LOCATION: (2041)..(2042)
<223> OTHER INFORMATION: UNA monomer
<220> FEATURE:
<221> NAME/KEY: modified_base
<222> LOCATION: (2046)..(2046)
<223> OTHER INFORMATION: UNA monomer
<220> FEATURE:
<221> NAME/KEY: modified_base
<222> LOCATION: (2048)..(2048)
<223> OTHER INFORMATION: UNA monomer
<220> FEATURE:
<221> NAME/KEY: modified_base
<222> LOCATION: (2052)..(2052)
<223> OTHER INFORMATION: UNA monomer
<220> FEATURE:
<221> NAME/KEY: modified_base
<222> LOCATION: (2060)..(2062)
<223> OTHER INFORMATION: UNA monomer
<220> FEATURE:
<221> NAME/KEY: modified_base
<222> LOCATION: (2064)..(2064)
<223> OTHER INFORMATION: UNA monomer
<220> FEATURE:
<221> NAME/KEY: modified_base
<222> LOCATION: (2070)..(2070)
<223> OTHER INFORMATION: UNA monomer
<220> FEATURE:
<221> NAME/KEY: modified_base
<222> LOCATION: (2073)..(2073)
<223> OTHER INFORMATION: UNA monomer
<220> FEATURE:
<221> NAME/KEY: modified_base
<222> LOCATION: (2076)..(2076)
<223> OTHER INFORMATION: UNA monomer
<220> FEATURE:
```

```
<221> NAME/KEY: modified_base
<222> LOCATION: (2078)..(2079)
<223> OTHER INFORMATION: UNA monomer
<220> FEATURE:
<221> NAME/KEY: modified_base
<222> LOCATION: (2085)..(2085)
<223> OTHER INFORMATION: UNA monomer
<220> FEATURE:
<221> NAME/KEY: modified_base
<222> LOCATION: (2089)..(2089)
<223> OTHER INFORMATION: UNA monomer
<220> FEATURE:
<221> NAME/KEY: modified_base
<222> LOCATION: (2092)..(2092)
<223> OTHER INFORMATION: UNA monomer
<220> FEATURE:
<221> NAME/KEY: modified_base
<222> LOCATION: (2094)..(2094)
<223> OTHER INFORMATION: UNA monomer
<220> FEATURE:
<221> NAME/KEY: modified_base
<222> LOCATION: (2098)..(2098)
<223> OTHER INFORMATION: UNA monomer
<220> FEATURE:
<221> NAME/KEY: modified_base
<222> LOCATION: (2102)..(2104)
<223> OTHER INFORMATION: UNA monomer
<220> FEATURE:
<221> NAME/KEY: modified_base
<222> LOCATION: (2121)..(2122)
<223> OTHER INFORMATION: UNA monomer
<220> FEATURE:
<221> NAME/KEY: modified_base
<222> LOCATION: (2124)..(2125)
<223> OTHER INFORMATION: UNA monomer

<400> SEQUENCE: 153 augaggqucc ugggugggcg cugcggggcg cugcuggcgu gucuccuccu agugcuuccc      60
gucucagagg caaacuuuug uuuauauuuu agaaaugauu uuauauacaa ccgugcaugc     120
auuucuguau uggucggcuu aucuggaugc aauuuuuucu auucuauaug cuuuuuguca     180
aagcaacagg cuucacaagu ccugguuagg aagcgucgug caaauucuuu acuugaagaa     240
accaaacagg guaaucuuga agagaaugc aucgaagaac ugugcaauaa agaagaagcc      300
agggaggucu uugaaaauga cccggaaacg gauuauuuuu auccaaaaua cuuaguuugu     360
cuucgcucuu uucaaacugg guuauucacu gcugcacguc agucaacuaa ugcuuauccu     420
gaccuaagaa gcugugucaa ugccauucca gaccagugua guccucugcc augcaaugaa     480
gauggauaua ugagcugcaa agauggaaaa gcuucuuuua cuugcacuug uaaaccaggu     540
uggcaaggag aaaaguguga auuugacaua aaugaaugca agaucccuc aaauauaaau      600 ggagguugca gucaaauuug ugauaauaca ccuggaaguu accacuguuc cuguaaaaau     660
gguuuuguua ugcuuucaaa uaagaaagau uguaaagaug uggaugaaug cucuuuugaag    720 ccaagcauuu guggcacagc ugugugcaag aacaucccag gagauuuga augugaaugc      780 cccgaaggcu acagauauaa ucucaaauca aagucuugug aagauauaga ugaaugcucu     840
gagaacaugu gugcucagcu uugugucaau uacccuggag guuacacuug cuauugugau     900
gggaagaaag gauucaaacu ugcccaagau cagaagaguu gugagguugu uucagugugc     960
cuucccuuga accuugacac aaaguaugaa uuacuuuacu uggcggagca guuugcaggg    1020
guuguuuuau auuuaaaauu ucguuugcca gaaaucagca gauuucagc agaauuugau     1080 uuccggacau augauucaga aggcgugaua cuguacgcag aaucuaucga ucacucagcg    1140
uggcuccuga uugcacuucg uggugaaag auugaaguuc agcuuaagaa ugaacauaca    1200
uccaaaauca caacuggagg ugauguuauu aauaauggc uauggaauau ggugucugug   1260
```

```
gaagaauuag aacauaguau uagcauuaaa auagcuaaag aagcugugau ggauauaaau    1320
aaaccuggac cccuuuuuaa gccggaaaau ggauugcugg aaaccaaagu auacuuugca    1380
ggauucccuc ggaaaguggaa aagugaacuc auuaaaccga uuaacccucg ucuagaugga   1440
uguauacgaa gcuggaauuu gaugaagcaa ggagcuucug gaauaaagga aauuauucaa    1500
gaaaaacaaa auaagcauug ccugguuacu guggagaagg gcuccacuaa uccgguucu     1560 ggaauugcuc aauuucacau agauuauaau aauguaucca gugcugaggg uuggcaugua    1620
aaugugaccu ugaauauucg uccauccacg ggcacuggug uuaugcuugc cuggyuucu    1680 gguaacaaca cagugcccuu ugcuguguccc uugguggacu ccaccucuga aaaaucacag   1740
gauauucugu uaucuguuga aaauacugua auauaucgga uacaggcccu aagucuaugu   1800
uccgaucaac aaucucaucu ggaauuuaga gucaacagaa acaaucugga uugucgaca    1860 ccacuuaaaa uagaaaccau cucccaugaa gaccuucaaa gacaacuugc cgucuuggac   1920
aaagcaauga aagcaaaagu ggccacauac cuggguggcc uuccagaugu uccauucagu   1980
gccacaccag ugaaugccuu uuauaauggc ugcauggaag ugaauauuaa ugguguacag   2040
uuggaucugg augaagccau uucuaaacau aaugauauua gagcucacuc auguccauca   2100
guuuggaaaa agacaaagaa uucuuaa                                       2127

<210> SEQ ID NO 154
<211> LENGTH: 1725
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(4)
<223> OTHER INFORMATION: UNA monomer
<220> FEATURE:
<221> NAME/KEY: modified_base
<222> LOCATION: (1722)..(1724)
<223> OTHER INFORMATION: UNA monomer

<400> SEQUENCE: 154
augucgaucc aggagaacau aucaucccug cagcuucggu caugggucuc uaagucccaa      60
agagacuuag caaaguccau ccugauuggg gcuccaggag ggccagcggg guaucugcgg    120
cgggccagug uggcccaacu gacccaggag cugggcacug ccuucuucca gcagcagcag    180
cugccagcug cuauggcaga caccuuccug gaacaccucu gccuacugga cauugacucc    240
gagcccgugg cugcucgcag uaccagcauc auugccacca ucgggccagc aucucgcucc    300
guggagcgcc ucaaggagau gaucaaggcc gggaugaaca uugcgcgacu caacuuucucc   360 cacggcuccc acgaguacca ugcugaguccc aucgccaacg uccgggaggc ggguggagagc    420 uuugcagguu ccccacucag cuaccggccc guggccaucg cccuggacac caagggaccg    480
gagauccgca cugggauccu gcagggggu ccagagucgg aaguggagcu gguugaagggc     540 ucccagguge uggugacugu ggacccccgcg uuccggacgc gggggaacgc gaacaccgug     600 ugggugggacu accccaauau ugucgggguc gugccggugc ggggccgcau cuacauugac    660
gacgggcuca ucucccuagu ggaccagaaa aucggccccag agggacuggu gacccaagug    720
gagaacggcg gcguccuggg cagccggaag ggcgugaacu ugccagggc ccagguggac    780 uugcccgggc uugccgagca ggacguccga gaccugcgcu ucggggugga gcaugggug     840 gacaucgucu uugccuccuu ugugcggaaa gccagcgacg uggcugccgu cagggcugcu   900
```

```
cuggguccgg aaggacacgg caucaagauc aucagcaaaa uugagaacca cgaaggcgug      960
aagagguuug augaaauccu ggaggugagc gacggcauca uggaggcacg gggggaccua     1020
ggcaucgaga ucccagcaga gaagguuuuc cuggcucaga agaugaugau ugggcgcugc     1080
aacuuggcgg gcaagccugu ugucugugcc acacagaugc uggagagcau gauuaccaag     1140
ccccggccaa cgagggcaga gacaagcgau gucgccaaug cugugcugga uggggcugac     1200
ugcaucaugc ugucagggga gacugccaag ggcaacuucc cuggaagc ggugaagaug       1260 cagcaugcga uugcccggga ggcagaggcc gcaguguacc accggcagcu guugaggag      1320 cuacgucggg cagcgccacu aagccgugau cccacgagg ucaccgccau uggugcugug      1380
gaggcugccu ucaagugcug ugcugcugcc aucauugugc ugaccacaac uggccgcuca     1440
gcccagcuuc ugucucggua ccgaccucgg gcagcaguca uugcugucac ccgcucugcc     1500
caggcugccc gccaggucca cuuaugccga ggagucuucc ccuugcuuua ccgugaaccu     1560
ccagaagcca ucugggcaga ugauguagau cgccggguc aauuuggcau ugaaaguggga    1620 aagcuccgug gcuuccuccg uguuggagac cuggugauu uggugacagg cuggcgaccu      1680
ggcuccggcu acaccaacau caugcgggug cuaagcauau ccuga                     1725
```

<210> SEQ ID NO 155  
<211> LENGTH: 1725  
<212> TYPE: RNA  
<213> ORGANISM: Artificial Sequence  
<220> FEATURE:  
<223> OTHER INFORMATION: Description of Artificial Sequence: Synthetic  
    polynucleotide  
<220> FEATURE:  
<221> NAME/KEY: modified_base  
<222> LOCATION: (2)..(2)  
<223> OTHER INFORMATION: UNA monomer  
<220> FEATURE:  
<221> NAME/KEY: modified_base  
<222> LOCATION: (4)..(4)  
<223> OTHER INFORMATION: UNA monomer  
<220> FEATURE:  
<221> NAME/KEY: modified_base  
<222> LOCATION: (8)..(8)  
<223> OTHER INFORMATION: UNA monomer  
<220> FEATURE:  
<221> NAME/KEY: modified_base  
<222> LOCATION: (20)..(20)  
<223> OTHER INFORMATION: UNA monomer  
<220> FEATURE:  
<221> NAME/KEY: modified_base  
<222> LOCATION: (22)..(22)  
<223> OTHER INFORMATION: UNA monomer  
<220> FEATURE:  
<221> NAME/KEY: modified_base  
<222> LOCATION: (25)..(25)  
<223> OTHER INFORMATION: UNA monomer  
<220> FEATURE:  
<221> NAME/KEY: modified_base  
<222> LOCATION: (29)..(29)  
<223> OTHER INFORMATION: UNA monomer  
<220> FEATURE:  
<221> NAME/KEY: modified_base  
<222> LOCATION: (35)..(36)  
<223> OTHER INFORMATION: UNA monomer  
<220> FEATURE:  
<221> NAME/KEY: modified_base  
<222> LOCATION: (40)..(40)  
<223> OTHER INFORMATION: UNA monomer  
<220> FEATURE:  
<221> NAME/KEY: modified_base  
<222> LOCATION: (43)..(43)  
<223> OTHER INFORMATION: UNA monomer  
<220> FEATURE:  
<221> NAME/KEY: modified_base -continued

```
<222> LOCATION: (47)..(47)
<223> OTHER INFORMATION: UNA monomer
<220> FEATURE:
<221> NAME/KEY: modified_base
<222> LOCATION: (49)..(49)
<223> OTHER INFORMATION: UNA monomer
<220> FEATURE:
<221> NAME/KEY: modified_base
<222> LOCATION: (51)..(51)
<223> OTHER INFORMATION: UNA monomer
<220> FEATURE:
<221> NAME/KEY: modified_base
<222> LOCATION: (55)..(55)
<223> OTHER INFORMATION: UNA monomer
<220> FEATURE:
<221> NAME/KEY: modified_base
<222> LOCATION: (67)..(68)
<223> OTHER INFORMATION: UNA monomer
<220> FEATURE:
<221> NAME/KEY: modified_base
<222> LOCATION: (76)..(76)
<223> OTHER INFORMATION: UNA monomer
<220> FEATURE:
<221> NAME/KEY: modified_base
<222> LOCATION: (80)..(80)
<223> OTHER INFORMATION: UNA monomer
<220> FEATURE:
<221> NAME/KEY: modified_base
<222> LOCATION: (83)..(83)
<223> OTHER INFORMATION: UNA monomer
<220> FEATURE:
<221> NAME/KEY: modified_base
<222> LOCATION: (86)..(87)
<223> OTHER INFORMATION: UNA monomer
<220> FEATURE:
<221> NAME/KEY: modified_base
<222> LOCATION: (93)..(93)
<223> OTHER INFORMATION: UNA monomer
<220> FEATURE:
<221> NAME/KEY: modified_base
<222> LOCATION: (112)..(112)
<223> OTHER INFORMATION: UNA monomer
<220> FEATURE:
<221> NAME/KEY: modified_base
<222> LOCATION: (114)..(114)
<223> OTHER INFORMATION: UNA monomer
<220> FEATURE:
<221> NAME/KEY: modified_base
<222> LOCATION: (116)..(116)
<223> OTHER INFORMATION: UNA monomer
<220> FEATURE:
<221> NAME/KEY: modified_base
<222> LOCATION: (129)..(129)
<223> OTHER INFORMATION: UNA monomer
<220> FEATURE:
<221> NAME/KEY: modified_base
<222> LOCATION: (131)..(131)
<223> OTHER INFORMATION: UNA monomer
<220> FEATURE:
<221> NAME/KEY: modified_base
<222> LOCATION: (140)..(140)
<223> OTHER INFORMATION: UNA monomer
<220> FEATURE:
<221> NAME/KEY: modified_base
<222> LOCATION: (152)..(152)
<223> OTHER INFORMATION: UNA monomer
<220> FEATURE:
<221> NAME/KEY: modified_base
<222> LOCATION: (159)..(159)
<223> OTHER INFORMATION: UNA monomer
<220> FEATURE:
<221> NAME/KEY: modified_base
<222> LOCATION: (163)..(164)
<223> OTHER INFORMATION: UNA monomer
<220> FEATURE:
<221> NAME/KEY: modified_base
<222> LOCATION: (166)..(167)
<223> OTHER INFORMATION: UNA monomer
<220> FEATURE:
```

-continued

```
<221> NAME/KEY: modified_base
<222> LOCATION: (182)..(182)
<223> OTHER INFORMATION: UNA monomer
<220> FEATURE:
<221> NAME/KEY: modified_base
<222> LOCATION: (189)..(189)
<223> OTHER INFORMATION: UNA monomer
<220> FEATURE:
<221> NAME/KEY: modified_base
<222> LOCATION: (192)..(192)
<223> OTHER INFORMATION: UNA monomer
<220> FEATURE:
<221> NAME/KEY: modified_base
<222> LOCATION: (194)..(194)
<223> OTHER INFORMATION: UNA monomer
<220> FEATURE:
<221> NAME/KEY: modified_base
<222> LOCATION: (205)..(206)
<223> OTHER INFORMATION: UNA monomer
<220> FEATURE:
<221> NAME/KEY: modified_base
<222> LOCATION: (209)..(209)
<223> OTHER INFORMATION: UNA monomer
<220> FEATURE:
<221> NAME/KEY: modified_base
<222> LOCATION: (218)..(218)
<223> OTHER INFORMATION: UNA monomer
<220> FEATURE:
<221> NAME/KEY: modified_base
<222> LOCATION: (220)..(220)
<223> OTHER INFORMATION: UNA monomer
<220> FEATURE:
<221> NAME/KEY: modified_base
<222> LOCATION: (224)..(224)
<223> OTHER INFORMATION: UNA monomer
<220> FEATURE:
<221> NAME/KEY: modified_base
<222> LOCATION: (227)..(227)
<223> OTHER INFORMATION: UNA monomer
<220> FEATURE:
<221> NAME/KEY: modified_base
<222> LOCATION: (233)..(234)
<223> OTHER INFORMATION: UNA monomer
<220> FEATURE:
<221> NAME/KEY: modified_base
<222> LOCATION: (238)..(238)
<223> OTHER INFORMATION: UNA monomer
<220> FEATURE:
<221> NAME/KEY: modified_base
<222> LOCATION: (248)..(248)
<223> OTHER INFORMATION: UNA monomer
<220> FEATURE:
<221> NAME/KEY: modified_base
<222> LOCATION: (252)..(252)
<223> OTHER INFORMATION: UNA monomer
<220> FEATURE:
<221> NAME/KEY: modified_base
<222> LOCATION: (255)..(255)
<223> OTHER INFORMATION: UNA monomer
<220> FEATURE:
<221> NAME/KEY: modified_base
<222> LOCATION: (261)..(261)
<223> OTHER INFORMATION: UNA monomer
<220> FEATURE:
<221> NAME/KEY: modified_base
<222> LOCATION: (269)..(269)
<223> OTHER INFORMATION: UNA monomer
<220> FEATURE:
<221> NAME/KEY: modified_base
<222> LOCATION: (272)..(273)
<223> OTHER INFORMATION: UNA monomer
<220> FEATURE:
<221> NAME/KEY: modified_base
<222> LOCATION: (281)..(281)
<223> OTHER INFORMATION: UNA monomer
<220> FEATURE:
<221> NAME/KEY: modified_base
<222> LOCATION: (292)..(292)
<223> OTHER INFORMATION: UNA monomer
```

-continued

```
<220> FEATURE:
<221> NAME/KEY: modified_base
<222> LOCATION: (294)..(294)
<223> OTHER INFORMATION: UNA monomer
<220> FEATURE:
<221> NAME/KEY: modified_base
<222> LOCATION: (298)..(298)
<223> OTHER INFORMATION: UNA monomer
<220> FEATURE:
<221> NAME/KEY: modified_base
<222> LOCATION: (302)..(302)
<223> OTHER INFORMATION: UNA monomer
<220> FEATURE:
<221> NAME/KEY: modified_base
<222> LOCATION: (311)..(311)
<223> OTHER INFORMATION: UNA monomer
<220> FEATURE:
<221> NAME/KEY: modified_base
<222> LOCATION: (320)..(320)
<223> OTHER INFORMATION: UNA monomer
<220> FEATURE:
<221> NAME/KEY: modified_base
<222> LOCATION: (323)..(323)
<223> OTHER INFORMATION: UNA monomer
<220> FEATURE:
<221> NAME/KEY: modified_base
<222> LOCATION: (335)..(335)
<223> OTHER INFORMATION: UNA monomer
<220> FEATURE:
<221> NAME/KEY: modified_base
<222> LOCATION: (341)..(342)
<223> OTHER INFORMATION: UNA monomer
<220> FEATURE:
<221> NAME/KEY: modified_base
<222> LOCATION: (350)..(350)
<223> OTHER INFORMATION: UNA monomer
<220> FEATURE:
<221> NAME/KEY: modified_base
<222> LOCATION: (355)..(356)
<223> OTHER INFORMATION: UNA monomer
<220> FEATURE:
<221> NAME/KEY: modified_base
<222> LOCATION: (358)..(358)
<223> OTHER INFORMATION: UNA monomer
<220> FEATURE:
<221> NAME/KEY: modified_base
<222> LOCATION: (367)..(367)
<223> OTHER INFORMATION: UNA monomer
<220> FEATURE:
<221> NAME/KEY: modified_base
<222> LOCATION: (376)..(376)
<223> OTHER INFORMATION: UNA monomer
<220> FEATURE:
<221> NAME/KEY: modified_base
<222> LOCATION: (381)..(381)
<223> OTHER INFORMATION: UNA monomer
<220> FEATURE:
<221> NAME/KEY: modified_base
<222> LOCATION: (384)..(384)
<223> OTHER INFORMATION: UNA monomer
<220> FEATURE:
<221> NAME/KEY: modified_base
<222> LOCATION: (388)..(388)
<223> OTHER INFORMATION: UNA monomer
<220> FEATURE:
<221> NAME/KEY: modified_base
<222> LOCATION: (392)..(392)
<223> OTHER INFORMATION: UNA monomer
<220> FEATURE:
<221> NAME/KEY: modified_base
<222> LOCATION: (401)..(401)
<223> OTHER INFORMATION: UNA monomer
<220> FEATURE:
<221> NAME/KEY: modified_base
<222> LOCATION: (413)..(413)
<223> OTHER INFORMATION: UNA monomer
<220> FEATURE:
<221> NAME/KEY: modified_base
<222> LOCATION: (421)..(423)
```

```
<223> OTHER INFORMATION: UNA monomer
<220> FEATURE:
<221> NAME/KEY: modified_base
<222> LOCATION: (429)..(430)
<223> OTHER INFORMATION: UNA monomer
<220> FEATURE:
<221> NAME/KEY: modified_base
<222> LOCATION: (437)..(437)
<223> OTHER INFORMATION: UNA monomer
<220> FEATURE:
<221> NAME/KEY: modified_base
<222> LOCATION: (442)..(442)
<223> OTHER INFORMATION: UNA monomer
<220> FEATURE:
<221> NAME/KEY: modified_base
<222> LOCATION: (452)..(452)
<223> OTHER INFORMATION: UNA monomer
<220> FEATURE:
<221> NAME/KEY: modified_base
<222> LOCATION: (458)..(458)
<223> OTHER INFORMATION: UNA monomer
<220> FEATURE:
<221> NAME/KEY: modified_base
<222> LOCATION: (464)..(464)
<223> OTHER INFORMATION: UNA monomer
<220> FEATURE:
<221> NAME/KEY: modified_base
<222> LOCATION: (485)..(485)
<223> OTHER INFORMATION: UNA monomer
<220> FEATURE:
<221> NAME/KEY: modified_base
<222> LOCATION: (492)..(492)
<223> OTHER INFORMATION: UNA monomer
<220> FEATURE:
<221> NAME/KEY: modified_base
<222> LOCATION: (497)..(497)
<223> OTHER INFORMATION: UNA monomer
<220> FEATURE:
<221> NAME/KEY: modified_base
<222> LOCATION: (500)..(500)
<223> OTHER INFORMATION: UNA monomer
<220> FEATURE:
<221> NAME/KEY: modified_base
<222> LOCATION: (510)..(510)
<223> OTHER INFORMATION: UNA monomer
<220> FEATURE:
<221> NAME/KEY: modified_base
<222> LOCATION: (517)..(517)
<223> OTHER INFORMATION: UNA monomer
<220> FEATURE:
<221> NAME/KEY: modified_base
<222> LOCATION: (524)..(524)
<223> OTHER INFORMATION: UNA monomer
<220> FEATURE:
<221> NAME/KEY: modified_base
<222> LOCATION: (530)..(530)
<223> OTHER INFORMATION: UNA monomer
<220> FEATURE:
<221> NAME/KEY: modified_base
<222> LOCATION: (533)..(533)
<223> OTHER INFORMATION: UNA monomer
<220> FEATURE:
<221> NAME/KEY: modified_base
<222> LOCATION: (541)..(541)
<223> OTHER INFORMATION: UNA monomer
<220> FEATURE:
<221> NAME/KEY: modified_base
<222> LOCATION: (548)..(548)
<223> OTHER INFORMATION: UNA monomer
<220> FEATURE:
<221> NAME/KEY: modified_base
<222> LOCATION: (551)..(551)
<223> OTHER INFORMATION: UNA monomer
<220> FEATURE:
<221> NAME/KEY: modified_base
<222> LOCATION: (554)..(554)
<223> OTHER INFORMATION: UNA monomer
<220> FEATURE:
<221> NAME/KEY: modified_base
```

```
<222> LOCATION: (558)..(558)
<223> OTHER INFORMATION: UNA monomer
<220> FEATURE:
<221> NAME/KEY: modified_base
<222> LOCATION: (560)..(560)
<223> OTHER INFORMATION: UNA monomer
<220> FEATURE:
<221> NAME/KEY: modified_base
<222> LOCATION: (571)..(572)
<223> OTHER INFORMATION: UNA monomer
<220> FEATURE:
<221> NAME/KEY: modified_base
<222> LOCATION: (599)..(599)
<223> OTHER INFORMATION: UNA monomer
<220> FEATURE:
<221> NAME/KEY: modified_base
<222> LOCATION: (601)..(601)
<223> OTHER INFORMATION: UNA monomer
<220> FEATURE:
<221> NAME/KEY: modified_base
<222> LOCATION: (605)..(605)
<223> OTHER INFORMATION: UNA monomer
<220> FEATURE:
<221> NAME/KEY: modified_base
<222> LOCATION: (610)..(610)
<223> OTHER INFORMATION: UNA monomer
<220> FEATURE:
<221> NAME/KEY: modified_base
<222> LOCATION: (618)..(618)
<223> OTHER INFORMATION: UNA monomer
<220> FEATURE:
<221> NAME/KEY: modified_base
<222> LOCATION: (620)..(621)
<223> OTHER INFORMATION: UNA monomer
<220> FEATURE:
<221> NAME/KEY: modified_base
<222> LOCATION: (623)..(623)
<223> OTHER INFORMATION: UNA monomer
<220> FEATURE:
<221> NAME/KEY: modified_base
<222> LOCATION: (629)..(629)
<223> OTHER INFORMATION: UNA monomer
<220> FEATURE:
<221> NAME/KEY: modified_base
<222> LOCATION: (632)..(632)
<223> OTHER INFORMATION: UNA monomer
<220> FEATURE:
<221> NAME/KEY: modified_base
<222> LOCATION: (638)..(638)
<223> OTHER INFORMATION: UNA monomer
<220> FEATURE:
<221> NAME/KEY: modified_base
<222> LOCATION: (650)..(650)
<223> OTHER INFORMATION: UNA monomer
<220> FEATURE:
<221> NAME/KEY: modified_base
<222> LOCATION: (652)..(652)
<223> OTHER INFORMATION: UNA monomer
<220> FEATURE:
<221> NAME/KEY: modified_base
<222> LOCATION: (656)..(657)
<223> OTHER INFORMATION: UNA monomer
<220> FEATURE:
<221> NAME/KEY: modified_base
<222> LOCATION: (668)..(668)
<223> OTHER INFORMATION: UNA monomer
<220> FEATURE:
<221> NAME/KEY: modified_base
<222> LOCATION: (671)..(671)
<223> OTHER INFORMATION: UNA monomer
<220> FEATURE:
<221> NAME/KEY: modified_base
<222> LOCATION: (673)..(673)
<223> OTHER INFORMATION: UNA monomer
<220> FEATURE:
<221> NAME/KEY: modified_base
<222> LOCATION: (677)..(677)
<223> OTHER INFORMATION: UNA monomer
<220> FEATURE:
```

```
<221> NAME/KEY: modified_base
<222> LOCATION: (680)..(680)
<223> OTHER INFORMATION: UNA monomer
<220> FEATURE:
<221> NAME/KEY: modified_base
<222> LOCATION: (683)..(683)
<223> OTHER INFORMATION: UNA monomer
<220> FEATURE:
<221> NAME/KEY: modified_base
<222> LOCATION: (692)..(692)
<223> OTHER INFORMATION: UNA monomer
<220> FEATURE:
<221> NAME/KEY: modified_base
<222> LOCATION: (707)..(707)
<223> OTHER INFORMATION: UNA monomer
<220> FEATURE:
<221> NAME/KEY: modified_base
<222> LOCATION: (710)..(710)
<223> OTHER INFORMATION: UNA monomer
<220> FEATURE:
<221> NAME/KEY: modified_base
<222> LOCATION: (719)..(719)
<223> OTHER INFORMATION: UNA monomer
<220> FEATURE:
<221> NAME/KEY: modified_base
<222> LOCATION: (734)..(734)
<223> OTHER INFORMATION: UNA monomer
<220> FEATURE:
<221> NAME/KEY: modified_base
<222> LOCATION: (737)..(737)
<223> OTHER INFORMATION: UNA monomer
<220> FEATURE:
<221> NAME/KEY: modified_base
<222> LOCATION: (755)..(755)
<223> OTHER INFORMATION: UNA monomer
<220> FEATURE:
<221> NAME/KEY: modified_base
<222> LOCATION: (760)..(761)
<223> OTHER INFORMATION: UNA monomer
<220> FEATURE:
<221> NAME/KEY: modified_base
<222> LOCATION: (776)..(776)
<223> OTHER INFORMATION: UNA monomer
<220> FEATURE:
<221> NAME/KEY: modified_base
<222> LOCATION: (781)..(782)
<223> OTHER INFORMATION: UNA monomer
<220> FEATURE:
<221> NAME/KEY: modified_base
<222> LOCATION: (791)..(791)
<223> OTHER INFORMATION: UNA monomer
<220> FEATURE:
<221> NAME/KEY: modified_base
<222> LOCATION: (793)..(793)
<223> OTHER INFORMATION: UNA monomer
<220> FEATURE:
<221> NAME/KEY: modified_base
<222> LOCATION: (806)..(806)
<223> OTHER INFORMATION: UNA monomer
<220> FEATURE:
<221> NAME/KEY: modified_base
<222> LOCATION: (815)..(815)
<223> OTHER INFORMATION: UNA monomer
<220> FEATURE:
<221> NAME/KEY: modified_base
<222> LOCATION: (820)..(821)
<223> OTHER INFORMATION: UNA monomer
<220> FEATURE:
<221> NAME/KEY: modified_base
<222> LOCATION: (827)..(827)
<223> OTHER INFORMATION: UNA monomer
<220> FEATURE:
<221> NAME/KEY: modified_base
<222> LOCATION: (834)..(834)
<223> OTHER INFORMATION: UNA monomer
<220> FEATURE:
<221> NAME/KEY: modified_base
<222> LOCATION: (839)..(839)
<223> OTHER INFORMATION: UNA monomer
```

```
<220> FEATURE:
<221> NAME/KEY: modified_base
<222> LOCATION: (845)..(845)
<223> OTHER INFORMATION: UNA monomer
<220> FEATURE:
<221> NAME/KEY: modified_base
<222> LOCATION: (848)..(848)
<223> OTHER INFORMATION: UNA monomer
<220> FEATURE:
<221> NAME/KEY: modified_base
<222> LOCATION: (850)..(852)
<223> OTHER INFORMATION: UNA monomer
<220> FEATURE:
<221> NAME/KEY: modified_base
<222> LOCATION: (856)..(856)
<223> OTHER INFORMATION: UNA monomer
<220> FEATURE:
<221> NAME/KEY: modified_base
<222> LOCATION: (859)..(861)
<223> OTHER INFORMATION: UNA monomer
<220> FEATURE:
<221> NAME/KEY: modified_base
<222> LOCATION: (863)..(863)
<223> OTHER INFORMATION: UNA monomer
<220> FEATURE:
<221> NAME/KEY: modified_base
<222> LOCATION: (881)..(881)
<223> OTHER INFORMATION: UNA monomer
<220> FEATURE:
<221> NAME/KEY: modified_base
<222> LOCATION: (885)..(885)
<223> OTHER INFORMATION: UNA monomer
<220> FEATURE:
<221> NAME/KEY: modified_base
<222> LOCATION: (890)..(890)
<223> OTHER INFORMATION: UNA monomer
<220> FEATURE:
<221> NAME/KEY: modified_base
<222> LOCATION: (897)..(897)
<223> OTHER INFORMATION: UNA monomer
<220> FEATURE:
<221> NAME/KEY: modified_base
<222> LOCATION: (900)..(900)
<223> OTHER INFORMATION: UNA monomer
<220> FEATURE:
<221> NAME/KEY: modified_base
<222> LOCATION: (902)..(902)
<223> OTHER INFORMATION: UNA monomer
<220> FEATURE:
<221> NAME/KEY: modified_base
<222> LOCATION: (906)..(906)
<223> OTHER INFORMATION: UNA monomer
<220> FEATURE:
<221> NAME/KEY: modified_base
<222> LOCATION: (923)..(923)
<223> OTHER INFORMATION: UNA monomer
<220> FEATURE:
<221> NAME/KEY: modified_base
<222> LOCATION: (929)..(929)
<223> OTHER INFORMATION: UNA monomer
<220> FEATURE:
<221> NAME/KEY: modified_base
<222> LOCATION: (932)..(932)
<223> OTHER INFORMATION: UNA monomer
<220> FEATURE:
<221> NAME/KEY: modified_base
<222> LOCATION: (941)..(942)
<223> OTHER INFORMATION: UNA monomer
<220> FEATURE:
<221> NAME/KEY: modified_base
<222> LOCATION: (959)..(959)
<223> OTHER INFORMATION: UNA monomer
<220> FEATURE:
<221> NAME/KEY: modified_base
<222> LOCATION: (967)..(969)
<223> OTHER INFORMATION: UNA monomer
<220> FEATURE:
<221> NAME/KEY: modified_base
<222> LOCATION: (972)..(972)
```

-continued

```
<223> OTHER INFORMATION: UNA monomer
<220> FEATURE:
<221> NAME/KEY: modified_base
<222> LOCATION: (977)..(977)
<223> OTHER INFORMATION: UNA monomer
<220> FEATURE:
<221> NAME/KEY: modified_base
<222> LOCATION: (980)..(980)
<223> OTHER INFORMATION: UNA monomer
<220> FEATURE:
<221> NAME/KEY: modified_base
<222> LOCATION: (986)..(986)
<223> OTHER INFORMATION: UNA monomer
<220> FEATURE:
<221> NAME/KEY: modified_base
<222> LOCATION: (998)..(998)
<223> OTHER INFORMATION: UNA monomer
<220> FEATURE:
<221> NAME/KEY: modified_base
<222> LOCATION: (1001)..(1001)
<223> OTHER INFORMATION: UNA monomer
<220> FEATURE:
<221> NAME/KEY: modified_base
<222> LOCATION: (1004)..(1004)
<223> OTHER INFORMATION: UNA monomer
<220> FEATURE:
<221> NAME/KEY: modified_base
<222> LOCATION: (1019)..(1019)
<223> OTHER INFORMATION: UNA monomer
<220> FEATURE:
<221> NAME/KEY: modified_base
<222> LOCATION: (1025)..(1025)
<223> OTHER INFORMATION: UNA monomer
<220> FEATURE:
<221> NAME/KEY: modified_base
<222> LOCATION: (1031)..(1031)
<223> OTHER INFORMATION: UNA monomer
<220> FEATURE:
<221> NAME/KEY: modified_base
<222> LOCATION: (1046)..(1049)
<223> OTHER INFORMATION: UNA monomer
<220> FEATURE:
<221> NAME/KEY: modified_base
<222> LOCATION: (1052)..(1052)
<223> OTHER INFORMATION: UNA monomer
<220> FEATURE:
<221> NAME/KEY: modified_base
<222> LOCATION: (1056)..(1056)
<223> OTHER INFORMATION: UNA monomer
<220> FEATURE:
<221> NAME/KEY: modified_base
<222> LOCATION: (1064)..(1064)
<223> OTHER INFORMATION: UNA monomer
<220> FEATURE:
<221> NAME/KEY: modified_base
<222> LOCATION: (1067)..(1067)
<223> OTHER INFORMATION: UNA monomer
<220> FEATURE:
<221> NAME/KEY: modified_base
<222> LOCATION: (1070)..(1071)
<223> OTHER INFORMATION: UNA monomer
<220> FEATURE:
<221> NAME/KEY: modified_base
<222> LOCATION: (1078)..(1078)
<223> OTHER INFORMATION: UNA monomer
<220> FEATURE:
<221> NAME/KEY: modified_base
<222> LOCATION: (1084)..(1085)
<223> OTHER INFORMATION: UNA monomer
<220> FEATURE:
<221> NAME/KEY: modified_base
<222> LOCATION: (1098)..(1098)
<223> OTHER INFORMATION: UNA monomer
<220> FEATURE:
<221> NAME/KEY: modified_base
<222> LOCATION: (1100)..(1101)
<223> OTHER INFORMATION: UNA monomer
<220> FEATURE:
<221> NAME/KEY: modified_base
```

```
<222> LOCATION: (1103)..(1103)
<223> OTHER INFORMATION: UNA monomer
<220> FEATURE:
<221> NAME/KEY: modified_base
<222> LOCATION: (1105)..(1105)
<223> OTHER INFORMATION: UNA monomer
<220> FEATURE:
<221> NAME/KEY: modified_base
<222> LOCATION: (1107)..(1107)
<223> OTHER INFORMATION: UNA monomer
<220> FEATURE:
<221> NAME/KEY: modified_base
<222> LOCATION: (1118)..(1118)
<223> OTHER INFORMATION: UNA monomer
<220> FEATURE:
<221> NAME/KEY: modified_base
<222> LOCATION: (1121)..(1121)
<223> OTHER INFORMATION: UNA monomer
<220> FEATURE:
<221> NAME/KEY: modified_base
<222> LOCATION: (1130)..(1130)
<223> OTHER INFORMATION: UNA monomer
<220> FEATURE:
<221> NAME/KEY: modified_base
<222> LOCATION: (1133)..(1134)
<223> OTHER INFORMATION: UNA monomer
<220> FEATURE:
<221> NAME/KEY: modified_base
<222> LOCATION: (1170)..(1170)
<223> OTHER INFORMATION: UNA monomer
<220> FEATURE:
<221> NAME/KEY: modified_base
<222> LOCATION: (1172)..(1172)
<223> OTHER INFORMATION: UNA monomer
<220> FEATURE:
<221> NAME/KEY: modified_base
<222> LOCATION: (1179)..(1179)
<223> OTHER INFORMATION: UNA monomer
<220> FEATURE:
<221> NAME/KEY: modified_base
<222> LOCATION: (1182)..(1182)
<223> OTHER INFORMATION: UNA monomer
<220> FEATURE:
<221> NAME/KEY: modified_base
<222> LOCATION: (1184)..(1184)
<223> OTHER INFORMATION: UNA monomer
<220> FEATURE:
<221> NAME/KEY: modified_base
<222> LOCATION: (1187)..(1187)
<223> OTHER INFORMATION: UNA monomer
<220> FEATURE:
<221> NAME/KEY: modified_base
<222> LOCATION: (1191)..(1191)
<223> OTHER INFORMATION: UNA monomer
<220> FEATURE:
<221> NAME/KEY: modified_base
<222> LOCATION: (1197)..(1197)
<223> OTHER INFORMATION: UNA monomer
<220> FEATURE:
<221> NAME/KEY: modified_base
<222> LOCATION: (1201)..(1201)
<223> OTHER INFORMATION: UNA monomer
<220> FEATURE:
<221> NAME/KEY: modified_base
<222> LOCATION: (1205)..(1205)
<223> OTHER INFORMATION: UNA monomer
<220> FEATURE:
<221> NAME/KEY: modified_base
<222> LOCATION: (1208)..(1208)
<223> OTHER INFORMATION: UNA monomer
<220> FEATURE:
<221> NAME/KEY: modified_base
<222> LOCATION: (1211)..(1211)
<223> OTHER INFORMATION: UNA monomer
<220> FEATURE:
<221> NAME/KEY: modified_base
<222> LOCATION: (1213)..(1213)
<223> OTHER INFORMATION: UNA monomer
<220> FEATURE:
```

```
<221> NAME/KEY: modified_base
<222> LOCATION: (1224)..(1224)
<223> OTHER INFORMATION: UNA monomer
<220> FEATURE:
<221> NAME/KEY: modified_base
<222> LOCATION: (1237)..(1238)
<223> OTHER INFORMATION: UNA monomer
<220> FEATURE:
<221> NAME/KEY: modified_base
<222> LOCATION: (1242)..(1242)
<223> OTHER INFORMATION: UNA monomer
<220> FEATURE:
<221> NAME/KEY: modified_base
<222> LOCATION: (1244)..(1244)
<223> OTHER INFORMATION: UNA monomer
<220> FEATURE:
<221> NAME/KEY: modified_base
<222> LOCATION: (1253)..(1253)
<223> OTHER INFORMATION: UNA monomer
<220> FEATURE:
<221> NAME/KEY: modified_base
<222> LOCATION: (1259)..(1259)
<223> OTHER INFORMATION: UNA monomer
<220> FEATURE:
<221> NAME/KEY: modified_base
<222> LOCATION: (1266)..(1266)
<223> OTHER INFORMATION: UNA monomer
<220> FEATURE:
<221> NAME/KEY: modified_base
<222> LOCATION: (1271)..(1272)
<223> OTHER INFORMATION: UNA monomer
<220> FEATURE:
<221> NAME/KEY: modified_base
<222> LOCATION: (1295)..(1295)
<223> OTHER INFORMATION: UNA monomer
<220> FEATURE:
<221> NAME/KEY: modified_base
<222> LOCATION: (1297)..(1297)
<223> OTHER INFORMATION: UNA monomer
<220> FEATURE:
<221> NAME/KEY: modified_base
<222> LOCATION: (1310)..(1310)
<223> OTHER INFORMATION: UNA monomer
<220> FEATURE:
<221> NAME/KEY: modified_base
<222> LOCATION: (1312)..(1314)
<223> OTHER INFORMATION: UNA monomer
<220> FEATURE:
<221> NAME/KEY: modified_base
<222> LOCATION: (1322)..(1322)
<223> OTHER INFORMATION: UNA monomer
<220> FEATURE:
<221> NAME/KEY: modified_base
<222> LOCATION: (1326)..(1326)
<223> OTHER INFORMATION: UNA monomer
<220> FEATURE:
<221> NAME/KEY: modified_base
<222> LOCATION: (1340)..(1340)
<223> OTHER INFORMATION: UNA monomer
<220> FEATURE:
<221> NAME/KEY: modified_base
<222> LOCATION: (1347)..(1347)
<223> OTHER INFORMATION: UNA monomer
<220> FEATURE:
<221> NAME/KEY: modified_base
<222> LOCATION: (1350)..(1350)
<223> OTHER INFORMATION: UNA monomer
<220> FEATURE:
<221> NAME/KEY: modified_base
<222> LOCATION: (1356)..(1356)
<223> OTHER INFORMATION: UNA monomer
<220> FEATURE:
<221> NAME/KEY: modified_base
<222> LOCATION: (1361)..(1361)
<223> OTHER INFORMATION: UNA monomer
<220> FEATURE:
<221> NAME/KEY: modified_base
<222> LOCATION: (1370)..(1371)
<223> OTHER INFORMATION: UNA monomer
```

-continued

```
<220> FEATURE:
<221> NAME/KEY: modified_base
<222> LOCATION: (1374)..(1374)
<223> OTHER INFORMATION: UNA monomer
<220> FEATURE:
<221> NAME/KEY: modified_base
<222> LOCATION: (1377)..(1377)
<223> OTHER INFORMATION: UNA monomer
<220> FEATURE:
<221> NAME/KEY: modified_base
<222> LOCATION: (1379)..(1379)
<223> OTHER INFORMATION: UNA monomer
<220> FEATURE:
<221> NAME/KEY: modified_base
<222> LOCATION: (1386)..(1386)
<223> OTHER INFORMATION: UNA monomer
<220> FEATURE:
<221> NAME/KEY: modified_base
<222> LOCATION: (1390)..(1391)
<223> OTHER INFORMATION: UNA monomer
<220> FEATURE:
<221> NAME/KEY: modified_base
<222> LOCATION: (1396)..(1396)
<223> OTHER INFORMATION: UNA monomer
<220> FEATURE:
<221> NAME/KEY: modified_base
<222> LOCATION: (1399)..(1399)
<223> OTHER INFORMATION: UNA monomer
<220> FEATURE:
<221> NAME/KEY: modified_base
<222> LOCATION: (1401)..(1401)
<223> OTHER INFORMATION: UNA monomer
<220> FEATURE:
<221> NAME/KEY: modified_base
<222> LOCATION: (1404)..(1404)
<223> OTHER INFORMATION: UNA monomer
<220> FEATURE:
<221> NAME/KEY: modified_base
<222> LOCATION: (1407)..(1407)
<223> OTHER INFORMATION: UNA monomer
<220> FEATURE:
<221> NAME/KEY: modified_base
<222> LOCATION: (1412)..(1412)
<223> OTHER INFORMATION: UNA monomer
<220> FEATURE:
<221> NAME/KEY: modified_base
<222> LOCATION: (1415)..(1416)
<223> OTHER INFORMATION: UNA monomer
<220> FEATURE:
<221> NAME/KEY: modified_base
<222> LOCATION: (1418)..(1418)
<223> OTHER INFORMATION: UNA monomer
<220> FEATURE:
<221> NAME/KEY: modified_base
<222> LOCATION: (1421)..(1421)
<223> OTHER INFORMATION: UNA monomer
<220> FEATURE:
<221> NAME/KEY: modified_base
<222> LOCATION: (1431)..(1431)
<223> OTHER INFORMATION: UNA monomer
<220> FEATURE:
<221> NAME/KEY: modified_base
<222> LOCATION: (1438)..(1438)
<223> OTHER INFORMATION: UNA monomer
<220> FEATURE:
<221> NAME/KEY: modified_base
<222> LOCATION: (1448)..(1449)
<223> OTHER INFORMATION: UNA monomer
<220> FEATURE:
<221> NAME/KEY: modified_base
<222> LOCATION: (1451)..(1451)
<223> OTHER INFORMATION: UNA monomer
<220> FEATURE:
<221> NAME/KEY: modified_base
<222> LOCATION: (1453)..(1453)
<223> OTHER INFORMATION: UNA monomer
<220> FEATURE:
<221> NAME/KEY: modified_base
<222> LOCATION: (1455)..(1455)
```

```
<223> OTHER INFORMATION: UNA monomer
<220> FEATURE:
<221> NAME/KEY: modified_base
<222> LOCATION: (1459)..(1459)
<223> OTHER INFORMATION: UNA monomer
<220> FEATURE:
<221> NAME/KEY: modified_base
<222> LOCATION: (1467)..(1467)
<223> OTHER INFORMATION: UNA monomer
<220> FEATURE:
<221> NAME/KEY: modified_base
<222> LOCATION: (1478)..(1478)
<223> OTHER INFORMATION: UNA monomer
<220> FEATURE:
<221> NAME/KEY: modified_base
<222> LOCATION: (1481)..(1482)
<223> OTHER INFORMATION: UNA monomer
<220> FEATURE:
<221> NAME/KEY: modified_base
<222> LOCATION: (1485)..(1485)
<223> OTHER INFORMATION: UNA monomer
<220> FEATURE:
<221> NAME/KEY: modified_base
<222> LOCATION: (1487)..(1487)
<223> OTHER INFORMATION: UNA monomer
<220> FEATURE:
<221> NAME/KEY: modified_base
<222> LOCATION: (1495)..(1495)
<223> OTHER INFORMATION: UNA monomer
<220> FEATURE:
<221> NAME/KEY: modified_base
<222> LOCATION: (1497)..(1497)
<223> OTHER INFORMATION: UNA monomer
<220> FEATURE:
<221> NAME/KEY: modified_base
<222> LOCATION: (1506)..(1506)
<223> OTHER INFORMATION: UNA monomer
<220> FEATURE:
<221> NAME/KEY: modified_base
<222> LOCATION: (1517)..(1517)
<223> OTHER INFORMATION: UNA monomer
<220> FEATURE:
<221> NAME/KEY: modified_base
<222> LOCATION: (1522)..(1523)
<223> OTHER INFORMATION: UNA monomer
<220> FEATURE:
<221> NAME/KEY: modified_base
<222> LOCATION: (1525)..(1525)
<223> OTHER INFORMATION: UNA monomer
<220> FEATURE:
<221> NAME/KEY: modified_base
<222> LOCATION: (1535)..(1535)
<223> OTHER INFORMATION: UNA monomer
<220> FEATURE:
<221> NAME/KEY: modified_base
<222> LOCATION: (1537)..(1538)
<223> OTHER INFORMATION: UNA monomer
<220> FEATURE:
<221> NAME/KEY: modified_base
<222> LOCATION: (1543)..(1544)
<223> OTHER INFORMATION: UNA monomer
<220> FEATURE:
<221> NAME/KEY: modified_base
<222> LOCATION: (1547)..(1549)
<223> OTHER INFORMATION: UNA monomer
<220> FEATURE:
<221> NAME/KEY: modified_base
<222> LOCATION: (1554)..(1554)
<223> OTHER INFORMATION: UNA monomer
<220> FEATURE:
<221> NAME/KEY: modified_base
<222> LOCATION: (1560)..(1560)
<223> OTHER INFORMATION: UNA monomer
<220> FEATURE:
<221> NAME/KEY: modified_base
<222> LOCATION: (1571)..(1571)
<223> OTHER INFORMATION: UNA monomer
<220> FEATURE:
<221> NAME/KEY: modified_base
```

```
<222> LOCATION: (1573)..(1573)
<223> OTHER INFORMATION: UNA monomer
<220> FEATURE:
<221> NAME/KEY: modified_base
<222> LOCATION: (1581)..(1581)
<223> OTHER INFORMATION: UNA monomer
<220> FEATURE:
<221> NAME/KEY: modified_base
<222> LOCATION: (1584)..(1584)
<223> OTHER INFORMATION: UNA monomer
<220> FEATURE:
<221> NAME/KEY: modified_base
<222> LOCATION: (1586)..(1586)
<223> OTHER INFORMATION: UNA monomer
<220> FEATURE:
<221> NAME/KEY: modified_base
<222> LOCATION: (1590)..(1590)
<223> OTHER INFORMATION: UNA monomer
<220> FEATURE:
<221> NAME/KEY: modified_base
<222> LOCATION: (1598)..(1598)
<223> OTHER INFORMATION: UNA monomer
<220> FEATURE:
<221> NAME/KEY: modified_base
<222> LOCATION: (1603)..(1605)
<223> OTHER INFORMATION: UNA monomer
<220> FEATURE:
<221> NAME/KEY: modified_base
<222> LOCATION: (1610)..(1611)
<223> OTHER INFORMATION: UNA monomer
<220> FEATURE:
<221> NAME/KEY: modified_base
<222> LOCATION: (1617)..(1617)
<223> OTHER INFORMATION: UNA monomer
<220> FEATURE:
<221> NAME/KEY: modified_base
<222> LOCATION: (1625)..(1625)
<223> OTHER INFORMATION: UNA monomer
<220> FEATURE:
<221> NAME/KEY: modified_base
<222> LOCATION: (1629)..(1629)
<223> OTHER INFORMATION: UNA monomer
<220> FEATURE:
<221> NAME/KEY: modified_base
<222> LOCATION: (1633)..(1634)
<223> OTHER INFORMATION: UNA monomer
<220> FEATURE:
<221> NAME/KEY: modified_base
<222> LOCATION: (1637)..(1637)
<223> OTHER INFORMATION: UNA monomer
<220> FEATURE:
<221> NAME/KEY: modified_base
<222> LOCATION: (1641)..(1641)
<223> OTHER INFORMATION: UNA monomer
<220> FEATURE:
<221> NAME/KEY: modified_base
<222> LOCATION: (1643)..(1644)
<223> OTHER INFORMATION: UNA monomer
<220> FEATURE:
<221> NAME/KEY: modified_base
<222> LOCATION: (1652)..(1652)
<223> OTHER INFORMATION: UNA monomer
<220> FEATURE:
<221> NAME/KEY: modified_base
<222> LOCATION: (1655)..(1655)
<223> OTHER INFORMATION: UNA monomer
<220> FEATURE:
<221> NAME/KEY: modified_base
<222> LOCATION: (1658)..(1659)
<223> OTHER INFORMATION: UNA monomer
<220> FEATURE:
<221> NAME/KEY: modified_base
<222> LOCATION: (1661)..(1661)
<223> OTHER INFORMATION: UNA monomer
<220> FEATURE:
<221> NAME/KEY: modified_base
<222> LOCATION: (1664)..(1664)
<223> OTHER INFORMATION: UNA monomer
<220> FEATURE:
```

-continued

```
<221> NAME/KEY: modified_base
<222> LOCATION: (1672)..(1672)
<223> OTHER INFORMATION: UNA monomer
<220> FEATURE:
<221> NAME/KEY: modified_base
<222> LOCATION: (1680)..(1680)
<223> OTHER INFORMATION: UNA monomer
<220> FEATURE:
<221> NAME/KEY: modified_base
<222> LOCATION: (1684)..(1684)
<223> OTHER INFORMATION: UNA monomer
<220> FEATURE:
<221> NAME/KEY: modified_base
<222> LOCATION: (1690)..(1690)
<223> OTHER INFORMATION: UNA monomer
<220> FEATURE:
<221> NAME/KEY: modified_base
<222> LOCATION: (1700)..(1700)
<223> OTHER INFORMATION: UNA monomer
<220> FEATURE:
<221> NAME/KEY: modified_base
<222> LOCATION: (1703)..(1703)
<223> OTHER INFORMATION: UNA monomer
<220> FEATURE:
<221> NAME/KEY: modified_base
<222> LOCATION: (1709)..(1709)
<223> OTHER INFORMATION: UNA monomer
<220> FEATURE:
<221> NAME/KEY: modified_base
<222> LOCATION: (1712)..(1712)
<223> OTHER INFORMATION: UNA monomer
<220> FEATURE:
<221> NAME/KEY: modified_base
<222> LOCATION: (1718)..(1718)
<223> OTHER INFORMATION: UNA monomer
<220> FEATURE:
<221> NAME/KEY: modified_base
<222> LOCATION: (1720)..(1720)
<223> OTHER INFORMATION: UNA monomer
<220> FEATURE:
<221> NAME/KEY: modified_base
<222> LOCATION: (1723)..(1723)
<223> OTHER INFORMATION: UNA monomer

<400> SEQUENCE: 155
augucgaucc aggagaacau aucaucccug cagcuucggu caugggucuc uaagucccaa      60
agagacuuag caaaguccau ccugauuggg gcuccaggag ggccagcggg guaucugcgg     120
cgggccagug uggcccaacu gacccaggag cugggcacug ccuucuucca gcagcagcag    180
cugccagcug cuauggcaga caccuuccug gaacaccucu gccuacugga cauugacucc    240
gagcccgugg cugcucgcag uaccagcauc auugccacca ucgggccagc aucucgcucc    300
guggagcgcc ucaaggagau gaucaaggcc gggaugaaca uugcgcgacu caacuucucc    360
cacggcuccc acgaguacca ugcugagucc aucgccaacg uccgggaggc gguggagagc    420
uuugcagguu ccccacucag cuaccggccc guggccaucg cccuggacac caagggaccg    480
gagauccgca cugggauccu gcagggggu ccagagucgg aaguggagcu ggugaagggc     540
ucccaggugc uggugacugu ggaccccgcg uucggacgc gggggaacgc gaacaccgug     600
uggugggacu accccaauau uguccgggu gugccggugg ggggccgcau cuacauugac     660
gacgggcuca ucucccuagu ggucagaaaa aucggcccag agggacuggu gacccaagug    720
gagaacggcg gcguccuggg cagccggaag ggcgugaacu ugccagggc ccagguggac     780 uugcccgggc uguccgagca ggacguccga gaccugcgcu cggggugga gcauggggug     840 gacaucgucu uugccuccuu gucgggaaaa gccagcgacg uggcugccgu cagggcugcu    900 cugggguccgg aaggacacgg caucaagauc ucagcaaaa uugagaacca cgaaggcgug     960
aagagguuug augaaauccu ggaggugagc gacggcauca ugguggcacg ggggaccua    1020
```

```
ggcaucgaga ucccagcaga gaagguuuuc cuggcucaga agaugaugau ugggcgcugc    1080
aacuuggcgg gcaagccugu ugucugugcc acacagaugc uggagagcau gauuaccaag    1140
ccccggccaa cgagggcaga gacaagcgau gucgccaaug cugugcugga ugggcugac     1200 ugcaucaugc ugucagggga gacugccaag ggcaacuucc cuguggaagc ggugaagaug    1260
cagcaugcga uugcccggga ggcagaggcc gcaguguacc accggcagcu guugaggag     1320 cuacgucggg cagcgccacu aagccgugau cccacgagg ucaccgccau ggugcugug      1380 gaggcugccu ucaagugcug gcugcugcc aucaugugc ugaccacaac uggccgcuca      1440
gcccagcuuc ugucucggua ccgaccucgg gcagcaguca uugcugucac ccgcucugcc    1500
caggcugccc gccaggucca cuuaugccga ggagucuucc ccuugcuuua ccgugaaccu    1560
ccagaagcca ucugggcaga ugauguagau cgccgggucg aauuuggcau ugaaagugga   1620
aagcuccgug gcuuccuccg uguuggagac cuggugauug uggugacagg cuggcgaccu    1680
ggcuccggcu acaccaacau caugcggguc uaagcauau ccuga                    1725
```

```
<210> SEQ ID NO 156
<211> LENGTH: 1359
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(4)
<223> OTHER INFORMATION: UNA monomer
<220> FEATURE:
<221> NAME/KEY: modified_base
<222> LOCATION: (1356)..(1358)
<223> OTHER INFORMATION: UNA monomer

<400> SEQUENCE: 156
```

```
auguccacug cgguccugga aaacccaggc uugggcagga aacucucuga cuuuggacag     60
gaaacaagcu auauugaaga caacugcaau caaaaugguc ccauaucacu gaucuucuca    120
cucaaagaag aaguuggugc auuggccaaa guauugcgcu auuugagga gaaugaugua     180 aaccugaccc acauugaauc uagaccuucu cguuuaaaga agaugaguda ugaauuuuuc    240
acccauuugg auaaacguag ccugccugcu cugacaaaca ucaucaagau cuugaggcau    300
gacauugguu ccacuguccu ugagcuuuca cgagauaaga agaaagacac aguggcccugg   360 uucccaagaa ccauucaaga gcuggacaga uuugccaauc agauucucag cuauggagcg    420
gaacuggaug cugaccaccc ugguuuuaaa gauccugugu accgugcaag acggaagcag    480
uuugcugaca uugccuacaa cuaccgccau gggcagccca ucccucgagu ggaauacaug    540
gaggaagaaa agaaaacaug gggcacagug uucaagacuc ugaagccuu guauaaaacc     600 caugcuugcu augaguacaa ucacauuuuu ccacuucuug aaaaguacug uggcuuccau    660
gaagauaaca uccccagcu ggaagacguu ucucaauucc gcagacuug cacugguuuc     720 cgccuccgac cuguggcugg ccugcuuucc ucucgggauu ucuggggugg ccuggccuuc    780
cgagucuucc acugcacaca guacaucaga caüggaücca agcccaugua uaccccgaa     840 ccugacaucu gccaugagcu guuggacau gugcccuugu uucagaucg cagcuuugcc      900 caguüuuccc aggaaauügg ccuügccucu cugggugcac cugaugaaua cauügaaaag    960 cucgccacaa üuuacugggu uacuguggag uuugggcucu gcaaacaagg agacuccaua   1020
aaggcauaug gugccugggcu ccugucaucc uuuggügaau uacaguacug cuuaucagag  1080
```

```
aagccaaagc uucucccccu ggagcuggag aagacagcca uccaaaauua cacugucacg   1140
gaguuccagc cccuguauua cguggcagag aguuuuaaug augccaagga gaaaguaagg   1200
aacuuugcug ccacaauacc ucggcccuuc ucaguucgcu acgacccaua cacccaaagg   1260
auugaggucu uggacaauac ccagcagcuu aagauuuugg cugauuccau uaacagugaa   1320
auuggaaucc uuugcagugc cuccagaaaa auaaaguaa                         1359
```

```
<210> SEQ ID NO 157
<211> LENGTH: 1360
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: UNA monomer
<220> FEATURE:
<221> NAME/KEY: modified_base
<222> LOCATION: (21)..(21)
<223> OTHER INFORMATION: UNA monomer
<220> FEATURE:
<221> NAME/KEY: modified_base
<222> LOCATION: (39)..(39)
<223> OTHER INFORMATION: UNA monomer
<220> FEATURE:
<221> NAME/KEY: modified_base
<222> LOCATION: (57)..(57)
<223> OTHER INFORMATION: UNA monomer
<220> FEATURE:
<221> NAME/KEY: modified_base
<222> LOCATION: (75)..(75)
<223> OTHER INFORMATION: UNA monomer
<220> FEATURE:
<221> NAME/KEY: modified_base
<222> LOCATION: (93)..(93)
<223> OTHER INFORMATION: UNA monomer
<220> FEATURE:
<221> NAME/KEY: modified_base
<222> LOCATION: (111)..(111)
<223> OTHER INFORMATION: UNA monomer
<220> FEATURE:
<221> NAME/KEY: modified_base
<222> LOCATION: (129)..(129)
<223> OTHER INFORMATION: UNA monomer
<220> FEATURE:
<221> NAME/KEY: modified_base
<222> LOCATION: (147)..(147)
<223> OTHER INFORMATION: UNA monomer
<220> FEATURE:
<221> NAME/KEY: modified_base
<222> LOCATION: (165)..(165)
<223> OTHER INFORMATION: UNA monomer
<220> FEATURE:
<221> NAME/KEY: modified_base
<222> LOCATION: (183)..(183)
<223> OTHER INFORMATION: UNA monomer
<220> FEATURE:
<221> NAME/KEY: modified_base
<222> LOCATION: (201)..(201)
<223> OTHER INFORMATION: UNA monomer
<220> FEATURE:
<221> NAME/KEY: modified_base
<222> LOCATION: (219)..(219)
<223> OTHER INFORMATION: UNA monomer
<220> FEATURE:
<221> NAME/KEY: modified_base
<222> LOCATION: (237)..(237)
<223> OTHER INFORMATION: UNA monomer
<220> FEATURE:
<221> NAME/KEY: modified_base
<222> LOCATION: (255)..(255)
<223> OTHER INFORMATION: UNA monomer
```

```
<220> FEATURE:
<221> NAME/KEY: modified_base
<222> LOCATION: (273)..(273)
<223> OTHER INFORMATION: UNA monomer
<220> FEATURE:
<221> NAME/KEY: modified_base
<222> LOCATION: (291)..(291)
<223> OTHER INFORMATION: UNA monomer
<220> FEATURE:
<221> NAME/KEY: modified_base
<222> LOCATION: (309)..(309)
<223> OTHER INFORMATION: UNA monomer
<220> FEATURE:
<221> NAME/KEY: modified_base
<222> LOCATION: (327)..(327)
<223> OTHER INFORMATION: UNA monomer
<220> FEATURE:
<221> NAME/KEY: modified_base
<222> LOCATION: (345)..(345)
<223> OTHER INFORMATION: UNA monomer
<220> FEATURE:
<221> NAME/KEY: modified_base
<222> LOCATION: (363)..(363)
<223> OTHER INFORMATION: UNA monomer
<220> FEATURE:
<221> NAME/KEY: modified_base
<222> LOCATION: (381)..(381)
<223> OTHER INFORMATION: UNA monomer
<220> FEATURE:
<221> NAME/KEY: modified_base
<222> LOCATION: (399)..(399)
<223> OTHER INFORMATION: UNA monomer
<220> FEATURE:
<221> NAME/KEY: modified_base
<222> LOCATION: (417)..(417)
<223> OTHER INFORMATION: UNA monomer
<220> FEATURE:
<221> NAME/KEY: modified_base
<222> LOCATION: (435)..(435)
<223> OTHER INFORMATION: UNA monomer
<220> FEATURE:
<221> NAME/KEY: modified_base
<222> LOCATION: (453)..(453)
<223> OTHER INFORMATION: UNA monomer
<220> FEATURE:
<221> NAME/KEY: modified_base
<222> LOCATION: (471)..(471)
<223> OTHER INFORMATION: UNA monomer
<220> FEATURE:
<221> NAME/KEY: modified_base
<222> LOCATION: (489)..(489)
<223> OTHER INFORMATION: UNA monomer
<220> FEATURE:
<221> NAME/KEY: modified_base
<222> LOCATION: (507)..(507)
<223> OTHER INFORMATION: UNA monomer
<220> FEATURE:
<221> NAME/KEY: modified_base
<222> LOCATION: (525)..(525)
<223> OTHER INFORMATION: UNA monomer
<220> FEATURE:
<221> NAME/KEY: modified_base
<222> LOCATION: (579)..(579)
<223> OTHER INFORMATION: UNA monomer
<220> FEATURE:
<221> NAME/KEY: modified_base
<222> LOCATION: (597)..(597)
<223> OTHER INFORMATION: UNA monomer
<220> FEATURE:
<221> NAME/KEY: modified_base
<222> LOCATION: (615)..(615)
<223> OTHER INFORMATION: UNA monomer
<220> FEATURE:
<221> NAME/KEY: modified_base
<222> LOCATION: (633)..(633)
<223> OTHER INFORMATION: UNA monomer
<220> FEATURE:
<221> NAME/KEY: modified_base
<222> LOCATION: (651)..(651)
```

```
<223> OTHER INFORMATION: UNA monomer
<220> FEATURE:
<221> NAME/KEY: modified_base
<222> LOCATION: (669)..(669)
<223> OTHER INFORMATION: UNA monomer
<220> FEATURE:
<221> NAME/KEY: modified_base
<222> LOCATION: (687)..(687)
<223> OTHER INFORMATION: UNA monomer
<220> FEATURE:
<221> NAME/KEY: modified_base
<222> LOCATION: (705)..(705)
<223> OTHER INFORMATION: UNA monomer
<220> FEATURE:
<221> NAME/KEY: modified_base
<222> LOCATION: (723)..(723)
<223> OTHER INFORMATION: UNA monomer
<220> FEATURE:
<221> NAME/KEY: modified_base
<222> LOCATION: (741)..(741)
<223> OTHER INFORMATION: UNA monomer
<220> FEATURE:
<221> NAME/KEY: modified_base
<222> LOCATION: (759)..(759)
<223> OTHER INFORMATION: UNA monomer
<220> FEATURE:
<221> NAME/KEY: modified_base
<222> LOCATION: (777)..(777)
<223> OTHER INFORMATION: UNA monomer
<220> FEATURE:
<221> NAME/KEY: modified_base
<222> LOCATION: (795)..(795)
<223> OTHER INFORMATION: UNA monomer
<220> FEATURE:
<221> NAME/KEY: modified_base
<222> LOCATION: (813)..(813)
<223> OTHER INFORMATION: UNA monomer
<220> FEATURE:
<221> NAME/KEY: modified_base
<222> LOCATION: (831)..(831)
<223> OTHER INFORMATION: UNA monomer
<220> FEATURE:
<221> NAME/KEY: modified_base
<222> LOCATION: (849)..(849)
<223> OTHER INFORMATION: UNA monomer
<220> FEATURE:
<221> NAME/KEY: modified_base
<222> LOCATION: (867)..(867)
<223> OTHER INFORMATION: UNA monomer
<220> FEATURE:
<221> NAME/KEY: modified_base
<222> LOCATION: (885)..(885)
<223> OTHER INFORMATION: UNA monomer
<220> FEATURE:
<221> NAME/KEY: modified_base
<222> LOCATION: (903)..(903)
<223> OTHER INFORMATION: UNA monomer
<220> FEATURE:
<221> NAME/KEY: modified_base
<222> LOCATION: (921)..(921)
<223> OTHER INFORMATION: UNA monomer
<220> FEATURE:
<221> NAME/KEY: modified_base
<222> LOCATION: (939)..(939)
<223> OTHER INFORMATION: UNA monomer
<220> FEATURE:
<221> NAME/KEY: modified_base
<222> LOCATION: (957)..(957)
<223> OTHER INFORMATION: UNA monomer
<220> FEATURE:
<221> NAME/KEY: modified_base
<222> LOCATION: (975)..(975)
<223> OTHER INFORMATION: UNA monomer
<220> FEATURE:
<221> NAME/KEY: modified_base
<222> LOCATION: (993)..(993)
<223> OTHER INFORMATION: UNA monomer
<220> FEATURE:
<221> NAME/KEY: modified_base
```

```
<222> LOCATION: (1011)..(1011)
<223> OTHER INFORMATION: UNA monomer
<220> FEATURE:
<221> NAME/KEY: modified_base
<222> LOCATION: (1029)..(1029)
<223> OTHER INFORMATION: UNA monomer
<220> FEATURE:
<221> NAME/KEY: modified_base
<222> LOCATION: (1047)..(1047)
<223> OTHER INFORMATION: UNA monomer
<220> FEATURE:
<221> NAME/KEY: modified_base
<222> LOCATION: (1065)..(1065)
<223> OTHER INFORMATION: UNA monomer
<220> FEATURE:
<221> NAME/KEY: modified_base
<222> LOCATION: (1083)..(1083)
<223> OTHER INFORMATION: UNA monomer
<220> FEATURE:
<221> NAME/KEY: modified_base
<222> LOCATION: (1101)..(1101)
<223> OTHER INFORMATION: UNA monomer
<220> FEATURE:
<221> NAME/KEY: modified_base
<222> LOCATION: (1119)..(1119)
<223> OTHER INFORMATION: UNA monomer
<220> FEATURE:
<221> NAME/KEY: modified_base
<222> LOCATION: (1137)..(1137)
<223> OTHER INFORMATION: UNA monomer
<220> FEATURE:
<221> NAME/KEY: modified_base
<222> LOCATION: (1155)..(1155)
<223> OTHER INFORMATION: UNA monomer
<220> FEATURE:
<221> NAME/KEY: modified_base
<222> LOCATION: (1173)..(1173)
<223> OTHER INFORMATION: UNA monomer
<220> FEATURE:
<221> NAME/KEY: modified_base
<222> LOCATION: (1191)..(1191)
<223> OTHER INFORMATION: UNA monomer
<220> FEATURE:
<221> NAME/KEY: modified_base
<222> LOCATION: (1209)..(1209)
<223> OTHER INFORMATION: UNA monomer
<220> FEATURE:
<221> NAME/KEY: modified_base
<222> LOCATION: (1227)..(1227)
<223> OTHER INFORMATION: UNA monomer
<220> FEATURE:
<221> NAME/KEY: modified_base
<222> LOCATION: (1245)..(1245)
<223> OTHER INFORMATION: UNA monomer
<220> FEATURE:
<221> NAME/KEY: modified_base
<222> LOCATION: (1263)..(1263)
<223> OTHER INFORMATION: UNA monomer
<220> FEATURE:
<221> NAME/KEY: modified_base
<222> LOCATION: (1281)..(1281)
<223> OTHER INFORMATION: UNA monomer
<220> FEATURE:
<221> NAME/KEY: modified_base
<222> LOCATION: (1299)..(1299)
<223> OTHER INFORMATION: UNA monomer
<220> FEATURE:
<221> NAME/KEY: modified_base
<222> LOCATION: (1317)..(1317)
<223> OTHER INFORMATION: UNA monomer
<220> FEATURE:
<221> NAME/KEY: modified_base
<222> LOCATION: (1335)..(1335)
<223> OTHER INFORMATION: UNA monomer
<220> FEATURE:
<221> NAME/KEY: modified_base
<222> LOCATION: (1353)..(1353)
<223> OTHER INFORMATION: UNA monomer
<220> FEATURE:
```

<221> NAME/KEY: modified_base
<222> LOCATION: (1359)..(1359)
<223> OTHER INFORMATION: UNA monomer

<400> SEQUENCE: 157

```
auguccacug cgguccugga aacccaggc uugggcagga aacucucuga cuuuggacag     60
gaaacaagcu auauugaaga caacugcaau caaaauggug ccauaucacu gaucuucuca    120
cucaaagaag aaguuggugc auuggccaaa guauugcgcu auuugagga gaaugaugua     180
aaccugaccc acauugaauc uagaccuucu cguuuaaaga aagaugagua ugaauuuuuc    240
acccauuugg auaaacguag ccugccugcu cugacaaaca ucaucaagau cuugaggcau    300
gacauuggug ccacugucca ugagcuuuca cgagauaaga agaaagacac agugcccugg    360
uucccaagaa ccauucaaga gcuggacaga uuugccaauc agauucucag cuauggagcg    420
gaacuggaug cugaccaccc ugguuuuaaa gauccugugu accgugcaag acggaagcag    480
uuugcugaca uugccuacaa cuaccgccau gggcagccca ucccucgagu ggaauacaug    540
gaggaagaaa agaaaacaug gggcacagug uucaagacuc ugaagcccuu guauaaaacc    600
caugcuugcu augaguacaa ucacauuuuu ccacuucuug aaaaguacug uggcuuccau    660
gaagauaaca uuccccagcu ggaagacguu ucucaauucc gcagacuug cacugguuuc    720
cgccuccgac cuguggcugg ccugcuuucc ucucgggauu ucuugggugg ccuggccuuc    780
cgagucuucc acugcacaca guacaucaga cauggaucca agcccaugua uacccccgaa    840
ccugacaucu gccaugagcu guugggacau gugcccuugu uucagaucg cagcuuugcc    900
caguuuuccc aggaaauugg ccuugccucu cugggugcac cugaugaaua cauugaaaag    960
cucgccacaa uuuacugguu uacuguggag uuugggcucu gcaaacaagg agacuccaua   1020
aaggcauaug gugcugggcu ccugucaucc uuuggugaau uacaguacug cuuaucagag   1080
aagccaaagc uucucccccu ggagcuggag aagacagcca uccaaaauua cacugucacg   1140
gaguccagc cccuguauua cguggcagag aguuuuaaug augccaagga ggaaaguaag    1200
gaacuuugcu gccacaauac cucggcccuu cucaguucgc uacgacccau acacccaaag   1260
gauugaggu uuggacaaua cccagcagcu uaagauuuug gcugauucca uuaacaguga   1320
aauuggaauc cuuugcagug cccuccagaa aauaaaguaa                         1360
```

<210> SEQ ID NO 158
<211> LENGTH: 1359
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (4)..(4)
<223> OTHER INFORMATION: UNA monomer
<220> FEATURE:
<221> NAME/KEY: modified_base
<222> LOCATION: (9)..(9)
<223> OTHER INFORMATION: UNA monomer
<220> FEATURE:
<221> NAME/KEY: modified_base
<222> LOCATION: (14)..(14)
<223> OTHER INFORMATION: UNA monomer
<220> FEATURE:
<221> NAME/KEY: modified_base
<222> LOCATION: (17)..(17)

```
<223> OTHER INFORMATION: UNA monomer
<220> FEATURE:
<221> NAME/KEY: modified_base
<222> LOCATION: (31)..(32)
<223> OTHER INFORMATION: UNA monomer
<220> FEATURE:
<221> NAME/KEY: modified_base
<222> LOCATION: (44)..(44)
<223> OTHER INFORMATION: UNA monomer
<220> FEATURE:
<221> NAME/KEY: modified_base
<222> LOCATION: (46)..(46)
<223> OTHER INFORMATION: UNA monomer
<220> FEATURE:
<221> NAME/KEY: modified_base
<222> LOCATION: (48)..(48)
<223> OTHER INFORMATION: UNA monomer
<220> FEATURE:
<221> NAME/KEY: modified_base
<222> LOCATION: (52)..(54)
<223> OTHER INFORMATION: UNA monomer
<220> FEATURE:
<221> NAME/KEY: modified_base
<222> LOCATION: (70)..(70)
<223> OTHER INFORMATION: UNA monomer
<220> FEATURE:
<221> NAME/KEY: modified_base
<222> LOCATION: (72)..(72)
<223> OTHER INFORMATION: UNA monomer
<220> FEATURE:
<221> NAME/KEY: modified_base
<222> LOCATION: (74)..(75)
<223> OTHER INFORMATION: UNA monomer
<220> FEATURE:
<221> NAME/KEY: modified_base
<222> LOCATION: (85)..(85)
<223> OTHER INFORMATION: UNA monomer
<220> FEATURE:
<221> NAME/KEY: modified_base
<222> LOCATION: (90)..(90)
<223> OTHER INFORMATION: UNA monomer
<220> FEATURE:
<221> NAME/KEY: modified_base
<222> LOCATION: (96)..(96)
<223> OTHER INFORMATION: UNA monomer
<220> FEATURE:
<221> NAME/KEY: modified_base
<222> LOCATION: (99)..(99)
<223> OTHER INFORMATION: UNA monomer
<220> FEATURE:
<221> NAME/KEY: modified_base
<222> LOCATION: (104)..(104)
<223> OTHER INFORMATION: UNA monomer
<220> FEATURE:
<221> NAME/KEY: modified_base
<222> LOCATION: (106)..(106)
<223> OTHER INFORMATION: UNA monomer
<220> FEATURE:
<221> NAME/KEY: modified_base
<222> LOCATION: (110)..(110)
<223> OTHER INFORMATION: UNA monomer
<220> FEATURE:
<221> NAME/KEY: modified_base
<222> LOCATION: (113)..(113)
<223> OTHER INFORMATION: UNA monomer
<220> FEATURE:
<221> NAME/KEY: modified_base
<222> LOCATION: (115)..(116)
<223> OTHER INFORMATION: UNA monomer
<220> FEATURE:
<221> NAME/KEY: modified_base
<222> LOCATION: (118)..(118)
<223> OTHER INFORMATION: UNA monomer
<220> FEATURE:
<221> NAME/KEY: modified_base
<222> LOCATION: (122)..(122)
<223> OTHER INFORMATION: UNA monomer
<220> FEATURE:
<221> NAME/KEY: modified_base
```

```
<222> LOCATION: (134)..(135)
<223> OTHER INFORMATION: UNA monomer
<220> FEATURE:
<221> NAME/KEY: modified_base
<222> LOCATION: (138)..(138)
<223> OTHER INFORMATION: UNA monomer
<220> FEATURE:
<221> NAME/KEY: modified_base
<222> LOCATION: (142)..(143)
<223> OTHER INFORMATION: UNA monomer
<220> FEATURE:
<221> NAME/KEY: modified_base
<222> LOCATION: (152)..(152)
<223> OTHER INFORMATION: UNA monomer
<220> FEATURE:
<221> NAME/KEY: modified_base
<222> LOCATION: (154)..(155)
<223> OTHER INFORMATION: UNA monomer
<220> FEATURE:
<221> NAME/KEY: modified_base
<222> LOCATION: (160)..(161)
<223> OTHER INFORMATION: UNA monomer
<220> FEATURE:
<221> NAME/KEY: modified_base
<222> LOCATION: (163)..(165)
<223> OTHER INFORMATION: UNA monomer
<220> FEATURE:
<221> NAME/KEY: modified_base
<222> LOCATION: (174)..(174)
<223> OTHER INFORMATION: UNA monomer
<220> FEATURE:
<221> NAME/KEY: modified_base
<222> LOCATION: (177)..(177)
<223> OTHER INFORMATION: UNA monomer
<220> FEATURE:
<221> NAME/KEY: modified_base
<222> LOCATION: (179)..(179)
<223> OTHER INFORMATION: UNA monomer
<220> FEATURE:
<221> NAME/KEY: modified_base
<222> LOCATION: (185)..(185)
<223> OTHER INFORMATION: UNA monomer
<220> FEATURE:
<221> NAME/KEY: modified_base
<222> LOCATION: (194)..(195)
<223> OTHER INFORMATION: UNA monomer
<220> FEATURE:
<221> NAME/KEY: modified_base
<222> LOCATION: (199)..(199)
<223> OTHER INFORMATION: UNA monomer
<220> FEATURE:
<221> NAME/KEY: modified_base
<222> LOCATION: (201)..(201)
<223> OTHER INFORMATION: UNA monomer
<220> FEATURE:
<221> NAME/KEY: modified_base
<222> LOCATION: (207)..(208)
<223> OTHER INFORMATION: UNA monomer
<220> FEATURE:
<221> NAME/KEY: modified_base
<222> LOCATION: (210)..(210)
<223> OTHER INFORMATION: UNA monomer
<220> FEATURE:
<221> NAME/KEY: modified_base
<222> LOCATION: (213)..(215)
<223> OTHER INFORMATION: UNA monomer
<220> FEATURE:
<221> NAME/KEY: modified_base
<222> LOCATION: (225)..(225)
<223> OTHER INFORMATION: UNA monomer
<220> FEATURE:
<221> NAME/KEY: modified_base
<222> LOCATION: (229)..(229)
<223> OTHER INFORMATION: UNA monomer
<220> FEATURE:
<221> NAME/KEY: modified_base
<222> LOCATION: (231)..(231)
<223> OTHER INFORMATION: UNA monomer
<220> FEATURE:
```

-continued

```
<221> NAME/KEY: modified_base
<222> LOCATION: (235)..(239)
<223> OTHER INFORMATION: UNA monomer
<220> FEATURE:
<221> NAME/KEY: modified_base
<222> LOCATION: (246)..(248)
<223> OTHER INFORMATION: UNA monomer
<220> FEATURE:
<221> NAME/KEY: modified_base
<222> LOCATION: (252)..(252)
<223> OTHER INFORMATION: UNA monomer
<220> FEATURE:
<221> NAME/KEY: modified_base
<222> LOCATION: (258)..(258)
<223> OTHER INFORMATION: UNA monomer
<220> FEATURE:
<221> NAME/KEY: modified_base
<222> LOCATION: (263)..(263)
<223> OTHER INFORMATION: UNA monomer
<220> FEATURE:
<221> NAME/KEY: modified_base
<222> LOCATION: (267)..(267)
<223> OTHER INFORMATION: UNA monomer
<220> FEATURE:
<221> NAME/KEY: modified_base
<222> LOCATION: (270)..(270)
<223> OTHER INFORMATION: UNA monomer
<220> FEATURE:
<221> NAME/KEY: modified_base
<222> LOCATION: (272)..(272)
<223> OTHER INFORMATION: UNA monomer
<220> FEATURE:
<221> NAME/KEY: modified_base
<222> LOCATION: (281)..(281)
<223> OTHER INFORMATION: UNA monomer
<220> FEATURE:
<221> NAME/KEY: modified_base
<222> LOCATION: (284)..(284)
<223> OTHER INFORMATION: UNA monomer
<220> FEATURE:
<221> NAME/KEY: modified_base
<222> LOCATION: (290)..(290)
<223> OTHER INFORMATION: UNA monomer
<220> FEATURE:
<221> NAME/KEY: modified_base
<222> LOCATION: (292)..(293)
<223> OTHER INFORMATION: UNA monomer
<220> FEATURE:
<221> NAME/KEY: modified_base
<222> LOCATION: (300)..(300)
<223> OTHER INFORMATION: UNA monomer
<220> FEATURE:
<221> NAME/KEY: modified_base
<222> LOCATION: (305)..(306)
<223> OTHER INFORMATION: UNA monomer
<220> FEATURE:
<221> NAME/KEY: modified_base
<222> LOCATION: (309)..(309)
<223> OTHER INFORMATION: UNA monomer
<220> FEATURE:
<221> NAME/KEY: modified_base
<222> LOCATION: (315)..(315)
<223> OTHER INFORMATION: UNA monomer
<220> FEATURE:
<221> NAME/KEY: modified_base
<222> LOCATION: (317)..(317)
<223> OTHER INFORMATION: UNA monomer
<220> FEATURE:
<221> NAME/KEY: modified_base
<222> LOCATION: (321)..(321)
<223> OTHER INFORMATION: UNA monomer
<220> FEATURE:
<221> NAME/KEY: modified_base
<222> LOCATION: (326)..(328)
<223> OTHER INFORMATION: UNA monomer
<220> FEATURE:
<221> NAME/KEY: modified_base
<222> LOCATION: (336)..(336)
<223> OTHER INFORMATION: UNA monomer
```

-continued

```
<220> FEATURE:
<221> NAME/KEY: modified_base
<222> LOCATION: (353)..(353)
<223> OTHER INFORMATION: UNA monomer
<220> FEATURE:
<221> NAME/KEY: modified_base
<222> LOCATION: (358)..(358)
<223> OTHER INFORMATION: UNA monomer
<220> FEATURE:
<221> NAME/KEY: modified_base
<222> LOCATION: (361)..(362)
<223> OTHER INFORMATION: UNA monomer
<220> FEATURE:
<221> NAME/KEY: modified_base
<222> LOCATION: (374)..(375)
<223> OTHER INFORMATION: UNA monomer
<220> FEATURE:
<221> NAME/KEY: modified_base
<222> LOCATION: (383)..(383)
<223> OTHER INFORMATION: UNA monomer
<220> FEATURE:
<221> NAME/KEY: modified_base
<222> LOCATION: (391)..(393)
<223> OTHER INFORMATION: UNA monomer
<220> FEATURE:
<221> NAME/KEY: modified_base
<222> LOCATION: (399)..(399)
<223> OTHER INFORMATION: UNA monomer
<220> FEATURE:
<221> NAME/KEY: modified_base
<222> LOCATION: (404)..(405)
<223> OTHER INFORMATION: UNA monomer
<220> FEATURE:
<221> NAME/KEY: modified_base
<222> LOCATION: (407)..(407)
<223> OTHER INFORMATION: UNA monomer
<220> FEATURE:
<221> NAME/KEY: modified_base
<222> LOCATION: (412)..(412)
<223> OTHER INFORMATION: UNA monomer
<220> FEATURE:
<221> NAME/KEY: modified_base
<222> LOCATION: (414)..(414)
<223> OTHER INFORMATION: UNA monomer
<220> FEATURE:
<221> NAME/KEY: modified_base
<222> LOCATION: (425)..(425)
<223> OTHER INFORMATION: UNA monomer
<220> FEATURE:
<221> NAME/KEY: modified_base
<222> LOCATION: (429)..(429)
<223> OTHER INFORMATION: UNA monomer
<220> FEATURE:
<221> NAME/KEY: modified_base
<222> LOCATION: (432)..(432)
<223> OTHER INFORMATION: UNA monomer
<220> FEATURE:
<221> NAME/KEY: modified_base
<222> LOCATION: (441)..(441)
<223> OTHER INFORMATION: UNA monomer
<220> FEATURE:
<221> NAME/KEY: modified_base
<222> LOCATION: (444)..(447)
<223> OTHER INFORMATION: UNA monomer
<220> FEATURE:
<221> NAME/KEY: modified_base
<222> LOCATION: (453)..(453)
<223> OTHER INFORMATION: UNA monomer
<220> FEATURE:
<221> NAME/KEY: modified_base
<222> LOCATION: (456)..(456)
<223> OTHER INFORMATION: UNA monomer
<220> FEATURE:
<221> NAME/KEY: modified_base
<222> LOCATION: (458)..(458)
<223> OTHER INFORMATION: UNA monomer
<220> FEATURE:
<221> NAME/KEY: modified_base
<222> LOCATION: (460)..(460)
```

```
<223> OTHER INFORMATION: UNA monomer
<220> FEATURE:
<221> NAME/KEY: modified_base
<222> LOCATION: (465)..(465)
<223> OTHER INFORMATION: UNA monomer
<220> FEATURE:
<221> NAME/KEY: modified_base
<222> LOCATION: (481)..(483)
<223> OTHER INFORMATION: UNA monomer
<220> FEATURE:
<221> NAME/KEY: modified_base
<222> LOCATION: (486)..(486)
<223> OTHER INFORMATION: UNA monomer
<220> FEATURE:
<221> NAME/KEY: modified_base
<222> LOCATION: (491)..(492)
<223> OTHER INFORMATION: UNA monomer
<220> FEATURE:
<221> NAME/KEY: modified_base
<222> LOCATION: (496)..(496)
<223> OTHER INFORMATION: UNA monomer
<220> FEATURE:
<221> NAME/KEY: modified_base
<222> LOCATION: (502)..(502)
<223> OTHER INFORMATION: UNA monomer
<220> FEATURE:
<221> NAME/KEY: modified_base
<222> LOCATION: (510)..(510)
<223> OTHER INFORMATION: UNA monomer
<220> FEATURE:
<221> NAME/KEY: modified_base
<222> LOCATION: (521)..(521)
<223> OTHER INFORMATION: UNA monomer
<220> FEATURE:
<221> NAME/KEY: modified_base
<222> LOCATION: (525)..(525)
<223> OTHER INFORMATION: UNA monomer
<220> FEATURE:
<221> NAME/KEY: modified_base
<222> LOCATION: (530)..(530)
<223> OTHER INFORMATION: UNA monomer
<220> FEATURE:
<221> NAME/KEY: modified_base
<222> LOCATION: (535)..(535)
<223> OTHER INFORMATION: UNA monomer
<220> FEATURE:
<221> NAME/KEY: modified_base
<222> LOCATION: (539)..(539)
<223> OTHER INFORMATION: UNA monomer
<220> FEATURE:
<221> NAME/KEY: modified_base
<222> LOCATION: (559)..(559)
<223> OTHER INFORMATION: UNA monomer
<220> FEATURE:
<221> NAME/KEY: modified_base
<222> LOCATION: (569)..(569)
<223> OTHER INFORMATION: UNA monomer
<220> FEATURE:
<221> NAME/KEY: modified_base
<222> LOCATION: (571)..(572)
<223> OTHER INFORMATION: UNA monomer
<220> FEATURE:
<221> NAME/KEY: modified_base
<222> LOCATION: (579)..(579)
<223> OTHER INFORMATION: UNA monomer
<220> FEATURE:
<221> NAME/KEY: modified_base
<222> LOCATION: (581)..(581)
<223> OTHER INFORMATION: UNA monomer
<220> FEATURE:
<221> NAME/KEY: modified_base
<222> LOCATION: (586)..(586)
<223> OTHER INFORMATION: UNA monomer
<220> FEATURE:
<221> NAME/KEY: modified_base
<222> LOCATION: (589)..(590)
<223> OTHER INFORMATION: UNA monomer
<220> FEATURE:
<221> NAME/KEY: modified_base
```

```
<222> LOCATION: (592)..(592)
<223> OTHER INFORMATION: UNA monomer
<220> FEATURE:
<221> NAME/KEY: modified_base
<222> LOCATION: (594)..(594)
<223> OTHER INFORMATION: UNA monomer
<220> FEATURE:
<221> NAME/KEY: modified_base
<222> LOCATION: (603)..(603)
<223> OTHER INFORMATION: UNA monomer
<220> FEATURE:
<221> NAME/KEY: modified_base
<222> LOCATION: (606)..(607)
<223> OTHER INFORMATION: UNA monomer
<220> FEATURE:
<221> NAME/KEY: modified_base
<222> LOCATION: (610)..(610)
<223> OTHER INFORMATION: UNA monomer
<220> FEATURE:
<221> NAME/KEY: modified_base
<222> LOCATION: (612)..(612)
<223> OTHER INFORMATION: UNA monomer
<220> FEATURE:
<221> NAME/KEY: modified_base
<222> LOCATION: (616)..(616)
<223> OTHER INFORMATION: UNA monomer
<220> FEATURE:
<221> NAME/KEY: modified_base
<222> LOCATION: (621)..(621)
<223> OTHER INFORMATION: UNA monomer
<220> FEATURE:
<221> NAME/KEY: modified_base
<222> LOCATION: (626)..(630)
<223> OTHER INFORMATION: UNA monomer
<220> FEATURE:
<221> NAME/KEY: modified_base
<222> LOCATION: (635)..(636)
<223> OTHER INFORMATION: UNA monomer
<220> FEATURE:
<221> NAME/KEY: modified_base
<222> LOCATION: (638)..(639)
<223> OTHER INFORMATION: UNA monomer
<220> FEATURE:
<221> NAME/KEY: modified_base
<222> LOCATION: (646)..(646)
<223> OTHER INFORMATION: UNA monomer
<220> FEATURE:
<221> NAME/KEY: modified_base
<222> LOCATION: (649)..(649)
<223> OTHER INFORMATION: UNA monomer
<220> FEATURE:
<221> NAME/KEY: modified_base
<222> LOCATION: (651)..(651)
<223> OTHER INFORMATION: UNA monomer
<220> FEATURE:
<221> NAME/KEY: modified_base
<222> LOCATION: (655)..(656)
<223> OTHER INFORMATION: UNA monomer
<220> FEATURE:
<221> NAME/KEY: modified_base
<222> LOCATION: (660)..(660)
<223> OTHER INFORMATION: UNA monomer
<220> FEATURE:
<221> NAME/KEY: modified_base
<222> LOCATION: (666)..(666)
<223> OTHER INFORMATION: UNA monomer
<220> FEATURE:
<221> NAME/KEY: modified_base
<222> LOCATION: (671)..(672)
<223> OTHER INFORMATION: UNA monomer
<220> FEATURE:
<221> NAME/KEY: modified_base
<222> LOCATION: (680)..(680)
<223> OTHER INFORMATION: UNA monomer
<220> FEATURE:
<221> NAME/KEY: modified_base
<222> LOCATION: (689)..(691)
<223> OTHER INFORMATION: UNA monomer
<220> FEATURE:
```

```
<221> NAME/KEY: modified_base
<222> LOCATION: (693)..(693)
<223> OTHER INFORMATION: UNA monomer
<220> FEATURE:
<221> NAME/KEY: modified_base
<222> LOCATION: (697)..(698)
<223> OTHER INFORMATION: UNA monomer
<220> FEATURE:
<221> NAME/KEY: modified_base
<222> LOCATION: (701)..(701)
<223> OTHER INFORMATION: UNA monomer
<220> FEATURE:
<221> NAME/KEY: modified_base
<222> LOCATION: (708)..(709)
<223> OTHER INFORMATION: UNA monomer
<220> FEATURE:
<221> NAME/KEY: modified_base
<222> LOCATION: (714)..(714)
<223> OTHER INFORMATION: UNA monomer
<220> FEATURE:
<221> NAME/KEY: modified_base
<222> LOCATION: (717)..(719)
<223> OTHER INFORMATION: UNA monomer
<220> FEATURE:
<221> NAME/KEY: modified_base
<222> LOCATION: (725)..(725)
<223> OTHER INFORMATION: UNA monomer
<220> FEATURE:
<221> NAME/KEY: modified_base
<222> LOCATION: (732)..(732)
<223> OTHER INFORMATION: UNA monomer
<220> FEATURE:
<221> NAME/KEY: modified_base
<222> LOCATION: (734)..(734)
<223> OTHER INFORMATION: UNA monomer
<220> FEATURE:
<221> NAME/KEY: modified_base
<222> LOCATION: (738)..(738)
<223> OTHER INFORMATION: UNA monomer
<220> FEATURE:
<221> NAME/KEY: modified_base
<222> LOCATION: (743)..(743)
<223> OTHER INFORMATION: UNA monomer
<220> FEATURE:
<221> NAME/KEY: modified_base
<222> LOCATION: (746)..(748)
<223> OTHER INFORMATION: UNA monomer
<220> FEATURE:
<221> NAME/KEY: modified_base
<222> LOCATION: (751)..(751)
<223> OTHER INFORMATION: UNA monomer
<220> FEATURE:
<221> NAME/KEY: modified_base
<222> LOCATION: (753)..(753)
<223> OTHER INFORMATION: UNA monomer
<220> FEATURE:
<221> NAME/KEY: modified_base
<222> LOCATION: (759)..(761)
<223> OTHER INFORMATION: UNA monomer
<220> FEATURE:
<221> NAME/KEY: modified_base
<222> LOCATION: (763)..(764)
<223> OTHER INFORMATION: UNA monomer
<220> FEATURE:
<221> NAME/KEY: modified_base
<222> LOCATION: (768)..(768)
<223> OTHER INFORMATION: UNA monomer
<220> FEATURE:
<221> NAME/KEY: modified_base
<222> LOCATION: (773)..(773)
<223> OTHER INFORMATION: UNA monomer
<220> FEATURE:
<221> NAME/KEY: modified_base
<222> LOCATION: (778)..(779)
<223> OTHER INFORMATION: UNA monomer
<220> FEATURE:
<221> NAME/KEY: modified_base
<222> LOCATION: (785)..(785)
<223> OTHER INFORMATION: UNA monomer
```

-continued

```
<220> FEATURE:
<221> NAME/KEY: modified_base
<222> LOCATION: (787)..(788)
<223> OTHER INFORMATION: UNA monomer
<220> FEATURE:
<221> NAME/KEY: modified_base
<222> LOCATION: (793)..(793)
<223> OTHER INFORMATION: UNA monomer
<220> FEATURE:
<221> NAME/KEY: modified_base
<222> LOCATION: (802)..(802)
<223> OTHER INFORMATION: UNA monomer
<220> FEATURE:
<221> NAME/KEY: modified_base
<222> LOCATION: (806)..(806)
<223> OTHER INFORMATION: UNA monomer
<220> FEATURE:
<221> NAME/KEY: modified_base
<222> LOCATION: (813)..(813)
<223> OTHER INFORMATION: UNA monomer
<220> FEATURE:
<221> NAME/KEY: modified_base
<222> LOCATION: (817)..(817)
<223> OTHER INFORMATION: UNA monomer
<220> FEATURE:
<221> NAME/KEY: modified_base
<222> LOCATION: (827)..(827)
<223> OTHER INFORMATION: UNA monomer
<220> FEATURE:
<221> NAME/KEY: modified_base
<222> LOCATION: (829)..(829)
<223> OTHER INFORMATION: UNA monomer
<220> FEATURE:
<221> NAME/KEY: modified_base
<222> LOCATION: (831)..(831)
<223> OTHER INFORMATION: UNA monomer
<220> FEATURE:
<221> NAME/KEY: modified_base
<222> LOCATION: (843)..(843)
<223> OTHER INFORMATION: UNA monomer
<220> FEATURE:
<221> NAME/KEY: modified_base
<222> LOCATION: (848)..(848)
<223> OTHER INFORMATION: UNA monomer
<220> FEATURE:
<221> NAME/KEY: modified_base
<222> LOCATION: (850)..(850)
<223> OTHER INFORMATION: UNA monomer
<220> FEATURE:
<221> NAME/KEY: modified_base
<222> LOCATION: (855)..(855)
<223> OTHER INFORMATION: UNA monomer
<220> FEATURE:
<221> NAME/KEY: modified_base
<222> LOCATION: (860)..(860)
<223> OTHER INFORMATION: UNA monomer
<220> FEATURE:
<221> NAME/KEY: modified_base
<222> LOCATION: (862)..(863)
<223> OTHER INFORMATION: UNA monomer
<220> FEATURE:
<221> NAME/KEY: modified_base
<222> LOCATION: (870)..(870)
<223> OTHER INFORMATION: UNA monomer
<220> FEATURE:
<221> NAME/KEY: modified_base
<222> LOCATION: (872)..(872)
<223> OTHER INFORMATION: UNA monomer
<220> FEATURE:
<221> NAME/KEY: modified_base
<222> LOCATION: (877)..(878)
<223> OTHER INFORMATION: UNA monomer
<220> FEATURE:
<221> NAME/KEY: modified_base
<222> LOCATION: (880)..(883)
<223> OTHER INFORMATION: UNA monomer
<220> FEATURE:
<221> NAME/KEY: modified_base
<222> LOCATION: (888)..(888)
```

```
<223> OTHER INFORMATION: UNA monomer
<220> FEATURE:
<221> NAME/KEY: modified_base
<222> LOCATION: (895)..(897)
<223> OTHER INFORMATION: UNA monomer
<220> FEATURE:
<221> NAME/KEY: modified_base
<222> LOCATION: (904)..(907)
<223> OTHER INFORMATION: UNA monomer
<220> FEATURE:
<221> NAME/KEY: modified_base
<222> LOCATION: (917)..(918)
<223> OTHER INFORMATION: UNA monomer
<220> FEATURE:
<221> NAME/KEY: modified_base
<222> LOCATION: (923)..(924)
<223> OTHER INFORMATION: UNA monomer
<220> FEATURE:
<221> NAME/KEY: modified_base
<222> LOCATION: (928)..(928)
<223> OTHER INFORMATION: UNA monomer
<220> FEATURE:
<221> NAME/KEY: modified_base
<222> LOCATION: (930)..(930)
<223> OTHER INFORMATION: UNA monomer
<220> FEATURE:
<221> NAME/KEY: modified_base
<222> LOCATION: (932)..(932)
<223> OTHER INFORMATION: UNA monomer
<220> FEATURE:
<221> NAME/KEY: modified_base
<222> LOCATION: (936)..(936)
<223> OTHER INFORMATION: UNA monomer
<220> FEATURE:
<221> NAME/KEY: modified_base
<222> LOCATION: (942)..(942)
<223> OTHER INFORMATION: UNA monomer
<220> FEATURE:
<221> NAME/KEY: modified_base
<222> LOCATION: (945)..(945)
<223> OTHER INFORMATION: UNA monomer
<220> FEATURE:
<221> NAME/KEY: modified_base
<222> LOCATION: (949)..(949)
<223> OTHER INFORMATION: UNA monomer
<220> FEATURE:
<221> NAME/KEY: modified_base
<222> LOCATION: (953)..(954)
<223> OTHER INFORMATION: UNA monomer
<220> FEATURE:
<221> NAME/KEY: modified_base
<222> LOCATION: (962)..(962)
<223> OTHER INFORMATION: UNA monomer
<220> FEATURE:
<221> NAME/KEY: modified_base
<222> LOCATION: (971)..(973)
<223> OTHER INFORMATION: UNA monomer
<220> FEATURE:
<221> NAME/KEY: modified_base
<222> LOCATION: (976)..(976)
<223> OTHER INFORMATION: UNA monomer
<220> FEATURE:
<221> NAME/KEY: modified_base
<222> LOCATION: (979)..(981)
<223> OTHER INFORMATION: UNA monomer
<220> FEATURE:
<221> NAME/KEY: modified_base
<222> LOCATION: (984)..(984)
<223> OTHER INFORMATION: UNA monomer
<220> FEATURE:
<221> NAME/KEY: modified_base
<222> LOCATION: (986)..(986)
<223> OTHER INFORMATION: UNA monomer
<220> FEATURE:
<221> NAME/KEY: modified_base
<222> LOCATION: (991)..(993)
<223> OTHER INFORMATION: UNA monomer
<220> FEATURE:
<221> NAME/KEY: modified_base
```

```
<222> LOCATION: (998)..(998)
<223> OTHER INFORMATION: UNA monomer
<220> FEATURE:
<221> NAME/KEY: modified_base
<222> LOCATION: (1000)..(1000)
<223> OTHER INFORMATION: UNA monomer
<220> FEATURE:
<221> NAME/KEY: modified_base
<222> LOCATION: (1015)..(1015)
<223> OTHER INFORMATION: UNA monomer
<220> FEATURE:
<221> NAME/KEY: modified_base
<222> LOCATION: (1019)..(1019)
<223> OTHER INFORMATION: UNA monomer
<220> FEATURE:
<221> NAME/KEY: modified_base
<222> LOCATION: (1027)..(1027)
<223> OTHER INFORMATION: UNA monomer
<220> FEATURE:
<221> NAME/KEY: modified_base
<222> LOCATION: (1029)..(1029)
<223> OTHER INFORMATION: UNA monomer
<220> FEATURE:
<221> NAME/KEY: modified_base
<222> LOCATION: (1032)..(1032)
<223> OTHER INFORMATION: UNA monomer
<220> FEATURE:
<221> NAME/KEY: modified_base
<222> LOCATION: (1035)..(1035)
<223> OTHER INFORMATION: UNA monomer
<220> FEATURE:
<221> NAME/KEY: modified_base
<222> LOCATION: (1040)..(1040)
<223> OTHER INFORMATION: UNA monomer
<220> FEATURE:
<221> NAME/KEY: modified_base
<222> LOCATION: (1043)..(1043)
<223> OTHER INFORMATION: UNA monomer
<220> FEATURE:
<221> NAME/KEY: modified_base
<222> LOCATION: (1045)..(1045)
<223> OTHER INFORMATION: UNA monomer
<220> FEATURE:
<221> NAME/KEY: modified_base
<222> LOCATION: (1048)..(1048)
<223> OTHER INFORMATION: UNA monomer
<220> FEATURE:
<221> NAME/KEY: modified_base
<222> LOCATION: (1051)..(1053)
<223> OTHER INFORMATION: UNA monomer
<220> FEATURE:
<221> NAME/KEY: modified_base
<222> LOCATION: (1056)..(1056)
<223> OTHER INFORMATION: UNA monomer
<220> FEATURE:
<221> NAME/KEY: modified_base
<222> LOCATION: (1060)..(1061)
<223> OTHER INFORMATION: UNA monomer
<220> FEATURE:
<221> NAME/KEY: modified_base
<222> LOCATION: (1066)..(1066)
<223> OTHER INFORMATION: UNA monomer
<220> FEATURE:
<221> NAME/KEY: modified_base
<222> LOCATION: (1069)..(1069)
<223> OTHER INFORMATION: UNA monomer
<220> FEATURE:
<221> NAME/KEY: modified_base
<222> LOCATION: (1072)..(1073)
<223> OTHER INFORMATION: UNA monomer
<220> FEATURE:
<221> NAME/KEY: modified_base
<222> LOCATION: (1075)..(1075)
<223> OTHER INFORMATION: UNA monomer
<220> FEATURE:
<221> NAME/KEY: modified_base
<222> LOCATION: (1091)..(1092)
<223> OTHER INFORMATION: UNA monomer
<220> FEATURE:
```

```
<221> NAME/KEY: modified_base
<222> LOCATION: (1094)..(1094)
<223> OTHER INFORMATION: UNA monomer
<220> FEATURE:
<221> NAME/KEY: modified_base
<222> LOCATION: (1100)..(1100)
<223> OTHER INFORMATION: UNA monomer
<220> FEATURE:
<221> NAME/KEY: modified_base
<222> LOCATION: (1106)..(1106)
<223> OTHER INFORMATION: UNA monomer
<220> FEATURE:
<221> NAME/KEY: modified_base
<222> LOCATION: (1121)..(1121)
<223> OTHER INFORMATION: UNA monomer
<220> FEATURE:
<221> NAME/KEY: modified_base
<222> LOCATION: (1128)..(1129)
<223> OTHER INFORMATION: UNA monomer
<220> FEATURE:
<221> NAME/KEY: modified_base
<222> LOCATION: (1134)..(1134)
<223> OTHER INFORMATION: UNA monomer
<220> FEATURE:
<221> NAME/KEY: modified_base
<222> LOCATION: (1136)..(1136)
<223> OTHER INFORMATION: UNA monomer
<220> FEATURE:
<221> NAME/KEY: modified_base
<222> LOCATION: (1144)..(1145)
<223> OTHER INFORMATION: UNA monomer
<220> FEATURE:
<221> NAME/KEY: modified_base
<222> LOCATION: (1154)..(1154)
<223> OTHER INFORMATION: UNA monomer
<220> FEATURE:
<221> NAME/KEY: modified_base
<222> LOCATION: (1156)..(1156)
<223> OTHER INFORMATION: UNA monomer
<220> FEATURE:
<221> NAME/KEY: modified_base
<222> LOCATION: (1158)..(1159)
<223> OTHER INFORMATION: UNA monomer
<220> FEATURE:
<221> NAME/KEY: modified_base
<222> LOCATION: (1163)..(1163)
<223> OTHER INFORMATION: UNA monomer
<220> FEATURE:
<221> NAME/KEY: modified_base
<222> LOCATION: (1173)..(1176)
<223> OTHER INFORMATION: UNA monomer
<220> FEATURE:
<221> NAME/KEY: modified_base
<222> LOCATION: (1179)..(1179)
<223> OTHER INFORMATION: UNA monomer
<220> FEATURE:
<221> NAME/KEY: modified_base
<222> LOCATION: (1182)..(1182)
<223> OTHER INFORMATION: UNA monomer
<220> FEATURE:
<221> NAME/KEY: modified_base
<222> LOCATION: (1196)..(1196)
<223> OTHER INFORMATION: UNA monomer
<220> FEATURE:
<221> NAME/KEY: modified_base
<222> LOCATION: (1204)..(1206)
<223> OTHER INFORMATION: UNA monomer
<220> FEATURE:
<221> NAME/KEY: modified_base
<222> LOCATION: (1209)..(1209)
<223> OTHER INFORMATION: UNA monomer
<220> FEATURE:
<221> NAME/KEY: modified_base
<222> LOCATION: (1217)..(1217)
<223> OTHER INFORMATION: UNA monomer
<220> FEATURE:
<221> NAME/KEY: modified_base
<222> LOCATION: (1221)..(1221)
<223> OTHER INFORMATION: UNA monomer
```

-continued

```
<220> FEATURE:
<221> NAME/KEY: modified_base
<222> LOCATION: (1228)..(1229)
<223> OTHER INFORMATION: UNA monomer
<220> FEATURE:
<221> NAME/KEY: modified_base
<222> LOCATION: (1231)..(1231)
<223> OTHER INFORMATION: UNA monomer
<220> FEATURE:
<221> NAME/KEY: modified_base
<222> LOCATION: (1235)..(1236)
<223> OTHER INFORMATION: UNA monomer
<220> FEATURE:
<221> NAME/KEY: modified_base
<222> LOCATION: (1240)..(1240)
<223> OTHER INFORMATION: UNA monomer
<220> FEATURE:
<221> NAME/KEY: modified_base
<222> LOCATION: (1249)..(1249)
<223> OTHER INFORMATION: UNA monomer
<220> FEATURE:
<221> NAME/KEY: modified_base
<222> LOCATION: (1262)..(1263)
<223> OTHER INFORMATION: UNA monomer
<220> FEATURE:
<221> NAME/KEY: modified_base
<222> LOCATION: (1268)..(1268)
<223> OTHER INFORMATION: UNA monomer
<220> FEATURE:
<221> NAME/KEY: modified_base
<222> LOCATION: (1270)..(1271)
<223> OTHER INFORMATION: UNA monomer
<220> FEATURE:
<221> NAME/KEY: modified_base
<222> LOCATION: (1278)..(1278)
<223> OTHER INFORMATION: UNA monomer
<220> FEATURE:
<221> NAME/KEY: modified_base
<222> LOCATION: (1289)..(1290)
<223> OTHER INFORMATION: UNA monomer
<220> FEATURE:
<221> NAME/KEY: modified_base
<222> LOCATION: (1295)..(1298)
<223> OTHER INFORMATION: UNA monomer
<220> FEATURE:
<221> NAME/KEY: modified_base
<222> LOCATION: (1302)..(1302)
<223> OTHER INFORMATION: UNA monomer
<220> FEATURE:
<221> NAME/KEY: modified_base
<222> LOCATION: (1305)..(1306)
<223> OTHER INFORMATION: UNA monomer
<220> FEATURE:
<221> NAME/KEY: modified_base
<222> LOCATION: (1310)..(1311)
<223> OTHER INFORMATION: UNA monomer
<220> FEATURE:
<221> NAME/KEY: modified_base
<222> LOCATION: (1317)..(1317)
<223> OTHER INFORMATION: UNA monomer
<220> FEATURE:
<221> NAME/KEY: modified_base
<222> LOCATION: (1322)..(1323)
<223> OTHER INFORMATION: UNA monomer
<220> FEATURE:
<221> NAME/KEY: modified_base
<222> LOCATION: (1328)..(1328)
<223> OTHER INFORMATION: UNA monomer
<220> FEATURE:
<221> NAME/KEY: modified_base
<222> LOCATION: (1331)..(1333)
<223> OTHER INFORMATION: UNA monomer
<220> FEATURE:
<221> NAME/KEY: modified_base
<222> LOCATION: (1338)..(1338)
<223> OTHER INFORMATION: UNA monomer
<220> FEATURE:
<221> NAME/KEY: modified_base
<222> LOCATION: (1343)..(1343)
```

<223> OTHER INFORMATION: UNA monomer
<220> FEATURE:
<221> NAME/KEY: modified_base
<222> LOCATION: (1352)..(1352)
<223> OTHER INFORMATION: UNA monomer
<220> FEATURE:
<221> NAME/KEY: modified_base
<222> LOCATION: (1357)..(1357)
<223> OTHER INFORMATION: UNA monomer

<400> SEQUENCE: 158

```
auguccacug cgguccugga aacccaggc uugggcagga aacucucuga cuuuggacag      60
gaaacaagcu auauugaaga caacugcaau caaaauggug ccauaucacu gaucuucuca    120
cucaaagaag aaguuggugc auuggccaaa guauugcgcu auuugagga gaaugaugua     180
aaccugaccc acauugaauc uagaccuucu cguuuaaaga aagaugagua ugaauuuuuc    240
acccauuugg auaaacguag ccugccugcu cugacaaaca ucaucaagau cuugaggcau    300
gacauuggug ccacugucca ugagcuuuca cgagauaaga agaaagacac agugcccugg    360
uucccaagaa ccauucaaga gcuggacaga uuugccaauc agauucucag cuauggagcg    420
gaacuggaug cugaccaccc uguuuuaaaa gauccugugu accgugcaag acggaagcag    480
uuugcugaca uugccuacaa cuaccgccau gggcagccca ucccucgagu ggaauacaug    540
gaggaagaaa agaaaacaug gggcacagug uucaagacuc ugaaguccuu guauaaaacc    600
caugcuugcu augaguacaa ucacauuuuu ccacuucuug aaaaguacug uggcuuccau    660
gaagauaaca uuccccagcu ggaagacguu ucucaauucc ugcagacuug cacugguuuc    720
cgccuccgac cuguggcugg ccugcuuucc ucucgggauu ucuugggugg ccuggccuuc    780
cgagucuucc acugcacaca guacaucaga cauggaucca agcccaugua uaccccgaa    840
ccugacaucu gccaugagcu guggacau gucccuugu uuucagaucg cagcuuugcc    900
caguuuuccc aggaaauugg ccuugccucu cugggugcac cugaugaaua cauugaaaag    960
cucgccacaa uuuacugguu uacuguggag uuugggcucu gcaaacaagg agacuccaua   1020
aaggcauaug gugcugggcu ccugucaucc uuuggugaau uacaguacug cuuaucagag   1080
aagccaaagc uucucccccu ggagcuggag aagacagcca uccaaaauua cacugucacg   1140
gaguccagc cccuguauua cguggcagag aguuuuaaug augccaagga gaaaguaagg   1200
aacuuugcug ccacaauacc ucggccuuuc ucaguucgcu acgacccaua cacccaaagg   1260
auugaggucu uggacaauac ccagcagcuu aagauuuugg cugauuccau uaacagugaa   1320
auuggaauuc uuugcagugc ccuccagaaa auaaaguaa              1359
```

<210> SEQ ID NO 159
<211> LENGTH: 132
<212> TYPE: RNA
<213> ORGANISM: Tobacco etch virus

<400> SEQUENCE: 159

```
ucaacacaac auaucaaaa acaaacgaau cucaagcaau caagcauucu acuucuauug      60
cagcaauuua aaucauuucu uuuaaagcaa aagcaauuuu cugaaaauuu ucaccauuua    120
cgaacgauag cc                                                        132
```

<210> SEQ ID NO 160
<211> LENGTH: 132
<212> TYPE: RNA
<213> ORGANISM: Artificial Sequence
<220> FEATURE:
<223> OTHER INFORMATION: Description of Artificial Sequence: Synthetic -continued

```
          polynucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (6)..(6)
<223> OTHER INFORMATION: UNA monomer
<220> FEATURE:
<221> NAME/KEY: modified_base
<222> LOCATION: (10)..(10)
<223> OTHER INFORMATION: UNA monomer
<220> FEATURE:
<221> NAME/KEY: modified_base
<222> LOCATION: (14)..(14)
<223> OTHER INFORMATION: UNA monomer
<220> FEATURE:
<221> NAME/KEY: modified_base
<222> LOCATION: (19)..(19)
<223> OTHER INFORMATION: UNA monomer
<220> FEATURE:
<221> NAME/KEY: modified_base
<222> LOCATION: (23)..(23)
<223> OTHER INFORMATION: UNA monomer
<220> FEATURE:
<221> NAME/KEY: modified_base
<222> LOCATION: (27)..(27)
<223> OTHER INFORMATION: UNA monomer
<220> FEATURE:
<221> NAME/KEY: modified_base
<222> LOCATION: (31)..(31)
<223> OTHER INFORMATION: UNA monomer
<220> FEATURE:
<221> NAME/KEY: modified_base
<222> LOCATION: (35)..(35)
<223> OTHER INFORMATION: UNA monomer
<220> FEATURE:
<221> NAME/KEY: modified_base
<222> LOCATION: (39)..(39)
<223> OTHER INFORMATION: UNA monomer
<220> FEATURE:
<221> NAME/KEY: modified_base
<222> LOCATION: (43)..(43)
<223> OTHER INFORMATION: UNA monomer
<220> FEATURE:
<221> NAME/KEY: modified_base
<222> LOCATION: (47)..(47)
<223> OTHER INFORMATION: UNA monomer
<220> FEATURE:
<221> NAME/KEY: modified_base
<222> LOCATION: (51)..(51)
<223> OTHER INFORMATION: UNA monomer
<220> FEATURE:
<221> NAME/KEY: modified_base
<222> LOCATION: (55)..(55)
<223> OTHER INFORMATION: UNA monomer
<220> FEATURE:
<221> NAME/KEY: modified_base
<222> LOCATION: (59)..(59)
<223> OTHER INFORMATION: UNA monomer
<220> FEATURE:
<221> NAME/KEY: modified_base
<222> LOCATION: (63)..(63)
<223> OTHER INFORMATION: UNA monomer
<220> FEATURE:
<221> NAME/KEY: modified_base
<222> LOCATION: (67)..(67)
<223> OTHER INFORMATION: UNA monomer
<220> FEATURE:
<221> NAME/KEY: modified_base
<222> LOCATION: (71)..(71)
<223> OTHER INFORMATION: UNA monomer
<220> FEATURE:
<221> NAME/KEY: modified_base
<222> LOCATION: (75)..(75)
<223> OTHER INFORMATION: UNA monomer
<220> FEATURE:
<221> NAME/KEY: modified_base
```

```
<222> LOCATION: (79)..(79)
<223> OTHER INFORMATION: UNA monomer
<220> FEATURE:
<221> NAME/KEY: modified_base
<222> LOCATION: (83)..(83)
<223> OTHER INFORMATION: UNA monomer
<220> FEATURE:
<221> NAME/KEY: modified_base
<222> LOCATION: (87)..(87)
<223> OTHER INFORMATION: UNA monomer
<220> FEATURE:
<221> NAME/KEY: modified_base
<222> LOCATION: (91)..(91)
<223> OTHER INFORMATION: UNA monomer
<220> FEATURE:
<221> NAME/KEY: modified_base
<222> LOCATION: (95)..(95)
<223> OTHER INFORMATION: UNA monomer
<220> FEATURE:
<221> NAME/KEY: modified_base
<222> LOCATION: (99)..(99)
<223> OTHER INFORMATION: UNA monomer
<220> FEATURE:
<221> NAME/KEY: modified_base
<222> LOCATION: (103)..(103)
<223> OTHER INFORMATION: UNA monomer
<220> FEATURE:
<221> NAME/KEY: modified_base
<222> LOCATION: (107)..(107)
<223> OTHER INFORMATION: UNA monomer
<220> FEATURE:
<221> NAME/KEY: modified_base
<222> LOCATION: (111)..(111)
<223> OTHER INFORMATION: UNA monomer
<220> FEATURE:
<221> NAME/KEY: modified_base
<222> LOCATION: (115)..(115)
<223> OTHER INFORMATION: UNA monomer
<220> FEATURE:
<221> NAME/KEY: modified_base
<222> LOCATION: (119)..(119)
<223> OTHER INFORMATION: UNA monomer
<220> FEATURE:
<221> NAME/KEY: modified_base
<222> LOCATION: (123)..(123)
<223> OTHER INFORMATION: UNA monomer
<220> FEATURE:
<221> NAME/KEY: modified_base
<222> LOCATION: (127)..(127)
<223> OTHER INFORMATION: UNA monomer
<220> FEATURE:
<221> NAME/KEY: modified_base
<222> LOCATION: (131)..(131)
<223> OTHER INFORMATION: UNA monomer

<400> SEQUENCE: 160
ucaacacaac auauacaaaa acaaacgaau cucaagcaau caagcauucu acuucuauug    60
cagcaauuua aaucauuucu uuuaaagcaa aagcauuuuu cugaaaauuu ucaccauuua   120
cgaacgauag cc                                                       132

<210> SEQ ID NO 161
<211> LENGTH: 132
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: UNA monomer
<220> FEATURE:
<221> NAME/KEY: modified_base
<222> LOCATION: (32)..(32)
<223> OTHER INFORMATION: UNA monomer
```

```
<220> FEATURE:
<221> NAME/KEY: modified_base
<222> LOCATION: (62)..(62)
<223> OTHER INFORMATION: UNA monomer
<220> FEATURE:
<221> NAME/KEY: modified_base
<222> LOCATION: (92)..(92)
<223> OTHER INFORMATION: UNA monomer
<220> FEATURE:
<221> NAME/KEY: modified_base
<222> LOCATION: (131)..(131)
<223> OTHER INFORMATION: UNA monomer

<400> SEQUENCE: 161
ucaacacaac auauacaaaa caaacgaauc ucaagcaauc aagcauucua cuucuauugc      60
agcaauuuaa aucauuucuu uuaaagcaaa agcaauuuuc ugaaaauuuu caccauuuac    120
gaacgauagc cc                                                         132

<210> SEQ ID NO 162
<211> LENGTH: 131
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(4)
<223> OTHER INFORMATION: UNA monomer
<220> FEATURE:
<221> NAME/KEY: modified_base
<222> LOCATION: (128)..(130)
<223> OTHER INFORMATION: UNA monomer

<400> SEQUENCE: 162
ucaacacaac auauacaaaa caaacgaauc ucaagcaauc aagcauucua cuucuauugc      60
agcaauuuaa aucauuucuu uuaaagcaaa agcaauuuuc ugaaaauuuu caccauuuac    120
gaacgauagc c                                                          131

<210> SEQ ID NO 163
<211> LENGTH: 131
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(1)
<223> OTHER INFORMATION: UNA monomer
<220> FEATURE:
<221> NAME/KEY: modified_base
<222> LOCATION: (12)..(12)
<223> OTHER INFORMATION: UNA monomer
<220> FEATURE:
<221> NAME/KEY: modified_base
<222> LOCATION: (14)..(14)
<223> OTHER INFORMATION: UNA monomer
<220> FEATURE:
<221> NAME/KEY: modified_base
<222> LOCATION: (29)..(29)
<223> OTHER INFORMATION: UNA monomer
<220> FEATURE:
<221> NAME/KEY: modified_base
<222> LOCATION: (31)..(31)
<223> OTHER INFORMATION: UNA monomer
<220> FEATURE:
<221> NAME/KEY: modified_base
<222> LOCATION: (39)..(39)
<223> OTHER INFORMATION: UNA monomer
<220> FEATURE:
```

```
<221> NAME/KEY: modified_base
<222> LOCATION: (46)..(47)
<223> OTHER INFORMATION: UNA monomer
<220> FEATURE:
<221> NAME/KEY: modified_base
<222> LOCATION: (49)..(49)
<223> OTHER INFORMATION: UNA monomer
<220> FEATURE:
<221> NAME/KEY: modified_base
<222> LOCATION: (52)..(53)
<223> OTHER INFORMATION: UNA monomer
<220> FEATURE:
<221> NAME/KEY: modified_base
<222> LOCATION: (55)..(55)
<223> OTHER INFORMATION: UNA monomer
<220> FEATURE:
<221> NAME/KEY: modified_base
<222> LOCATION: (57)..(58)
<223> OTHER INFORMATION: UNA monomer
<220> FEATURE:
<221> NAME/KEY: modified_base
<222> LOCATION: (66)..(68)
<223> OTHER INFORMATION: UNA monomer
<220> FEATURE:
<221> NAME/KEY: modified_base
<222> LOCATION: (72)..(72)
<223> OTHER INFORMATION: UNA monomer
<220> FEATURE:
<221> NAME/KEY: modified_base
<222> LOCATION: (75)..(77)
<223> OTHER INFORMATION: UNA monomer
<220> FEATURE:
<221> NAME/KEY: modified_base
<222> LOCATION: (79)..(82)
<223> OTHER INFORMATION: UNA monomer
<220> FEATURE:
<221> NAME/KEY: modified_base
<222> LOCATION: (96)..(99)
<223> OTHER INFORMATION: UNA monomer
<220> FEATURE:
<221> NAME/KEY: modified_base
<222> LOCATION: (101)..(101)
<223> OTHER INFORMATION: UNA monomer
<220> FEATURE:
<221> NAME/KEY: modified_base
<222> LOCATION: (107)..(110)
<223> OTHER INFORMATION: UNA monomer
<220> FEATURE:
<221> NAME/KEY: modified_base
<222> LOCATION: (116)..(118)
<223> OTHER INFORMATION: UNA monomer
<220> FEATURE:
<221> NAME/KEY: modified_base
<222> LOCATION: (127)..(127)
<223> OTHER INFORMATION: UNA monomer

<400> SEQUENCE: 163
ucaacacaac auauacaaaa caaacgaauc ucaagcaauc aagcauucua cuucuauugc      60
agcaauuuaa aucauuucuu uuaaagcaaa agcaauuuuc ugaaaauuuu caccauuuac     120
gaacgauagc c                                                         131

<210> SEQ ID NO 164
<211> LENGTH: 131
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(131)
<223> OTHER INFORMATION: UNA monomer

<400> SEQUENCE: 164
```

```
ucaacacaac auauacaaaa caaacgaauc ucaagcaauc aagcauucua cuucuauugc      60
agcaauuuaa aucauuucuu uuaaagcaaa agcaauuuuc ugaaaauuuu caccauuuac     120
gaacgauagc c                                                         131

<210> SEQ ID NO 165
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
cttcctactc aggctttatt caaagacca                                       29

<210> SEQ ID NO 166
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'- Phosphorylation
<220> FEATURE:
<221> NAME/KEY: modified_base
<222> LOCATION: (26)..(30)
<223> OTHER INFORMATION: UNA monomer
<220> FEATURE:
<223> OTHER INFORMATION: 3'-(C3 Spacer)

<400> SEQUENCE: 166
aaaaaaaaaa aaaaaaaaaa aaaaaaaaaa                                      30
```